(12) United States Patent
Cravatt et al.

(10) Patent No.: US 10,859,585 B2
(45) Date of Patent: Dec. 8, 2020

(54) LIPID PROBES AND USES THEREOF

(71) Applicant: THE SCRIPPS RESEARCH INSTITUTE, La Jolla, CA (US)

(72) Inventors: Benjamin F. Cravatt, La Jolla, CA (US); Micah J. Niphakis, San Diego, CA (US); Kenneth Lum, San Diego, CA (US); Bruno Correia, Blemblens (CH); Armand Cognetta, San Diego, CA (US); Jonathan Hulce, Libertyville, IL (US)

(73) Assignee: The Scripps Research Institute, La Jolla, CA (US)

(*) Notice: Subject to any disclaimer, the term of this patent is extended or adjusted under 35 U.S.C. 154(b) by 0 days.

(21) Appl. No.: 16/235,096

(22) Filed: Dec. 28, 2018

(65) Prior Publication Data

US 2019/0293666 A1 Sep. 26, 2019

Related U.S. Application Data

(62) Division of application No. 15/080,767, filed on Mar. 25, 2016, now Pat. No. 10,168,342.

(60) Provisional application No. 62/139,576, filed on Mar. 27, 2015.

(51) Int. Cl.
*G01N 33/92* (2006.01)
*G01N 33/68* (2006.01)

(52) U.S. Cl.
CPC ........ *G01N 33/92* (2013.01); *G01N 33/6842* (2013.01); *G01N 2500/04* (2013.01); *G01N 2570/00* (2013.01)

(58) Field of Classification Search
None
See application file for complete search history.

(56) References Cited

U.S. PATENT DOCUMENTS

2011/0020837 A1* 1/2011 Haberkant .......... C07K 1/1077
435/7.1

OTHER PUBLICATIONS

Peng et al (JACS 137:556-9) (Year: 2015).*
Peng et al (JACS 137:556-9 supporting information) (Year: 2015).*

* cited by examiner

*Primary Examiner* — Christopher M Gross
(74) *Attorney, Agent, or Firm* — Thomas Fitting; Hugh Wang

(57) ABSTRACT

Disclosed herein are methods, compositions, probes, assays and kits for identifying a lipid binding protein as a drug binding target. Also disclosed herein are methods, compositions, and probes for mapping a ligand binding site on a lipid binding protein, identification of lipid binding proteins, generating drug-lipid binding protein profiles, high throughput drug screening, and identification of drugs as potential lipid binding protein ligands.

20 Claims, 25 Drawing Sheets

Specification includes a Sequence Listing.

Fig. 4
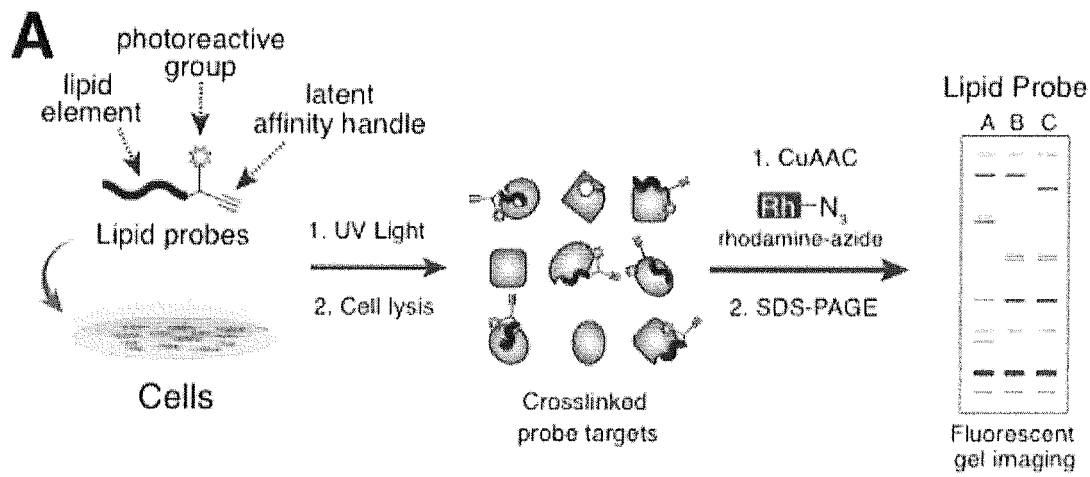
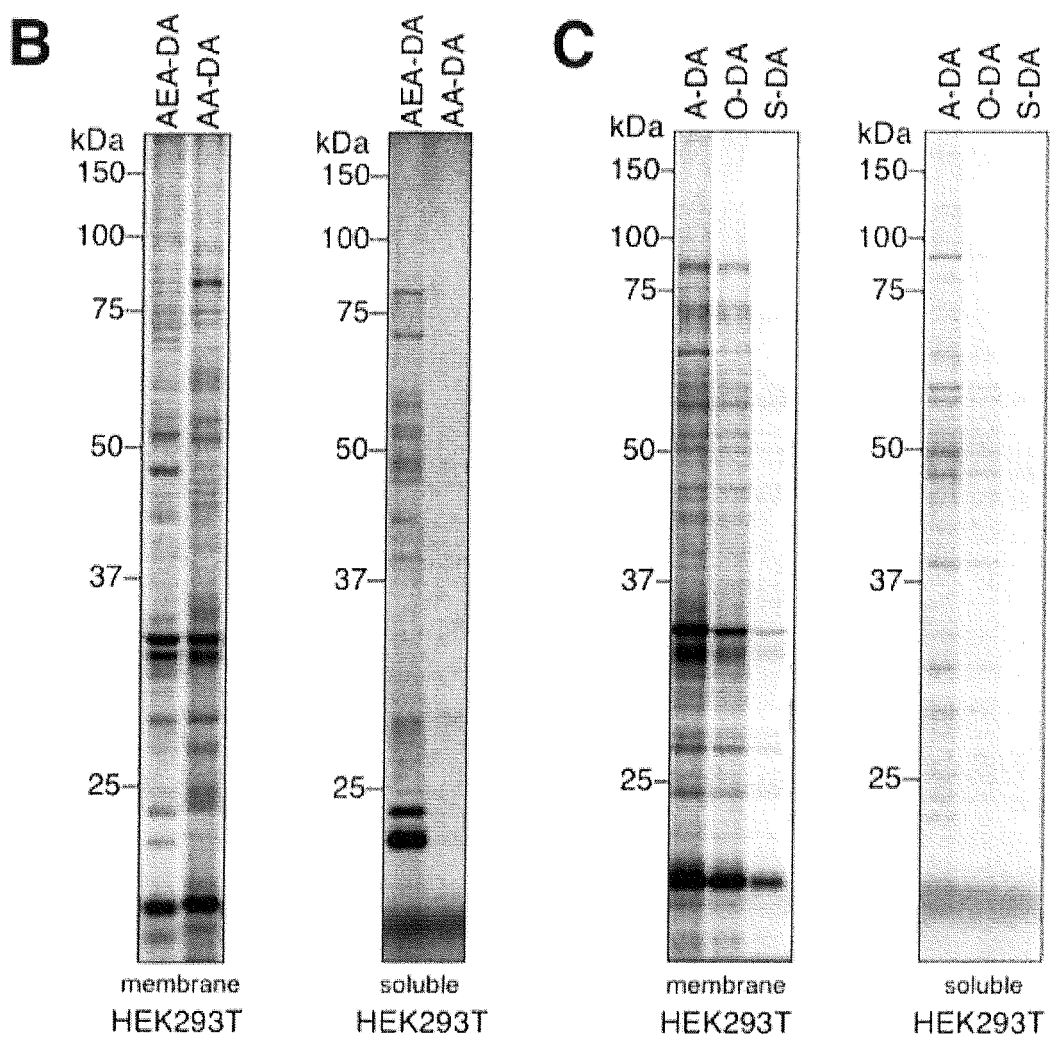

Fig. 17
a
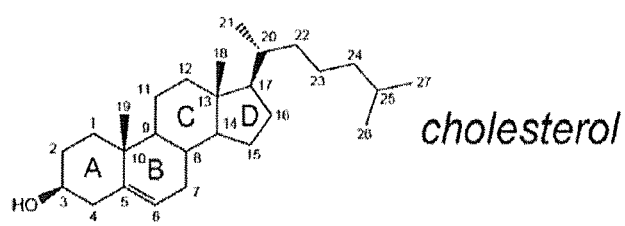 *cholesterol*
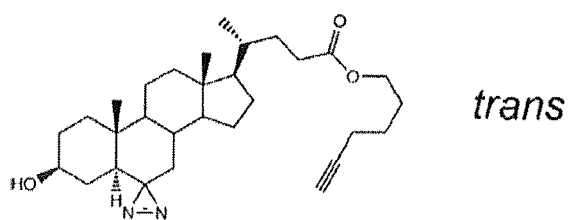 *trans*
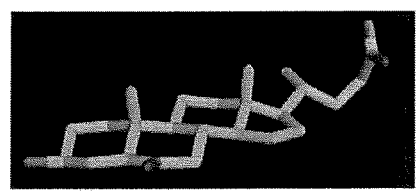
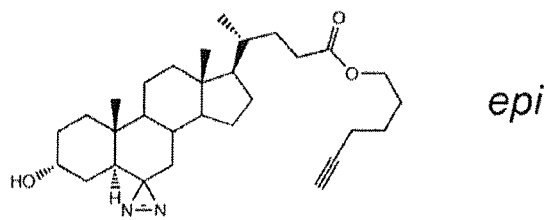 *epi*
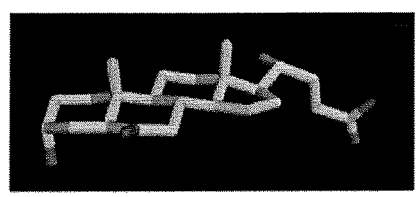
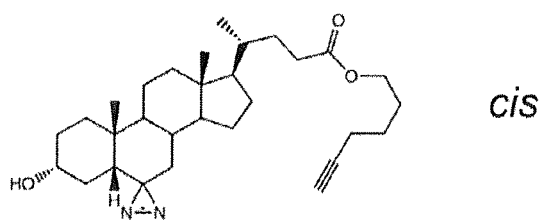 *cis*
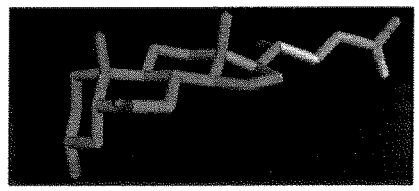
b

LIPID PROBES AND USES THEREOF

CROSS-REFERENCES

The subject application is a continuation of U.S. patent application Ser. No. 15/080,767, filed Mar. 25, 2016, which claims priority to U.S. Provisional Patent Application No. 62/139,576, filed Mar. 27, 2015, the disclosure of which is incorporated herein by reference.

STATEMENT OF GOVERNMENT LICENSE RIGHTS

This invention was made with government support under grant numbers CA132630 and DA032541 awarded by the National Institues of Health. The government has certain rights in the invention.

SEQUENCE LISTING

The instant application contains a Sequence Listing which has been submitted electronically in ASCII format and is hereby incorporated by reference in its entirety. Said ASCII copy, created on Mar. 16, 2016, is named 1702_1C1_SequenceListing.txt and is 27,141 bytes in size.

INCORPORATION BY REFERENCE OF TABLE SUBMITTED AS TEXT FILE VIA EFS-WEB

The instant application contains Table 3, which has been submitted as a computer readable text file in ASCII format via EFS-Web and is hereby incorporated in its entirety by reference herein. The text file, created date of Mar. 27, 2015, is named 1702_1C1_Table3.txt and is 196,718 bytes in size.

LENGTHY TABLES

The patent contains a lengthy table section. A copy of the table is available in electronic form from the USPTO web site (http://seqdata.uspto.gov/?pageRequest=docDetail&DocID=US10859585B2). An electronic copy of the table will also be available from the USPTO upon request and payment of the fee set forth in 37 CFR 1.19(b)(3).

BACKGROUND OF THE INVENTION

Small-molecule metabolites modulate various components of life. In some instances, their biological functions are mediated and regulated by interactions with proteins. In some cases, these metabolite-protein interactions include ligand-receptor, substrate-enzyme, and client-carrier relationships, many of which represent key nodes in biochemical networks that regulate cell physiology and disease. Eukaryotic and prokaryotic cells harbor numerous structurally distinct metabolites. Among these natural products, lipids display a capacity to interact with and to affect the functions of proteins.

SUMMARY OF THE INVENTION

Disclosed herein, in certain embodiments, is a method of identifying a lipid binding protein as a drug binding target, comprising: (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the lipid binding proteins from the set of lipid probe-protein complexes; (d) based on the value assigned in c), identifying a lipid binding protein as a drug binding target. In some embodiments, the sample comprises a first cell solution and a second cell solution. In some embodiments, the method further comprises contacting the first cell solution with a first lipid probe and contacting the second cell solution with a second lipid probe. In some embodiments, the first lipid probe and the second lipid probe are the same. In some embodiments, the second cell solution comprises a drug. In some embodiments, the second cell solution further comprises a buffer or a media. In some embodiments, the method further comprises treating the first cell solution and the second cell solution by a photoreactive means to generate a first group of lipid probe-protein complexes and a second group of lipid probe-protein complexes, wherein the first group and the second group of lipid probe-protein complexes comprise the set of lipid probe-protein complexes. In some embodiments, the method further comprises contacting the first cell solution with a first set of lipid probes wherein each of the lipid probes comprises a lipid, a photoreactive group, and an affinity handle, and wherein each lipid probe is different within the set. In some embodiments, the method further comprises contacting the second cell solution with a second set of lipid probes wherein each of the lipid probes comprises a lipid, a photoreactive group, and an affinity handle, and wherein each lipid probe is different within the set. In some embodiments, the first set of lipid probes and the second set of lipid probes are the same. In some embodiments, the method further comprises treating the first cell solution and the second cell solution by a photoreactive means to generate a third group of lipid probe-protein complexes and a fourth group of lipid probe-protein complexes. In some embodiments, the lipid is a bioactive lipid. In some embodiments, the lipid comprises fatty acyls, glycerolipids, glycerophospholipids, sphingolipids, sterol lipids, prenol lipids, saccharolipids, or polyketides. In some embodiments, the lipid is a member of the fatty acyls group. In some embodiments, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some embodiments, the lipid is a fatty acid. In some embodiments, the fatty acid comprises a saturated fatty acid, a monounsaturated fatty acid, or a polyunsaturated fatty acid. In some embodiments, the saturated fatty acid comprises propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid, or hexatriacontanoic acid. In some embodiments, the monounsaturated fatty acid comprises palmitoleic acid, vaccenic acid, oleic acid, eicosenoic acid, erucic acid, gadoleic acid, myristoleic acid, or nervonic acid. In some embodiments, the polyunsaturated fatty acid comprises omega-3 fatty acids, omega-6 fatty acids, omega-9 fatty acids, or conjugated fatty acids. In some embodiments, the polyunsaturated fatty acid comprises hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, mead acid, rumenic acid, alpha-calendic acid, beta-calendic acid, jacaric acid, alpha-eleostearic acid, beta-eleostearic acid, catalpic acid, punicic acid, rumelenic acid, alpha-parinaric acid, beta-parinaric acid, bosseopentaenoic acid, pinolenic acid, or podocarpic acid. In some embodiments, the lipid is a sterol lipid. In some embodiments, the sterol lipid comprises sterols, steroids, secosteroids, or bile acids. In some embodiments, the sterol comprises cholesterol, ergosterol, C24-propyl sterols, or stanol. In some embodiments, the photoreactive group comprises azides, benzophenone, diazo compounds, diazirines, diazonium salts, or diaryl ketones. In some embodiments, the photoreactive group is diazirine, or its derivatives thereof. In some embodiments, the photoreactive group further comprises a linker. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the affinity handle comprises an alkyne or an azide group. In some embodiments, the affinity handle is conjugated to the terminal carbon atom of the lipid probe. In some embodiments, the photoreactive group and the affinity handle are conjugated to the same site of the lipid probe. In some embodiments, the photoreactive group and the affinity handle are conjugated to different sites of the lipid probe. In some embodiments, the photoreactive means comprises ultraviolet light. In some embodiments, the affinity handle is further conjugated to an affinity ligand. In some embodiments, the affinity ligand comprises a chromophore, a labeling group, or a combination thereof. In some embodiments, the chromophore comprises fluorochrome, non-fluorochrome chromophore, quencher, an absorption chromophore, fluorophore, organic dye, inorganic dye, metal chelate, or a fluorescent enzyme substrate. In some embodiments, the fluorophore comprises rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol, aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-toluidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TAMRA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705. In some embodiments, the labeling group is biotin moiety, streptavidin moiety, bead, resin, a solid support, or a combination thereof. In some embodiments, the lipid probe comprises: a lipid selected from arachidonoyl, arachidoyl, oleoyl, palmitoyl, or stearoyl fatty acyls; a photoreactive linker; and an affinity handle. In some embodiments, the lipid probe is a lipid probe of Formula (I):

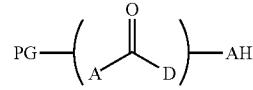

Formula (I)

wherein:
A is $C_{16}$-$C_{20}$alkyl or $C_{16}$-$C_{20}$alkenyl;
D is —OH, —NH$_2$, —NHR$^7$, or —OR$^8$;
  R$^7$ is $C_1$-$C_4$alkyl, ($C_1$-$C_5$alkyl)OH, or ($C_1$-$C_5$)SO$_3$M;
  R$^8$ is (CH$_2$OH)n;
  M is monovalent or divalent cation;
  n is 1, 2, or 3;
PG is a photoreactive group; and
AH is an affinity handle;
wherein PG is attached to A or D and AH is attached to A or D.

In some embodiments, the lipid probe has one of the following structures as illustrated in Table 1. In some embodiments, the lipid binding protein is an enzyme, a transporter, a receptor, an adaptor, a channel protein, or a chaperone. In some embodiments, the lipid binding protein is a protein encoded by a gene of Table 3, a protein encoded by a gene of Table 4, or a protein encoded by a gene of Table 5. In some embodiments, the first cell solution further comprises a control. In some embodiments, the control is dimethyl sulfoxide (DMSO). In some embodiments, the proteomic analysis means comprises a mass spectroscopy method. In some embodiments, the value assigned to each of the lipid binding protein in step c) is the area-under-the curve from a plot of signal intensity as a function of mass-to-charge ratio. In some embodiments, the identifying in step d) further comprises (i) locating a first value assigned to a lipid binding protein from the first group of lipid probe-protein complex and a second value of the same lipid binding protein from the second group of lipid probe-protein complex; and (ii) calculating a ratio between the two values assigned to the same lipid binding protein. In some embodiments, the ratio of greater than 2 indicates that the lipid binding protein is a candidate for interacting with the drug. In some embodiments, the ratio of greater than 3 indicates that the lipid binding protein is a candidate for interacting with the drug. In some embodiments, the method further comprises contacting the second cell solution with an additional drug. In some embodiments, the method further comprises generating a drug-lipid binding protein profile. In some embodiments, the drug-lipid binding protein profile is a profile that indicates the array of lipid binding proteins that interact with the drug. In some embodiments, the method further comprises classifying the drug as a specific inhibitor or a pan inhibitor. In some embodiments, the cell is obtained from a tumor cell line. In some embodiments, the cell is obtained from a Neuro2a or A549 cell line. In some embodiments, the cell is obtained from a tumor sample. In some embodiments, the sample is a tissue sample. In some embodiments, the method is an in situ method.

Described herein is a method of mapping a ligand binding site on a lipid binding protein, comprising (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; and (c) based on step b), locating a ligand binding site on the lipid binding protein. In some embodiments, step b) further comprises treating the set of lipid probe-protein complexes with a protease to generate a set of protein fragments. In some embodiments, each protein fragment is attached to a lipid probe. In some embodiments, locating further comprises determining the sequence of the set of protein fragments. In some embodiments, the protein fragment correlates to a ligand binding site on a lipid binding protein. In some embodiments, the sample comprises a first cell solution and a second cell solution. In some embodiments, the second cell solution comprises a drug. In some embodiments, the second cell solution further comprises a buffer or a media. In some embodiments, the method further comprises treating the first cell solution and the second cell solution by a photoreactive means to generate a first group of lipid probe-protein complexes and a second group of lipid probe-protein complexes, wherein the first group and the second group of lipid probe-protein complexes comprise the set of lipid probe-protein complexes. In some embodiments, the lipid is a bioactive lipid. In some embodiments, the lipid comprises fatty acyls, glycerolipids, glycerophospholipids, sphingolipids, sterol lipids, prenol lipids, saccharolipids, or polyketides. In some embodiments, the lipid is a member of the fatty acyls group. In some embodiments, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some embodiments, the lipid is a sterol lipid. In some embodiments, the photoreactive group comprises azides, benzophenone, diazo compounds, diazirines, diazonium salts, or diaryl ketones. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the lipid probe comprises a lipid selected from arachidonoyl, arachidoyl, oleoyl, palmitoyl, or stearoyl fatty acyls; a photoreactive linker; and an affinity handle. In some embodiments, the lipid probe is a lipid probe of Formula (I):

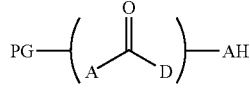

Formula (I)

wherein:
A is $C_{16}$-$C_{20}$alkyl or $C_{16}$-$C_{20}$alkenyl;
D is —OH, —NH$_2$, —NHR$^7$, or —OR$^8$;
R$^7$ is $C_1$-$C_4$alkyl, ($C_1$-$C_5$alkyl)OH, or ($C_1$-$C_5$)SO$_3$M;
R$^8$ is (CH$_2$OH)n;
M is monovalent or divalent cation;
n is 1, 2, or 3;
PG is a photoreactive group; and
AH is an affinity handle;
wherein PG is attached to A or D and AH is attached to A or D.

In some embodiments, the lipid probe has one of the following structures as illustrated in Table 1. In some embodiments, the lipid binding protein is a soluble protein or a membrane protein. In some embodiments, the lipid binding protein is an enzyme, a transporter, a receptor, an adaptor, a channel protein, or a chaperone. In some embodiments, the lipid binding protein is a protein encoded by a gene of Table 3, a protein encoded by a gene of Table 4, or a protein encoded by a gene of Table 5. In some embodiments, the proteomic analysis means comprises a mass spectroscopy method. In some embodiments, the sample is a tissue sample.

Described herein, in certain embodiments, is a lipid probe-protein composition comprising a lipid probe and a lipid binding protein. In some embodiments, the lipid binding protein is an enzyme, a transporter, a receptor, an adaptor, a channel protein, or a chaperone. In some embodiments, the lipid binding protein is a protein encoded by a gene of Table 3, a protein encoded by a gene of Table 4, a protein encoded by a gene of Table 5, or a protein encoded by a gene of Table 6. In some embodiments, the lipid binding protein is nucleobindin-1 (NUCB1). In some embodiments, the lipid binding protein is a protein fragment. In some embodiments, the protein fragment is a protein fragment of Table 6. In some embodiments, the lipid is a bioactive lipid. In some embodiments, the lipid comprises fatty acyls, glycerolipids, glycerophospholipids, sphingolipids, sterol lipids, prenol lipids, saccharolipids, or polyketides. In some embodiments, the lipid is a member of the fatty acyls group. In some embodiments, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some embodiments, the lipid is a fatty acid. In some embodiments, the lipid is a sterol lipid. In some embodiments, the sterol lipid comprises sterols, steroids, secosteroids, or bile acids. In some embodiments, the sterol comprises cholesterol, ergosterol, C24-propyl sterols, or stanol. In some embodiments, the photoreactive group comprises azides, benzophenone, diazo compounds, diazirines, diazonium salts, or diaryl ketones. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the lipid probe comprises: a lipid selected from arachidonoyl, arachidoyl, oleoyl, palmitoyl, or stearoyl fatty acyls; a photoreactive linker; and an affinity handle. In some embodiments, the lipid probe is a lipid probe of Formula (I):

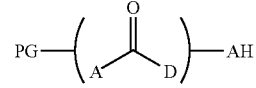

Formula (I)

wherein:
A is $C_{16}$-$C_{20}$alkyl or $C_{16}$-$C_{20}$alkenyl;
D is —OH, —NH$_2$, —NHR$^7$, or —OR$^8$;
R$^7$ is $C_1$-$C_4$alkyl, ($C_1$-$C_5$alkyl)OH, or ($C_1$-$C_5$)SO$_3$M;
R$^8$ is (CH$_2$OH)n;
M is monovalent or divalent cation;
n is 1, 2, or 3;
PG is a photoreactive group; and
AH is an affinity handle;
wherein PG is attached to A or D and AH is attached to A or D.

In some embodiments, the lipid probe has one of the following structures as illustrated in Table 1.

Described herein, in certain embodiments, is a lipid probe-protein composition produced by a process comprising contacting a sample with a lipid probe, and treating the sample comprising the lipid probe by a photoreactive means, wherein the treating time is from about 5 minutes to about 1 hour. In some embodiments, the treating time is about 10 minutes. In some embodiments, the lipid probe comprises a lipid, a photoreactive group, and an affinity handle. In some embodiments, the lipid is a bioactive lipid. In some embodiments, the lipid comprises fatty acyls, glycerolipids, glycerophospholipids, sphingolipids, sterol lipids, prenol lipids, saccharolipids, or polyketides. In some embodiments, the lipid is a member of the fatty acyls group. In some embodiments, the photoreactive group comprises azides, benzophenone, diazo compounds, diazirines, diazonium salts, or diaryl ketones. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the lipid probe comprises a lipid selected from arachidonoyl, arachidoyl, oleoyl, palmitoyl, or stearoyl fatty acyls; a photoreactive linker; and an affinity handle. In some embodiments, the lipid probe is a lipid probe of Formula (I):

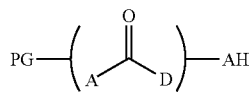

Formula (I)

wherein:
A is $C_{16}$-$C_{20}$alkyl or $C_{16}$-$C_{20}$alkenyl;
D is —OH, —NH$_2$, —NHR$^7$, or —OR$^8$;
R$^7$ is $C_1$-$C_4$alkyl, ($C_1$-$C_5$alkyl)OH, or ($C_1$-$C_5$)SO$_3$M;
R$^8$ is (CH$_2$OH)n;
M is monovalent or divalent cation;
n is 1, 2, or 3;
PG is a photoreactive group; and
AH is an affinity handle;
wherein PG is attached to A or D and AH is attached to A or D.

In some embodiments, the lipid probe has one of the following structures as illustrated in Table 1. In some embodiments, the protein from the lipid probe-protein composition is a lipid binding protein. In some embodiments, the lipid binding protein is an enzyme, a transporter, a receptor, an adaptor, a channel protein, or a chaperone. In some embodiments, the lipid binding protein is a protein encoded by a gene of Table 3, a protein encoded by a gene of Table 4, a protein encoded by a gene of Table 5, or a protein encoded by a gene of Table 6. In some embodiments, the lipid binding protein is nucleobindin-1 (NUCB1). In some embodiments, the method further comprises treating the lipid probe-protein composition with a protease. In some embodiments, the protein of the protease treated lipid probe-protein composition is a protein fragment. In some embodiments, the protein fragment is a protein fragment of Table 6. In some embodiments, the photoreactive means comprises ultraviolet light. In some embodiments, the sample is a cell solution sample. In some embodiments, the sample is a tissue sample.

Described herein, in certain embodiments, is a composition comprising an isolated sample wherein the isolated sample is an isolated cell or a tissue sample; and a lipid probe to be assayed for its ability to interact with a lipid binding protein expressed in the isolated sample. In some embodiments, the composition further comprises a drug as a test compound. In some embodiments, the lipid probe is assayed for its ability to interact with a lipid binding protein expressed in the sample in the presence of the drug.

Described herein, in certain embodiments, is an isolated treated cell comprising a lipid probe attached to a lipid binding protein. In some embodiments, the lipid probe is attached to the lipid binding protein through a covalent bond. In some embodiments, the isolated treated cell further comprises a set of lipid probes wherein each of the lipid probes is attached to a lipid binding protein. In some embodiments, each lipid probe within the set is different. In some embodiments, each lipid probe within the set is the same.

Described herein, in certain embodiments, is an isolated treated population of cells comprising a set of lipid probes attached to lipid binding proteins. In some embodiments, each of the lipid probes is attached to a lipid binding protein through a covalent bond. In some embodiments, each lipid probe within the set is different. In some embodiments, each lipid probe within the set is the same.

Described herein, in certain embodiments, is a lipid probe comprising a lipid, a photoreactive group, and an affinity handle wherein the lipid probe is constructed for detecting a drug-lipid binding protein interaction. In some embodiments, the lipid is a bioactive lipid. In some embodiments, the lipid comprises fatty acyls, glycerolipids, glycerophospholipids, sphingolipids, sterol lipids, prenol lipids, saccharolipids, or polyketides. In some embodiments, the lipid is a member of the fatty acyls group. In some embodiments, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some embodiments, the lipid is a sterol lipid. In some embodiments, the photoreactive group comprises azides, benzophenone, diazo compounds, diazirines, diazonium salts, or diaryl ketones. In some embodiments, the photoreactive group is diazirine, or its derivatives thereof. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the lipid probe comprises a lipid selected from arachidonoyl, arachidoyl, oleoyl, palmitoyl, or stearoyl fatty acyls; a photoreactive linker; and an affinity handle. In some embodiments, the lipid probe is a lipid probe of Formula (I):

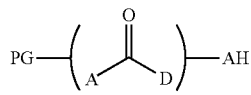

Formula (I)

wherein:
A is $C_{16}$-$C_{20}$alkyl or $C_{16}$-$C_{20}$alkenyl;
D is —OH, —$NH_2$, —$NHR^7$, or —$OR^8$;
  $R^7$ is $C_1$-$C_4$alkyl, ($C_1$-$C_5$alkyl)OH, or ($C_1$-$C_5$)$SO_3$M;
  $R^8$ is ($CH_2OH$)n;
  M is monovalent or divalent cation;
  n is 1, 2, or 3;
PG is a photoreactive group; and
AH is an affinity handle;
wherein PG is attached to A or D and AH is attached to A or D.

In some embodiments, PG is attached to A. In some embodiments, AH is attached to A. In some embodiments, the lipid probe has one of the following structures as illustrated in Table 1. In some embodiments, the probe is a lipid binding protein ligand. In some embodiments, the probe is a competitive ligand for interaction with a lipid binding protein in the presence of a drug. In some embodiments, the lipid binding protein is an enzyme, a transporter, a receptor, an adaptor, a channel protein, or a chaperone. In some embodiments, the lipid binding protein is a protein encoded by a gene of Table 3, a protein encoded by a gene of Table 4, or a protein encoded by a gene of Table 5. In some embodiments, the lipid binding protein is nucleobindin-1 (NUCB1).

Described herein, in certain embodiments, is an isolated and purified polypeptide comprising at least 90% sequence identity to at least seven contiguous amino acids of an amino acid sequence selected from Table 6, wherein the isolated and purified polypeptide is at most 50 amino acids in length. In some embodiments, the isolated and purified polypeptide comprising at least 95% sequence identity to at least seven contiguous amino acids of an amino acid sequence selected from Table 6, wherein the isolated and purified polypeptide is at most 50 amino acids in length. In some embodiments, the isolated and purified polypeptide comprising 100% sequence identity to at least seven contiguous amino acids of an amino acid sequence selected from Table 6, wherein the isolated and purified polypeptide is at most 50 amino acids in length. In some embodiments, the isolated and purified polypeptide consisting 100% sequence identity to the full length of an amino acid sequence selected from Table 6, wherein the isolated and purified polypeptide is at most 50 amino acids in length.

Described herein, in certain embodiments, is a nucleic acid encoding a polypeptide comprising at least 90% sequence identity at least seven contiguous amino acids of an amino acid sequence selected from Table 6. In some embodiments, the nucleic acid encoding a polypeptide comprising at least 95% sequence identity at least seven contiguous amino acids of an amino acid sequence selected from Table 6. In some embodiments, the nucleic acid encoding a polypeptide comprising 100% sequence identity at least seven contiguous amino acids of an amino acid sequence selected from Table 6. In some embodiments, the nucleic acid encoding a polypeptide consisting 100% sequence identity to the full length of an amino acid sequence selected from Table 6.

Described herein, in certain embodiments, is a method of screening a drug for interaction with a lipid binding protein, comprising: (a) contacting a solution comprising a purified recombinant lipid binding protein and a drug with a lipid probe, wherein the lipid probe comprises a lipid and a fluorophore; and (b) detecting a change in fluorescence polarization relative to a control, wherein the change in fluorescence polarization indicates an interaction between the drug and the lipid binding protein. In some embodiments, the lipid is a bioactive lipid. In some embodiments, the lipid comprises fatty acyls, glycerolipids, glycerophospholipids, sphingolipids, sterol lipids, prenol lipids, saccharolipids, or polyketides. In some embodiments, the lipid is a member of the fatty acyls group. In some embodiments, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some embodiments, the lipid is a fatty acid. In some embodiments, the lipid is a sterol lipid. In some embodiments, the sterol lipid comprises sterols, steroids, secosteroids, or bile acids. In some embodiments, the sterol comprises cholesterol, ergosterol, C24-propyl sterols, or stanol. In some embodiments, the lipid probe further comprises a photoreactive group. In some embodiments, the photoreactive group comprises azides, benzophenone, diazo compounds, diazirines, diazonium salts, or diaryl ketones. In some embodiments, the photoreactive group is diazirine, or its derivatives thereof. In some embodiments, the photoreactive group further comprises a linker. In some embodiments, the fluorophore comprises rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol, aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-toluidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TAMRA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705. In some embodiments, the fluorophore is conjugated to the hydrophilic portion of the lipid probe. In some embodiments, the photoreactive group and the fluorophore are conjugated to different sites of the lipid probe. In some embodiments, the lipid probe comprises an arachidonic acid and a fluorophore. In some embodiments, the lipid binding protein is a soluble protein or a membrane protein. In some embodiments, the lipid binding protein is an enzyme, a transporter, a receptor, an adaptor, a channel protein, or a chaperone. In some embodiments, the lipid binding protein is a protein encoded by a gene of Table 3, a protein encoded by a gene of Table 4, or a protein encoded by a gene of Table 5. In some embodiments, the lipid binding protein is nucleobindin-1 (NUCB1). In some embodiments, the method further comprises conjugating the lipid probe to the isolated recombinant lipid binding protein through a photoreactive means. In some embodiments, the photoreactive means comprises ultraviolet light. In some embodiments, the method further comprises contacting the solution with an additional drug. In some embodiments, the method further comprises generating a drug-lipid binding protein profile. In some embodiments, the drug-lipid binding protein profile is a profile that indicates the array of lipid binding proteins that interact with the drug. In some embodiments, the method further comprises classifying the drug as a specific inhibitor or a pan inhibitor. In some embodiments, the method is a high throughput screening method.

Described herein, in certain embodiments, is a lipid probe comprising a lipid and a fluorophore wherein the lipid probe is constructed for detecting a drug-lipid binding protein interaction. In some embodiments, the lipid is a bioactive lipid. In some embodiments, the lipid comprises fatty acyls, glycerolipids, glycerophospholipids, sphingolipids, sterol lipids, prenol lipids, saccharolipids, or polyketides. In some embodiments, the lipid is a member of the fatty acyls group. In some embodiments, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some embodiments, the lipid is a sterol lipid. In some embodiments, the lipid probe further comprises a photoreactive group. In some embodiments, the photoreactive group comprises azides, benzophenone, diazo compounds, diazirines, diazonium salts, or diaryl ketones. In some embodiments, the photoreactive group is diazirine, or its derivatives thereof. In some embodiments, the fluorophore is conjugated to the hydrophilic portion of the lipid probe. In some embodiments, the lipid probe comprises arachidonic acid and a fluorophore. In some embodiments, the lipid probe is 2-(6-(Dimethylamino)-3-(dimethyliminio)-3H-xanthen-9-yl)-5-((5-((5Z,8Z,11Z,14Z)-icosa-5,8,11,14-tetraenamido)pentyl)carbamoyl)benzoate. In some embodiments, the probe is a ligand for a lipid binding protein. In some embodiments, the lipid binding protein is an enzyme, a transporter, a receptor, an adaptor, a channel protein, or a chaperone. In some embodiments, the lipid binding protein is a protein encoded by a gene of Table 3, a protein encoded by a gene of Table 4, or a protein encoded by a gene of Table 5. In some embodiments, the lipid binding protein is nucleobindin-1 (NUCB1).

Described herein, in certain embodiments, is a lipid probe comprising a lipid and a fluorophore wherein the lipid probe is constructed for detecting a drug-nucleobindin-1 (NUCB1) interaction. In some embodiments, the lipid is a bioactive lipid. In some embodiments, the lipid comprises fatty acyls, glycerolipids, glycerophospholipids, sphingolipids, sterol lipids, prenol lipids, saccharolipids, or polyketides. In some embodiments, the lipid probe comprises arachidonic acid and a fluorophore. In some embodiments, the lipid probe is 2-(6-(Dimethylamino)-3-(dimethyliminio)-3H-xanthen-9-yl)-5-((5-((5Z,8Z,11Z,14Z)-icosa-5,8,11,14-tetraenamido)pentyl)carbamoyl)benzoate.

Described herein, in certain embodiments, is a compound of Formula (II), or a pharmaceutically acceptable salt, or solvate thereof:

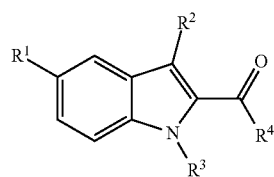

Formula (II)

wherein:
$R^1$ is H, halogen, —CN, —OH, $C_1$-$C_4$alkoxy, $C_1$-$C_4$fluoroalkoxy, —$NO_2$, —S—$C_1$-$C_4$alkyl, —S(=O)—$C_1$-$C_4$alkyl, or —S(=O)$_2$—$C_1$-$C_4$alkyl;

$R^2$ is H, halogen, $C_1$-$C_4$alkyl, $C_3$-$C_6$cycloalkyl, or substituted or unsubstituted phenyl, where if $R^2$ is substituted then $R^2$ is substituted with 1 or 2 $R^5$;
   each $R^5$ is independently selected from the group consisting of H, halogen, —CN, —$NO_2$, —OH, —$SR^6$, —S(=O)$R^6$, —S(=O)$_2R^6$, —C(=O)$R^6$, —$CO_2$H, —$CO_2R^6$, —$NH_2$, —$NHR^6$, —$N(R^6)_2$, —C(=O)$NH_2$, —C(=O)$NHR^6$, —C(=O)$N(R^6)_2$, $C_1$-$C_4$alkyl, $C_1$-$C_4$fluoroalkyl, $C_1$-$C_4$alkoxy, $C_1$-$C_4$fluoroalkoxy, $C_3$-$C_6$cycloalkyl, $C_2$-$C_6$heterocycloalkyl, phenyl, and phenoxy;

$R^3$ is H, or $C_1$-$C_4$alkyl;

$R^4$ is hydrogen, $C_1$-$C_4$alkyl, $C_1$-$C_4$alkoxy, —$NHNH_2$, —$NH_2$, —$NHR^6$, or —$N(R^6)_2$;

each $R^6$ is independently selected from the group consisting of $C_1$-$C_6$alkyl, $C_1$-$C_6$fluoroalkyl, $C_3$-$C_6$cycloalkyl, a substituted or unsubstituted phenyl, or substituted or unsubstituted benzyl;

or two $R^6$ groups attached to the same N atom are taken together with the N atom to which they are attached to form a $C_2$-$C_6$heterocycloalkyl that is unsubstituted or substituted with $C_1$-$C_4$alkyl or $C_3$-$C_6$cycloalkyl.

In some embodiments,
$R^1$ is H, $C_1$, —$NO_2$, or —S(=O)$_2$—$CH_3$;
$R^3$ is H, or —$CH_3$.
In some embodiments,
$R^4$ is —$NHNH_2$, —$NH_2$, —$NHR^6$, or —$N(R^6)_2$.
In some embodiments, the compound has the following structure of Formula (III):

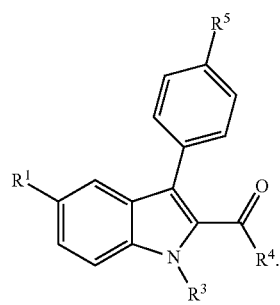

Formula (III)

In some embodiments,
each $R^6$ is independently selected from the group consisting of $C_1$-$C_6$alkyl, $C_1$-$C_6$fluoroalkyl, $C_3$-$C_6$cycloalkyl, or benzyl;
or two $R^6$ groups attached to the same N atom are taken together with the N atom to which they are attached to form a $C_2$-$C_6$heterocycloalkyl that is unsubstituted or substituted with $C_1$-$C_4$alkyl or $C_3$-$C_6$cycloalkyl, wherein the $C_2$-$C_6$heterocycloalkyl is pyrrolidinyl, piperidinyl, morpholinyl, thiomorpholinyl, piperazinyl, aziridinyl, or azetidinyl.

In some embodiments, the compound has one of the following structures as illustrated in Table 2. In some embodiments, the compound is a nucleobindin-1 (NUCB1) ligand.

Described herein, in certain embodiments, is a composition comprising a compound of Formula (II), or a pharmaceutically acceptable salt or solvate thereof; and an excipient. In some embodiments, the composition is formulated for administration to a mammal by intravenous administration, subcutaneous administration, oral administration, inhalation, nasal administration, dermal administration, or ophthalmic administration. In some embodiments, the composition is in the form of a tablet, a pill, a capsule, a liquid, a suspension, a gel, a dispersion, a solution, an emulsion, an ointment, or a lotion.

Described herein, in certain embodiments, is a method of identifying a lipid binding protein, comprising (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the proteins from the set of lipid probe-protein complexes; and (d) based on the value assigned in c), identifying a protein as a lipid binding protein. In some embodiments, the sample comprises a first cell solution and a second cell solution. In some embodiments, the method further comprises contacting the first cell solution with a first lipid probe and contacting the second cell solution with a second lipid probe. In some embodiments, the first lipid probe and the second lipid probe are the same. In some embodiments, the second cell solution comprises a buffer or a media. In some embodiments, the method further comprises treating the first cell solution by a photoreactive means. In some embodiments, the method further comprises contacting the first cell solution with a first set of lipid probes wherein each of the lipid probes comprises a lipid, a photoreactive group, and an affinity handle, and wherein each lipid probe is different within the set. In some embodiments, the method further comprises contacting the second cell solution with a second set of lipid probes wherein each of the lipid probes comprises a lipid, a photoreactive group, and an affinity handle, and wherein each lipid probe is different within the set. In some embodiments, the first set of lipid probes and the second set of lipid probes are the same. In some embodiments, the method further comprises treating the first cell solution by a photoreactive means. In some embodiments, the set of lipid probe-protein complexes further comprises a first group of lipid probe-protein complexes from the first cell solution and a second group of lipid probe-protein complexes from the second cell solution. In some embodiments, the lipid is a bioactive lipid. In some embodiments, the lipid comprises fatty acyls, glycerolipids, glycerophospholipids, sphingolipids, sterol lipids, prenol lipids, saccharolipids, or polyketides. In some embodiments, the lipid is a member of the fatty acyls group. In some embodiments, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some embodiments, the lipid is a fatty acid. In some embodiments, the fatty acid comprises a saturated fatty acid, a monounsaturated fatty acid, or a polyunsaturated fatty acid. In some embodiments, the lipid is a sterol lipid. In some embodiments, the sterol lipid comprises sterols, steroids, secosteroids, or bile acids. In some embodiments, the sterol comprises cholesterol, ergosterol, C24-propyl sterols, or stanol. In some embodiments, the photoreactive group comprises azides, benzophenone, diazo compounds, diazirines, diazonium salts, or diaryl ketones. In some embodiments, the photoreactive group is diazirine, or its derivatives thereof. In some embodiments, the photoreactive group further comprises a linker. In some embodiments, the affinity handle is a bioorthogonal affinity handle. In some embodiments, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the affinity handle comprises an alkyne or an azide group. In some embodiments, the affinity handle is conjugated to the terminal carbon atom of the lipid probe. In some embodiments, the photoreactive group and the affinity handle are conjugated to the same site of the lipid probe. In some embodiments, the photoreactive group and the affinity handle are conjugated to different sites of the lipid probe. In some embodiments, the lipid probe comprises: a lipid selected from arachidonoyl, arachidoyl, oleoyl, palmitoyl, or stearoyl fatty acyls; a photoreactive linker; and an affinity handle. In some embodiments, the lipid probe is a lipid probe of Formula (I):

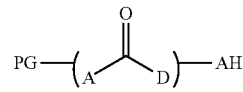

Formula (I)

wherein:
A is $C_{16}$-$C_{20}$alkyl or $C_{16}$-$C_{20}$alkenyl;
D is —OH, —$NH_2$, —$NHR^7$, or —$OR^8$;
$R^7$ is $C_1$-$C_4$alkyl, ($C_1$-$C_5$alkyl)OH, or ($C_1$-$C_5$)$SO_3$M;
$R^8$ is ($CH_2OH$)n;
M is monovalent or divalent cation;
n is 1, 2, or 3;
PG is a photoreactive group; and
AH is an affinity handle;
  wherein PG is attached to A or D and AH is attached to A or D.

In some embodiments, the lipid probe has one of the following structures as illustrated in Table 1. In some embodiments, the protein is a soluble protein or a membrane protein. In some embodiments, the protein is an enzyme, a transporter, a receptor, an adaptor, a channel protein, or a chaperone. In some embodiments, the protein is a protein encoded by a gene of Table 3, a protein encoded by a gene of Table 4, or a protein encoded by a gene of Table 5. In some embodiments, the photoreactive means comprises ultraviolet light. In some embodiments, the affinity handle is further conjugated to an affinity ligand. In some embodiments, the affinity ligand comprises a chromophore, a labeling group, or a combination thereof. In some embodiments, the chromophore comprises fluorochrome, non-fluorochrome chromophore, quencher, an absorption chromophore, fluorophore, organic dye, inorganic dye, metal chelate, or a fluorescent enzyme substrate. In some embodiments, the labeling group is biotin moiety, streptavidin moiety, bead, resin, a solid support, or a combination thereof. In some embodiments, the first cell solution further comprises a control. In some embodiments, the control is dimethyl sulfoxide (DMSO). In some embodiments, the value assigned to each of the protein in step c) is the area-under-the curve from a plot of signal intensity as a function of mass-to-charge ratio. In some embodiments, the identifying in step d) further comprises (i) locating a first value assigned to a protein from the first group of lipid probe-protein complex and a second value of the same protein from the second group of lipid probe-protein complex; and (ii) calculating a ratio between the two values. In some embodiments, the ratio of greater than 2 indicates that the protein is a candidate for interacting with the lipid probe. In some embodiments, the ratio of greater than 3 indicates that the protein is a candidate for interacting with the lipid probe. In some embodiments, the cell is obtained from a tumor cell line. In some embodiments, the cell is obtained from a Neuro2a or A549 cell line. In some embodiments, the cell is obtained from a tumor sample. In some embodiments, the sample is a tissue sample. In some embodiments, the method is an in situ method.

Described herein, in certain embodiments, is a method of identifying a fatty acyl binding protein, comprising: (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the proteins from the set of lipid probe-protein complexes; and (d) based on the value assigned in c), identifying a protein as a fatty acyl binding protein.

Described herein, in certain embodiments, is a method of identifying a fatty acyl binding protein as a drug binding target, comprising: (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the fatty acyl binding proteins from the set of lipid probe-protein complexes; and (d) based on the value assigned in c), identifying a fatty acyl binding protein as a drug binding target.

Described herein, in certain embodiments, is a method of generating a drug-lipid binding protein profile, comprising: (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the lipid binding proteins to generate a set of values; and (d) based on the set of values assigned in c), generate a drug-lipid binding protein profile. In some embodiments, the drug-lipid binding protein profile is a profile that indicates the array of lipid binding proteins that interacts with the drug.

Described herein, in certain embodiments, is a method of evaluating the selectivity of a drug for binding to a lipid binding protein, comprising: (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the lipid binding proteins from the first and second sets of lipid probe-protein complexes; and (d) based on the value assigned in c), classifying the drug as a specific inhibitor of a lipid binding protein or as a pan inhibitor.

Described herein, in certain embodiments, is a method of mapping a drug-induced metabolic change in a cell, comprising: (a) contacting a sample with a lipid binding protein ligand; (b) harvesting a set of lipids from a sample; (c) analyzing the set of metabolites by a proteomic analysis means; (d) based on step c), assigning a value to each of the metabolites from the set; and (e) based on step c), identifying one or more metabolites those expression levels have been changed relative to a control, wherein the changes in the one or more metabolite levels correlate to the drug-induced metabolic change in the cell. In some embodiments, the control is the expression levels of the one or more metabolites in the absence of the drug.

Described herein, in certain embodiments, is a method of monitoring the metabolic change of a cell with incubation of two or more drugs, comprising: (a) contacting a sample with a lipid binding protein ligand; (b) harvesting a set of lipids from a sample; (c) analyzing the set of metabolites by a proteomic analysis means; (d) based on step c), assigning a value to each of the metabolites from the set; and (e) based on step d), identifying one or more metabolites those expression levels have been changed relative to a control, wherein the changes in the one or more metabolite levels correlate to the metabolic change of the cell with incubation of two or more drugs. In some embodiments, the control is the expression levels of the one or more metabolites in the absence of the two or more drugs.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 4 illustrates chemical proteomic probes for mapping lipid-binding proteins in cells. (A) Experimental workflow for gel-based profiling of lipid-binding proteins in mammalian cells. Cells are incubated with lipid probes for 30 min prior to crosslinking with UV light (10 min, 4° C.) and subsequent cell lysis. Probe-labeled proteins are then conjugated a rhodamineazide (Rh—N3) reporter tag by copper-catalyzed azide-alkyne cycloaddition (CuAAC or "click") chemistry to allow for visualization of probe-labeled targets by SDS-PAGE and in-gel fluorescent scanning. (B) Membrane and soluble protein labeling profiles for the AEA-DA and AA-DA probes (20 μM) in HEK293T cells. Note that the AA-DA probe almost exclusively labels membrane proteins, whereas the AEA-DA probe interacts with both membrane and soluble proteins. (C) Comparative protein labeling profiles of the A-DA, 0-DA and S-DA probes in HEK293T cells, revealing a greater degree of labeling by the A-DA versus 0-DA or S-DA probes.

Ligand targets are designated as proteins that show light/heavy ratios of ≥3.0. (C) Chemical structures of the dual PTGS1/2-inhibitor (±)-flurbiprofen and PTGS2-selective inhibitor rofecoxib and representative peptide MS1 chromatograms for PTGS1 and PTGS2 in Neuro2a and A549 cells, respectively, showing that (±)-flurbiprofen (25 μM) competes A-DA (5 μM) labeling of both PTGS1 and PTGS2, whereas rofecoxib (25 μM) selectively competes PTGS2 labeling. (D) SILAC ratio plots for in situ competition experiments of A-DA (5 μM) labeling by (±)-flurbiprofen (25 μM) and rofecoxib (25 μM) validating target engagement and selectivity across PTGS isoforms and other lipid probe targets.

Figure 10:
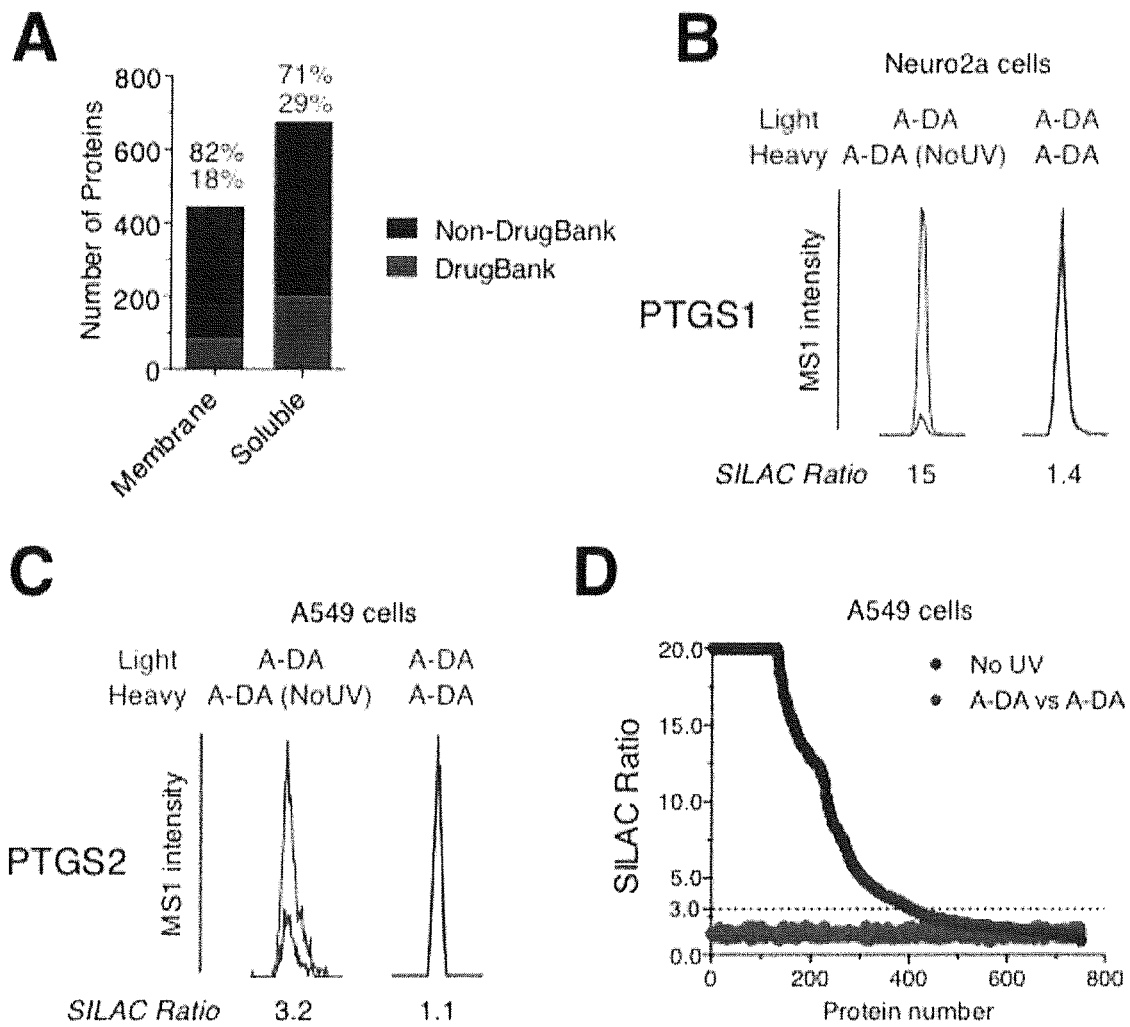

FIG. 10 illustrates potential drug targets within the lipid-interaction proteome. (A) Categorization of lipid probe targets according to their classification as membrane or soluble proteins and by their presence or absence in DrugBank. (B, C) Representative peptide MS1 chromatograms for PTGS1 (A) and PTGS2 (B) enriched from A-DA-treated Neuro2a and A549 cells, respectively, with or without UV-irradiation, confirming PTGS1 and PTGS2 as UV-dependent A-DA targets. (D) Heavy/Light SILAC ratio plots of No UV (blue) and probe-versus-probe (red) experiments for A-DA (5 μM) in A549 cells showing several hundred UV-dependent targets (SILAC ratio ≥3.0), including PTGS2 (ratio=3.2). See Table 3 (48054-701-101Table3.txt) for complete list of UV dependent targets.

Figure 11:
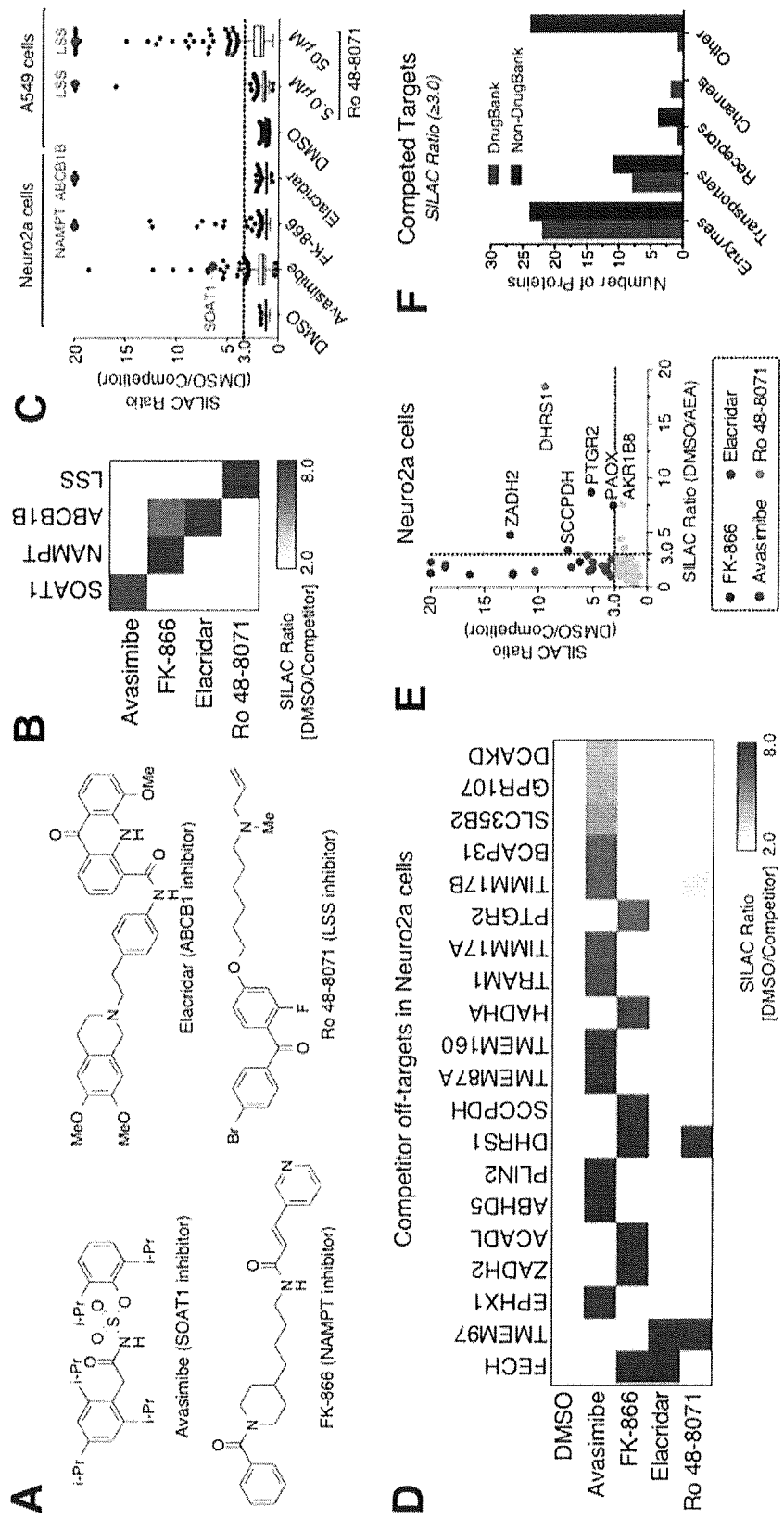

FIG. 11 illustrates in situ drug profiling with lipid probes. (A) Structures of compounds analyzed by competitive profiling with lipid probes. (B) Heatmap showing SILAC ratios for primary targets of drugs (25 μM), except for Ro 48-8071, which was assayed at 5 μM) from competitive profiling experiments performed in Neuro2a and A549 cells. All drugs were profiled in both cell lines, and target engagement for SOAT1, NAMPT, and ABCB1B is shown for Neuro2a cells with the AEA-DA probe (5 μM) and, for LSS, in A549 cells with the A-DA probe (5 μM) (also see Table 5,). (C) Box-whisker plots of protein SILAC ratios from in situ competition experiments showing on-(red) and off-(blue) targets (ratios ≥3.0) for tested drugs. (D) Heatmap of competed off-targets for tested drugs measured with the AEA-DA probe in Neuro2a cells. (E) Plot of SILAC ratios from AEA-DA competition experiments with tested drugs (25 μM) versus the lipid competitor AEA (200 μM). For simplicity, only the highest drug competition SILAC ratio is plotted for each target. (F) Categorization of drug-competed lipid probe targets based on their presence or absence in DrugBank and by protein class (also see Table 5).

Figure 12:
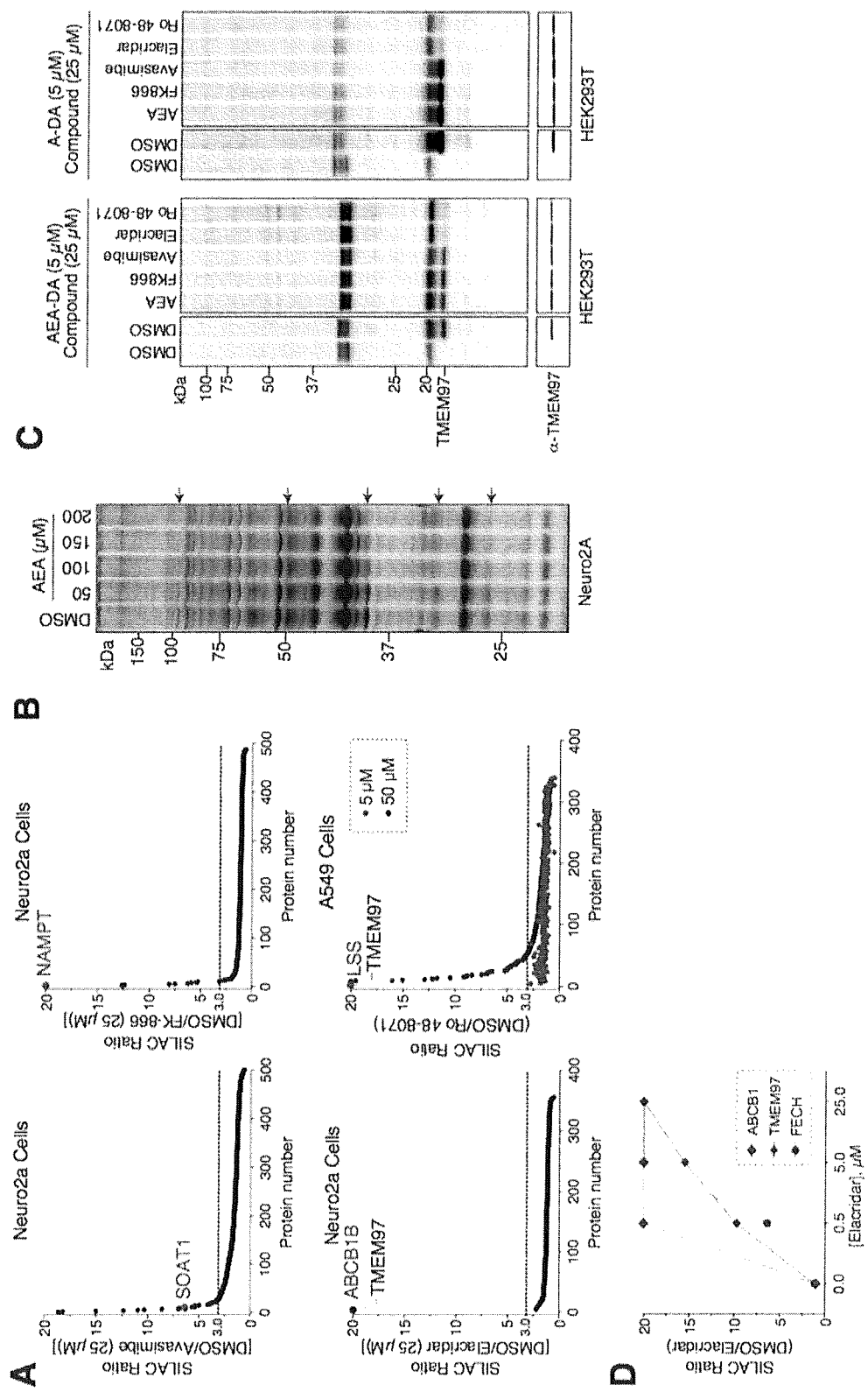

FIG. 12 shows in situ drug profiling with lipid probes. (A) SILAC ratio plots for in situ competition experiments performed with avasimibe (25 μM), FK-866 (25 μM), elacridar (25 μM), and Ro 48-8071 (5 and 50 μM) measured with the AEADA (5 μM) or A-DA (for Ro 48-8071) probe in the indicated cell lines. Data correspond to measurements plotted in FIG. 11C. The known target of each drug is highlighted in red. (B) In situ competitive profiles for the lipid competitor AEA (50-200 μM) measured with the AEA-DA probe (10 μM) in Neuro2a cells. Red arrows highlight AEA-competed proteins. (C) In situ competition profiles of arachidonoyl probe (AEA-DA or A-DA; 5 μM) labeling of recombinant TMEM97 with AEA, FK-866, avasimibe, elacridar or Ro 48-8071 (25 μM each) in HEK293T cells transiently transfected with TMEM97. TMEM97 competition was observed for elacridar and Ro 48-8071, but not other competitors, matching the MS-based competition profiles of endogenous TMEM97 in Neuro2a and A549 cells (See FIG. 11D and Table 5). (D) Concentration-dependent competition of AEA-DA (5 μM) probe labeling of ABCB1, TMEM97, and FECH by elacridar in Neuro2a cells.

Figure 13:
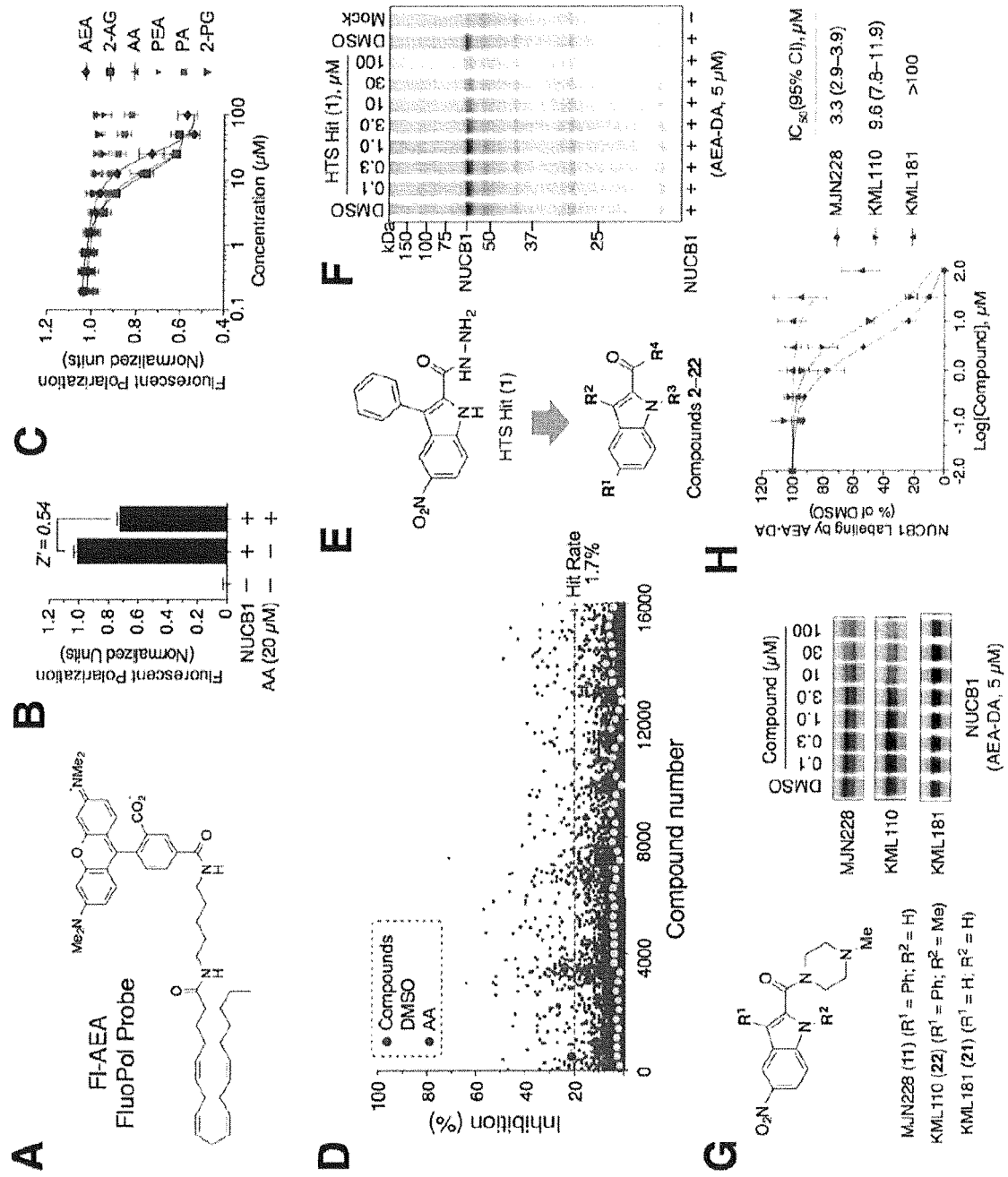

FIG. 13 shows modified lipid probes for high throughput screening (HTS) for the discovery of NUCB1 ligands. (A) Structure of Fl-AEA probe. (B) Incubation of the Fl-AEA probe (0.5 μM) with recombinant human NUCB1 (1.0 μM) produced a strong FluoPol signal that was significantly suppressed by the competitive lipid AA (20 μM; Z'=0.54). (C) Concentration-dependent suppression of the NUCB1-FluoPol signal by arachidonoyl lipids AEA, 2-AG and AA, but not palmitoyl lipids PEA, 2-palmitoyl glycerol (2-PG) or palmitic acid (PA). See FIG. 14A for profiling of additional lipids. (D) Screen of 16,000 compounds identified small molecules that inhibited the NUCB1-FluoPol signal by 20% or greater (dotted black line). (E) Structure of confirmed HTS hit 1 and positions modified for medicinal chemistry optimization. See FIG. 16B-D for summary of medicinal chemistry optimization of NUCB1 ligands. (F) Concentration-dependent blockade of AEA-DA (5 μM) labeling of purified, recombinant NUCB1 (0.25 μM) doped into HEK293T lysates (0.75 mg/mL) by HTS hit 1 (0.1-100 μM). (G, H) Structures and competitive profiling results (G) and IC50 curves and values (H) for NUCB1 ligands MJN228 and KML110 and the inactive control compound KML181. Data in B, C, and H represent mean values ±SD from at least three independent experiments.

Figure 14:
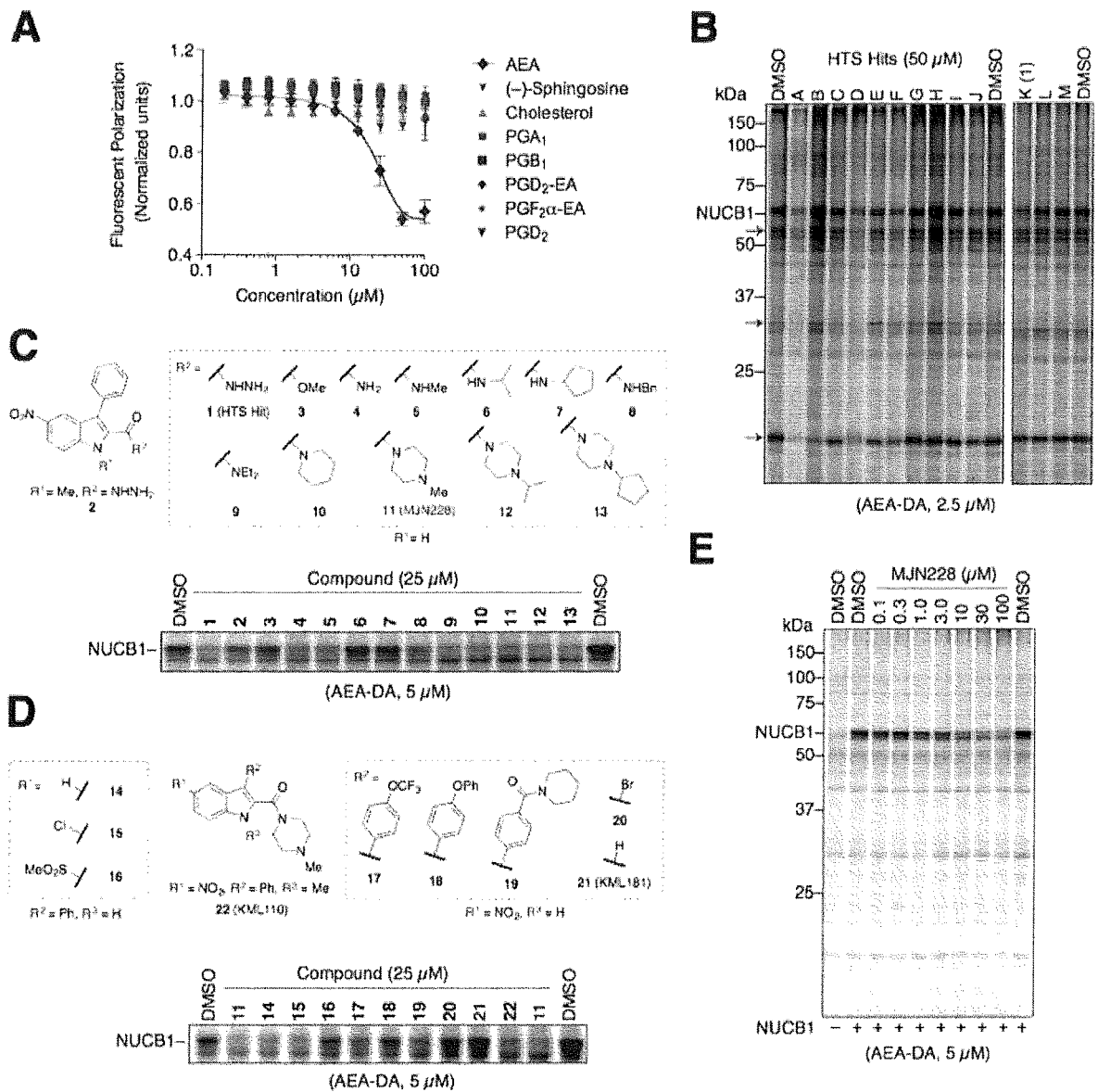

FIG. 14 shows optimization of NUCB1 ligands. (A) A panel of lipids, including sphingosine, cholesterol, prostaglandins ($A_1$, $B_1$ and $D_2$) and prostamide species ($PGD_2$-EA and $PGF_2\alpha$-EA), shows minimal blockade of Fl-AEA binding to recombinant NUCB1 as determined using a FluoPol assay. Error bars represent standard deviation (n=5). (B) Gel profile of competition experiment performed with select HTS hits (A-M) (50 μM each) versus the AEA-DA probe (2.5 μM) in NUCB1-transfected HEK293T cell lysates, identifying HTS hit 1 (K) as a selective NUCB1 ligand. (C, D) Structures and competition gel profiles of amide and ester analogs HTS hit 1 (25 μM) (C) and analogs of optimized NUCB1 ligand MJN228 (11) (D). Competition assays were performed with 25 μM of each competitor against the AEA-DA probe (5 μM) in HEK293T lysates (0.75 mg/mL) doped with purified, recombinant human NUCB1 (0.25 μM). (E) Full gel profile for competition experiment performed with MJN228 (1.0-100 μM) versus the AEA-DA probe (5 μM) in HEK293T lysates (0.75 mg/mL) doped with purified, recombinant human NUCB1 (0.25 μM).

Figure 15:
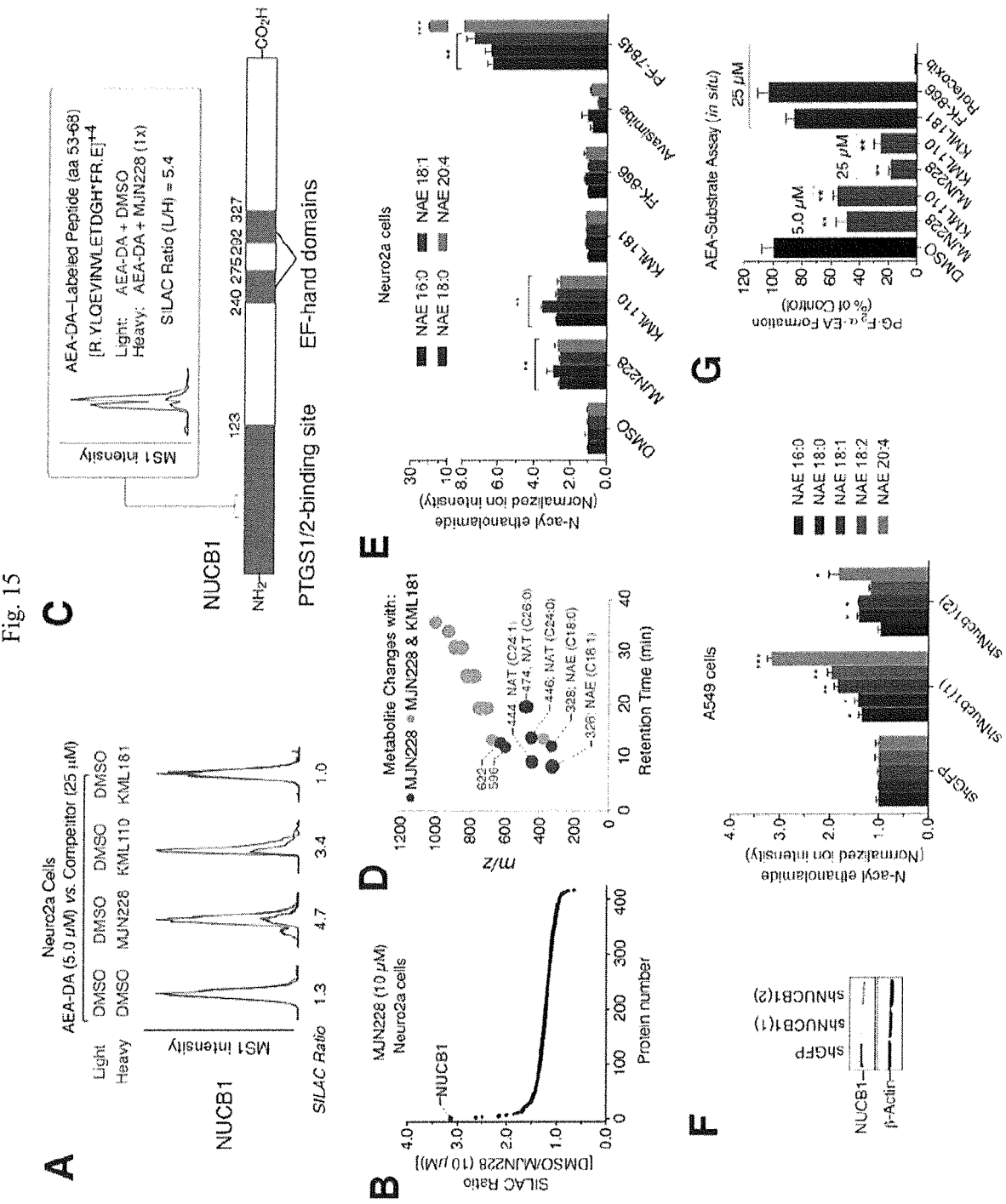

FIG. 15 shows target engagement and lipid metabolism effects of NUCB1 ligands. (A) Representative peptide MS1 chromatograms showing blockade of AEA-DA probe labeling of endogenous NUCB1 in Neuro2a cells by MJN228 and KML110, but not KML181. (B) SILAC ratio plot for in situ competition experiment performed with MJN228 (10 μM) and the AEA-DA probe (5 μM). (C) LC-MS/MS identification of a MJN228-sensitive, AEA-DA-modified NUCB1 peptide (aa 53-68) in Neuro2a cells. (D) Untargeted metabolite profiling reveals that Neuro2a cells treated with MJN228 (10 μM) show elevated fatty acid amides (NAEs and NATs) compared to cells treated with DMSO or KML181 (10 μM) (P<0.0001, n=5 per condition). See also Table 7. (E) Targeted MRM measurements showing elevations in NAEs in Neuro2a cells treated with NUCB1 ligands MJN228 and KML110 (10 μM, 6 h), but not KML181, FK-866, or avasimibe. See FIG. 16G for MRM measurements of NATs. (F) Left, Western blot showing knockdown of NUCB1 in shNUCB1 A549 cell lines compared to a control cell line (shGFP). Right, both shNUCB1 cells show significant elevations in NAEs compared to the control shGFP cell line.

(G) NUCB1 ligands MJN228 and KML110 (5 and 25 µM), but not KML181 or FK-866 (25 µM each), suppress the conversion of exogenous AEA (20 µM, 30 min) to PGF$_2\alpha$-EA in PMAstimulated A549 cells. Rofecoxib (25 µM) also blocked PGF$_{2alpha}$-EA synthesis. For (E-G), data represent mean values ±SEM; n=3-4/group. *P<0.05, P<0.01, *P<0.001 for DMSO-treated (E) or shGFP cells (F) versus compound-treated (E) or shNUCB1 (F) cells.

Figure 16:
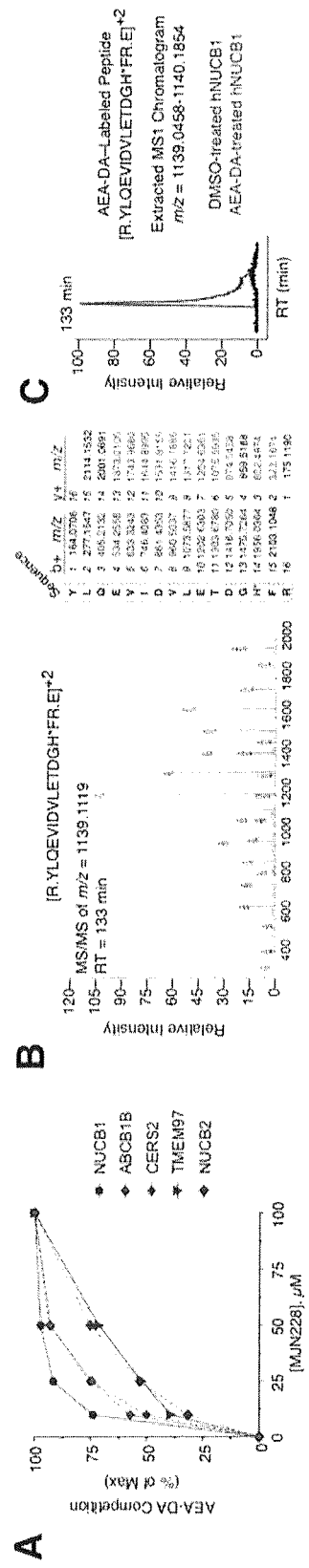
Figure 16:
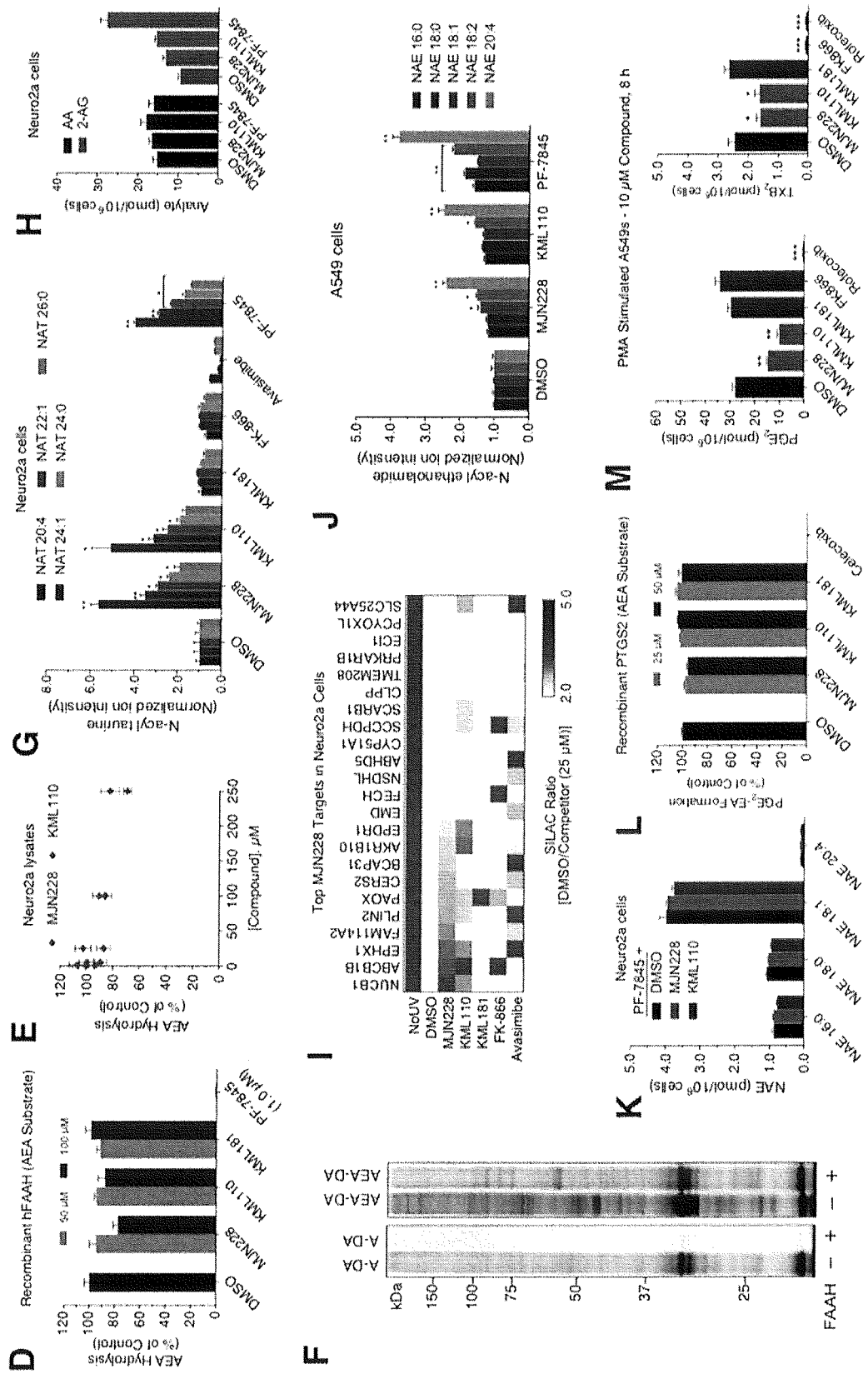

FIG. 16 shows cellular target engagement and lipid metabolism effects of NUCB1 ligands. (A) Concentration-dependent competition of AEA-DA (5 µM) probe labeling of NUCB1 and select off-targets (ABCB1B, TMEM97, CERS2, NUCB2) by MJN228 in Neuro2a cells. Data are normalized to the maximal competition value for each protein, which provides an estimate of fractional target engagement across the tested drug concentration range. (B) MS/MS spectrum of AEA-DA-modified NUCB1 peptide localizes probe crosslinking to His67. Purified, recombinant hNUCB1 was treated with DMSO or AEA-DA (10 µM), irradiated with UV light and subjected to proteolytic digestion, whereupon tryptic peptides were analyzed by LC-MS/MS and the resulting mass spectra were extracted using the ProLuCID algorithm designating a variable peptide modification of (+343.2511) for all residues. (C) Extracted ion chromatogram for m/z value of the NUCB1 AEA-DA-modified peptide described in (B) showing signals in AEA-DA-treated (red trace), but not DMSO-treated NUCB1. (D) AEA-hydrolysis assay using purified, recombinant humanized rat FAAH (Mileni et al., 2008) showing that MJN228, KML110, and KLM181 (50 or 100 µM) do not substantially inhibit FAAH activity. (E) AEA-hydrolysis assay in Neuro2a lysates showing minimal inhibition of FAAH activity by MJN228 and KML110 up to 250 µM. (F) Gel profiles of AEA-DA (20 µM) and A-DA (20 µM) probe labeling of HEK293T cells transiently transfected with hFAAH or empty vector. The clear differences in gel bands detected in FAAH-transfected cells suggest that the AEA-DA and A-DA probes are metabolized by FAAH. (G) Targeted MRM measurements showing NUCB1 ligands (MJN228 and KML110, 10 µM) and FAAH inhibitor PF-7845 (1 µM), but not inactive control compounds KML181, FK-866 or avasimibe (10 µM each), produce elevations in N-acyl taurines (NATs) in Neuro2a cells. (H) MJN228 and KML110 (10 µM) do not affect AA levels in Neuro2a cells, but produce a modest increase in 2-AG that is also observed to a greater degree with the selective FAAH inhibitor PF-7845 (1 µM). (I) Heatmap of drug targets in Neuro2a cells as measured by competitive profiling with the AEA-DA probe (5 µM). Note that MJN228 and KML110 both target NUCB1 whereas all other compounds do not, and, conversely, many of the additional targets of MJN228 and KML110 are shared by the other tested drugs. (J) Targeted MRM measurements of NAEs derived from A549 cells treated with MJN228 (10 µM), KML110 (10 µM) or PF-7845 (1 µM) for 6 h. (K) NUCB1 ligands MJN228 and KML110 (10 µM) do not produce elevations in NAEs when co-treated with PF-7845 (1 µM). (L) AEA oxygenation to PGE2-EA by purified, recombinant hPTGS2 is inhibited by celecoxib, but not MJN228 or KML110 (25 or 50 µM). (M) NUCB1 ligands MJN228 and KML110, but not KML181, suppress PGE2 (left) and TXB2 (right) synthesis from endogenous pools of AA in A549 cells pre-treated with the indicated compound (10 µM), 30 min) and then stimulated with PMA for 6 h. FK-866 selectively suppressed TXB2, but not PGE2 synthesis. Data are presented as means±SEM; n=3/group. *P<0.05, P<0.01, *P<0.001 for DMSO-treated versus compound-treated cells.

FIG. 17 illustrates clickable photoreactive sterol probes. Panel A shows structures of cholesterol and three diastereomeric sterol chemoproteomic probes. Panel B shows three-dimensional structures of cholesterol and sterol probes as determined by x-ray crystallography; cholesterol structure derived from PDBID: 3GKI24. In A and B, from top to bottom; cholesterol, trans-sterol probe, epi-sterol probe, cis-sterol probe.

Figure 18:
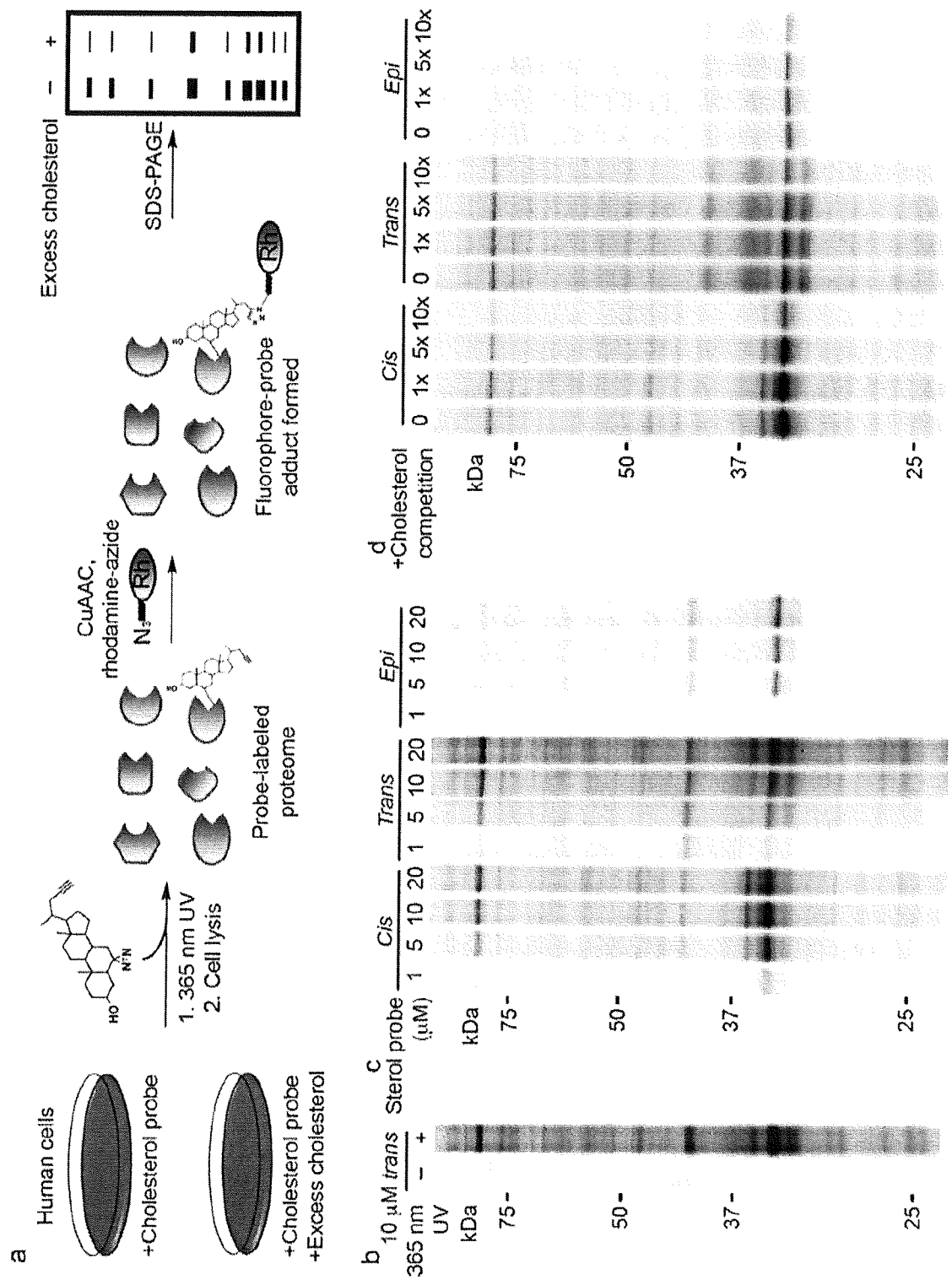

FIG. 18 shows a gel-based profiling of sterol-binding proteins in HeLa cells. Panel A shows a scheme for treatment of live cells with sterol probes and competitive treatments. Panel B shows HeLa cells treated with 10 µM trans-sterol probe, with and without 365 UV irradiation before click chemistry and SDS-PAGE analysis. Panel C shows concentration-dependent labeling of live HeLa cells with each probe (cis, epi, trans) at 1, 5, 10, and 20 µM. Panel D shows competition of sterol probe labeling profiles (10 µM probes) with increasing cholesterol from 0, 10 (1×), 50 (5×), and 100 µM (10×). Fluorescence gel images are shown in grayscale.

Figure 19:
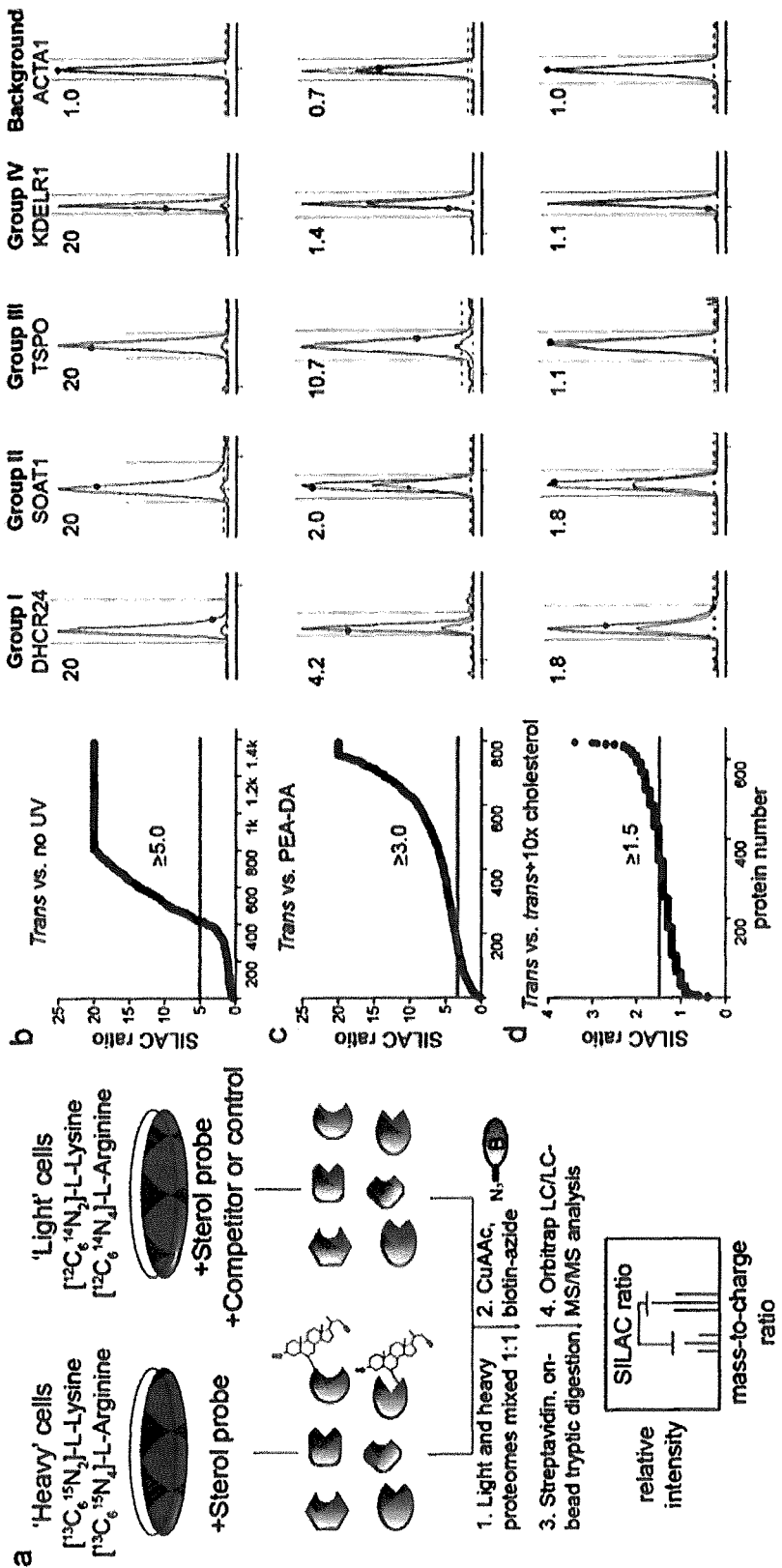
Figure 19:
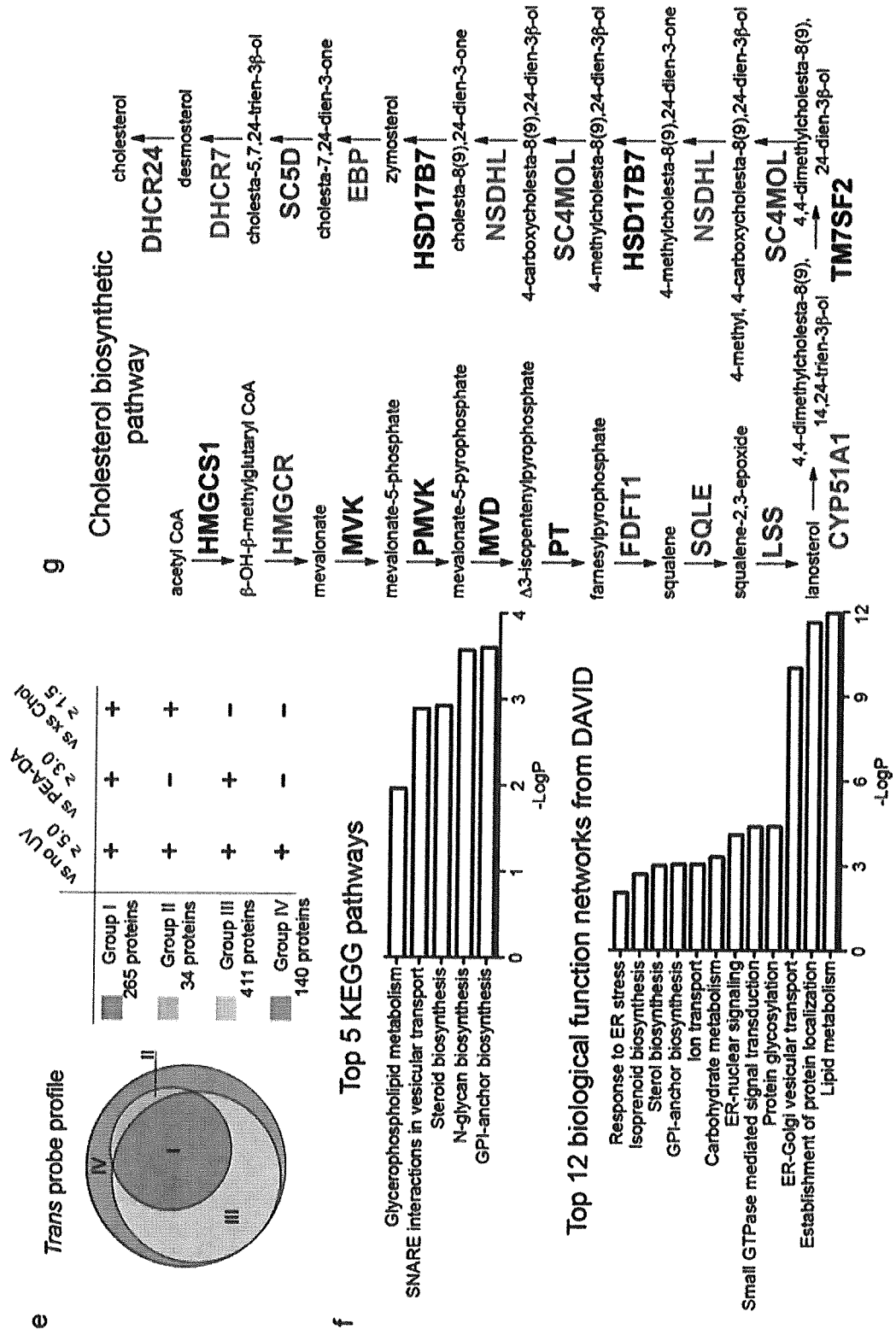

FIG. 19 illustrates MS-based profiling of sterol-binding proteins in HeLa cells. Panel A illustrates a scheme for enrichment and analysis of sterol probe labeling profiles in mammalian cells by biotin-streptavidin methods and SILAC MS analysis. Panels B-D show heavy/light ratio plots for total proteins identified in experiments that compared the labeling profiles of the trans-sterol probe versus no-UV light control (B; 20 µM trans probe/20 µM trans probe with no UV), the PEA-DA probe (C; 20 µM trans probe/20 µM PEA-DA probe), and 10× cholesterol competition (D; 10 µM trans probe/10 µM trans probe+100 µM cholesterol). Representative MS1 traces with calculated ratios for proteins that fall into Groups I-IV, as well as the MS1 traces for a non-specific background protein, are shown to the right of the global ratio plots. Ratios of >20 are listed as 20. Panel E illustrates a Venn diagram showing the distribution of Group I-IV proteins for the trans-sterol probe labeling profile. Final F shows top-five pathways determined by searching Group I proteins on the KEGG database, and top-12 biological function networks determined by searching Group I proteins on the DAVID gene ontology server. Panel G shows trans-sterol probe labeling profile for the cholesterol biosynthetic pathway, with colors reflecting each enzyme's Group designation (black: not detected).

Figure 20:
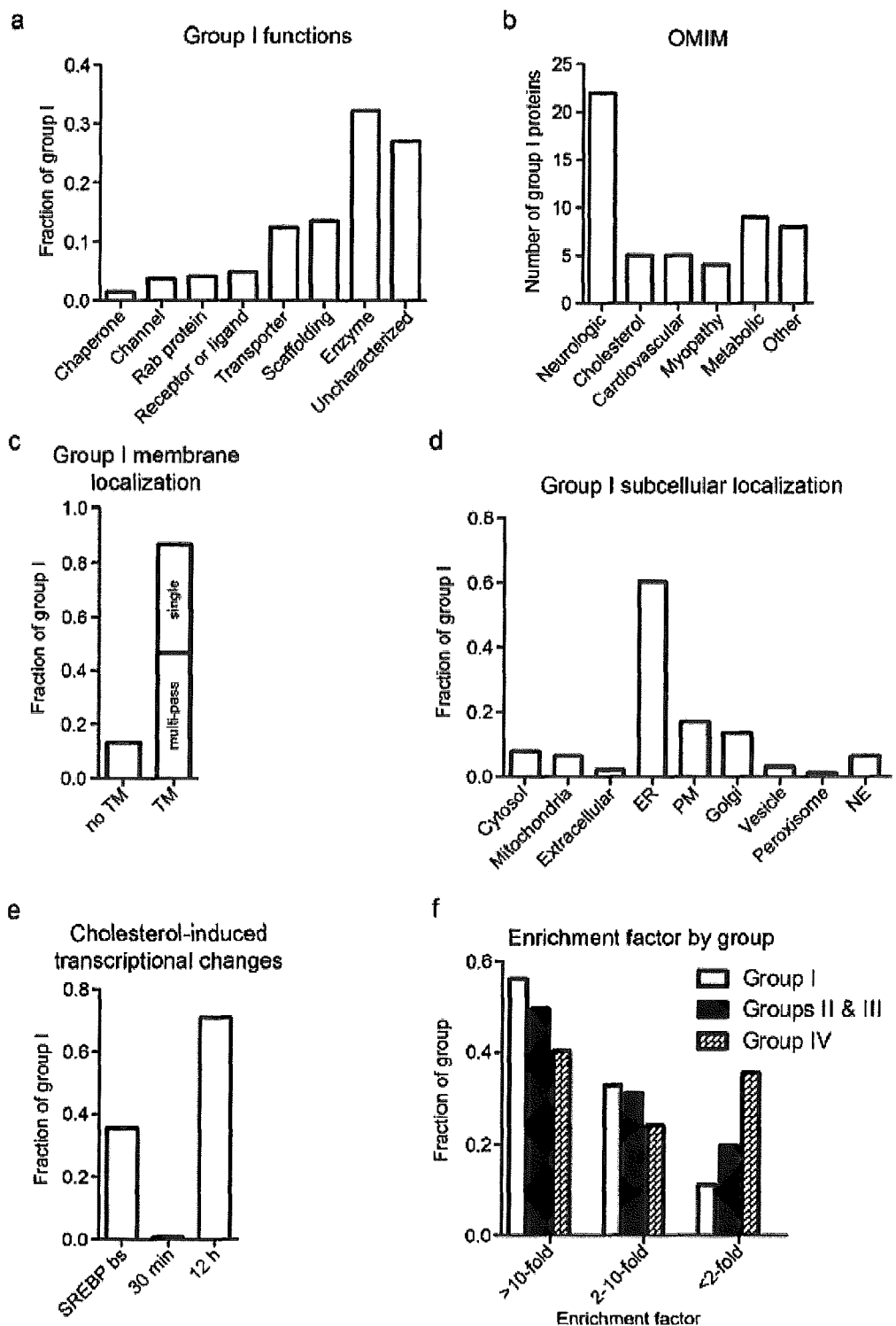

FIG. 20 shows analysis of Group I proteins. Panel A shows breakdown of Group I proteins by biochemical functions. Panel B shows group I proteins known to be genetically associated with human disease based on the OMIM database; the 'cholesterol' group represents diseases from all other groups that are known to manifest via aberrant cholesterol homeostasis. Panel C shows fraction of Group I proteins that possess known or predicted transmembrane (TM) domains. TM proteins are further divided into single-versus multipass TM proteins. Panel D shows known or predicted subcellular localization of Group I proteins. Subcellular localization predictions were made by examining protein sequences by the PSORT II algorithm (http://psort.hgc.jp/form2.html). Panel E shows cholesterol regulation of Group I proteins at the mRNA level. 'SREBP bs' denotes the fraction of Group I proteins with SREBP transcription factor binding sites in the gene/promoter regions based on the Qiagen SABiosciences transcription factor database (http://www.sabiosciences.com/chipqpersearch.php?app=TFBS). '30 min' and '12 h' denote the fraction of Group I proteins with substantial (≥two-fold) changes in mRNA levels after 100 µM cholesterol treatment for the indicated time. Panel F shows levels of enrichment (≥2-fold, 2-10 fold, ≥10-fold)

of Groups I, II & III, and IV proteins in trans-sterol probe data sets compared to their abundance in unenriched membranes.

DETAILED DESCRIPTION OF THE INVENTION

Certain Terminology

Unless defined otherwise, all technical and scientific terms used herein have the same meaning as is commonly understood to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, ranges and amounts can be expressed as "about" a particular value or range. About also includes the exact amount. Hence "about 5 µL" means "about 5 µL" and also "5 µL." Generally, the term "about" includes an amount that would be expected to be within experimental error.

The section headings used herein are for organizational purposes only and are not to be construed as limiting the subject matter described.

Overview

Disclosed herein, in certain embodiments, are methods, compositions, probes, assays, kits, and services for identifying a lipid binding protein as a drug binding target, mapping a ligand binding site on a lipid binding protein, identifying a protein as a lipid binding protein, and generating drug profiles with the use of a lipid probe. Also disclosed herein are methods, assays, compositions, and probes for screening a drug for interaction with a lipid binding protein utilizing recombinant proteins and a lipid probe described herein.

In some instances, described herein is a method which comprises harvesting a sample incubated in the presence of a lipid probe and a drug, and utilizes a proteomic means for analysis to identify drug binding targets. In some embodiments, the method further comprises comparing the data with a control. In some instances, the control is a sample incubated in the presence of a lipid probe but in the absence of a drug.

In some embodiments, the drug is a small molecule, its fragment or derivatives thereof; a polypeptide; a nucleic acid molecule; or combinations thereof. In some instances, the drug is a small molecule, its fragments or derivatives thereof. In some cases, the drug is a test compound. In some cases, the test compound has a therapeutic effect. In other cases, the test compound does not have a therapeutic effect. In some instances, the drug is a polypeptide (e.g., an antibody or an antibody conjugate). In additional cases, the drug is a nucleic acid molecule (e.g., a naked nucleic acid molecule or a nucleic acid molecule conjugate). In some instances, the drug has a therapeutic effect. In other instances, the drug does not have a therapeutic effect.

In some embodiments, the sample is a cell sample. In some instances, the sample is a tissue sample. In some embodiments, the cell sample comprises a cell solution. In some instances, the cell sample comprises a first cell solution and a second cell solution. In some embodiments, the method further comprises contacting the first cell solution with a first lipid probe and contacting the second cell solution with a second lipid probe. In some instances, the first lipid probe and the second lipid probe are the same. In some cases, the first and second lipid probes are different. In some instants, the cell solution comprises a buffer. In some instances, the cell solution comprises a media. In some embodiments, the second cell solution further comprises a drug. In some instances, the second cell solution further comprises a drug and a media. In some embodiments, the second cell solution further comprises a drug and an enriched media. In some instances, the method further comprises treating the first cell solution and the second cell solution by a photoreactive means to generate a first group of lipid probe-protein complexes and a second group of lipid probe-protein complexes, wherein the first group and the second group of lipid probe-protein complexes comprise the set of lipid probe-protein complexes.

In some instances, a first set of lipid probes are added to the first cell solution and a second set of lipid probes are added to the second cell solution. In some cases, each lipid probe is different within the set. In some instances, the first set of lipid probes is the same as the second set of lipid probes. In some cases, the method further comprises treating the first cell solution and the second cell solution by a photoreactive means to generate a third group of lipid probe-protein complexes and a fourth group of lipid probe-protein complexes.

In some instances, the photoreactive means comprises visible light or ultraviolet light. In some cases, after treatment by a photoreactive means, the sample is harvested and lysed and the lipid probe-protein complexes are collected for analysis by a proteomic analysis means. In some instances, the proteomic analysis means involve analysis by a mass spectroscopy, by gel electrophoresis, an antibody based detection method, and the like. In some instances, the lipid probe-protein complexes are further enriched on a bead, such as an affinity tagged bead (e.g. streptavidin-coupled beads), and then subjected to a mass spectroscopic analysis.

In some cases, a value is assigned to each of the lipid binding protein from the lipid probe-protein complexes after proteomic analysis. In some instances, the value is an area-under-the curve from a plot of signal intensity as a function of mass-to-charge ratio. In some embodiments, a first value is assigned to a lipid binding protein from the first group of lipid probe-protein complex of the first cell solution and a second value of the same lipid binding protein from the second group of lipid probe-protein complex of the second cell solution. In some instances, a ratio is then calculated between the two values, the first value and the second value, assigned to the same lipid binding protein. In some instances, a ratio of greater than 2 indicates that the lipid binding protein is a candidate for interacting with the drug. In some instances, the ratio is greater than 2.5, 3, 3.5, 4, 4.5, 5, 6, 7, 8, 9, or 10. In some cases, the ratio is at most 20. In some instances, the same lipid probe interacts with a number of lipid binding proteins in the presence of a drug. In some instances, the drug will modulate the interaction of a lipid probe with its lipid binding protein partners. In some instances, the spectrum of ratios for a lipid probe with its interacting protein partners in the presence of a drug indicates the specificity of the drug toward the protein. In some instances, the spectrum of ratio indicates whether the drug is a specific inhibitor to a protein or a pan inhibitor. In some instances, the method is an in-situ method.

In some embodiments, also described herein is a method of identifying a lipid binding protein as a drug binding target, comprising: (a) contacting a first sample with a first lipid probe and a second sample with a second lipid probe and a drug, wherein the first lipid probe and the second lipid probe are the same; (b) harvesting a first set of lipid probe-protein complexes from the first sample and a second set of lipid probe-protein complexes from the second sample; (c) analyzing the first and second sets of lipid probe-protein complexes by a proteomic analysis means; (d) based on step c), assigning a value to each of the lipid binding proteins from the first and second sets of lipid probe-protein complexes; and (e) based on the value assigned in d), identifying a lipid binding protein as a drug binding target.

In some embodiments, described herein is a method of identifying a lipid binding protein as a drug binding target, comprising: (a) harvesting a first set of lipid probe-protein complexes from a first cell solution and a second set of lipid probe-protein complexes from a second cell solution wherein the second cell solution comprises enriched media and a drug; (b) analyzing the first and second sets of lipid probe-protein complexes by a proteomic analysis means; (c) based on step b), assigning a value to each of the lipid binding proteins from the first and second sets of lipid probe-protein complexes; and (d) based on the value assigned in c), identifying a lipid binding protein as a drug binding target.

In some embodiments, described herein is a method of identifying a fatty acyl binding protein as a drug binding target, comprising: (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the fatty acyl binding proteins from the set of lipid probe-protein complexes; and (d) based on the value assigned in c), identifying a fatty acyl binding protein as a drug binding target.

In some instances, described herein are methods which allow for identification of novel targets for drugs, such as for example new protein targets for drugs with previous known targets. In some instances, the methods described herein are used to identify and/or evaluate off-target effects of one or more drugs. In some instances, the methods described herein are used for off-target screening of therapeutic compounds.

In some embodiments, also described herein is a method of mapping a ligand binding site on a lipid binding protein, comprising (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; and (c) based on step b), locating a ligand binding site on the lipid binding protein.

In some embodiments, a method of mapping a ligand binding site on a lipid binding protein described herein comprises (a) contacting a first cell solution with a first lipid probe and a second cell solution with a second lipid probe and a drug, wherein the first lipid probe and the second lipid probe are the same; (b) harvesting a first set of lipid probe-protein complexes from the first sample and a second set of lipid probe-protein complexes from the second sample; (c) treating the first set of lipid probe-protein complexes and the second set of lipid probe-protein complexes by a protease; (d) harvesting the treated first set of lipid probe-protein complexes and the treated second set of lipid probe-protein complexes; (e) analyzing the first and second sets of treated lipid probe-protein complexes by a proteomic analysis means; (f) based on step e), assigning a value to each of the lipid binding proteins from the first and second sets of lipid probe-protein complexes; and (g) based on the value assigned in f), identifying a lipid binding protein as a drug binding target.

In some embodiments, a method of mapping a ligand binding site on a lipid binding protein described herein comprises (a) harvesting a first set of lipid probe-protein complexes from a first cell solution and a second set of lipid probe-protein complexes from a second cell solution wherein the second cell solution comprises enriched media and a drug; (b) treating the first set of lipid probe-protein complexes and the second set of lipid probe-protein complexes by a protease; (c) harvesting the treated first set of lipid probe-protein complexes and the treated second set of lipid probe-protein complexes; (d) analyzing the first and second sets of treated lipid probe-protein complexes by a proteomic analysis means; (e) based on step d), assigning a value to each of the lipid binding proteins from the first and second sets of lipid probe-protein complexes; and (f) based on the value assigned in e), identifying a lipid binding protein as a drug binding target.

In some embodiments, further described herein is a method of identifying a lipid binding protein, comprising: (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the proteins from the set of lipid probe-protein complexes; (d) based on the value assigned in c), identifying a protein as a lipid binding protein. In some instances, described is a method of identifying a fatty acyl binding protein, comprising: (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the proteins from the set of lipid probe-protein complexes; and (d) based on the value assigned in c), identifying a protein as a fatty acyl binding protein.

In some embodiments, additionally described herein are methods of generating a drug-lipid binding protein profile and evaluating the selectivity of a drug for binding to a lipid binding protein. In some instances, a method of generating a drug-lipid binding protein profile comprises (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the lipid binding proteins to generate a set of values; and (d) based on the set of values assigned in c), generate a drug-lipid binding protein profile. In some instances, a method of evaluating the selectivity of a drug for binding to a lipid binding protein, comprises (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; (c) based on step b), assigning a value to each of the lipid binding proteins from the first and second sets of lipid probe-protein complexes; and (d) based on the value assigned in c), classifying the drug as a specific inhibitor of a lipid binding protein or as a pan inhibitor.

In some embodiments, also disclosed herein are cells, populations of cells, compositions, and probes to a lipid probe described herein and a lipid binding protein.

In some embodiments, further disclosed herein are assay and kits that utilize one or more of the methods described herein.

Lipid Probe

In some embodiments, the lipid probe comprises a lipid, a photoreactive group, and an affinity handle. Lipid is a broad family of small molecules capable of forming structures such as vesicles, multilamellar/unilamellar liposomes, or membranes in an aqueous environment. In some embodiments, the lipid is a bioactive lipid. In some embodiments, the lipid is an amphipathic lipid. In some instances, the lipid is a hydrophobic lipid.

In some instances, the lipids described herein comprise fatty acyls, glycerolipids, glycerophospholipids, sphingolipids, sterol lipids, prenol lipids, saccharolipids, or polyketides. In some instances, the lipid is a lipid derived from a cell membrane.

In some embodiments, the lipid is a member of the fatty acyls group. In some embodiments, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides.

In some embodiments, the lipid is a fatty acid. In some instances, the fatty acid comprises straight chain fatty acids or branched fatty acids. In some instances, the fatty acid comprises hydroperoxy, hydroxy, oxo, epoxy, methoxy, halogenated, amino, cyano, nitro, thia, carbocyclic, heterocyclic fatty acid, or its derivatives thereof.

In some instances, the fatty acid or its derivative thereof comprises a C3-C36 fatty acid or derivative thereof in some instances, the fatty acid or its derivative thereof comprises a C5-C30, C10-C25, or C15-C21 fatty acid or derivative thereof. In some instances, the fatty acid or its derivative comprises a C16, C17, C18, C19, or C20 fatty acid or derivative thereof.

In some cases, the fatty acid comprises a saturated fatty acid, a monounsaturated fatty acid, or a polyunsaturated fatty acid.

Exemplary saturated fatty acid includes, but is not limited to, propanoic acid, butanoic acid, pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, henatriacontanoic acid, dotriacontanoic acid, tritriacontanoic acid, tetratriacontanoic acid, pentatriacontanoic acid, or henatriacontanoic acid.

Exemplary monounsaturated fatty acid includes, but is not limited to, palmitoleic acid, vaccenic acid, oleic acid, eicosenoic acid, erucic acid, gadoleic acid, myristoleic acid, or nervonic acid.

In some instances, the polyunsaturated fatty acid comprises omega-3 fatty acids, omega-6 fatty acids, omega-9 fatty acids, or conjugated fatty acids. Exemplary polyunsaturated fatty acid includes, but is not limited to, hexadecatrienoic acid, alpha-linolenic acid, stearidonic acid, eicosatrienoic acid, eicosatetraenoic acid, eicosapentaenoic acid, heneicosapentaenoic acid, docosapentaenoic acid, docosahexaenoic acid, tetracosapentaenoic acid, tetracosahexaenoic acid, linoleic acid, gamma-linolenic acid, eicosadienoic acid, dihomo-gamma-linolenic acid, arachidonic acid, docosadienoic acid, adrenic acid, docosapentaenoic acid, tetracosatetraenoic acid, tetracosapentaenoic acid, mead acid, rumenic acid, alpha-calendic acid, beta-calendic acid, jacaric acid, alpha-eleostearic acid, beta-eleostearic acid, catalpic acid, punicic acid, rumelenic acid, alpha-parinaric acid, beta-parinaric acid, bosseopentaenoic acid, pinolenic acid, or podocarpic acid.

In some instances, the lipid is an eicosanoid, such as prostaglandin, leukotriene, thromboxane, lipoxin, hydroxy/hydroperoxyeicosatrienoic acid, hydroxy/hydroperoxyeicosatetraenoic acid, hydroxy/hydroperoxyeicosapentaenoic acid, epoxyeicosatrienoic acid, hepoxilin, levuglandin, isoprostane, calvulone, or its derivatives thereof.

In some embodiments, the lipid is a sterol lipid. In some instances, the sterol lipid comprises sterols, steroids, secosteroids, or bile acids. In some instances, the sterol comprises cholesterol, ergosterol, C24-propyl sterols, or stanol. In some instances, the lipid is cholesterol.

In some embodiments, the lipid is a glycerolipid. Glycerolipids comprise of mono-, di-, and tri-substituted glycerols. In some instances, the glycerolipids comprise monoradylglycerols, diradylglycerols, triadylglycerols, glycosylmonoradylglycerols, or glycosyldiradylglycerols.

In some embodiments, the lipid is a glycerophospholipid. Glycerophospholipids or phospholipids serve as key components of the lipid bilayer. In some instances, the glycerophospholipid or phospholipids comprise glycerophosphocholines, glycerophosphoethanolamines, glycerophosphoserines, glycerophosphoglycerols, glycerophosphoglycerophosphate, glycerophosphoinositols, glycerophosphoinositol monophosphates, glycerophosphoinositol bisphosphates, glycerophosphoinositol trisphosphates, glycerophosphates, glyceropyrophosphates, glycerophosphoglycerophosphoglycerols, CDP-glycerols, glycosylglycerophospholipids, glycerophosphoinositolglycans, glycerophosphonocholines, glycerophosphonoethanolamines, di-glycerol tetraether phospholipids (caldarchaeols), glycerol-nonitol tetraether phospholipids, or oxidized glycerophospholipids.

In some embodiments, the lipid is a sphingolipid. Sphingolipids are a family of lipid molecules that share a common sphingoid base backbone which is synthesized de novo from serine and a long-chain fatty acyl CoA. In some instances, the sphingoid base is referred to as sphingosine. In some embodiments, sphingolipids are further subdivided into ceramides, phosphosphingolipids, phosphonosphingolipids, glycosphingolipids, or arsenosphingolipids. In some instances, the glycosphingolipid is a neutral glycosphingolipid, an acidic glycosphingolipid, a basic glycosphingolipid, or an amphoteric glycosphingolipid.

In some embodiments, the lipid is a prenol lipid. Prenol lipids are synthesized from isopentenyl diphosphate and dimethylallyl diphosphate. In some embodiments, the prenol lipids comprise isoprenoids, quinones and hydroquinones, or polyprenols.

In some embodiments, the lipid is a saccharolipid. Saccharolipids are lipid molecules which comprise of fatty acids covalently attached to sugar backbones. In some instances, the saccharolipid comprise an acylated glucosamine precursor of a Lipid A component of lipopolysaccharide.

In some embodiments, the lipid is a polyketide. Polyketides are a class of structurally diverse secondary metabolites which are further divided into type I polyketides (macrolides from multimodular megasyntheses), type II polyketides (aromatic molecules from iterative action of dissociated enzymes), and type III polyketides (small aromatic molecules from fungal species). In some instances, polyketides include geldanamycin, doxycycline, erythromycin, and aflatoxin B1.

In some embodiments, a lipid is further classified as a neutral lipid, a cationic lipid, or an anionic lipid. In some embodiments, a neutral lipid is any of a number of lipid species which exist either in an uncharged or neutral zwitterionic form at physiological pH. Such lipids include, for example diacyl phosphatidylcholine, diacylphosphatidylethanolamine, ceramide, sphingomyelin, dihydrosphingomyelin, cephalin, and cerebrosides.

Cationic lipids, which carry a net positive charge at about physiological pH, include, but are not limited to, N,N-dioleoyl-N,N-dimethylammonium chloride ("DODAC"); N-(2,3-dioleoyloxy)propyl-N,N—N-triethylammonium chloride ("DOTMA"); N,N-distearyl-N,N-dimethylammonium bromide ("DDAB"); N-(2,3-dioleoyloxy)propyl)-N,N, N-trimethylammomum chloride ("DOTAP"); 1,2-Dioleoyloxy-3-trimethylaminopropane chloride salt ("DOTAP.C1"); 3β-(N',N'-dimethylaminoethane)-carbamoyl)cholesterol ("DC-Chol"), N-(1-(2,3-dioleoyloxy)propyl)-N-2-(sperminecarboxamido)ethyl)-N,N-dimethylammonium trifluoroacetate ("DOSPA"), dioctadecylamidoglycyl carboxyspermine ("DOGS"), 1,2-dileoyl-sn-3-phosphoethanolamine ("DOPE"), 1,2-dioleoyl-3-dimethylammonium propane ("DODAP"), N,N-dimethyl-2,3-dioleoyloxy)propylamine ("DODMA"), and N-(1,2-dimydstyloxyprop-3-yl)-N,N-dimethyl-N-hydroxyethyl ammonium bromide ("DMRIE").

Anionic lipids include, but are not limited to, phosphatidylglycerol, cardiolipin, diacylphosphatidylserine, diacylphosphatidic acid N-dodecanoyl phosphatidylethanoloamine, N-succinyl phosphatidylethanolamine, N-glutaryl phosphatidylethanolamine, lysylphosphatidylglycerol.

In some embodiments, a lipid probe disclosed herein comprises a) a lipid such as fatty acyl, glycerolipid, glycerophospholipid or phospholipid, sphingolipid, sterol lipid, prenol lipid, saccharolipid, or polyketide, b) a photoreactive group, and c) an affinity handle. In some instances, the lipid probe comprises a fatty acyl, a photoreactive group, and an affinity handle. In some instances, the lipid probe comprises a glycerolipid, a photoreactive group, and an affinity handle. In some embodiments, the lipid probe comprises a phospholipid, a photoreactive group, and an affinity handle. In some instances, the lipid probe comprises a sphingolipid, a photoreactive group, and an affinity handle. In some instances, the lipid probe comprises a sterol lipid, a photoreactive group, and an affinity handle.

In some embodiments, the lipid probe comprises a) a lipid selected from an arachidonoyl, arachidoyl, oleoyl, palmitoyl, or stearoyl fatty acyls, b) a photoreactive group, and c) an affinity handle. In some embodiments, the lipid probe comprises an arachidonoyl fatty acyl, a photoreactive group, and an affinity handle. In some embodiments, the lipid probe comprises an arachidoyl fatty acyl, a photoreactive group, and an affinity handle. In some embodiments, the lipid probe comprises an oleoyl fatty acyl, a photoreactive group, and an affinity handle. In some embodiments, the lipid probe comprises a palmitoyl fatty acyl, a photoreactive group, and an affinity handle. In some embodiments, the lipid probe comprises a stearoyl fatty acyl, a photoreactive group, and an affinity handle.

As used herein, the term "lipid" includes any suitable naturally occurring lipid and its derivatives thereof. For example in some instances, the term "lipid" includes arachidonic acid, a polyunsaturated omega-6 fatty acid, and its derivatives such as for example, (5Z,8Z,11Z)—N-(2-hydroxyethyl)-14-(3-(pent-4-yn-1-yl)-3H-diazirin-3-yl)tetradeca-5,8,11-trienamide (AEA-DA), (5Z,8Z,11Z)-14-(3-(pent-4-yn-1-yl)-3H-diazirin-3-yl)tetradeca-5,8,11-trienoic acid (AA-DA), (5Z,8Z,11Z,14Z)—N-(2-(3-methyl-3H-diazirin-3-yl)ethyl)icosa-5,8,11,14-tetraen-19-ynamide (A-DA), (5Z,8Z,11Z)-14-(3-(pent-4-yn-1-yl)-3H-diazirin-3-yl)tetradeca-5,8,11-trienamide (ANH$_2$-DA), potassium 2-((5Z,8Z,11Z)-14-(3-(pent-4-yn-1-yl)-3H-diazirin-3-yl) tetradeca-5,8,11-trienamido)ethane-1-sulfonate (AT-DA), or 1,3-dihydroxypropan-2-yl (5Z,8Z,11Z)-14-(3-(pent-4-yn-1-yl)-3H-diazirin-3-yl)tetradeca-5,8,11-trienoate (2-AG-DA).

Photoreactive Group

In some instances, the photoreactive group comprises azides, benzophenone, diazo compounds, diazirines, diazonium salts, or diaryl ketones.

In some instances, the photoreactive group is diazirine, or its derivatives thereof.

In some instances, the photoreactive group is attached at the hydrophobic portion of the lipid. In some instances, the photoreactive group is attached to the hydrophilic terminus of the lipid. In some instances, the photoreactive group is attached to an internal carbon of the lipid. In some instances, the photoreactive group is attached to an internal main carbon backbone of the lipid. In some instances, the photoreactive group is attached to an internal side chain group of the lipid.

In some embodiments, the photoreactive group is attached to a fatty acyl, a glycerolipids, a glycerophospholipid, a sphingolipid, a sterol lipid, a prenol lipid, a saccharolipid, or a polyketide. In some instances, the photoreactive group is attached to a fatty acyl (e.g. a fatty acid). In some instances, the photoreactive group is attached at C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C35, C35, or C36 position of the fatty acyl. In some instances, the photoreactive group is attached at C11, C12, C13, C14, C15, C16, C17, or C18 position.

In some instances, the photoreactive group further comprises a linker. In some instances, the linker bridges the lipid and the photoreactive group.

In some instances, the linker comprises a saturated, monosaturated, or polysaturated carbon chain group. In some instances, the linker is from about 1 to about 30 carbons long. In some instances, the linker is from about 2 to about 25, from about 3 to about 20, or from about 4 to about 14 carbons long.

As used herein, the term "photoreactive group" refers to a group capable of becoming covalently bound to another molecule upon irradiation by light. In some instances, the light is visible light. In some instances, the light is ultraviolet light. In some instances, the term "photoreactive means" refers to ultraviolet light. In some cases, upon irradiation such as by ultraviolet light, the photoreactive group further undergoes photolysis. As used herein, photolysis refers to the activation of the photoreactive group (e.g. diazirine) to generate a reactive species (e.g. carbene), which interact with a molecule in close proximity to form a covalent binding with the molecule.

Affinity Handle

In some embodiments, the affinity handle is a bioorthogonal affinity ligand. In some embodiments, the affinity handle utilizes bioorthogonal chemistry. As used herein, bioorthogonal chemistry refers to any chemical reaction that occurs inside of a living system (e.g. a cell) without interfering with native biochemical processes.

In some instances, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some instances, the affinity handle is an alkyne group, or an azide group.

In some instances, the affinity handle is an alkyne group. The term "alkyne group" as used in the context of an affinity handle refers to a group with a chemical formula of H—C≡C—R, HC$_2$R, R$_1$—C≡C—R$_2$, or R$_1$C$_2$R$_2$. In the context of the present chemical formula, R, R$_1$, and R$_2$ are independently a lipid described herein, a lipid precursor, a lipid portion such that the alkyne group is at an internal site within the lipid, a linker, or a combination thereof. In some cases, the alkyne group is capable of being covalently linked in a chemical reaction with a molecule containing an azide. In some instances, the affinity handle is an azide group.

In some instances, the affinity handle (e.g. alkyne group or azide group) serve as nonnative and non-perturbed bioorthogonal chemical handles. In some instances, the affinity handle (e.g. alkyne group or azide group) is further derivatized through chemical reactions such as click chemistry. In some instances, the click chemistry is a copper(I)-catalyzed [3+2]-Huisgen 1,3-dipolar cyclo-addition of alkynes and azides leading to 1,2,3-triazoles. In other instances, the click chemistry is a copper free variant of the above reaction.

In some instances, the affinity handle is attached to the hydrophilic terminus of the lipid. In some instances, the affinity handle is attached to an internal site of the lipid. In some instances, the affinity handle is attached to an internal main carbon backbone of the lipid. In some instances, the affinity handle is attached to an internal side chain group of the lipid.

In some embodiments, the affinity handle is attached to a fatty acyl, a glycerolipids, a glycerophospholipid, a sphingolipid, a sterol lipid, a prenol lipid, a saccharolipid, or a polyketide. In some instances, the affinity handle is attached to a fatty acyl (e.g. a fatty acid). In some instances, the affinity handle is attached at C3, C4, C5, C6, C7, C8, C9, C10, C11, C12, C13, C14, C15, C16, C17, C18, C19, C20, C21, C22, C23, C24, C25, C26, C27, C28, C29, C30, C31, C32, C33, C35, C35, or C36 position of the fatty acyl. In some instances, the affinity handle is attached to a terminal carbon atom.

In some instances, the affinity handle further comprises a linker. In some instances, the linker bridges the lipid and the affinity handle.

In some instances, the linker comprises a saturated, monosaturated, or polysaturated carbon chain group. In some instances, the linker is from about 1 to about 30 carbons long. In some instances, the linker is from about 2 to about 25, from about 3 to about 20, or from about 4 to about 14 carbons long.

In some instances, the photoreactive group and the affinity handle are conjugated to the same site on the lipid probe.

In some cases, the photoreactive group and the affinity handle are conjugated to different sites of the lipid probe.

In some instances, the affinity handle is further conjugated to an affinity ligand. In some embodiments, the affinity ligand comprises a chromophore, a labeling group, or a combination thereof. In some instances, the chromophore comprises fluorochrome, non-fluorochrome chromophore, quencher, an absorption chromophore, fluorophore, organic dye, inorganic dye, metal chelate, or a fluorescent enzyme substrate.

In some instances, the fluorophore comprises rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol, aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethylaminonaphthyl-5-sulfonate, 1-anilino-8-naphthalene sulfonate, 2-p-toluidinyl-6-naphthalene sulfonate, 3-phenyl-7-isocyanatocoumarin, N-(p-(2-benzoxazolyl)phenyl)maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TAMRA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705.

In some cases, the labeling group is a biotin moiety, a streptavidin moiety, bead, resin, a solid support, or a combination thereof. In some instances, the labeling group is a biotin moiety. In some instances, the biotin moiety further comprises a linker such as a 5, 6, 7, 8, 9, 10, 11, 12, 13, 14, 15 or more residues in length. In some instances, as described elsewhere herein, the linker further comprises a cleavage site, such as a protease cleavage site. In some cases, the biotin moiety interacts with a streptavidin moiety. In some instances, the biotin moiety is further attached to a bead, such as a streptavidin-coupled bead. In some instances, the biotin moiety is further attached to a resin or a solid support, such as a streptavidin-coupled resin or a streptavidin-coupled solid support. In some instances, the solid support is a plate, a platform, a cover slide, a microfluidic channel, and the like.

Lipid Probes of Formula I

In some embodiments, the lipid probe is a lipid probe of Formula I,

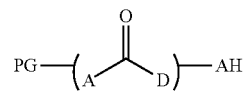

Formula (I)

wherein:
A is C$_{16}$-C$_{20}$alkyl or C$_{16}$-C$_{20}$alkenyl;
D is —OH, —NH$_2$, —NHR$^7$, or —OR$^8$;
R$^7$ is C$_1$-C$_4$alkyl, (C$_1$-C$_5$alkyl)OH, or (C$_1$-C$_5$)SO$_3$M;
R$^8$ is (CH$_2$OH)n;
M is monovalent or divalent cation;
n is 1, 2, or 3;
PG is a photoreactive group; and
AH is an affinity handle;
  wherein PG is attached to A or D and AH is attached to A or D.

In some instances, PG is a photoreactive group described supra. In some embodiments, PG comprises azides, benzophenone, diazo compounds, diazirines, diazonium salts, or diaryl ketones. In some instances, PG is diazirine, or its derivatives thereof. In some instances, PG is attached to A. In some instances, PG is attached to at a terminal site in A.

In some instances, PG is attached to an internal site in A. In some instances, PG is attached to D.

In some cases, AH is an affinity handle described supra. In some cases, AH is a bioorthogonal affinity handle. In some cases, AH is a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some instances, the affinity handle is an alkyne group, or an azide group. In some instances, AH is attached to A. In some instances, AH is attached to at a terminal site in A. In some instances, AH is attached to an internal site in A. In some cases, AH is attached to D.

Figure 1:
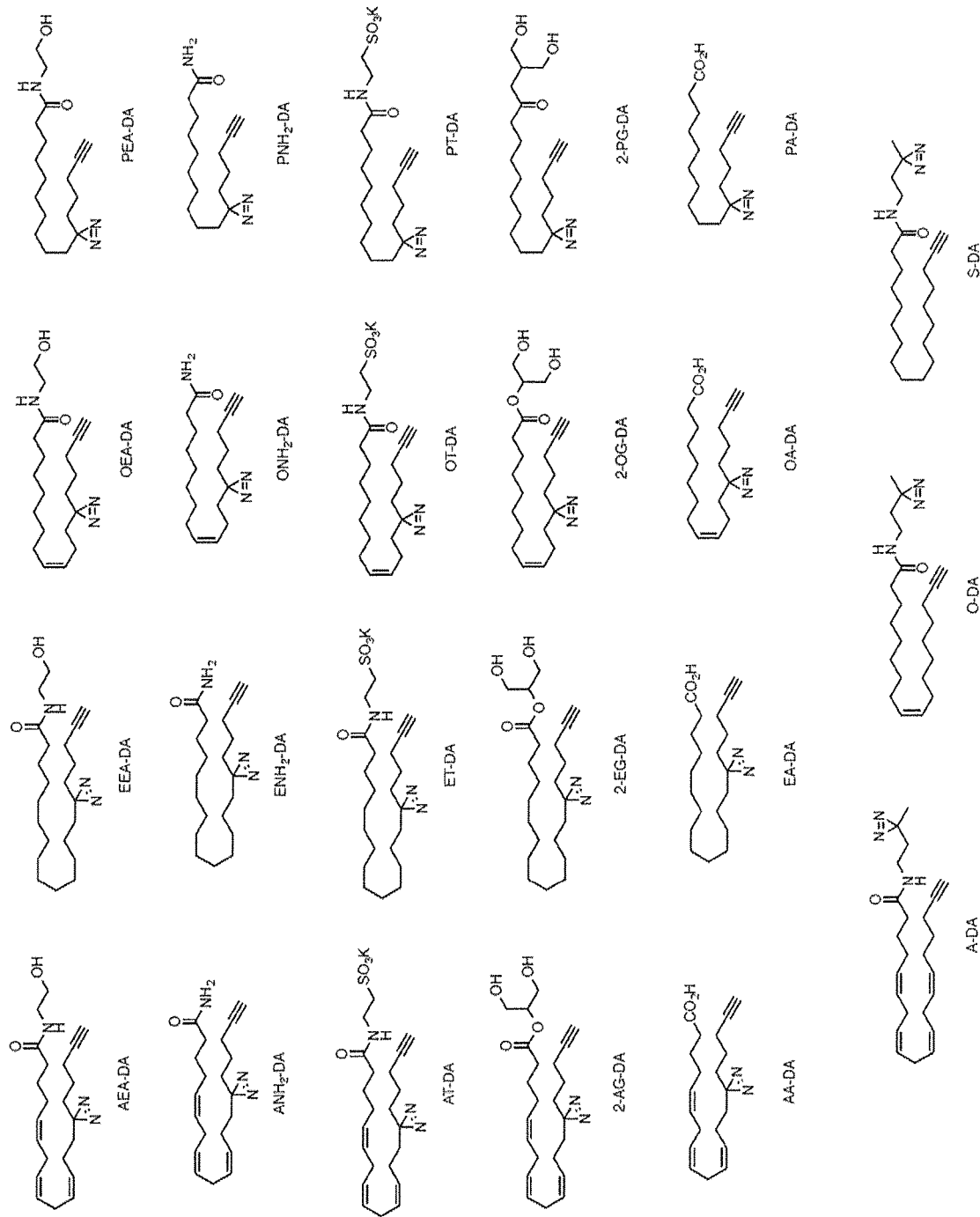
FIG. 1 illustrates structural representations of lipid probes described herein.

In some instances, the lipid probe has one of the following structures as illustrated in FIG. 1. In some instances, the lipid probe is a lipid probe from FIG. 1. In some instances, the lipid probe is a lipid probe selected from Table 1.

TABLE 1

| | Lipid Probe | Chemical Name |
|---|---|---|
| 1. | AEA-DA | (5Z,8Z,11Z)-N-(2-hydroxyethyl)-14-(3-(pent-4-yn-1-yl)-3H-diazirin-3-yl)tetradeca-5,8,11-trienamide |
| 2. | AA-DA | (5Z,8Z,11Z)-14-(3-(pent-4-yn-1-yl)-3H-diazirin-3-yl)tetradeca-5,8,11-trienoic acid |
| 3. | A-DA | (5Z,8Z,11Z,14Z)-N-(2-(3-methyl-3H-diazirin-3-yl)ethyl)icosa-5,8,11,14-tetraen-19-ynamide |
| 4. | ANH$_2$-DA | (5Z,8Z,11Z)-14-(3-(pent-4-yn-1-yl)-3H-diazirin-3-yl)tetradeca-5,8,11-trienamide |
| 5. | AT-DA | potassium 2-((5Z,8Z,11Z)-14-(3-(pent-4-yn-1-yl)-3H-diazirin-3-yl)tetradeca-5,8,11-trienamido)ethane-1-sulfonate |
| 6. | 2-AG-DA | 1,3-dihydroxypropan-2-yl (5Z,8Z,11Z)-14-(3-(pent-4-yn-1-yl)-3H-diazirin-3-yl)tetradeca-5,8,11-trienoate |
| 7. | EEA-DA | N-(2-hydroxyethyl)-14-(3-(pent-4-yn-1-yl)-3H-diazirin-3-yl)tetradecanamide |
| 8. | ENH$_2$-DA | 14-(3-(pent-4-yn-1-yl)-3H-diazirin-3-yl)tetradecanamide |
| 9. | ET-DA | potassium 2-(14-(3-(pent-4-yn-1-yl)-3H-diazirin-3-yl)tetradecanamido)ethane-1-sulfonate |
| 10. | 2-EG-DA | 1,3-dihydroxypropan-2-yl 14-(3-(pent-4-yn-1-yl)-3H-diazirin-3-yl)tetradecanoate |
| 11. | EA-DA | 14-(3-(pent-4-yn-1-yl)-3H-diazirin-3-yl)tetradecanoic acid |
| 12. | OEA-DA | (Z)-N-(2-hydroxyethyl)-12-(3-(pent-4-yn-1-yl)-3H-diazirin-3-yl)dodec-9-enamide |
| 13. | ONH$_2$-DA | (Z)-12-(3-(pent-4-yn-1-yl)-3H-diazirin-3-yl)dodec-9-enamide |
| 14. | OT-DA | potassium (Z)-2-(12-(3-(pent-4-yn-1-yl)-3H-diazirin-3-yl)dodec-9-enamido)ethane-1-sulfonate |
| 15. | 2-OG-DA | 1,3-dihydroxypropan-2-yl (Z)-12-(3-(pent-4-yn-1-yl)-3H-diazirin-3-yl)dodec-9-enoate |
| 16. | OA-DA | (Z)-12-(3-(pent-4-yn-1-yl)-3H-diazirin-3-yl)dodec-9-enoic acid |
| 17. | O-DA | (Z)-N-(2-(3-methyl-3H-diazirin-3-yl)ethyl)octadec-9-en-17-ynamide |
| 18. | PEA-DA | N-(2-hydroxyethyl)-10-(3-(pent-4-yn-1-yl)-3H-diazirin-3-yl)decanamide |
| 19. | PNH$_2$-DA | 10-(3-(pent-4-yn-1-yl)-3H-diazirin-3-yl)decanamide |
| 20. | PT-DA | potassium 2-(10-(3-(pent-4-yn-1-yl)-3H-diazirin-3-yl)decanamido)ethane-1-sulfonate |
| 21. | 2-PG-DA | 1-hydroxy-2-(hydroxymethyl)-13-(3-(pent-4-yn-1-yl)-3H-diazirin-3-yl)tridecan-4-one |
| 22. | PA-DA | 10-(3-(pent-4-yn-1-yl)-3H-diazirin-3-yl)decanoic acid |
| 23. | S-DA | N-(2-(3-Methyl-3H-diazirin-3-yl)ethyl)octadec-17-ynamide |

In some instances, the lipid probe is selected from (5Z,8Z,11Z)—N-(2-hydroxyethyl)-14-(3-(pent-4-yn-1-yl)-3H-diazirin-3-yl)tetradeca-5,8,11-trienamide (AEA-DA), (5Z,8Z,11Z)-14-(3-(pent-4-yn-1-yl)-3H-diazirin-3-yl)tetradeca-5,8,11-trienoic acid (AA-DA), (5Z,8Z,11Z,14Z)—N-(2-(3-methyl-3H-diazirin-3-yl)ethyl)icosa-5,8,11,14-tetraen-19-ynamide (A-DA), (Z)—N-(2-hydroxyethyl)-12-(3-(pent-4-yn-1-yl)-3H-diazirin-3-yl)dodec-9-enamide (OEA-DA), (Z)—N-(2-(3-methyl-3H-diazirin-3-yl)ethyl)octadec-9-en-17-ynamide (0-DA), N-(2-hydroxyethyl)-10-(3-(pent-4-yn-1-yl)-3H-diazirin-3-yl)decanamide (PEA-DA), and N-(2-(3-Methyl-3H-diazirin-3-yl)ethyl)octadec-17-ynamide (S-DA). In some instances, the lipid probe is (5Z,8Z,11Z)—N-(2-hydroxyethyl)-14-(3-(pent-4-yn-1-yl)-3H-diazirin-3-yl)tetradeca-5,8,11-trienamide (AEA-DA). In some instances, the lipid probe is (5Z,8Z,11Z)-14-(3-(pent-4-yn-1-yl)-3H-diazirin-3-yl)tetradeca-5,8,11-trienoic acid (AA-DA). In some instances, the lipid probe is (5Z,8Z,11Z,14Z)—N-(2-(3-methyl-3H-diazirin-3-yl)ethyl)icosa-5,8,11,14-tetraen-19-ynamide (A-DA). In some instances, the lipid probe is (Z)—N-(2-hydroxyethyl)-12-(3-(pent-4-yn-1-yl)-3H-diazirin-3-yl)dodec-9-enamide (OEA-DA). In some instances, the lipid probe is (Z)—N-(2-(3-methyl-3H-diazirin-3-yl)ethyl)octadec-9-en-17-ynamide (0-DA). In some instances, the lipid probe is N-(2-hydroxyethyl)-10-(3-(pent-4-yn-1-yl)-3H-diazirin-3-yl)decanamide (PEA-DA). In some instances, the lipid probe is N-(2-(3-Methyl-3H-diazirin-3-yl)ethyl)octadec-17-ynamide (S-DA).

As used herein in the context of lipid probe of Formula I, the term "alkyl" refers to a straight chain or branched, noncyclic or cyclic, saturated aliphatic hydrocarbons. Exemplary saturated straight chain alkyls include methyl, ethyl, n-propyl, n-butyl, n-pentyl, n-hexyl, and the like; saturated branched alkyls include isopropyl, sec-butyl, isobutyl, tert-butyl, isopentyl, and the like. Exemplary saturated cyclic alkyls include cyclopropyl, cyclobutyl, cyclopentyl, cyclohexyl, and the like; unsaturated cyclic alkyls include cyclopentenyl and cyclohexenyl, and the like.

The term "alkenyl" refers to an alkyl, as defined above, containing at least one double bond between adjacent carbon atoms. Alkenyls include both cis and trans isomers. Exemplary straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

Illustrative examples of cation include lithium ($Li^+$), sodium ($Na^+$), potassium ($K^+$), cesium ($Cs^+$), iron ($Fe^{2+}$ $Fe^{3+}$), calcium ($Ca^{2+}$), vanadium ($V^{4+}$), zinc ($Zn^{2+}$), cadmium ($Cd^{2+}$), silver ($Ag^+$), aluminum ($Al^{3+}$), and the like.

Lipid Interacting Proteins

In some instances, the lipid binding protein is a soluble protein or a membrane protein. In some instances, the lipid binding protein is involved in one or more of a biological process such as protein transport, lipid metabolism, apoptosis, transcription, electron transport, mRNA processing, or host-virus interaction. In some instances, the lipid binding protein is associated with one or more of diseases such as cancer or one or more disorders or conditions such as immune, metabolic, developmental, reproductive, neurological, psychiatric, renal, cardiovascular, or hematological disorders or conditions. In some cases, the lipid binding protein is an enzyme, a transporter, a receptor, an adaptor, a channel protein, or a chaperone.

An enzyme is a protein molecule that accelerates or catalyzes chemical reaction. Exemplary enzymes include, but are not limited to, AARS Alanine-tRNA ligase, cytoplasmic; ABCB1 multidrug resistant protein 1; ABHD10 Abhydrolase domain-containing protein 10, mitochondrial; ABHD12 Monoacylglycerol lipase ABHD12; ABHD16A Abhydrolase domain-containing protein 16A; ABHD6 Monoacylglycerol lipase ABHD6; ACAD9 Acyl-CoA dehydrogenase family member 9, mitochondrial; ACAD1 Long-chain specific acyl-CoA dehydrogenase, mitochondrial; ACAT2 Acetyl-CoA acetyltransferase, cytosolic; ACLY ATP-citrate synthase; ACOT2 Acyl-coenzyme A thioesterase 2, mitochondrial; ACP2 Lysosomal acid phosphatase; ACP6 Lysophosphatidic acid phosphatase type 6; ACSL1 Long-chain-fatty-acid-CoA ligase 1; ACSL3 Long-chain-fatty-acid-CoA ligase 3; ACSL4 Long-chain-fatty-acid-CoA ligase 4; ACSL6 Long-chain-fatty-acid-CoA ligase 6; ADK Adenosine kinase; ADPGK ADP-dependent glucokinase; ADSS Adenylosuccinate synthetase isozyme 2; AFG3L2 AFG3-like protein 2; AGK Acylglycerol kinase, mitochondrial; AGPAT1 1-acyl-sn-glycerol-3-phosphate acyltransferase alpha; Agpat2 1-acyl-sn-glycerol-3-phosphate acyltransferase beta; Agpat4 1-acyl-sn-glycerol-3-phosphate acyltransferase delta; AGPAT5 1-acyl-sn-glycerol-3-phosphate acyltransferase epsilon; AGPAT6 Glycerol-3-phosphate acyltransferase 4; Agpat9 Glycerol-3-phosphate acyltransferase 3; AGPS Alkyldihydroxyacetonephosphate synthase, peroxisomal; AHCY Adenosylhomocysteinase; AIFM1 Apoptosis-inducing factor 1, mitochondrial; AIFM2 Apoptosis-inducing factor 2; Akr1b8 Aldose reductase-related protein 2; Akr1c13 Aldo-keto reductase family 1 member $C_{13}$; ALDH18A1 Delta-1-pyrroline-5-carboxylate synthase; ALDH1A2 Retinal dehydrogenase 2; ALDH1B1 Aldehyde dehydrogenase X, mitochondrial; ALDH2 Aldehyde dehydrogenase, mitochondrial; ALDH3A2 Fatty aldehyde dehydrogenase; Aldh3b1 Aldehyde dehydrogenase family 3 member B1; ALDH7A1 Alpha-aminoadipic semialdehyde dehydrogenase; ALG1 Chitobiosyldiphosphodolichol beta-mannosyltransferase; ALG10 Dol-β-Glc:Glc(2)Man(9)GlcNAc(2)-PP-Dol alpha-1,2-glucosyltransferase; ALG11 GDP-Man:Man(3)GlcNAc(2)-PP-Dol alpha-1,2-mannosyltransferase; ALG12 Dol-β-Man:Man(7)GlcNAc(2)-PP-Dol alpha-1,6-mannosyltransferase; Alg2 Alpha-1,3/1,6-mannosyltransferase ALG2; ALG5 Dolichyl-phosphate beta-glucosyltransferase; ALG6 Dolichyl pyrophosphate Man9GlcNAc2 alpha-1,3-glucosyltransferase; ALG9 Alpha-1,2-mannosyltransferase ALG9; AMFR E3 ubiquitin-protein ligase AMFR; ASAH1 acid ceramidase; ASNS Asparagine synthetase; ASPH Aspartyl/asparaginyl beta-hydroxylase; ATAD1 ATPase family AAA domain-containing protein 1; ATIC Bifunctional purine biosynthesis protein PURH; ATL2 Atlastin-2; ATP13A1 Probable cation-transporting ATPase 13A1; ATP1A1 Sodium/potassium-transporting ATPase subunit alpha; ATP1A3 Sodium/potassium-transporting ATPase subunit alpha; ATP2A2 Sarcoplasmic/endoplasmic reticulum calcium ATPase; ATP2B1 MCG13663, isoform CRA_a; ATP4A Potassium-transporting ATPase alpha chain 1; ATP5B ATP synthase subunit beta, mitochondrial; B3GNT1 N-acetyllactosaminide beta-1,3-N-acetylglucosaminy; BDH1 D-beta-hydroxybutyrate dehydrogenase, mitochondrial; CAD CAD protein; CBS cystathionine beta-synthase; CLPP putative ATP-dependent Clp protease proteolytic subunit; COMT catechol O-methyltransferase; COPS5 COPS signalosome complex subunit 5; COQ5 2-methoxy-6-polyprenyl-1,4-benzoquinol methylase; CPT1A Carnitine O-palmitoyltransferase 1, liver isoform; CPT2 Carnitine O-palmitoyltransferase 2, mitochondrial; CPVL Probable serine carboxypeptidase CPVL; CSNK1A1 casein kinase I isoform alpha; CTH cystathionine gamma-lyase; CTPS1 CTP synthase 1; CTSA Lysosomal protective protein; CTSB Cathepsin B; CTSD Cathepsin D; CYB5R3 NADH-cytochrome b5 reductase 3; Cyp20a1 Cytochrome P450 20A1; CYP51A1 Lanosterol 14-alpha demethylase; DAD1 Dolichyl-diphosphooligosaccharide-protein glycosyltransferase; DCTPP1 dCTP pyrophosphatase 1; DCXR L-xylulose reductase; DDOST Dolichyl-diphosphooligosaccharide-protein glycosyltransferase; DDX17 Probable ATP-dependent RNA helicase DDX17; DCTN1 Dynactin subunit 1; DDX17 Probable ATP-dependent RNA helicase DDX17; DDX20 Probable ATP-dependent RNA helicase DDX20; DDX3X ATP-dependent RNA helicase DDX3X; DDXS Probable ATP-dependent RNA helicase DDXS; DEGS1 Sphingolipid delta (4)-desaturase DES1; DHCR24 Delta(24)-sterol reductase; DHCR7 7-dehydrocholesterol reductase; DHFR Dihydrofolate reductase; DHODH Dihydroorotate dehydrogenase (quinone), mitochondrial; DHRS1 Dehydrogenase/reductase SDR family member 1; DHRS3 Short-chain dehydrogenase/reductase 3; DHRS7 Dehydrogenase/reductase SDR family member 7; DHRS7B Dehydrogenase/reductase SDR family member 7B; DHX15 Putative pre-mRNA-splicing factor ATP-dependent RN; DHX30 Putative ATP-dependent RNA helicase DHX30; DHX9 ATP-dependent RNA helicase A; DLD Dihydrolipoyl dehydrogenase, mitochondrial; DNM1L Dynamin-1-like protein; DNM2 Dynamin-2; DOLK Dolichol kinase; DOLPP1 Dolichyldiphosphatase 1; DPM1 Dolichol-phosphate mannosyltransferase; Dpp7 Dipeptidyl peptidase 2; DPY19L1 Protein dpy-19 homolog 1; EBP 3-beta-hydroxysteroid-Delta(8), Delta(7)-isomerase; ECE1 Endothelin-converting enzyme 1; ECH1 Delta(3,5)-Delta(2,4)-dienoyl-CoA isomerase, mitochondrial; ECHS1 Enoyl-CoA hydratase, mitochondrial; Ecil Enoyl-CoA delta isomerase 1, mitochondrial; EIF3F Eukaryotic translation initiation factor 3 subunit; EIF4A1 Eukaryotic initiation factor 4A-I; EIF4A2 Eukaryotic initiation factor 4A-II; ELOVL2 Elongation of very long chain fatty acids protein; ENDOD1 Endonuclease domain-containing 1 protein; EPHX1 Epoxide hydrolase 1; EPHX2 Bifunctional epoxide hydrolase 2; ERMP1 Endoplasmic reticulum metallopeptidase 1; ERO1L ERO1-like protein alpha; Fadsl Fatty acid desaturase 1; FADS2 Fatty acid desaturase 2; FADS3 Fatty acid desaturase 3; FAH fumarylacetoacetase; Fkbp11 Peptidyl-prolyl cis-trans isomerase FKBP11; FKBP1A Peptidyl-prolyl cis-trans isomerase FKBP1A; Fkbp2 Peptidyl-prolyl cis-trans isomerase FKBP2; FKBP4 Peptidyl-prolyl cis-trans isomerase FKBP4; FKBP8 Peptidyl-prolyl cis-trans isomerase FKBP8; FNTB Protein farnesyltransferase subunit beta; G6PD Glucose-6-phosphate 1-dehydrogenase; GAA Lysosomal alpha-glucosidase; GALNT1 Polypeptide N-acetylgalactosaminyltransferase 1; GANAB Neutral alpha-glucosidase AB; GARS Glycine-tRNA ligase; GART Trifunctional purine biosynthetic protein adenosine; GBA Glucosylceramidase; GDPD1 Glycerophosphodiester phosphodiesterase domain-containing 1; GK Glycerol kinase; GLA Alpha-galactosidase A; GLB1 Beta-galactosidase; GLO1 Lactoylglutathione lyase; GLT8D1 Glycosyltransferase 8 domain-containing protein 1; GMPPB Mannose-1-phosphate guanyltransferase beta; GMPS GMP synthase; GNPAT Dihydroxyacetone phosphate acyltransferase; GPD2 Glycerol-3-phosphate dehydrogenase, mitochondrial; GPX8 Probable glutathione peroxidase 8; GSR Glutathione reductase, mitochondrial; GSTM1 Glutathione S-transferase Mu 1; GSTM2 Glutathione S-transferase Mu 2; GSTO1 Glutathione S-transferase omega-1; GSTP1 Glutathione S-transferase P; HACL1 2-hydroxyacyl-CoA lyase 1; HADH Hydroxyacyl-coenzyme A dehydrogenase, mitochondrial; HADHA Trifunctional enzyme subunit alpha, mitochondrial; HADHB Trifunctional enzyme subunit beta, mitochondrial; HARS Histidine-tRNA ligase, cytoplasmic; HAT1 Histone acetyltransferase type B catalytic subunit; HK1 Hexokinase-1; HK2 Hexokinase-2; HM13 Minor histocompatibility antigen H13; HMGCS1 Hydroxymethylglutaryl-CoA synthase, cytoplasmic; HMOX2 Heme oxygenase 2; HPRT1 Hypoxanthine-guanine phosphoribosyltransferase; HSD17B10 3-hydroxyacyl-CoA dehydrogenase type-2; HSD17B11 Estradiol 17-beta-dehydrogenase 11; HSD17B12 Estradiol 17-beta-dehydrogenase 12; HSD17B4 Peroxisomal multifunctional enzyme type 2; HSD17B7 3-keto-steroid reductase; HSDL2 Hydroxysteroid dehydrogenase-like protein 2; HUWE1 E3 ubiquitin-protein ligase HUWE1; TARS Isoleucine-tRNA ligase, cytoplasmic; IARS2 Isoleucine-tRNA ligase, mitochondrial; ICMT Protein-S-isoprenylcysteine O-methyltransferase; IDH1 Isocitrate dehydrogenase; IDH2 Isocitrate dehydrogenase; IFI30 Gamma-interferon-inducible lysosomal thiol reductase; ILVBL Acetolactate synthase-like protein; IMPDH2 Inosine-5-monophosphate dehydrogenase 2; INPP5K Inositol polyphosphate 5-phosphatase K; KDM1B Lysine-specific histone demethylase 1B; KDSR 3-ketodihydrosphingosine reductase; KDM1B Lysine-specific histone demethylase 1B; KDSR 3-ketodihydrosphingosine reductase; L2HGDH L-2-hydroxyglutarate dehydrogenase, mitochondrial; LARS Leucine-tRNA ligase, cytoplasmic; LCLAT1 Lysocardiolipin acyltransferase 1; LNPEP Leucyl-cystinyl aminopeptidase; LPCAT1 Lysophosphatidylcholine acyltransferase 1; LPCAT2 Lysophosphatidylcholine acyltransferase 2; LPCAT3 Lysophospholipid acyltransferase 5; LPGAT1 Acyl-CoA:lysophosphatidylglycerol acyltransferase; LSS Lanosterol synthase; LTA4H Leukotriene A-4 hydrolase; MAOA Amine oxidase; MARCHS E3 ubiquitin-protein ligase MARCHS; MARCH6 E3 ubiquitin-protein ligase MARCH6; MBLAC2 Metallo-beta-lactamase domain-containing protein 2; MBOAT7 Lysophospholipid acyltransferase 7; MCCC2 Methylcrotonoyl-CoA carboxylase beta chain, mitochondrial; MCEE Methylmalonyl-CoA epimerase; MCM2 DNA replication licensing factor MCM2; MCM4 DNA replication licensing factor MCM4; MCM6 DNA replication licensing factor MCM6; MCM7 DNA replication licensing factor MCM7; MEST Mesoderm-specific transcript protein; METAP1 Methionine aminopeptidase 1; METTL7A Methyltransferase-like protein 7A; MGEAS Bifunctional protein NCOAT; MGST1 Microsomal glutathione S-transferase 1; MIF Macrophage migration inhibitory factor; MOGS Mannosyl-oligosaccharide glucosidase; MOV10 Putative helicase MOV-10; MPI Mannose-6-phosphate isomerase; MSMO1 Methylsterol monooxygenase 1; MT-CO1 Cytochrome c oxidase subunit 1; MT-ND1 NADH-ubiquinone oxidoreductase chain 1; MT-ND2 NADH-ubiquinone oxidoreductase chain 2; MT-ND5 NADH-ubiquinone oxidoreductase chain 5; MTAP S-methyl-5-thioadenosine phosphorylase; MTHFD1 C-1-tetrahydrofolate synthase, cytoplasmic; NAMPT Nicotinamide phosphoribosyltransferase; NDUFS1 NADH-ubiquinone oxidoreductase 75 kDa subunit, mitochondrial; NDUFS2 NADH dehydrogenase; NDUFS3 NADH dehydrogenase; NDUFS7 NADH dehydrogenase; NLN Neurolysin, mitochondrial; NME2 Nucleoside diphosphate kinase B; NNT NAD(P) transhydrogenase, mitochondrial; NPEPPS Puromycin-sensitive aminopeptidase; NRD1 Nardilysin; NSDHL Sterol-4-alpha-carboxylate 3-dehydrogenase, decarboxylating; NSUN2 tRNA (cytosine(34)-C(5))-methyltransferase; NT5C3L Cytosolic 5-nucleotidase III-like protein; NT5DC2 5-nucleotidase domain-containing protein 2; NTMT1 N-terminal Xaa-Pro-Lys N-methyltransferase 1; NUDT1 7,8-dihydro-8-oxoguanine triphosphatase; NUDT9 ADP-ribose pyrophosphatase, mitochondrial; NXN Nucleoredoxin; OAT Ornithine aminotransferase, mitochondrial; OPA1 Dynamin-like 120 kDa protein, mitochondrial; OTUB1 Ubiquitin thioesterase OTUB1; P4HA1 Prolyl 4-hydroxylase subunit alpha-1; P4HA2 Prolyl 4-hydroxylase subunit alpha-2; P4HB Protein disulfide-isomerase; P4HTM Transmembrane prolyl 4-hydroxylase; PAICS Multifunctional protein ADE2; PANK4 Pantothenate kinase 4; PAOX Peroxisomal N(1)-acetyl-spermine/spermidine oxidase; PAPSS1 Bifunctional 3-phosphoadenosine 5-phosphosulfate; PARL Presenilins-associated rhomboid-like protein, mitochondrial; PCK2 Phosphoenolpyruvate carboxykinase; PCYOX1 Prenylcysteine oxidase 1; PCYOX1L Prenylcysteine oxidase-like; PCYT1A Choline-phosphate cytidylyltransferase A; PDIA6 Protein disulfide-isomerase A6; PDP1; Pdss1 Decaprenyl-diphosphate synthase subunit 1; PFKL 6-phosphofructokinase, liver type PFKP 6-phosphofructokinase type C PGAM5 Serine/threonine-protein phosphatase PGAM5, mitochondrial; PHGDH D-3-phosphoglycerate dehydrogenase; PI4 KB Phosphatidylinositol 4-kinase beta; PIGK GPI-anchor transamidase; PIGM GPI mannosyltransferase 1; PISD Phosphatidylserine decarboxylase proenzyme; PITRM1 Presequence protease, mitochondrial; PKM Pyruvate kinase isozymes M1/M2; Pla2g15 Group XV phospholipase A2; PLBD2 Putative phospholipase B-like 2; PLD3 Phospholipase D3; PLOD1 Procollagen-lysine, 2-oxoglutarate 5-dioxygenase 1; PLOD3 Procollagen-lysine, 2-oxoglutarate 5-dioxygenase 3; PMPCA Mitochondrial-processing peptidase subunit alpha; PMPCB Mitochondrial-processing peptidase subunit beta; PNPLA2 Patatin-like phospholipase domain-containing protein; PNPLA6 Neuropathy target esterase; POLR2B DNA-directed RNA polymerase II subunit RPB2; POLRMT DNA-directed RNA polymerase, mitochondrial; PON2 Serum paraoxonase/arylesterase 2; POR NADPH-cytochrome P450 reductase; PPAPDC2 Presqualene diphosphate phosphatase; PPAT Amidophosphoribosyltransferase; PPM1L Protein phosphatase 1L; PPT1 Palmitoyl-protein thioesterase 1; PRCP Lysosomal Pro-X carboxypeptidase; PRDX1 Peroxiredoxin-1; PRDX3 Thioredoxin-dependent peroxide reductase, mitochondrial; PREP Prolyl endopeptidase; PREPL Prolyl endopeptidase-like; PRKDC DNA-dependent protein kinase catalytic subunit; PRMT1 Protein arginine N-methyltransferase 1; PSMA4 Proteasome subunit alpha type-4; PSMA6 Proteasome subunit alpha type-6; PSMB1 Proteasome subunit beta type-1; PSMB2 Proteasome subunit beta type-2; PSMB3 Proteasome subunit beta type-3; PSMB4 Proteasome subunit beta type-4; PSMB5 Proteasome subunit beta type-5; PSMB6 Proteasome subunit beta type-6; PSMB7 Proteasome subunit beta type-7; PSMB8 Proteasome subunit beta type-8; PSMD14 26S proteasome non-ATPase regulatory subunit 14; PTDSS1 Phosphatidylserine synthase 1; PTDSS2 Phosphatidylserine synthase 2; PTGES2 Prostaglandin E synthase 2; PTGR2 Prostaglandin reductase 2; PTGS1 Prostaglandin G/H synthase 1; PTPLAD1 3-hydroxyacyl-CoA dehydratase 3; PTPLB 3-hydroxyacyl-CoA dehydratase 2; PTPN1 Tyrosine-protein phosphatase non-receptor type 1; PTRH2 Peptidyl-tRNA hydrolase 2, mitochondrial; QPCTL Glutaminyl-peptide cyclotransferase-like protein; RABGGTB Geranylgeranyl transferase type-2 subunit beta; RANBP2 E3 SUMO-protein ligase RanBP2; RARS Arginine-tRNA ligase, cytoplasmic; RDH10 Retinol dehydrogenase 10; RDH11 Retinol dehydrogenase 11; RDH13 Retinol dehydrogenase 13; RDH14 Retinol dehydrogenase 14; RETSAT All-trans-retinol 13,14-reductase; RHOT1 Mitochondrial Rho GTPase 1; RHOT2 Mitochondrial Rho GTPase 2; RNF14 E3 ubiquitin-protein ligase RNF14; RPN1 Dolichyl-diphosphooligosaccharide-protein glycosyltransferase; RPN2 Dolichyl-diphosphooligosaccharide-protein glycosyltransferase; RPS3 40S ribosomal protein S3; RPS6KA1 Ribosomal protein S6 kinase alpha-1; RPS6KA2 Ribosomal protein S6 kinase alpha-2; RPS6KA3 Ribosomal protein S6 kinase alpha-3; RRM2 Ribonucleoside-diphosphate reductase subunit M2; RUVBL1 RuvB-like 1; RUVBL2 RuvB-like 2; SACM1L Phosphatidylinositide phosphatase SAC1; SCCPDH Saccharopine dehydrogenase-like oxidoreductase; SCD Acyl-CoA desaturase; SCD2 Acyl-CoA desaturase 2; SCP2 Non-specific lipid-transfer protein; SCPEP1 Retinoid-inducible serine carboxypeptidase; SDHA Succinate dehydrogenase; SDHB Succinate dehydrogenase; SEC11A Signal peptidase complex catalytic subunit SEC11A; SEC11C Signal peptidase complex catalytic subunit SEC11C; SGPL1 Sphingosine-1-phosphate lyase 1; SHMT1 Serine hydroxymethyltransferase, cytosolic; SHMT2 Serine hydroxymethyltransferase, mitochondrial; SLC27A2 Very long-chain acyl-CoA synthetase; SLC27A3 Long-chain fatty acid transport protein 3; SMPD4 Sphingomyelin phosphodiesterase 4; SNRNP200 U5 small nuclear ribonucleoprotein 200 kDa helicase; SOAT1 Sterol O-acyltransferase 1; SPCS2 Signal peptidase complex subunit 2; SPTLC1 Serine palmitoyltransferase 1; SPTLC2 Serine palmitoyltransferase 2; SQLE Squalene monooxygenase; SRM Spermidine synthase; SPTLC1 Serine palmitoyltransferase 1; SPTLC2 Serine palmitoyltransferase 2; SQLE Squalene monooxygenase; SRM Spermidine synthase; STT3A Dolichyl-diphosphooligosaccharide-protein glycosyltransferase; STT3B Dolichyl-diphosphooligosaccharide-protein glycosyltransferase; SYVN1 E3 ubiquitin-protein ligase synoviolin; TECR Trans-2,3-enoyl-CoA reductase; THOP1 Thimet oligopeptidase; TM7SF2 Delta (14)-sterol reductase; TMPPE Transmembrane protein with metallophosphoesterase; TMX3 Protein disulfide-isomerase TMX3; TOR1A Torsin-1A; TOR1B Torsin-1B; TPI1 Triosephosphate isomerase; TPP1 Tripeptidyl-peptidase 1; TRIM28 Transcription intermediary factor 1-beta; UGCG Ceramide glucosyltransferase; UGT8 2-hydroxyacylsphingosine 1-beta-galactosyltransferase; UQCRFS1 Cytochrome b-c1 complex subunit Rieske, mitochondrial; USP28 Ubiquitin carboxyl-terminal hydrolase 28; USP47 Ubiquitin carboxyl-terminal hydrolase 47; USP5 Ubiquitin carboxyl-terminal hydrolase 5; USP7 Ubiquitin carboxyl-terminal hydrolase 7; VAT1 Synaptic vesicle membrane protein VAT-1 homolog; VAT1L Synaptic vesicle membrane protein VAT-1 homolog-likeVCP Transitional endoplasmic reticulum ATPase; VKORC1L1 Vitamin K epoxide reductase complex subunit 1-like; VKORC1L1 Vitamin K epoxide reductase complex subunit 1-like; WHSC1 Probable histone-lysine N-methyltransferase NSD2; XPNPEP1 Xaa-Pro aminopeptidase 1; XRCC5 X-ray repair cross-complementing protein 5; XRCC6 X-ray repair cross-complementing protein 6; YKT6 Synaptobrevin homolog YKT6; YME1L1 ATP-dependent zinc metalloprotease YME1L1; ZADH2 Zinc-binding alcohol dehydrogenase domain-containing 2; and ZMPSTE24 CAAX prenyl protease 1 homolog.

In some embodiments, one or more lipid probes described herein interact or bind to one or more of the enzymes described above and elsewhere herein.

A transporter, also referred to as a transmembrane pump, transporter protein, escort protein, acid transport protein, cation transport protein, or anion transport protein, is a protein molecule that moves materials (e.g. ions, small molecules, macromolecules, proteins) within an organism, such as across a biological membrane. Exemplary transporters include, but are not limited to, AAAS Aladin; ABCB1 multidrug resistant protein 1; ABCB10 ATP-binding cassette sub-family B member 10, mitochondrial; ABCB7 ATP-binding cassette sub-family B member 7, mitochondrial; ABCD3 ATP-binding cassette sub-family D member 3; ACBD5 Acyl-CoA-binding domain-containing protein 5; ACTN4 alpha-actinin-4; AMFR E3 ubiquitin-protein ligase AMFR; AP3B1 AP-3 complex subunit beta-1; AP3M1 AP-3 complex subunit mu-1; APOL2 Apolipoprotein L2; APOO Apolipoprotein O; APOOL Apolipoprotein O-like; ARF1 ADP-ribosylation factor 1; ARF3 ADP-ribosylation factor 3; ARF4 ADP-ribosylation factor 4; ARF5 ADP-ribosylation factor 5; ARFGAP1 ADP-ribosylation factor GTPase-activating protein; ASNA1 ATPase ASNA1; ATP13A1 Probable cation-transporting ATPase 13A1; ATP1A1 Sodium/potassium-transporting ATPase subunit alpha; ATP1A3 Sodium/potassium-transporting ATPase subunit alpha; ATP2A2 Sarcoplasmic/endoplasmic reticulum calcium ATPase; ATP2B1 MCG13663, isoform CRA_a; ATP4A Potassium-transporting ATPase alpha chain 1; ATP5A1 ATP synthase subunit alpha, mitochondrial; ATP5B ATP synthase subunit beta, mitochondrial; ATP5C1 ATP synthase subunit gamma, mitochondrial; ATP5F1 ATP synthase subunit b, mitochondrial; ATP5H ATP synthase subunit d, mitochondrial; ATP5I ATP synthase subunit e, mitochondrial; ATP5J2 ATP synthase subunit f, mitochondrial; ATP5L ATP synthase subunit g, mitochondrial; ATP5O ATP synthase subunit 0, mitochondrial; ATP6AP1 V-type proton ATPase subunit S1; ATP6VOA1 V-type proton ATPase 116 kDa subunit a isoform 1; ATP6VOA2 V-type proton ATPase 116 kDa subunit a isoform 2; ATP6VOC V-type proton ATPase 16 kDa proteolipid subunit; ATP6V1B2 V-type proton ATPase subunit B, brain isoform; BAG6 Large proline-rich protein BAG6; BCAP29 B-cell receptor-associated protein 29; BCAP31 B-cell receptor-associated protein 31; BNIP1 vesicle transport protein SEC20; CDIPT CDP-diacylglycerol-inositol 3-phosphatidyltransferase; CDKAL1 Threonylcarbamoyladenosine tRNA methylthiotransferase; CDS2 Phosphatidate cytidylyltransferase 2; CEPT1 Choline/ethanolaminephosphotransferase 1; CERS5 ceramide synthase 5; CERS6 ceramide synthase 6; CHDH choline dehydrogenase, mitochondrial; CHUK inhibitor of nuclear factor kappa-B kinase subunit; CKB creatine kinase B-type; COPB1 coatomer subunit beta; COPE coatomer subunit epsilon; CPT1A Carnitine O-palmitoyltransferase 1, liver isoform; CPT2 Carnitine O-palmitoyltransferase 2, mitochondrial; CSE1L exportin-2; CYB5A Cytochrome b5; CYB5B Cytochrome b5 type B; CYC1 Cytochrome cl, heme protein, mitochondrial; DCTN1 Dynactin subunit 1; DERL1 Derlin-1; DYNC1H1 Cytoplasmic dynein 1 heavy chain 1; ERGIC1 Endoplasmic reticulum-Golgi intermediate compartment; ERGIC2 Endoplasmic reticulum-Golgi intermediate compartment; ESYT1 Extended synaptotagmin-1; ESYT2 Extended synaptotagmin-2; ETFDH Electron transfer flavoprotein-ubiquinone oxidoreductase; FABP5 Fatty acid-binding protein, epidermal; FADS1 Fatty acid desaturase 1; FADS2 Fatty acid desaturase 2; FADS3 Fatty acid desaturase 3; FMR1 Fragile X mental retardation protein 1 homolog; GET4 Golgi to ER traffic protein 4 homolog; GOLIM4 Golgi integral membrane protein 4; GOLPH3 Golgi phosphoprotein 3; GOLT1B Vesicle transport protein GOT1B; GOPC Golgi-associated PDZ and coiled-coil motif-containing; GOSR1 Golgi SNAP receptor complex member 1; GPR89B Golgi pH regulator B; HIGD1A HIG1 domain family member 1A; HNRNPA1 Heterogeneous nuclear ribonucleoprotein A1; HNRNPA1L2 Heterogeneous nuclear ribonucleoprotein A1-like 2; IGF2BP1 Insulin-like growth factor 2 mRNA-binding protein; IGF2BP3 Insulin-like growth factor 2 mRNA-binding protein; IPO11 Importin-11; IPO4 Importin-4; IPO5 Importin-5; IPO7 Importin-7; IPO9 Importin-9; KDELR1 ER lumen protein retaining receptor 1; KDELR2 ER lumen protein retaining receptor 2; KDELR3 ER lumen protein retaining receptor 3; KHSRP Far upstream element-binding protein 2; KPNA2 Importin subunit alpha-2; KPNB1 Importin subunit beta-1; LAPTM4A Lysosomal-associated transmembrane protein 4A; LMAN1 Protein ERGIC-53 LMAN2 Vesicular integral-membrane protein VIP36; LRPPRC Leucine-rich PPR motif-containing protein, mitochondrial; MAGT1 Magnesium transporter protein 1; MCFD2 Multiple coagulation factor deficiency protein 2; MICU1 Calcium uptake protein 1, mitochondrial; MMGT1 Membrane magnesium transporter 1; MPC2 Mitochondrial pyruvate carrier 2; MT-ATP6 ATP synthase subunit a; MT-CO1 Cytochrome c oxidase subunit 1; MT-CO2 Cytochrome c oxidase subunit 2; MT-ND1 NADH-ubiquinone oxidoreductase chain 1; MT-ND2 NADH-ubiquinone oxidoreductase chain 2; MT-ND5 NADH-ubiquinone oxidoreductase chain 5; MTCH1 Mitochondrial carrier homolog 1; MTCH2 Mitochondrial carrier homolog 2; MTTP Microsomal triglyceride transfer protein large subunit; MTX1 Metaxin-1; MTX2 Metaxin-2; NASP Nuclear autoantigenic sperm protein; NCBP1 Nuclear cap-binding protein subunit 1; NDUFA10 NADH dehydrogenase; NDUFA11 NADH dehydrogenase; NDUFA13 NADH dehydrogenase; NDUFA4 NADH dehydrogenase; NDUFA8 NADH dehydrogenase; NDUFA9 NADH dehydrogenase; NDUFB10 NADH dehydrogenase; NDUFB6 NADH dehydrogenase; NDUFB8 NADH dehydrogenase; NDUFB9 NADH dehydrogenase; NDUFS1 NADH-ubiquinone oxidoreductase 75 kDa subunit, mitochondrial; NDUFS2 NADH dehydrogenase; NDUFS3 NADH dehydrogenase; NDUFS7 NADH dehydrogenase; NUP133 Nuclear pore complex protein Nup133; NUP155 Nuclear pore complex protein Nup155; NUP160 Nuclear pore complex protein Nup160; NUP205 Nuclear pore complex protein Nup205; NUP210 Nuclear pore membrane glycoprotein 210; NUP37 Nucleoporin Nup37; NUP93 Nuclear pore complex protein Nup93; OSBPL8 Oxysterol-binding protein-related protein 8; PDCD6IP Programmed cell death 6-interacting protein; PEX14 Peroxisomal membrane protein PEX14; PITPNB Phosphatidylinositol transfer protein beta isoform; PLIN3 Perilipin-3; PRAF2 PRA1 family protein 2; PREB Prolactin regulatory element-binding protein; RAB10 Ras-related protein Rab-10; RAB11A Ras-related protein Rab-11A; RAB11B Ras-related protein Rab-11B; RAB18 Ras-related protein Rab-18; RAB1A Ras-related protein Rab-1A; RAB1B Ras-related protein Rab-1B; RAB2A Ras-related protein Rab-2A; RAB9A Ras-related protein Rab-9A; RANBP2 E3 SUMO-protein ligase RanBP2; RBP1 Retinol-binding protein 1; RFT1 Protein RFT1 homolog; RTN3 Reticulon-3; SAR1A GTP-binding protein SAR1a; SAR1B GTP-binding protein SAR1b; SCAMPI Secretory carrier-associated membrane protein 1; SCAMP2 Secretory carrier-associated membrane protein 2; SCAMP3 Secretory carrier-associated membrane protein 3; SCP2 Non-specific lipid-transfer protein; SDHA Succinate dehydrogenase; SDHB Succinate dehydrogenase; SDHC Succinate dehydrogenase cytochrome b560 subunit, mitochondrial; SDHD Succinate dehydrogenase; SEC13 Protein SEC13 homolog; SEC22B Vesicle-trafficking protein SEC22b; SEC23A Protein transport protein Sec23A; SEC23B Protein transport protein Sec23B; SEC61A1 Protein transport protein Sec61 subunit alpha isoform; SEC61A2 Protein transport protein Sec61 subunit alpha isoform; SEC63 Translocation protein SEC63 homolog; SFXN1 Sideroflexin-1; SFXN4 Sideroflexin-4; SIGMAR1 Sigma non-opioid intracellular receptor 1; SIGMAR1 Sigma non-opioid intracellular receptor 1; SLC16A1 Monocarboxylate transporter 1; SLC1A5 Neutral amino acid transporter B(0); SLC25A1 Tricarboxylate transport protein, mitochondrial; SLC25A10 Mitochondrial dicarboxylate carrier; SLC25A11 Mitochondrial 2-oxoglutarate/malate carrier protein; SLC25A12 Calcium-binding mitochondrial carrier protein Aral; SLC25A13 Calcium-binding mitochondrial carrier protein Aral; SLC25A15 Mitochondrial ornithine transporter 1; SLC25A16 Graves disease carrier protein homolog; SLC25A17 Peroxisomal membrane protein PMP34; SLC25A19 Mitochondrial thiamine pyrophosphate carrier; SLC25A20 Mitochondrial carnitine/acylcarnitine carrier protein; SLC25A21 Mitochondrial 2-oxodicarboxylate carrier; SLC25A22 Mitochondrial glutamate carrier 1; SLC25A24 Calcium-binding mitochondrial carrier protein SCaM; SLC25A25 Calcium-binding mitochondrial carrier protein SCaM; SLC25A26 S-adenosylmethionine mitochondrial carrier protein; SLC25A3 Phosphate carrier protein, mitochondrial; SLC25A32 Mitochondrial folate transporter/carrier; SLC25A33 Solute carrier family 25 member 33; SLC25A4 ADP/ATP translocase 1; SLC25A44 Solute carrier family 25 member 44; SLC25A5 ADP/ATP translocase 2; SLC25A51 Solute carrier family 25 member 51; SLC25A6 ADP/ATP translocase 3; SLC29A3 Equilibrative nucleoside transporter 3; SLC2A3 Solute carrier family 2, facilitated glucose transporter; SLC30A6 Zinc transporter 6; SLC30A7 Zinc transporter 7; SLC33A1 Acetyl-coenzyme A transporter 1; SLC35B2 Adenosine 3-phospho 5-phosphosulfate transporter; SLC35E1 Solute carrier family 35 member E1; SLC38A2 Sodium-coupled neutral amino acid transporter 2; SLC39A7 Zinc transporter SLC39A7; SLC7A1 High affinity cationic amino acid transporter 1; SLC7A3 Cationic amino acid transporter 3; SNX1 Sorting nexin-1; SNX2 Sorting nexin-2; SNX27 Sorting nexin-27; SNX5 Sorting nexin-5; SNX6 Sorting nexin-6; SNX9 Sorting nexin-9; SPNS1 Protein spinster homolog 1; STX18 Syntaxin-18; Stx5 Syntaxin-5; SV2C Synaptic vesicle glycoprotein 2C; TIMM17A Mitochondrial import inner membrane translocase subunit; TIMM17B Mitochondrial import inner membrane translocase subunit; TIMM22 Mitochondrial import inner membrane translocase subunit; TIMM23 Mitochondrial import inner membrane translocase subunit; TIMM44 Mitochondrial import inner membrane translocase subunit; TIMM50 Mitochondrial import inner membrane translocase subunit; TMED1 Transmembrane emp24 domain-containing protein 1; TMED10 Transmembrane emp24 domain-containing protein 10; TMED2 Transmembrane emp24 domain-containing protein 2; TMED3 Transmembrane emp24 domain-containing protein 3; TMED4 Transmembrane emp24 domain-containing protein 4; TMED5 Transmembrane emp24 domain-containing protein 5; TMED7 Transmembrane emp24 domain-containing protein 7; TMED9 Transmembrane emp24 domain-containing protein 9; TMEM38B Trimeric intracellular cation channel type B; TMEM48 Nucleoporin NDC1; Tmem66 Store-operated calcium entry-associated regulatory; TMX1 Thioredoxin-related transmembrane protein 1; TMX4 Thioredoxin-related transmembrane protein 4; TNPO1 Transportin-1; TNPO2 Transportin-2; TNPO3 Transportin-3; TOMM20 Mitochondrial import receptor subunit TOM20 homolog; TOMM22 Mitochondrial import receptor subunit TOM22 homolog; TOMM40 Mitochondrial import receptor subunit TOM40 homolog; TPR Nucleoprotein TPR; TRAM1 Translocating chain-associated membrane protein 1; TSPO Translocator protein; TTYH3 Protein tweety homolog 3; TUSC3 Tumor suppressor candidate 3; UNC119 Protein unc-119 homolog A; UNC119B Protein unc-119 homolog B; UQCR10 Cytochrome b-cl complex subunit 9; UQCRC1 Cytochrome b-cl complex subunit 1, mitochondrial; UQCRC2 Cytochrome b-cl complex subunit 2, mitochondrial; UQCRFS1 Cytochrome b-cl complex subunit Rieske, mitochondrial; UQCRQ Cytochrome b-cl complex subunit 8; VCP Transitional endoplasmic reticulum ATPase; VDAC1 Voltage-dependent anion-selective channel protein; VDAC2 Voltage-dependent anion-selective channel protein; VDAC3 Voltage-dependent anion-selective channel protein; VPS35 Vacuolar protein sorting-associated protein 35; XPO1 Exportin-1; XPO5 Exportin-5; XPOT Exportin-T; YIF1A Protein YIF1A; and YKT6 Synaptobrevin homolog YKT6.

In some embodiments, one or more lipid probes described herein interact or bind to one or more of the transporters described above and elsewhere herein.

A receptor is a protein molecule that is embedded within the plasma membrane of a cell. In some instances, the receptor upon receiving a signal, such as a chemical signal, respond by producing a change in the cell. In some embodiments, a receptor is further divided into type 1 receptors or ionotropic receptors which are targeted by fast neurotransmitters such as acetylcholine (nicotinic) and GABA; type 2 receptors or G protein-coupled receptors (GPCRs); type 3 receptors or kinase linked and related receptors such as tyrosine kinase receptor and enzyme-linked receptor; and type 4 receptors or nuclear receptors. Exemplary receptors include, but are not limited to, ITGB1 Integrin beta-1, KDELR1 ER lumen protein retaining receptor 1, KDELR2 ER lumen protein retaining receptor 2, KDELR3 ER lumen protein retaining receptor 3, LBR Lamin-B receptor, LMBR1 Limb region 1 protein homolog, NGFR Tumor necrosis factor receptor superfamily member, NR3C1 Glucocorticoid receptor, PGRMC1 Membrane-associated progesterone receptor component, PGRMC2 Membrane-associated progesterone receptor component, PHB2 Prohibitin-2, SCARB1 Scavenger receptor class B member 1, SCARB2 Lysosome membrane protein 2, SIGMAR1 Sigma non-opioid intracellular receptor 1, SLC1A5 Neutral amino acid transporter B(0), SRPRB Signal recognition particle receptor subunit beta, and TFRC Transferrin receptor protein 1.

In some embodiments, one or more lipid probes described herein interact or bind to one or more of the receptors described above and elsewhere herein.

An adaptor is an accessory protein molecule which mediates specific protein-protein interactions that drive the formation of protein complexes. In some instances, an adaptor protein lacks intrinsic enzymatic activity. Exemplary adaptor proteins include, but are not limited to, adaptor protein complex 1, adaptor protein complex 2, Casitas B-lineage lymphoma (Cbl) adaptor protein, Lck-interacting molecule (LIME), non-catalytic region of tyrosine kinase (Nck) adaptor protein, BAIAP2 Brain-specific angiogenesis inhibitor 1-associated; MPP6 MAGUK p55 subfamily member 6; SPTAN1 spectrin alpha chain, non-erythrocytic 1; YWHAB 14-3-3 protein beta/alpha; YWHAE 14-3-3 protein epsilon; YWHAG 14-3-3 protein gamma; YWHAH 14-3-3 protein eta; YWHAQ 14-3-3 protein theta; and YWHAZ 14-3-3 protein zeta/delta.

In some embodiments, one or more lipid probes described herein interact or bind to one or more of the adaptors described above and elsewhere herein.

A channel protein is a pore-forming membrane protein which allows the transport of molecules such as ions and small molecules across a cell membrane. In some instances, a channel protein is a ligand-gated, voltage-gated, or mechanically-gated channel protein. In some instances, a channel protein allows for passive diffusion of molecules such as ions and small molecules. Exemplary channel proteins include, but are not limited to, VDAC1 Voltage-dependent anion-selective channel protein, VDAC2 Voltage-dependent anion-selective channel protein, and VDAC3 Voltage-dependent anion-selective channel protein.

In some embodiments, one or more lipid probes described herein interact or bind to one or more of the channel proteins described above and elsewhere herein.

A chaperone is a protein molecule that assists in folding or unfolding of protein molecules and/or assembly or disassembly of macromolecular structures. Exemplary chaperones include, but are not limited to, ABCE1 ATP-binding cassette sub-family E member 1; AHSA1 Activator of 90 kDa heat shock protein ATPase homolog 1; ANP32B acidic leucine-rich nuclear phosphoprotein 32 family; BAG6 Large proline-rich protein BAG6; BCS1L mitochondrial chaperone BCS1; CALR calreticulin; CANX calnexin; CCT2 T-complex protein 1 subunit beta; CCT3 T-complex protein 1 subunit gamma; CCT4 T-complex protein 1 subunit delta; CCT5 T-complex protein 1 subunit epsilon; CCT6A T-complex protein 1 subunit zeta; CCT7 T-complex protein 1 subunit eta; CD74 H-2 class II histocompatibility antigen gamma chai; CDC37 Hsp90 co-chaperone Cdc37; CLGN calmegin; DNAJA1 DnaJ homolog subfamily A member 1; DNAJC1 DnaJ homolog subfamily C member 1; DNAJC11 DnaJ homolog subfamily C member 11; HSP90AA1 Heat shock protein HSP 90-alpha; HSP90AB1 Heat shock protein HSP 90-beta; HSP90B1 Endoplasmin; HSPA1B Heat shock 70 kDa protein 1A/1B; HSPA2 Heat shock-related 70 kDa protein 2; HSPA8 Heat shock cognate 71 kDa protein; HSPA9 Stress-70 protein, mitochondrial; HSPD1 60 kDa heat shock protein, mitochondrial; HYOU1 Hypoxia up-regulated protein 1; NDUFAF2 Mimitin, mitochondrial; SCO1 Protein SCO1 homolog, mitochondrial; SCO2 Protein SCO2 homolog, mitochondrial; ST13 Hsc70-interacting protein; TBCD Tubulin-specific chaperone D; TCP1 T-complex protein 1 subunit alpha; TIMMDC1 Translocase of inner mitochondrial membrane domain; and TMEM126B Transmembrane protein 126B.

In some embodiments, one or more lipid probes described herein interact or bind to one or more of the chaperones described above and elsewhere herein.

In some embodiments, the lipid binding protein is an enzyme, a transporter, a receptor, an adaptor, a channel protein, or a chaperone described supra. In other embodiments, the lipid binding protein is a protein disclosed in Tables 3-6 (which are incorporated in files 48054-701-101Table3.txt, 48054-701-101Table4.txt, 48054-701-101Table5.txt, and 48054-701-101Table6.txt). Sometimes, the lipid binding protein is an enzyme, a transporter, a receptor, an adaptor, a channel protein, or a chaperone described in Tables 3-6.

In some embodiments, one or more lipid probes interact or bind to one or more of the lipid binding proteins disclosed in Tables 3-6. In some instances, one or more lipid probes interact or bind to one or more of the enzyme, transporter, receptor, adaptor, channel protein, or chaperone described in Tables 3-6.

Samples, Analytical Techniques, and Instrumentation

In certain embodiments, one or more of the methods disclosed herein comprise a sample. In some embodiments, the sample is a cell sample or a tissue sample. In some instances, the sample is a cell sample. In some embodiments, the sample for use with the methods described herein is obtained from cells of an animal. In some instances, the animal cell includes a cell from a marine invertebrate, fish, insects, amphibian, reptile, or mammal. In some instances, the mammalian cell is a primate, ape, equine, bovine, porcine, canine, feline, or rodent. In some instances, the mammal is a primate, ape, dog, cat, rabbit, ferret, or the like. In some cases, the rodent is a mouse, rat, hamster, gerbil, hamster, chinchilla, or guinea pig. In some embodiments, the bird cell is from a canary, parakeet or parrots. In some embodiments, the reptile cell is from a turtles, lizard or snake. In some cases, the fish cell is from a tropical fish. In some cases, the fish cell is from a zebrafish (e.g. *Danio rerio*). In some cases, the worm cell is from a nematode (e.g. *C. elegans*). In some cases, the amphibian cell is from a frog. In some embodiments, the arthropod cell is from a tarantula or hermit crab.

In some embodiments, the sample for use with the methods described herein is obtained from a mammalian cell. In some instances, the mammalian cell is an epithelial cell, connective tissue cell, hormone secreting cell, a nerve cell, a skeletal muscle cell, a blood cell, or an immune system cell.

Exemplary mammalian cells include, but are not limited to, 293A cell line, 293FT cell line, 293F cells, 293H cells, HEK 293 cells, CHO DG44 cells, CHO—S cells, CHO-K1 cells, Expi293F™ cells, Flp-In™ T-REx™ 293 cell line, Flp-In™-293 cell line, Flp-In™-3T3 cell line, Flp-In™-BHK cell line, Flp-In™—CHO cell line, Flp-In™-CV-1 cell line, Flp-In™-Jurkat cell line, FreeStyle™ 293-F cells, FreeStyle™ CHO—S cells, GripTite™ 293 MSR cell line, GS-CHO cell line, HepaRG™ cells, T-REx™ Jurkat cell line, Per.C6 cells, T-REx™-293 cell line, T-REx™—CHO cell line, T-REx™-HeLa cell line, NC-HIMT cell line, and PC12 cell line.

In some instances, the sample for use with the methods described herein is obtained from cells of a tumor cell line. In some instances, the sample is obtained from cells of a solid tumor cell line. In some instances, the solid tumor cell line is a sarcoma cell line. In some instances, the solid tumor cell line is a carcinoma cell line. In some embodiments, the sarcoma cell line is obtained from a cell line of alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epitheioid cell differentiation, osteosarcoma, parosteal osteosarcoma, neoplasm with perivascular epitheioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, or telangiectatic osteosarcoma.

In some embodiments, the carcinoma cell line is obtained from a cell line of adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, or vulvar cancer.

In some instances, the sample is obtained from cells of a hematologic malignant cell line. In some instances, the hematologic malignant cell line is a T-cell cell line. In some instances, B-cell cell line. In some instances, the hematologic malignant cell line is obtained from a T-cell cell line of: peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, or treatment-related T-cell lymphomas.

In some instances, the hematologic malignant cell line is obtained from a B-cell cell line of: acute lymphoblastic leukemia (ALL), acute myelogenous leukemia (AML), chronic myelogenous leukemia (CML), acute monocytic leukemia (AMoL), chronic lymphocytic leukemia (CLL), high-risk chronic lymphocytic leukemia (CLL), small lymphocytic lymphoma (SLL), high-risk small lymphocytic lymphoma (SLL), follicular lymphoma (FL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some embodiments, the sample for use with the methods described herein is obtained from a tumor cell line. Exemplary tumor cell line includes, but is not limited to, 600MPE, AU565, BT-20, BT-474, BT-483, BT-549, Evsa-T, Hs578T, MCF-7, MDA-MB-231, SkBr3, T-47D, HeLa, DU145, PC3, LNCaP, A549, H1299, NCI-H460, A2780, SKOV-3/Luc, Neuro2a, RKO, RKO-AS45-1, HT-29, SW1417, SW948, DLD-1, SW480, Capan-1, MC/9, B72.3, B25.2, B6.2, B38.1, DMS 153, SU.86.86, SNU-182, SNU-423, SNU-449, SNU-475, SNU-387, Hs 817.T, LMH, LMH/2A, SNU-398, PLHC-1, HepG2/SF, OCI-Lyl, OCI-Ly2, OCI-Ly3, OCI-Ly4, OCI-Ly6, OCI-Ly7, OCI-Ly10, OCI-Ly18, OCI-Ly19, U2932, DB, HBL-1, RIVA, SUDHL2, TMD8, MEC1, MEC2, 8E5, CCRF-CEM, MOLT-3, TALL-104, AML-193, THP-1, BDCM, HL-60, Jurkat, RPMI 8226, MOLT-4, RS4, K-562, KASUMI-1, Daudi, GA-10, Raji, JeKo-1, NK-92, and Mino.

In some embodiments, the sample for use in the methods is from any tissue or fluid from an individual. Samples include, but are not limited to, tissue (e.g. connective tissue, muscle tissue, nervous tissue, or epithelial tissue), whole blood, dissociated bone marrow, bone marrow aspirate, pleural fluid, peritoneal fluid, central spinal fluid, abdominal fluid, pancreatic fluid, cerebrospinal fluid, brain fluid, ascites, pericardial fluid, urine, saliva, bronchial lavage, sweat, tears, ear flow, sputum, hydrocele fluid, semen, vaginal flow, milk, amniotic fluid, and secretions of respiratory, intestinal or genitourinary tract. In some embodiments, the sample is a tissue sample, such as a sample obtained from a biopsy or a tumor tissue sample. In some embodiments, the sample is a blood serum sample. In some embodiments, the sample is a blood cell sample containing one or more peripheral blood mononuclear cells (PBMCs). In some embodiments, the sample contains one or more circulating tumor cells (CTCs). In some embodiments, the sample contains one or more disseminated tumor cells (DTC, e.g., in a bone marrow aspirate sample).

In some embodiments, the samples are obtained from the individual by any suitable means of obtaining the sample using well-known and routine clinical methods. Procedures for obtaining tissue samples from an individual are well known. For example, procedures for drawing and processing tissue sample such as from a needle aspiration biopsy is well-known and is employed to obtain a sample for use in the methods provided. Typically, for collection of such a tissue sample, a thin hollow needle is inserted into a mass such as a tumor mass for sampling of cells that, after being stained, will be examined under a microscope.

Sample Preparation and Analysis

In some embodiments, the sample is a sample solution. In some instances, the sample solution comprises a solution such as a buffer (e.g. phosphate buffered saline) or a media. In some instances, the sample solution is a cell solution.

In some embodiments, the sample (e.g. cells or a cell solution) is incubated with a lipid probe for analysis of protein lipid probe interactions. In some instances, the sample is further compared with a control. In some instances, a difference is observed in a set of lipid probe protein interactions between the sample and the control. In some instances, the difference correlates to a set of lipid binding proteins that interacts with a lipid probe.

In some instances, the sample (e.g. cells or a cell solution) is incubated with a drug for analysis of protein lipid probe interactions and lipid binding protein-drug interactions. In some cases, the sample is further compared with a control. In some instances, a difference is observed in a set of lipid probe protein interactions between the sample and the control. In some instances, the difference correlates to a set of lipid binding proteins that interacts with a drug. In some instances, one lipid binding protein is observed to interact with a drug. In some instances, multiple lipid binding proteins are observed to interact with a drug. In some aspects, a drug is a specific inhibitor of a lipid binding protein. In some instances, a drug is a pan-inhibitor of a lipid binding protein. In some instances, the drug is a competitor of a lipid probe for interaction with a lipid binding protein.

In some embodiments, the sample (e.g. cells or a cell solution) is further labeled for analysis of protein lipid probe interactions and lipid binding protein-drug interactions. In some instances, the sample (e.g. cells or a cell solution) is labeled with an enriched media. In some cases, the sample (e.g. cells or a cell solution) is labeled with isotope-labeled amino acids, such as $^{13}C$ or $^{15}N$-labeled amino acids. In some cases, the labeled sample is further compared with a non-labeled sample to detect differences in protein lipid probe interactions between the two samples. In some instances, this difference is a difference of a protein and its interaction with a lipid probe in the labeled sample versus the non-labeled sample. In some instances, the difference is an increase, decrease or a lack of protein lipid probe interaction in the two samples. In some instances, the isotope-labeled method is termed SILAC, stable isotope labeling using amino acids in cell culture.

In some instances, the sample is divided into a first cell solution and a second cell solution. In some instances, the first cell solution is contacted with a first lipid probe and a second cell solution is contacted with a second lipid probe. In some embodiments, the first lipid probe and the second lipid probe are the same. In some instances, the second cell solution comprises an enriched media and a drug. In some embodiments, enriched cell culture media is a stable isotope labeled media. In some instances, the enriched cell culture media contains $^{13}C$ labeled amino acids, $^{15}N$ labeled amino acids, or a combination thereof. In some embodiments, the first cell solution comprises unlabeled media, such as a fetal bovine serum based or serum-free media.

In some instances, upon incubation with a lipid probe and/or a drug, the first cell solution and/or second cell solution are then treated by visible light or ultraviolet light to cross-link the lipid probe with its binding partner from the cell solutions. In some instances, both cell solutions are treated by a photoreactive means (e.g. ultraviolet light). In some instances, only one of the cell solutions is treated by a photoreactive means.

In some instances, when a drug is added to the second cell solution for determining a lipid binding protein as a drug binding target, both cell solutions are treated by a photoreactive means (e.g. ultraviolet light). In some cases, a drug competes with a lipid probe for interaction with a lipid binding protein. In some instances, lipid probe and protein interaction from both the first cell solution and second cell solution are analyzed and the difference (e.g. the lack or decreased lipid probe and protein interaction due to a drug competition effect in the second cell solution) in lipid probe and protein interaction between the two cell solutions allow for identification of the lipid binding proteins as drug targets.

In some instances, a control (e.g. dimethyl sulfoxide (DMSO)) is added to the first cell solution or the second cell solution.

In some embodiments, only the first cell solution is treated by a photoreactive means (e.g. ultraviolet light). In some instances, both cell solutions are then further processed to identify proteins as lipid binding proteins. In some instances, the difference between the two cell solutions, e.g. the lack or decreased lipid probe and protein interaction due to an absence of photolysis in the second cell population, allows for identification of proteins as lipid binding proteins.

In some instances, after treatment by a photoreactive means, the cell solutions are then treated by conventional means to harvest the lipid probe-protein complexes. In some instances, the lipid probe-protein complexes are harvested involving centrifugation; lysis such as by vortex, homogenization, or freeze-thaw step; filtration step; and enrichment steps such as concentration, chemical extraction, or affinity based extraction. In some instances, the cell lysate generated from the cell solutions is further separated into a solution fraction and a membrane fraction and lipid probe-protein complexes are harvested from the two fractions.

In some embodiments, the lipid probe-protein complex is further conjugated to a chromophore, such as a fluorophore. In some instances, the lipid probe-protein complex is separated and visualized utilizing an electrophoresis system, such as through a gel electrophoresis, or a capillary electrophoresis. Exemplary gel electrophoresis includes agarose based gels, polyacrylamide based gels, or starch based gels. In some instances, the lipid probe-protein is subjected to a native electrophoresis condition. In some instances, the lipid probe-protein is subjected to a denaturing electrophoresis condition.

In some instances, the lipid probe-protein is further fragmentized to generate protein fragments. In some instances, fragmentation is generated through mechanical stress, pressure, or chemical means. In some instances, the protein from the lipid probe-protein complexes is fragmented by a chemical means. In some instances, the chemical means is a protease. Exemplary proteases include, but are not limited to, serine proteases such as chymotrypsin A, penicillin G acylase precursor, dipeptidase E, DmpA aminopeptidase, subtilisin, prolyl oligopeptidase, D-Ala-D-Ala peptidase C, signal peptidase I, cytomegalovirus assemblin, Lon-A peptidase, peptidase Clp, *Escherichia coli* phage K1F endosialidase, CIMCD self-cleaving protein, nucleoporin 145, lactoferrin, murein tetrapeptidase LD-carboxypeptidase, or rhomboid-1; threonine proteases such as ornithine acetyltransferase; cysteine proteases such as TEV protease, amidophosphoribosyltransferase precursor, gamma-glutamyl hydrolase (*Rattus norvegicus*), hedgehog protein, DmpA aminopeptidase, papain, bromelain, cathepsin K, calpain, caspase-1, separase, adenain, pyroglutamyl-peptidase I, sortase A, hepatitis C virus peptidase 2, sindbis virus-type nsP2 peptidase, dipeptidyl-peptidase VI, or DeSI-1 peptidase; aspartate proteases such as beta-secretase 1 (BACE1), beta-secretase 2 (BACE2), cathepsin D, cathepsin E, chymosin, napsin-A, nepenthesin, pepsin, plasmepsin, presenilin, or renin; glutamic acid proteases such as AfuGprA; and metalloproteases such as peptidase_M48.

In some instances, the fragmentation is a random fragmentation. In some instances, the fragmentation generates specific lengths of protein fragments, or the shearing occurs at particular sequence of amino acid regions.

In some instances, the protein fragments are further analyzed by a proteomic method such as by liquid chromatography (LC) (e.g. high performance liquid chromatography), liquid chromatography-mass spectrometry (LC-MS), gas chromatography-mass spectrometry (GC-MS), capillary electrophoresis-mass spectrometry (CE-MS), or nuclear magnetic resonance imaging (NMR).

In some embodiments, the LC method is any suitable LC methods well known in the art, for separation of a sample into its individual parts. This separation occurs based on the interaction of the sample with the mobile and stationary phases. Since there are many stationary/mobile phase combinations that are employed when separating a mixture, there are several different types of chromatography that are classified based on the physical states of those phases. In some embodiments, the LC is further classified as normal-phase chromatography, reverse-phase chromatography, size-exclusion chromatography, ion-exchange chromatography, affinity chromatography, displacement chromatography, partition chromatography, flash chromatography, chiral chromatography, and aqueous normal-phase chromatography.

In some embodiments, the LC method is a high performance liquid chromatography (HPLC) method. In some embodiments, the HPLC method is further categorized as normal-phase chromatography, reverse-phase chromatography, size-exclusion chromatography, ion-exchange chromatography, affinity chromatography, displacement chromatography, partition chromatography, chiral chromatography, and aqueous normal-phase chromatography.

In some embodiments, the HPLC method of the present disclosure is performed by any standard techniques well known in the art. Exemplary HPLC methods include hydrophilic interaction liquid chromatography (HILIC), electrostatic repulsion-hydrophilic interaction liquid chromatography (ERLIC) and reverse phase liquid chromatography (RPLC).

In some embodiments, the LC is coupled to a mass spectroscopy as a LC-MS method. In some embodiments, the LC-MS method includes ultra-performance liquid chromatography-electrospray ionization quadrupole time-of-flight mass spectrometry (UPLC-ESI-QTOF-MS), ultra-performance liquid chromatography-electrospray ionization tandem mass spectrometry (UPLC-ESI-MS/MS), reverse phase liquid chromatography-mass spectrometry (RPLC-MS), hydrophilic interaction liquid chromatography-mass spectrometry (HILIC-MS), hydrophilic interaction liquid chromatography-triple quadrupole tandem mass spectrometry (HILIC-QQQ), electrostatic repulsion-hydrophilic interaction liquid chromatography-mass spectrometry (ERLIC-MS), liquid chromatography time-of-flight mass spectrometry (LC-QTOF-MS), liquid chromatography-tandem mass spectrometry (LC-MS/MS), multidimensional liquid chromatography coupled with tandem mass spectrometry (LC/LC-MS/MS). In some instances, the LC-MS method is LC/LC-MS/MS. In some embodiments, the LC-MS methods of the present disclosure are performed by standard techniques well known in the art.

In some embodiments, the GC is coupled to a mass spectroscopy as a GC-MS method. In some embodiments, the GC-MS method includes two-dimensional gas chromatography time-of-flight mass spectrometry (GC-GC-TOFMS), gas chromatography time-of-flight mass spectrometry (GC-QTOF-MS) and gas chromatography-tandem mass spectrometry (GC-MS/MS).

In some embodiments, CE is coupled to a mass spectroscopy as a CE-MS method. In some embodiments, the CE-MS method includes capillary electrophoresis-negative electrospray ionization-mass spectrometry (CE-ESI-MS), capillary electrophoresis-negative electrospray ionization-quadrupole time of flight-mass spectrometry (CE-ESI- QTOF-MS) and capillary electrophoresis-quadrupole time of flight-mass spectrometry (CE-QTOF-MS).

In some embodiments, the nuclear magnetic resonance (NMR) method is any suitable method well known in the art for the detection of one or more lipid binding proteins or protein fragments disclosed herein. In some embodiments, the NMR method includes one dimensional (1D) NMR methods, two dimensional (2D) NMR methods, solid state NMR methods and NMR chromatography. Exemplary 1D NMR methods include $^{1}$Hydrogen, $^{13}$Carbon, $^{15}$Nitrogen, $^{17}$Oxygen, $^{19}$Fluorine, $^{31}$Phosphorus, $^{39}$Potassium, $^{23}$Sodium, $^{33}$Sulfur, $^{87}$Strontium, $^{27}$Aluminium, $^{43}$Calcium, $^{35}$Chlorine, $^{37}$Chlorine, $^{63}$Copper, $^{65}$Copper, $^{57}$Iron, $^{25}$Magnesium, $^{199}$Mercury or $^{67}$Zinc NMR method, distortionless enhancement by polarization transfer (DEPT) method, attached proton test (APT) method and 1D-incredible natural abundance double quantum transition experiment (IN-ADEQUATE) method. Exemplary 2D NMR methods include correlation spectroscopy (COSY), total correlation spectroscopy (TOCSY), 2D-INADEQUATE, 2D-adequate double quantum transfer experiment (ADEQUATE), nuclear overhauser effect spectroscopy (NOSEY), rotating-frame NOE spectroscopy (ROESY), heteronuclear multiple-quantum correlation spectroscopy (HMQC), heteronuclear single quantum coherence spectroscopy (HSQC), short range coupling and long range coupling methods. Exemplary solid state NMR method include solid state $^{13}$Carbon NMR, high resolution magic angle spinning (HR-MAS) and cross polarization magic angle spinning (CP-MAS) NMR methods. Exemplary NMR techniques include diffusion ordered spectroscopy (DOSY), DOSY-TOCSY and DOSY-HSQC.

In some embodiments, the protein fragments are analyzed by method as described in Weerapana et al., "Quantitative reactivity profiling predicts functional cysteines in proteomes," *Nature*, 468:790-795 (2010).

In some embodiments, a value is assigned to each of the protein from the lipid probe-protein complex. In some instances, the value is the area-under-the curve from a plot of signal intensity as a function of mass-to-charge ratio. In some embodiments, a first value is assigned to the protein obtained from the first cell solution and a second value is assigned to the same protein obtained from the second cell solution. In some instances, a ratio is calculated between the two values. In some instances, a ratio of greater than 2 indicates that the protein is a candidate for interacting with a drug or that the protein is a lipid binding protein. In some instances, the ratio is greater than 2.5, 3, 3.5, 4, 4.5, 5, 6, 7, 8, 9, 10, 11, 12, 13, 14, 15, 16, 17, 18, 19, or 20. In some cases, the ratio is at most 20.

In some instances, the ratio is calculated based on averaged values. In some instances, the averaged value is an average of at least two, three, or four values of the protein from each cell solution, or that the protein is observed at least two, three, or four times in each cell solution and a value is assigned to each observed time. In some instances, the ratio further has a standard deviation of less than 12, 10, or 8.

In some instances, a value is not an averaged value. In some instances, the ratio is calculated based on value of a protein observed only once in a cell population. In some instances, the ratio is assigned with a value of 20.

In some embodiments, in the context of identifying a lipid binding protein as a drug binding target, a first ratio is obtained from two cell solutions in which both cell solutions have been treated by photoreactive means and the second cell solution is incubated with a drug. In some instances, the first ratio is further compared to a second ratio in which both cell solutions have been treated by photoreactive means in the absence of a drug. In some instances, the first ratio is greater than 0.5, 1, 1.5, 2, 2.5, 3, 3.5, 4, 4.5, 5, 6, 7, 8, 9, 10, 11, 12, 13, 14, 15, 16, 17, 18, 19, or 20. In some instances, the second ratio is greater than 0.5, 1, 1.5, 2, 2.5, 3, 3.5, 4, 4.5, 5, 6, 7, 8, 9, 10, 11, 12, 13, 14, 15, 16, 17, 18, 19, or 20. In some instances, if the first ratio is greater than 2, 2.5, 3, 3.5, 4, 4.5, 5, 6, 7, 8, 9, 10, 11, 12, 13, 14, 15, 16, 17, 18, 19, or 20 and the second ratio is from about 0.5 to about 2, the two ratios indicate that a protein is a drug binding target.

In some embodiments, in the context of identifying a protein as a lipid binding protein, a first ratio is obtained from two cell solutions in which both cell solutions have been treated by photoreactive means. In some instances, the first ratio is further compared to a second ratio in which one of the cell solutions (e.g. the first cell solution) is treated by a photoreactive means. In some instances, the first ratio is greater than 0.5, 1, 1.5, 2, 2.5, 3, 3.5, 4, 4.5, 5, 6, 7, 8, 9, 10, 11, 12, 13, 14, 15, 16, 17, 18, 19, or 20. In some instances, the second ratio is greater than 0.5, 1, 1.5, 2, 2.5, 3, 3.5, 4, 4.5, 5, 6, 7, 8, 9, 10, 11, 12, 13, 14, 15, 16, 17, 18, 19, or 20. In some instances, if the first ratio is from about 0.5 to about 2, and the second ratio is greater than 2, 2.5, 3, 3.5, 4, 4.5, 5, 6, 7, 8, 9, 10, 11, 12, 13, 14, 15, 16, 17, 18, 19, or 20, the two ratios indicate that a protein is a lipid binding protein.

Method of Mapping Ligand Binding Site on a Lipid Binding Protein

In some instances, also disclosed herein is a method of mapping the ligand binding site on a lipid binding protein. In some embodiments, the method comprises (a) harvesting a set of lipid probe-protein complexes from a sample wherein the lipid probe comprises a lipid, a photoreactive group, and an affinity handle; (b) analyzing the set of lipid probe-protein complexes by a proteomic analysis means; and (c) based on step b), locating a ligand binding site on the lipid binding protein.

In some embodiments, the method further comprises treating the set of lipid probe-protein complexes with a protease to generate a set of protein fragments. The protease is a serine protease, a threonine protease, a cysteine protease, an aspartate protease, a glutamic acid protease, or a metalloprotease. In some instances, the protease is a serine protease. In some instances, the protease is trypsin. In some instances, lipid probe-protein complex is further attached to a labeling group such as a biotin moiety. In some instances, the labeling group such as a biotin moiety further comprises a linker. In some instances, the linker is a peptide. In some instances, the peptide linker is about 7, 8, 9, 10, 11, 12, 13, 14, 15, 16, 17, 18, 19, 20 or more amino acid residues in length. In some instances, the peptide linker contains a cleavage site. A non-limiting list of cleavage sites includes Tobacco Etch Virus (TEV), thrombin (Thr), enterokinase (EKT), activated Factor X (Xa), or human Rhinovirus 3C protease (3C/PreScission). In some instances, the peptide linker contains a TEV protease cleavage site. In some instances, the TEV protease cleavage site comprises the following sequence Gly-Gln-Phe-Tyr-Leu-Asn-Glu. In some instances, the biotin moiety is further coupled to a bead (e.g. a streptavidin-coupled bead).

In some instances, the protein from the lipid probe-protein complex attached to the bead (via a biotin moiety comprising a linker and attached to a streptavidin-coupled bead) is digested with trypsin, and the immobilized peptide or protein fragment is further separated and collected. In some instances, the collected peptide or protein fragment is then digested by a protease (e.g. TEV protease), and the treated protein fragment is then separated, and collected for analysis. In some instances, the analysis is a proteomic analysis as described above and elsewhere herein. In some instances, the sequence of the protein fragment is further determined. In some instances, the protein fragment correlates to a drug binding site on the lipid binding protein.

In some embodiments, the sequence of the protein fragment correlates to a sequence as illustrated in Table 6. In some instances, the sequence as shown in Table 6 correlates to a site on the full length protein as a drug binding site. In some instances, the sequence as shown in Table 6 correlates to a drug binding site. In some instances, polypeptides comprising one or more of the sequences as shown in Table 6 serve as probes for drug screening.

In some embodiments, the lipid probe comprises a lipid, a photoreactive group, and an affinity handle. In some embodiments, the lipid is a bioactive lipid. In some instances, the lipid comprises fatty acyls, glycerolipids, glycerophospholipids, sphingolipids, sterol lipids, prenol lipids, saccharolipids, or polyketides. In some cases, the lipid is a member of the fatty acyls group. In some cases, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some instances, the lipid is a sterol lipid.

In some embodiments, the photoreactive group comprises azides, benzophenone, diazo compounds, diazirines, diazonium salts, or diaryl ketones. In some embodiments, the photoreactive group is a diazirine or its derivatives thereof.

In some embodiments, the affinity handle is a bioorthogonal affinity handle. In some instances, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group. In some embodiments, the affinity handle comprises an alkyne group or an azide group.

In some embodiments, the lipid probe comprises: a lipid selected from arachidonoyl, arachidoyl, oleoyl, palmitoyl, or stearoyl fatty acyls; a photoreactive linker; and an affinity handle.

In some embodiments, the lipid probe is a lipid probe of Formula (I):

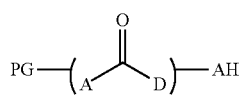

Formula (I)

wherein:
A is $C_{16}$-$C_{20}$alkyl or $C_{16}$-$C_{20}$alkenyl;
D is —OH, —NH$_2$, —NHR$^7$, or —OR$^8$;
R$^7$ is $C_1$-$C_4$alkyl, ($C_1$-$C_5$alkyl)OH, or ($C_1$-$C_5$)SO$_3$M;
R$^8$ is (CH$_2$OH)n;
M is monovalent or divalent cation;
n is 1, 2, or 3;
PG is a photoreactive group; and
AH is an affinity handle;
  wherein PG is attached to A or D and AH is attached to A or D.

In some embodiments, the lipid probe has one of the following structures as exemplified in FIG. 1 and in Table 1. In some embodiments, the lipid binding protein is a soluble protein or a membrane protein. In some instances, the lipid binding protein is an enzyme, a transporter, a receptor, an adaptor, a channel protein, or a chaperone. In some instances, the lipid binding protein is a protein encoded by a gene of Table 3, a protein encoded by a gene of Table 4, or a protein encoded by a gene of Table 5.

In some instances, the sample comprises a cell sample or a tissue sample. In some instances, the sample is a cell sample. In some instances, the cell sample comprises a first cell solution and a second cell solution. In some cases, the second cell solution comprises an enriched media and a drug. In some cases, the enriched media is a stable isotope labeled media. In some instances, the first cell solution and the second cell solution are further treating by a photoreactive means to generate a first group of lipid probe-protein complexes and a second group of lipid probe-protein complexes, wherein the first group and the second group of lipid probe-protein complexes comprise the set of lipid probe-protein complexes.

Compositions, Process of Producing a Lipid Probe-Protein Composition, and Lipid Probes In some embodiments, disclosed herein include compositions of the lipid probe-protein complex, and compositions that comprises a lipid probe-protein complex and a sample.

In some embodiments, disclosed herein is a lipid probe-protein composition which comprises a lipid probe and a lipid binding protein. In some embodiments, also described herein is a lipid probe-protein composition produced by a process which comprises contacting a sample with a lipid probe, and treating the sample which comprises the lipid probe by a photoreactive means, wherein the treating time is from about 5 minutes to about 1 hour. In some instances, the treating time is from about 5, 6, 7, 8, 9, 10, 11, 12, 15, 20, 30, 40, 50, or 60 minutes. In some instances, the treating time is about 10 minutes. In some instances, the treating temperature is at about 0° C., 1° C., 2° C., 3° C., 4° C., 5° C., 10° C., 15° C., 20° C., 25° C., 30° C., 37° C., or 40° C. In some instances, the treating temperature is at about 4° C.

In some instances, the lipid binding protein is an enzyme, a transporter, a receptor, an adaptor, a channel protein, or a chaperone. In some embodiments, the lipid binding protein is a protein encoded by a gene of Table 3, a protein encoded by a gene of Table 4, a protein encoded by a gene of Table 5, or a protein encoded by a gene of Table 6. In some instances, the lipid binding protein is nucleobindin-1 (NUCB1). In some cases, the lipid binding protein is a protein fragment. In some cases, the protein fragment is a protein fragment of Table 6.

In some embodiments, the lipid is a bioactive lipid. In some instances, the lipid comprises fatty acyls, glycerolipids, glycerophospholipids, sphingolipids, sterol lipids, prenol lipids, saccharolipids, or polyketides. In some instances, the lipid is a member of the fatty acyls group. In some instances, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some cases, the lipid is a fatty acid. In some cases, the lipid is a sterol lipid. In some instances, the sterol lipid comprises sterols, steroids, secosteroids, or bile acids. In some instances, the sterol comprises cholesterol, ergosterol, C24-propyl sterols, or stanol.

In some embodiments, the photoreactive group comprises azides, benzophenone, diazo compounds, diazirines, diazonium salts, or diaryl ketones. In some embodiments, the affinity handle is a bioorthogonal affinity handle. In some instances, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group.

In some instances, the lipid probe comprises: a lipid selected from arachidonoyl, arachidoyl, oleoyl, palmitoyl, or stearoyl fatty acyls; a photoreactive linker; and an affinity handle.

In some embodiments, the lipid probe is a lipid probe of Formula (I):

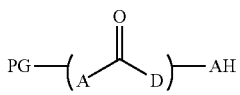

Formula (I)

wherein:
A is $C_{16}$-$C_{20}$alkyl or $C_{16}$-$C_{20}$alkenyl;
D is —OH, —NH$_2$, —NHR$^7$, or —OR$^8$;
R$^7$ is $C_1$-$C_4$alkyl, ($C_1$-$C_5$alkyl)OH, or ($C_1$-$C_5$)SO$_3$M;
R$^8$ is (CH$_2$OH)n;
M is monovalent or divalent cation;
n is 1, 2, or 3;
PG is a photoreactive group; and
AH is an affinity handle;
    wherein PG is attached to A or D and AH is attached to A or D.

In some instances, the lipid probe has one of the following structures as exemplified in FIG. 1 and in Table 1.

In some embodiments, disclosed herein is a composition which comprises an isolated sample wherein the isolated sample is an isolated cell or a tissue sample; and a lipid probe to be assayed for its ability to interact with a lipid binding protein expressed in the isolated sample. In some instances, the composition further comprises a drug as a test compound. In some cases, the lipid probe is assayed for its ability to interact with a lipid binding protein expressed in the sample in the presence of the drug.

In some embodiments, also described herein is an isolated treated cell which comprises a lipid probe attached to a lipid binding protein. In some embodiments, the lipid probe is attached to the lipid binding protein through a covalent bond. In some instances, the isolated treated cell further comprises a set of lipid probes wherein each of the lipid probes is attached to a lipid binding protein. In some cases, each lipid probe within the set is different. In other cases, each lipid probe within the set is the same.

In some embodiments, further described herein is an isolated treated population of cells which comprises a set of lipid probes attached to lipid binding proteins. In some instances, each of the lipid probes is attached to a lipid binding protein through a covalent bond. In some cases, each lipid probe within the set is different. In other cases, each lipid probe within the set is the same.

In some embodiments, disclosed herein is a lipid probe which comprises a lipid, a photoreactive group, and an affinity handle wherein the lipid probe is constructed for detecting a drug-lipid binding protein interaction. In some instances, the lipid is a bioactive lipid. In some cases, the lipid comprises fatty acyls, glycerolipids, glycerophospholipids, sphingolipids, sterol lipids, prenol lipids, saccharolipids, or polyketides. In some instances, the lipid is a member of the fatty acyls group. In some cases, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In other instances, the lipid is a sterol lipid. In some embodiments, the photoreactive group comprises azides, benzophenone, diazo compounds, diazirines, diazonium salts, or diaryl ketones. In some cases, the photoreactive group is diazirine, or its derivatives thereof. In some instances, the affinity handle is a bioorthogonal affinity handle. In some cases, the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group.

In some embodiments, the lipid probe comprises: a lipid selected from arachidonoyl, arachidoyl, oleoyl, palmitoyl, or stearoyl fatty acyls; a photoreactive linker; and an affinity handle.

In some embodiments, the lipid probe is a lipid probe of Formula (I):

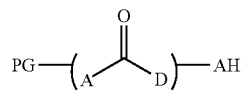

Formula (I)

wherein:
A is $C_{16}$-$C_{20}$alkyl or $C_{16}$-$C_{20}$alkenyl;
D is —OH, —NH$_2$, —NHR$^7$, or —OR$^8$;
R$^7$ is $C_1$-$C_4$alkyl, ($C_1$-$C_5$alkyl)OH, or ($C_1$-$C_5$)SO$_3$M;
R$^8$ is (CH$_2$OH)n;
M is monovalent or divalent cation;
n is 1, 2, or 3;
PG is a photoreactive group; and
AH is an affinity handle;
    wherein PG is attached to A or D and AH is attached to A or D.

In some instances, PG is attached to A. In some cases, AH is attached to A. In some cases, the lipid probe has one of the following structures as exemplified in FIG. 1 and Table 1. In some cases, the probe is a lipid binding protein ligand. In some instances, the probe is a competitive ligand for interaction with a lipid binding protein in the presence of a drug. In some cases, the lipid binding protein is an enzyme, a transporter, a receptor, an adaptor, a channel protein, or a chaperone. In some cases, the lipid binding protein is a protein encoded by a gene of Table 3, a protein encoded by a gene of Table 4, or a protein encoded by a gene of Table 5. In some cases, the lipid binding protein is nucleobindin-1 (NUCB1).

Lipid Binding Protein Fragments as Ligand Interaction Sites

In some embodiments, described herein includes an isolated and purified polypeptide that is derived from a lipid binding protein and serves as a ligand interaction site. In some instances, the isolated and purified polypeptide comprises at least 90% sequence identity to at least seven contiguous amino acids of an amino acid sequence selected from Table 6, wherein the isolated and purified polypeptide is at most 50 amino acids in length. In some instances, the isolated and purified polypeptide comprises at least 95% sequence identity to at least seven contiguous amino acids of an amino acid sequence selected from Table 6, wherein the isolated and purified polypeptide is at most 50 amino acids in length. In some instances, the isolated and purified polypeptide comprises 100% sequence identity to at least seven contiguous amino acids of an amino acid sequence selected from Table 6, wherein the isolated and purified polypeptide is at most 50 amino acids in length. In some instances, the isolated and purified polypeptide consists of 100% sequence identity to the full length of an amino acid sequence selected from Table 6, wherein the isolated and purified polypeptide is at most 50 amino acids in length.

In some instances after the generation of a polypeptide, the polypeptide is subjected to one or more rounds of purification steps to remove impurities. In some instances, the purification step is a chromatographic step utilizing separation methods such as affinity-based, size-exclusion based, ion-exchange based, or the like. In some cases, the polypeptide is at most 30%, 40%, 50%, 60%, 70%, 80%, 90%, 95%, 99%, 99.9%, or 100% pure or without the presence of impurities. In some cases, the polypeptide is at least 30%, 40%, 50%, 60%, 70%, 80%, 90%, 95%, 99%, 99.9%, or 100% pure or without the presence of impurities.

In some embodiments, described herein includes nucleic acid encoding a polypeptide that is derived from a lipid binding protein and serves as a ligand interaction site. In some embodiments, described herein includes nucleic acid encoding a polypeptide comprising at least 90% sequence identity to at least seven contiguous amino acids of an amino acid sequence selected from Table 6. In some cases, the nucleic acid encoding a polypeptide comprising at least 95% sequence identity to at least seven contiguous amino acids of an amino acid sequence selected from Table 6. In some cases, the nucleic acid encoding a polypeptide comprising 100% sequence identity to at least seven contiguous amino acids of an amino acid sequence selected from Table 6. In some cases, the nucleic acid encoding a polypeptide consisting 100% sequence identity to the full length of an amino acid sequence selected from Table 6.

In some instances, the nucleic acid is subjected to one or more rounds of purification steps to remove impurities. In some instances, the purification step is a chromatographic step utilizing separation methods such as affinity-based, size-exclusion based, ion-exchange based, or the like. In some cases, the nucleic acid is at most 30%, 40%, 50%, 60%, 70%, 80%, 90%, 95%, 99%, 99.9%, or 100% pure or without the presence of impurities. In some cases, the nucleic acid is at least 30%, 40%, 50%, 60%, 70%, 80%, 90%, 95%, 99%, 99.9%, or 100% pure or without the presence of impurities.

As used herein, a polypeptide includes natural amino acids, unnatural amino acids, or a combination thereof. In some instances, an amino acid residue refers to a molecule containing both an amino group and a carboxyl group. Suitable amino acids include, without limitation, both the D- and L-isomers of the naturally-occurring amino acids, as well as non-naturally occurring amino acids prepared by organic synthesis or other metabolic routes. The term amino acid, as used herein, includes, without limitation, α-amino acids, natural amino acids, non-natural amino acids, and amino acid analogs.

The term "α-amino acid" refers to a molecule containing both an amino group and a carboxyl group bound to a carbon which is designated the α-carbon.

The term "β-amino acid" refers to a molecule containing both an amino group and a carboxyl group in a β configuration.

"Naturally occurring amino acid" refers to any one of the twenty amino acids commonly found in peptides synthesized in nature, and known by the one letter abbreviations A, R, N, C, D, Q, E, G, H, I, L, K, M, F, P, S, T, W, Y and V.

The following table shows a summary of the properties of natural amino acids:

| Amino Acid | 3-Letter Code | 1-Letter Code | Side-chain Polarity | Side-chain charge (pH 7.4) | Hydropathy Index |
|---|---|---|---|---|---|
| Alanine | Ala | A | nonpolar | neutral | 1.8 |
| Arginine | Arg | R | polar | positive | −4.5 |
| Asparagine | Asn | N | polar | neutral | −3.5 |
| Aspartic acid | Asp | D | polar | negative | −3.5 |
| Cysteine | Cys | C | polar | neutral | 2.5 |
| Glutamic acid | Glu | E | polar | negative | −3.5 |
| Glutamine | Gln | Q | polar | neutral | −3.5 |
| Glycine | Gly | G | nonpolar | neutral | −0.4 |
| Histidine | His | H | polar | positive (10%) neutral (90%) | −3.2 |
| Isoleucine | Ile | I | nonpolar | neutral | 4.5 |
| Leucine | Leu | L | nonpolar | neutral | 3.8 |
| Lysine | Lys | K | polar | positive | −3.9 |
| Methionine | Met | M | nonpolar | neutral | 1.9 |
| Phenylalanine | Phe | F | nonpolar | neutral | 2.8 |
| Proline | Pro | P | nonpolar | neutral | −1.6 |
| Serine | Ser | S | polar | neutral | −0.8 |
| Threonine | Thr | T | polar | neutral | −0.7 |
| Tryptophan | Trp | W | nonpolar | neutral | −0.9 |
| Tyrosine | Tyr | Y | polar | neutral | −1.3 |
| Valine | Val | V | nonpolar | neutral | 4.2 |

"Hydrophobic amino acids" include small hydrophobic amino acids and large hydrophobic amino acids. "Small hydrophobic amino acid" are glycine, alanine, proline, and analogs thereof. "Large hydrophobic amino acids" are valine, leucine, isoleucine, phenylalanine, methionine, tryptophan, and analogs thereof. "Polar amino acids" are serine, threonine, asparagine, glutamine, cysteine, tyrosine, and analogs thereof "Charged amino acids" are lysine, arginine, histidine, aspartate, glutamate, and analogs thereof.

The term "amino acid analog" refers to a molecule which is structurally similar to an amino acid and which is substituted for an amino acid in the formation of a peptidomimetic macrocycle. Amino acid analogs include, without limitation, (3-amino acids and amino acids where the amino or carboxy group is substituted by a similarly reactive group (e.g., substitution of the primary amine with a secondary or tertiary amine, or substitution of the carboxy group with an ester).

The term "non-natural amino acid" refers to an amino acid which is not one of the twenty amino acids commonly found in peptides synthesized in nature, and known by the one letter abbreviations A, R, N, C, D, Q, E, G, H, I, L, K, M, F, P, S, T, W, Y and V.

In some instances, amino acid analogs include β-amino acid analogs. Examples of β-amino acid analogs include, but are not limited to, the following: cyclic β-amino acid analogs; β-alanine; (R)-β-phenylalanine; (R)-1,2,3,4-tetrahydro-isoquinoline-3-acetic acid; (R)-3-amino-4-(1-naphthyl)-butyric acid; (R)-3-amino-4-(2,4-dichlorophenyl) butyric acid; (R)-3-amino-4-(2-chlorophenyl)-butyric acid; (R)-3-amino-4-(2-cyanophenyl)-butyric acid; (R)-3-amino-4-(2-fluorophenyl)-butyric acid; (R)-3-amino-4-(2-furyl)-butyric acid; (R)-3-amino-4-(2-methylphenyl)-butyric acid; (R)-3-amino-4-(2-naphthyl)-butyric acid; (R)-3-amino-4-(2-thienyl)-butyric acid; (R)-3-amino-4-(2-trifluoromethylphenyl)-butyric acid; (R)-3-amino-4-(3,4-dichlorophenyl)butyric acid; (R)-3-amino-4-(3,4-difluorophenyl)butyric acid; (R)-3-amino-4-(3-benzothienyl)-butyric acid; (R)-3-amino-4-(3-chlorophenyl)-butyric acid; (R)-3-amino-4-(3-cyanophenyl)-butyric acid; (R)-3-amino-4-(3-fluorophenyl)-butyric acid; (R)-3-amino-4-(3-methylphenyl)-butyric acid; (R)-3-amino-4-(3-pyridyl)-butyric acid; (R)-3-amino-4-(3-thienyl)-butyric acid; (R)-3-amino-4-(3-trifluoromethylphenyl)-butyric acid; (R)-3-amino-4-(4-bromophenyl)-butyric acid; (R)-3-amino-4-(4-chlorophenyl)-butyric acid; (R)-3-amino-4-(4-cyanophenyl)-butyric acid; (R)-3-amino-4-(4-fluorophenyl)-butyric acid; (R)-3-amino-4-(4-iodophenyl)-butyric acid; (R)-3-amino-4-(4-methylphenyl)-butyric acid; (R)-3-amino-4-(4-nitrophenyl)-butyric acid; (R)-3-amino-4-(4-pyridyl)-butyric acid; (R)-3-amino-4-(4-trifluoromethylphenyl)-butyric acid; (R)-3-amino-4-pentafluoro-phenylbutyric acid; (R)-3-amino-5-hexenoic acid; (R)-3-amino-5-hexynoic acid; (R)-3-amino-5-phenylpentanoic acid; (R)-3-amino-6-phenyl-5-hexenoic acid; (S)-1,2,3,4-tetrahydro-isoquinoline-3-acetic acid; (S)-3-amino-4-(1-naphthyl)-butyric acid; (S)-3-amino-4-(2,4-dichlorophenyl)butyric acid; (S)-3-amino-4-(2-chlorophenyl)-butyric acid; (S)-3-amino-4-(2-cyanophenyl)-butyric acid; (S)-3-amino-4-(2-fluorophenyl)-butyric acid; (S)-3-amino-4-(2-furyl)-butyric acid; (S)-3-amino-4-(2-methylphenyl)-butyric acid; (S)-3-amino-4-(2-naphthyl)-butyric acid; (S)-3-amino-4-(2-thienyl)-butyric acid; (S)-3-amino-4-(2-trifluoromethylphenyl)-butyric acid; (S)-3-amino-4-(3,4-dichlorophenyl)butyric acid; (S)-3-amino-4-(3,4-difluorophenyl)butyric acid; (S)-3-amino-4-(3-benzothienyl)-butyric acid; (S)-3-amino-4-(3-chlorophenyl)-butyric acid; (S)-3-amino-4-(3-cyanophenyl)-butyric acid; (S)-3-amino-4-(3-fluorophenyl)-butyric acid; (S)-3-amino-4-(3-methylphenyl)-butyric acid; (S)-3-amino-4-(3-pyridyl)-butyric acid; (S)-3-amino-4-(3-thienyl)-butyric acid; (S)-3-amino-4-(3-trifluoromethylphenyl)-butyric acid; (S)-3-amino-4-(4-bromophenyl)-butyric acid; (S)-3-amino-4-(4-chlorophenyl) butyric acid; (S)-3-amino-4-(4-cyanophenyl)-butyric acid; (S)-3-amino-4-(4-fluorophenyl) butyric acid; (S)-3-amino-4-(4-iodophenyl)-butyric acid; (S)-3-amino-4-(4-methylphenyl)-butyric acid; (S)-3-amino-4-(4-nitrophenyl)-butyric acid; (S)-3-amino-4-(4-pyridyl)-butyric acid; (S)-3-amino-4-(4-trifluoromethylphenyl)-butyric acid; (S)-3-amino-4-pentafluoro-phenylbutyric acid; (S)-3-amino-5-hexenoic acid; (S)-3-amino-5-hexynoic acid; (S)-3-amino-5-phenylpentanoic acid; (S)-3-amino-6-phenyl-5-hexenoic acid; 1,2,5,6-tetrahydropyridine-3-carboxylic acid; 1,2,5,6-tetrahydropyridine-4-carboxylic acid; 3-amino-3-(2-chlorophenyl)-propionic acid; 3-amino-3-(2-thienyl)-propionic acid; 3-amino-3-(3-bromophenyl)-propionic acid; 3-amino-3-(4-chlorophenyl)-propionic acid; 3-amino-3-(4-methoxyphenyl)-propionic acid; 3-amino-4,4,4-trifluoro-butyric acid; 3-aminoadipic acid; D-β-phenylalanine; β-leucine; L-β-homoalanine; L-β-homoaspartic acid γ-benzyl ester; L-β-homoglutamic acid δ-benzyl ester; L-β-homoisoleucine; L-β-homoleucine; L-β-homomethionine; L-β-homophenylalanine; L-β-homoproline; L-β-homotryptophan; L-β-homovaline; L-Nω-benzyloxycarbonyl-β-homolysine; Nω-L-β-homoarginine; O-benzyl-L-β-homohydroxyproline; O-benzyl-L-β-homoserine; O-benzyl-L-β-homothreonine; O-benzyl-L-β-homotyrosine; γ-trityl-L-β-homoasparagine; (R)-β-phenylalanine; L-β-homoaspartic acid γ-t-butyl ester; L-β-homoglutamic acid δ-t-butyl ester; L-Nω-β-homoly sine; Nδ-trityl-L-β-homoglutamine; Nω-2,2,4,6,7-pentamethyl-dihydrobenzofuran-5-sulfonyl-L-β-homoarginine; O-t-butyl-L-β-homohydroxy-proline; O-t-butyl-L-β-homoserine; O-t-butyl-L-β-homothreonine; O-t-butyl-L-β-homotyrosine; 2-aminocyclopentane carboxylic acid; and 2-aminocyclohexane carboxylic acid.

In some instances, amino acid analogs include analogs of alanine, valine, glycine or leucine. Examples of amino acid analogs of alanine, valine, glycine, and leucine include, but are not limited to, the following: α-methoxyglycine; α-allyl-L-alanine; α-aminoisobutyric acid; α-methyl-leucine; β-(1-naphthyl)-D-alanine; β-(1-naphthyl)-L-alanine; β-(2-naphthyl)-D-alanine; β-(2-naphthyl)-L-alanine; β-(2-pyridyl)-D-alanine; β-(2-pyridyl)-L-alanine; β-(2-thienyl)-D-alanine; β-(2-thienyl)-L-alanine; β-(3-benzothienyl)-D-alanine; β-(3-benzothienyl)-L-alanine; β-(3-pyridyl)-D-alanine; β-(3-pyridyl)-L-alanine; β-(4-pyridyl)-D-alanine; β-(4-pyridyl)-L-alanine; β-chloro-L-alanine; β-cyano-L-alanin; β-cyclohexyl-D-alanine; β-cyclohexyl-L-alanine; β-cyclopenten-1-yl-alanine; β-cyclopentyl-alanine; β-cyclopropyl-L-Ala-OH.dicyclohexylammonium salt; β-t-butyl-D-alanine; β-t-butyl-L-alanine; γ-aminobutyric acid; L-α,β-diaminopropionic acid; 2,4-dinitro-phenylglycine; 2,5-dihydro-D-phenylglycine; 2-amino-4,4,4-trifluorobutyric acid; 2-fluoro-phenylglycine; 3-amino-4,4,4-trifluoro-butyric acid; 3-fluoro-valine; 4,4,4-trifluoro-valine; 4,5-dehydro-L-leu-OH.dicyclohexylammonium salt; 4-fluoro-D-phenylglycine; 4-fluoro-L-phenylglycine; 4-hydroxy-D-phenylglycine; 5,5,5-trifluoro-leucine; 6-aminohexanoic acid; cyclopentyl-D-Gly-OH.dicyclohexylammonium salt; cyclopentyl-Gly-OH.dicyclohexylammonium salt; D-α,β-diaminopropionic acid; D-α-aminobutyric acid; D-α-t-butylglycine; D-(2-thienyl)glycine; D-β-thienyl)glycine; D-2-aminocaproic acid; D-2-indanylglycine; D-allylglycine-dicyclohexylammonium salt; D-cyclohexylglycine; D-norvaline; D-phenylglycine; β-aminobutyric acid; β-aminoisobutyric acid; (2-bromophenyl)glycine; (2-methoxyphenyl)glycine; (2-methylphenyl)glycine; (2-thiazoyl)glycine; (2-thienyl)glycine; 2-amino-3-(dimethylamino)-propionic acid; L-α,β-diaminopropionic acid; L-α-aminobutyric acid; L-α-t-butylglycine; L-β-thienyl)glycine; L-2-amino-3-(dimethylamino)-propionic acid; L-2-aminocaproic acid dicyclohexyl-ammonium salt; L-2-indanylglycine; L-allylglycine.dicyclohexyl ammonium salt; L-cyclohexylglycine; L-phenylglycine; L-propargylglycine; L-norvaline; N-α-aminomethyl-L-alanine; D-α,γ-diaminobutyric acid; L-α,γ-diaminobutyric acid; β-cyclopropyl-L-alanine; (N-β-(2,4-dinitrophenyl))-L-α,β-diaminopropionic acid; (N-β-1-(4,4-dimethyl-2,6-dioxocyclohex-1-ylidene) ethyl)-D-α,β-diaminopropionic acid; (N-β-1-(4,4-dimethyl-2,6-dioxocyclohex-1-ylidene)ethyl)-L-α,β-diaminopropionic acid; (N-β-4-methyltrityl)-L-α,β-diaminopropionic acid; (N-β-allyloxycarbonyl)-L-α,β-diaminopropionic acid; (N-γ-1-(4,4-dimethyl-2,6-dioxocyclohex-1-ylidene)ethyl)-D-α,γ-diaminobutyric acid; (N-γ-1-(4,4-dimethyl-2,6-dioxocyclohex-1-ylidene)ethyl)-L-α,γ-diaminobutyric acid; (N-γ-4-methyltrityl)-D-α,γ-diaminobutyric acid; (N-γ-4-methyltrityl)-L-α,γ-diaminobutyric acid; (N-γ-allyloxycarbonyl)-L-α,γ-diaminobutyric acid; D-α, γ-diaminobutyric acid; 4,5-dehydro-L-leucine; cyclopentyl-D-Gly-OH; cyclopentyl-Gly-OH; D-allylglycine; D-homocyclohexylalanine; L-1-pyrenylalanine; L-2-aminocaproic acid; L-allylglycine; L-homocyclohexylalanine; and N-(2-hydroxy-4-methoxy-Bzl)-Gly-OH.

In some instances, amino acid analogs include analogs of arginine or lysine. Examples of amino acid analogs of arginine and lysine include, but are not limited to, the following: citrulline; L-2-amino-3-guanidinopropionic acid; L-2-amino-3-ureidopropionic acid; L-citrulline; Lys(Me)$_2$-OH; Lys(N$_3$)—OH; Nδ-benzyloxycarbonyl-L-ornithine; Nω-nitro-D-arginine; Nω-nitro-L-arginine; α-methyl-ornithine; 2,6-diaminoheptanedioic acid; L-ornithine; (Nδ-1-(4,4-dimethyl-2,6-dioxo-cyclohex-1-ylidene)ethyl)-D-ornithine; (Nδ-1-(4,4-dimethyl-2,6-dioxo-cyclohex-1-ylidene) ethyl)-L-ornithine; (Nδ-4-methyltrityl)-D-ornithine; (Nδ-4-methyltrityl)-L-ornithine; D-ornithine; L-ornithine; Arg(Me)(Pbf)-OH; Arg(Me)$_2$-OH (asymmetrical); Arg(Me)2-OH (symmetrical); Lys(ivDde)-OH; Lys(Me)$_2$-OH.HCl; Lys(Me3)-OH chloride; Nω-nitro-D-arginine; and Nω-nitro-L-arginine.

In some instances, amino acid analogs include analogs of aspartic or glutamic acids. Examples of amino acid analogs of aspartic and glutamic acids include, but are not limited to, the following: α-methyl-D-aspartic acid; α-methyl-glutamic acid; α-methyl-L-aspartic acid; γ-methylene-glutamic acid; (N-γ-ethyl)-L-glutamine; [N-α-(4-aminobenzoyl)]-L-glutamic acid; 2,6-diaminopimelic acid; L-α-aminosuberic acid; D-2-aminoadipic acid; D-α-aminosuberic acid; α-aminopimelic acid; iminodiacetic acid; L-2-aminoadipic acid; threo-β-methyl-aspartic acid; γ-carboxy-D-glutamic acid γ,γ-di-t-butyl ester; γ-carboxy-L-glutamic acid γ,γ-di-t-butyl ester; Glu(OAll)-OH; L-Asu(OtBu)-OH; and pyroglutamic acid.

In some instances, amino acid analogs include analogs of cysteine and methionine. Examples of amino acid analogs of cysteine and methionine include, but are not limited to, Cys(farnesyl)-OH, Cys(farnesyl)-OMe, α-methyl-methionine, Cys(2-hydroxyethyl)-OH, Cys(3-aminopropyl)-OH, 2-amino-4-(ethylthio)butyric acid, buthionine, buthionine-sulfoximine, ethionine, methionine methylsulfonium chloride, selenomethionine, cysteic acid, [2-(4-pyridyl)ethyl]-DL-penicillamine, [2-(4-pyridyl)ethyl]-L-cysteine, 4-methoxybenzyl-D-penicillamine, 4-methoxybenzyl-L-penicillamine, 4-methylbenzyl-D-penicillamine, 4-methylbenzyl-L-penicillamine, benzyl-D-cysteine, benzyl-L-cysteine, benzyl-DL-homocysteine, carbamoyl-L-cysteine, carboxyethyl-L-cysteine, carboxymethyl-L-cysteine, diphenylmethyl-L-cysteine, ethyl-L-cysteine, methyl-L-cysteine, t-butyl-D-cysteine, trityl-L-homocysteine, trityl-D-penicillamine, cystathionine, homocystine, L-homocystine, (2-aminoethyl)-L-cysteine, seleno-L-cystine, cystathionine, Cys(StBu)-OH, and acetamidomethyl-D-penicillamine.

In some instances, amino acid analogs include analogs of phenylalanine and tyrosine. Examples of amino acid analogs of phenylalanine and tyrosine include β-methyl-phenylalanine, β-hydroxyphenylalanine, α-methyl-3-methoxy-DL-phenylalanine, α-methyl-D-phenylalanine, α-methyl-L-phenylalanine, 1,2,3,4-tetrahydroisoquinoline-3-carboxylic acid, 2,4-dichloro-phenylalanine, 2-(trifluoromethyl)-D-phenylalanine, 2-(trifluoromethyl)-L-phenylalanine, 2-bromo-D-phenylalanine, 2-bromo-L-phenylalanine, 2-chloro-D-phenylalanine, 2-chloro-L-phenylalanine, 2-cyano-D-phenylalanine, 2-cyano-L-phenylalanine, 2-fluoro-D-phenylalanine, 2-fluoro-L-phenylalanine, 2-methyl-D-phenylalanine, 2-methyl-L-phenylalanine, 2-nitro-D-phenylalanine, 2-nitro-L-phenylalanine, 2;4;5-trihydroxy-phenylalanine, 3,4,5-trifluoro-D-phenylalanine, 3,4,5-trifluoro-L-phenylalanine, 3,4-dichloro-D-phenylalanine, 3,4-dichloro-L-phenylalanine, 3,4-difluoro-D-phenylalanine, 3,4-difluoro-L-phenylalanine, 3,4-dihydroxy-L-phenylalanine, 3,4-dimethoxy-L-phenylalanine, 3,5,3'-triiodo-L-thyronine, 3,5-diiodo-D-tyrosine, 3,5-diiodo-L-tyrosine, 3,5-diiodo-L-thyronine, 3-(trifluoromethyl)-D-phenylalanine, 3-(trifluoromethyl)-L-phenylalanine, 3-amino-L-tyrosine, 3-bromo-D-phenylalanine, 3-bromo-L-phenylalanine, 3-chloro-D-phenylalanine, 3-chloro-L-phenylalanine, 3-chloro-L-tyrosine, 3-cyano-D-phenylalanine, 3-cyano-L-phenylalanine, 3-fluoro-D-phenylalanine, 3-fluoro-L-phenylalanine, 3-fluoro-tyrosine, 3-iodo-D-phenylalanine, 3-iodo-L-phenylalanine, 3-iodo-L-tyrosine, 3-methoxy-L-tyrosine, 3-methyl-D-phenylalanine, 3-methyl-L-phenylalanine, 3-nitro-D-phenylalanine, 3-nitro-L-phenylalanine, 3-nitro-L-tyrosine, 4-(trifluoromethyl)-D-phenylalanine, 4-(trifluoromethyl)-L-phenylalanine, 4-amino-D-phenylalanine, 4-amino-L-phenylalanine, 4-benzoyl-D-phenylalanine, 4-benzoyl-L-phenylalanine, 4-bis(2-chloroethyl)amino-L-phenylalanine, 4-bromo-D-phenylalanine, 4-bromo-L-phenylalanine, 4-chloro-D-phenylalanine, 4-chloro-L-phenylalanine, 4-cyano-D-phenylalanine, 4-cyano-L-phenylalanine, 4-fluoro-D-phenylalanine, 4-fluoro-L-phenylalanine, 4-iodo-D-phenylalanine, 4-iodo-L-phenylalanine, homophenylalanine, thyroxine, 3,3-diphenylalanine, thyronine, ethyl-tyrosine, and methyl-tyrosine.

In some instances, amino acid analogs include analogs of proline. Examples of amino acid analogs of proline include, but are not limited to, 3,4-dehydro-proline, 4-fluoro-proline, cis-4-hydroxy-proline, thiazolidine-2-carboxylic acid, and trans-4-fluoro-proline.

In some instances, amino acid analogs include analogs of serine and threonine. Examples of amino acid analogs of serine and threonine include, but are not limited to, 3-amino-2-hydroxy-5-methylhexanoic acid, 2-amino-3-hydroxy-4-methylpentanoic acid, 2-amino-3-ethoxybutanoic acid, 2-amino-3-methoxybutanoic acid, 4-amino-3-hydroxy-6-methylheptanoic acid, 2-amino-3-benzyloxypropionic acid, 2-amino-3-benzyloxypropionic acid, 2-amino-3-ethoxypropionic acid, 4-amino-3-hydroxybutanoic acid, and α-methylserine.

In some instances, amino acid analogs include analogs of tryptophan. Examples of amino acid analogs of tryptophan include, but are not limited to, the following: α-methyl-tryptophan; β-(3-benzothienyl)-D-alanine; β-(3-benzothienyl)-L-alanine; 1-methyl-tryptophan; 4-methyl-tryptophan; 5-benzyloxy-tryptophan; 5-bromo-tryptophan; 5-chloro-tryptophan; 5-fluoro-tryptophan; 5-hydroxy-tryptophan; 5-hydroxy-L-tryptophan; 5-methoxy-tryptophan; 5-methoxy-L-tryptophan; 5-methyl-tryptophan; 6-bromo-tryptophan; 6-chloro-D-tryptophan; 6-chloro-tryptophan; 6-fluoro-tryptophan; 6-methyl-tryptophan; 7-benzyloxy-tryptophan; 7-bromo-tryptophan; 7-methyl-tryptophan; D-1,2,3,4-tetrahydro-norharman-3-carboxylic acid; 6-methoxy-1,2,3,4-tetrahydronorharman-1-carboxylic acid; 7-azatryptophan; L-1,2,3,4-tetrahydro-norharman-3-carboxylic acid; 5-methoxy-2-methyl-tryptophan; and 6-chloro-L-tryptophan.

In some instances, amino acid analogs are racemic. In some instances, the D isomer of the amino acid analog is used. In some cases, the L isomer of the amino acid analog is used. In some instances, the amino acid analog comprises chiral centers that are in the R or S configuration. Sometimes, the amino group(s) of a β-amino acid analog is substituted with a protecting group, e.g., tert-butyloxycarbonyl (BOC group), 9-fluorenylmethyloxycarbonyl (FMOC), tosyl, and the like. Sometimes, the carboxylic acid functional group of a β-amino acid analog is protected, e.g., as its ester derivative. In some cases, the salt of the amino acid analog is used.

In some embodiments, nucleic acid molecules refer to at least two nucleotides covalently linked together. In some instances, a nucleic acid described herein contains phosphodiester bonds, although in some cases, as outlined below (for example in the construction of primers and probes such as label probes), nucleic acid analogs are included that have alternate backbones, comprising, for example, phosphoramide (Beaucage et al., Tetrahedron 49(10):1925 (1993) and references therein; Letsinger, J. Org. Chem. 35:3800 (1970); Sprinzl et al, Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al, Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid (also referred to herein as "PNA") backbones and linkages (see Egholm, J. Am. Chem. Soc. 114:1895 (1992); Meier et al., Chem. Int, Ed, Engl. 31:1008 (1992); Nielsen, Nature. 365:566 (1993); Carlsson et al., Nature 380:207 (1996), all of which are incorporated by reference). Other analog nucleic acids include those with bicyclic structures including locked nucleic acids (also referred to herein as "LNA"), Koshkin et al., J. Am. Chem. Soc. 12.0.13252 3 (1998); positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & amp; Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al, Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169 176). Several nucleic acid analogs are described in Rawls, C & E News Jun. 2, 1997 page 35. "Locked nucleic acids" are also included within the definition of nucleic acid analogs. LNAs are a class of nucleic acid analogues in which the ribose ring is "locked" by a methylene bridge connecting the 2'-O atom with the 4'-C atom. All of these references are hereby expressly incorporated by reference. In some instances, these modifications of the ribose-phosphate backbone are done to increase the stability and half-life of such molecules in physiological environments. For example, PNA:DNA and LNA-DNA hybrids exhibit higher stability and thus are used in some embodiments. The target nucleic acids are single stranded or double stranded, as specified, or contain portions of both double stranded or single stranded sequence. Depending on the application, the nucleic acids are DNA (including, e.g., genomic DNA, mitochondrial DNA, and cDNA), RNA (including, e.g., mRNA and rRNA) or a hybrid, where the nucleic acid contains any combination of deoxyribo- and ribo-nucleotides, and any combination of bases, including uracil, adenine, thymine, cytosine, guanine, inosine, xathanine hypoxathanine, isocytosine, isoguanine, etc.

High Throughput Method of Screening Utilizing Recombinant Proteins

In some instances, disclosed herein are methods of screening a drug utilizing recombinant lipid binding proteins. In some embodiments, the method comprises (a) contacting a solution comprising a purified recombinant lipid binding protein and a drug with a lipid probe, wherein the lipid probe comprises a lipid and a fluorophore; and (b) detecting a change in fluorescence polarization relative to a control, wherein the change in fluorescence polarization indicates an interaction between the drug and the lipid binding protein. In some instances, the method is a high throughput method.

In some instances, the change in fluorescence polarization is an increase in fluorescence polarization relative to a control. In some instances, the change in fluorescence polarization is a decrease in fluorescence polarization relative to a control. In some instances, the decrease in fluorescence polarization correlates to an interaction between the drug and the lipid binding protein. As used in this context, the control is the fluorescence polarization of a lipid probe in the presence of a recombinant protein in the absence of a drug.

In some instances, the lipid probe comprises a bioactive lipid. In some instances, the lipid probe comprises a fatty acyl, glycerolipid, glycerophospholipid, sphingolipid, sterol lipid, prenol lipid, saccharolipid, or polyketide. In some instances, the lipid probe comprises a lipid from a member of the fatty acyls group. In some instances, the fatty acyls comprise fatty acids, octadecanoids, eicosanoids, docosanoids, fatty alcohols, fatty aldehydes, fatty esters, fatty amides, fatty nitriles, fatty ethers, or fatty acyl glycosides. In some instances, the lipid is a fatty acid. In some instances, the lipid probe comprises a sterol lipid. In some instances, the sterol lipid comprises sterols, steroids, secosteroids, or bile acids. In some cases, the sterol comprises cholesterol, ergosterol, C24-propyl sterols, or stanol.

In some instances, the lipid probe further comprises a photoreactive group, such as azides, benzophenone, diazo compounds, diazirines, diazonium salts, or diaryl ketones. In some instances, the photoreactive group further comprises a linker.

In some instances, the lipid probe comprises a fluorophore such as rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol, aminorhodamine, carboxyrhodamine, chlororhodamine, methylrhodamine, sulforhodamine, thiorhodamine, cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine, bilirubin 1-dimethyl-aminonaphthyl-5-sulfonate, 1-anilino-8-naphthalene sulfonate, 2-p-toluidinyl-6-naphthalene sulfonate, 3-phenyl-7-isocyanatocoumarin, N-(p-(2-benzoxazolyl)phenyl) maleimide, stilbenes, pyrenes, 6-FAM (Fluorescein), 6-FAM (NHS Ester), 5(6)-FAM, 5-FAM, Fluorescein dT, 5-TAMRA-cadavarine, 2-aminoacridone, HEX, JOE (NHS Ester), MAX, TET, ROX, TAMRA, TAMRA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, or TYE™ 705.

In some instances, the fluorophore is conjugated to the hydrophilic portion of the lipid probe. In some instances, the photoreactive group and the fluorophore are conjugated to different sites of the lipid probe.

In some instances, the lipid probe comprises a lipid selected from arachidonoyl, arachidoyl, oleoyl, palmitoyl, or stearoyl fatty acyls and a fluorophore. In some instances, the lipid probe comprises an arachidonoyl fatty acyl and a fluorophore. In some instances, the lipid probe comprises an arachidoyl fatty acyl and a fluorophore. In some instances, the lipid probe comprises an oleoyl fatty acyl and a fluorophore. In some instances, the lipid probe comprises a palmitoyl fatty acyl and a fluorophore. In some instances, the lipid probe comprises a stearoyl fatty acyl and a fluorophore.

In some instances, the lipid probe comprises a lipid probe such as those described in Table 1 in which the lipid probe is conjugated to a fluorophore.

In some instances, the lipid probe comprises arachidonic acid and a fluorophore. In some instances, the lipid probe is 2-(6-(Dimethylamino)-3-(dimethyliminio)-3H-xanthen-9-yl)-5-((5-((5Z,8Z,11Z,14Z)-icosa-5,8,11,14-tetraenamido)pentyl)carbamoyl)benzoate.

In some embodiments, a recombinant protein is constructed, expressed, and purified using methods well known in the art. In some instances, the vector is any suitable vectors derived from either a eukaryotic or prokaryotic sources. In some instances, vectors include bacteria (e.g. *E. coli*), insects, yeast (e.g. *Pichia pastoris*), or mammalian source.

In some instances, bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2. In some instances the vector is pET21 from *E. coli*. Insect vector may include pFastBac1, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some instances, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 *Pichia* vector, pFLD1 Pichi *pastoris* vector, pGAPZA,B, & C *Pichia pastoris* vector, pPIC3.5K *Pichia* vector, pPIC6 A, B, & C *Pichia* vector, pPIC9K *Pichia* vector, pTEF1/Zeo, pYES2 yeast vector, pYES2/CT yeast vector, pYES2/NT A, B, & C yeast vector, or pYES3/CT yeast vector.

In some instances, mammalian vectors include transient expression vectors or stable expression vectors. In some cases, mammalian transient expression vectors include p3xFLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4. In some instances, mammalian stable expression vector include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some instances, any suitable protein expression and purification methodologies are applicable for expression and purification of a recombinant protein described herein. In some instances, protein purification includes a purification tag, such as a HIS(6)-Tag, HA-tag, Myc-tag, V5-tag, FLAG-tag, maltose binding protein (MBP) tag, and the like. In some instances, the purification utilizes affinity chromatographic methods, extraction methods, precipitation methods, and the like.

In some instances, the lipid binding protein is an enzyme, a transporter, a receptor, an adaptor, a channel protein, or a chaperone. In some cases, the lipid binding protein is a protein encoded by a gene of Table 3, a protein encoded by a gene of Table 4, or a protein encoded by a gene of Table 5. In some instances, the lipid binding protein is nucleobindin-1 (NUCB1). NUCB1 is a small calcium-binding EF-hand protein and participate in Golgi calcium homeostatis and $Ca^{2+}$ regulated signal transduction events. In some instances, NUCB1 serves as a repressor of the S1P-mediated ATF6 activation. TF6 is a bZIP transcription factor that plays a major role in UPR transcriptional induction via binding to the ER stress response elements in the promoter of target genes. In some instances, the NUCB1 gene is an endoplasmic reticulum (ER) stress-indicible gene.

Lipid Probe for Use in a High Throughput Screening Method Utilizing Recombinant Proteins In some instances, also described herein is a lipid probe which comprises a lipid and a fluorophore wherein the lipid probe is constructed for detecting a drug-lipid binding protein interaction. As described above, the lipid probe comprises a lipid such as a bioactive lipid (e.g. a fatty acyl). In some instances, the lipid probe further comprises a photoreactive group. In some instances, the lipid probe comprises a lipid selected from arachidonoyl, arachidoyl, oleoyl, palmitoyl, or stearoyl fatty acyls and a fluorophore. In some instances, the lipid probe comprises an arachidonoyl fatty acyl and a fluorophore. In some instances, the lipid probe comprises an arachidoyl fatty acyl and a fluorophore. In some instances, the lipid probe comprises an oleoyl fatty acyl and a fluorophore. In some instances, the lipid probe comprises a palmitoyl fatty acyl and a fluorophore. In some instances, the lipid probe comprises a stearoyl fatty acyl and a fluorophore.

In some instances, the lipid probe comprises a lipid probe such as those described in Table 1 in which the lipid probe is conjugated to a fluorophore.

In some instances, the lipid probe comprises arachidonic acid and a fluorophore. In some instances, the lipid probe is 2-(6-(Dimethylamino)-3-(dimethyliminio)-3H-xanthen-9-yl)-5-((5-((5Z,8Z,11Z,14Z)-icosa-5,8,11,14-tetraenamido)pentyl)carbamoyl)benzoate.

In some instances, the lipid probe is a ligand for a lipid binding protein. In some instances, the lipid probe is a ligand to an enzyme, a transporter, a receptor, an adaptor, a channel protein, or a chaperone. In some instances, the lipid probe is a ligand to a protein encoded by a gene of Table 3, a protein encoded by a gene of Table 4, or a protein encoded by a gene of Table 5. In some instances, the lipid probe is a ligand to nucleobindin-1 (NUCB1).

In some instances, also described herein is a lipid probe which comprises a lipid and a fluorophore wherein the lipid probe is constructed for detecting a drug-nucleobindin-1 (NUCB1) interaction. In some instances, the lipid probe comprises arachidonic acid and a fluorophore. In some instances, the lipid probe is 2-(6-(Dimethylamino)-3-(dimethyliminio)-3H-xanthen-9-yl)-5-((5-((5Z,8Z,11Z,14Z)-icosa-5,8,11,14-tetraenamido)pentyl)carbamoyl)benzoate.

NUCB1 Ligand

In some embodiments, disclosed herein is a NUCB1 ligand. In some instances, the NUCB1 ligand is a compound of Formula (II), or a pharmaceutically acceptable salt, or solvate thereof:

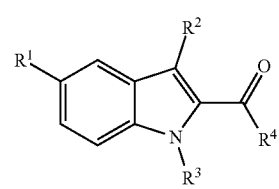

Formula (II)

wherein:
- R¹ is H, halogen, —CN, —OH, C₁-C₄alkoxy, C₁-C₄fluoroalkoxy, —NO₂, —S—C₁-C₄alkyl, —S(=O)—C₁-C₄alkyl, or —S(=O)₂—C₁-C₄alkyl;
- R² is H, halogen, C₁-C₄alkyl, C₃-C₆cycloalkyl, or substituted or unsubstituted phenyl, where if R² is substituted then R² is substituted with 1 or 2 R⁵;
  - each R⁵ is independently selected from the group consisting of H, halogen, —CN, —NO₂, —OH, —SR⁶, —S(=O)R⁶, —S(=O)₂R⁶, —C(=O)R⁶, —CO₂H, —CO₂R⁶, —NH₂, —NHR⁶, —N(R⁶)₂, —C(=O)NH₂, —C(=O)NHR⁶, —C(=O)N(R⁶)₂, C₁-C₄alkyl, C₁-C₄fluoroalkyl, C₁-C₄alkoxy, C₁-C₄fluoroalkoxy, C₃-C₆cycloalkyl, C₂-C₆heterocycloalkyl, phenyl, and phenoxy;
- R³ is H, or C₁-C₄alkyl;
- R⁴ is hydrogen, C₁-C₄alkyl, C₁-C₄alkoxy, —NHNH₂, —NH₂, —NHR⁶, or —N(R⁶)₂;
- each R⁶ is independently selected from the group consisting of C₁-C₆alkyl, C₁-C₆fluoroalkyl, C₃-C₆cycloalkyl, a substituted or unsubstituted phenyl, or substituted or unsubstituted benzyl;
- or two R⁶ groups attached to the same N atom are taken together with the N atom to which they are attached to form a C₂-C₆heterocycloalkyl that is unsubstituted or substituted with C₁-C₄alkyl or C₃-C₆cycloalkyl.

In some instances, R¹ is H, C₁, —NO₂, or —S(=O)₂—CH₃; R³ is H, or —CH₃.

In some instances, R⁴ is —NHNH₂, —NH₂, —NHR⁶, or —N(R⁶)₂.

In some instances, the compound has the following structure of Formula (III):

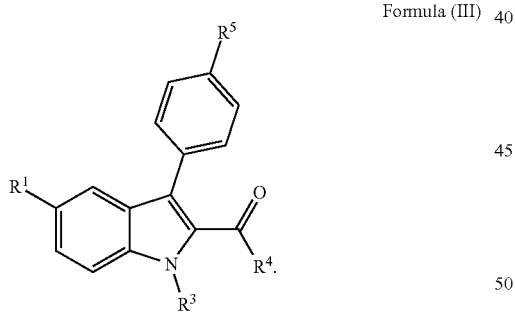

Formula (III)

In some instances,
- each R⁶ is independently selected from the group consisting of C₁-C₆alkyl, C₁-C₆fluoroalkyl, C₃-C₆cycloalkyl, or benzyl;
- or two R⁶ groups attached to the same N atom are taken together with the N atom to which they are attached to form a C₂-C₆heterocycloalkyl that is unsubstituted or substituted with C₁-C₄alkyl or C₃-C₆cycloalkyl, wherein the C₂-C₆heterocycloalkyl is pyrrolidinyl, piperidinyl, morpholinyl, thiomorpholinyl, piperazinyl, aziridinyl, or azetidinyl.

In some embodiments, the NUCB1 ligand has a structure selected from Table 2.

TABLE 2

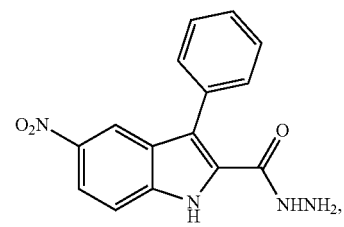 [SMILES: NNC(=O)c1[nH]c2ccc([N+](=O)[O-])cc2c1-c1ccccc1]

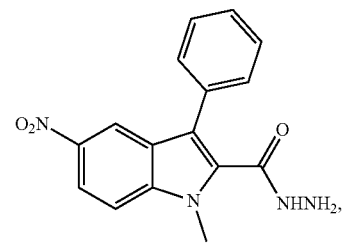 [SMILES: Cn1c(C(=O)NN)c(-c2ccccc2)c2cc([N+](=O)[O-])ccc21]

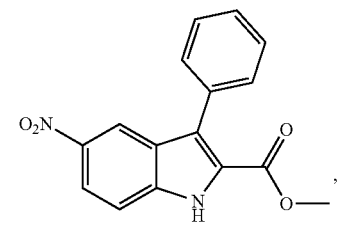 [SMILES: COC(=O)c1[nH]c2ccc([N+](=O)[O-])cc2c1-c1ccccc1]

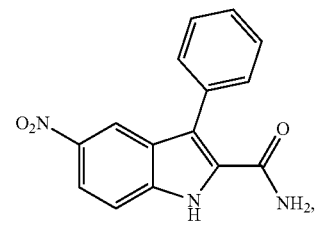 [SMILES: NC(=O)c1[nH]c2ccc([N+](=O)[O-])cc2c1-c1ccccc1]

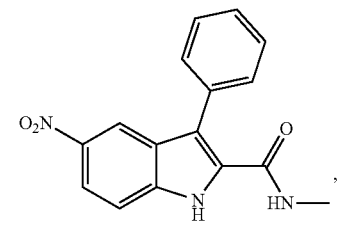

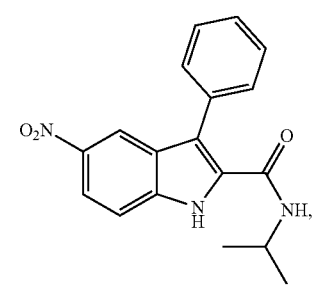 [SMILES: CC(C)NC(=O)c1[nH]c2ccc([N+](=O)[O-])cc2c1-c1ccccc1]

TABLE 2-continued
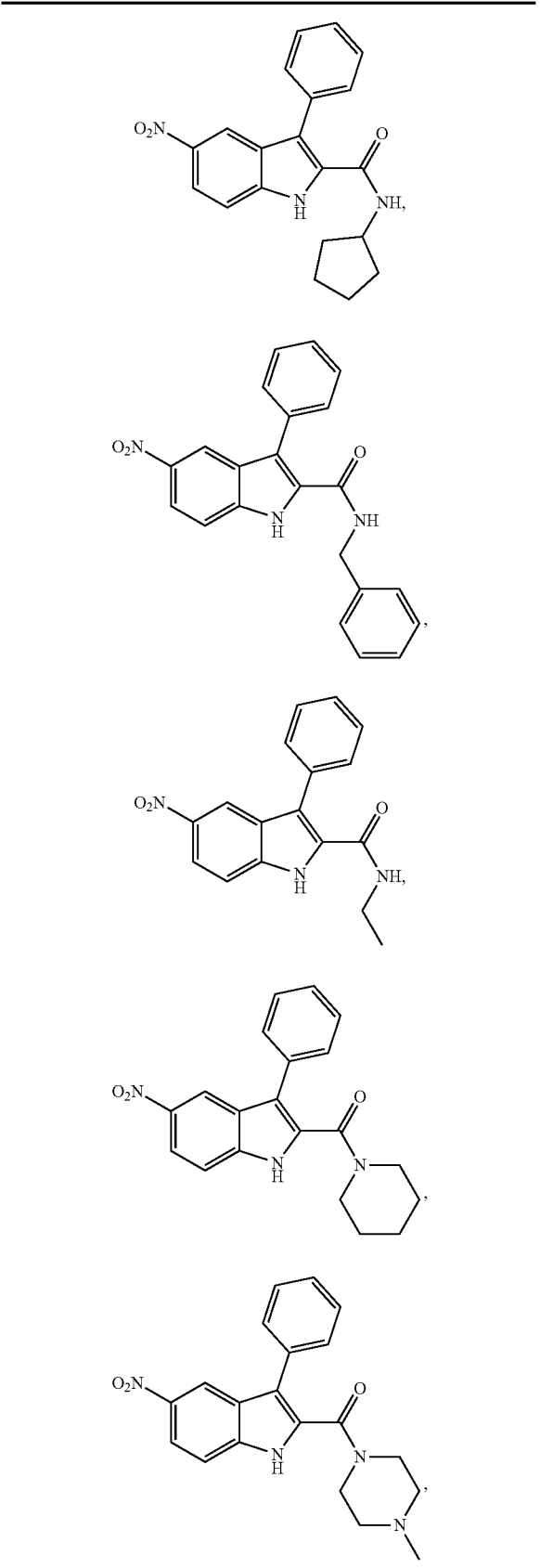
TABLE 2-continued
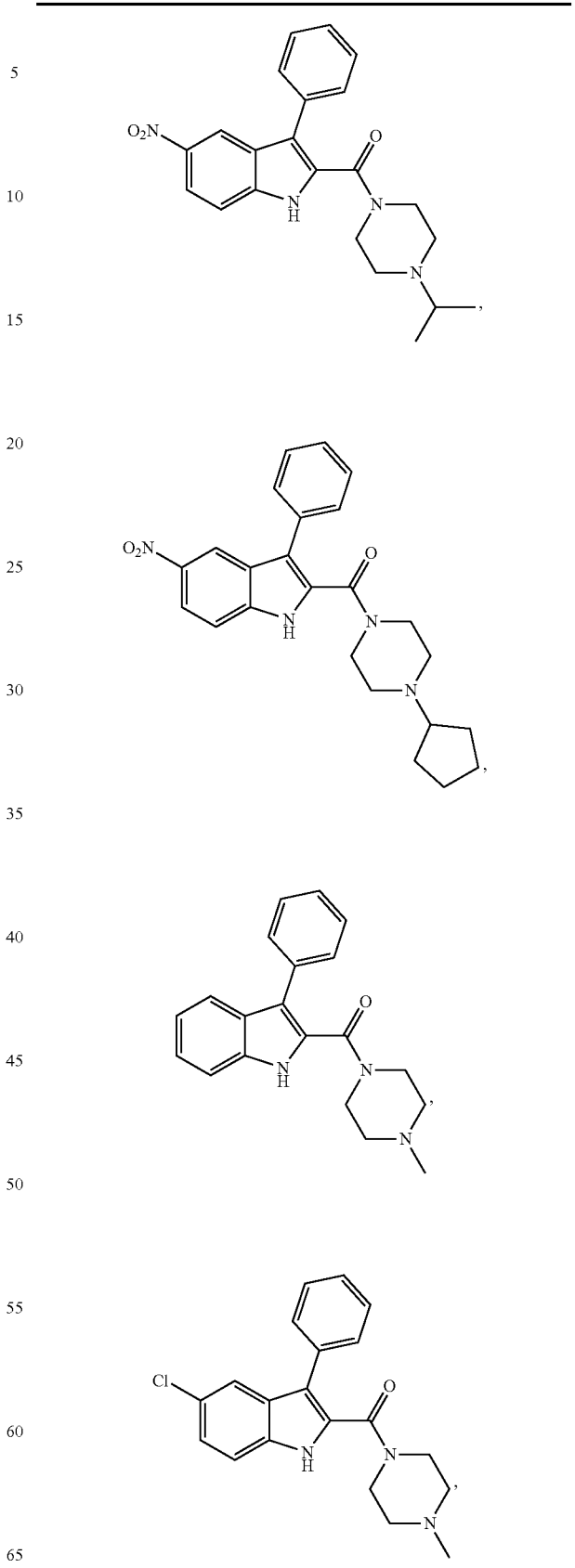

TABLE 2-continued

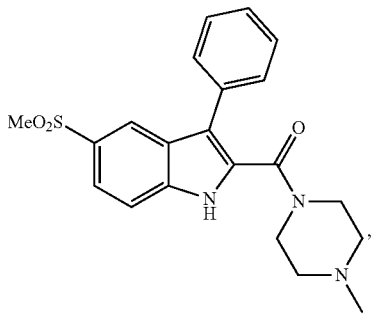 [SMILES: CN1CCN(C(=O)c2[nH]c3ccc(S(C)(=O)=O)cc3c2-c2ccccc2)CC1]

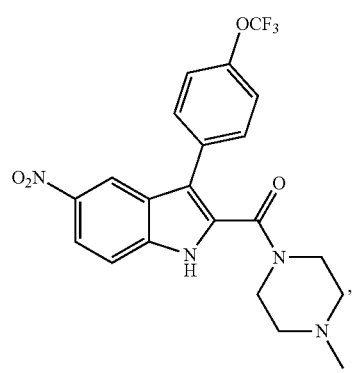 [SMILES: CN1CCN(C(=O)c2[nH]c3ccc([N+](=O)[O-])cc3c2-c2ccc(OC(F)(F)F)cc2)CC1]

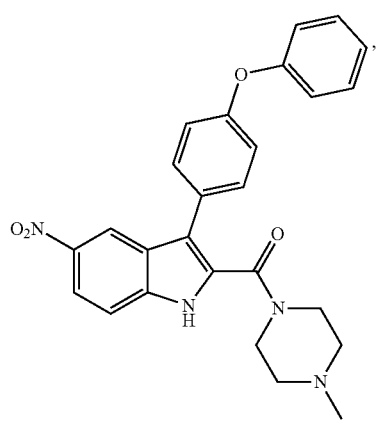 [SMILES: CN1CCN(C(=O)c2[nH]c3ccc([N+](=O)[O-])cc3c2-c2ccc(Oc3ccccc3)cc2)CC1]

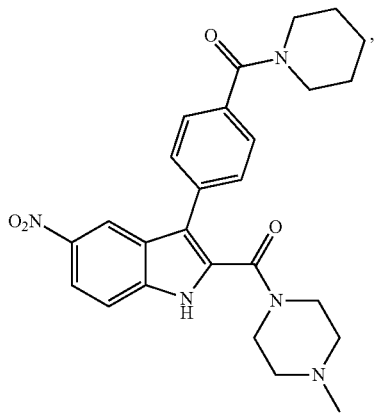 [SMILES: CN1CCN(C(=O)c2[nH]c3ccc([N+](=O)[O-])cc3c2-c2ccc(C(=O)N3CCCCC3)cc2)CC1]

TABLE 2-continued

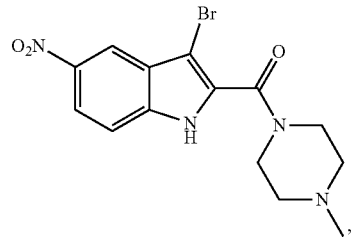 [SMILES: CN1CCN(C(=O)c2[nH]c3ccc([N+](=O)[O-])cc3c2Br)CC1]

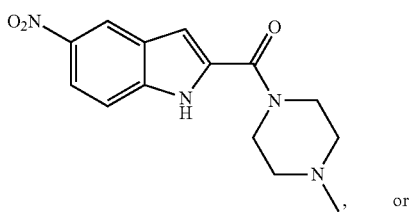 [SMILES: CN1CCN(C(=O)c2cc3cc([N+](=O)[O-])ccc3[nH]2)CC1]

or

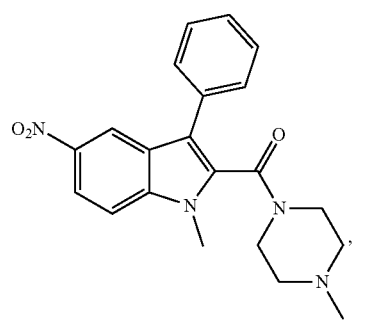 [SMILES: CN1CCN(C(=O)c2c(-c3ccccc3)c3cc([N+](=O)[O-])ccc3n2C)CC1]

In some instances, further disclosed herein is a composition which comprises a compound such as a NUCB1 ligand or a pharmaceutically acceptable salt or solvate thereof, and an excipient.

In some instances, any suitable excipient is used. A summary of pharmaceutical compositions described herein may be found, for example, in *Remington: The Science and Practice of Pharmacy*, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms and Drug Delivery Systems*, Seventh Ed. (Lippincott Williams & Wilkins 1999).

In some instances, the composition further comprises of carriers, stabilizers, diluents, dispersing agents, suspending agents, and/or thickening agents.

A "carrier" or "carrier materials" include any commonly used excipients in pharmaceutics and should be selected on the basis of compatibility with compounds disclosed herein, such as, compounds of ibrutinib, and the release profile properties of the desired dosage form. Exemplary carrier materials include, e.g., binders, suspending agents, disintegration agents, filling agents, surfactants, solubilizers, stabilizers, lubricants, wetting agents, diluents, and the like. "Pharmaceutically compatible carrier materials" include, but are not limited to, acacia, gelatin, colloidal silicon dioxide, calcium glycerophosphate, calcium lactate, maltodextrin, glycerine, magnesium silicate, polyvinylpyrrolidone (PVP), cholesterol, cholesterol esters, sodium caseinate, soy lecithin, taurocholic acid, phosphotidylcholine, sodium chloride, tricalcium phosphate, dipotassium phosphate, cellulose and cellulose conjugates, sugars sodium stearoyl lactylate, carrageenan, monoglyceride, diglyceride, pregelatinized starch, and the like. See, e.g., *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins1999).

"Dispersing agents," and/or "viscosity modulating agents" include materials that control the diffusion and homogeneity of a drug through liquid media or a granulation method or blend method. In some embodiments, these agents also facilitate the effectiveness of a coating or eroding matrix. Exemplary diffusion facilitators/dispersing agents include, e.g., hydrophilic polymers, electrolytes, Tween® 60 or 80, PEG, polyvinylpyrrolidone (PVP; commercially known as Plasdone®), and the carbohydrate-based dispersing agents such as, for example, hydroxypropyl celluloses (e.g., HPC, HPC-SL, and HPC-L), hydroxypropyl methylcelluloses (e.g., HPMC K100, HPMC K4M, HPMC K15M, and HPMC K100M), carboxymethylcellulose sodium, methylcellulose, hydroxyethylcellulose, hydroxypropylcellulose, hydroxypropylmethylcellulose phthalate, hydroxypropylmethylcellulose acetate stearate (HPMCAS), non-crystalline cellulose, magnesium aluminum silicate, triethanolamine, polyvinyl alcohol (PVA), vinyl pyrrolidone/vinyl acetate copolymer (S630), 4-(1,1,3,3-tetramethylbutyl)-phenol polymer with ethylene oxide and formaldehyde (also known as tyloxapol), poloxamers (e.g., Pluronics F68®, F88®, and F108®, which are block copolymers of ethylene oxide and propylene oxide); and poloxamines (e.g., Tetronic 908®, also known as Poloxamine 908®, which is a tetrafunctional block copolymer derived from sequential addition of propylene oxide and ethylene oxide to ethylenediamine (BASF Corporation, Parsippany, N.J.)), polyvinylpyrrolidone K 12, polyvinylpyrrolidone K17, polyvinylpyrrolidone K25, or polyvinylpyrrolidone K30, polyvinylpyrrolidone/vinyl acetate copolymer (S-630), polyethylene glycol, e.g., the polyethylene glycol has a molecular weight of about 300 to about 6000, or about 3350 to about 4000, or about 7000 to about 5400, sodium carboxymethylcellulose, methylcellulose, polysorbate-80, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, polysorbate-80, sodium alginate, polyethoxylated sorbitan monolaurate, polyethoxylated sorbitan monolaurate, povidone, carbomers, polyvinyl alcohol (PVA), alginates, chitosans and combinations thereof. Plasticizers such as cellulose or triethyl cellulose are also used as dispersing agents. Dispersing agents particularly useful in liposomal dispersions and self-emulsifying dispersions are dimyristoyl phosphatidyl choline, natural phosphatidyl choline from eggs, natural phosphatidyl glycerol from eggs, cholesterol and isopropyl myristate.

"Suspending agents" include compounds such as polyvinylpyrrolidone, e.g., polyvinylpyrrolidone K12, polyvinylpyrrolidone K17, polyvinylpyrrolidone K25, or polyvinylpyrrolidone K30, vinyl pyrrolidone/vinyl acetate copolymer (S630), polyethylene glycol, e.g., the polyethylene glycol have a molecular weight of about 300 to about 6000, or about 3350 to about 4000, or about 7000 to about 5400, sodium carboxymethylcellulose, methylcellulose, hydroxypropylmethylcellulose, hydroxymethylcellulose acetate stearate, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Thickening agent or viscosity enhancing agents include, e.g., methyl cellulose, xanthan gum, carboxymethyl cellulose, hydroxypropyl cellulose, hydroxypropylmethyl cellulose, hydroxypropylmethyl cellulose acetate stearate, hydroxypropylmethyl cellulose phthalate, carbomer, polyvinyl alcohol, alginates, acacia, chitosans and combinations thereof.

In some instances, the composition further comprises one or more pH adjusting agents or buffering agents, including acids such as acetic, boric, citric, lactic, phosphoric and hydrochloric acids; bases such as sodium hydroxide, sodium phosphate, sodium borate, sodium citrate, sodium acetate, sodium lactate and tris-hydroxymethylaminomethane; and buffers such as citrate/dextrose, sodium bicarbonate and ammonium chloride. Such acids, bases and buffers are included in an amount required to maintain pH of the composition in an acceptable range.

In some instances, the composition also includes one or more salts in an amount required to bring osmolality of the composition into an acceptable range. Such salts include those having sodium, potassium or ammonium cations and chloride, citrate, ascorbate, borate, phosphate, bicarbonate, sulfate, thiosulfate or bisulfite anions; suitable salts include sodium chloride, potassium chloride, sodium thiosulfate, sodium bisulfite and ammonium sulfate.

In some instances, the composition is formulated for administration to a mammal by intravenous administration, subcutaneous administration, oral administration, inhalation, nasal administration, dermal administration, or ophthalmic administration.

In some instances, the composition is in the form of a tablet, a pill, a capsule, a liquid, a suspension, a gel, a dispersion, a solution, an emulsion, an ointment, or a lotion. In some instances, the compositions described herein are formulated into any suitable dosage form, including but not limited to, aqueous oral dispersions, liquids, gels, syrups, elixirs, slurries, suspensions and the like, for oral ingestion by an individual to be treated, solid oral dosage forms, aerosols, controlled release formulations, fast melt formulations, effervescent formulations, lyophilized formulations, tablets, powders, pills, dragees, capsules, delayed release formulations, extended release formulations, pulsatile release formulations, multiparticulate formulations, and mixed immediate release and controlled release formulations. In some embodiments, the compositions are formulated into capsules. In some embodiments, the compositions are formulated into solutions (for example, for intravenous (IV) administration). In some instances, the dosage form further comprises acceptable additives such as a compatible carrier, binder, filling agent, suspending agent, flavoring agent, sweetening agent, disintegrating agent, dispersing agent, surfactant, lubricant, colorant, diluent, solubilizer, moistening agent, plasticizer, stabilizer, penetration enhancer, wetting agent, anti-foaming agent, antioxidant, preservative, or one or more combination thereof.

As used in the context of Formula II and Formula III, the terms below, as used herein, have the following meanings, unless indicated otherwise:

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a C1-C6 alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl, ethyl, s-butyl, or 1-ethyl-propyl. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —$CH_2$—, —$CH_2CH_2$—, or —$CH_2CH_2CH_2$—. In some embodiments, the alkylene is —$CH_2$—. In some embodiments, the alkylene is —$CH_2CH_2$—. In some embodiments, the alkylene is —$CH_2CH_2CH_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloakyls having from three to ten carbon atoms, from three to eight carbon atoms, from three to six carbon atoms, or from three to five carbon atoms. Monocyclic cyclcoalkyl radicals include, for example, cyclopropyl, cyclobutyl, cyclopentyl, cyclohexyl, cycloheptyl, and cyclooctyl. In some embodiments, the monocyclic cyclcoalkyl is cyclopropyl, cyclobutyl, cyclopentyl or cyclohexyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Heterocycloalkyl" or "heterocyclyl" or "heterocyclic ring" refers to a stable 3- to 14-membered non-aromatic ring radical comprising 2 to 13 carbon atoms and from one to 6 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. In some embodiments the heterocycloalkyl is morpholinyl, thiomorpholinyl, piperidinyl, or pyrrolidinyl. In some embodiments the heterocycloalkyl is morpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g. —$NH_2$, —NHR, —$N(R)_2$), and the protected derivatives thereof. In some embodiments, optional substituents are independently selected from alkyl, alkoxy, haloalkyl, cycloalkyl, halogen, —CN, —$NH_2$, —$NH(CH_3)$, —$N(CH_3)_2$, —OH, —$CO_2H$, and —$CO_2$alkyl. In some embodiments, optional substituents are independently selected from fluoro, chloro, bromo, iodo, —$CH_3$, —$CH_2CH_3$, —$CF_3$, —$OCH_3$, and —$OCF_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

Kits and Articles of Manufacture

Disclosed herein, in certain embodiments, are kits and articles of manufacture for use with one or more methods described herein. In some embodiments, described herein is a kit for identifying a lipid binding protein as a drug binding target. In some instances, also described herein is a kit for mapping binding sites on a lipid binding protein. In some cases, described herein is a kit for identifying lipid binding proteins. In some embodiments, also described herein is a kit for a high throughput screening of a drug for interaction with a lipid binding protein.

In some embodiments, such kit includes lipid probes such as the lipid probes described herein, test compounds such as drugs and/or controls, and reagents suitable for carrying out one or more of the methods described herein. In some instances, the kit further comprises samples, such as a cell sample, and suitable solutions such as buffers or media. In some embodiments, the kit further comprises recombinant proteins for use in one or more of the methods described herein. In some embodiments, additional components of the kit comprises a carrier, package, or container that is compartmentalized to receive one or more containers such as vials, tubes, and the like, each of the container(s) comprising one of the separate elements to be used in a method described herein. Suitable containers include, for example, bottles, vials, plates, syringes, and test tubes. In one embodiment, the containers are formed from a variety of materials such as glass or plastic.

The articles of manufacture provided herein contain packaging materials. Examples of pharmaceutical packaging materials include, but are not limited to, bottles, tubes, bags, containers, and any packaging material suitable for a selected formulation and intended mode of use.

For example, the container(s) include lipid probes, test compounds, and one or more reagents for use in a method disclosed herein. Such kits optionally include an identifying description or label or instructions relating to its use in the methods described herein.

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

Services

The methods provided herein may also be performed as a service. In some instances, a service provider obtain from the customer a plurality of drug candidates for analysis with one or more of the lipid probes for screening. In some embodiments, the service provider screens the drug candidates using one or more of the methods described herein, and then provide the results to the customer. In some instances, the service provider provides the appropriate reagents to the customer for analysis utilizing one or more of the lipid probes and one or more of the methods described herein. In some cases, the customer performs one or more of the methods described herein and then provide the results to the service provider for analysis. In some embodiments, the service provider then analyzes the results and provides the results to the costumer. In some cases, the customer further analyze the results by interacting with software installed locally (at the customer's location) or remotely (e.g., on a server reachable through a network). Exemplary customers include pharmaceutical companies, clinical laboratories, physicians, patients, and the like. In some instances, a customer is any suitable customer or party with a need or desire to use the methods, systems, compositions, and kits described herein.

Digital Processing Device

In some embodiments, the methods described herein include a digital processing device, or use of the same. In further embodiments, the digital processing device includes one or more hardware central processing units (CPU) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device.

In accordance with the description herein, suitable digital processing devices include, but are not limited to, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Suitable tablet computers include those with booklet, slate, or convertible configurations.

In some embodiments, the digital processing device includes an operating system configured to perform executable instructions. The operating system is, for example, software, including programs and data, which manages the device's hardware and provides services for execution of applications. Suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux, and Palm® WebOS®. Suitable media streaming device operating systems include, by way of non-limiting examples, Apple TV®, Roku®, Boxee®, Google TV®, Google Chromecast®, Amazon Fire®, and Samsung® HomeSync®. Suitable video game console operating systems include, by way of non-limiting examples, Sony® PS3®, Sony® PS4®, Microsoft® Xbox 360®, Microsoft Xbox One, Nintendo® Wii®, Nintendo® Wii U®, and Ouya®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes a display to send visual information to a user. In some embodiments, the display includes a cathode ray tube (CRT), a liquid crystal display (LCD), a thin film transistor liquid crystal display (TFT-LCD), an organic light emitting diode (OLED) display, a plasma display, a video projector, or a combination thereof.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect™, Leap Motion™, or the like. In still further embodiments, the input device is a combination of devices such as those disclosed herein.

In some embodiments, the systems and methods disclosed herein include one or more non-transitory computer readable storage media encoded with a program including instructions executable by the operating system of an optionally networked digital processing device. In further embodiments, a computer readable storage medium is a tangible component of a digital processing device. In still further embodiments, a computer readable storage medium is optionally removable from a digital processing device. In some embodiments, a computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

In some embodiments, the systems and methods disclosed herein include at least one computer program, or use of the same. A computer program includes a sequence of instructions, executable in the digital processing device's CPU, written to perform a specified task. In some embodiments, computer readable instructions are implemented as program modules, such as functions, objects, Application Programming Interfaces (APIs), data structures, and the like, that perform particular tasks or implement particular abstract data types.

In some embodiments, the functionality of the computer readable instructions are combined or distributed as desired in various environments. In some embodiments, a computer program comprises one sequence of instructions. In some embodiments, a computer program comprises a plurality of sequences of instructions. In some embodiments, a computer program is provided from one location. In other embodiments, a computer program is provided from a plurality of locations. In various embodiments, a computer program includes one or more software modules. In various embodiments, a computer program includes, in part or in whole, one or more web applications, one or more mobile applications, one or more standalone applications, one or more web browser plug-ins, extensions, add-ins, or add-ons, or combinations thereof.

In some embodiments, a computer program includes a web application. A web application, in various embodiments, utilizes one or more software frameworks and one or more database systems. In some embodiments, a web application is created upon a software framework such as Microsoft® .NET or Ruby on Rails (RoR). In some embodiments, a web application utilizes one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. A web application, in various embodiments, is written in one or more versions of one or more languages. In some embodiments, a web application is written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). In some embodiments, a web application is written to some extent in a presentation definition language such as Cascading Style Sheets (CSS). In some embodiments, a web application is written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application is written to some extent in a database query language such as Structured Query Language (SQL). In some embodiments, a web application integrates enterprise server products such as IBM® Lotus Domino®. In some embodiments, a web application includes a media player element. In various further embodiments, a media player element utilizes one or more of many suitable multimedia technologies including, by way of non-limiting examples, Adobe® Flash®, HTML 5, Apple® QuickTime®, Microsoft® Silverlight®, Java™, and Unity®.

In some embodiments, a computer program includes a mobile application provided to a mobile digital processing device. In some embodiments, the mobile application is provided to a mobile digital processing device at the time it is manufactured. In other embodiments, the mobile application is provided to a mobile digital processing device via the computer network described herein.

In view of the disclosure provided herein, a mobile application is created by techniques using hardware, languages, and development environments. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

In some embodiments, commercial forums for distribution of mobile applications include, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

In some embodiments, a computer program includes a standalone application, which is a program that is run as an independent computer process, not an add-on to an existing process, e.g., not a plug-in. In some instances, standalone applications are compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable compiled applications.

In some embodiments, the computer program includes a web browser plug-in. In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. In some instances, web browser plug-ins include Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer®Mobile, Amazon® Kindle® Basic Web, Nokia® Browser, Opera Software® Opera® Mobile, and Sony® PSP™ browser.

In some embodiments, the systems and methods disclosed herein include software, server, and/or database modules, or use of the same. In view of the disclosure provided herein, software modules are created and implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

In some embodiments, the methods and systems disclosed herein include one or more databases, or use of the same. In view of the disclosure provided herein, databases are suitable for storage and retrieval of analytical information described elsewhere herein. In various embodiments, suitable databases include, by way of non-limiting examples, relational databases, non-relational databases, object oriented databases, object databases, entity-relationship model databases, associative databases, and XML databases. In some embodiments, a database is internet-based. In further embodiments, a database is web-based. In still further embodiments, a database is cloud computing-based. In other embodiments, a database is based on one or more local computer storage devices.

Server

Figure 2:
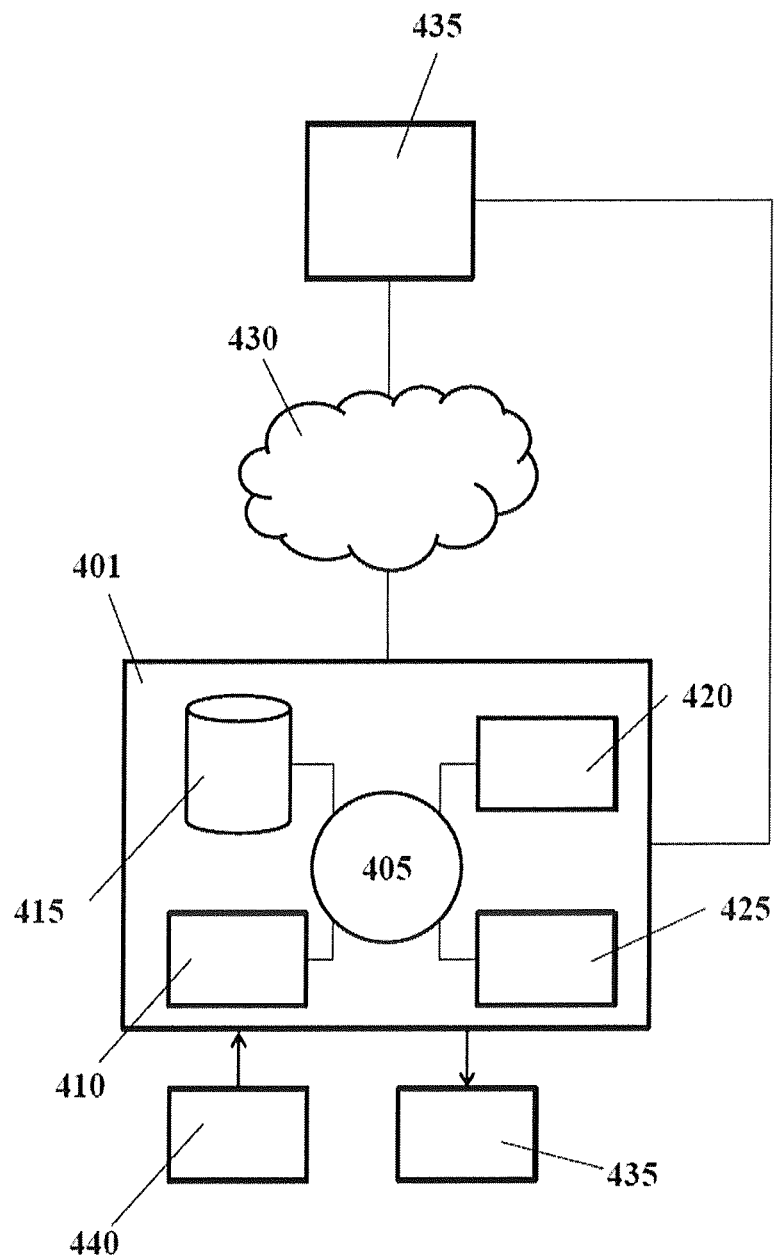
FIG. 2 illustrates a conceptual schematic of an exemplary computer server to be used for processing a method described herein.

In some embodiments, the methods provided herein are processed on a server or a computer server (FIG. 2). In some embodiments, the server 401 includes a central processing unit (CPU, also "processor") 405 which is a single core processor, a multi core processor, or plurality of processors for parallel processing. In some embodiments, a processor used as part of a control assembly is a microprocessor. In some embodiments, the server 401 also includes memory 410 (e.g. random access memory, read-only memory, flash memory); electronic storage unit 415 (e.g. hard disk); communications interface 420 (e.g. network adaptor) for communicating with one or more other systems; and peripheral devices 425 which includes cache, other memory, data storage, and/or electronic display adaptors. The memory 410, storage unit 415, interface 420, and peripheral devices 425 are in communication with the processor 405 through a communications bus (solid lines), such as a motherboard. In some embodiments, the storage unit 415 is a data storage unit for storing data. The server 401 is operatively coupled to a computer network ("network") 430 with the aid of the communications interface 420. In some embodiments, a processor with the aid of additional hardware is also operatively coupled to a network. In some embodiments, the network 430 is the Internet, an intranet and/or an extranet, an intranet and/or extranet that is in communication with the Internet, a telecommunication or data network. In some embodiments, the network 430 with the aid of the server 401, implements a peer-to-peer network, which enables devices coupled to the server 401 to behave as a client or a server. In some embodiments, the server is capable of transmitting and receiving computer-readable instructions (e.g., device/system operation protocols or parameters) or data (e.g., sensor measurements, raw data obtained from detecting metabolites, analysis of raw data obtained from detecting metabolites, interpretation of raw data obtained from detecting metabolites, etc.) via electronic signals transported through the network 430. Moreover, in some embodiments, a network is used, for example, to transmit or receive data across an international border.

In some embodiments, the server 401 is in communication with one or more output devices 435 such as a display or printer, and/or with one or more input devices 440 such as, for example, a keyboard, mouse, or joystick. In some embodiments, the display is a touch screen display, in which case it functions as both a display device and an input device. In some embodiments, different and/or additional input devices are present such an enunciator, a speaker, or a microphone. In some embodiments, the server uses any one of a variety of operating systems, such as for example, any one of several versions of Windows®, or of MacOS®, or of Unix®, or of Linux®.

In some embodiments, the storage unit 415 stores files or data associated with the operation of a device, systems or methods described herein.

In some embodiments, the server communicates with one or more remote computer systems through the network 430. In some embodiments, the one or more remote computer systems include, for example, personal computers, laptops, tablets, telephones, smart phones, or personal digital assistants.

In some embodiments, a control assembly includes a single server 401. In other situations, the system includes multiple servers in communication with one another through an intranet, extranet and/or the Internet.

In some embodiments, the server 401 is adapted to store device operation parameters, protocols, methods described herein, and other information of potential relevance. In some embodiments, such information is stored on the storage unit 415 or the server 401 and such data are transmitted through a network.

EXAMPLES

These examples are provided for illustrative purposes only and not to limit the scope of the claims provided herein.

Example I

Materials

Internal standards for LC/MS analysis (AEA-$d_4$, PEA-$d_4$, AA-$d_8$, 2-AG-$d_5$, PGE$_2$-$d_9$, PGD$_2$-$d_9$, TXB$_2$-$d_4$, PGE$_2$-EA-$d_4$) were purchased from Cayman Chemical Company. Lipid standards and competitors, including (+)-flurbiprofen, rofecoxib, avasimibe, FK-866 and Ro 48-8071 were purchased from Cayman Chemical Company and used without further purification. Lipid probes and NUCB1 ligands were synthesized according to methods outlined below.

Cell Culture

HEK293T and Neuro2a cells were maintained in high-glucose DMEM supplemented with 10% (v/v) fetal bovine serum (FBS), penicillin (100 U/mL), streptomycin (100 µg/mL) and Lglutamine (2 mM). A549 cells were grown in RPMI-1640 (Mediatech) supplemented as above. All cell lines were grown at 37° C. in a humidified 5% $CO_2$ atmosphere. For SILAC experiments, each cell line was passaged at least six times in either SILAC DMEM or SILAC RPMI-1640 (Thermo), which lack L-lysine and L-arginine, and supplemented with 10% (v/v) dialyzed FBS (Gemini), PSQ (as above), and either [$^{13}C_6$, $^{15}N_2$]-L-lysine and [$^{13}C_6$, $^{15}N_4$]-Larginine (Sigma) (100 µg/mL each) or L-lysine.HCl and L-arginine.HCl (Sigma) (100 µg/mL each). Heavy and light cells were maintained in parallel and cell aliquots were frozen after six passages in SILAC media and stored in liquid N2 until needed. When thawed, cells were passaged at least three times before use in experiments.

Live Cell Labeling with Clickable Photoaffinity Probes

At ~80-90% confluency, cells were trypsinized and counted using an automated cell counter (Bio-Rad). For gel-based analysis, cells were plated at a density of 2.5×10$^6$ cells/6 cm plate and grown for 18-24 h before labeling. The indicated photoaffinity probe and, if applicable, competitors or vehicle were dissolved in fresh media (1.5 mL) in a glass vial and warmed to 37° C. in a water bath. For competition experiments, serum-free media was used, whereas for probe-probe comparisons, standard growth media containing 10% (v/v) FBS was used. The media from each 6 cm plate was then aspirated and the cells were washed with DPBS (2×3.0 mL) before adding media containing probes and/or competitors. In some instances, media was either poured directly from the glass vials onto the cells or transferred using a glass Pasteur pipette. Cells were incubated at 37° C. for 30 min before the media was removed and the cells were either directly exposed to 365 nm light for 10 min at 4° C. (Stratagene, UV Stratalinker™ 1800 Crosslinker) or incubated at 4° C. for 10 min in ambient light (No UV control experiments).

For MS-based experiments, cell labeling was performed in a similar manner as above. Modifications to this protocol included using isotopically light and heavy SILAC cells and increasing the cell count to increase protein yield. Specifically, SILAC cells were plated at a density of 4×10$^6$ cells/10 cm plate and grown to near complete confluency prior to labeling. Additionally, probe and, if applicable, vehicles or competitors were dissolved together in 4.0 mL of fresh, serum-free SILAC media in glass vials. Isotopically light cells were labeled with the arachidinoyl probe (AEA-DA or A-DA) and irradiated with UV for 10 min at 4° C. "Heavy" cells were subjected to variable conditions as specified in each experiment, including treatments with alternative lipid probes (OEA-DA, PEA-DA, O-DA or S-DA) or competitors.

Proteome Preparation for Gel- and MS-Based Analyses

Cells were then harvested by scraping in cold DPBS (1.5 mL) and cell pellets isolated by centrifugation (1,400×g, 3 min) and then washed by addition of cold DPBS (1.0 mL), vortexing and re-centrifugation (1,400×g, 3 min). To the cell pellets was added cold DPBS (100-500 µL) and the cells were lysed by probe sonication using a Branson Sonifier probe sonicator (10 pulses, 50% duty cycle, output setting=3). In some instances, PMA-stimulated SILAC A549 cells were lysed in DPBS containing indomethacin (10 µM) to inhibit PTGS2 prior to mixing heavy and light proteomes in order to prevent non-UV dependent covalent adduction of this enzyme. When analyzing soluble and membrane components separately, cell lysates were then centrifuged (100,000×g, 45 min) to provide the soluble (supernatant) and membrane (pellet) fractions. For SILAC experiments, isotopically "heavy" and "light" cell lysates were mixed in equal proportions (2.0 mg of protein each) prior to fractionation.

For gel-based analysis, after sonicating the membrane pellets in cold DPBS, protein concentrations of each fraction were determined using the BCA protein assay (Bio-Rad) and a microplate reader (Tecan, Infinite F500).

Gel-Based Analysis of Crosslinked Proteins

Proteomes were diluted to 1.0 mg/mL (total protein concentration) and 50 µL of each proteome was transferred to separate wells in a 96-well plate. To each proteome sample was added 6 µL of a freshly prepared "click" reagent mixture containing TBTA (3 µL/sample, 1.7 mM in 4:1 DMSO:t-BuOH), CuSO4 (1.0 µL/sample, 50 mM in $H_2O$), TCEP (1.0 µL/sample, 50 mM in DPBS and Rh-N3 (1.0 µL/sample, 1.25 mM in DMSO). Upon addition of the "click" mixture, each reaction was mixed by pipetting up-and-down several times and then allowed to react at room temperature. After 1 h, each reaction was quenched with 4×SDS loading buffer (17 µL), and proteins were resolved using SDS-PAGE (10% acrylamide 13 gel) and analyzed by in-gel fluorescent scanning on a Hitachi FMBIO-II flatbed fluorescence scanner.

MS-Based Analysis of Crosslinked Proteins

Isotopically heavy and light proteomes from derived from probe labeled cells were mixed in equal proportions (1.0 mg each) and diluted to a final volume of 1.0 mL with DPBS. A mixture of TBTA (60 µL/sample, 1.7 mM in 4:1 DMSO:t-BuOH), CuSO4 (20 µL/sample, 50 mM in $H_2O$), TCEP (20 µL/sample, 50 mM in DPBS and Biotin-N3 (10 µL/sample, 10 mM in DMSO) was added and the proteome was vortexed and placed on a rotator at room temperature. After 1 h, cold MeOH (2 mL), $CHCl_3$ (0.5 mL) and DPBS (1 mL) were added sequentially and the cloudy mixture was vortexed and then centrifuged (5,000×g, 15 min, 4° C.). The organic and aqueous layers were aspirated leaving a protein disc which had formed between phases. The protein disc was washed with cold 1:1 MeOH:$CHCl_3$ (3×1 mL) while intact and then probe sonicated in cold 4:1 MeOH:$CHCl_3$ (2.5 mL). Insoluble proteins were pelleted via centrifugation (5,000×g, 15 min, 4° C.) and the supernatant was removed. The remaining pellet was redissolved in a freshly prepared solution of urea (500 µL, 6 M in DPBS). When analyzing membrane proteomes, 10% (w/v) SDS (20 µL) was added and the solution was warmed to 37° C. to facilitate the dissolution of poorly soluble proteins. TCEP (50 µL, 100 mM in DBPS, pH 7) was next added, and after the proteome solution was incubated for 30 min at 37° C., iodoacetamide (70 µL, 400 mM in DPBS) was added. After incubating for an additional 30 min at room temperature, 10% (w/v) SDS (120 µL) was added followed by DPBS (5.5 mL) and then pre-washed streptavidin beads (100 µL, 1:1, Pierce). Proteomes were rotated with the beads for 1.5 h at room temperature and the beads were pelleted by centrifugation (1,000×g, 2 min) and sequentially washed with 0.25% SDS (3×10 mL), DPBS (3×10 mL) and dd$H_2O$ (3×10 mL). The beads were transferred to a Protein LoBind tube (Eppendorf) and enriched proteins were trypsinized by addition of urea (200 µL, 2.0 M in DPBS), CaCl2 (2.0 µL, 100 mM in $H_2O$) and sequence grade porcine trypsin (Promega). After digesting overnight at 37° C., the supernatant was transferred to a clean Protein LoBind tube, acidified with $HCO_2H$ (16 µL) and stored at −20° C. until the analyzed by LC/LC-MS/MS.

Proteomic analysis by mass spectrometry and data analysis

Proteomic samples were analyzed using a Thermo Orbitrap Velos mass spectrometer according to Weerapana et al., "Quantitative reactivity profiling predicts functional cysteines in proteomes," *Nature* 468:790-795 (2010). Peptides from on-bead tryptic digests were pressure loaded onto a 250 µm (inner diameter) fused silica capillary column packed with 4 cm C18 resin (5 µm, Phenomenex). Peptides were then eluted onto a 100 µm (inner diameter) fused silica capillary column packed with 3 cm strong cation exchange (SCX) resin followed by 10 cm C18 resin. Chromatographically separation of the peptide mixture was achieved using a 5-step multidimensional LC-MS (MudPIT) according to Washburn et al., "Large-scale analysis of the yeast proteome by multidimensional protein identification technology," *Nat Biotechnol* 19:242-247 (2001) in which Washburn et al. teaches of 0%, 25%, 50%, 80% and 100% salt bumps of $NH_4OAc$ (500 mM) salt bumps followed by an increasing gradient of $CH_3CN$ (0.1% $HCO_2H$) in $H_2O$. Peptides were analyzed by a Thermo Orbitrap Velos mass spectrometer set in data-dependent acquisition mode where two MS1 microscans [400-1800 mass to charge ratio (m/z)] were followed by 30 data-dependent fragmentation (MS2) scans. Dynamic exclusion (repeat count of 1, exclusion duration of 20 s) and monoisotopic precursor selection were enabled, whereas all other parameters were left at default values. MS2 spectra were extracted from raw data files using RAW Xtractor and searched using the ProLuCID algorithm against mouse and human, reverse-concatenated non-redundant (gene-centric) FASTA databases that were assembled from the Uniprot database (www.uniprot.org). The precursor-ion mass tolerance was set to 50 ppm and the fragment-ion mass tolerance was the default assignment of 0. Searches allowed for oxidation of methionine (+15.9949 m/z) as a variable modification and specified static modification of cysteine residues (+57.0215 m/z; iodoacetamide alkylation). Datasets were independently searched with light and heavy parameter files where light searches applied default masses to each amino acid and heavy searches specified static modifications on lysine (+8.0142 m/z) and arginine (+10.0082 m/z). Matched MS2 spectra from ProLuCID searches were assembled by protein and filtered using DTASelect (version 2.0.47) which allowed only half-tryptic or fully-tryptic peptides for identification and quantification. Peptides were restricted to a specified false positive rate of 1%. Redundant peptide identifications, if common between multiple proteins, were allowed, as database entries were limited to a single consensus splice variant. SILAC ratios were determined using in-house software (CIMAGE) (Weerapana et al., 2010)]. Briefly, MS1 ion chromatograms (+10 ppm) from "light" and "heavy" target peptide masses (m/z) were generated using a retention time window (+10 min) centered at the time the peptide ion was selected for MS/MS fragmentation, and subsequently identified. The ratio of "light" and "heavy" peptide peak areas are then calculated. To ensure the correct peak-pair is used for quantification, CIMAGE applies a co-elution correlation score filter ($R2 \geq 0.8$) for "heavy" and "light" peptide peaks to exclude target peptides with bad co-elution profiles. Furthermore, an "envelope correlation score" filter is applied to ensure the experimentally observed high-resolution MS1 spectrum matches ($R2 > 0.8$) the predicted isotopic distribution. Peptides detected as singletons, where only the heavy or light isotopically labeled peptide was detected and sequenced, but which passed all other filters described above, were given a standard ratio of 20, which is the maximum SILAC ratio reported here.

Proteomics Data Filtering

SILAC results for identification of UV-dependent probe targets and comparison of structurally related lipid probes in HEK293T and Neuro2a represents data combined from 2-3 separate biological replicates. The soluble and membrane fractions from each biological replicate were analyzed separately to improve protein coverage. Median peptide SILAC ratios were then filtered to assure each protein ratio was derived from three or more unique and quantified peptides and that the combined quantified peptide ratios possessed a standard deviation of less than 10. SILAC ratios complying with these criteria were then averaged with ratios acquired from replicates and the alternate fraction (membrane or soluble) to provide a final value which is reported in Table 3 (48054-701-101Table3.txt). If no replicate values were detected, the SILAC ratio from this single occurrence was included only if each target was also quantified in probe-versus-probe experiments according to the above criteria. Data from instances where a target was identified in a single replicate was included due to the analysis of probe-versus-No UV data where a >90% confirmation was found in the UV-dependence (SILAC ratio ≥3.0) of targets identified across multiple replicates. In some instances, a subpopulation of these singly quantified targets was also identified in both cell lines (Neuro2a and HEK293T). See Table 6 for a list of individual peptide sequences.

UV-dependent lipid probe targets were defined as proteins that complied with the following criteria: 1) the protein was identified and quantified (according to the above criteria) in both probe-versus-probe and probe-versus-No UV datasets; 2) the protein exhibited a mean SILAC ratio of ≥3.0 in probe-versus-No UV experiments; 3) the protein exhibited a mean SILAC ratio of <2.0 and >0.5 in probe-versus-probe. Only UV-dependent targets are shown in Table 3. For competition experiments, SILAC results were derived from 1-3 experiments. Only proteins that qualified as UV-dependent targets according to the above criteria were included in the analysis (see Table 4 and 5; 48054-701-101Table4.txt, 48054-701-101Table5.txt). Furthermore, SILAC ratios for each competition experiment were only included if they were derived from two or more unique and quantified peptides.

Lipid Probe Target Meta-Analysis

Figure 5:
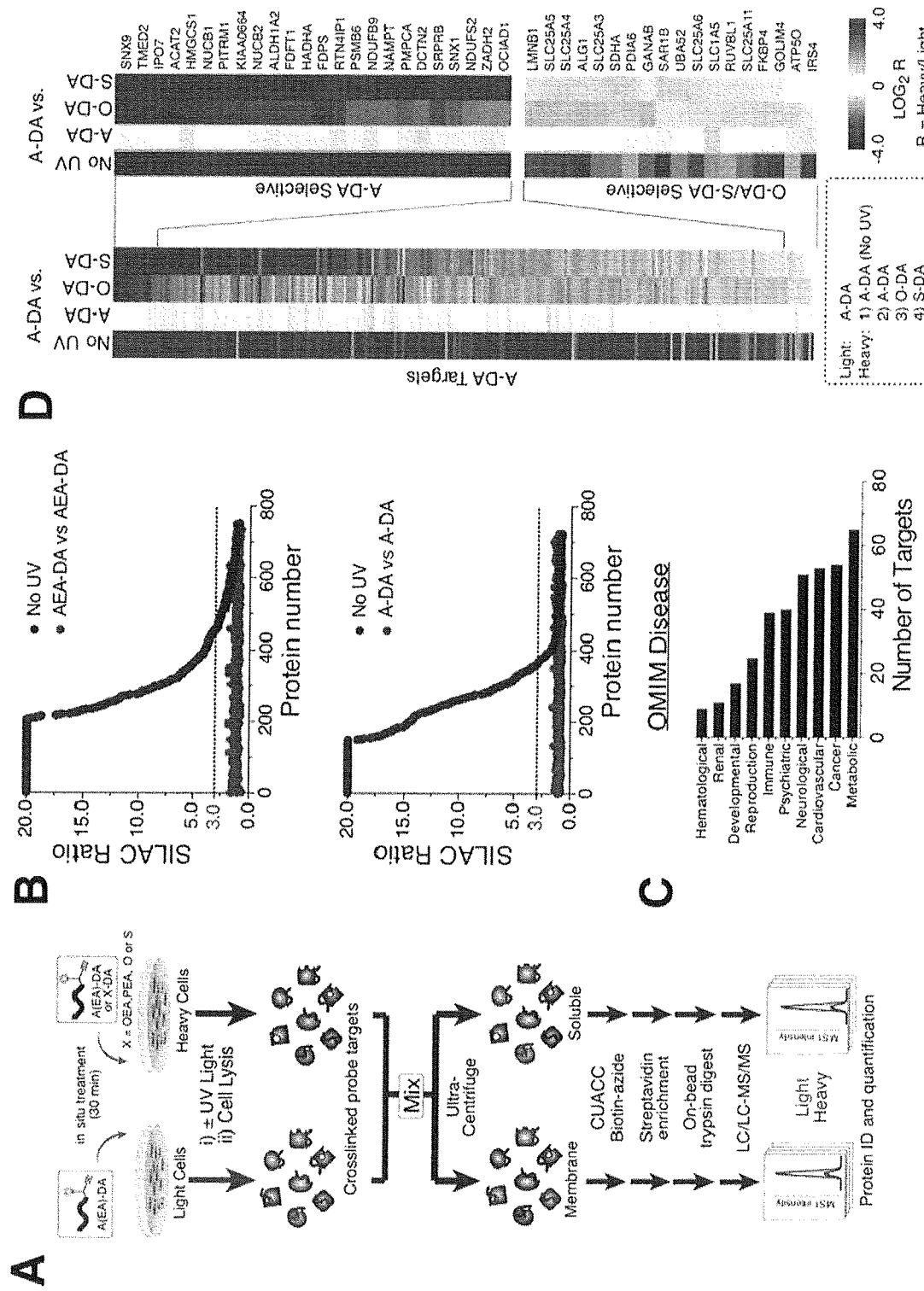
FIG. 5 shows protein targets of lipid probes mapped by quantitative MS-based proteomics. (A) Depiction of experimental workflow for mapping lipid-binding proteins in cells by quantitative MS-based profiling. Light- and heavy amino acid-labeled SILAC cells were first treated with the indicated lipid probe (20 μM) and comparison condition in complete media supplemented with fetal bovine serum (10%). After 30 min, the media was removed and the cells were irradiated for 10 min at 4° C. Heavy and light proteomes from the treated cells were mixed in equal proportions and the combined proteome was separated into membrane and soluble fractions by ultracentrifugation. Probe-labeled proteins were then conjugated to a biotin tag using CuAAC. Following streptavidin enrichment, probe targets were then digested on-bead and the resulting tryptic peptides were analyzed by multidimensional (strong cation exchange/reverse phase) liquid chromatography and tandem mass spectrometry. Targets were defined as proteins with ≥3 unique quantified peptides and SILAC ratios ≥3 in probe-versus-No UV experiments and ≤2 in probe-probe control experiments. (B) Heavy/light SILAC ratio plots for total proteins identified in experiments comparing the labeling profiles of the indicated lipid probe (20 μM) versus no-UV light (No UV; 20 μM probe without UV irradiation) or probe (both heavy and light cells treated with 20 μM probe) controls in Neuro2A cells. Dashed lines mark threshold ratio values (≥3-fold in No UV experiments and ≤2-fold in probe-probe experiments) for designation of lipid probe targets in Neuro2a cells. (C) Lipid probe targets that have been genetically linked to human diseases based on searches of the OMIM database. (D) Heat map showing the relative enrichment values for lipid probe targets by the A-DA probe compared to O-DA and S-DA probes, as well as compared to the A-DA probe itself with (A-DA) or without UV irradiation (No UV) as controls, in HEK293T cells. See also Table 3 (48054-701-101Table3.txt) for complete list of lipid probe targets and SILAC ratios from each indicated experiment. (E) Peptide MS1 chromatograms for representative AEA-DA-selective (HEATR3) and PEADA-selective (LSS) targets.
Figure 5:
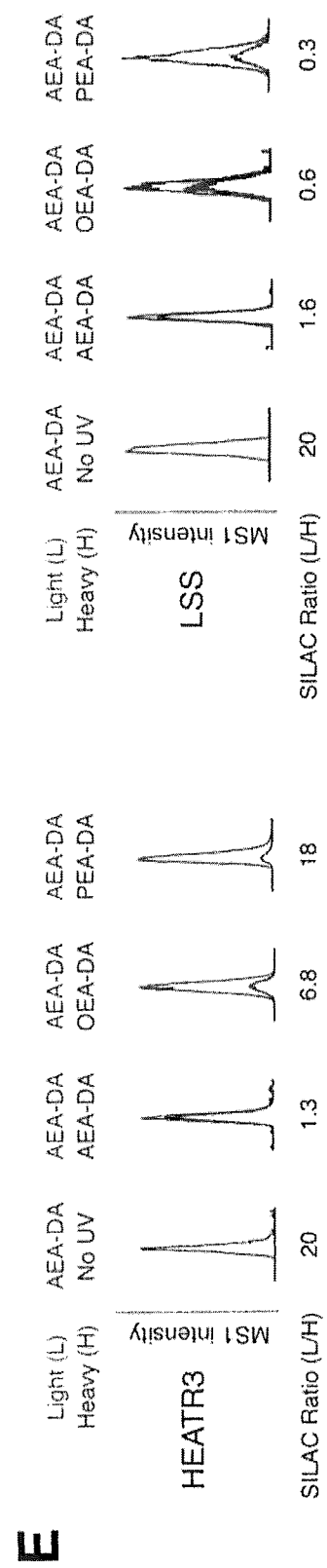
Figure 6:
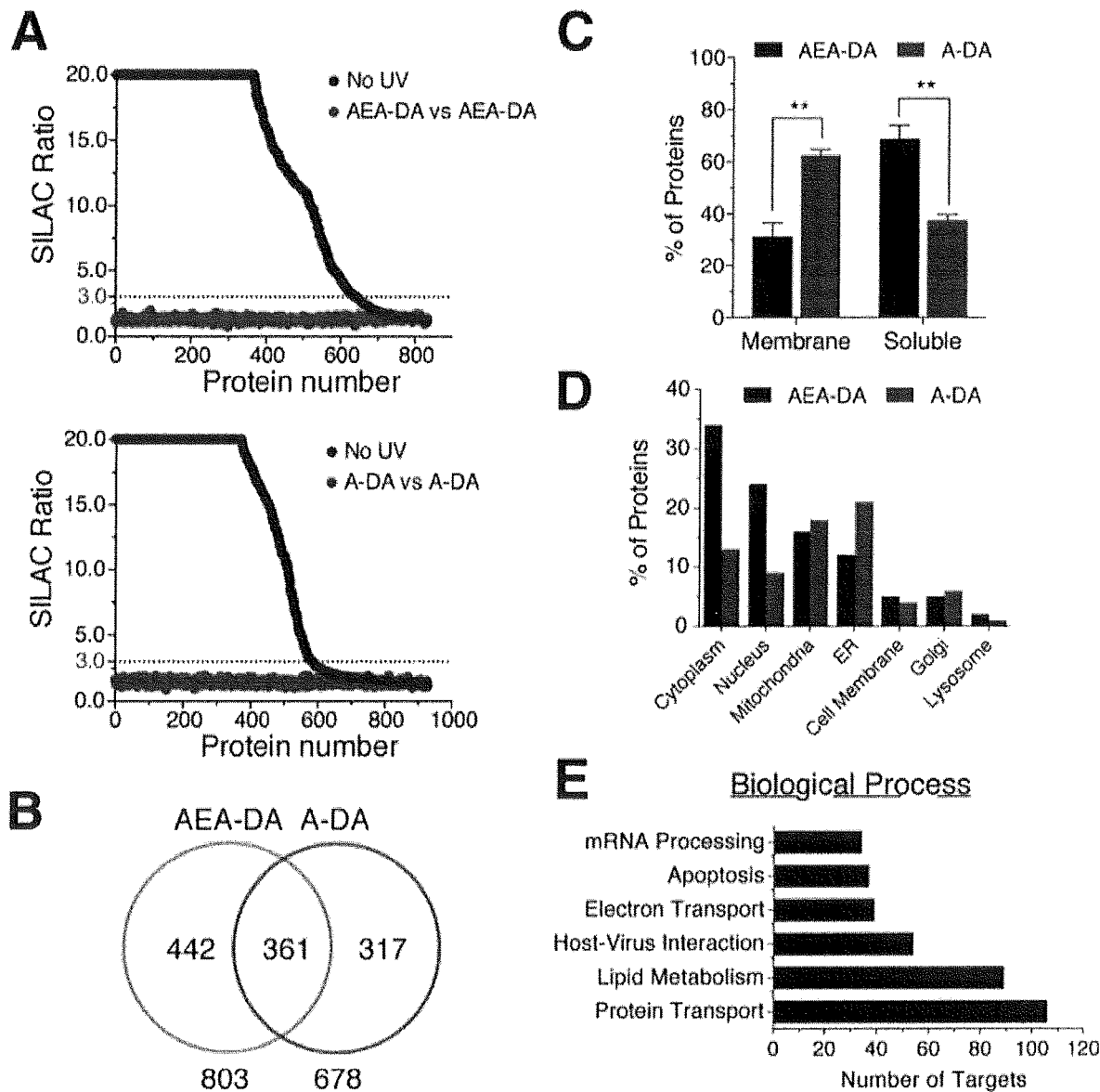
FIG. 6 illustrates protein targets of lipid probes mapped by quantitative proteomics. (A) Heavy/light SILAC ratio plots for total proteins identified in experiments comparing the labeling profiles of lipid probes (20 μM) versus a 'No UV' control (20 μM probe without UV irradiation) or the equivalent probe (both heavy and light cells treated with 20 μM of the same probe) in HEK293T cells. Dashed lines mark threshold ratio values (≥3-fold in No UV experiments) for designation of lipid probe targets (also see FIG. 5). (B) Venn diagram of shared and unique protein targets of AEA-DA and A-DA in HEK293T and Neuro2a cells. (C—F) Analysis of lipid probe targets based on (C) presence (membrane) or absence (soluble) of known/predicted transmembrane domains; (D) known/predicted subcellular distribution; (E) involvement in specific biological processes; and (F) protein class distribution. Categories were assigned based on UniProt annotations. (G) Diagram highlighting lipid probe targets (red) in major fatty acid metabolic pathways. SILAC ratios from probe-versus-No UV experiments are indicated in parentheses next to gene names (data shown are for the A-DA probe in HEK293T cells except for CPT1A, which was detected with the A-DA probe in Neuro2a cells). For instances where multiple isoforms of a given protein is enriched (i.e., ACSL and GPAT), the highest ratio across all isoforms is presented. (H) Heat map showing the relative protein enrichment values for the AEA-DA probe compared to OEA-DA and PEA-DA probes, as well as compared to the AEA probe itself with (AEA-DA) or without UV irradiation (No UV) as controls, in HEK293T cells. See FIG. 5D for a similar analysis of the A-DA probe series and Table 3 for complete list of lipid probe targets.
Figure 6:
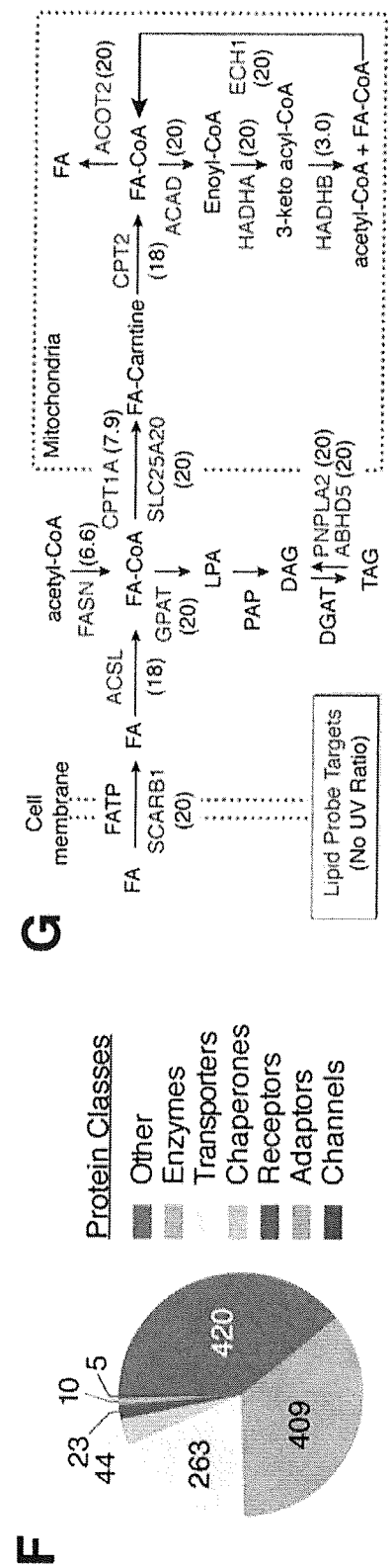
Figure 6:
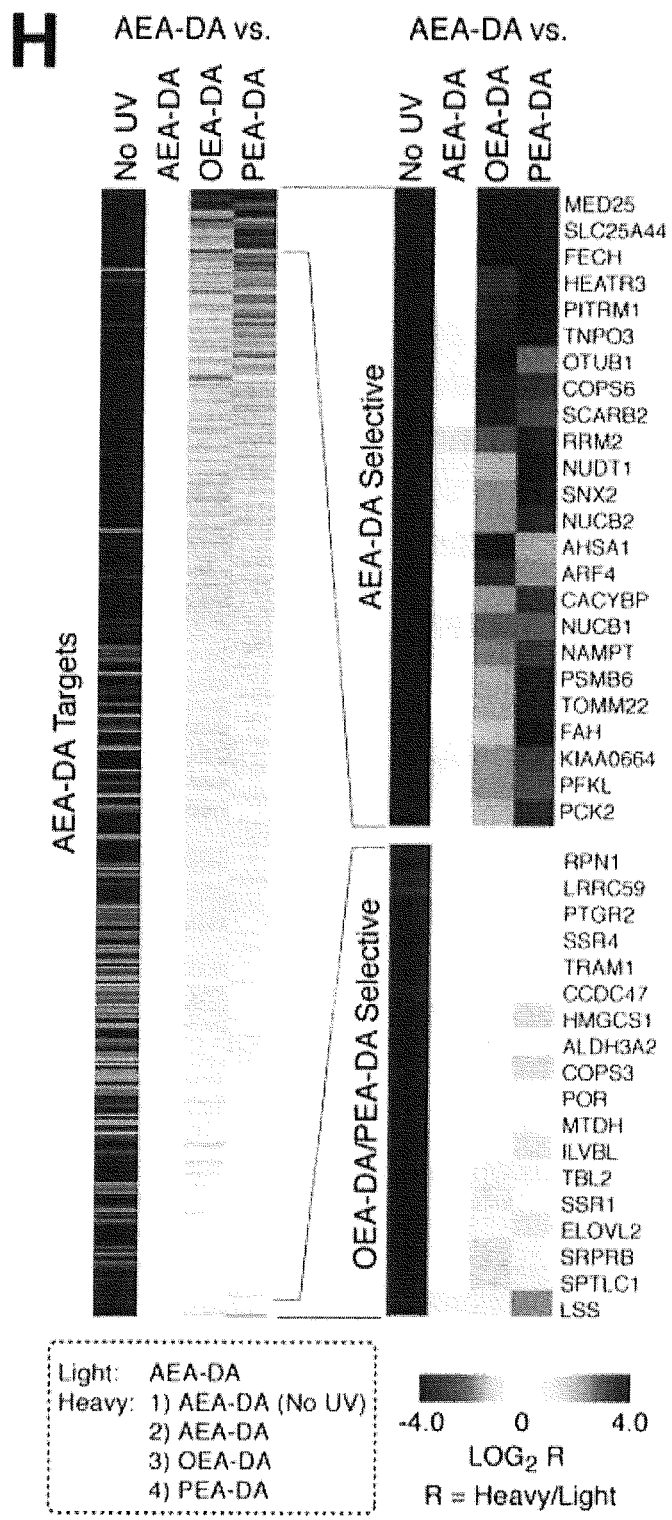

Analyses of the final lipid probe target list as found in Table 3 and FIGS. 5 and 6 were conducted using the ID Mapping feature of UniProt Database (http://www.uniprot.org/uploadlists/) with the exception of the OMIM analysis which was performed using the DAVID Bioinformatics Database (http://david.abcc.ncifcrf.gov/tools.jsp). Membrane proteins were defined as proteins possessing known or predicted transmembrane domains (UniProt analysis), and the remaining targets were considered soluble. Statistical analysis of membrane and soluble targets for each probe were determined by combining No UV datasets from HEK293T (n=2) and Neuro2a (n=2) cell lines for AEA-DA and A-DA probes, and calculating the percent of total probe-enriched targets (SILAC ratio ≥3.0) that possess or lack transmembrane domains (i.e. membrane or soluble, respectively). Data are presented as the mean percentage of total probe targets±SEM; n=4/group. **$P<0.01$ for AEA-DA versus A-DA probe targets.

Transient Protein Expression in HEK293T Cells

Full-length cDNAs encoding for the each protein of interest were subcloned into pcDNA3.1 myc-His A (Invitrogen) or used directly for transfections if available in a eukaryotic expression vector. HEK293T cells were grown to ~70% confluence under standard growth conditions before adding the appropriate cDNA [control cells ("mock") received an equal amount of empty pcDNA3.1 myc-His A vector] and FuGENE 6 or X-tremeGENE HP (Roche) transfection reagent according to the manufacturer's instructions. Cells were incubated for 36-48 hours before labeling in situ or harvesting for in vitro experiments.

Recombinant NUCB1 Expression and Purification

Human NUCB1 lacking the N-terminal signal sequence (M1-A26) was subcloned into pET45b(+) vector (Novagen) using the following PCR primers for amplification: 5'-CAT CAA TTG TGT GCC CCT GGA GAG AG-3' and 5'-AGC AAG CTT TAC AGA TGT TGG GGC ACC-3'. Following transformation of *Escherichia coli* strain BL21 (DE3) with hNucb1ΔSSpET45b(+), a single colony was isolated and grown in Terrific Broth containing carbenicillin (100 mg/L) at 37° C. to an $OD_{600}$ of 0.8. Protein expression was induced with IPTG (1.0 mM) and the cells were incubated at 20° C. with shaking overnight. After centrifugation, cells pellets were resuspended in cold buffer containing HEPES (0.05M), NaCl (0.03 M), imidazole (5.0 mM), DNase (0.1 mg/mL), MgCl2 (1.0 mM), CaCl2 (1.0 mM) and EDTA-free Complete Protease Inhibitor Cocktail and lysed using a microfluidizer. Cell lysates were centrifuged (8,000×g, 30 min, 4° C.) and the supernatant was stirred with Talon cobalt affinity resin (0.4 mL/g cells) (Clontech) for 1 h at 4° C. The suspension was applied to a column and the retained resin was washed with HEPES buffer containing 500 mM NaCl until the eluent was clean of DNA and protein (A280/260) and then with HEPES buffer containing 10 mM imidazole (5 mL/1 mL resin). Protein was then slowly eluted with HEPES buffer containing 50 mM imidazole in 1.0 mL fractions and the combined fractions containing hNUCB1 were passed through a Sephadex G-25M column to remove imidazole and concentrated in an Amicon centrifugal filter device (Millipore). These conditions produced hNUCB1 at approximately 10 mg/L of culture; however, several lower molecular weight fragments were also present in this preparation. hNUCB1 was further purified by size exclusion chromatography.

FluoPol Assay Optimization

FluoPol conditions were optimized by screening various concentrations of Fl-AEA, hNUCB1, $CaCl_2$ and Pluronic F-127 against positive and negative controls. Arachidonic acid (20 μM final) was used as a positive control, and DMSO as a negative. Additionally, protein-free controls were used to normalize for background signal. Optimal conditions were selected based on maximal probe competition, and were found to be: 1.0 μM hNucb1, 0.5 μM Fl-AEA, 20 μM $CaCl_2$, and 0.01% Pluronic F-127, using DPBS as a buffer system. The Z'-factor for these conditions was determined to be 0.54, indicating a high signal to noise assay.

High Throughput Screen

A 10 μL solution of hNUCB1 (1 μM), Fl-AEA (0.5 μM), $CaCl_2$ (20 μM), and Pluronic F-127 (0.01%) was added to a Greiner 384-well plate. Additionally, in some wells protein was omitted to serve as a blank control for background signal. To the protein containing wells 16,000 compounds (50 nL in DMSO, 2 mM) from the Maybridge Hitfinder library were added by a pin-tool robot. Additionally, on each plate to some wells arachidonic acid (20 μM final) or DMSO were added as positive and negative controls to allow normalization between plates. The plates were allowed to incubate for 5 minutes at room temperature, then fluorescence polarization was measured by measuring fluorescence intensity through polarized 595 nm filters. Hits were selected based on maximal probe competition.

In Vitro Gel-Based Competition Lipid Probes

Cell lysates (1.0 mg/mL), the indicated lipid probe (2.5 or 5 μM) and, for recombinant NUCB1 competition experiments, purified hNUCB1 (250 nM) and CaCl2 (100 μM) were mixed on ice. DMSO or competitors were then added to the proteome mixture (50 µM) in 96-well plates and each sample was incubated for 15 min at 37° C. The samples were then irradiated with UV light and subjected to previously described click chemistry conditions. As before, each reaction was quenched with 4×SDS loading buffer (17 µL), and proteins were resolved using SDS-PAGE (10% acrylamide gel) and analyzed by in-gel fluorescent scanning on a Hitachi FMBIO-II flatbed fluorescence scanner. NUCB1 competition was quantitatively assessed by measuring the fluorescent intensity of the corresponding gel band using ImageJ 1.48 v and normalizing this value by a non-competed gel band to control for loading differences. Because residual, non-competitive NUCB1 labeling were observed at the highest concentration of the tested NUCB1 ligands, the IC50's were determined by calculating the percent of maximal competition (100 µM, MJN228) rather than percent of the background signal in lanes without recombinant NUCB1 added.

Mapping Probe-Modified Peptides

Mapping Probe-Modified Peptides with Purified NUCB1:

To a solution of recombinant hNUCB1 (50 µL, 5.0 mg/mL) in DPBS and $CaCl_2$ (100 µM) was added either DMSO or AEADA (50 µM final concentration). After incubating at 37° C. for 15 min, the mixture was irradiated with UV light for 10 min at 4° C. Standard reduction and alkylation steps were omitted because of the absence of cysteine residues in hNUCB1. Thus, the probe crosslinked hNUCB1 solution was diluted with urea (150 µL, 8.0 M in DPBS) and trypsinized by addition of sequence grade porcine trypsin (5.0 µg, Promega) and incubation overnight at 37° C. The samples were then acidified with $HCO_2H$ (16 µL) and a 10 µL aliquot was pressure loaded onto a 100 µm (inner diameter) fused silica capillary column with a 5 µm tip containing 10 cm C18 resin (5 µm, Phenomenex). Peptides were eluted from the column using a 180 min gradient from 0% to 50% Buffer B (Buffer A: 5% acetonitrile, 95% water, 0.1% formic acid; Buffer B: 80% acetonitrile, 20% water, 0.1% formic acid) and analyzed on an LTQ-Orbitrap mass spectrometer (ThermoFisher).

Mapping Probe-Modified Peptides in Cells:

Experiments were performed as described above using the AEA-DA probe (100 µM) in 3.0 mL of DMEM (serum-free) and Neuro2A cells without (twelve replicates; ten biological; two technical). For the ligand competition study, cells were treated with the AEA-DA probe (50 µM) and DMSO or MJN228 (50 µM) treatment. Cells were harvested and processed as described above. Whole cell lysates (500 µL at 1.5 mg/mL) were processed for MS analysis using the previously described isoTOPABPP protocol (Speers and Cravatt, 2005). In brief, for global mapping of AEA-DA-modified peptides, proteomes were split into two fractions, which were subjected to click chemistry conditions with either light or heavy isotopically labeled TEV-tags. For the MJN288 competition study, proteomes were subjected to click chemistry conditions with either light (DMSO) or heavy (MJN228-treated) TEV-tags. Light and heavy-tagged proteomes in each experiment were then combined, and, following enrichment of probe-labeled targets using streptavidin beads, proteins were digested on-bead with trypsin and remaining immobilized peptides released with a subsequent TEV protease digestion. The resulting probe-modified peptides were collected for MS analysis, which was performed as described above with differences in the salt bumps applied in the chromatographic gradients which were 0%, 30%, 60%, 90% and 100% NH4OAc (500 mM). The protein identification searches of the MS data were performed using the same software packages described above with the following changes applied to identify the peptides modified with AEA-DA and the cleaved TEV tag. All amino acids were considered as possible residues for modification. To facilitate the computational searches, sets of up to 3 amino acids were searched using ProLuCID and filtered with DTASelect as described above. The mass of the modification used to search for probe-modified peptides was +727.4745 m/z for the probe plus the light TEV-tag and +733.4831 m/z for the heavy counterpart. The isoTOP ratios for probe labeled peptides were quantified using the in-house software CIMAGE (Weerapana et al., 2010). For global mapping experiments, AEA-DA-modified peptides were expected to show a ratio of "heavy" and "light" signals of ~1.0 (0.5<ratio<2.0) and were required to have been detected in at least two of the twelve replicate experiments. Proteins containing probe-modified peptides were further categorized as having: i) one principal probe-modified peptide (where only a single probe-modified peptide was identified for the protein or the protein possessed a probe-modified peptide that was detected in at least 75% of the experiments and no other probe-modified peptide that was detected in more than 33% of the experiments); ii) two probe-modified peptides; or iii) three or more probe-modified peptides.

Untargeted Metabolomics

Discovery metabolite profiling was performed as described by Saghatelian et al., "Assignment of endogenous substrates to enzymes by global metabolite profiling," *Biochemistry* 43:14332-14339 (2004) with several modifications. Neuro2a cells were plated at a density of $4 \times 10^6$ cells/10 cm plate and grown for 18 h. In glass vials, solutions of vehicle or test compounds were prepared in serum- and dye-free DMEM and warmed to 37° C. in a water bath. The media from the cells was removed and cells were washed with DPBS (2×5.0 mL) before adding freshly prepared media solutions containing vehicle or compound. After incubating for 6 h at 37° C. and subsequent removal of the media, the cells were harvested by scrapping in cold DPBS (3 mL) and pelleted by centrifugation in glass vials. The pellets were washed once with cold DPBS (3 mL) and then cold $CH_3Cl$:MeOH (2:1) (3 mL) was added. After vortexing, the vials were centrifuged (3,000×g, 10 min, 4° C.) and the bottom (organic) layer was transferred to a new glass vial and concentrated under a stream of $N_2$. Samples were stored at −80° C. until the day of analysis when they were reconstituted in Mobile Phase A (100 µL, see below).

Lipid extracts were analyzed by LC/MS in both positive and negative modes using an Agilent 6520 QTOF instrument and LC separation performed on a Kinetex reversed phase $C_{18}$ column (50×4.6 mm, 2.6 µm particle size, 100A). Mobile phase A was composed of 5:1:4 isopropanol:methanol:water and Mobile phase B was composed of 99:1 isopropanol:water. Both mobile phases also contained 0.1% AcOH and $NH_4OAc$ (5 mM) to facilitate ionization and LC separation. Following injection (20 µL), samples were eluted with a constant flow rate (350 µL/min) using the following gradient: Mobile Phase A (100%), 1-3 min; Mobile Phase B increased linearly to 20%, 3-5 min; Mobile Phase B increased linearly to 30%, 5-25 min; Mobile Phase B increased linearly to 95%, 25-35 min Mobile Phase B held constant at 95%, 35-40 min. To minimize carryover, LC solvents were cycled between 100% Mobile Phase A and 100% Mobile Phase B over 5 min after each run. Data analysis was performed using XCMS (Smith et al., 2006) software which is freely available online (https://xcmsonline.scripps.edu).

In Vitro Enzyme Activity Assays

FAAH activity was measured by AEA hydrolysis: The membrane fraction of Neuro2a lysates (200 µL, 2.0 mg/mL) was incubated with DMSO or the test compound (1.0-250 µM) at 37° C. After 15 min, AEA-$d_8$ (25 µM) was added and the samples were incubated for an additional 30 min and then quenched by the addition of two volumes of $CHCl_3$: MeOH (2:1) containing pentadecanoic acid (PDA) (1.0 nmol) as an internal standard. After centrifuging (2,000×g, 5 min, 4° C.) to separate the organic and aqueous layers, the lower organic layer was transferred to a clean vial and analyzed by LC/MS as previously described. (Long et al., 2009) Pure humanized rat FAAH (Mileni et al., 2008) (5.0 ng/µL) was assayed in the same manner. Product levels were quantified by determining peak areas in relation to PDA.

PTGS2 activity was measured by MS-based analysis of AEA oxidation: human recombinant PTGS2 (Cayman) was reconstituted in DPBS (1:200) containing EDTA (5 mM), phenol (2 mM), and hemin (1 µM) at 0° C. An aliquot of this mixture (200 µL) was incubated with DMSO or the test compound (25 or 50 µM) at 37° C. After 30 min, freshly purified AEA (25 µM) was added and the samples were incubated for an additional 30 min and then quenched by the addition of two volumes of $CHCl_3$:MeOH (2:1) containing $PGE_2$-EA-$d_9$ (320 nmol respectively) as an internal standard. After centrifuging (3,000×g, 5 min, 4° C.) to separate the organic and aqueous layers, the lower organic layer was transferred to a clean vial and analyzed by LC/MS as previously described. MS analysis of prostamides was performed as described below. $PGE_2$-EA levels formed from AEA oxidation were quantified by determining peak areas in relation to $PGE_2$-$d_9$.

LC-MS Analysis of Lipids from Neuro2a Cells

Neuro2a cells were treated and lipids extracted as described above. A mixture of internal standards [AEA-$d_4$ (10 pmol), 2-AG-$d_5$ (100 pmol), AA-$d_8$ (100 pmol), PEA-$d_4$ (100 pmol), PDA (1.0 nmol)] was added to the organic phase prior to extracting cells. NAEs, MAGs, AA and NATs were analyzed similarly to previously described methods (Saghatelian et al., 2004). The following MS parameters were used to measure the indicated metabolites by MRM (precursor ion, product ion, collision energy, polarity): NAE 20:4 (AEA) (348, 62, 12, positive), AEA-$d_4$ (352, 66, 12, positive), NAE 16:0 (PEA) (300, 62, 12, positive), PEA-$d_4$ (304, 62, 12, positive), NAE 18:0 (328, 62, 12, positive), NAE 18:1 (326, 62, 12, positive), NAE 18:2 (324, 62, 12, positive), 2-AG (379, 287, 8, positive), 2-AG-$d_5$ (384, 287, 8, positive), AA (303, 259, 4, negative), AA-$d_8$ (311, 267, 4, negative), NAT 20:4 (410, 80, 35, negative), NAT 22:1 (444, 80, 35, negative), NAT 24:1 (472, 80, 35, negative), NAT 24:0 (474, 80, 35, negative), NAT 26:0 (502, 80, 35, negative). The indicated lipids were quantified by measuring the area under the peak relative to an internal standard (AEA-$d_4$ for AEA and NAE 18:2; PEA-$d_4$ for PEA, NAE 18:1 and NAE 18:0; 2-AG-$d_5$ for 2-AG; AA-$d_8$ for AA and 20:4 NAT; PDA for all other NATs).

RNA Interference of NUCB1 in A549 Cells

Knockdown of NUCB1 in A549 cells was accomplished using short-hairpin RNA constructs (pLKO.1-puro vectors: Sigma-Aldrich) with the following sequences:

```
shNUCB1(1):
5'-CCGGGAACACGAGAGACGGCGTTATCTCGAGATAACGCCGTCTCTCGT
GTTCTTTTTG-3';

shNUCB1(2):
5'-CCGGCCCAATGTACAGGTGGATCATCTCGAGATGATCCACCTGTACAT
TGGGTTTTTG-3'.
```

To generate lentivirus particles, HEK293T cells were cotransfected with the appropriate pLKO.1 vector along with VSVG and dVPR helper vectors using X-tremeGENE HP (Roche). After 36 h, media from the transfected HEK293T cells was used to transduce A549 cells which were grown for 4 days in media containing puromycin (1.0 µg/mL). Infected cells were then expanded for metabolite analysis and confirmation of knockdown by Western blot. Prior to extraction of lipids, old media was removed and replaced with serum-free RPMI and cells were incubated for 6 h before harvesting. Lipids were extracted and measured as described above.

Oxidative Metabolism of AEA in A549 Cells

A549 cells were seeded in 6 cm plates at a density of 2.5×10$^6$ cells/plate, incubated for 12-18 h and then stimulated with PMA (10 nM) for 6 h. In glass vials, solutions of vehicle or compound were prepared in serum- and dye-free RPMI-1640 and warmed to 37° C. in a water bath. The media from the PMA-stimulated cells was removed and cells were washed with DPBS (2×3 mL) before adding freshly prepared media solutions containing vehicle or compound (2 mL/plate). After incubating for 30 min at 37° C., a solution of BHT-stabilized AEA (60 µM AEA; 60 µM BHT) in the same media was added to the cells (1.0 mL/plate) and incubated for 1 h. The media from the cells was then transferred to glass vials containing MS internal standards [$PGE_2$-EA-$d_4$ (25 pmol)], centrifuged (1,500×g, 5 min) to remove detached cells and then loaded onto pre-equilibrated reversed phase SPE cartridges (Phenomenex, Strata-X 33 µm, 60 mg/3 mL). After washing cartridges with 5% MeOH/$H_2O$ (3 mL), prostamides were eluted with MeOH (1.0 mL) and the eluent was concentrated under a stream of $N_2$. Concentrated samples were stored at −80° C. until the day of analysis when they were reconstituted in Mobile Phase A [100 µL, 30% $CH_3CN$ in $H_2O$ (0.1% AcOH, 5.0 mM $NH_4OAc$)].

Media extracts were analyzed by LC/MS/MS with LC separation performed on a Kinetex reversed phase C18 column (50×4.6 mm, 2.6 µm particle size, 100A). Mobile phase A was composed of 30% (v/v) $CH_3CN$ in $H_2O$ and Mobile phase B was composed of 50% (v/v) $CH_3CN$ in i-PrOH. Both mobile phases also contained 0.1% AcOH and $NH_4OAc$ (5 mM) to facilitate ionization and LC separation. Following injection (20 µL), samples were eluted with a constant flow rate (350 µL/min) using the following gradient: Mobile Phase A (100%), 1-3 min; Mobile Phase B increased linearly to 20%, 3-5 min; Mobile Phase B increased linearly to 50%, 5-7 min; Mobile Phase B held constant at 50%, 7-8 min; Mobile Phase B increased linearly to 75%, 8-9 min; Mobile Phase B held constant at 75%, 9-11 min; Mobile Phase B increased linearly to 100%, 11-12 min; Mobile Phase B held constant at 100%, 12-15 min. To minimize carryover, LC solvents were cycled between 100% Mobile Phase A and 100% Mobile Phase B over 5 min after each run.

MS analysis of prostamides was performed on an Agilent 6460 Triple Quadrupole LC/MS System with operating conditions as follows: gas temperature (300° C.); gas flow (9 L·min$^{-1}$); nebulizer (45 psi); sheath gas temperature (300° C.); sheath gas flow (12 L·min$^{-1}$); positive and negative capillary voltage (3.5 kV). Analysis was achieved using multiple reaction monitoring with precursor to product ion transitions, optimized collision energies (CE) as listed below and prostamide quantification was achieved by normalized of analyte peaks relative to a deuterated prostamide internal standard ($PGE_2$-EA-$d_4$) to account for differences in extraction efficiency. The following MS parameters were used to measure the indicated metabolites by MRM (precursor ion, product ion, collision energy, polarity): PGF$_2\alpha$-EA (380, 344, 4, positive), PGE$_2$-EA-d$_4$ (382, 66, 25, positive), PGE$_2$-EA (378, 62, 25, positive). A non-deuterated PGF$_2\alpha$-EA standard (Cayman) was used to confirm the retention time and fragmentation of PGF$_2\alpha$-EA generated by A549 cells.

Determination of Prostaglandin Production in A549 Cells

A549 cells were seeded in 6 cm plates at a density of 4×10$^6$ cells/plate, incubated for 12-18 h to allow cells to adhere. In glass vials, solutions of vehicle (DMSO) or compound (10 μM each) were prepared in serum- and dye-free RPMI-1640 and warmed to 37° C. in a water bath. The old media was removed from each plate and cells were washed with DPBS (2×3 mL) before adding freshly prepared media solutions containing vehicle or compound (3 mL/plate). After incubating for 30 min at 37° C., cells were then stimulated with PMA (10 nM) for 8 h. The media from the cells was then transferred to glass vials containing MS internal standards [PGE2-d$_9$ (10 pmol), PGD$_2$-d$_9$ (10 pmol) and TXB$_2$-d$_4$ (10 pmol)], centrifuged (1,500×g, 5 min) to remove detached cells and then loaded onto preequilibrated reversed phase SPE cartridges (Phenomenex, Strata-X 33 μm, 60 mg/3 mL). After washing cartridges with 5% MeOH/H2O (3 mL), analytes were eluted with MeOH (1.0 mL) and the eluent was concentrated under a stream of N2. Concentrated samples were stored at −80° C. until the day of analysis when they were reconstituted in Mobile Phase A [100 μL, 30% CH$_3$CN in H$_2$O (0.1% AcOH)]. Media extracts were analyzed by LC/MS/MS with LC separation performed on a Kinetex reversed phase C18 column (50×4.6 mm, 2.6 μm particle size, 100 Å). Mobile phase gradients were identical to those described above for prostamide analysis and the composition Mobile phases A and B differed only by lacking NH$_4$OAc (5 mM). The following MS parameters were used to measure the indicated metabolites by MRM (precursor ion, product ion, collision energy, polarity): PGE2 (351, 271, 12, negative), PGE$_2$-d$_9$ (360, 280, 12, negative), TXB$_2$ (369, 169, 6, negative), TXB$_2$-d$_4$ (373, 173, 6, negative). PGE2 and TXB$_2$ levels were quantified by determining peak areas in relation to their deuterated internal standard.

Statistical Analysis

Metabolite data are shown as mean±SEM (n=3-5/group). Differences between two groups were determined using Student's t test (unpaired, two-tailed) and significance was denoted for P values <0.05. IC50 values for NENF and NUCB1 ligands were determined using GraphPad Prism software to calculate 95% confidence intervals (CI).

Chemical Proteomic Probes for Mapping Lipid-Protein Interactions

Figure 3:
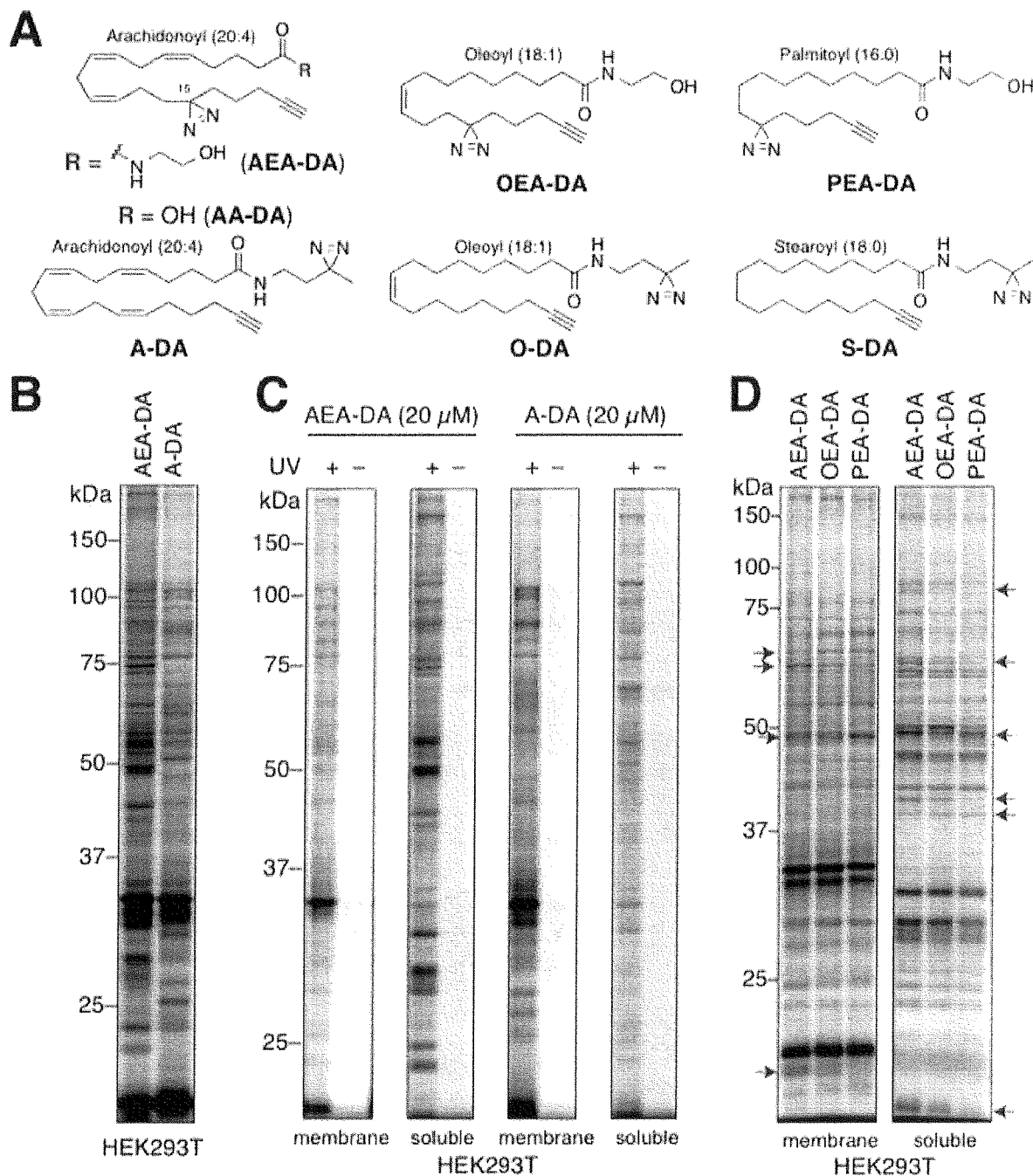
FIG. 3 illustrates chemical proteomic probes for mapping lipid-binding proteins in cells. (A) Structures of lipid probes featuring arachidonoyl (AEA-DA, AA-DA and A-DA), oleoyl (OEADA and O-DA), palmitoyl (PEA-DA) and stearoyl (S-DA) acyl chains, as well as photoreactive (diazirine) and alkyne groups. (B) AEA-DA and A-DA probes which show overlapping, but distinct protein interaction profiles in HEK293T cells. Cells were treated with each probe (20 µM) for 30 min in situ before photocrosslinking and analysis of probe-modified proteins as described in FIG. 4. (C) Arachidonoyl probe labeling of membrane and soluble proteins depend on UV irradiation of cells. (D) Comparative labeling profiles of lipid probes (20 µM, 30 min) in HEK293T cells. Red and blue arrows mark representative proteins preferentially labeled by arachidonoyl and oleoyl/palmitoyl probes, respectively. See FIG. 4C for profiles of A-DA, O-DA and S-DA.

In some embodiments, chemical proteomic probes described herein offer a tool to globally map the cellular targets of both natural and unnatural small molecules in native biological systems. In some instances, a probe relies on innate chemical reactivity with protein residues. In other instances, a probe exploits binding affinity and light-induced crosslinking reactions to capture a protein. In some embodiments, the latter group typically possesses: (i) a photoreactive element that converts reversible small molecule-protein interactions into stable, covalent adducts upon ultraviolet (UV) light irradiation; (ii) an alkyne, which serves as a sterically minimized surrogate reporter allowing late-stage conjugation to azide tags by copper-catalyzed azide-alkyne cycloaddition (CuAAC or "click") chemistry; and (iii) a binding element that directs the probe towards proteins that recognize particular structural features. In some instances, a set of lipid probes are prepared for identifying proteins that interact with fatty acid-derived lipids in cells. In some embodiments, a set of probes are prepared that contain a diazirine photoreactive group, an alkyne handle, and lipids, such as for example, arachidonic (C20:4), oleic (C18:1), palmitic (C16:0), and stearic (C18:0) (FIG. 3A).

In some instances, within the arachidonoyl subset of probes, fatty acid- and fatty acid amide-based probes (AA-DA and AEA-DA, respectively) were synthesized and their potential were evaluated to bind and covalently modify (under UV-light exposure) proteins in human cells by gel-based profiling. For example, HEK293T cells were treated with probe (AA-DA or AEA-DA; 20 μM, 30 min), irradiated with UV light (10 min, 4° C.), lysed and the cell proteomes fractionated into membrane and soluble components by centrifugation prior to conjugation to a fluorescent reporter tag (Rh-N3) using CuAAC (FIG. 4A). Analysis of probe targets by SDS-PAGE and in-gel fluorescence scanning revealed distinct protein labeling profiles for each probe (FIG. 4B). The AA-DA probe showed almost exclusive labeling of membrane proteins. In some instances, this was a consequence of rapid sequestration of this probe into membranes through its metabolic incorporation into phospho/neutral-lipids or into lipidated proteins. The AEA-DA probe showed substantial labeling of both soluble and membrane proteins in HEK293T cells (FIG. 4B). In some instances, the labeling profile of the AEA-DA probe reflected a limited capacity of the cell to metabolize this amidated probe, which undergoes enzyme-mediated hydrolysis prior to incorporation into other lipids or proteins. In some instances, the fatty acid amide probes were selected for chemical proteomic mapping of lipid-binding proteins in cells.

A set of lipid probes that featured intact acyl chains and a diazirineamide head group (A-DA; O-DA, S-DA; FIG. 3A) was also prepared. In some instances, the diazirine group was positioned at different locations (e.g. acyl chain and head group). In some instances, the differing positions of the diazirine group provide wider range of interaction with lipid binding proteins. In some instances, the AEA-DA and A-DA probes showed overlapping, but distinct protein labeling profiles in HEK293T cells (FIG. 3B). The protein-labeling events for both probes were UV light-dependent, and in some instances, reflect reversible binding interactions between the probes and cellular proteins (FIG. 3C). The polyunsaturated arachidonoyl probes (AEA-DA and A-DA) also showed a more extensive proteomic labeling profiles compared to the monounsaturated (OEA-DA, O-DA) or saturated (PEA-DA, S-DA) lipid probes (FIG. 3D and FIG. 4C).

Landscape of Lipid-Binding Proteins in Cells

The protein targets of the AEA-DA and A-DA probes were identified using stable-isotope labeling by amino acids in cell culture (SILAC) and liquid chromatography-tandem mass spectrometry (LC-MS/MS). Isotopically "light" cells served as a static control for each experiment and were treated with either AEA-DA or A-DA (20 μM, 30 min) before UV irradiation (FIG. 5A). Isotopically "heavy" cells served as comparison groups and were treated with: (i) the same conditions as the "light" cells (probe-versus-probe control); (ii) the same probe as the "light" cells, but not crosslinked with UV light (probe-versus-No UV); or (iii) the corresponding oleoyl (18:1, OEA-DA or O-DA) or fully-saturated (C16:0, PEA-DA; C18:0, S-DA) probes. Performing these SILAC experiments in both a human (HEK293T) and mouse (Neuro2a) cell line provided an extensive inventory of lipid probe targets-defined as proteins with at least three unique quantifiable peptides that were labeled by either A-DA or AEA-DA in a UV-dependent manner (SILAC ratio ≥3.0 in probe versus-No UV experiments) and not enriched in probe-versus-probe control experiments (SILAC ratio <2.0) (FIG. 6A and FIG. 5B).

In some instances, more than 1000 proteins were enriched from HEK293T and Neuro2a cells by the A-DA and AEA-DA probes. In some cases, a set of probe-specific targets were identified for both AEA-DA and A-DA (442 and 317, respectively; FIG. 6B). In some instances, the AEA-DA and A-DA probes target both soluble and membrane proteins, (FIG. 6C), which correspond to an enrichment of these protein targets in cytoplasmic/nuclear and endoplasmic reticulum (ER) compartments (FIG. 6D). In some embodiments, these differences reflect the lipophilicity (i.e., c Log P) of the A-DA probe, promoting its localization in membranes.

In some embodiments, categorizing the lipid probe targets in relation to their functions in biological pathways reveal enrichment of proteins involved in various membrane biology processes, including protein transport, lipid metabolism, and host-virus interactions (FIG. 6E). Analysis of the probe targets through the Online Mendelian Inheritance in Man (OMIM) database revealed links to numerous diseases, including metabolic disorders, cancer, and cardiovascular and neurological disease (FIG. 5C). Proteins from different functional classes were enriched by the lipid probes (FIG. 6F). In some instances, protein targets include enzymes and lipid carriers involved at almost every node of fatty acid uptake (SCARB1), transport (SLC25A20), biosynthesis (FASN, PNPLA2) and catabolism (ACADs, HADHA) (FIG. 6G). Additional targets include arachidonoyl lipid carrier proteins (e.g., FABP5) and metabolizing enzymes (e.g., PTGS1 or COX1). In some instances, targets include proteins without prior links to lipid biology (Table 3). In some instances, the LC-MS analysis of the lipid probe set is consistent with the gel profiles displayed by these probes. In some instances, more lipid probe targets interact with the AEA-DA and A-DA probes compared to either monounsaturated (OEA-DA, O-DA) or saturated (PEA-DA, S-DA) probes (FIGS. 6H, 5D, 5E, and Table 3).

Validation and Characterization of Lipid Probe-Protein Interactions

Figure 7:
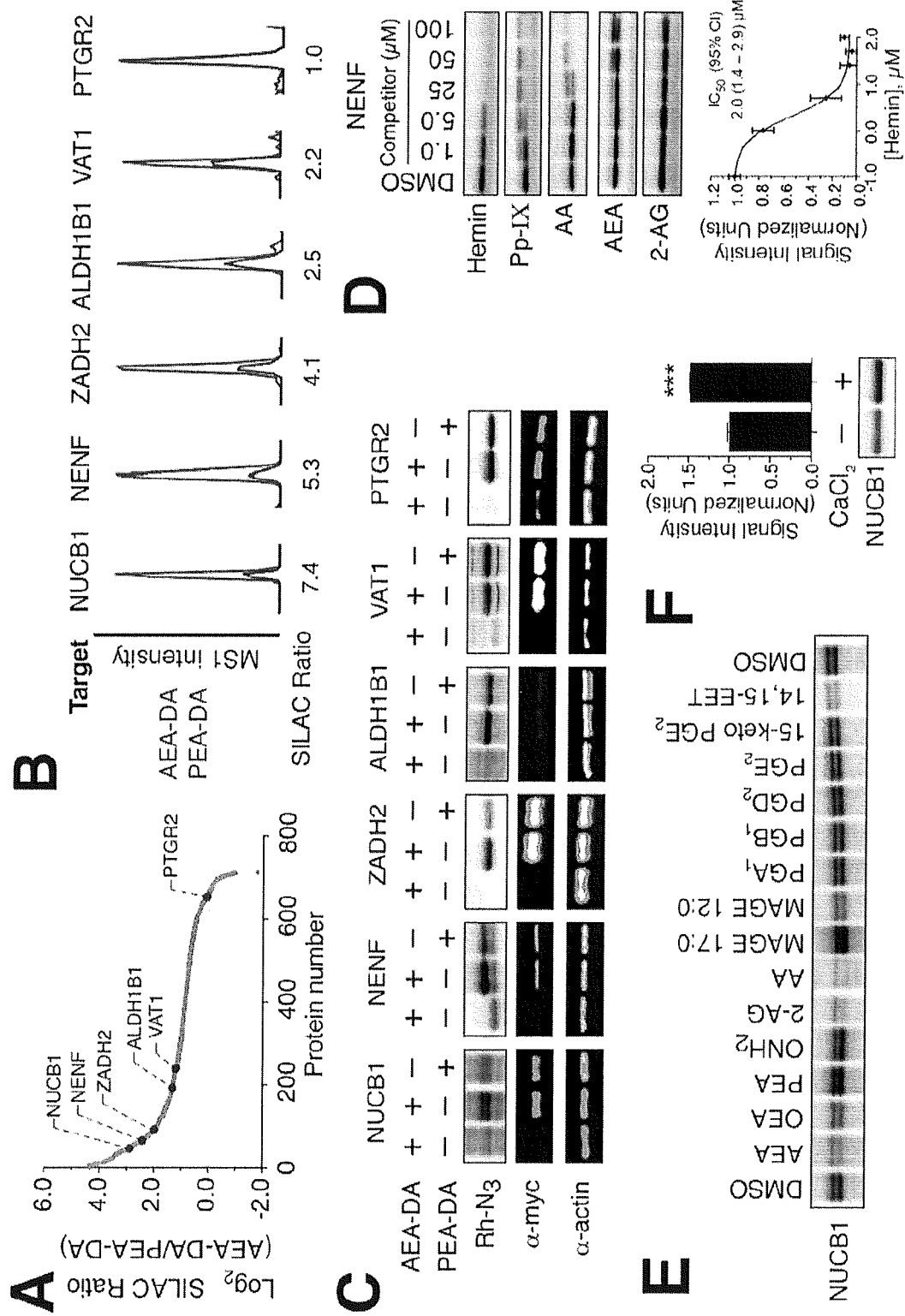
FIG. 7 shows experimental validation of representative lipid probe targets. (A) SILAC ratio plot for AEA-DA versus PEA-DA (20 μM) probe labeling in HEK293T cells highlighting targets selected for experimental validation. (B) Representative peptide MS1 chromatograms for selected targets showing relative labeling by AEA-DA and PEA-DA probes. (C) Lipid probe labeling of Myc-tagged recombinant proteins expressed by transient transfection in HEK293T cells. Top panels show in situ labeling profiles for the AEA-DA and PEA-DA probes with indicated targets (lane 1, mock-transfected cells; lanes 2 & 3, target-transfected cells; see FIG. 10A for full gel profiles). Middle panels, anti-Myc blotting. Lower panels, anti-actin blotting as a loading control. (D) Upper panel shows in vitro competition profiles of AEA-DA probe labeling of NENF by hemin, protoporphyrin IX (Pp-IX), and the arachidonoyl lipids AA, AEA and 2-AG (1-100 μM) (experiments performed in NENF-transfected HEK293T lysates). Lower panel shows concentration-dependent inhibition of AEA-DA labeling of NENF by hemin (CI=95% confidence interval) as determined from gel profiles. Data represent mean values ±SD from three independent experiments. (E) In vitro competition profiles of NUCB1 labeling by the AEA-DA (5.0 μM) probe using various lipids (20×) as competitors. Experiments were performed in lysates from NUCB1-transfected HEK293T cells. (F) Calcium-dependent enhancement of NUCB1 labeling by the AEA-DA probe. Data represent mean values ±SEM; n=3/condition.***P<0.001 for untreated versus CaCl2 (100 μM)-treated samples.

Six probe targets were selected, including both novel (e.g., NUCB1, NENF) and known (e.g., PTGR2) lipid-interacting proteins for further interaction studies with the AEA-DA and PEA-DA probes (FIGS. 7A and 7B). In situ probe treatment of HEK293T cells expressing Myc-tagged proteins showed protein-lipid interaction (FIG. 7C). NUCB1, NENF, and ZADH2 all showed labeling by the AEA-DA versus PEA-DA probe, while ALDH1B 1, VAT1, and PTGR2 exhibited similar extents of interaction with each probe, and in some instances, matching the lipid interaction profiles observed for endogenous forms of these proteins (compare FIGS. 7B and 7C).

Figure 8:
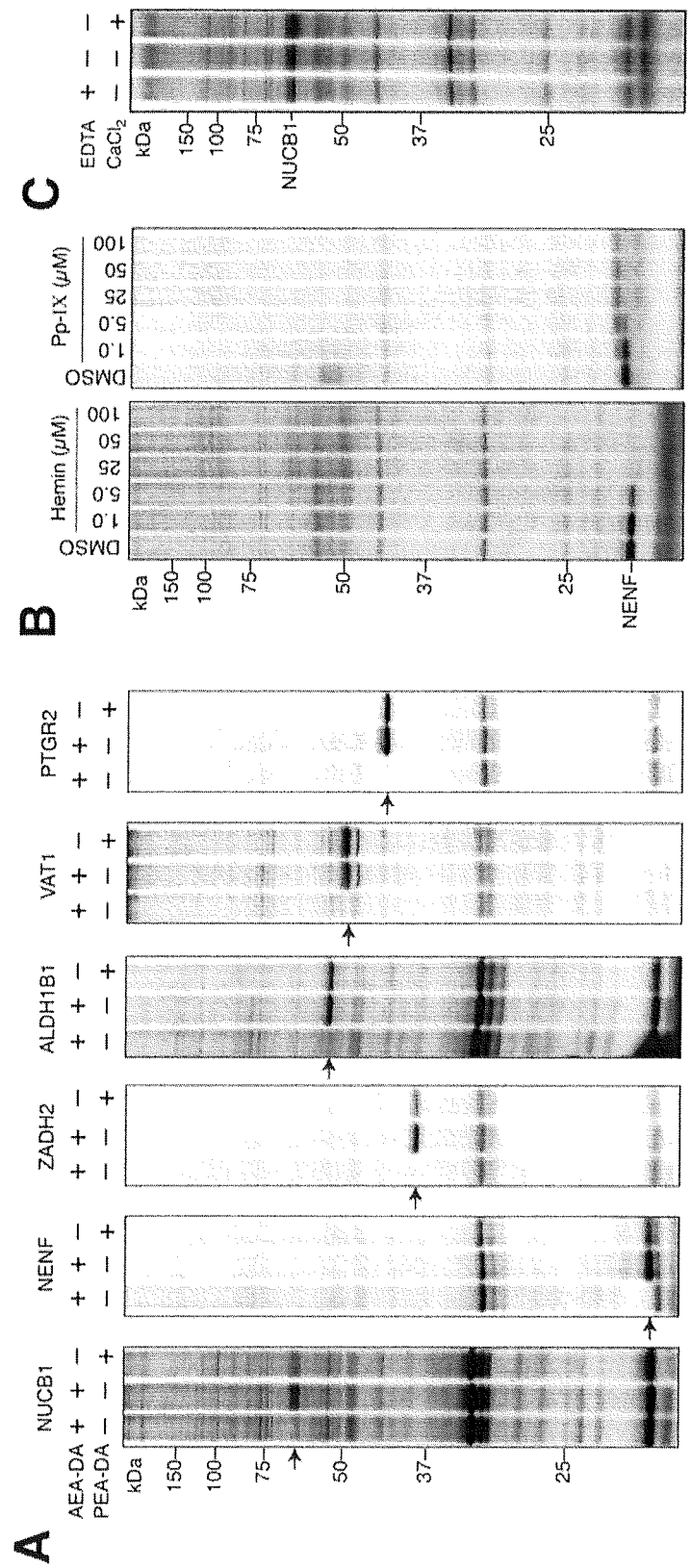
FIG. 8 illustrates experimental validation of representative lipid probe targets. (A) Full gel profiles of cropped images found in top panels of FIG. 7A showing in situ probe labeling profiles for the indicated targets. (B) Full gel profiles of cropped images found in FIG. 7D showing in vitro competition of NENF labeling by AEA-DA. Note that hemin competes NENF-labeling but in some instances does not compete with other probe-labeled targets. (C) Calcium-dependent enhancement of NUCB1 labeling by AEA-DA (experiments performed in lysates from NUCB1-transfected HEK293T cells). In contrast, CaCl2 treatment did not affect the AEA-DA-labeling of most other proteins in HEK293T lysates. Note that EDTA-treated samples were supplemented with an equivalent amount of CuSO4 (relative to EDTA) prior to fluorophore conjugation in order to prevent EDTA from quenching the CuAAC reaction.

NENF, also called neudesin, is a secreted protein from the cytochrome b5-like heme/steroid-binding family that promotes the survival of neurons (Kimura et al., 2008). NENF has been shown to bind hemin and protoporphyrin IX (Pp-IX) and these interactions promote neurotrophic activity. In some instances, hemin and protoporphyrin IX (Pp-IX) inhibited in a concentration-dependent manner the labeling of recombinant NENF by the AEA-DA probe (FIG. 7D), and the hemin-NENF interaction (IC50=2 µM), in some cases, is selective (FIG. 8B). AA and AEA, but not 2-AG, competitively blocked AEADA probe labeling of NENF (FIG. 7D).

The nucleobindin proteins NUCB1 and NUCB2, in some cases, are not known to bind small-molecule ligands. However, in some instances, NUCB1 has been shown to interact with the prostaglandin biosynthetic enzymes PTGS 1 and PTGS2 enzymes and enhance PTGS2-mediated prostaglandin synthesis in vitro. In some instances, AEA-DA probe labeling of recombinant NUCB1 was blocked by arachidonoyl lipids (AEA, AA and 2-AG) over saturated/shorter chain analogs [OEA, PEA, oleamide (ONH2)] and prostaglandins (FIG. 7E). Nucleobindins feature two EF-hand domains that undergo conformational change upon binding to calcium (de Alba and Tjandra, 2004). Using both purified, recombinant NUCB1 (FIG. 7F) and NUCB1-transfected HEK293T cell lysates (FIG. 8C), it was found that $CaCl_2$ (100 µM) selectively increased AEA-DA probe-labeling of NUCB1, whereas EDTA appeared to reduce this interaction.

In Situ Drug Profiling with Lipid Probes

Figure 9:
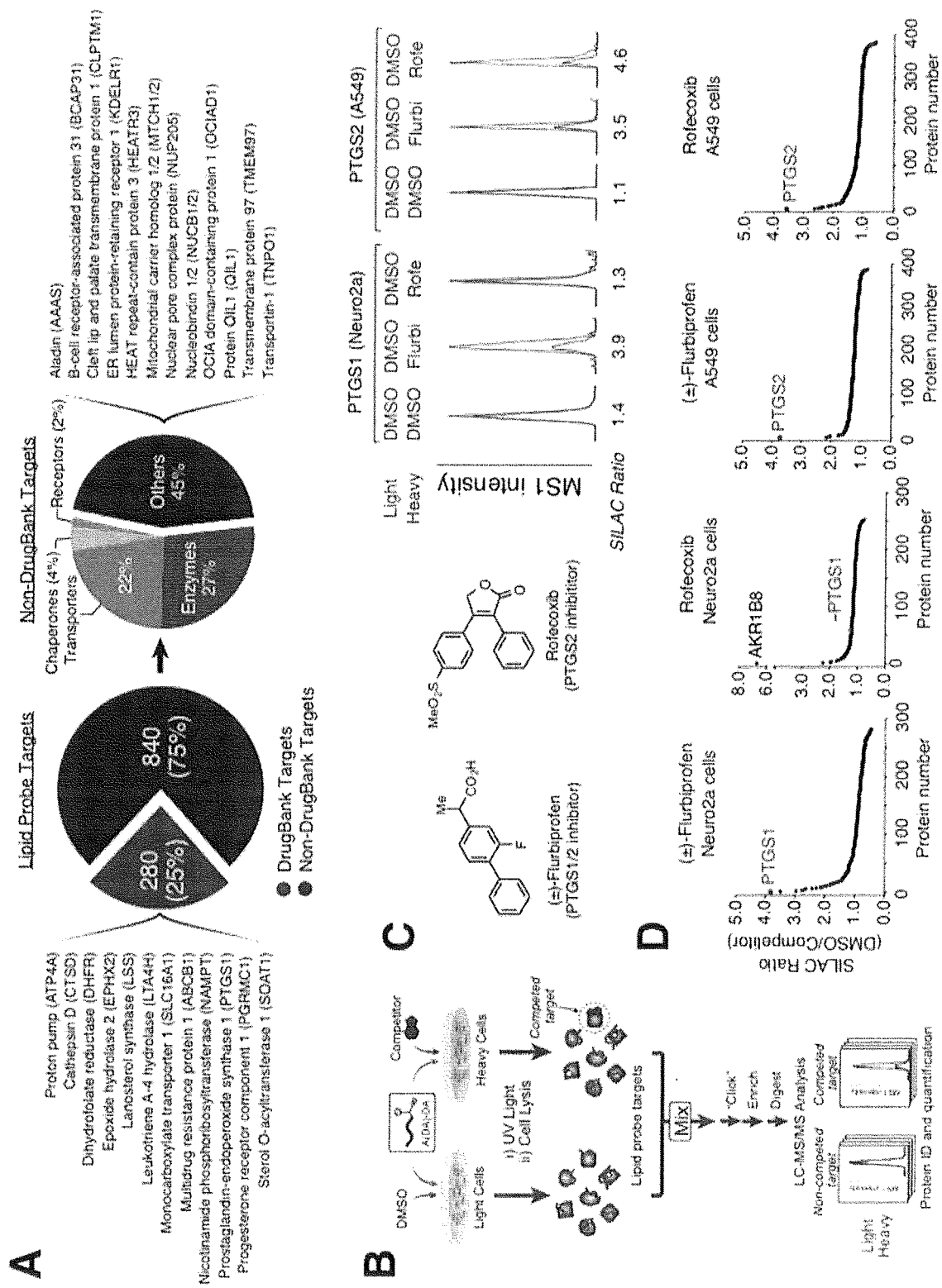
FIG. 9 shows the lipid-interaction proteome is rich in drug targets. (A) Categorization of lipid probe targets based on distribution in DrugBank (left pie chart) and further analysis of non-DrugBank targets by protein classes considered ligandable (e.g., enzymes, receptors, transporters) or not (Others). (B) Scheme for in situ competitive profiling of ligands using lipid probes. Isotopically light and heavy cells are treated with vehicle (DMSO) or competitor ligand, respectively, along with a lipid probe for 30 min. Cells are then UV-irradiated, lysed, and light and heavy lysates combined, enriched, and digested for LC-MS/MS analysis.

The lipid-interaction proteome was substantially enriched in known drug targets (~25%, or 280 proteins; FIG. 9A and Table 4) compared to the total fraction of the human proteome represented in the Drugbank database (~12%). The fraction of DrugBank proteins present among membrane and soluble probe targets were similar (FIG. 10A; 18% and 29%, respectively) and included proteins from multiple functional classes, such as enzymes (e.g., LSS, PTGS1, SOAT1), transporters (e.g., ABCB1, ATP4A, VDAC1-3), and receptors (e.g., SCARB1, PGRMC1). The remaining lipid-probe targets not found in DrugBank corresponded to additional proteins that are considered "ligandable" (e.g. enzymes, receptors, etc.), and proteins not predicted to interact with small molecules based on either their ascribed biochemical activities or lack of functional characterization (FIG. 9A and Table 4). In some instances, these findings suggested that the lipid probes exhibit a preferential capacity to interact with known drug-binding proteins in cells and, by extension, might facilitate the discovery of many additional proteins with the potential to bind small-molecule ligands. In some instances, for both known and newly identified ligandable proteins, the lipid probes provide a method to determine drug target engagement and the selectivity of these interactions in cells.

In some instances, the prostaglandin biosynthetic enzymes PTGS 1 and PTGS2 were selected for interaction with dual PTGS 1/PTGS2 and selective PTGS2 inhibitors. PTGS 1 was detected as a lipid probe target in Neuro2A cells (FIG. 10B), but PTGS2 was not enriched from this cell line or from HEK293T cells. In some instances, drug interactions with PTGS2 was carried out in phorbol-12-myristate-13-acetate (PMA)-stimulated A549 cells (FIGS. 10C and 10D). Drug-competition profiles were generated with the lipid probes by co-treating heavy and light cells with the A DA probe (5 µM) and either DMSO (light) or drug competitor (25 µM; heavy) for 30 min (FIG. 9B). The cells were then irradiated with UV light, harvested and lysed, whereupon the heavy and light proteomes were mixed in equal proportions. Following CuAAC conjugation with biotin-N3, streptavidin enrichment, and on-bead tryptic digestion, probe-labeled proteins were analyzed by LC/LC-MS/MS. Drug-competed proteins were defined as those showing a substantial (≥3-fold) reduction in signal in drug-treated (heavy) versus DMSO-treated (light). The dual PTGS1/2 inhibitor (±)-flurbiprofen competitively blocked A-DA-labeling of both PTGS1 and PTGS2 in cells, whereas the selective PTGS2 inhibitor rofecoxib disrupted A-DA-labeling of PTGS2, but not PTGS 1 (FIG. 9C). Both drugs showed selectivity for PTGS enzymes in Neuro2A and A549 cells (FIG. 9D and Table 4). Some additional competed targets were also, identified, including aldose reductase-related protein 2 (AKR1B8), which showed reductions in A-DA labeling in rofecoxib-, but not (±)-flurbiprofen-treated Neuro2A cells (FIG. 9D and Table 4). AKR1B8 is a mouse ortholog of the human aldo-keto reductase AKR1B10, which is modified and inhibited by electrophilic prostaglandins. In some instances, the results provide further support that these enzymes specifically interact with arachidonoyl related lipids and drugs.

The analysis of drug action in cells were expanded to include several additional lipid probe targets with known ligands—sterol O-acyltransferase (SOAT1), nicotinamide phosphoribosyltransferase (NAMPT), lanosterol synthase (LSS), and multidrug resistance protein 1(ABCB1) and their respective inhibitors, avasimibe, FK-866, Ro 48-8071, and elacridar (FIG. 11A). Some of these targets were chosen because they represent integral membrane proteins (LSS, SOAT1, ABCB1) and in some instances pose technical challenges for other drug interaction profiling methods that measure ligand-induced changes in proteolytic or thermal stability. Each ligand was initially assayed at 25 µM in Neuro2a cells, as this concentration was predicted to fully engage the primary drug target and also facilitate a broader prospecting of the lipid-interaction proteome for other ligandable proteins. The drug—Ro 48-8071—was tested across a concentration range of about 5 to about 50 µM to assess potency of interactions and facilitate identification of additional drug-protein interactions. The "heavy" and "light" cells were treated with drug and DMSO, respectively, followed by the arachidonoyl probes (5 µM), UV irradiation, sample processing, protein enrichment, and MS-based analysis. For each tested drug, the drug interacted with its primary established target and little cross-reactivity with the other three established targets under investigation (FIG. 11B and FIG. 12A). One exception was FK-866, which competed probe-labeling of both its established target NAMPT and ABCB1B (FIG. 11B).

A survey of the lipid-interaction proteome revealed a unique set of additional targets for each drug (FIG. 11C and FIG. 12A), many of which were competed by one of the four tested drugs (FIG. 11D). Clear concentration-dependent increases in the target landscape were observed for Ro 48-8071, with the target, LSS, being fully competed at 5 µM along with only two off-targets (TMEM97 and EBP), whereas, at 50 µM, Ro 48-8071 suppressed probe labeling of several additional targets (FIGS. 11C and 12A). The drug competition profiles were also compared to that of the endogenous lipid transmitter AEA tested at 200 µM, which was found to be a suitable concentration for competitive profiling by gel-based analysis (FIG. 12B). AEA competed with several targets of the drugs FK-866 (e.g. PTGR2) and Ro 48-8071 (e.g. DHRS1), both of which possess lipid-like scaffolds, but not the targets of avasimibe or elacridar (FIG. 11E).

Additional profiling of drugs in Neuro2a and A549 cells using both A-DA and AEA-DA probes to maximize coverage provided a rich set of competed targets (Table 5). Only ~30% of the identified drug targets were listed in DrugBank, and, of the non-DrugBank targets, a substantial portion (~40%) were uncharacterized proteins or proteins that belonged to classes that would traditionally be considered challenging to ligand based on their sparse representation in DrugBank (FIG. 11F and Table 5). Some proteins interacted strongly with multiple drugs, such as ferrochelatase (FECH), which has recently been found to bind several kinase inhibitors in cells using thermal proteome profiling. Lipid probe labeling of FECH, along with ABCB1B and TMEM97, was blocked by elacridar at concentrations as low as 0.5 µM (FIG. 12D), indicating that these drug-protein interactions are high affinity events. Both elacridar and Ro 48-8071 were confirmed to block AEA-DA probe labeling of recombinantly expressed TMEM97 in transfected HEK293T cells (FIG. 12C). In some instances, these data suggest that FECH and TMEM97 are ligandable proteins, as reflected by their capacity to interact with multiple small-molecule chemotypes in cells.

Discovery of Selective Ligands for the Lipid-Binding Protein Nucleobindin 1

In some embodiments, a high-throughput method is used for screening and identifying novel ligand-binding proteins. In some instances, NUCB1 is selected. In some instances, a fluorescent arachidonoyl lipid probe (Fl-AEA; FIG. 13A) was synthesized and confirmed that it bound to recombinant, purified human NUCB1 (hNUCB1) protein to produce a substantial increase in fluorescence polarization (FluoPol) signal (FIG. 13B). This FluoPol signal was significantly reduced by arachidonoyl, but not palmitoyl (FIG. 13C) or other (FIG. 14A) competitor lipids, recapitulating the selectivity observed by gel- and MS-based profiling with photoreactive lipid probes (FIG. 7E).

The FluoPol assay was optimized to provide a Z' score of >0.5 (compared to assays performed with AA as a competitor ligand; FIG. 13B) and used to screen 16,000 compounds from the Maybridge library at 10 µM in 384 well-plate format. 272 compounds produced a 20% or greater reduction in FluoPol signal (on par or greater than the reduction caused by AA) to give a hit rate of 1.7% (FIG. 13D). Chemoinformatic analysis to remove frequent hit compounds and compounds with structural alerts yielded 100 compounds that were assayed by gel-based competitive profiling with the AEA-DA probe against recombinant hNUCB1 doped into HEK293T cell lysates. This analysis identified hydrazide 1 (FIG. 13E) as a strong competitor of NUCB1 labeling that showed selectivity across other AEA-DA targets detected in the HEK293T proteome (FIG. 13F and FIG. 14B), and, in some instances, this compound was chosen for further optimization (FIG. 14), culminating in the discovery of the N-methylpiperidine amide MJN228 (11; FIG. 13G), which blocked AEA-DA probe labeling of NUCB1 with an IC50 value of 3.3 µM (FIG. 13H) and did not appear to disrupt other arachidonoyl probe-protein interactions in HEK293T cell lysates (FIG. 14E). A second NUCB1-active ligand was developed that contained a methyl substituent on the indole nitrogen (22, KML110), which only caused a slight reduction in potency (IC50=9.6 µM), as well as a structurally related inactive control compound KML181, which displayed markedly reduced potency for NUCB1 (IC50>100 µM; FIGS. 13G and 13H).

In some embodiments, the ligands are tested for their interaction to NUCB1 in cells. Treatment of Neuro2a cells with MJN228 or KML110 (25 µM) produced substantial (~3-5-fold) reductions in lipid probe enrichment of NUCB1, while KML181 had no effect (FIG. 15A). MJN228 inhibited lipid probe binding to NUCB1 at concentrations as low as 10 µM, with near-maximal inhibition observed at ~25 µM (FIG. 16A). An analysis of the lipid-interaction proteome revealed that NUCB1 was the most competed protein among the ~400 AEA-DA probe targets detected in Neuro2a cells (FIG. 15B). The site of arachidonoyl probe (and MJN228) binding to NUCB1 was mapped in cells, which was accomplished by treating Neuro2A cells with the AEA-DA probe (50 µM) in the presence of DMSO or MJN228 (50 µM), followed by UV irradiation, CuAAC conjugation of AEA-DA-labeled proteins to isotopically light (DMSO-treated cells) and heavy (MJN228-treated cells) azide-biotin tags featuring a TEV protease-cleavable linker, and LCMS/MS analysis using a previously described platform, termed isoTOP-ABPP, for mapping probe-modified peptides in proteomes (Speers and Cravatt, 2005). A AEA-DA labeled peptide was identified for NUCB1 (aa 53-68) in DMSO-treated cells and the signals for this peptide were substantially (>5-fold) reduced in MJN228-treated cells (FIG. 15C). This AEA-DA labeling site was confirmed using recombinant, purified hNUCB1 and tandem MS analysis which narrowed down the site of probe modification to His67 (FIGS. 16B and 16C). The MJN228-sensitive, AEA-DA-modified peptide resides within the previously mapped PTGS1/2-binding domain of NUCB1 (aa 1-123; FIG. 15C), in some instances, indicating that this region is responsible for both the lipid- and protein-protein interactions displayed by NUCB1.

Deeper profiling of Neuro2a cells using the isoTOP-ABPP platform identified AEA-DA modified peptides for an additional ~150 proteins (Table 6), which accounted for ~40% of the total AEA-DA targets mapped in this cell line.

NUCB1 Ligands Perturb Multiple Lipid Pathways in Cells

Having established that NUCB1 is a principal target of MJN228 in cells, the metabolic consequences of this ligand-protein interaction was investigated by performing a lipidomic analysis of Neuro2a cells treated with DMSO, MJN228 (10 µM), or the inactive control probe KML181 (10 µM). Following a 6 h incubation with each compound, cells were harvested, lysed, and their lipids isolated by organic extraction and analyzed by untargeted LC-MS in both positive and negative ion modes. Using XCMS software to quantitate differences between compound- and DMSO-treated samples, a group of metabolites were identified that were significantly elevated in MJN228-treated Neuro2a cells (≥2 fold, P<0.0001) but not in cells treated with KML181 (FIG. 15D and Table 7). The chromatographic and tandem MS profiles of these lipids enabled their structural assignment as N-acyl ethanolamines (NAEs) and N-acyl taurines (NATs). NAEs and NATs are hydrolytically metabolized by the enzyme fatty acid amide hydrolase (FAAH) (Saghatelian et al., 2006). However, neither MJN228 nor KML110 showed substantial inhibitory activity against purified recombinant FAAH or endogenous FAAH in Neuro2a lysates (IC50 values >100 µM, FIGS. 16D and 16E), suggesting that the compounds did not increase NAE or NAT levels through direct interactions with FAAH in cells. In some instances, signals above background were not detected for this enzyme in the chemical proteomic data sets. In some instances, the poor labeling of FAAH is due to the lipid probes serving as substrates for this enzyme, and an overall loss in probe labeling of proteins in cells that overexpress FAAH (FIG. 16F).

In some instances, targeted metabolite analysis is used to evaluate the effects of NUCB1 ligands and control compounds on the fatty acid amide content of cells. Both NUCB1 ligands (MJN228 and KML110), and the FAAH inhibitor PF-7845 elevated the cellular concentrations of NAEs and NATs, including the endocannabinoid anandamide (C20:4 NAE, or AEA) and the TRPV4 ligand C20:4 NAT (FIG. 15E and FIG. 16G). Other arachidonoyl lipids, including AA and 2-AG, were either unaffected or slightly elevated by NUCB1 ligands in comparison (FIG. 16H). KML181 and the additional control compounds avasimibe and FK-866 did not interact with the recombinant NUCB1 protein (FIG. 16I and Table 4), or altered NAE/NAT content in cells (FIG. 15E and FIG. 16G). In some instances, the NUCB1 ligands elevated fatty acid amides in a human cell line (A549 cells; FIG. 16J). In some instances, RNA interference was used to stably lower the expression of NUCB1 in A549 cells using two distinct shRNA probes [shNUCB1 (1) and shNUCB1(2)] (FIG. 15F). Multiple NAEs, including AEA and OEA, were elevated in the shNUCB1-A549 cell lines, but not in the control shRNA (shGFP-A549) cell line (FIG. 15F).

In some instances, the pharmacological and RNA-interference data illustrate that NUCB1 plays a role in facilitating the metabolism of fatty acid amides, possibly by serving as an intracellular carrier to deliver these lipids to FAAH. Treatment of cells with both a NUCB1 ligand and the FAAH inhibitor PF-7845 did not produce larger changes in NAEs than treatment with the PF-7845 alone (FIG. 16K). AEA is not only a substrate for FAAH, but also PTGS2, which converts this endocannabinoid into bioactive prostamides. In some instances, NUCB1 ligands are tested to determine if they perturb the oxidative metabolism of AEA by PTSG2. In some cases, NUCB1 ligands are not PTGS2 inhibitors (FIG. 16L). In some cases, PMA-stimulated A549 cells are then treated with NUCB1 ligands (MJN228 and KML110) and control compounds (KML181 and FK-866) followed by exogenous AEA (20 µM) and measured the formation of prostamides. Both NUCB1 ligands, but not the control compounds, produced a significant, concentration-dependent reduction in PGF2α-EA in A549 cells (FIG. 15G). In some instances, NUCB1 bound AA in the biochemical assays (see FIG. 7E and FIG. 13B). In some cases, NUCB1 ligands were tested to determine if they affect prostaglandin production in A549 cells treated with PMA. The PMA-stimulated generation of PGE2 and $TXB_2$ was attenuated by NUCB1 ligands, but not the control compound KML181 (FIG. 16M). The additional control compound FK-866 exhibited a curious profile, showing no effect on PGE2, but complete suppression of $TXB_2$ (FIG. 16M). In some instances, FK-866, either through inhibiting its primary target NAMPT or another protein in A549 cells, impairs $TXB_2$ production. In some instances, alterations in prostamides and prostaglandins were not observed in shNUCB1 cells, which indicate that a more substantial reduction in NUCB1 expression than that achieved by RNA-interference is needed to perturb NUCB1-PTGS2 crosstalk in cells.

Mapping On-Target and Off-Target Effects of Lipid-Binding Protein Inhibitors

In some embodiments, drugs assayed by one or more of the methods described herein showed off-target profiles (FIG. 11D and Table 5). In some instances, about 50% or more of the liganded proteins discovered herein showed interaction with more than one small-molecule competitor (Table 5). In some instances, this shows that the ligand-binding content of the lipid-interaction proteome is not saturated. The off targets for specific drugs, in some cases, share functionality. For example, three targets of Ro 48-8071 are sequence-unrelated, membrane-bound enzymes LSS and EBP and protein TMEM97 which is involved in the metabolism and regulation of cholesterol. In some instances, a single inhibitor, such as Ro 48-8071, targets one or more proteins which operate in different pathways. In some instances, a single inhibitor modulates multiple distinct lipid pathways.

Example II

Materials:

All chemicals were obtained from commercial suppliers and were used without further purification. Anhydrous solvents were obtained by passing solvents through activated alumina columns. Merck silica gel TLC plates (0.25 mm, 60 F254) were used to monitor reactions. Flash chromatography was performed using SiliaFlash F60 silica gel (40-63

Synthesis of AA-DA and AEA-DA

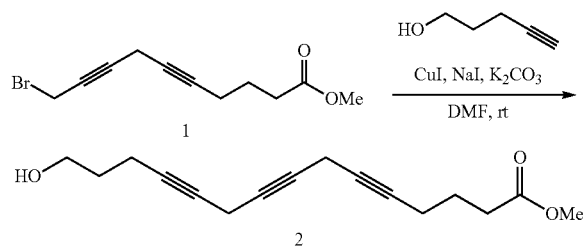

Methyl 15-hydroxypentadeca-5,8,11-triynoate (2)

To a stirring heterogeneous mixture of K$_2$CO$_3$ (567 mg, 4.1 mmol, 1.0 equiv.), CuI (781 mg, 4.1 mmol, 1.0 equiv.), anhydrous NaI (615 mg, 4.1 mmol, 1.0 equiv.) in anhydrous DMF (10 mL) was added methyl ester 1 (Li et al., 2005) (340 mg, 4.1 mmol, 1.0 equiv.) and 4-pentyn-1-ol (0.34 g, 4.1 mmol, 1.0 equiv.) under N$_2$. The reaction mixture was stirred for 12 h at ambient temperature before diluting with EtOAc:hexanes (100 mL, 1:1) and passed through a pad of Celite to remove insoluble material. The filtrate was then added to a separatory funnel and washed with saturated NH$_4$Cl (aq.) (100 mL) and brine (2×100 mL). The organic layer was then dried over anhydrous Na$_2$SO$_4$ and concentrated under reduced pressure. The remaining residue was purified by SiO$_2$ flash chromatography (20-30% EtOAc/hexanes) providing the title compound as a colorless oil (888 mg, 75%): $^1$H NMR (300 MHz, CDCl$_3$) δ 3.74 (t, J=6.2 Hz, 2H), 3.67 (s, 3H), 3.12 (s, 4H), 2.42 (t, J=7.5 Hz, 2H), 2.31-2.19 (m, 4H), 1.85-1.69 (m, 4H); MS (ESI+) m/z calc'd for C$_{16}$H$_{21}$O$_3$ [M+H]$^+$: 261.2, found 261.3.

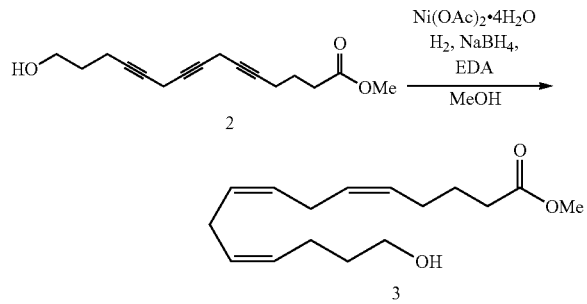

Methyl (5Z,8Z,11Z)-15-hydroxypentadeca-5,8,11-trienoate (3)

To a stirring mixture of Ni(OAc)$_4$.4H$_2$O (2.86 g, 11.5 mmol, 3.0 equiv.) in MeOH (90 mL) under N$_2$ was added NaBH$_4$ (435 mg, 11.5 mmol, 3.0 equiv.) in small portions over 10 minutes. The reaction vessel was then purged with H2 and the mixture stirred for 30 min at ambient temperature. Ethylenediamine (3.1 mL, 46.1 mmol, 12 equiv.) was then added to the reaction mixture, followed by triyne 2 (1.0 g, 3.84 mmol, 1.0 equiv.). When the mass of the starting material was no longer detected by mass spectrometry (Agilent 1100 Series LC/MSD), the reaction was filtered through a pad of Celite and the filtrate was concentrated under reduced pressure. The remaining residue was purified by SiO$_2$—AgNO$_3$ (10%) flash chromatography (30-80% EtOAc/hexanes) providing the title compound as a colorless oil (774 mg, 76%): $^1$H NMR (400 MHz, CDCl$_3$) δ 5.47-5.31 (m, 6H), 3.66 (s, 3H), 3.66 (t, J=6.4 Hz, 2H), 2.93-2.67 (m, 4H), 2.43 (s, 1H), 2.32 (t, J=7.5 Hz, 2H), 2.17 (q, J=6.9 Hz, 2H), 2.11 (q, J=7.1 Hz, 2H), 1.75-1.60 (m, 4H); HRMS (ESI-TOF+) m/z calc'd for C$_{16}$H$_{27}$O$_3$ [M+H]$^+$: 267.1955, found 267.1956.

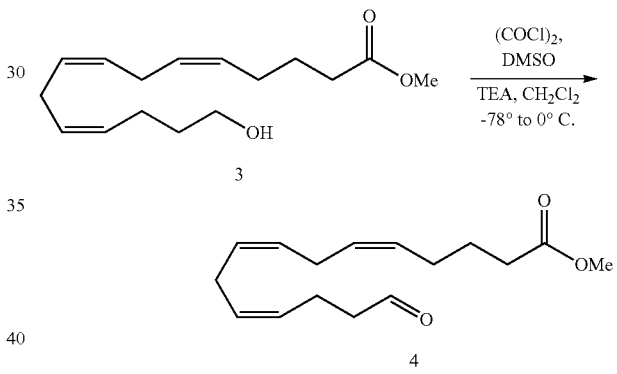

Methyl (5Z,8Z,11Z)-15-oxopentadeca-5,8,11-trienoate (4)

In an oven-dried RBF, oxalyl chloride (0.39 mL, 4.5 mmol, 2.0 equiv) was added to anhydrous CH$_2$Cl$_2$ (20 mL) at −78° C. under N$_2$. To this solution was added DMSO (0.64 mL, 9.0 mmol, 4.0 equiv.) drop-wise. After 30 min of stirring at −78° C., alcohol 3 (600 mg, 2.25 mmol, 1.0 equiv.) in anhydrous CH$_2$Cl$_2$ (5.0 mL) was added over 5 min and the reaction was stirred for another 30 min. TEA (1.3 mL, 9.0 mmol, 4.0 equiv.) was then added and the reaction was stirred for 30 min at −78° C. before warming to 0° C. in an ice bath. After 30 min, the reaction was diluted with 25% EtOAc/hexanes and reaction mixture was passed through a silica plug. Following evaporation of the eluent the remaining residue was purified by SiO$_2$ flash chromatography (5% EtOAc/hexanes) providing the title compound as a colorless oil (548 mg, 92%): $^1$H NMR (400 MHz, CDCl$_3$) δ 9.78 (s, 1H), 5.39 (td, J=15.0, 14.5, 5.2 Hz, 6H), 3.67 (s, 3H), 2.87-2.76 (m, 4H), 2.52 (t, J=7.2 Hz, 2H), 2.41 (q, J=6.7 Hz, 2H), 2.33 (t, J=7.5 Hz, 2H), 2.11 (q, J=6.8 Hz, 2H), 1.71 (p, J=7.4 Hz, 2H); $^{13}$C NMR (101 MHz, CDCl$_3$) δ 202.02, 174.09, 129.45, 129.07, 128.80, 128.46, 127.89, 127.76, 51.56, 43.74, 33.48, 26.62, 25.68, 25.65, 24.83, 20.13; MS (ESI+) m/z calc'd for $C_{16}H_{25}O_3$ [M+H]$^+$: 265.2, found 265.2.

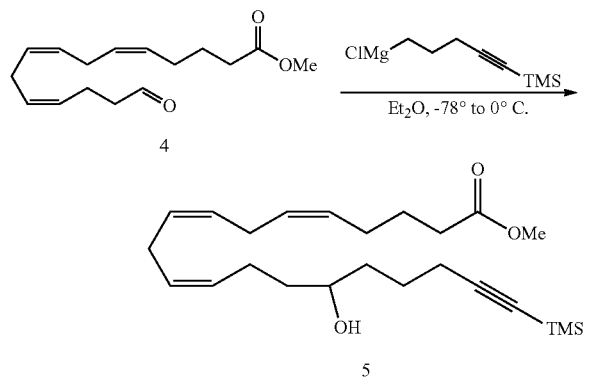

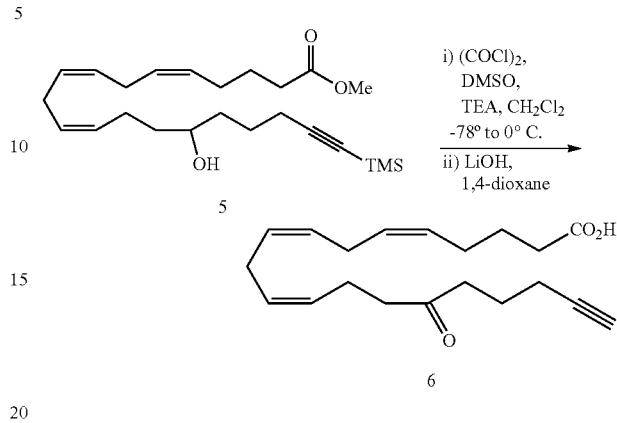

Methyl (5Z,8Z,11Z)-15-hydroxy-20-(trimethylsilyl)icosa-5,8,11-trien-19-ynoate (5)

Synthesis of (5-(trimethylsilyl)pent-4-yn-1-yl)magnesium chloride

Magnesium turnings (208 mg, 8.55 mmol, 1.5 equiv.) were etched with the back of a glass pipette and added to a flame-dried, two-neck RBF containing a stir bar and fitted with an oven-dried reflux condenser. After purging the reaction vessel with argon, a small bead of $I_2$ (~10 mg) was added to the magnesium turnings followed by anhydrous THF (3.0 mL) and the resulting mixture was stirred for 15 min at room temperature. A few drops of (5-chloropent-1-yn-1-yl)trimethylsilane (1.0 g, 5.7 mmol, 1.0 equiv) dissolved in anhydrous THF (7.0 mL) was then added to the mixture and the mixture was heated to reflux. The remaining (5-chloropent-1-yn-1-yl)trimethylsilane solution was then slowly added to the refluxing reaction mixture over 30 min. When the addition was complete, the reaction was refluxed for an additional 3 h before cooling to room temperature and determining the Grignard reagent concentration by titration using menthol and 1,10-phenanthroline.

Grignard Addition.

Aldehyde 4 (479 mg, 1.81 mmol, 1.0 equiv.) was dissolved in anhydrous Et$_2$O (25 mL) and cooled to −78° C. under N$_2$. (5-(Trimethylsilyl)pent-4-yn-1-yl)magnesium chloride (3.4 mL, 1.81 mmol, 0.53 M in THF, 1.0 equiv.) was then added drop-wise over 10 min and after stirring for an additional 1 h at −78° C., the reaction mixture was allowed to cool to 0° C. After stirring for 1 h at 0° C., the reaction was quenched with the addition of sat. NH$_4$Cl (aq.) (10 mL) and the product was extracted with Et$_2$O (3×25 mL). The combined organic layers were then dried over anhydrous Na$_2$SO$_4$ and concentrated under reduced pressure. The remaining residue was purified by SiO$_2$ flash chromatography (20% EtOAc/hexanes) providing the title compound as a colorless oil (349 mg, 48%): $^1$H NMR (400 MHz, CDCl$_3$) δ 5.44-5.28 (m, 6H), 3.64 (s, 3H), 3.67-3.59 (m, 1H), 2.86-2.73 (m, 4H), 2.30 (t, J=7.5 Hz, 2H), 2.23 (t, J=6.6 Hz, 2H), 2.21-2.13 (m, 2H), 2.09 (q, J=7.0 Hz, 2H), 1.76-1.62 (m, 4H), 1.59-1.45 (m, 4H), 0.12 (s, 9H); $^{13}$C NMR (101 MHz, CDCl$_3$) δ 174.23, 129.78, 128.99, 128.96, 128.40, 128.31, 128.23, 107.37, 84.82, 70.99, 51.62, 37.31, 36.66, 33.51, 26.63, 25.71, 24.84, 23.69, 19.92, 0.25; MS (ESI+) m/z calc'd for $C_{24}H_{41}O_3Si$ [M+H]$^+$: 405.3, found 405.4.

(5Z,8Z,11Z)-15-oxoicosa-5,8,11-trien-19-ynoic acid (6)

In an oven-dried RBF, oxalyl chloride (0.15 mL, 1.72 mmol, 2.0 equiv) was added to anhydrous CH$_2$Cl$_2$ (5.0 mL) at −78° C. under N$_2$. To this solution was added DMSO (0.25 mL, 3.45 mmol, 4.0 equiv.) drop-wise. After 30 min of stirring at −78° C., alcohol 5 (349 mg, 0.862 mmol, 1.0 equiv.) in anhydrous CH$_2$Cl$_2$ (2.0 mL) was added over 5 min and the reaction was stirred for another 30 min. TEA (0.48 mL, 3.45 mmol, 4.0 equiv.) was then added and the reaction was stirred for 30 min at −78° C. before warming to 0° C. in an ice bath. After 30 min, the reaction was diluted with 25% EtOAc/hexanes and reaction mixture was passed through a silica plug. Following evaporation of the eluent the remaining residue was redissolved in 1,4-dioxane (3.0 mL) and LiOH (1.0 mL, 2 M in H$_2$O) was added. After stirring for 6 h, the reaction was quenched by pouring it into a separatory funnel containing EtOAc (25 mL) and 0.5 M HCl (aq.) (25 mL) and the product was extracted with EtOAc (3×25 mL). The combined organic layers were then dried over anhydrous Na$_2$SO$_4$ and concentrated under reduced pressure. The remaining residue was purified by SiO$_2$ flash chromatography (20% EtOAc/hexanes, 0.5% HCO$_2$H) providing the title compound as a colorless oil (172 mg, 75%): $^1$H NMR (400 MHz, CDCl$_3$) δ 5.46-5.26 (m, 6H), 2.81 (q, J=6.4 Hz, 4H), 2.57 (t, J=7.2 Hz, 2H), 2.50 (t, J=7.4 Hz, 2H), 2.35 (p, J=7.2 Hz, 4H), 2.22 (td, J=6.8, 2.5 Hz, 2H), 2.13 (q, J=7.2 Hz, 2H), 1.96 (t, J=2.5 Hz, 1H), 1.79 (p, J=7.3 Hz, 2H), 1.70 (p, J=7.3 Hz, 2H); $^{13}$C NMR (101 MHz, CDCl$_3$) δ 210.52, 165.59, 129.18, 129.15, 128.88, 128.35, 128.26, 128.13, 83.69, 69.21, 42.73, 41.38, 33.40, 26.55, 25.76, 25.72, 24.58, 22.30, 21.78, 17.88; HRMS (ESI-TOF+) m/z calc'd for $C_{20}H_{29}O_3$ [M+H]$^+$: 317.2111, found 317.2110.

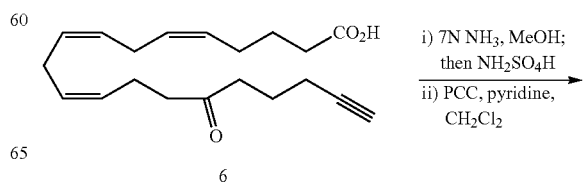

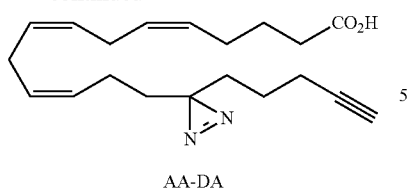

AA-DA

(5Z,8Z,1Z)-14-(3-(pent-4-yn-1-yl)-3H-diazirin-3-yl)tetradeca-5,8,11-trienoic acid (AA-DA)

Diaziridine formation was accomplished using a method reported by (Bond et al., 2009). Ketone 6 (172 mg, 0.54 mmol, 1.0 equiv.) was dissolved in a solution of $NH_3$ (2.0 mL, 7.0 N in MeOH) at 0° C. in a RBF under $N_2$. After stirring for 3 h at 0° C., a solution of hydroxylamine-O-sulfonic acid (70 mg, 0.62 mmol, 1.15 equiv.) in anhydrous MeOH (2.0 mL) was added drop-wise over 10 min. The reaction mixture was allowed to slowly warm to room temperature while stirring overnight (~12 h). The reaction was then concentrated under a stream of $N_2$ and the remaining residue was redissolved in $Et_2O$ (10 mL) and filtered through a pad of Celite using additional $Et_2O$ (5 mL) for washes. The combined filtrate was then concentrated under reduced pressure providing the crude diaziridine intermediate which was used without further purification.

Diazirine formation was accomplished using a method reported by (Sanderson et al., 2005). The crude diaziridine intermediate (see above) was redissolved in anhydrous $CH_2Cl_2$ (5.0 mL) and pyridine (0.5 mL) in a RBF charged with a stir bar and flushed with $N_2$. Pyridinium chlorochromate (116 mg, 0.54 mmol, 1.0 equiv.) was then added in small portions over 20 min while the reaction mixture was cooled to 0° C. The reaction was then allowed to warm to room temperature and stirred for an additional 1 h before diluting with 50% EtOAc/hexanes (25 mL) and $HCO_2H$ (0.5 mL). The resulting solution was passed through a silica plug and the was filtrate concentrated and purified further by $SiO_2$ flash chromatography (15% EtOAc/hexanes, 1.0% $HCO_2H$) providing the title compound as a colorless oil (45 mg, 28%, 2 steps): $^1H$ NMR (500 MHz, $CDCl_3$) δ 5.43-5.26 (m, 6H), 2.81-2.75 (m, 4H), 2.37 (t, J=7.5 Hz, 2H), 2.16 (td, J=7.0, 2.7 Hz, 2H), 2.13 (q, J=7.3 Hz, 2H), 1.95 (t, J=2.6 Hz, 1H), 1.86 (q, J=7.6 Hz, 2H), 1.73 (p, J=7.5 Hz, 2H), 1.54-1.44 (m, 4H), 1.33 (p, J=7.1 Hz, 2H); $^{13}C$ NMR (126 MHz, $CDCl_3$) δ 173.38, 129.11, 129.06, 129.03, 128.43, 128.41, 128.14, 83.54, 69.08, 33.85, 33.08, 31.97, 28.43, 26.64, 25.75, 24.84, 22.87, 21.86, 18.08, 15.59; HRMS (ESI-TOF+) m/z calc'd for $C_{20}H_{29}N_2O_2$ [M+H]$^+$: 329.2223, found 329.2226.

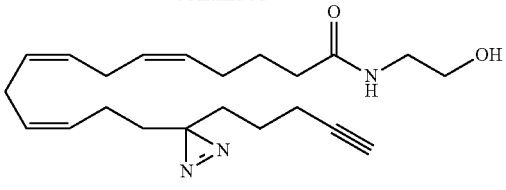

AEA-DA

(5Z,8Z,11Z)—N-(2-hydroxyethyl)-14-(3-(pent-4-yn-1-yl)-3H-diazirin-3-yl)tetradeca-5,8,11-trienamide (AEA-DA)

To a stirring solution of AA-DA (18 mg, 0.054 mmol, 1.0 equiv.) and N-hydroxysuccinimide (6.8 mg, 0.059 mmol, 1.1 equiv) in anhydrous $CH_2Cl_2$ (2.0 mL) was added EDCI (11 mg, 0.059, 1.1 equiv.). The reaction mixture was stirred for 12 h at which point the starting material was completely consumed as judged by TLC (30% EtOAc/hexanes, 1.0% $HCO_2H$). The reaction mixture was poured into a separatory funnel with brine (25 mL) and product extracted with $CH_2Cl_2$ (3×25 mL). The combined organic layers were then dried over anhydrous $Na_2SO_4$ and concentrated under reduced pressure and this crude NHS ester was used without further purification.

The above-synthesized NHS ester (23 mg, 0.054 mmol, 1.0 equiv.) was dissolved in $CH_2Cl_2$ (1.0 mL) before adding TEA (40 μL, 0.27 mmol, 5.0 equiv.) and ethanolamine (17 μL, 0.27 mmol, 5.0 equiv.). After stirring for 1 h at room temperature, the reaction was concentrated under reduced pressure and the remaining residue was purified by $SiO_2$ flash chromatography (80:15:5 EtOAc:hexanes:MeOH) providing the title compound as a colorless oil (18 mg, 92%): $^1H$ NMR (500 MHz, $CDCl_3$) δ 5.94 (bs, 1H), 5.44-5.24 (m, 6H), 3.73 (t, J=4.9 Hz, 2H), 3.43 (q, J=5.4 Hz, 2H), 2.82-2.74 (m, 4H), 2.61 (bs, 1H), 2.22 (t, J=7.8 Hz, 2H), 2.16 (td, J=7.0, 2.5 Hz, 2H), 2.11 (q, J=7.0 Hz, 2H), 1.95 (t, J=2.5 Hz, 1H), 1.86 (q, J=7.4 Hz, 2H), 1.74 (p, J=7.4 Hz, 2H), 1.55-1.44 (m, 4H), 1.33 (p, J=7.0 Hz, 2H); $^{13}C$ NMR (126 MHz, $CDCl_3$) δ 174.38, 129.21, 129.08, 128.91, 128.41, 128.37, 128.12, 83.52, 69.11, 62.65, 42.63, 36.07, 33.03, 31.97, 28.50, 26.79, 25.78, 25.75, 25.61, 22.86, 21.85, 18.07; HRMS (ESI-TOF+) m/z calc'd for $C_{22}H_{34}N_3O_2$ [M+H]$^+$: 372.2645, found 372.2644.

Synthesis of OEA-DA

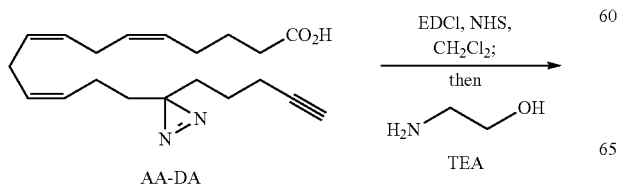

AA-DA

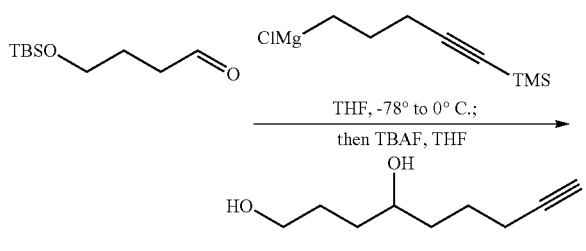

Non-8-yne-1,4-diol (8)

To a stirring solution of 4-((tert-butyldimethylsilyl)oxy)butanal (Asano and Matsubara, 2011) (1.38 g, 6.82 mmol, 1.0 equiv.) in anhydrous Et₂O (100 mL) at −78° C. under N₂ was added (5-(trimethylsilyl)pent-4-yn-1-yl)magnesium chloride (15 mL, 7.5 mmol, 0.50 M in THF, 1.1 equiv.) over 10 min. The reaction was then allowed to warm to room temperature. After stirring for 1 h at room temperature, the reaction was quenched with sat. NH₄Cl (aq.) and the product was extracted with EtOAc (3×100 mL). The combined organic layers were dried over anhydrous Na₂SO₄ and concentrated under reduced pressure. The remaining residue was redissolved in anhydrous THF and cooled to 0° C. before adding TBAF (20.5 mL, 20.5 mmol, 1.0 M in THF, 3.0 equiv). The reaction was stirred for 2 h at room temperature and quenched by addition of silica gel (~25 g) directly into the reaction mixture. The solvent was then removed under reduced pressure and the remaining free-flowing solid was loaded directly onto a column for purification by SiO₂ flash chromatography (100% EtOAc) providing the title compound as a colorless oil (843 mg, 79%): ¹H NMR (500 MHz, CDCl₃) δ 3.74-3.63 (m, 3H), 3.60 (bs, 2H), 2.27 (td, J=6.3, 2.7 Hz, 2H), 2.01 (t, J=2.6 Hz, 1H), 1.78-1.48 (m, 8H); ¹³C NMR (126 MHz, CDCl₃) δ 84.49, 71.22, 68.63, 62.76, 36.50, 34.60, 29.08, 24.77, 18.46; MS (ESI+) m/z calc'd for C₉H₁₇O₂ [M+H]⁺: 157.1, found 157.2.

Wittig Reaction.

To a stirring solution of phosphonium salt 10 (Gunn, 1985) (208 mg, 0.37 mmol, 1.0 equiv.) anhydrous THF (15 mL) at 0° C. under N₂ was added NaHMDS (0.47 mL, 0.47 mmol, 1.0 M in THF, 1.0 equiv.) drop-wise over 15 min. The resulting orange solution was stirring at room temperature for an additional 1 h. In a separate RBF, aldehyde 9 (86 mg, 0.56 mmol, 1.2 equiv.) was dissolved in anhydrous THF (15 mL) and cooled to −78° C. under N₂. The ylide solution was then slowly added to the aldehyde solution over 45 min and after stirring for an additional 1 h at −78° C., the reaction mixture was allowed to warm to room temperature overnight (~12 h). The reaction was then concentrated under reduced pressure and the remaining residue was purified by SiO₂ flash chromatography (10% EtOAc/hexanes) providing the title compound as a colorless oil (48 mg, 42%): ¹H NMR (400 MHz, CDCl₃) δ 5.43-5.21 (m, 2H), 3.66 (s, 3H), 2.55 (t, J=7.2 Hz, 2H), 2.45 (t, J=7.4 Hz, 2H), 2.33-2.26 (m, 4H), 2.22 (td, J=6.9, 2.7 Hz, 2H), 2.01 (q, J=6.8 Hz, 2H), 1.95 (t, J=2.7 Hz, 1H), 1.78 (p, J=7.1 Hz, 2H), 1.61 (dd, J=14.1, 6.9 Hz, 2H), 1.38-1.23 (m, 8H); ¹³C NMR (101 MHz, CDCl₃) δ 210.05, 174.48, 131.35, 127.88, 83.78, 69.19, 51.63, 42.97, 41.34, 34.27, 29.72, 29.32, 29.28, 29.25, 27.32, 25.11, 22.38, 21.86, 17.94; HRMS (ESI-TOF+) m/z calc'd for C₁₉H₃₁O₃ [M+H]⁺: 307.2268, found 305.2271.

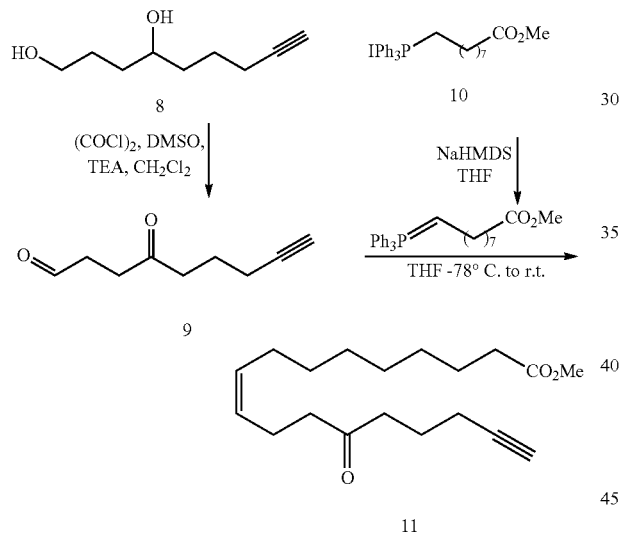

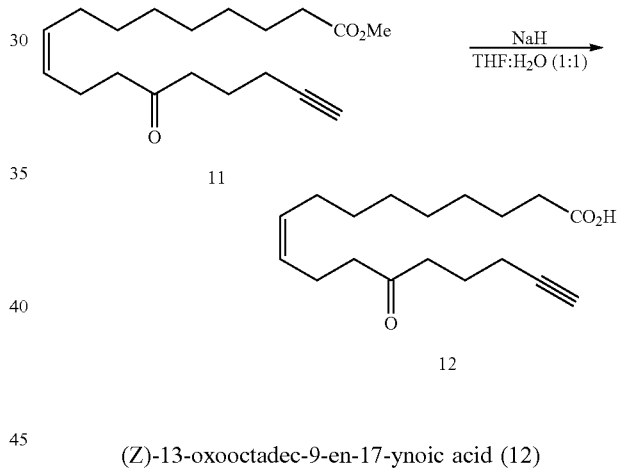

(Z)-13-oxooctadec-9-en-17-ynoic acid (12)

Methyl (Z)-13-oxooctadec-9-en-17-ynoate (11)

Synthesis of 4-oxonon-8-ynal (9)

In an oven-dried RBF, oxalyl chloride (1.1 mL, 12.8 mmol, 4.0 equiv) was added to anhydrous CH₂Cl₂ (50 mL) at −78° C. under N₂. To this solution was added DMSO (1.8 mL, 25.6 mmol, 8.0 equiv.) drop-wise. After 30 min of stirring at −78° C., diol 8 (500 mg, 3.2 mmol, 1.0 equiv.) in anhydrous CH₂Cl₂ (10 mL) was added over 15 min and the reaction was stirred for another 30 min. TEA (3.6 mL, 25.6 mmol, 8.0 equiv.) was then added and the reaction was stirred for 30 min at −78° C. before warming to 0° C. in an ice bath. After 30 min, the reaction was diluted with 30% EtOAc/hexanes and reaction mixture was passed through a silica plug. The eluent was then concentrated and used without further purification.

Methyl ester 11 (140 mg, 0.46 mmol, 1.0 equiv.) was dissolved in THF (1.0 mL), and NaOH (91 mg, 2.28 mmol, 5.0 equiv.) in H₂O (1.0 mL) was added. The reaction mixture was stirred at room temperature for 8 h and then transferred to a separatory funnel containing EtOAc (25 mL) and 0.1 M HCl (25 mL). The product was extracted with EtOAc (3×25 mL) and the combined organic layers were dried over anhydrous Na₂SO₄ and concentrated under reduced pressure. The remaining residue was purified by SiO₂ flash chromatography (20% EtOAc/hexanes, 1% HCO₂H) providing the title compound as a colorless oil (110 mg, 82%): ¹H NMR (500 MHz, CDCl₃) δ 5.41-5.34 (m, 1H), 5.32-5.25 (m, 1H), 2.55 (t, J=7.2 Hz, 2H), 2.46 (t, J=7.4 Hz, 2H), 2.37-2.26 (m, 4H), 2.22 (td, J=6.9, 2.6 Hz, 2H), 2.02 (q, J=7.1 Hz, 2H), 1.95 (t, J=2.6 Hz, 1H), 1.78 (p, J=7.1 Hz, 2H), 1.62 (p, J=7.3 Hz, 2H), 1.38-1.23 (m, 8H); ¹³C NMR (126 MHz, CDCl₃) δ 210.43, 180.30, 131.57, 128.13, 84.01, 69.42, 43.20, 41.58, 34.44, 29.91, 29.48, 29.43, 29.38, 27.52, 25.05, 22.62, 22.10, 18.17; HRMS (ESI-TOF+) m/z calc'd for C₁₈H₂₉O₃ [M+H]⁺: 293.2111, found 293.2110.

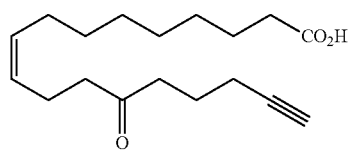

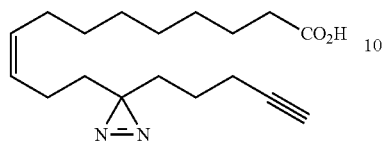

OA-DA (Z)-12-(3-(pent-4-yn-1-yl)-3H-diazirin-3-yl)dodec-9-enoic acid (OA-DA)

Diaziridine formation was accomplished using a method reported by (Bond et al., 2009). Ketone 12 (100 mg, 0.34 mmol, 1.0 equiv.) was dissolved in a solution of $NH_3$ (2.0 mL, 7.0 N in MeOH) at 0° C. in a RBF under $N_2$. After stirring for 3 h at 0° C., a solution of hydroxylamine-O-sulfonic acid (45 mg, 0.39 mmol, 1.15 equiv.) in anhydrous MeOH (2.0 mL) was added drop-wise over 10 min. The reaction mixture was allowed to slowly warm to room temperature while stirring overnight (~12 h). The reaction was then concentrated under a stream of $N_2$ and the remaining residue was redissolved in $Et_2O$ (10 mL) and filtered through a pad of Celite using additional $Et_2O$ (5 mL) for washes. The combined filtrate was then concentrated under reduced pressure providing the crude diaziridine intermediate which was used without further purification.

Diazirine formation was accomplished using a method reported by (Sanderson et al., 2005). The crude diaziridine intermediate (see above) was redissolved in anhydrous $CH_2Cl_2$ (4.0 mL) and pyridine (0.4 mL) in a RBF charged with a stir bar and flushed with $N_2$. Pyridinium chlorochromate (147 mg, 0.68 mmol, 2.0 equiv.) was then added in small portions over 20 min while the reaction mixture was cooled to 0° C. The reaction was then allowed to warm to room temperature and stirred for an additional 1 h before diluting with 50% EtOAc/hexanes (25 mL) and $HCO_2H$ (0.4 mL). The resulting solution was passed through a silica plug and the was filtrate concentrated and purified further by $SiO_2$ flash chromatography (15% EtOAc/hexanes, 1.0% $HCO_2H$) providing the title compound as a colorless oil (27 mg, 26%, 2 steps): $^1$H NMR (500 MHz, $CDCl_3$) δ 5.40-5.34 (m, 1H), 5.27-5.21 (m, 1H), 2.35 (t, J=7.5 Hz, 2H), 2.16 (td, J=7.0, 2.7 Hz, 2H), 1.98 (q, J=7.4 Hz, 2H), 1.94 (t, J=2.6 Hz, 1H), 1.82 (q, J=7.3 Hz, 2H), 1.63 (p, J=7.4 Hz, 2H), 1.54-1.47 (m, 2H), 1.46-1.39 (m, 2H), 1.38-1.24 (m, 10H); $^{13}$C NMR (126 MHz, $CDCl_3$) δ 180.02, 131.25, 127.88, 83.56, 69.04, 34.13, 33.21, 31.95, 29.60, 29.25, 29.18, 29.14, 28.47, 27.29, 24.79, 22.88, 21.82, 18.08; HRMS (ESI-TOF+) m/z calc'd for $C_{18}H_{27}N_2O_2$ [M+H]$^+$: 305.2223, found 305.2211.

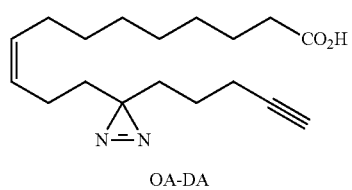 

OA-DA            TEA

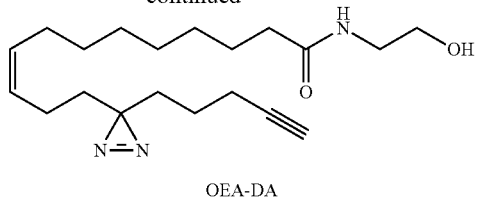

OEA-DA (Z)—N-(2-hydroxyethyl)-12-(3-(pent-4-yn-1-yl)-3H-diazirin-3-yl)dodec-9-enamide (OEA-DA)

To a stirring solution of OA-DA (15 mg, 0.049 mmol, 1.0 equiv.) and N-hydroxysuccinimide (8.5 mg, 0.074 mmol, 1.5 equiv) in anhydrous $CH_2Cl_2$ (2.0 mL) was added EDCI (14 mg, 0.074, 1.5 equiv.). The reaction mixture was stirred for 12 h at which point the starting material was completely consumed as judged by TLC (30% EtOAc/hexanes, 1.0% $HCO_2H$). The reaction mixture was poured into a separatory funnel with brine (25 mL) and product extracted with $CH_2Cl_2$ (3×25 mL). The combined organic layers were then dried over anhydrous $Na_2SO_4$ and concentrated under reduced pressure and this crude NHS ester was used without further purification.

A portion of the above-synthesized NHS ester (9.8 mg, 0.025 mmol, 1.0 equiv.) was dissolved in $CH_2Cl_2$ (1.0 mL) before adding TEA (17 µL, 0.125 mmol, 5.0 equiv.) and ethanolamine (7.5 µL, 0.125 mmol, 5.0 equiv.). After stirring for 1 h at room temperature, the reaction was concentrated under reduced pressure and the remaining residue was purified by $SiO_2$ flash chromatography (2% MeOH/EtOAc) providing the title compound as a white solid (6.2 mg, 71%): $^1$H NMR (500 MHz, $CDCl_3$) δ 5.90 (bs, 1H), 5.41-5.33 (m, 1H), 5.28-5.21 (m, 1H), 3.74 (t, J=4.8 Hz, 2H), 3.43 (q, J=4.4 Hz, 2H), 2.60 (bs, 1H), 2.21 (t, J=7.8 Hz, 2H), 2.16 (td, J=7.0, 2.6 Hz, 2H), 1.98 (q, J=7.5 Hz, 2H), 1.95 (t, J=2.7 Hz, 1H), 1.82 (q, J=8.4 Hz, 2H), 1.64 (p, J=7.6 Hz, 2H), 1.54-1.48 (m, 2H), 1.46-1.41 (m, 2H), 1.37-1.26 (m, 10H); $^{13}$C NMR (151 MHz, $CDCl_3$) δ 174.66, 131.28, 127.86, 83.58, 69.07, 62.93, 42.66, 36.80, 33.20, 31.95, 29.60, 29.35, 29.33, 29.20, 28.53, 27.29, 25.82, 22.88, 21.82, 18.09; HRMS (ESI-TOF+) m/z calc'd for $C_{20}H_{34}N_3O_2$ [M+H]$^+$: 348.2645, found 348.2645.

Synthesis of PEA-DA

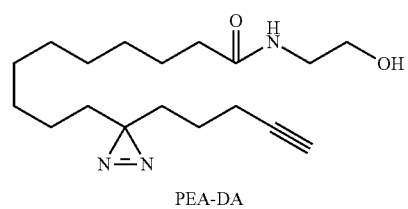

PEA-DA

N-(2-hydroxyethyl)-10-(3-(pent-4-yn-1-yl)-3H-diazirin-3-yl)decanamide (PEA-DA)

Synthetic protocols and analytical data for the synthesis of PEA-DA have been previously reported. (Hulce et al., 2013) The same methods were used herein.

Synthesis of A-DA

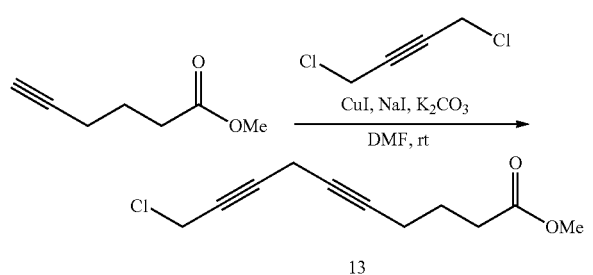

Methyl 10-chlorodeca-5,8-diynoate (13)

To a stirring heterogeneous mixture of $K_2CO_3$ (6.3 g, 45.6 mmol, 1.0 equiv.), CuI (8.7 g, 45.6 mmol, 1.0 equiv.), anhydrous NaI (6.84 g, 45.6 mmol, 1.0 equiv.) in anhydrous DMF (100 mL) was added 1,4-dichloro-2-butyne (18.0 mL, 184.4 mmol, 5.0 equiv.) and methyl 5-hexynoate (6.0 mL, 45.6 mmol, 1.0 equiv.) under $N_2$. The reaction mixture was stirred for 12 h at ambient temperature before diluting with EtOAc:hexanes (500 mL, 1:1) and passed through a pad of Celite to remove insoluble material. The filtrate was then added to a separatory funnel and washed with saturated $NH_4Cl$ (aq.) (500 mL) and then brine (2×500 mL). The organic layer was then dried over anhydrous $Na_2SO_4$ and concentrated under reduced pressure. The remaining residue was purified by $SiO_2$ flash chromatography (5% EtOAc/hexanes) providing the title compound as a colorless oil (5.33 g, 55%): $^1$H NMR (500 MHz, CDCl$_3$) δ 4.21 (t, J=2.2 Hz, 2H), 3.76 (s, 3H), 3.28 (p, J=2.3 Hz, 2H), 2.51 (t, J=7.4 Hz, 2H), 2.32 (t, J=6.9 Hz, 2H), 1.90 (p, J=7.4 Hz, 2H); $^{13}$C NMR (126 MHz, CDCl$_3$) δ 173.72, 81.64, 80.16, 75.22, 73.99, 51.72, 32.98, 30.82, 23.94, 18.29, 10.11; HRMS (ESI-TOF+) m/z calc'd for $C_{11}H_{14}ClO_2$ [M+H]$^+$: 213.0677, found 213.0676.

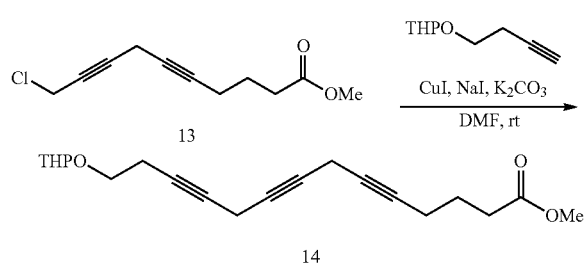

Methyl 14-((tetrahydro-2H-pyran-2-yl)oxy)tetradeca-5,8,11-triynoate (14)

To a stirring heterogeneous mixture of $K_2CO_3$ (1.55 g, 11.2 mmol, 1.0 equiv.), CuI (2.13 g, 11.2 mmol, 1.0 equiv.), anhydrous NaI (1.68 g, 11.2 mmol, 1.0 equiv.) in anhydrous DMF (50 mL) was added 2-(3-butynyloxy)tetrahydropyran (1.76 mL, 11.2 mmol, 1.0 equiv.) and diyne 13 (2.39 g, 11.2 mmol, 1.0 equiv.) under $N_2$. The reaction mixture was stirred for 12 h at ambient temperature before diluting with EtOAc: hexanes (250 mL, 1:1) and passed through a pad of Celite to remove insoluble material. The filtrate was then added to a separatory funnel and washed with saturated $NH_4Cl$ (aq.) (250 mL) and then brine (2×250 mL). The organic layer was then dried over anhydrous $Na_2SO_4$ and concentrated under reduced pressure. The remaining residue was purified by $SiO_2$ flash chromatography (5-10% EtOAc/hexanes) providing the title compound as a colorless oil (2.63 g, 71%): $^1$H NMR (500 MHz, CDCl$_3$) δ 4.61 (t, J=3.4 Hz, 1H), 3.89-3.82 (m, 1H), 3.80-3.73 (m, 1H), 3.65 (s, 3H), 3.54-3.41 (m, 2H), 3.13-3.06 (m, 4H), 2.47-2.42 (m, 2H), 2.40 (t, J=7.5 Hz, 2H), 2.23-2.17 (m, 2H), 1.84-1.74 (m, 3H), 1.72-1.64 (m, 1H), 1.60-1.44 (m, 4H); $^{13}$C NMR (126 MHz, CDCl$_3$) δ 173.70, 98.80, 79.53, 77.64, 74.96, 74.85, 74.81, 74.75, 65.81, 62.28, 51.63, 32.93, 30.65, 25.53, 23.93, 20.27, 19.51, 18.26, 9.88, 9.82; MS (ESI+) m/z calc'd for $C_{20}H_{27}NO_4$ [M+H]$^+$: 331.2, found 331.2.

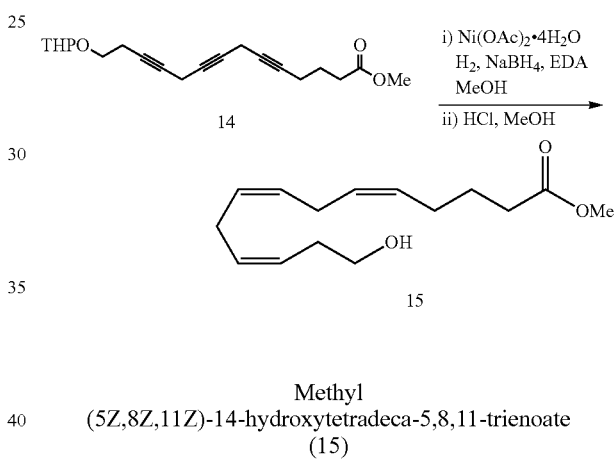

Methyl (5Z,8Z,11Z)-14-hydroxytetradeca-5,8,11-trienoate (15)

To a stirring mixture of Ni(OAc)$_4$.4H$_2$O (1.92 g, 7.73 mmol, 2.55 equiv.) in anhydrous MeOH (100 mL) under $N_2$ was added NaBH$_4$ (344 mg, 9.09 mmol, 3.0 equiv.) in small portions over 15 minutes. The reaction vessel was then purged with H2 and the mixture stirred for 30 min at ambient temperature. Ethylenediamine (0.45 mL, 6.7 mmol, 2.2 equiv.) was then added to the reaction mixture, followed by triyne 14 (1.0 g, 3.03 mmol, 1.0 equiv.). When the mass of the starting material was no longer detected by mass spectrometry (Agilent 1100 Series LC/MSD), the reaction was filtered through a pad of Celite, concentrated under reduced pressure and then passed through a pad of silica gel with (25% EtOAc/hexanes). The filtrate was then concentrated under reduced pressure and the remaining residue was redissolved in cold methanolic HCl (25 mL, 0.1 M) and stirred for 1 h at room temperature. The reaction mixture was then concentrated under a stream of $N_2$ and the crude product was purified by $SiO_2$—AgNO$_3$ (10%) flash chromatography (25-75% EtOAc/hexanes) providing the title compound as a colorless oil (428 mg, 56%): $^1$H NMR (500 MHz, CDCl$_3$) δ 5.55-5.46 (m, 1H), 5.43-5.29 (m, 5H), 3.64 (s, 3H), 3.62 (t, J=6.6 Hz, 2H), 2.83 (t, J=6.4 Hz, 2H), 2.78 (t, J=5.6 Hz, 2H), 2.34 (q, J=6.6 Hz, 2H), 2.31 (t, J=7.5 Hz, 2H), 2.09 (q, J=7.1 Hz, 2H), 1.68 (p, J=7.5 Hz, 2H); $^{13}$C NMR (126 MHz, CDCl$_3$) δ 174.24, 130.94, 129.00, 128.89, 128.39, 128.03, 125.78, 62.25, 51.60, 33.51, 30.96, 26.63, 25.84, 25.71, 24.83; HRMS (ESI-TOF+) m/z calc'd for $C_{15}H_{25}O_3$ [M+H]$^+$: 253.1798, found 253.1799.

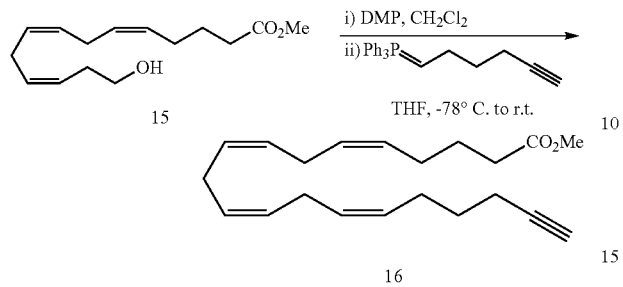

Methyl (5Z,8Z,11Z,14Z)-icosa-5,8,11,14-tetraen-19-ynoate (16)

Formation of Aldehyde.

A solution of methyl triene 15 (109 mg, 0.43 mmol, 1.0 equiv.) in anhydrous $CH_2Cl_2$ (5.0 mL) was cooled to 0° C. and DMP (220 mg, 0.52 mmol, 1.2 equiv.) was added. The reaction mixture was allowed to warm to room temperature and then stirred for an additional 1 h. The reaction was then cooled to 0° C. and quenched with sat. $NaHCO_3$ (5 mL) and sat. $Na_2S_2O_3$ (5 mL) and transferred to a separatory funnel. The product was extracted with $CH_2Cl_2$ (3×20 mL) and the combined organic layers were dried over anhydrous $Na_2SO_4$ and concentrated under reduced pressure providing methyl (5Z,8Z,11Z)-14-oxotetradeca-5,8,11-trienoate which was used immediately in the following Wittig reaction.

Wittig Reaction.

To a mixture of hex-5-yn-1-yltriphenylphosphonium iodide (Luo et al., 2013) (362 mg, 0.77 mmol, 1.8 equiv.) in anhydrous THF (10 mL) at −78° C. under $N_2$ was added NaHMDS (0.69 mL, 0.69 mmol, 1.0 M in THF, 1.6 equiv.). The resulting orange solution was allowed to warm to room temperature. After stirring for an additional 2 h at room temperature, the reaction mixture was cooled to −100° C. and freshly prepared methyl (5Z,8Z,11Z)-14-oxotetradeca-5,8,11-trienoate (108 mg, 0.43 mmol, 1.0 equiv.) in anhydrous THF (3.0 mL) was added drop-wise over 15 min and after stirring for an additional 1 h at −100° C., the reaction mixture was allowed to warm to room temperature overnight (~12 h). The reaction was then concentrated under reduced pressure and the remaining residue was purified by $SiO_2$ flash chromatography (5% EtOAc/hexanes) providing the title compound as a colorless oil (38 mg, 28%): $^1$H NMR (500 MHz, CDCl$_3$) δ 5.45 (s, 8H), 3.74 (s, 3H), 2.96-2.83 (m, 6H), 2.40 (t, J=7.3 Hz, 2H), 2.34-2.14 (m, 6H), 2.03 (s, 1H), 1.78 (p, J=7.2 Hz, 2H), 1.68 (p, J=7.0 Hz, 2H); $^{13}$C NMR (126 MHz, CDCl$_3$) δ 174.44, 129.34 (2C), 129.24 (2C), 128.73, 128.61, 128.54, 128.44, 84.75, 68.81, 51.89, 33.85, 28.73, 26.96, 26.56, 26.06, 26.03, 26.01, 25.18, 18.27; HRMS (ESI-TOF+) m/z calc'd for $C_{21}H_{31}O_2$ [M+H]$^+$: 315.2319, found 215.2317; MS (ESI+) m/z calc'd for $C_{21}H_{31}O_2$ [M+H]$^+$: 315.23, found 315.26.

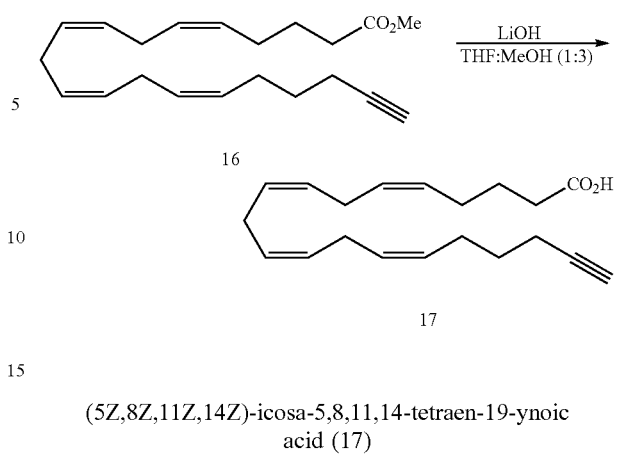

(5Z,8Z,11Z,14Z)-icosa-5,8,11,14-tetraen-19-ynoic acid (17)

Methyl ester 16 (38 mg, 0.12 mmol, 1.0 equiv.) was dissolved in THF (1.0 mL) and MeOH (3.0 mL), and LiOH (1.2 mL, 1.2 mmol, 1.0 M in $H_2O$, 10.0 equiv.) was added. The reaction mixture was stirred at room temperature for 4 h and then transferred to a separatory funnel containing EtOAc (25 mL) and 0.1 M HCl (25 mL). The product was extracted with EtOAc (3×25 mL) and the combined organic layers were dried over anhydrous $Na_2SO_4$ and concentrated under reduced pressure. The remaining residue was purified by $SiO_2$ flash chromatography (20% EtOAc/hexanes, 0.5% $HCO_2H$) providing the title compound as a colorless oil (34 mg, 94%). The NMR spectra matched those reported by (Milne et al., 2010).

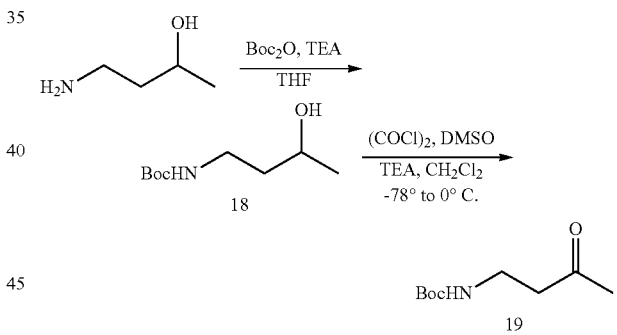

tert-Butyl (3-oxobutyl)carbamate (19)

To a stirring solution of 4-amino-2-butanol (0.50 mL, 5.22 mmol, 1.0 equiv.) and TEA (0.87 mL, 6.26 mmol, 1.2 equiv.) in THF (20 mL) was added $Boc_2O$ (1.25 g, 5.74 mmol, 1.1 equiv.) in small portions over 10 min. The reaction mixture was stirred for 1 h at room temperature and then quenched with ice cold 0.5 N HCl (20 mL). The product was extracted with EtOAc (3×100 mL) and the combined organic layers were dried over anhydrous $Na_2SO_4$ and concentrated under reduced pressure. The remaining residue was used without further purification.

In an oven-dried RBF, oxalyl chloride (0.91 mL, 10.4 mmol, 2.0 equiv) was added to anhydrous $CH_2Cl_2$ (100 mL) at −78° C. under $N_2$. To this solution was added DMSO (1.48 mL, 20.9 mmol, 4.0 equiv.) drop-wise. After 30 min of stirring at −78° C., tert-butyl (3-hydroxybutyl)carbamate (18) in anhydrous $CH_2Cl_2$ (10 mL) was added over 15 min and the reaction was stirred for another 30 min. TEA (2.91 mL, 20.9 mmol, 4.0 equiv.) was then added and the reaction was stirred for 30 min at −78° C. before warming to 0° C. in an ice bath. After 30 min, the reaction was diluted with Et₂O and reaction mixture was passed through a silica plug. After concentrating the eluent under reduced pressure the remaining residue was purified by SiO₂ flash chromatography (50% EtOAc/hexanes) providing the title compound as a colorless oil (826 mg, 85%); ¹H NMR (600 MHz, CDCl₃) δ 5.00 (bs, 1H), 3.31 (q, J=5.6 Hz, 2H), 2.64 (t, J=5.6 Hz, 2H), 2.13 (s, 3H), 1.39 (s, 9H); ¹³C NMR (151 MHz, CDCl₃) δ 208.29, 155.97, 79.30, 43.60, 35.23, 30.26, 28.46 (3C); MS (ESI+) m/z calc'd for $C_9H_{18}NO_3$ [M+H]⁺: 188.1, found 188.2.

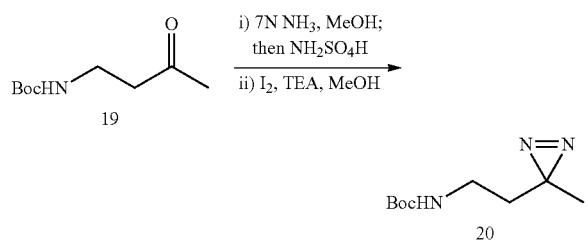

tert-Butyl (2-(3-methyl-3H-diazirin-3-yl)ethyl)carbamate (20)

Diazirine formation was accomplished using a method reported by Bond et al. (Bond et al., 2009) Ketone 19 (0.83 g, 4.43 mmol, 1.0 equiv.) was dissolved in a solution of NH₃ (10 mL, 7.0 N in MeOH) at 0° C. in a RBF under N₂. After stirring for 3 h at 0° C., a solution of hydroxylamine-O-sulfonic acid (577 mg, 5.10 mmol, 1.15 equiv.) in anhydrous MeOH (10 mL) was added drop-wise over 10 min. The reaction mixture was allowed to slowly warm to room temperature while stirring overnight (~12 h). The reaction was then concentrated under a stream of N₂ and the remaining residue was redissolved in Et₂O (10 mL) and filtered through a pad of Celite using additional Et₂O (5 mL) for washes. The combined filtrate was then concentrated under reduced pressure and redissolved in anhydrous MeOH (5.0 mL) in an amber RBF under N₂ and cooled to 0° C. TEA (0.93 mL, 6.65 mmol, 1.5 equiv.) was then added and the reaction mixture was stirred for 5 min. Keeping the reaction mixture at 0° C., iodine (1.24 g, 4.87 mmol, 1.1 equiv.) was slowly added as a solid over 30 min until the red-brown color persisted. The reaction mixture was stirred for an additional 30 min at 0° C. before quenching with sat. Na₂S₂O₃ (aq.) (50 mL). After vigorously stirring the quenched reaction mixture for 10 min, it was diluted further with EtOAc (100 mL) and the product was extracted with EtOAc (3×100 mL). The combined organic layers were dried over anhydrous Na₂SO₄ and concentrated under reduced pressure. The remaining residue was purified by SiO₂ flash chromatography (35% EtOAc/hexanes) providing the title compound as a light yellow oil (222 mg, 25%): ¹H NMR (500 MHz, CDCl₃) δ 4.71 (bs, 1H), 2.97 (q, J=6.3 Hz, 2H), 1.48 (t, J=6.9 Hz, 2H), 1.36 (s, 9H), 0.97 (s, 3H); ¹³C NMR (126 MHz, CDCl₃) δ 156.10, 79.63, 36.03, 35.00, 28.61, 24.66, 20.15; MS (ESI+) m/z calc'd for $C_9H_{18}N_3O_2$ [M+H]⁺: 200.1, found 200.2.

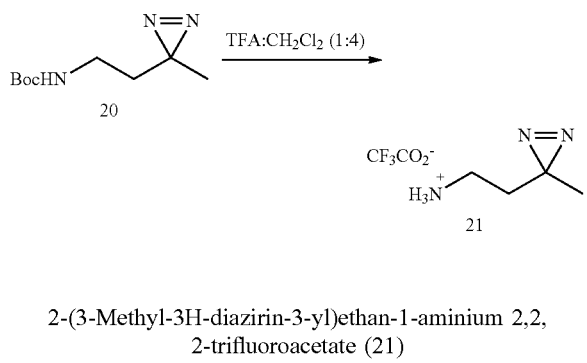

2-(3-Methyl-3H-diazirin-3-yl)ethan-1-aminium 2,2,2-trifluoroacetate (21)

Note: The title compound was synthesized immediately before coupling to alkyne fatty acids (see below). Diazirine 20 (0.1-0.4 mmol) was dissolved in anhydrous CH₂Cl₂ (2.0 mL/mmol of starting material) and cooled to 0° C. While stirring, TFA (0.5 mL/mmol of starting material) was added and the reaction was monitored by TLC. Upon complete consumption of starting material, the reaction mixture was concentrated under a stream of N₂. To remove residual amounts of TFA, the residue was repetitively redissolved in CH₂Cl₂ (~5 mL) and concentrated (3×) and finally placed under high vacuum for 1 h. The remaining residue was used in subsequent reactions without further purification.

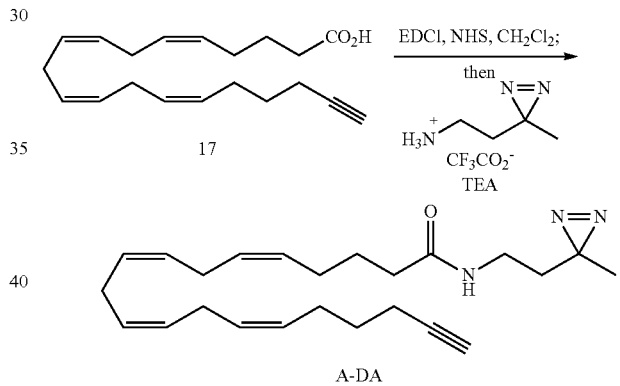

(5Z,8Z,11Z,14Z)—N-(2-(3-methyl-3H-diazirin-3-yl)ethyl)icosa-5,8,11,14-tetraen-19-ynamide (A-DA)

To a stirring solution of carboxylic acid 17 (34 mg, 0.113 mmol, 1.0 equiv.) and N-hydroxysuccinimide (20 mg, 0.170 mmol, 1.5 equiv) in anhydrous CH₂Cl₂ (2.0 mL) was added EDCI (33 mg, 0.170, 1.5 equiv.). The reaction mixture was stirred for 12 h at which point the starting material was completely consumed as judged by TLC (30% EtOAc/hexanes, 1.0% HCO₂H). The reaction mixture was poured into a separatory funnel with brine (25 mL) and product extracted with CH₂Cl₂ (3×25 mL). The combined organic layers were then dried over anhydrous Na₂SO₄ and concentrated under reduced pressure and this crude NHS ester was used without further purification.

The above-synthesized NHS ester was dissolved in CH₂Cl₂ (1.0 mL) before adding TEA (32 μL, 0.226 mmol, 2.0 equiv.) and amine 21 (48 mg, 0.226 mmol, 2.0 equiv.) in CH₂Cl₂ (1.0 mL). After stirring for 1 h at room temperature, the reaction was concentrated under reduced pressure and the remaining residue was purified by SiO₂ flash chromatography (50% EtOAc/hexanes) providing the title compound as a colorless oil (37 mg, 85%): $^1$H NMR (500 MHz, CDCl$_3$) δ 5.45 (bs, 1H), 5.43-5.31 (m, 8H), 3.16 (q, J=6.7 Hz, 2H), 2.86-2.74 (m, 6H), 2.22-2.15 (m, 6H), 2.12 (q, J=6.3 Hz, 2H), 1.96 (t, J=2.7 Hz, 1H), 1.72 (p, J=7.5 Hz, 2H), 1.63-1.57 (m, 4H), 1.05 (s, 3H); $^{13}$C NMR (151 MHz, CDCl$_3$) δ 172.96, 129.24, 129.09, 128.97, 128.91, 128.50, 128.33, 128.32, 128.15, 84.53, 68.58, 36.22, 34.75, 34.23, 28.46, 26.81, 26.30, 25.80, 25.79 (2C), 25.57, 24.65, 19.96, 18.00; HRMS (ESI-TOF+) m/z calc'd for C$_{24}$H$_{36}$N$_3$O [M+H]$^+$: 382.2853, found 382.2854.

Synthesis of O-DA

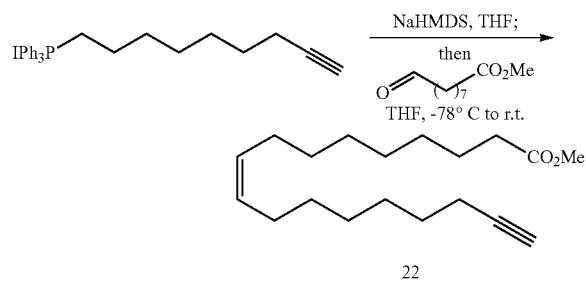

Methyl (Z)-octadec-9-en-17-ynoate (22)

To a mixture of non-8-yn-1-yltriphenylphosphonium iodide (2.45 g, 4.79 mmol, 1.8 equiv.) in anhydrous THF (30 mL) at −78° C. under N$_2$ was added NaHMDS (4.3 mL, 4.26 mmol, 1.0 M in THF, 1.6 equiv.). The resulting orange solution was allowed to warm to room temperature. After stirring for an additional 2 h at room temperature, the reaction mixture was cooled to −100° C. and freshly prepared methyl 9-oxononanoate (Zhang et al., 2006) (495 mg, 2.66 mmol, 1.0 equiv.) in anhydrous THF (25.0 mL) was added drop-wise over 15 min and after stirring for an additional 1 h at −100° C., the reaction mixture was allowed to warm to room temperature overnight (~12 h). The reaction was then concentrated under reduced pressure and the remaining residue was purified by SiO$_2$ flash chromatography (5% EtOAc/hexanes) providing the title compound as a colorless oil (335 mg, 43%): $^1$H NMR (600 MHz, CDCl$_3$) δ 5.33 (t, J=4.8 Hz, 2H), 3.65 (s, 3H), 2.29 (t, J=7.5 Hz, 2H), 2.17 (td, J=7.0, 2.0 Hz, 2H), 1.99 (p, J=6.0 Hz, 4H), 1.92 (s, 1H), 1.60 (p, J=6.8 Hz, 2H), 1.51 (p, J=7.2 Hz, 2H), 1.39 (p, J=7.4 Hz, 2H), 1.36-1.25 (m, 12H); $^{13}$C NMR (151 MHz, CDCl$_3$) δ 175.12, 130.74, 130.60, 85.55, 68.92, 52.27, 34.93, 30.51, 30.41, 30.00, 29.96, 29.92, 29.57, 29.48, 29.30, 28.00, 27.96, 25.78, 19.23; HRMS (ESI-TOF+) m/z calc'd for C$_{19}$H$_{33}$O$_2$ [M+H]$^+$: 293.2475, found 293.2476.

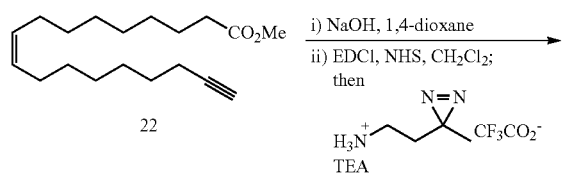

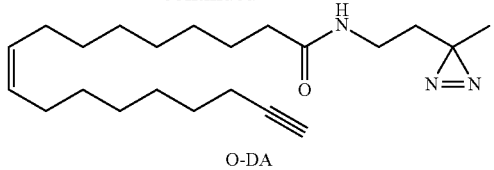

(Z)—N-(2-(3-methyl-3H-diazirin-3-yl)ethyl)octadec-9-en-17-ynamide (O-DA)

Hydrolysis of methyl ester. Methyl ester 22 (127 mg, 0.43 mmol, 1.0 equiv.) was dissolved in 1,4-dioxane (3.0 mL), and NaOH (2.2 mL, 2.2 mmol, 1.0 M in H$_2$O, 5.0 equiv.) was added. The reaction mixture was stirred at room temperature for 4 h and then transferred to a separatory funnel containing EtOAc (25 mL) and 0.1 M HCl (25 mL). The product was extracted with EtOAc (3×25 mL) and the combined organic layers were dried over anhydrous Na$_2$SO$_4$ and concentrated under reduced pressure. The remaining residue was passed through a silica plug (50% EtOAc/hexanes, 1% HCO$_2$H) and used without further purification.

NHS-Carbamate Formation.

To a stirring solution of (Z)-octadec-9-en-17-ynoic acid (57 mg, 0.20 mmol, 1.0 equiv.) and N-hydroxysuccinimide (26 mg, 0.31 mmol, 1.5 equiv) in anhydrous CH$_2$Cl$_2$ (2.0 mL) was added EDCI (59 mg, 0.31, 1.5 equiv.). The reaction mixture was stirred for 12 h at which point the starting material was completely consumed as judged by TLC (30% EtOAc/hexanes, 1.0% HCO$_2$H). The reaction mixture was poured into a separatory funnel with brine (25 mL) and product extracted with CH$_2$Cl$_2$ (3×25 mL). The combined organic layers were then dried over anhydrous Na$_2$SO$_4$ and concentrated under reduced pressure and this crude NHS ester was used without further purification.

Amide Formation.

The above-synthesized NHS ester was dissolved in CH$_2$Cl$_2$ (1.0 mL) before adding TEA (56 μL, 0.40 mmol, 2.0 equiv.) and amine 21 (85 mg, 0.40 mmol, 2.0 equiv.) in CH$_2$Cl$_2$ (1.0 mL). After stirring for 1 h at room temperature, the reaction was concentrated under reduced pressure and the remaining residue was purified by SiO$_2$ flash chromatography (50% EtOAc/hexanes) providing the title compound as a colorless oil (63 mg, 87%): $^1$H NMR (600 MHz, CDCl$_3$) δ 5.54 (bs, 1H), 5.36-5.29 (m, 2H), 3.15 (q, J=6.1 Hz, 2H), 2.15 (q, J=7.1 Hz, 4H), 2.03-1.96 (m, 4H), 1.93 (s, 1H), 1.65-1.56 (m, 4H), 1.50 (p, J=7.0 Hz, 2H), 1.39 (p, J=6.1 Hz, 2H), 1.35-1.22 (m, 12H), 1.03 (s, 3H); $^{13}$C NMR (151 MHz, CDCl$_3$) δ 173.27, 130.01, 129.88, 84.88, 68.21, 36.90, 34.69, 34.22, 29.80, 29.68, 29.37 (2C), 29.25, 28.84, 28.75, 28.57, 27.29, 27.23, 25.79, 24.62, 19.93, 18.50; HRMS (ESI-TOF+) m/z calc'd for C$_{22}$H$_{38}$N$_3$O [M+H]$^+$: 360.3009, found 360.3008.

Synthesis of S-DA

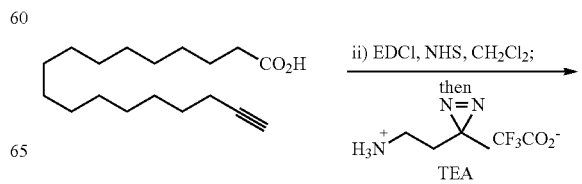

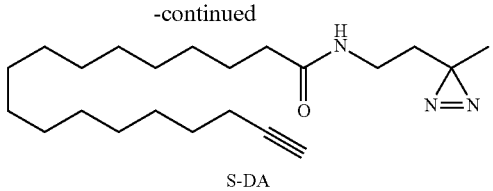

N-(2-(3-Methyl-3H-diazirin-3-yl)ethyl)octadec-17-ynamide (S-DA)

NHS-Carbamate Formation.

To a stirring solution of commercially available 17-octadecynoic acid (10 mg, 0.036 mmol, 1.0 equiv.) and N-hydroxysuccinimide (6.1 mg, 0.053 mmol, 1.5 equiv) in anhydrous $CH_2Cl_2$ (1.0 mL) was added EDCI (10 mg, 0.053, 1.5 equiv.). The reaction mixture was stirred for 12 h at which point the starting material was completely consumed as judged by TLC (35% EtOAc/hexanes, 1.0% $HCO_2H$). The reaction mixture was poured into a separatory funnel with brine (25 mL) and product extracted with $CH_2Cl_2$ (3×25 mL). The combined organic layers were then dried over anhydrous $Na_2SO_4$ and concentrated under reduced pressure and this crude NHS ester was used without further purification.

Amide Formation.

The above-synthesized NHS ester was dissolved in $CH_2Cl_2$ (1.0 mL) before adding TEA (10 μL, 0.072 mmol, 2.0 equiv.) amine 21 (15 mg, 0.072 mmol, 2.0 equiv.) in $CH_2Cl_2$ (1.0 mL). After stirring for 1 h at room temperature, the reaction was concentrated under reduced pressure and the remaining residue was purified by $SiO_2$ flash chromatography (50% EtOAc/hexanes) providing the title compound as a white solid (10 mg, 77%): $^1H$ NMR (500 MHz, $CDCl_3$) δ 5.43 (bs, 1H), 3.17 (q, J=6.7 Hz, 2H), 2.22-2.13 (m, 4H), 1.93 (t, J=2.6 Hz, 1H), 1.68-1.56 (m, 4H), 1.52 (q, J=7.1 Hz, 2H), 1.39 (p, J=7.8 Hz, 2H), 1.31-1.23 (m, 20H), 1.05 (s, 3H); $^{13}C$ NMR (126 MHz, $CDCl_3$) δ 173.32, 84.99, 68.17, 36.99, 34.73, 34.25, 29.85, 29.79, 29.75, 29.65, 29.64, 29.50, 29.44, 29.27, 28.92, 28.65, 25.84, 24.67, 19.98, 18.55; HRMS (ESI-TOF+) m/z calc'd for $C_{22}H_{40}N_3O$ $[M+H]^+$: 362.3166, found 362.3168.

F1-AEA Synthesis

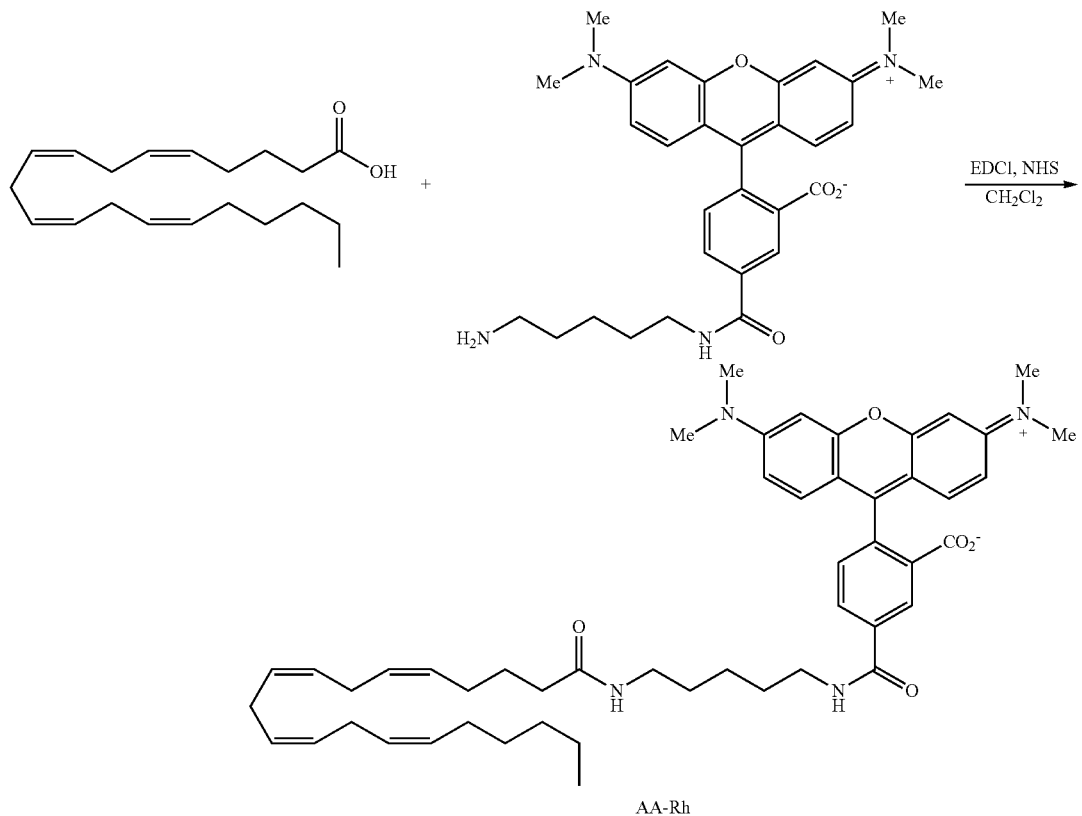

2-(6-(Dimethylamino)-3-(dimethyliminio)-3H-xanthen-9-yl)-5-((5-((5Z,8Z,11Z,14Z)-icosa-5,8,11,14-tetraenamido)pentyl)carbamoyl)benzoate (F1-AEA)

To a stirring solution of arachidonic acid (420 mg, 1.38 mmol, 1.0 equiv.) and N-hydroxysuccinimide (238 mg, 2.07 mmol, 1.5 equiv) in anhydrous $CH_2Cl_2$ (10 mL) was added EDCI (397 mg, 2.07, 1.5 equiv.). The reaction mixture was stirred for 12 h at which point the starting material was completely consumed as judged by TLC (30% EtOAc/hexanes, 1.0% $HCO_2H$). The reaction mixture was poured into a separatory funnel with brine (25 mL) and product extracted with $CH_2Cl_2$ (3×25 mL). The combined organic layers were then dried over anhydrous $Na_2SO_4$ and concentrated under reduced pressure and the resulting residue passed through a pad of silica (50% EtOAc/hexanes). A portion of the concentrated eluent was used in the following step.

The above-synthesized NHS ester (15 mg, 0.038 mmol, 2.0 equiv.) was dissolved in $CH_2Cl_2$ (2.0 mL) and 5-TAMRA-cadavarine 21 (10 mg, 0.019 mmol, 1.0 equiv.) in $CH_2Cl_2$ (1.0 mL). After stirring overnight at room temperature under $N_2$, the reaction was concentrated under reduced pressure and the remaining residue was purified by prep. TLC (15% $MeOH/CH_2Cl_2$) providing the title compound as a dark red oil (9.2 mg, 60%): $^1H$ NMR (600 MHz, $CDCl_3$) δ 8.41 (s, 1H), 8.20 (dd, J=8.0, 1.6 Hz, 1H), 7.25 (d, J=8.0 Hz, 1H), 6.82 (t, J=5.5 Hz, 1H), 6.57 (d, J=8.8 Hz, 2H), 6.48 (d, J=2.5 Hz, 2H), 6.38 (dd, J=8.9, 2.6 Hz, 2H), 5.61 (t, J=5.4 Hz, 1H), 5.43-5.29 (m, 8H), 3.50 (q, J=6.5 Hz, 2H), 3.26 (q, J=6.6 Hz, 2H), 2.98 (s, 12H), 2.84-2.76 (m, 6H), 2.18 (t, J=7.5 Hz, 2H), 2.08 (q, J=6.6 Hz, 2H), 2.04 (q, J=7.2 Hz, 2H), 1.69 (p, J=7.3 Hz, 4H), 1.55 (p, J=7.0 Hz, 2H), 1.42 (p, J=7.5 Hz, 2H), 1.37-1.26 (m, 6H), 0.88 (t, J=6.9 Hz, 3H); $^{13}C$ NMR (151 MHz, $CDCl_3$) δ 173.33, 169.30, 166.30, 155.41, 153.13, 152.37, 136.39, 134.36, 130.66, 129.31, 128.85, 128.82, 128.73, 128.35, 128.33, 128.28, 128.00, 127.66, 124.81, 123.02, 108.90, 106.32, 98.62, 40.39, 40.17, 39.08, 36.31, 31.66, 29.85, 29.47, 28.90, 27.37, 26.83, 25.78, 25.77, 24.01, 22.72, 14.24.

Example III

NUCB1 Ligand Synthesis

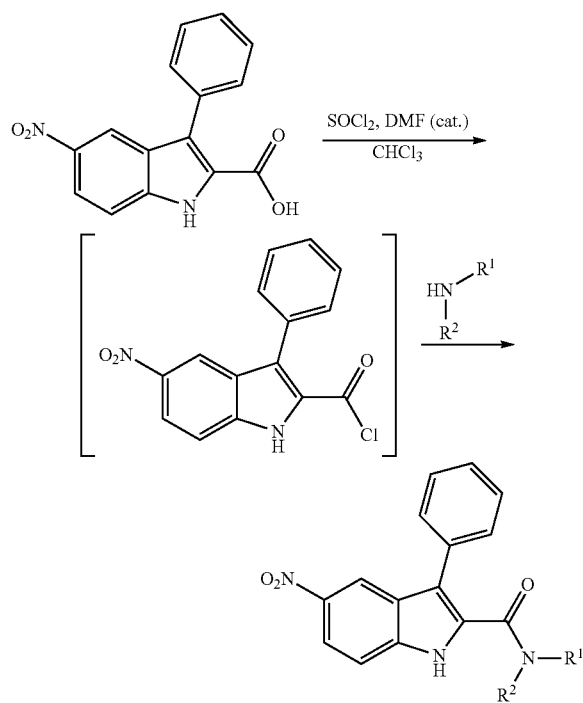

Representative Procedure A:

Acyl Chloride Formation:

To a stirring mixture of 5-nitro-3-phenyl-1H-indole-2-carboxylic acid (110 mg, 0.39 mmol, 1.0 equiv.) in $CHCl_3$ (5.0 mL) under $N_2$ was added $SOCl_2$ (37 µL, 0.51 mmol, 1.3 equiv.) followed by DMF (~10 µL). The reaction mixture was heated to reflux for 1 h and then concentrated under a stream of $N_2$ and then under reduced pressure providing the crude acyl chloride which was used without further purification.

Amide Formation:

To a stirring solution of amine (0.18 mmol, 2.0 equiv.) and NMM (42 µL, 0.36 mmol, 4.0 equiv.) in $CH_2Cl_2$ (2.0 mL) was added a solution of 5-nitro-3-phenyl-1H-indole-2-carbonyl chloride (27 mg, 0.09 mmol, 1.0 equiv.) in $CH_2Cl_2$ (1.0 mL). The reaction was stirred for 1 h at room temperature and then concentrated under a stream of N2. The crude product was purified by prep. TLC.

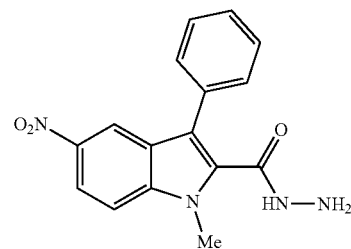 [SMILES: Cn1c(C(=O)NN)c(-c2ccccc2)c2cc([N+](=O)[O-])ccc21]

1-Methyl-5-nitro-3-phenyl-1H-indole-2-carbohydrazide (2)

To a stirring solution of methyl 1-methyl-5-nitro-3-phenyl-1H-indole-2-carboxylate (25 mg, 0.081 mmol, 1.0 equiv.) in MeOH (3.0 mL) was added hydrazine monohydrate (41 mg, 0.81 mmol, 10 equiv.). The reaction mixture was then heated to 50° C., stirred overnight and concentrated under a stream of N2. The product was purified by prep. TLC [MeOH:EtOAc:$CH_2Cl_2$ (5:45:50)] providing the title compound as a yellow solid (19 mg, 76%): $^1H$ NMR (600 MHz, $CDCl_3$) δ 8.51 (d, J=2.1 Hz, 1H), 8.24 (dd, J=9.2, 2.1 Hz, 1H), 7.61-7.38 (m, 6H), 6.87 (bs, 1H), 4.07 (s, 3H); $^{13}C$ NMR (151 MHz, $CDCl_3$) δ 163.38, 143.45, 141.18, 132.52, 131.09, 130.63, 130.35, 129.45, 126.44, 122.11, 120.65, 119.31, 111.12, 30.55; HRMS (ESI-TOF+) m/z calc'd for $C_{16}H_{15}N_4O_3$ $[M+H]^+$: 311.1144, found 311.1142.

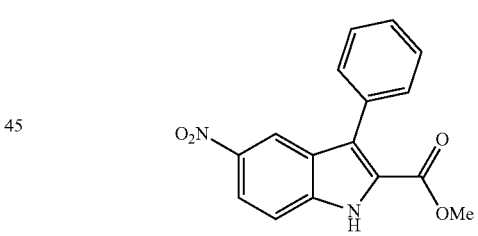

Methyl 5-nitro-3-phenyl-1H-indole-2-carboxylate (3)

In a RBF, anhydrous MeOH (10 mL) was cooled to 0° C. and acetyl chloride (2.0 mL) was carefully added drop-wise over 10 min while the reaction was vigorously stirred. The resulting methanolic HCl solution was then allowed to warm to room temperature and stirred for 15 min before adding 5-nitro-3-phenyl-1H-indole-2-carboxylic acid (99 mg, 0.35 mmol, 1.0 equiv.). The reaction mixture was then heated to 50° C., stirred overnight and concentrated under a stream of N2. The product was purified by prep. TLC (20% EtOAc/$CH_2Cl_2$) providing the title compound as a yellow solid (75 mg, 72%): $^1H$ NMR (600 MHz, 9:1 $CDCl_3$:$CD_3OD$) δ 8.48 (d, J=2.2 Hz, 1H), 8.14 (dd, J=9.1, 2.2 Hz, 1H), 7.58-7.32 (m, 6H), 3.42 (s, 3H); $^{13}C$ NMR (151 MHz, $D_2O$) δ 162.08, 142.40, 138.94, 132.16, 130.36, 128.20, 127.90, 127.08, 126.24, 125.67, 120.53, 119.37, 112.48, 52.05; HRMS (ESI-TOF+) m/z calc'd for $C_{16}H_{13}N_2O_4$ [M+H]$^+$: 297.0875, found 297.0869.

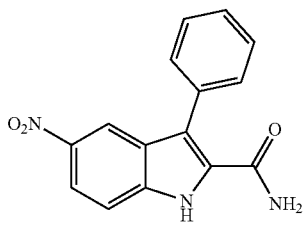 [SMILES: NC(=O)c1[nH]c2ccc([N+](=O)[O-])cc2c1-c1ccccc1]

5-Nitro-3-phenyl-1H-indole-2-carboxamide (4)

The title compound was synthesized according to Representative Procedure A from ammonium hydroxide (36 μL, 0.90 mmol, 10 equiv.) and 5-nitro-3-phenyl-1H-indole-2-carbonyl chloride (27 mg, 0.09 mmol, 1.0 equiv.). Purification of the crude product by prep. TLC (20% EtOAc/CH$_2$Cl$_2$) provided the title compound as a yellow solid (21 mg, 83%): $^1$H NMR (600 MHz, 9:1 CDCl$_3$:CD$_3$OD) δ 8.35 (d, J=2.2 Hz, 1H), 8.14 (dd, J=9.1, 2.2 Hz, 1H), 7.61-7.43 (m, 6H); $^{13}$C NMR (151 MHz, 9:1 CDCl$_3$:CD$_3$OD) δ 143.04, 139.21, 132.78, 131.06, 130.34, 129.86, 129.65, 128.26, 122.44, 120.73, 119.35, 113.26; HRMS (ESI-TOF+) m/z calc'd for $C_{15}H_{12}N_3O_3$ [M+H]$^+$: 282.0879, found 282.0873.

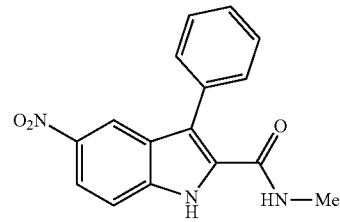 [SMILES: CNC(=O)c1[nH]c2ccc([N+](=O)[O-])cc2c1-c1ccccc1]

N-Methyl-5-nitro-3-phenyl-1H-indole-2-carboxamide (5)

The title compound was synthesized according to Representative Procedure A from methylamine (225 μL, 0.45 mmol, 2.0 M in THF, 5.0 equiv.) and 5-nitro-3-phenyl-1H-indole-2-carbonyl chloride (27 mg, 0.09 mmol, 1.0 equiv.). Purification of the crude product by prep. TLC (20% EtOAc/CH$_2$Cl$_2$) provided the title compound as a yellow solid (23 mg, 87%): $^1$H NMR (600 MHz, 9:1 CDCl$_3$:CD$_3$OD) δ 8.27 (d, J=2.2 Hz, 1H), 8.04 (dd, J=9.1, 2.3 Hz, 1H), 7.47-7.37 (m, 6H), 2.68 (s, 3H); $^{13}$C NMR (151 MHz, 9:1 CDCl$_3$:CD$_3$OD) δ 161.96, 142.16, 138.16, 131.89, 130.15, 129.51, 129.43, 128.75, 127.27, 120.24, 119.66, 118.27, 112.30, 26.08; HRMS (ESI-TOF+) m/z calc'd for $C_{16}H_{14}N_3O_3$ [M+H]$^+$: 296.1035, found 296.1030.

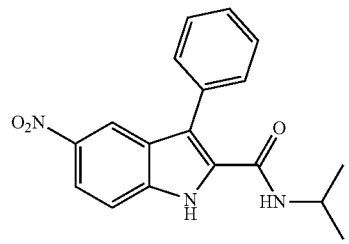 [SMILES: CC(C)NC(=O)c1[nH]c2ccc([N+](=O)[O-])cc2c1-c1ccccc1]

N-Isopropyl-5-nitro-3-phenyl-1H-indole-2-carboxamide (6)

The title compound was synthesized according to Representative Procedure A from isopropylamine (15 μL, 0.18 mmol, 2.0 equiv.), NMM (42 μL, 0.36 mmol, 4.0 equiv.) and 5-nitro-3-phenyl-1H-indole-2-carbonyl chloride (27 mg, 0.09 mmol, 1.0 equiv.). Purification of the crude product by prep. TLC (20% EtOAc/CH$_2$Cl$_2$) provided the title compound as a yellow solid (25 mg, 86%): $^1$H NMR (600 MHz, CDCl$_3$) δ 8.44 (d, J=2.2 Hz, 1H), 8.21 (dd, J=9.0, 2.2 Hz, 1H), 7.68-7.43 (m, 6H), 5.90 (d, J=7.8 Hz, 1H), 4.23 (hept, J=6.7 Hz, 1H), 1.06 (d, J=6.6 Hz, 6H); $^{13}$C NMR (151 MHz, CDCl$_3$) δ 160.40, 142.62, 138.18, 132.09, 130.63, 130.63, 129.97, 129.73, 129.71, 129.22, 127.75, 120.34, 120.04, 118.59, 112.47, 77.16, 42.16, 22.47; HRMS (ESI-TOF+) m/z calc'd for $C_{18}H_{18}N_3O_3$ [M+H]$^+$: 324.1343, found 324.1341.

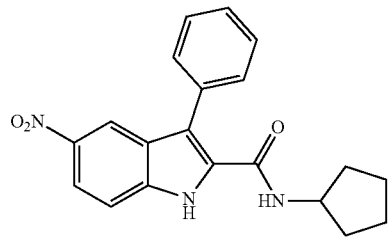 [SMILES: O=C(NC1CCCC1)c1[nH]c2ccc([N+](=O)[O-])cc2c1-c1ccccc1]

N-Cyclopentyl-5-nitro-3-phenyl-1H-indole-2-carboxamide (7)

The title compound was synthesized according to Representative Procedure A from cyclopentylamine (18 μL, 0.18 mmol, 2.0 equiv.), NMM (42 μL, 0.36 mmol, 4.0 equiv.) and 5-nitro-3-phenyl-1H-indole-2-carbonyl chloride (27 mg, 0.09 mmol, 1.0 equiv.). Purification of the crude product by prep. TLC (20% EtOAc/CH$_2$Cl$_2$) provided the title compound as a yellow solid (27 mg, 87 $^1$H NMR (600 MHz, CDCl$_3$) δ 10.92 (s, 1H), 8.42 (d, J=2.2 Hz, 1H), 8.21 (dd, J=9.1, 2.2 Hz, 1H), 7.66-7.45 (m, 6H), 6.03 (d, J=7.4 Hz, 1H), 4.37 (dtd, J=11.9, 7.0, 5.0 Hz, 1H), 1.94-1.84 (m, 2H), 1.61-1.52 (m, 2H), 1.46-1.36 (m, 2H), 1.29-1.19 (m, 2H); $^{13}$C NMR (151 MHz, CDCl$_3$) δ 160.54, 142.63, 138.07, 132.18, 130.60, 130.04, 129.76, 129.25, 127.83, 120.26, 120.04, 118.56, 112.45, 77.16, 51.75, 33.07, 23.42, 23.39; HRMS (ESI-TOF+) m/z calc'd for $C_{20}H_{20}N_3O_3$ [M+H]$^+$: 350.1499, found 350.1500.

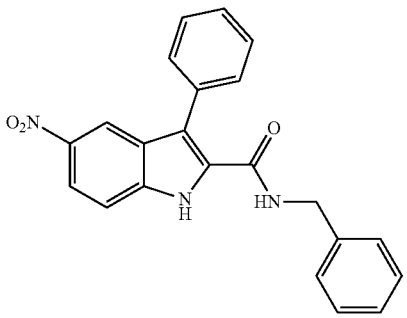 [SMILES: O=C(NCc1ccccc1)c1[nH]c2ccc([N+](=O)[O-])cc2c1-c1ccccc1]

N-Benzyl-5-nitro-3-phenyl-1H-indole-2-carboxamide (8)

The title compound was synthesized according to Representative Procedure A from benzylamine (20 μL, 0.18 mmol, 2.0 equiv.), NMM (42 μL, 0.36 mmol, 4.0 equiv.) and 5-nitro-3-phenyl-1H-indole-2-carbonyl chloride (27 mg, 0.09 mmol, 1.0 equiv.). Purification of the crude product by prep. TLC (20% EtOAc/CH$_2$Cl$_2$) provided the title compound as a yellow solid (30 mg, 90%): $^1$H NMR (600 MHz, CDCl$_3$) δ 8.41 (d, J=2.2 Hz, 1H), 8.15 (dd, J=9.1, 2.2 Hz, 1H), 7.54-7.46 (m, 5H), 7.42 (d, J=9.1 Hz, 1H), 7.35-7.28 (m, 3H), 7.16-7.11 (m, 2H), 6.44 (t, J=5.5 Hz, 1H), 4.57 (d, J=5.7 Hz, 2H); $^{13}$C NMR (151 MHz, CDCl$_3$) δ 161.32, 142.67, 138.18, 137.13, 131.87, 130.50, 129.85, 129.42, 129.22, 128.93, 127.85, 127.77, 127.35, 120.84, 120.23, 118.66, 112.54, 77.16, 43.98; HRMS (ESI-TOF+) m/z calc'd for C$_{22}$H$_{18}$N$_3$O$_3$ [M+H]$^+$: 372.1343, found 372.1345.

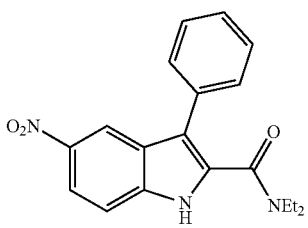

N,N-Diethyl-5-nitro-3-phenyl-1H-indole-2-carboxamide (9)

The title compound was synthesized according to Representative Procedure A from diethylamine (18 μL, 0.18 mmol, 2.0 equiv.), NMM (42 μL, 0.36 mmol, 4.0 equiv.) and 5-nitro-3-phenyl-1H-indole-2-carbonyl chloride (27 mg, 0.09 mmol, 1.0 equiv.). Purification of the crude product by prep. TLC (20% EtOAc/CH$_2$Cl$_2$) provided the title compound as a yellow solid (24 mg, 78%): $^1$H NMR (600 MHz, CDCl$_3$) δ 10.21 (s, 1H), 8.71 (d, J=2.2 Hz, 1H), 8.16 (dd, J=9.0, 2.2 Hz, 1H), 7.56-7.46 (m, 5H), 7.45-7.39 (m, 1H), 3.54 (s, 2H), 3.05 (s, 2H), 1.18 (s, 3H), 0.66 (s, 3H); $^{13}$C NMR (151 MHz, CDCl$_3$) δ 163.46, 142.11, 138.25, 132.19, 130.19, 128.78, 128.65, 127.47, 125.10, 118.68, 118.21, 117.35, 111.41, 42.65, 38.87, 12.84, 11.69; HRMS (ESI-TOF+) m/z calc'd for C$_{19}$H$_{20}$N$_3$O$_3$ [M+H]$^+$: 338.1499, found 338.1496.

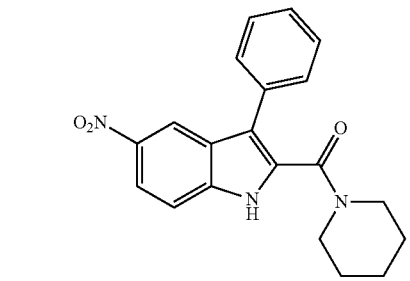 [SMILES: O=C(c1[nH]c2ccc([N+](=O)[O-])cc2c1-c1ccccc1)N1CCCCC1]

(5-Nitro-3-phenyl-1H-indol-2-yl)(piperidin-1-yl)methanone (10)

The title compound was synthesized according to Representative Procedure A from piperidine (18 μL, 0.18 mmol, 2.0 equiv.), NMM (42 μL, 0.36 mmol, 4.0 equiv.) and 5-nitro-3-phenyl-1H-indole-2-carbonyl chloride (27 mg, 0.09 mmol, 1.0 equiv.). Purification of the crude product by prep. TLC (20% EtOAc/CH$_2$Cl$_2$) provided the title compound as a yellow solid (16 mg, 51%): $^1$H NMR (600 MHz, 9:1 CDCl$_3$:CD$_3$OD) δ 8.71 (d, J=2.1 Hz, 1H), 8.18 (d, J=8.9 Hz, 1H), 7.51 (d, J=6.2 Hz, 5H), 7.45-7.39 (m, 1H), 3.61 (s, 2H), 3.08-3.00 (m, 2H), 1.64-1.36 (m, 4H), 0.85 (s, 2H); $^{13}$C NMR (151 MHz, 9:1 CDCl$_3$:CD$_3$OD) δ 163.21, 142.42, 139.11, 132.82, 130.20, 129.27, 129.25, 127.86, 125.43, 119.08, 117.85, 112.14, 48.38, 43.37, 25.27, 25.08, 24.15; HRMS (ESI-TOF+) m/z calc'd for C$_{20}$H$_{20}$N$_3$O$_3$ [M+H]$^+$: 350.1499, found 350.1503.

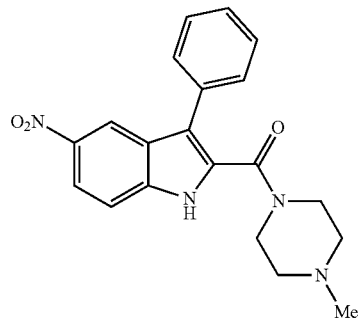 [SMILES: CN1CCN(C(=O)c2[nH]c3ccc([N+](=O)[O-])cc3c2-c2ccccc2)CC1]

(4-Methylpiperazin-1-yl)(5-nitro-3-phenyl-1H-indol-2-yl)methanone (11, MJN228)

The title compound was synthesized according to Representative Procedure A from 1-methylpiperazine (20 μL, 0.18 mmol, 2.0 equiv.), NMM (42 μL, 0.36 mmol, 4.0 equiv.) and 5-nitro-3-phenyl-1H-indole-2-carbonyl chloride (27 mg, 0.09 mmol, 1.0 equiv.). Purification of the crude product by prep. TLC (20% EtOAc/CH$_2$Cl$_2$) provided the title compound as a yellow solid (26 mg, 79%): $^1$H NMR (600 MHz, 9:1 CDCl$_3$:CD$_3$OD) δ 8.60 (d, J=2.2 Hz, 1H), 8.09 (dd, J=9.1, 2.2 Hz, 1H), 7.49-7.32 (m, 6H), 3.61 (bs, 2H), 3.06 (bs, 2H), 2.27 (bs, 2H), 2.05 (s, 3H), 1.56 (bs, 2H); $^{13}$C NMR (151 MHz, 9:1 CDCl$_3$:CD$_3$OD) δ 164.00, 143.13, 139.90, 133.42, 130.26, 130.12, 130.03, 128.69, 126.03, 120.17, 119.91, 118.52, 112.96, 54.45, 47.53, 46.28, 42.65; HRMS (ESI-TOF+) m/z calc'd for C$_{20}$H$_{21}$N$_4$O$_3$ [M+H]$^+$: 365.1614, found 365.1607.

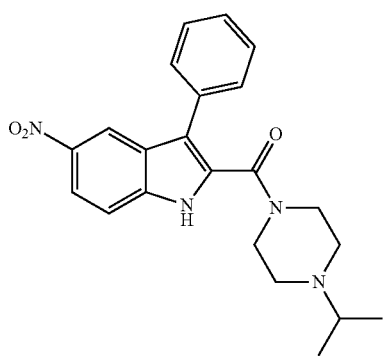 [SMILES: CC(C)N1CCN(C(=O)c2[nH]c3ccc([N+](=O)[O-])cc3c2-c2ccccc2)CC1]

(4-Isopropylpiperazin-1-yl)(5-nitro-3-phenyl-1H-indol-2-yl)methanone (12)

The title compound was synthesized according to Representative Procedure A from 1-isopropylpiperazine (9.4 μL, 0.066 mmol, 1.9 equiv.), NMM (10 μL, 0.091 mmol, 2.6 equiv.) and 5-nitro-3-phenyl-1H-indole-2-carboxylic acid (9.8 mg, 0.035 mmol, 1.0 equiv.). Purification of the crude product by prep. TLC (20% EtOAc/CH$_2$Cl$_2$) provided the title compound as a yellow solid (9.3 mg, 68%): $^1$H NMR (400 MHz, CDCl$_3$) δ 10.78 (s, 1H), 8.67 (s, 1H), 8.17 (dd, J=9.1, 2.2 Hz, 1H), 7.59-7.47 (m, 5H), 7.43 (t, J=7.1 Hz, 1H), 3.75 (bs, 2H), 3.15 (bs, 2H), 2.64-2.51 (m, 1H), 2.46 (bs, 2H), 1.72 (bs, 2H), 0.89 (d, J=6.5 Hz, 6H); $^{13}$C NMR (101 MHz, CDCl$_3$) δ 163.14, 142.69, 139.09, 132.80, 129.59, 129.56, 128.18, 125.69, 119.96, 119.50, 118.03, 112.19, 18.25; HRMS (ESI-TOF+) m/z calc'd for C$_{22}$H$_{25}$N$_4$O$_3$ [M+H]$^+$: 393.1921, found 393.1921.

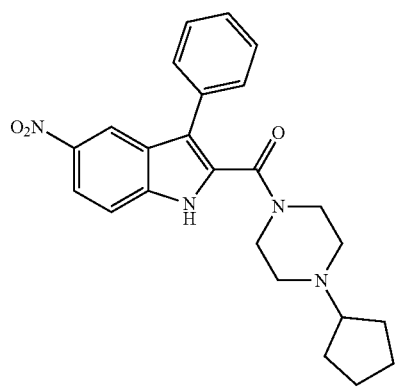 [SMILES: O=C(c1[nH]c2ccc([N+](=O)[O-])cc2c1-c1ccccc1)N1CCN(C2CCCC2)CC1]

(4-Cyclopentylpiperazin-1-yl)(5-nitro-3-phenyl-1H-indol-2-yl)methanone (13)

The title compound was synthesized according to Representative Procedure A from 1-cyclopentylpiperazine (6.9 μL, 0.044 mmol, 1.2 equiv.), NMM (5 μL, 0.045 mmol, 1.2 equiv.) and 5-nitro-3-phenyl-1H-indole-2-carboxylic acid (10.4 mg, 0.046 mmol, 1.0 equiv.). Purification of the crude product by prep. TLC (10% MeOH/CH$_2$Cl$_2$ then 10% MeOH/EtOAc) provided the title compound as a yellow solid (8.9 mg, 57%): $^1$H NMR (400 MHz, CDCl$_3$) δ 10.54 (s, 1H), 8.68 (d, J=2.2 Hz, 1H), 8.18 (dd, J=9.0, 2.2 Hz, 1H), 7.56-7.47 (m, 5H), 7.47-7.40 (m, 1H), 3.76 (s, 2H), 3.13 (s, 2H), 2.44 (s, 2H), 2.32 (p, J=8.1 Hz, 1H), 1.73 (d, J=17.9 Hz, 3H), 1.66-1.58 (m, 1H), 1.54-1.42 (m, 2H), 1.25 (s, 4H); HRMS (ESI-TOF+) m/z calc'd for C$_{24}$H$_{27}$N$_4$O$_3$ [M+H]$^+$: 419.2078, found 419.2077.

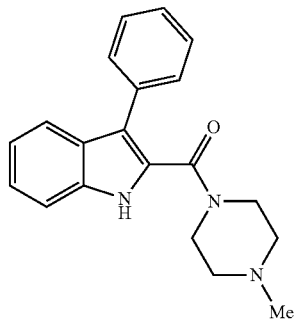 [SMILES: CN1CCN(C(=O)c2[nH]c3ccccc3c2-c2ccccc2)CC1]

(4-Methylpiperazin-1-yl)(3-phenyl-1H-indol-2-yl)methanone (14)

The title compound was synthesized according to Representative Procedure A from 1-methylpiperazine (30 μL, 0.266 mmol, 2.6 equiv.) and 3-phenyl-1H-indole-2-carboxylic acid (24.7 mg, 0.104 mmol, 1.0 equiv.). Purification of the crude product by prep. TLC (20% EtOAc/CH$_2$Cl$_2$) provided the title compound as a white foam (27.5 mg, 83%): $^1$H NMR (500 MHz, CDCl$_3$) δ 9.92 (m, 1H), 7.75 (d, J=8.1 Hz, 1H), 7.52-7.49 (m, 2H), 7.45 (t, J=7.8 Hz, 3H), 7.37-7.32 (m, 1H), 7.28 (ddd, J=8.2, 7.0, 1.1 Hz, 1H), 7.15 (ddd, J=8.0, 7.0, 1.0 Hz, 1H), 3.72 (bs, 2H), 3.14 (bs, 2H), 2.32 (bs, 2H), 2.11 (s, 3H), 1.63 (bs, 2H); $^{13}$C NMR (126 MHz, DMSO) δ 164.35, 136.20, 134.47, 129.66, 129.07, 127.20, 126.65, 126.16, 124.11, 120.78, 120.28, 117.92, 112.00, 77.16, 53.93, 47.09 (b), 45.71, 42.28 (b); HRMS (ESI-TOF+) m/z calc'd for C$_{20}$H$_{21}$N$_4$O$_3$ [M+H]$^+$: 320.1757, found 320.1757.

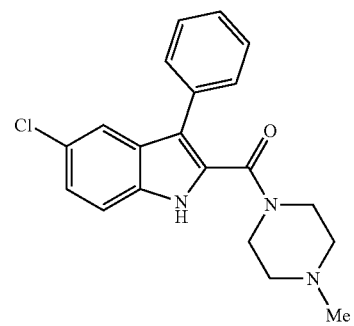 [SMILES: CN1CCN(C(=O)c2[nH]c3ccc(Cl)cc3c2-c2ccccc2)CC1]

(5-Chloro-3-phenyl-1H-indol-2-yl)(4-methylpiperazin-1-yl)methanone (15)

The title compound was synthesized according to Representative Procedure A from 1-methylpiperazine (30 μL, 0.266 mmol, 2.4 equiv.) and 5-chloro-3-phenyl-1H-indole-2-carboxylic acid (30.6 mg, 0.113 mmol, 1.0 equiv.). Purification of the crude product by prep. TLC (10% MeOH/EtOAc) provided the title compound as a white solid (29.9 mg, 75% over two steps): $^1$H NMR (500 MHz, CDCl$_3$) δ 10.27 (s, 1H), 7.69 (d, J=2.0 Hz, 1H), 7.51-7.43 (m, 4H), 7.41-7.34 (m, 2H), 7.21 (dd, J=8.7, 2.0 Hz, 1H), 3.73 (bs, 2H), 3.12 (bs, 2H), 2.33 (bs, 2H), 2.11 (s, 3H), 1.63 (bs, 2H). HRMS (ESI-TOF+) m/z calc'd for $C_{20}H_{21}ClN_3O$ [M+H]$^+$: 354.1368, found 354.1370.

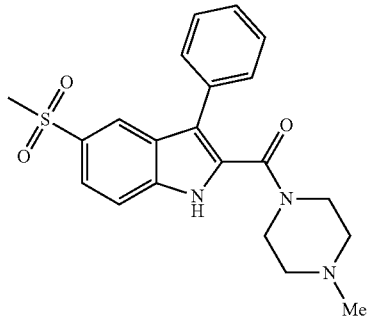 [SMILES: CN1CCN(C(=O)c2[nH]c3ccc(S(C)(=O)=O)cc3c2-c2ccccc2)CC1]

(4-Methylpiperazin-1-yl)(5-(methylsulfonyl)-3-phenyl-1H-indol-2-yl)methanone (16)

The title compound was synthesized in three steps beginning with methyl 5-(methylsulfonyl)-1H-indole-2-carboxylate:

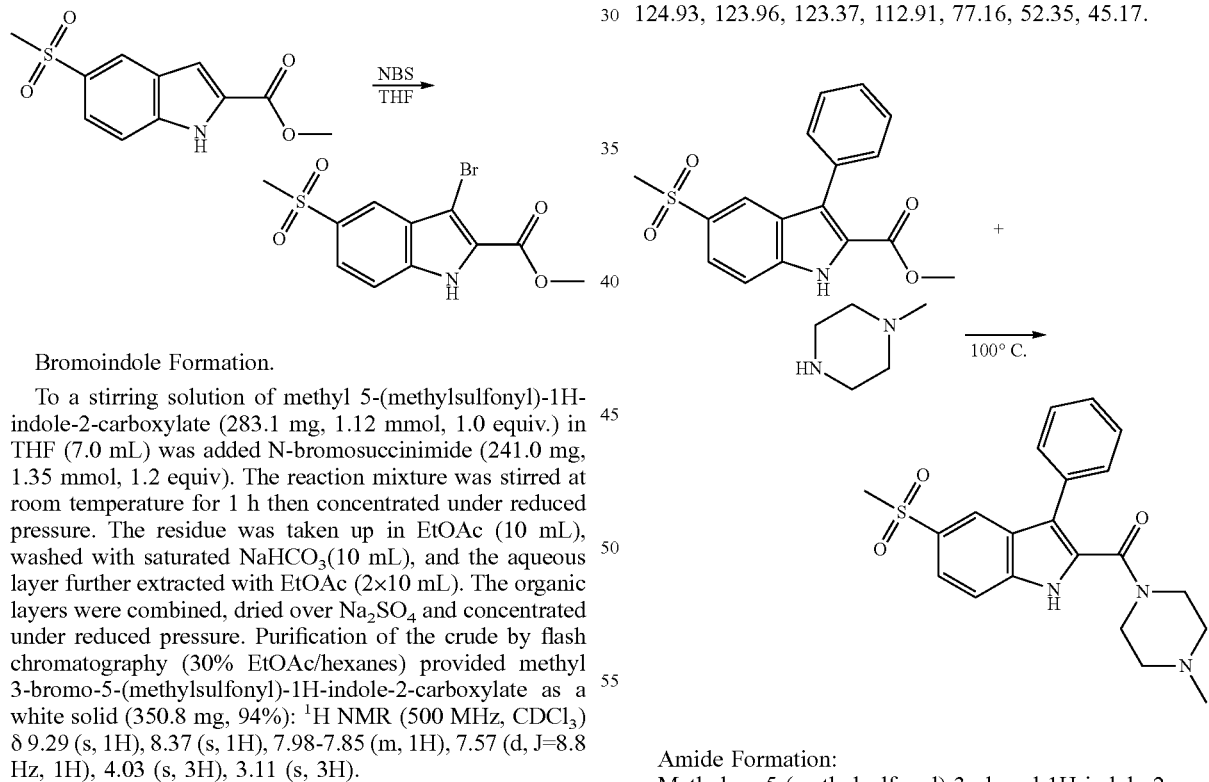

Bromoindole Formation.

To a stirring solution of methyl 5-(methylsulfonyl)-1H-indole-2-carboxylate (283.1 mg, 1.12 mmol, 1.0 equiv.) in THF (7.0 mL) was added N-bromosuccinimide (241.0 mg, 1.35 mmol, 1.2 equiv). The reaction mixture was stirred at room temperature for 1 h then concentrated under reduced pressure. The residue was taken up in EtOAc (10 mL), washed with saturated NaHCO$_3$(10 mL), and the aqueous layer further extracted with EtOAc (2×10 mL). The organic layers were combined, dried over Na$_2$SO$_4$ and concentrated under reduced pressure. Purification of the crude by flash chromatography (30% EtOAc/hexanes) provided methyl 3-bromo-5-(methylsulfonyl)-1H-indole-2-carboxylate as a white solid (350.8 mg, 94%): $^1$H NMR (500 MHz, CDCl$_3$) δ 9.29 (s, 1H), 8.37 (s, 1H), 7.98-7.85 (m, 1H), 7.57 (d, J=8.8 Hz, 1H), 4.03 (s, 3H), 3.11 (s, 3H).

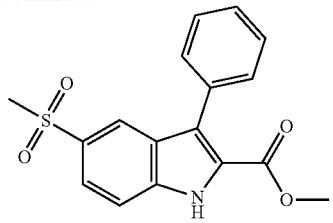

Phenylindole Formation:

Methyl 3-bromo-5-(methylsulfonyl)-1H-indole-2-carboxylate (99.0 mg, 0.307 mmol, 1 equiv.), phenylboronic acid (74.9 mg, 0.614 mmol, 2 equiv.), sodium carbonate (65.1 mg, 0.614 mmol, 2 equiv.), and tetrakis(triphenylphosphine)palladium(0) (10 mg, 3 mol %) were suspended in toluene (2 mL) and water (1 mL) under N$_2$. The mixture was heated to 60° C. and stirred for 18 h. The mixture was extracted with EtOAc (5×5 mL) and the combined organic layers dried over Na$_2$SO$_4$ then concentrated under reduced pressure. Purification of the crude by flash chromatography (2-5% EtOAc/CH$_2$Cl$_2$) provided methyl 5-(methylsulfonyl)-3-phenyl-1H-indole-2-carboxylate as a white solid (26.9 mg, 27%): $^1$H NMR (400 MHz, CDCl$_3$) δ 9.45 (s, 1H), 8.28 (dt, J=1.7, 0.7 Hz, 1H), 7.89 (dd, J=8.7, 1.8 Hz, 1H), 7.60 (dd, J=8.7, 0.7 Hz, 1H), 7.55-7.41 (m, 5H), 3.84 (s, 3H), 3.06 (s, 3H); $^{13}$C NMR (101 MHz, CDCl$_3$) δ 161.96, 137.76, 133.39, 132.02, 130.52, 128.40, 128.14, 127.77, 125.72, 124.93, 123.96, 123.37, 112.91, 77.16, 52.35, 45.17.

Amide Formation:

Methyl 5-(methylsulfonyl)-3-phenyl-1H-indole-2-carboxylate (5.0 mg, 0.0152 mmol, 1 equiv.) was dissolved in 1-methylpiperaine (300 μL) and heated at 100° C. for 48 h in a tightly-capped vial under N$_2$. The reaction mixture was cooled to room temperature and concentrated under reduced pressure. Purification of the crude by prep. TLC (10% MeOH/CH$_2$Cl$_2$) provided the title compound as a white solid (1.9 mg, 31%): $^1$H NMR (400 MHz, CDCl$_3$) δ 9.34 (s, 1H), 8.38 (d, J=1.8 Hz, 1H), 7.84 (dd, J=8.6, 1.8 Hz, 1H), 7.58 (dd, J=8.6, 0.7 Hz, 1H), 7.54-7.46 (m, 4H), 7.45-7.39 (m, 1H), 3.71 (bs, 2H), 3.09 (bs, 2H), 2.33 (bs, 2H), 2.13 (s, 3H), 1.65 (bs, 3H); HRMS (ESI-TOF+) m/z calc'd for $C_{21}H_{24}N_3O_3S$ [M+H]$^+$: 398.1533, found 398.1537.

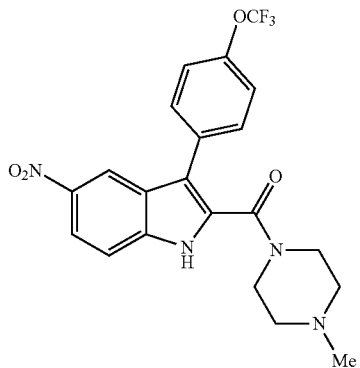 [SMILES: CN1CCN(C(=O)c2[nH]c3ccc([N+](=O)[O-])cc3c2-c2ccc(OC(F)(F)F)cc2)CC1]

(4-Methylpiperazin-1-yl)(5-nitro-3-(4-(trifluoromethoxy)phenyl)-1H-indol-2-yl)methanone (17)

Bromoindole 20 (9.0 mg, 0.0245 mmol, 1.0 equiv.), (4-(trifluoromethoxy)phenyl)boronic acid (9.0 mg, 0.0437 mmol, 1.8 equiv.), and tetrakis(triphenylphosphine)palladium(0) (10 mg, 3 mol %) were dissolved in 1:1:1 water:toluene:ethanol (1 mL) and heated at 100° C. for 24 h in a tightly-capped vial under $N_2$. After cooling to room temperature, the reaction mixture was diluted with saturated sodium bicarbonate (5 mL), extracted with $CH_2Cl_2$ (3×5 mL). The combined organic layers were dried over $Na_2SO_4$ then concentrated under reduced pressure. Purification of the crude by prep. TLC (10% MeOH/EtOAc) provided the title compound as a yellow solid (4.5 mg, 41%): $^1$H NMR (400 MHz, CDCl$_3$) δ 9.65 (s, 1H), 8.64 (s, 1H), 8.22 (ddd, J=9.0, 2.2, 1.2 Hz, 1H), 7.56-7.50 (m, 3H), 7.43-7.38 (m, 2H), 3.71 (bs, 1H), 3.15 (bs, 1H), 2.34 (bs, 1H), 2.14 (s, 3H), 1.59 (bs, 4H), 1.25 (bs, 1H); HRMS (ESI-TOF+) m/z calc'd for $C_{21}H_{20}F_3N_4O_4$ [M+H]$^+$: 449.1431, found 449.1430.

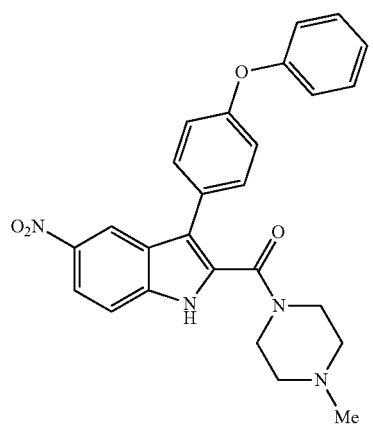 [SMILES: CN1CCN(C(=O)c2[nH]c3ccc([N+](=O)[O-])cc3c2-c2ccc(Oc3ccccc3)cc2)CC1]

(4-Methylpiperazin-1-yl)(5-nitro-3-(4-phenoxyphenyl)-1H-indol-2-yl)methanone (18)

Bromoindole 20 (29.8 mg, 0.0812 mmol, 1.0 equiv.), (4-phenoxyphenyl)boronic acid (35.1 mg, 0.164 mmol, 2.0 equiv.), lithium chloride (~10 mg) and tetrakis(triphenylphosphine)palladium(0) (10.1 mg, 10 mol %) were dissolved in 1:1:1 2M sodium bicarbonate:toluene:ethanol (1 mL) and heated at 80° C. for 24 h in a tightly-capped vial under $N_2$. After cooling to room temperature, the reaction mixture was diluted with saturated sodium bicarbonate (5 mL), extracted with $CH_2Cl_2$ (3×5 mL). The combined organic layers were dried over $Na_2SO_4$ then concentrated under reduced pressure. Purification of the crude by prep. TLC (10% MeOH/EtOAc) provided the title compound as a yellow solid (8.9 mg, 24%): $^1$H NMR (600 MHz, CDCl$_3$) δ 10.15 (s, 1H), 8.67 (s, 1H), 8.19 (dd, J=9.0, 2.1 Hz, 1H), 7.50 (d, J=8.8 Hz, 1H), 7.47-7.38 (m, 4H), 7.21-7.10 (m, 5H), 3.76 (bs, 2H), 3.19 (bs, 2H), 2.38 (bs, 2H), 2.21 (s, 3H), 1.80 (bs, 2H); $^{13}$C NMR (151 MHz, CDCl$_3$) δ 163.14, 157.85, 156.63, 142.77, 138.89, 130.86, 130.11, 129.33, 127.27, 125.88, 124.10, 119.69, 119.63, 119.52, 119.42, 118.05, 112.11, 77.16, 54.24, 47.38 (b), 46.02, 42.58 (b); HRMS (ESI-TOF+) m/z calc'd for $C_{26}H_{25}N_4O_4$ [M+H]$^+$: 457.1870, found 457.1872.

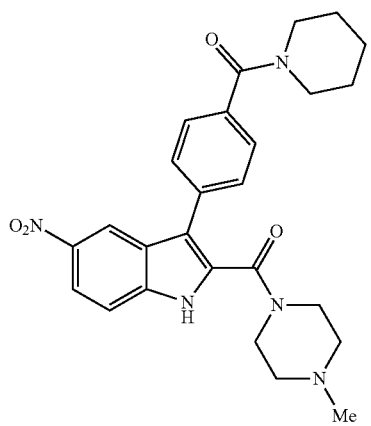 [SMILES: CN1CCN(C(=O)c2[nH]c3ccc([N+](=O)[O-])cc3c2-c2ccc(C(=O)N3CCCCC3)cc2)CC1]

(4-Methylpiperazin-1-yl)(5-nitro-3-(4-(piperidine-1-carbonyl)phenyl)-1H-indol-2-yl)methanone (19)

Bromoindole 20 (10.0 mg, 0.0272 mmol, 1.0 equiv.), (4-(piperidine-1-carbonyl)phenyl)boronic acid (16.3 mg, 0.0699 mmol, 2.6 equiv.), lithium chloride (~10 mg) and tetrakis(triphenylphosphine)palladium(0) (3 mg, 10 mol %) were dissolved in 1:1:1 2M sodium bicarbonate:toluene:ethanol (1 mL) and heated at 80° C. for 24 h in a tightly-capped vial under $N_2$. After cooling to room temperature, the reaction mixture was diluted with saturated sodium bicarbonate (5 mL), extracted with $CH_2Cl_2$ (3×5 mL). The combined organic layers were dried over $Na_2SO_4$ then concentrated under reduced pressure. Purification of the crude by prep. TLC (10% MeOH/CH$_2$Cl$_2$) provided the title compound as a yellow solid (4.1 mg, 32%): $^1$H NMR (400 MHz, CDCl$_3$) δ 9.65 (s, 1H), 8.70 (s, 1H), 8.22 (d, J=9.2 Hz, 1H), 7.60-7.48 (m, 5H), 3.75 (bs, 4H), 3.47 (bs, 2H), 3.15 (bs, 2H), 2.35 (bs, 3H), 2.14 (s, 2H), 1.67 (m, 8H); HRMS (ESI-TOF+) m/z calc'd for $C_{26}H_{30}N_5O_4$ [M+H]$^+$: 476.2292, found 476.2292.

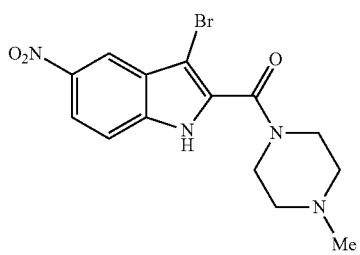 [SMILES: CN1CCN(C(=O)c2[nH]c3ccc([N+](=O)[O-])cc3c2Br)CC1]

(3-Bromo-5-nitro-1H-indol-2-yl)(4-methylpiperazin-1-yl)methanone (20)

The title compound was synthesized according to Representative Procedure A from 1-methylpiperazine (58 µL, 0.64 mmol, 1.8 equiv.), NMM (76 µL, 0.70 mmol, 2.0 equiv.) and 5-nitro-3-bromo-1H-indole-2-carboxylic acid (101.9 mg, 0.35 mmol, 1.0 equiv.). Purification of the crude product by flash chromatography (10% EtOAc/MeOH) provided the title compound as a yellow solid (115.4 mg, 88% over two steps): $^1$H NMR (600 MHz, DMSO-d6) δ 8.35 (d, J=2.2 Hz, 1H), 8.13 (dd, J=9.0, 2.3 Hz, 1H), 7.62 (d, J=9.0 Hz, 1H), 3.68 (bs, 2H), 3.41 (bs, 2H), 2.44-2.30 (bm, 4H), 2.21 (s, 3H); $^{13}$C NMR (151 MHz, DMSO-d6) δ 160.25, 141.77, 138.29, 133.47, 125.46, 118.77, 115.84, 113.43, 90.71, 55.04, 54.13, 46.86, 45.60, 41.72, 39.52; HRMS (ESI-TOF+) m/z calc'd for $C_{14}H_{16}BrN_4O_3$ [M+H]$^+$: 367.0400, found 367.0398.

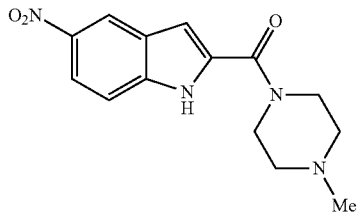 [SMILES: CN1CCN(C(=O)c2cc3cc([N+](=O)[O-])ccc3[nH]2)CC1]

(4-Methylpiperazin-1-yl)(5-nitro-1H-indol-2-yl)methanone (21)

The title compound was synthesized in three steps beginning with ethyl 5-nitro-1H-indole-2-carboxylate:

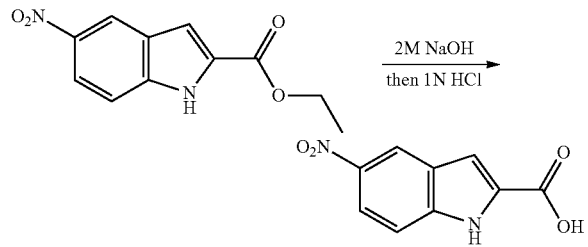

Ester Hydrolysis:

A stirring suspension of ethyl 5-nitro-1H-indole-2-carboxylate (190 mg, 0.811 mmol, 1.0 equiv.) in 2M NaOH (2 mL, 4.9 equiv.) was heated to reflux until the solids dissolved and then for an additional 1 h. The solution was allowed to cool to room temperature and 1N HCl (4 mL) was added dropwise till no further precipitation of a pale yellow solid was observed. The crude was collected by filtration and dried under reduced pressure to give quantitative yield of the acid which was carried on to the next step without further purification.

Acyl Chloride and Amide Formation:

Synthesis of the title compound was completed according to Representative Procedure A from 1-methylpiperazine (30 µL, 0.27 mmol, 2.7 equiv.), NMM (30 µL, 0.27 mmol, 2.7 equiv.) and 5-nitro-1H-indole-2-carboxylic acid (29 mg, 0.10 mmol, 1.0 equiv.). Purification of the crude product by prep. TLC (10% MeOH/EtOAc) provided the title compound as a pale yellow solid (9.9 mg, 33% over two steps): $^1$H NMR (600 MHz, CDCl$_3$) δ 9.91 (s, 1H), 8.63 (d, J=2.1 Hz, 1H), 8.18 (dd, J=9.1, 2.2 Hz, 1H), 7.48 (d, J=9.0 Hz, 1H), 6.94 (d, J=2.0 Hz, 1H), 3.97 (bs, 4H), 2.53 (dd, J=5.0 Hz, 4H), 2.37 (s, 3H); 13C NMR (151 MHz, CDCl$_3$) δ 161.63, 142.54, 138.67, 132.52, 126.70, 119.76, 119.42, 112.15, 107.16, 55.08, 47.42 (b), 46.17, 43.09 (b); HRMS (ESI-TOF+) m/z calc'd for $C_{14}H_{17}N_4O_3$ [M+H]$^+$: 289.1295, found 289.1294.

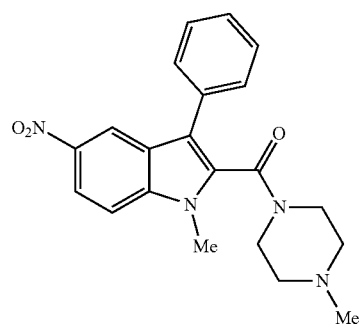 [SMILES: CN1CCN(C(=O)c2c(-c3ccccc3)c3cc([N+](=O)[O-])ccc3n2C)CC1]

(1-Methyl-5-nitro-3-phenyl-1H-indol-2-yl)(4-methylpiperazin-1-yl)methanone (22)

The title compound was synthesized in three steps beginning with 5-nitro-3-phenyl-1H-indole-2-carboxylic acid:

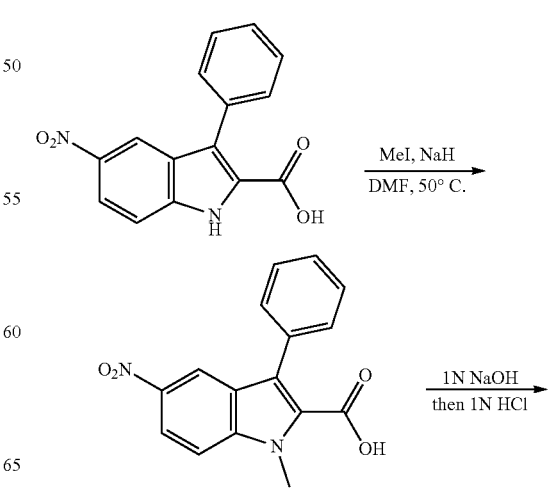

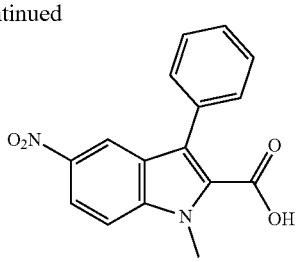

Per-Methylation and Hydrolysis:

To a stirring solution of 5-nitro-3-phenyl-1H-indole-2-carboxylic acid (48.8 mg, 0.173 mmol, 1.0 equiv.) in DMF (2 mL) was sodium hydride (60% dispersion in mineral oil, 24 mg, 0.36 mmol, 3.5 equiv.) portion-wise. After 10 min, methyl iodide (105 μL, 1.69 mmol, 9.8 equiv.) was added and the reaction mixture heated to 50° C. for 16 h. The reaction mixture was concentrated to dryness under reduced pressure. The crude from the methylation reaction was taken up in aqueous NaOH (1 N, 2 mL) and heated to 80° C. for 24 h. After allowing the mixture to cool to room temperature, aqueous HCl was added (4 mL) until no further precipitation was observed. The crude product was collected by filtration, washed with Et$_2$O (3×5 mL), and dried under reduced pressure to give quantitative yield of 1-methyl-5-nitro-3-phenyl-1H-indole-2-carboxylic acid as a yellow solid. LRMS (ESI–) m/z calc'd for $C_{16}H_{11}N_2O_4$ [M–H]$^-$: 295, found 295. The crude product was used in the next step without purification.

Acyl Chloride and Amide Formation:

Synthesis of the title compound was completed according to Representative Procedure A from 1-methylpiperazine (15 μL, 0.133 mmol, 1.2 equiv.), NMM (15 μL, 0.136 mmol, 1.3 equiv.) and crude 1-methyl-5-nitro-3-phenyl-1H-indole-2-carboxylic acid (31.7 mg, 0.107 mmol, 1.0 equiv.). Purification of the crude product by prep. TLC (10% MeOH/EtOAc) provided the title compound as a yellow solid (28.0 mg, 69% over two steps): $^1$H NMR (600 MHz, CDCl$_3$) δ 8.70 (d, J=2.2 Hz, 1H), 8.20 (dd, J=9.1, 2.2 Hz, 1H), 7.48 (d, J=4.4 Hz, 4H), 7.42 (d, J=9.1 Hz, 1H), 7.41-7.37 (m, 1H), 3.87 (s, 3H), 3.85-3.82 (m, 1H), 3.67-3.60 (m, 1H), 3.21-3.14 (m, 1H), 3.03-2.97 (m, 1H), 2.44-2.37 (m, 1H), 2.22-2.15 (m, 1H), 2.09 (s, 3H), 2.02-1.95 (m, 1H), 1.27-1.18 (m, 1H); $^{13}$C NMR (151 MHz, CDCl$_3$) δ 161.82, 142.60, 140.14, 132.56, 132.47, 129.39, 129.10, 127.89, 124.91, 118.94, 118.46, 117.85, 110.09, 110.04, 77.16, 54.20, 54.06, 46.81, 45.86, 41.90, 31.60; HRMS (ESI-TOF+) m/z calc'd for $C_{21}H_{23}N_4O_3$ [M+H]$^+$: 379.1765, found 379.1767.

Example IV

Synthesis of Sterol Probes

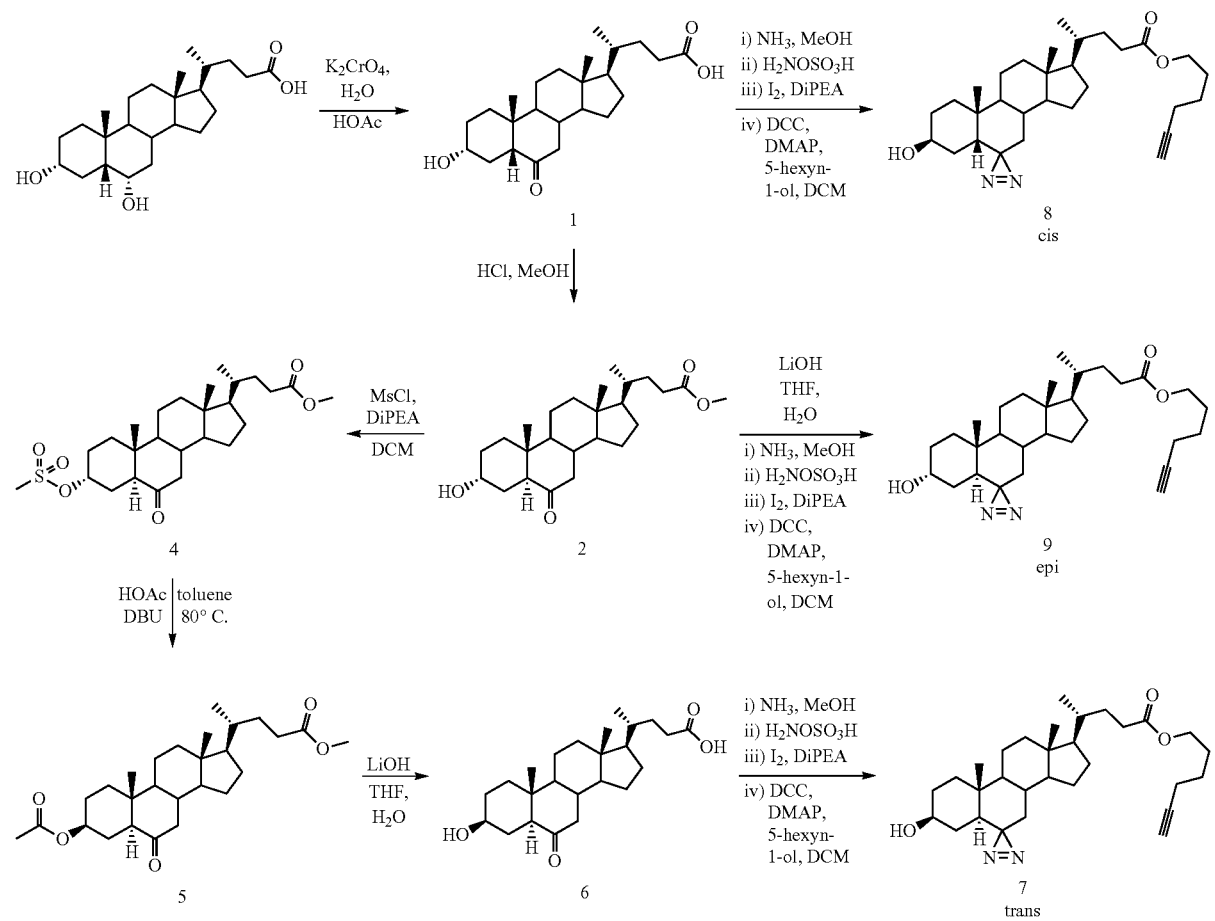

(4R)-4-((3R,5R,10R,13R,17R)-3-hydroxy-10,13-dimethyl-6-oxohexadecahydro-1H-cyclopenta[a]phenanthren-17-yl)pentanoic acid (1)

To a stirred solution of hyodeoxycholic acid (10.0 g, 25.5 mmol, 1 equiv) in glacial acetic acid (135 ml) was added an aqueous solution of potassium chromate (4.95 g, 1 equiv, in 12 ml) dropwise at room temperature. The resulting solution was stirred at room temperature overnight, before being diluted slowly with sat. aq. NaHCO$_3$(100 ml) and water (200 ml) on ice. The resulting suspension was stirred to room temperature for 1 h before being extracted with CH$_2$Cl$_2$ (3×). The combined organic extracts were dried over Na$_2$SO$_4$ and concentrated under reduced pressure. The residue was purified by SiO$_2$ flash chromatography (5% MeOH/CH$_2$Cl$_2$) to provide the title compound (6.18 g, 62%). The title compound was recrystallized from aqueous MeOH by vapor diffusion to obtain a diffraction-quality crystal, and its structure was determined by X-ray diffraction (FIG. 17b, purple). $^1$H NMR (600 MHz, CDCl$_3$) δ 3.64 (bm, 1H), 2.39 (m 1H), 2.27 (m, 1H), 2.18 (m, 1H), 2.12 (m, 1H), 2.04 (m, 1H), 1.0-1.91 (mm, 23H), 0.94 (d, J=6 Hz, 3H), 0.84 (s, 3H), 0.65 (s, 3H); $^{13}$C NMR (150 MHz, CDCl$_3$) δ 214.7, 179.4, 71.1, 60.2, 57.7, 56.6, 44.0, 43.8, 40.8, 40.5, 39.5, 37.9, 36.1, 35.8, 35.5, 31.5, 31.0, 28.9, 24.8, 24.0, 21.7, 19.1, 12.8, 0.9; HRMS (ESI-TOF+) m/z calc'd for C$_{24}$H$_{39}$O$_4$ [M+H]$^+$: 391.2843, found 391.2846.

(4R)-methyl 4-((3R,5S,10R,13R,17R)-3-hydroxy-10,13-dimethyl-6-oxohexadecahydro-1H-cyclopenta[a]phenanthren-17-yl)pentanoate (2)

Intermediate 1 (1.0 g, 2.56 mmol, 1 equiv) was dissolved in anhydrous 2 N HCl in MeOH (10 ml), and the resulting solution was allowed to equilibrate overnight. At this time, the solution was neutralized carefully with sat. aq. NaHCO$_3$ (20 ml) and the mixed diastereomers were extracted with CH$_2$Cl$_2$ (3×). The combined organic extracts were dried over Na$_2$SO$_4$ and concentrated in vacuo. The title compound was obtained (537 mg, 52%) as a single diastereomer (>95% by $^1$H NMR) after two recrystallizations from aqueous MeOH. $^1$H NMR (600 MHz, CDCl$_3$) δ 4.16 (sm, 1H), 3.66 (s, 3H), 2.71 (m, 1H) 2.30 (m, 1H), 2.28 (m, 1H), 2.21 (m, 1H), 2.00 (m, 2H), 1.87 (m, 1H), 1.79 (m, 2H), 1.70 (m, 2H), 1.0-1.69 (mm, 17H), 0.92 (d, J=6 Hz, 3H), 0.72 (s, 3H), 0.65 (s, 3H); $^{13}$C NMR (150 MHz, CDCl$_3$) δ 213.6, 175.5, 66.3, 57.6, 56.7, 54.6, 52.5, 52.4, 48.7, 44.6, 42.2, 40.1, 38.8, 35.7, 32.5, 31.9, 31.8, 28.8, 28.6, 28.5, 24.8, 21.9, 19.1, 13.2, 12.9; HRMS (ESI-TOF+) m/z calc'd for C$_{25}$H$_{40}$O$_4$ [M+H]$^+$: 405.2999, found 405.2998.

(4R)-4-((3R,5S,10R,13R,17R)-3-hydroxy-10,13-dimethyl-6-oxohexadecahydro-1H-cyclopenta[a]phenanthren-17-yl)pentanoic acid (3)

The title compound was prepared using the base hydrolysis procedure described in the preparation of 6. Intermediate 2 (76.1 mg, 0.171 mmol, 1 equiv) yielded 3 (63 mg, 94%), which was used without further purification. A diffraction-quality crystal was obtained by recrystallization of the crude material from CH$_2$Cl$_2$ and pentane by vapor diffusion and the structure of the title compound was determined by X-ray diffraction (FIG. 17b, cyan). $^1$H NMR (600 MHz, D$_3$OD/CDCl$_3$) d 4.03 (sm, 1H), 2.74 (m, 1H), 2.20 (m, 2H), 2.07 (m, 2H), 1.88 (m, 1H), 1.78 (m, 2H), 1.0-1.67 (mm, 20H), 0.96 (d, J=6 Hz, 3H), 0.72 (s, 3H), 0.70 (s, 3H); $^{13}$C NMR (150 MHz, D$_3$OD/CDCl$_3$) d 215.1, 175.0, 65.5, 57.4, 56.9, 54.5, 52.3, 47.1, 42.1, 40.3, 38.9, 36.6, 35.8, 33.3, 32.3, 28.5, 28.2, 27.9, 24.4, 21.6, 18.3, 12.1, 11.9; HRMS (ESI-TOF+) m/z calc'd for C$_{24}$H$_{38}$O$_4$ [M+H]$^+$: 391.2843, found 391.3843.

(4R)-methyl 4-((3R,5S,10R,13R,17R)-10,13-dimethyl-3-((methylsulfonyl)oxy)-6-oxohexadecahydro-1H-cyclopenta[a]phenanthren-17-yl)pentanoate (4)

To a stirred solution of 2 (537 mg, 1.33 mmol, 1 equiv) in CH$_2$Cl$_2$ (7 ml) at 0° C. was added Hunig's base (515 ml, 3 equiv), catalytic DMAP and mesyl chloride (160 ml, 1.5 equiv; dropwise). The resulting solution was warmed to room temperature and stirred for 4 h before dilution with CH$_2$Cl$_2$ (10 ml) and subsequently quenched by vigorous stirring in water (10 ml). The phases from the quenched reaction were separated, and the organic phase was washed with sat. aq. NaHCO$_3$, dried over Na$_2$SO$_4$ and concentrated in vacuo. The title compound (640 mg, 99%) was obtained as a following purification by SiO$_2$ flash chromatography (40% EtOAc/hexanes). $^1$H NMR (600 MHz, CDCl$_3$) δ 5.04 (sm, 1H), 3.66 (s, 3H), 2.99 (s, 3H), 2.63 (m, 1H), 2.38 (m, 1H), 2.31 (m, 1H), 2.25 (m, 1H), 1.0-2.04 (mm, 22H), 0.93 (d, J=6 Hz, 3H), 0.74 (s, 3H), 0.66 (s, 3H); $^{13}$C NMR (150 MHz, CDCl$_3$) δ 211.2, 174.7, 78.8, 56.7, 55.7, 53.5, 51.9, 51.5, 46.6, 43.0, 41.1, 38.5, 37.9, 37.2, 35.3, 31.7, 31.0, 30.9, 27.9, 26.2, 25.7, 23.3, 22.2, 18.2, 12.5, 12.0; HRMS (ESI-TOF+) m/z calc'd for C$_{26}$H$_{42}$O$_6$S [M+Na]$^+$: 505.2594, found 505.2597.

(4R)-methyl 4-((3S,5S,10R,13R,17R)-3-acetoxy-10,13-dimethyl-6-oxohexadecahydro-1H-cyclopenta[a]phenanthren-17-yl)pentanoate (5)

To a stirred solution of 4 (640 mg, 1.33 mmol, 1 equiv) in toluene (2.8 ml) was added a pre-mixed solution of DBU (640 ml, 3 equiv) and glacial acetic acid (504 ml, 6 equiv) in toluene (1 ml) dropwise. The resulting solution was heated with stirring at 80° C. for 6 h. The solution was then cooled to room temperature, diluted with EtOAc (10 ml), and washed first with aq. 1 N HCl, water, and then with sat. aq. NaHCO$_3$. The resulting organic phase was dried (Na$_2$SO$_4$) and concentrated in vacuo. The remaining residue was purified by SiO$_2$ flash chromatography (20% EtOAc/hexanes) to provide the title compound (503 mg, 85%). $^1$H NMR (600 MHz, CDCl$_3$) δ 4.67 (bm, 1H), 3.66 (s, 1H), 2.3 (m, 4H), 2.04 (m, 1H), 2.02 (s, 3H), 1.0-2.0 (mm, 23H), 0.93 (d, J=6 Hz, 3H), 0.76 (s, 3H), 0.66 (s, 3H); $^{13}$C NMR (150 MHz, CDCl$_3$) δ 210.3, 174.7, 170.6, 72.8, 56.6, 56.5, 55.7, 53.8, 51.5, 46.6, 43.2, 41.0, 39.4, 37.8, 35.3, 34.8, 31.0, 30.9, 26.8, 26.1, 26.0, 24.9, 24.8, 23.9, 18.2, 13.0, 12.0; HRMS (ESI-TOF+) m/z calc'd for C$_{27}$H$_{42}$O$_5$ [M+H]$^+$: 447.3105, found 447.3108.

(4R)-4-((3S,5S,10R,13R,17R)-3-hydroxy-10,13-dimethyl-6-oxohexadecahydro-1H-cyclopenta[a]phenanthren-17-yl)pentanoic acid (6)

To a solution of 5 (503 mg, 1.12 mmol, 1 equiv) in THF (2.8 ml) was added 2 N aqueous LiOH (2.8 ml). The resulting mixture was stirred vigorously overnight and then neutralized by the addition of 1 N aq. HCl (12 ml) on an ice bath. The product was extracted with CH$_2$Cl$_2$ (3×), dried over Na$_2$SO$_4$, concentrated under reduced pressure. The remaining residue was recrystallized once from aqueous MeOH to provide the title compound (250 mg, 57%). The title compound was recrystallized from aqueous EtOH by vapor diffusion to obtain a diffraction-quality crystal, and its structure was determined by X-ray diffraction (FIG. 17b, green). $^1$H NMR (600 MHz, CDCl$_3$) δ 3.54 (bm, 1H), 2.37 (m, 1H). 2.29 (m, 1H), 2.22 (m, 2H), 2.03 (m, 1H), 1.96 (m, 1H), 1.76-1.92 (mm, 6H), 1.62 (m, 1H), 1.54 (m, 1H), 1.0-1.52 (mm, 14H), 0.94 (d, J=6 Hz, 3H), 0.75 (s, 3H), 0.67 (s, 3H); $^{13}$C NMR (150 MHz, CDCl$_3$) δ 212.0, 177.0, 70.3, 56.8, 56.7, 55.9, 53.9, 49.5, 46.7, 43.1, 41.4, 39.5, 38.0, 36.7, 35.3, 31.2, 31.0, 30.7, 29.2, 24.8, 21.7, 18.2, 13.1, 12.0; HRMS (ESI-TOF+) m/z calc'd for C$_{24}$H$_{38}$O$_4$ [M+H]$^+$: 391.2843, found 391.2848.

(4R)-hex-5-yn-1-yl 4-((3S,5S,10R,13R,17R)-3-hydroxy-10,13-dimethyl-1,2,3,4,5,7,8,9,10,11,12,13,14,15,16,17-hexadecahydrospiro[cyclopenta[a]phenanthrene-6,3'-diazirin]-17-yl)pentanoate (trans probe) (7)

A round bottom flask containing 6 (100 mg, 0.256 mmol, 1 equiv) was cooled to 0° C. under N$_2$, 7N NH$_3$ in MeOH (2.5 ml) was added slowly, and the resulting solution was stirred at 0° C. for 3 h. At this time, an anhydrous methanolic solution of hydroxylamine-O-sulfonic acid (41 mg, 1.4 eq, in 0.3 ml) was added dropwise at 0° C. The resulting solution was allowed to stir to room temperature overnight, and became increasingly turbid. The following day, the mixture was evaporated to dryness in the reaction vessel under a stream of dry N2, and the resulting residue was then resuspended in anhydrous MeOH. The mixture was filtered, and the filter cake washed with additional dry MeOH. The total filtrate was then concentrated under reduced pressure, and re-dissolved in dry methanol (2.5 ml) in an amber flask. The solution was cooled to 0° C., and Hunig's base was added (0.1 ml), followed by iodine in small portions, until a dark brown color persisted in the solution for more than 30 minutes, indicating total oxidation of the previously formed diaziridine. The solution was then diluted with EtOAc, and washed successively with 1 N aq. HCl and then sat. aq. Na$_2$S$_2$O$_3$ until the organic phase was clarified (2×). The organic phase was then dried (Na$_2$SO$_4$) and concentrated in vacuo in an amber flask to yield the crude diazirine acid, which was immediately esterified without further purification. The crude residue was dissolved in CH$_2$Cl$_2$ (2 ml), cooled to 0° C., and 5-hexyn-ol (75 mg, 3 eq), a catalytic amount of DMAP, followed by DCC (69 mg, 1.3 eq) were added. The resulting solution was stirred to room temperature overnight and then filtered and concentrated under reduced pressure. The trans probe was then obtained (41 mg, 33% over three steps) by SiO$_2$ flash chromatography (92.5:7.5:0.5, CH$_2$Cl$_2$:EtOAc:MeOH). $^1$H NMR (600 MHz, CDCl$_3$) δ 4.08 (t, J=6 Hz, 2H), 3.47 (bm, 1H), 2.34 (m, 1H), 2.21 (m, 3H) 2.00 (m, 1H), 1.96 (sm, 1H), 0.75-1.75 (mm, 24H), 1.1 (s, 3H), 0.92 (d, J=6 Hz, 3H), 0.79 (m, 2H), 0.69 (s, 3H), 0.42 (m, 2H); $^{13}$C NMR (150 MHz, CDCl$_3$) δ 174.3, 83.9, 71.0, 68.7, 63.7, 56.0, 55.8, 53.6, 45.2, 43.1, 39.9, 37.5, 37.4, 36.3, 33.8, 33.1, 31.5, 31.4, 31.3, 29.2, 27.8, 27.7, 25.0, 24.9, 23.9, 21.2, 18.2, 18.1, 13.0, 12.1; HRMS (ESI-TOF+) m/z calc'd for C$_{30}$H$_{46}$N$_2$O$_3$ [M+H]$^+$: 483.3581, found 483.3575.

Example V

Cell Culture and Live Cell Labeling

HeLa cells were grown at 37° C. under a humidified 5% CO$_2$ atmosphere, in a culture medium consisting of high-glucose DMEM (HyClone) supplemented with 10% fetal bovine serum (FBS; Gemini) and penicillin, streptomycin, and glutamine (Cellgro; PSQ). For SILAC experiments, the culture medium was replaced with SILAC DMEM (Thermo) supplemented instead with 10% dialyzed FBS, PSQ, and 100 μg/ml [$^{13}$C$_6$, $^{15}$N$_4$] L-arginine-HCl and [$^{13}$C$_6$, $^{15}$N$_2$]L-lysine-HCl (Sigma-Aldrich). Cells were passaged at least six times in isotopically labeled media before being utilized for analysis by LC-MS/MS.

To facilitate delivery to cells, all sterols and steroids, including the sterol probes, were complexed in aqueous solution to mβCD (Sigma-Aldrich) for at least twelve hours before dilution in culture medium for labeling. The desired amount of sterol or steroid was added to a saturated aqueous mβCD (38 mM) solution to generate a concentrated stock, and agitated at room temperature overnight; solutions were filtered prior to use the following day. Aqueous stock solutions of the trans probe were prepared at 2 mM; the cis and epi probes were prepared at 1.2 mM; cholesterol and other sterols for competition were prepared at 4 mM; steroids were prepared at 5 mM. Non-steroidal lipids, C$_{17}$-MAGE, and di-C$_{15}$-DAG, as well as the PEA-DA probe were suspended in DMSO (10 mM) and diluted to working concentrations directly in culture medium.

Prior to live-cell labeling, aqueous stock solutions of each sterol probe or competitor (or DMSO stock solution of lipids) were combined in opaque centrifuge tubes, and then diluted to final working concentrations in culture medium under dim ambient light. Unmodified culture medium was then removed from the cells, and replaced with probe-containing medium. Cells were then incubated at 37° C. for 30 minutes in the dark to load the cells with sterol probe and competitors. After this time, cells were washed quickly with cold PBS, and then irradiated for five minutes under 365 nm ultraviolet light in a FB-UVXL-1000 UV Crosslinker (Fisher) in cold PBS. Cells were then harvested by scraping, and the cell pellet frozen at −80° C. until processing for gel or LC-MS/MS analysis.

Sample Processing for Analysis by SDS-PAGE or LC-MS/MS

Frozen cell pellets were thawed on ice and lysed in PBS by sonication. Protein concentrations of cell lysates were determined using the BCA protein assay on a microplate reader. Click chemistry was then performed directly in whole-cell lysates in PBS. For analysis by gel, 50 μg of protein was used, adjusted to a protein concentration of 1 mg/ml (50 μl), and was mixed with 20 μM rhodamine-azide, 1 mM Tris(2-carboxyethyl)phosphine (TCEP, Sigma-Aldrich), 100 μM Tris[(1-benzyl-1H-1,2,3-triazol-4-yl)methyl]amine (TBTA) (Sigma-Aldrich), and 1 mM CuSO4 in PBS at room temperature. After 1 hour, samples were mixed with SDS sample loading buffer and loaded without boiling on a 10% SDS-PAGE gel, separated, and imaged using a Hitachi FMBIO-II flatbed fluorescence scanner.

For proteomic analysis, 1 mg of both heavy and light lysates were mixed in a 1:1 ratio, and then combined with 500 μM biotin-azide, 100 μM TBTA, 1 mM TCEP, and 1 mM CuSO4 in 400 μl PBS for 1 hour. Water (100 μl), methanol (500 μl) and chloroform (125 μl) were then added directly to the reaction mixture and mixed vigorously by vortexing. The biphasic solution was then centrifuged at 4000 rpm for 20 minutes at 4° C., and protein was pelleted at the phase interface as a solid disk. Liquid layers were discarded, and the protein was washed further by sonication into 1:1 methanol/chloroform (500 μl first wash, 250 μl second wash) followed by centrifugation at 13.3 k rpm for 10 minutes at 4° C. to re-pellet. The protein pellets were air-dried briefly, and then resuspended by sonication into 500 µl water containing 25 mM ammonium bicarbonate and 6 M urea. To this solution, 5 µl of a 1 M DTT solution in water was added, followed by 140 µl 10% SDS in water, and the solution was heated at 65° C. for 15 minutes. The samples were cooled briefly on ice, and then 40 µl of a 0.5 M iodoacetamide (Sigma-Aldrich) solution in water was added, and the samples were incubated at room temperature for 30 minutes in the dark. The samples were then diluted to 6 ml with PBS, and enriched over streptavidin (Thermo) (100 µl slurry) for 2 hours at room temperature. The beads were washed once with 10 ml 1% SDS in PBS, then three more times with 10 ml PBS. The beads were then transferred to a 1.5 ml screw-cap tube in 200 µl 25 mM ammonium bicarbonate/2 M urea in water, with 1 mM calcium chloride and 2 µg sequencing grade porcine trypsin (Promega), and then digested at 37° C. overnight. The digest supernatant was then collected by filtration of the resin, which was washed additionally with 100 µl PBS. The combined filtrate and wash for each sample was then acidifed with 16 µl formic acid, and then pressure-loaded onto a biphasic (strong cation exchange/reverse phase) capillary column for analysis by two-dimensional liquid chromatography separation in combination with tandem mass spectrometry (2D-LC-MS/MS). Unenriched samples were processed in the same fashion, but the enrichment step was omitted, and instead, 200 µg of processed protein was committed to tryptic digestion and MudPIT analysis.

Mass Spectrometry and Data Processing

Mass spectrometry was performed using a Thermo Orbitrap Velos mass spectrometer. Peptides were eluted using a 5-step multidimensional LC-MS (MudPIT) protocol (using 0%, 25%, 50%, 80%, and 100% salt bumps of 500 mM aqueous ammonium acetate, followed by an increasing gradient of aqueous acetonitrile/0.1% formic acid in each step) and data were collected in data-dependent acquisition mode (2 MS1 microscans (400-1800 m/z) and 30 data-dependent MS2 scans) with dynamic exclusion enabled (repeat count of 1, exclusion duration of 20 s) with monoisotopic precursor selection enabled. All other parameters were left at default values. Unenriched membrane preparations were eluted using the same chromatographic steps and instrument settings. SEQUEST searches allowed for variable oxidation of methionine (+15.9949), static modification of cysteine residues (+57.0215; iodoacetamide alkylation), and no enzyme specificity. Each data set was independently searched with light and heavy parameters files; for the light search, all other amino acids were left at default masses; for the heavy search, static modifications on lysine (+8.0142) and arginine (+10.0082) were specified. The precursor ion mass tolerance was set to 50 ppm and the fragment ion mass tolerance was the default assignment of 0. The data was searched using a human reverse-concatenated non-redundant (gene-centric) FASTA database that combines IPI and Ensembl identifiers. The resulting matched MS2 spectra were assembled into protein identifications, then filtered using DTASelect (version 2.0.47), and only half- or fully-tryptic peptides were accepted for identification, and only fully-tryptic peptides were considered for quantification. Peptides were restricted to a specified false positive rate of 1%. Redundant peptide identifications common between multiple proteins were allowed, but the database was restricted to a single consensus splice variant. SILAC ratios were quantified using in-house software as described (CIMAGE). Briefly, extracted MS 1 ion chromatograms (+/−10 ppm) from both 'light' and 'heavy' target peptide masses (m/z) are generated using a retention time window (+/−10 minutes) centered on the time when the peptide ion was selected for MS/MS fragmentation, and subsequently identified. Next, the ratio of the peak areas under the light and heavy signals (signal-to-noise ratio S/N>2.5) are calculated. Computational filters used to ensure that the correct peak-pair is used for quantification include a co-elution correlation score filter ($R^2 \geq 0.8$), removing target peptides with bad co-elution profile, and an "envelope correlation score" filter ($R^2 > 0.8$) that eliminates target peptides whose predicted pattern of the isotopic envelope distribution does not match the experimentally observed high-resolution MS 1 spectrum. Also, peptides detected as singletons, where only the heavy or light isotopically labeled peptide is detected and sequenced, but which pass all other filtering parameters, were given a standard ratio of 20, which is the maximum SILAC ratio reported herein. All reported SILAC experiments were run in duplicate, except the cholesterol competition, which was run in quadruplicate.

After automated processing, data sets were further filtered and analyzed manually based on more stringent and experiment-specific criteria. Only proteins which showed at least 2 unique identified and quantified peptides between four control runs (trans probe versus vehicle and versus "no UV", each in duplicate), and that showed at least ratio of 5.0 when the heavy, trans probe-enriched signal was compared to the background signal, were considered for further analysis by comparison to the PEA-DA labeling profile, and to cholesterol competition. Only proteins that showed at least a ratio of 3.0 when trans probe-labeled cells were compared to PEA-DA-labeled cells were considered "selective" and could be considered Group III or higher, and only proteins that showed at least a ratio of 1.5 when competed by 10× cholesterol, and showed at least 2 quantified unique peptides across four competition runs were considered "sensitive" for further analysis and consideration as Group II or higher. All experimental SILAC ratios presented are the mean of the median ratios of all quantified peptides for each protein from each replicate for each experiment.

Meta-analyses in FIG. 20 of the sensitive and selective group of trans probe targets were performed using several online resources and servers. Automated gene ontology and pathway enrichment analyses were performed by uploading the Group I protein list to the DAVID bioinformatics website and performing enrichment analyses. Protein annotations in FIG. 20 were obtained from primary literature sources, GeneCards.com, the Qiagen SABiosciences transcription factor database, and the OMIM database. Transmembrane domains were predicted, as necessary, by PSORT II and TMHMM prediction servers.

Microarray Analysis of Cholesterol-Induced Transcriptional Changes

To verify that the observed cholesterol competition is due to direct physical competition of probe binding, and not due to cholesterol-mediated expression changes for each sensitive target, HeLa cells were incubated with or without 20 µM cis probe and 100 µM cholesterol for 30 minutes and 12 hours, then harvested total cellular mRNA from each treatment using the Qiagen RNEasy kit, and submitted 8 µg total mRNA (combination of three biological replicates) per sample the TSRI DNA Array core facility, for quantitative transcriptomic analysis by microarray, using the HU133 Set GeneChip (Affymetrix), and the Affymetrix GeneChip Expression 3' Amplification One-Cycle protocol.

Recombinant Expression and Validation Cholesterol Competition of Novel Targets

To validate protein-cholesterol interactions identified by the trans sterol probe for which there is no previous evidence of cholesterol binding, SQLE, FDFT1, PGRMC1, POR, ADPGK, CYP20A1, and JAGN1 cDNAs were obtained (OpenBiosystems), and were recombinantly over-expressed as the full-length, unmodified proteins (except JAGN1, which was expressed with a C-terminal myc-his epitope-tag) in HeLa cells via transfection with Fugene HD according to the manufacturer's protocol. 48 hours post-transfection, cells were labeled in situ with either 5 or 10 uM trans probe, with or without 10× (50 μM or 100 μM) cholesterol. Both the competed and non-competed transfected samples were compared to a control transfected with a distinct protein, on a 10% SDS-PAGE gel, and equal expression of the protein of interest between competed and non-competed samples was verified via western blot of the same samples on a gradient (4-20%) gel using commercial antibodies specific to each protein. Antibodies used in this study were: monoclonal mouse α-myc (1:10,000; Invitrogen), monoclonal rabbit α-POR (1:1000; Sigma-Aldrich), monoclonal mouse α-FDFT1 (1:1000; Sigma-Aldrich), monoclonal mouse α-ADPGK (1:1000; Sigma-Aldrich), monoclonal rabbit α-PGRMC1 (1:2000; Sigma-Aldrich), monoclonal mouse α-SQLE (1:1000; Sigma-Aldrich), monoclonal mouse α-actin (1:2000; Sigma-Aldrich), and polyclonal rabbit α-CYP20A1 (1:100; Thermo).

Design of Clickable, Photoreactive Sterol Probes

In some embodiments, a set of sterol probes (FIG. 17a) was designed to contains a photoactivatable diazirine group at the 6-position of the steroid core (using standard numbering), which minimally perturb the biophysical properties of cholesterol, and an alkyne incorporated via an ester linkage into the alkyl side-chain of cholesterol. In some instances, the probes differ in the diastereomeric relationship between the C3-alcohol and C5-hydrogen groups appended to the cholesterol core (termed cis, trans, and epi hereafter) and were synthesized from a common precursor—the bile acid hyodeoxycholic acid X-ray structures of the keto-acid intermediates corresponding to each cholesterol probe were obtained to verify their relative and absolute stereochemistry (FIG. 17b). As compared to the three-dimensional structure of cholesterol (extracted from a structure in complex with NPC1, FIG. 17b), the trans probe exhibits the most similarity to cholesterol in terms of stereochemistry and molecular topology. Due to its 3α-OH stereochemistry, the epi probe instead most resembles epicholesterol. The cis probe, while appearing bent in the crystal structure (FIG. 17b), is more flexible due to its structurally distinct cis-decalin-type A-B ring fusion. This ring fusion stereochemistry, along with its 3α-OH stereochemistry, in some instances, allows for the cis probe to adopt bent cholesterol-like conformations in solution that retain the equatorial orientation of the $C_3$ hydroxyl group.

Gel Profiling of Sterol-Binding Proteins in Human Cells

Sterol probe labeling of cellular proteins was assessed using SDS-PAGE analysis (FIG. 18a). Probe labeling for virtually all detected proteins was found to be UV-irradiation dependent (FIG. 18b), indicating that these interactions reflect non-covalent binding events (versus the post-translational modification of proteins by cholesterol). Concentration-dependent increases in protein labeling were observed for all three probes (1-20 μM probe), with the cis- and trans-sterol probes showing stronger overall protein-labeling profiles than the epi probe (FIG. 18c).

MS Profiling of Sterol-Binding Proteins in Human Cells

Biotin-streptavidin methods coupled with SILAC (stable isotope labeling by amino acids in cell culture) MS were used to distinguish proteins that specifically interact with sterol probes and assess the sensitivity of these interactions to competition by excess cholesterol (FIG. 19a). Isotopically 'heavy' HeLa cells were treated with the trans-sterol probe (20 μM) for 30 min and irradiated with UV light (5 min), while 'light' cells received either no probe treatment prior to UV light exposure (vehicle control), or received the trans-sterol probe (20 μM), but were not irradiated (no-UV control). Cells were then harvested, their heavy and light proteomes mixed 1:1, and probe-labeled proteins conjugated to an azide-biotin tag by click chemistry and enriched using streptavidin chromatography. Enriched proteins were then digested on-bead with trypsin and the resulting tryptic peptide mixture analyzed by LC-MS methods. Proteins that exhibited heavy:light SILAC ratios of ≥5 for trans-sterol probe versus both vehicle and no-UV light control reactions were designated as sterol-interacting proteins. About 850 proteins met these criteria (FIG. 19b).

The proteome-labeling profiles of the trans-sterol probe were compared with the cis and epi probes by SILAC. The mean labeling intensity ratio for probe-enriched proteins in the trans-versus-cis comparison was 0.9 (trans/cis; standard deviation=0.57) indicating that the trans and cis probes display similar protein-interaction profiles in cells. In contrast, the mean ratio, as well as the standard deviation, of the trans-versus-epi comparison were higher (2.1 and 1.2 for trans/epi, respectively), suggesting that the stereochemistry of the sterol hydroxyl group impacts probe-protein interactions in a variable manner.

In some instances, about 700 of the identified sterol-binding proteins showed strong selectivity (≥3-fold higher signals) for the trans-sterol probe over a non-steroidal neutral lipid probe containing a diazirine and alkyne group embedded within an N-palmitoylethanolamine structure [N-palmitoylethanolamine-diazirine-alkyne (PEA-DA) (FIG. 19c). In some cases, about 18 proteins from the sterol-binding group showed the opposite profile, exhibiting greater labeling with the PEA-DA probe (heavy/light signal ratio <1.0) (FIG. 19c).

Competitive profiling experiments were performed where the trans-sterol probe was evaluated for protein labeling in cells treated with excess cholesterol. Light and heavy-labeled HeLa cells were treated with the trans-sterol probe (10 μM) in the presence or absence of 10× (100 μM) cholesterol, respectively. In some cases, about 300 proteins showed at least a 50% decrease in trans-sterol probe labeling intensity in cells treated with excess cholesterol (FIG. 19d). In some instances, about 250 of these cholesterol-sensitive targets also showed selective labeling by the trans-sterol probe compared to the PEA-DA probe, and the majority (>60%) of the competed proteins also showed evidence of cholesterol competition in experiments performed with the cis-sterol probe. In some cases, parallel DNA microarray experiments were performed and that cholesterol-sensitive proteins showed no evidence of gene expression changes at the 30 min time point of competitive analysis.

The level of isotopically labeled amino acid incorporation was controlled in the SILAC experiments by treating heavy and light HeLa cells each with 20 uM trans-sterol probe, and combining and processing their proteomes as described above. The overall median and mean ratio for proteins detected in this experiment was 1.0, in some cases, indicative of about >95% heavy amino acid incorporation.

In some embodiments, the MS experiments enabled distribution of the proteins that interacted with the trans-sterol probe into four groups: 1) Group I, which were both sensitive to cholesterol competition and selective for the trans-sterol probe over the PEA-probe (265 total proteins), 2) Group II, which were sensitive, but not selective (34 total proteins), 3) Group III, which were selective, but not sensitive (411 total proteins), and 4) Group IV, which were neither sensitive nor selective (140 total proteins) (FIG. 19e). Representative MS1 traces for sterol-interacting proteins from each group are shown in FIG. 19b-d.

Analysis of Group I Cholesterol-Binding Proteins

In some instances, Group I contains many proteins that are known to bind to cholesterol. In some instances, the Group I proteins include Scap, caveolin (CAV1), tetraspanin CD82, the sterol transport protein ARV1, and the sterol biosynthetic enzymes, HMG-CoA reductase (HMGCR). In some instances, the trans-sterol probe interacted with additional enzymes in the sterol biosynthetic pathway (FIGS. 19f and g). In some cases, FDFT1 and SQLE, two upstream enzymes in the sterol biosynthetic pathway that do not directly handle sterols as substrates or products were identified in Group I (FIG. 19g). Group II-IV also contained additional proteins known to interact with cholesterol, including, for instance, the lysosomal sterol transporter NPC1.

Additional proteins in Group I include, but are not limited to, G-protein coupled receptors, a class of receptors that have been proposed to bind cholesterol to stabilize certain functional conformations; ion channels; transporters; and enzymes (FIG. 20a). Glycerophospholipid metabolic enzymes, protein glycosylation and degradation pathways, and protein networks that regulate membrane structure and dynamics, in some instances, are also included in Group I proteins (FIG. 19f).

Evaluation of the subcellular distribution of Group I proteins, in some cases, revealed that the vast majority (87%) are known or predicted integral membrane proteins (FIG. 20c). In some cases, these proteins were near-equally distributed between single- and multi-pass transmembrane proteins (FIG. 20c) and were dispersed across all subcellular membrane compartments with a notable enrichment in known or predicted ER proteins (FIG. 20d).

In some instances, the OMIM database is used to analyze the set of Group I proteins in relation to human diseases. In some instances, the human diseases include, but are not limited to, neurological disorders, cardiovascular diseases, and metabolic diseases (FIG. 20b).

Example VI

Tables 3-7 are illustrated below. Table 3 illustrates a list of lipid probe targets and SILAC ratios. Table 4 illustrates proteomic data set for lipid probe competition experiments. Data represents SILAC ratios from individual datasets except for MJN228 (10 and 25 uM), FK-866, avasimibe and AEA in Neuro2a cells, and (±)-flurbiprofen and rofecoxib in A549 cells which display the mean SILAC ratio from 2-3 experiments. All data are filtered to remove targets which were not UV-dependent. Table 5 illustrates aligned proteomic data for competed targets in Neuro2a and A549 cells. Table 6 illustrates a list of AEA-DA-modified peptides which are identified using the isoTOP-ABPP platform. The isoTOP-ABPP platform was applied to Neuro2a cells treated with the AEA-DA probe (100 μM). Data represented 12 replicates (10 biological and 2 technical). Table 7 illustrates untargeted metabolomic data for MJN228- and KML181-treated Neuro2a cells. Data represent XCMS-identified features from untargeted LC-MS analysis of organic-soluble extracts from Neuro2a cells treated with DMSO, MJN228 (10 μM), or KML181 (10 μM) for 6 h (n-5 per condition).

TABLE 4A

| Neuro2a (A-DA) Competition | | | | | |
|---|---|---|---|---|---|
| Gene Name | Accession | No UV | DMSO | Flurbiprofen (25 μM) | Rofecoxib (25 μM) |
| Kdsr | Q6GV12 | 20.0 | 0.9 | 0.7 | 1.2 |
| Tmem97 | Q8VD00 | 20.0 | 1.0 | 1.0 | 1.0 |
| Ech1 | O35459 | 20.0 | 0.9 | 0.5 | 1.2 |
| Ppt1 | O88531 | 20.0 | 1.2 | | 1.0 |
| Scarb1 | Q61009 | 20.0 | 0.9 | 1.3 | 1.5 |
| Cpt2 | P52825 | 20.0 | 1.0 | 0.9 | 1.2 |
| Akr1b8 | P45377 | 20.0 | 1.2 | 0.9 | 6.7 |
| UPF0554 | Q8BVA5 | 20.0 | 1.0 | 1.0 | 1.0 |
| Timm17a | Q9Z0V8 | 20.0 | 1.0 | 0.8 | 1.2 |
| Timm17b | Q9Z0V7 | 20.0 | 1.0 | 0.7 | 1.1 |
| Slc25a20 | Q9Z2Z6 | 20.0 | 1.0 | 1.1 | 2.0 |
| Gpr107 | Q8BUV8 | 20.0 | 0.9 | 0.8 | 1.0 |
| Ptgs1 | P22437 | 11.8 | 1.6 | 3.8 | 1.2 |
| Acadl | P51174 | 20.0 | 1.1 | 3.5 | 1.1 |
| Pcyox1 | Q9CQF9 | 20.0 | 1.2 | 0.9 | 1.2 |
| Tmem173 | Q3TBT3 | 20.0 | 0.8 | 1.2 | 1.3 |
| Tram1 | Q91V04 | 20.0 | 1.1 | 0.7 | 1.1 |
| Apmap | Q9D7N9 | 20.0 | 1.2 | 0.5 | 1.5 |
| Plin2 | P43883 | 20.0 | 0.9 | 1.4 | 1.3 |
| Dhrs1 | Q99L04 | 16.6 | 1.1 | 0.9 | 1.4 |
| Dhodh | O35435 | 20.0 | 1.1 | 3.0 | |
| Fam114a2 | Q8VE88 | 20.0 | 1.2 | 0.9 | 1.1 |
| Mospd2 | Q9CWP6 | 20.0 | 1.2 | 0.6 | 1.6 |
| Scd2 | P13011 | 6.0 | 1.1 | 2.8 | |
| Sdhb | Q9CQA3 | 14.1 | 1.1 | 2.7 | 1.1 |
| Lss | Q8BLN5 | 15.2 | 1.1 | 1.1 | 1.0 |
| Bsg | P18572 | 20.0 | 1.3 | 2.6 | 1.4 |
| Lbr | Q3U9G9 | 12.0 | 1.0 | 0.7 | 1.0 |
| Cers2 | Q924Z4 | 16.4 | 1.1 | 0.7 | 1.2 |
| Agps | Q8C0I1 | 20.0 | 1.0 | 2.4 | 1.4 |
| Hmox2 | O70252 | 18.7 | 1.1 | 0.9 | 1.2 |
| Nptn | P97300 | 20.0 | 1.2 | | |
| Ephx1 | Q9D379 | 17.3 | 1.0 | 0.7 | 1.4 |
| Pcyox1l | Q8C7K6 | 20.0 | 1.2 | 1.0 | 1.9 |
| Cyb5b | Q9CQX2 | 12.5 | 1.2 | 1.1 | 1.1 |
| Slc30a6 | Q8BJM5 | 20.0 | 1.1 | 0.7 | 1.1 |
| Gnpat | P98192 | 20.0 | 1.0 | 2.3 | |
| Fech | P22315 | 20.0 | 1.0 | | 2.2 |
| Sec11a | Q9R0P6 | 20.0 | 1.0 | 0.7 | 1.2 |
| Por | P37040 | 20.0 | 1.1 | 2.1 | 1.2 |
| Tmem199 | Q5SYH2 | 20.0 | 1.1 | 0.8 | 1.1 |
| Dnajc1 | Q61712 | 20.0 | 1.1 | 0.7 | |
| Ndufs2 | Q91WD5 | 14.4 | 1.0 | 2.1 | 0.9 |
| Opa3 | Q505D7 | 20.0 | 1.0 | | 1.1 |
| Aldh3a2 | P47740 | 20.0 | 1.0 | | 1.1 |
| Scarb2 | O35114 | 20.0 | 1.0 | 0.6 | 1.0 |
| Tor1b | Q9ER41 | 20.0 | 1.0 | | |
| Gpd2 | Q64521 | 14.1 | 1.0 | 2.0 | 0.9 |
| Cox4i1 | P19783 | 20.0 | 1.2 | 0.5 | 1.2 |
| Vdac1 | Q60932 | 20.0 | 1.2 | 0.6 | 1.1 |
| Psap | Q61207 | 20.0 | 1.0 | 1.0 | 0.9 |
| Ptges2 | Q8BWM0 | 15.5 | 1.1 | 0.7 | 1.0 |
| Fads1 | Q920L1 | 3.1 | 1.1 | 1.9 | 1.2 |
| Qil1 | Q8R404 | 20.0 | 1.1 | 1.1 | 1.1 |
| Ssr1 | Q9CY50 | 20.0 | 1.1 | 0.9 | 1.1 |
| Acsl6 | Q91WC3 | 20.0 | 1.0 | 0.7 | 1.2 |
| Emb | P21995 | 20.0 | 1.0 | 0.6 | 1.3 |
| Rtn3 | Q9ES97 | 14.3 | 1.0 | 1.2 | 1.1 |
| Sgpl1 | Q8R0X7 | 16.2 | 1.0 | 0.5 | 1.2 |
| Atp2a2 | O55143 | 16.9 | 1.2 | 0.8 | 1.1 |
| Asah1 | Q9WV54 | 15.7 | 1.1 | 0.7 | 1.0 |
| Tusc3 | Q8BTV1 | 10.9 | 0.9 | | |
| Cyp51a1 | Q8K0C4 | 14.1 | 1.3 | 0.5 | 1.1 |
| Vat1 | Q62465 | 5.4 | 1.1 | 1.2 | 1.3 |
| Ttyh3 | Q6P5F7 | 20.0 | 0.9 | 1.8 | 1.1 |
| Ano10 | Q8BH79 | 20.0 | 1.2 | 0.7 | 1.3 |
| Ptgr2 | Q8VDQ1 | 20.0 | 1.1 | 0.9 | 1.5 |
| Ggt7 | Q99JP7 | 15.9 | 1.0 | 1.1 | 1.2 |
| Fam162a | Q9D6U8 | 20.0 | 1.0 | 1.8 | 1.2 |
| Acad9 | Q8JZN5 | 14.5 | 1.0 | 0.8 | 1.1 |
| Tbl2 | Q9R099 | 20.0 | 0.9 | | 1.8 |
| Ghitm | Q91VC9 | 20.0 | 1.0 | 0.5 | 1.2 |
| Ermp1 | Q3UVK0 | 16.1 | 0.9 | 1.7 | 1.6 |
| Sar1a | P36536 | 20.0 | 1.1 | 0.7 | 1.1 |
| Hsd17b11 | Q9EQ06 | 20.0 | 1.0 | 1.0 | 1.3 |

TABLE 4A-continued

Neuro2a (A-DA) Competition

| Gene Name | Accession | No UV | DMSO | Flurbiprofen (25 μM) | Rofecoxib (25 μM) |
|---|---|---|---|---|---|
| Ckap4 | Q8BMK4 | 16.9 | 1.2 | 0.9 | 1.3 |
| Vdac2 | Q60930 | 15.7 | 1.2 | 0.7 | 1.0 |
| Tmed7 | D3YZZ5 | 20.0 | 1.1 | | 0.9 |
| Vim | P20152 | 3.5 | 1.2 | 1.7 | 0.9 |
| Sqle | P52019 | 20.0 | 1.3 | 1.2 | 1.7 |
| Ccdc47 | Q9D024 | 15.0 | 1.1 | 0.9 | 1.2 |
| Dpm1 | O70152 | 12.2 | 1.0 | | 1.7 |
| Bcap31 | Q61335 | 20.0 | 1.3 | 0.8 | 1.4 |
| Mmgt1 | Q8K273 | 20.0 | 1.1 | | 1.1 |
| Sccpdh | Q8R127 | 17.4 | 1.1 | 0.7 | 1.3 |
| Phb2 | O35129 | 14.3 | 1.1 | 0.9 | 1.0 |
| Ankle2 | Q6P1H6 | 20.0 | 0.9 | 0.9 | 1.2 |
| Msmo1 | Q9CRA4 | 17.6 | 1.2 | 0.6 | 1.1 |
| Mtdh | Q80WJ7 | 17.1 | 1.1 | 0.9 | 1.4 |
| Atp13a1 | Q9EPE9 | 20.0 | 0.9 | 0.9 | 1.2 |
| Ndufb10 | Q9DCS9 | 20.0 | 1.3 | 1.6 | |
| Ostc | Q78XF5 | 14.6 | 1.2 | 0.9 | 1.1 |
| Eci1 | P42125 | 3.8 | 1.1 | | 1.0 |
| Sar1b | Q9CQC9 | 15.9 | 1.0 | 0.7 | 1.3 |
| Arf1 | P84078 | 4.9 | 1.1 | 1.0 | 1.3 |
| Arf3 | P61205 | 8.6 | 1.1 | 1.0 | |
| Fam210a | Q8BGY7 | 20.0 | 1.1 | | |
| Atp5l | Q9CPQ8 | 6.8 | 1.2 | 1.3 | 1.1 |
| Laptm4a | Q60961 | 16.1 | 1.0 | 1.4 | 1.2 |
| Hsd17b4 | P51660 | 10.7 | 1.0 | 1.4 | |
| Gm364 | A2AFI6 | 4.5 | 1.0 | | 1.5 |
| Coq4 | Q8BGB8 | 14.2 | 1.0 | 1.6 | 1.2 |
| Faf2 | Q3TDN2 | 20.0 | 0.9 | 0.8 | 1.6 |
| Cisd1 | Q91WS0 | 15.1 | 1.1 | 0.7 | 1.1 |
| Pgrmc2 | Q80UU9 | 16.7 | 1.2 | 0.9 | 1.2 |
| Sec63 | Q8VHE0 | 14.3 | 0.9 | 0.9 | 1.1 |
| Prph | P15331 | 3.0 | 1.1 | 1.5 | 1.1 |
| Pdss1 | Q33DR2 | 18.8 | 0.9 | 0.7 | 1.1 |
| Gm20425 | E9Q035 | 17.4 | 1.2 | | 1.2 |
| Oxa1l | Q8BGA9 | 20.0 | 1.1 | 0.8 | |
| Slc25a24 | Q8BMD8 | 20.0 | 1.0 | 0.8 | 1.1 |
| Tmem48 | Q8VCB1 | 20.0 | 0.9 | 0.7 | 1.1 |
| Canx | P35564 | 14.8 | 1.2 | 0.9 | 1.1 |
| Stt3a | P46978 | 18.5 | 1.1 | 0.7 | 1.1 |
| Alg9 | Q8VDI9 | 20.0 | 0.9 | 0.7 | 1.5 |
| Tmem209 | Q8BRG8 | 14.5 | 1.0 | 0.8 | 1.1 |
| Cers5 | Q9D6K9 | 15.1 | 1.2 | 0.9 | 1.2 |
| Stip1 | Q60864 | 6.1 | 1.0 | 1.5 | 1.2 |
| Acsl1 | P41216 | 4.4 | 1.0 | 0.8 | 1.2 |
| Gm20671 | F6TVX7 | 20.0 | 1.1 | | 1.0 |
| Pisd | Q8BSF4 | 20.0 | 1.1 | 1.0 | 1.0 |
| Lpcat3 | Q91V01 | 19.1 | 1.0 | 0.9 | 1.2 |
| Nsdhl | Q9R1J0 | 16.2 | 1.2 | 0.7 | 1.2 |
| Ncln | Q8VCM8 | 4.9 | 0.9 | | 1.1 |
| Coq9 | Q8K1Z0 | 20.0 | 0.9 | 0.7 | |
| Tmpo | Q61033 | 11.8 | 1.1 | 0.8 | 1.1 |
| Tmpo | Q61029 | 12.0 | 1.1 | 0.8 | 1.2 |
| Emc1 | Q8C7X2 | 14.3 | 1.0 | 1.1 | |
| Acsl3 | Q9CZW4 | 12.9 | 1.0 | 0.9 | 1.2 |
| Ghdc | Q99J23 | 16.0 | 0.9 | 1.0 | 1.2 |
| Rtn4ip1 | Q924D0 | 20.0 | 1.1 | 0.8 | 1.1 |
| Agpat6 | Q8K2C8 | 20.0 | 0.9 | 1.4 | 1.1 |
| Abhd16a | Q9Z1Q2 | 12.4 | 0.9 | 0.9 | 1.4 |
| Zmpste24 | Q80W54 | 20.0 | 1.1 | 0.8 | 1.1 |
| Tmx2 | Q9D710 | 15.0 | 1.3 | 0.9 | 1.2 |
| Tmed10 | Q9D1D4 | 9.7 | 1.2 | 1.0 | 1.0 |
| Uba52 | P62984 | 3.9 | 1.1 | | 1.1 |
| Vmp1 | Q99KU0 | 18.0 | 1.0 | 0.7 | |
| Kdelr1 | Q99JH8 | 20.0 | 1.1 | 0.9 | 1.1 |
| Ndufa4 | Q62425 | 5.8 | 1.1 | 1.4 | |
| Sdhd | Q9CXV1 | 4.3 | 1.0 | 1.4 | 1.3 |
| Cyb5r3 | Q9DCN2 | 4.9 | 1.2 | 1.0 | 1.2 |
| Bri3bp | Q8BXV2 | 20.0 | 1.1 | 0.8 | 1.2 |
| Lmf2 | Q8C3X8 | 14.9 | 1.1 | 0.7 | 1.2 |
| Tomm22 | Q9CPQ3 | 20.0 | 1.1 | 0.7 | 1.1 |
| Tmed2 | Q9R0Q3 | 20.0 | 1.2 | 0.8 | 1.1 |
| Pmpca | Q9DC61 | 4.9 | 1.0 | 0.8 | 1.1 |
| Mogs | Q80UM7 | 3.9 | 1.0 | 1.4 | |
| Derl1 | Q99J56 | 20.0 | 1.2 | 0.7 | 1.2 |
| Hsd17b7 | O88736 | 20.0 | 1.0 | 0.7 | 1.0 |
| Uqcrfs1 | Q9CR68 | 3.5 | 1.1 | 1.4 | |
| Nrm | Q8VC65 | 16.5 | 1.1 | | 1.3 |
| Mest | Q07646 | 12.8 | 1.1 | 0.9 | 1.2 |
| Ssr4 | Q62186 | 10.8 | 1.1 | 0.9 | 1.2 |
| Cers4 | Q9D6J1 | 20.0 | 1.0 | 0.6 | 1.1 |
| Clptm1 | Q8VBZ3 | 18.7 | 1.1 | 1.0 | 1.2 |
| Gaa | P70699 | 7.6 | 1.0 | 1.0 | |
| Rab2a | P53994 | 3.3 | 1.1 | 0.9 | 1.1 |
| Hadha | Q8BMS1 | 9.5 | 1.2 | 1.2 | 1.1 |
| Adpgk | Q8VDL4 | 18.0 | 1.2 | 0.7 | 1.2 |
| ptplad1 | Q8K2C9 | 16.7 | 1.0 | | 1.2 |
| Fkbp8 | O35465 | 3.0 | 1.1 | 1.3 | |
| Atl2 | Q6PA06 | 15.8 | 1.0 | | |
| Cyc1 | Q9D0M3 | 8.6 | 1.1 | 1.3 | 1.1 |
| Pigt | Q8BXQ2 | 11.4 | 1.2 | | 1.3 |
| Slc25a17 | O70579 | 11.7 | 1.0 | | |
| Atp1a1 | Q8VDN2 | 4.0 | 1.0 | 1.1 | 1.1 |
| Tmed1 | Q3V009 | 14.0 | 1.2 | 1.0 | |
| Apoo | Q9DCZ4 | 13.6 | 1.1 | 0.9 | 1.0 |
| Tmem68 | Q9D850 | 20.0 | 1.0 | | 1.3 |
| Kdelr2 | Q9CQM2 | 20.0 | 1.0 | 1.0 | 1.1 |
| Pnpla2 | Q8BJ56 | 20.0 | 0.9 | 1.3 | |
| Slc25a32 | Q8BMG8 | 20.0 | 1.1 | 0.7 | 1.3 |
| Acp6 | Q8BP40 | 20.0 | 1.0 | | 1.3 |
| Cox5a | P12787 | 3.1 | 1.1 | | 1.2 |
| Acsl4 | Q9QUJ7 | 5.2 | 1.1 | 0.9 | 1.2 |
| Stoml2 | Q99JB2 | 4.7 | 1.0 | 0.9 | 1.1 |
| Cend1 | Q9JKC6 | 7.2 | 1.2 | 1.3 | 1.1 |
| Pigs | Q6PD26 | 10.8 | 1.1 | 0.9 | 1.3 |
| Dcakd | Q8BHC4 | 13.8 | 1.1 | 0.9 | 1.2 |
| Tmx4 | Q8C0L0 | 12.8 | 1.0 | 0.9 | 1.1 |
| Slc39a7 | Q31125 | 20.0 | 0.9 | | 1.3 |
| Dhcr24 | Q8VCH6 | 20.0 | 1.1 | 0.6 | 1.3 |
| Ddost | O54734 | 4.8 | 1.0 | 1.1 | 1.2 |
| Atp5i | Q06185 | 14.2 | 1.1 | 1.1 | |
| Itgb1 | P09055 | 4.2 | 1.3 | 1.2 | |
| Agpat4 | Q8K4X7 | 11.8 | 0.9 | 1.0 | 1.2 |
| Fdft1 | P53798 | 20.0 | 0.9 | | |
| Tecr | Q9CY27 | 20.0 | 1.1 | 0.8 | 1.2 |
| Rtn4 | Q99P72 | 14.9 | 1.1 | 1.0 | 1.0 |
| Parl | Q5XJY4 | 7.2 | 1.1 | 0.8 | 1.2 |
| Pgrmc1 | O55022 | 13.5 | 1.1 | 0.7 | 1.2 |
| Sec22b | O08547 | 11.6 | 1.1 | 0.9 | 1.2 |
| Abcb10 | Q9JI39 | 5.1 | 1.1 | 1.2 | |
| Pla2g15 | Q8VEB4 | 20.0 | 1.1 | 1.2 | |
| Surf4 | Q64310 | 9.4 | 1.2 | 0.9 | 1.1 |
| Ctsd | P18242 | 20.0 | 1.0 | 0.7 | 0.8 |
| Atp5f1 | Q9CQQ7 | 8.7 | 1.1 | 1.0 | 1.1 |
| Alg2 | Q9DBE8 | 5.2 | 0.9 | | |
| Tmx1 | Q8VBT0 | 7.1 | 1.2 | 0.8 | 1.2 |
| Atp6v0c | P63082 | 3.0 | 1.1 | | 1.0 |
| Emd | O08579 | 20.0 | 1.2 | 0.9 | 1.2 |
| Ociad1 | Q9CRD0 | 14.7 | 1.1 | 1.0 | 1.0 |
| Tmem214 | Q8BM55 | 14.2 | 0.9 | 0.9 | 1.1 |
| Phb | P67778 | 9.1 | 1.1 | 0.8 | 1.1 |
| Slc25a33 | Q3TZX3 | 14.7 | 1.0 | 0.5 | 1.1 |
| Slc25a19 | Q9DAM5 | 20.0 | 1.2 | 0.7 | 1.1 |
| Baiap2 | Q8BKX1 | 20.0 | 1.1 | 1.2 | |
| Slc25a16 | Q8C0K5 | 20.0 | 1.1 | 1.2 | |
| Ncstn | P57716 | 20.0 | 1.0 | | 1.2 |
| Tlcd1 | Q99JT6 | 20.0 | 1.0 | 1.1 | 1.2 |
| Tmem33 | Q9CR67 | 7.4 | 1.2 | 0.8 | 1.2 |
| Lman2 | Q9DBH5 | 6.1 | 1.0 | 1.2 | 0.9 |
| Sec61a1 | P61620 | 6.3 | 1.1 | 0.9 | 1.2 |
| Rdh11 | Q9QYF1 | 6.2 | 1.1 | 1.0 | 1.1 |
| Esyt2 | Q3TZZ7 | 20.0 | 0.9 | 1.0 | 1.2 |
| Slc25a25 | A2ASZ8 | 20.0 | 1.0 | 0.9 | 1.1 |
| Far1 | Q922J9 | 3.7 | 1.0 | 1.2 | 1.1 |
| Immt | Q8CAQ8 | 9.9 | 1.1 | 1.1 | 1.2 |
| Stt3b | Q3TDQ1 | 7.7 | 0.9 | 0.7 | 1.2 |
| Timm50 | Q9D880 | 9.4 | 1.1 | 1.0 | 1.1 |
| Mcm6 | P97311 | 3.2 | 1.3 | 1.2 | |
| Hm13 | Q9D8V0 | 20.0 | 1.2 | 0.8 | 1.2 |
| Timm22 | Q9CQ85 | 20.0 | 1.2 | 1.2 | 1.1 |
| Timm44 | O35857 | 10.9 | 1.3 | 1.0 | 1.2 |

TABLE 4A-continued

Neuro2a (A-DA) Competition

| Gene Name | Accession | No UV | DMSO | Flurbiprofen (25 μM) | Rofecoxib (25 μM) |
|---|---|---|---|---|---|
| Abhd5 | Q9DBL9 | 20.0 | 1.0 | 1.2 | |
| Tomm40 | Q9QYA2 | 8.0 | 1.1 | 0.9 | 1.2 |
| Lrrc59 | Q922Q8 | 6.7 | 1.2 | 1.0 | 1.2 |
| Abcd3 | P55096 | 3.0 | 0.9 | 1.1 | 1.1 |
| Abhd12 | Q99LR1 | 14.8 | 1.2 | 0.7 | 1.2 |
| Amfr | Q9R049 | 20.0 | 1.2 | 1.2 | |
| Pigu | Q8K358 | 20.0 | 1.0 | 0.9 | 1.2 |
| Yif1b | Q9CX30 | 13.8 | 0.9 | 0.7 | 1.2 |
| Mtch2 | Q791V5 | 13.6 | 1.1 | 0.7 | 1.1 |
| Slc25a1 | Q8JZU2 | 9.2 | 1.0 | | 1.0 |
| Nup210 | Q9QY81 | 20.0 | 1.0 | | |
| Hsd17b12 | O70503 | 7.1 | 1.2 | 0.8 | 1.2 |
| Jagn1 | Q5XKN4 | 20.0 | 1.0 | 0.7 | 1.2 |
| Rpn2 | Q9DBG6 | 4.0 | 1.0 | 0.9 | 1.1 |
| Rpn1 | Q91YQ5 | 12.6 | 1.2 | 1.1 | 1.1 |
| Slc25a4 | P48962 | 4.8 | 1.2 | 0.8 | 1.0 |
| Sec61a2 | Q9JLR1 | 4.3 | 1.0 | 0.9 | 1.1 |
| Agk | Q9ESW4 | 14.0 | 0.9 | 1.0 | 1.1 |
| Dhrs7 | Q9CXR1 | 20.0 | 0.9 | 1.1 | 1.1 |
| Nnt | Q61941 | 11.9 | 1.0 | 0.7 | 1.0 |
| Comt | O88587 | 7.2 | 0.9 | 0.8 | 1.1 |
| Slc25a10 | Q9QZD8 | 5.6 | 1.0 | 0.8 | 1.1 |
| Slc25a12 | Q8BH59 | 5.2 | 1.0 | 1.0 | 1.1 |
| Tmem43 | Q9DBS1 | 5.1 | 1.0 | | 1.1 |
| Trabd | Q99JY4 | 17.0 | 0.9 | 0.9 | 1.1 |
| March5 | Q3KNM2 | 20.0 | 0.9 | 0.6 | 1.1 |
| Slc25a26 | Q5U680 | 20.0 | 1.0 | | 1.1 |
| Alg5 | Q9DB25 | 6.9 | 1.1 | 1.0 | 1.1 |
| Dnajc11 | Q5U458 | 8.6 | 1.1 | 1.0 | 1.1 |
| Slc25a5 | P51881 | 4.2 | 1.2 | 0.8 | 1.0 |
| Sacm1l | Q9EP69 | 4.5 | 1.0 | 1.0 | 1.1 |
| Atp1a3 | Q6PIC6 | 3.7 | 1.2 | | 1.1 |
| Ptrh2 | Q8R2Y8 | 10.2 | 1.1 | 0.8 | 1.1 |
| Aifm2 | Q8BUE4 | 20.0 | 1.0 | | 1.1 |
| Asna1 | O54984 | 9.7 | 1.2 | 0.8 | 0.8 |
| Aifm1 | Q9Z0X1 | 13.2 | 1.3 | | |
| Nucb1 | Q02819 | 20.0 | 1.2 | 0.7 | 1.1 |
| Dolpp1 | Q9JMF7 | 14.3 | 1.2 | 0.7 | 1.1 |
| Pex16 | Q91XC9 | 16.1 | 1.1 | 1.0 | 1.1 |
| Hsdl1 | Q8BTX9 | 14.6 | 1.1 | 0.7 | 1.1 |
| Samm50 | Q8BGH2 | 10.2 | 1.1 | 0.9 | 1.1 |
| Tmx3 | Q8BXZ1 | 6.8 | 1.0 | 0.8 | 1.1 |
| Bdh1 | Q80XN0 | 3.7 | 1.0 | 1.0 | 1.0 |
| Atad3 | Q925I1 | 14.1 | 1.1 | 0.9 | 1.1 |
| Rab1b | Q9D1G1 | 3.3 | 1.1 | 1.1 | |
| Atp6v0a1 | Q9Z1G4 | 11.2 | 0.9 | 0.7 | 1.1 |
| Tomm70a | Q9CZW5 | 3.0 | 1.1 | 1.1 | 1.0 |
| Mtch1 | Q791T5 | 8.7 | 0.9 | 0.8 | 1.0 |
| Slc25a22 | Q9D6M3 | 5.2 | 1.1 | 0.8 | 1.0 |
| Odr4 | Q4PJX1 | 3.3 | 1.1 | 1.1 | |
| Spcs2 | Q9CYN2 | 16.7 | 1.1 | | 1.0 |
| Vkorc1l1 | Q6TEK5 | 20.0 | 1.1 | 0.5 | 1.0 |
| Ubqln2 | Q9QZM0 | 3.5 | 1.6 | 1.0 | |
| Sfxn1 | Q99JR1 | 4.9 | 1.1 | 0.9 | 1.0 |
| Slc7a3 | P70423 | 4.9 | 1.0 | 0.9 | 1.0 |
| Timm23 | Q9WTQ8 | 20.0 | 1.1 | 0.9 | 1.0 |
| Apool | Q78IK4 | 16.9 | 1.1 | 0.8 | |
| Cdipt | Q8VDP6 | 10.0 | 1.0 | 0.6 | 1.0 |
| Agpat1 | O35083 | 5.6 | 0.9 | 0.9 | 1.0 |
| Rab10 | P61027 | 3.2 | 1.0 | 0.9 | 1.0 |
| Tmem66 | Q8R3Q0 | 20.0 | 1.1 | 1.0 | |
| Ubc | P0CG50 | 3.5 | 1.2 | 1.0 | |
| Cox15 | Q8BJ03 | 7.2 | 0.8 | 0.6 | 1.0 |
| Abcb7 | Q61102 | 3.5 | 0.9 | | |
| Dhcr7 | O88455 | 5.7 | 1.1 | 0.8 | 1.0 |
| Tmem165 | P52875 | 11.5 | 1.1 | 0.9 | |
| Cpt1a | P97742 | 7.9 | 0.9 | 0.8 | |
| Slc25a51 | Q5HZI9 | 20.0 | 1.0 | 0.9 | |
| Atad1 | Q9D5T0 | 4.5 | 1.2 | 0.9 | |
| Gdpd1 | Q9CRY7 | 5.8 | 1.1 | 0.9 | |
| Mtap | Q9CQ65 | 5.2 | 1.1 | 0.7 | |
| Agpat9 | Q8CON2 | 20.0 | 1.2 | 0.9 | |
| Aup1 | P70295 | 6.4 | 1.0 | 0.9 | |
| Rab11b | P46638 | 13.2 | 1.1 | 0.9 | |
| Mtx2 | O88441 | 8.9 | 1.0 | | 0.9 |
| Them6 | Q80ZW2 | 20.0 | 1.1 | 0.9 | |
| Tmem160 | Q9D938 | 20.0 | 1.0 | 0.9 | |
| Arl6ip1 | Q9JKW0 | 12.6 | 1.1 | 0.9 | |
| Degs1 | O09005 | 4.7 | 1.0 | 0.9 | |
| Pigk | Q9CXY9 | 9.8 | 0.9 | 0.9 | |
| Stx5 | Q8K1E0 | 4.4 | 1.0 | 0.9 | |
| Bcap29 | Q61334 | 20.0 | 0.9 | 0.8 | |
| Vapb | Q9QY76 | 20.0 | 0.9 | | 0.8 |
| Sel1l | Q9Z2G6 | 20.0 | 1.1 | 0.8 | |
| Lnp | Q7TQ95 | 13.8 | 1.0 | 0.8 | |
| Abhd6 | Q8R2Y0 | 14.7 | 0.9 | 0.8 | |
| Ebp | P70245 | 20.0 | 0.9 | | 0.8 |
| Agpat5 | Q9D1E8 | 6.9 | 1.0 | 0.8 | |
| Lmf1 | Q3U3R4 | 20.0 | 1.1 | 0.8 | |
| Golph3 | Q9CRA5 | 20.0 | 1.0 | | |
| Letm1 | Q9Z2I0 | 7.6 | 1.2 | 0.8 | |
| Mttp | O08601 | 20.0 | 1.1 | 0.7 | |
| Erlin2 | Q8BFZ9 | 13.2 | 1.0 | 0.7 | |
| Dhrs7b | Q99J47 | 10.7 | 1.0 | 0.7 | |
| Mpv17l2 | Q8VIK2 | 20.0 | 1.0 | 0.7 | |
| Letmd1 | Q924L1 | 14.7 | 0.9 | 0.7 | |
| Coq5 | Q9CXI0 | 12.4 | 1.1 | 0.5 | |
| Reep2 | Q8VCD6 | 20.0 | 0.9 | 0.5 | |

TABLE 4B

Neuro2a (AEA-DA) Competition

| Gene Name | No UV | DMSO | AEA (200 μM) | FK866 (25 μM) | Avasimibe (25 μM) | Elacridar (25 μM) | Ro 48-8071 (25 μM) | MJN228 (10 μM) | MJN228 (25 μM) | MJN228 (50 μM) | MJN228 (100 μM) | KML110 (25 μM) | KML181 (25 μM) |
|---|---|---|---|---|---|---|---|---|---|---|---|---|---|
| Fech | 20.0 | 1.0 | 1.3 | 20.0 | 0.2 | 20.0 | 1.4 | 1.0 | 2.4 | 3.0 | 2.9 | 2.2 | 1.4 |
| Abcb1b | 20.0 | 1.1 | 2.3 | 5.4 | 1.8 | 20.0 | 1.7 | 2.6 | 4.0 | 9.4 | 20.0 | 5.7 | 1.1 |
| Tmem97 | 20.0 | 1.1 | 1.8 | 1.0 | 1.7 | 18.7 | 10.0 | 1.4 | 1.7 | 2.1 | 3.2 | 1.6 | 1.0 |
| Ephx1 | 4.0 | 1.0 | 2.1 | 1.4 | 18.6 | 1.8 | 2.4 | 2.5 | 3.8 | 8.2 | 11.5 | 3.4 | 1.3 |
| Dhrs1 | 20.0 | 1.1 | 18.4 | 8.0 | 2.1 | 1.5 | 9.5 | 1.4 | 1.8 | 2.4 | 4.4 | 2.7 | 1.5 |
| Nampt | 20.0 | 1.4 | 1.1 | 16.4 | 1.3 | 1.1 | 0.9 | | 1.2 | 1.0 | | 2.0 | 0.8 |
| Zadh2 | 20.0 | 1.0 | 4.8 | 12.6 | 1.8 | 1.2 | 1.0 | 1.4 | 1.5 | 2.3 | 6.0 | 1.5 | 0.9 |
| Acad1 | 20.0 | 1.0 | 1.1 | 12.4 | 1.0 | 1.3 | 1.4 | 1.8 | 2.0 | 2.4 | 1.8 | 0.9 | |
| Abhd5 | 20.0 | 1.3 | 1.3 | 1.1 | 12.3 | 1.3 | 1.4 | 1.6 | 2.2 | 4.0 | 14.3 | 2.0 | 1.0 |
| Plin2 | 20.0 | 1.0 | 1.4 | 1.0 | 10.3 | 1.5 | 1.8 | 1.8 | 3.2 | 20.0 | 20.0 | 2.7 | 0.8 |
| Ptgr2 | 20.0 | 1.2 | 8.7 | 5.2 | 1.4 | 1.2 | 1.1 | 1.2 | 1.2 | 1.0 | 1.5 | 1.5 | 1.0 |
| Akr1b8 | 20.0 | 1.3 | 7.7 | 1.7 | 2.3 | 1.2 | 1.4 | | 1.9 | 2.1 | 2.7 | 3.1 | 1.1 |
| Paox | 20.0 | 1.2 | 7.5 | 3.2 | 1.7 | 1.5 | 2.4 | 2.1 | 3.2 | 4.5 | 13.5 | 2.9 | 4.8 |
| Sccpdh | 20.0 | 1.1 | 3.4 | 7.3 | 2.5 | 1.3 | 1.6 | 1.4 | 2.1 | 3.3 | 5.9 | 2.6 | 1.0 |

TABLE 4B-continued

Neuro2a (AEA-DA) Competition

| Gene Name | No UV | DMSO | AEA (200 μM) | FK866 (25 μM) | Avasimibe (25 μM) | Elacridar (25 μM) | Ro 48-8071 (25 μM) | MJN228 (10 μM) | MJN228 (25 μM) | MJN228 (50 μM) | MJN228 (100 μM) | KML110 (25 μM) | KML181 (25 μM) |
|---|---|---|---|---|---|---|---|---|---|---|---|---|---|
| Tmem87a | 20.0 | 1.4 | 1.8 | 1.1 | 7.0 | 1.4 | 2.3 | 1.3 | 1.9 | 1.6 | 2.7 | 1.8 | 1.1 |
| Tmem160 | 13.4 | 1.5 |  | 1.2 | 6.9 | 1.4 | 1.2 | 1.2 | 1.5 |  | 3.5 | 1.3 | 0.9 |
| Soat1 | 6.1 | 1.2 |  | 2.3 | 6.4 | 1.5 | 1.8 | 1.2 | 2.6 |  |  |  | 1.2 |
| Hadha | 20.0 | 1.2 | 2.3 | 6.2 | 2.2 | 2.2 | 1.0 | 1.4 | 1.7 | 2.0 | 2.9 | 2.0 | 1.1 |
| Tram1 | 20.0 | 1.1 | 2.9 | 1.2 | 5.5 | 1.2 | 1.8 | 1.3 | 1.8 | 1.9 | 5.4 | 1.7 | 1.0 |
| Timm17a | 20.0 | 1.7 | 1.5 | 1.1 | 5.4 | 1.5 | 2.7 | 1.1 | 1.4 | 1.4 | 2.7 | 1.5 | 0.9 |
| Timm17b | 20.0 | 1.4 | 1.6 | 1.2 | 5.1 | 1.5 | 2.8 | 1.3 | 1.5 | 2.2 | 3.6 | 1.8 | 1.0 |
| Bcap31 | 12.0 | 1.3 | 2.3 | 1.6 | 5.0 | 1.5 | 1.4 | 2.1 | 2.5 | 3.8 | 4.0 | 2.0 | 1.1 |
| Akr1b10 | 20.0 | 1.1 | 4.5 | 1.9 | 2.4 | 1.3 | 1.5 | 2.1 | 2.8 | 2.6 | 3.2 | 3.9 | 1.3 |
| Slc35b2 | 13.4 | 1.3 | 1.9 | 1.0 | 4.2 | 1.2 | 0.9 | 1.0 | 1.1 | 1.6 | 1.2 | 1.3 | 0.9 |
| Gpr107 | 20.0 | 1.1 | 1.6 | 1.0 | 3.9 | 1.1 | 1.8 | 1.1 | 1.3 | 2.1 | 2.9 | 1.5 | 1.1 |
| Dcakd | 9.0 | 1.2 | 1.9 | 1.1 | 3.7 | 1.2 | 1.0 | 1.2 | 1.4 | 1.5 | 1.9 | 1.4 | 0.9 |
| Timm22 | 13.6 | 1.5 | 1.3 | 1.2 | 3.6 | 1.3 | 1.1 | 1.0 | 1.3 | 1.0 | 1.8 | 1.4 | 0.9 |
| Kdsr | 19.4 | 1.4 | 3.6 | 1.1 | 2.1 | 1.3 | 1.6 | 1.1 | 1.5 | 1.3 | 1.7 | 1.6 | 0.9 |
| Fads2 | 10.5 | 1.4 | 2.5 | 1.2 | 3.4 | 1.5 | 1.2 | 1.3 | 1.8 | 1.9 | 2.8 | 1.4 | 0.8 |
| Trabd | 12.0 | 1.4 | 1.0 | 1.2 | 3.4 | 1.1 | 1.0 | 1.1 | 1.3 | 1.4 | 1.7 | 1.5 | 1.0 |
| Gm20425 | 16.5 | 1.3 | 2.3 | 1.2 | 3.3 | 1.2 | 1.2 | 1.3 | 1.7 | 1.7 | 2.9 | 1.5 | 0.9 |
| Tmem48 | 14.5 | 1.3 | 1.9 | 1.2 | 3.3 | 1.2 | 1.1 | 1.3 | 1.5 | 1.9 | 2.8 | 1.6 | 1.0 |
| Hmox2 | 4.0 | 1.1 | 3.2 | 1.0 | 2.1 | 1.2 | 1.3 | 1.1 | 1.4 | 1.3 | 1.7 | 1.5 | 1.0 |
| Pgrmc2 | 16.3 | 1.2 | 2.0 | 1.2 | 3.2 | 1.3 | 1.3 | 1.2 | 1.5 | 1.7 | 2.0 | 1.6 | 0.9 |
| Sec11a | 5.4 | 1.2 | 1.9 | 1.1 | 3.1 | 1.3 | 1.6 | 1.2 | 1.6 | 1.7 | 2.3 | 1.6 | 0.9 |
| March5 | 20.0 | 1.6 |  | 1.3 | 3.1 | 1.0 | 1.1 | 1.1 | 1.1 | 1.0 | 1.1 | 1.5 | 0.8 |
| Emd | 20.0 | 1.3 | 1.4 | 1.4 | 3.1 | 1.3 | 1.3 | 1.8 | 2.4 | 2.5 | 4.5 | 1.7 | 1.0 |
| Cpt2 | 20.0 | 1.1 | 1.1 | 3.1 | 1.1 | 1.3 | 2.1 | 1.3 | 1.7 | 2.7 | 5.5 | 1.5 | 0.9 |
| Abhd6 | 20.0 | 1.4 | 2.3 | 1.7 | 3.0 | 1.5 | 1.2 | 1.2 | 1.7 | 2.3 | 2.9 | 2.6 | 1.0 |
| Tomm22 | 20.0 | 1.5 | 1.4 | 1.1 | 3.0 | 1.3 | 1.0 | 1.1 | 1.2 | 1.2 | 1.8 | 1.3 | 0.8 |
| Cers2 | 17.1 | 1.2 | 2.4 | 1.2 | 3.0 | 1.3 | 1.6 | 2.0 | 3.1 | 5.2 | 6.8 | 2.2 | 1.1 |
| Opa3 | 20.0 | 1.2 |  | 1.1 | 3.0 | 1.3 | 1.4 | 1.4 | 1.4 | 1.5 | 1.9 | 1.6 | 0.9 |
| Nsdhl | 9.4 | 1.4 | 2.0 | 1.3 | 3.0 | 1.3 | 1.3 | 1.7 | 2.3 | 3.0 | 4.0 | 1.7 | 0.9 |
| Tmpo | 12.9 | 1.2 | 2.0 | 1.0 | 2.9 | 1.2 | 1.2 | 1.1 | 1.4 | 1.4 | 2.1 | 1.5 | 0.8 |
| Scarb1 | 20.0 | 1.3 | 1.6 | 2.3 | 1.4 | 1.3 | 2.9 | 1.6 | 2.0 | 3.2 | 4.9 | 2.8 | 1.2 |
| Scg2 | 20.0 | 1.3 | 1.2 | 1.0 | 2.9 | 2.0 | 1.1 | 1.3 | 1.5 | 1.2 | 1.1 | 1.4 | 0.9 |
| Sar1a | 11.9 | 1.2 |  | 1.0 | 2.9 | 1.6 | 1.1 | 1.3 | 1.7 | 1.7 | 2.2 | 1.4 | 0.8 |
| Tmpo | 12.3 | 1.2 | 1.9 | 1.1 | 2.8 | 1.2 | 1.2 | 1.1 | 1.4 | 1.3 | 2.0 | 1.5 | 0.8 |
| Acp6 | 20.0 | 1.2 | 2.5 | 1.2 | 2.8 | 1.1 | 0.9 | 1.5 | 1.5 | 1.8 | 2.3 | 1.6 | 0.9 |
| Dnajc1 | 20.0 | 1.3 | 2.1 | 1.4 | 2.8 |  | 1.2 | 1.0 | 1.6 | 1.5 |  |  | 1.1 |
| Ccdc47 | 13.2 | 1.2 | 1.7 | 1.3 | 2.8 | 1.4 | 1.4 | 1.4 | 1.8 | 1.9 | 3.1 | 1.7 | 0.9 |
| Hsdl1 | 11.6 | 1.3 | 2.5 | 1.0 | 2.8 | 1.3 | 0.9 | 1.1 | 1.2 | 1.0 | 1.5 | 1.4 | 0.7 |
| Dolpp1 | 20.0 | 1.1 | 2.2 | 1.2 | 2.7 | 1.3 | 1.3 | 1.2 | 1.6 | 1.9 | 3.3 | 1.6 | 0.9 |
| Ssr4 | 5.2 | 1.3 | 1.8 | 1.2 | 2.7 | 1.7 | 1.2 | 1.5 | 1.9 | 2.4 | 2.6 | 1.5 | 1.0 |
| Slc25a32 | 20.0 | 1.4 | 1.5 | 1.1 | 2.7 | 1.1 | 1.1 | 1.5 | 1.5 | 1.5 | 1.9 | 1.5 | 0.9 |
| Gstm2 | 20.0 | 1.3 | 2.7 | 1.5 | 2.2 |  | 1.3 | 1.6 | 1.6 |  | 2.2 |  | 1.1 |
| Sgpl1 | 20.0 | 1.0 | 2.7 | 1.7 | 2.1 | 1.2 | 1.2 | 1.3 | 1.5 | 1.8 | 2.7 | 1.4 | 1.0 |
| Fam114a2 | 20.0 | 1.4 | 1.4 | 1.0 | 2.7 | 1.5 | 1.6 | 1.6 | 3.5 | 4.1 | 7.6 | 2.2 | 1.1 |
| Cdipt | 3.2 | 1.1 | 1.8 | 1.1 | 2.7 | 1.0 | 0.7 | 1.0 | 1.0 | 0.7 | 0.8 | 0.9 | 0.9 |
| Rtn3 | 4.3 | 1.0 | 2.7 | 1.1 | 1.7 | 1.3 | 1.2 | 1.2 | 1.4 | 1.4 | 1.7 | 1.3 | 1.0 |
| Aldh1b1 | 19.0 | 1.0 | 2.7 | 1.3 | 1.2 | 1.3 | 1.6 | 1.2 | 1.6 | 2.0 | 2.6 | 1.7 | 2.3 |
| Ssr1 | 17.7 | 1.6 | 1.9 | 1.3 | 2.6 | 1.4 | 1.3 | 1.3 | 1.7 | 1.8 | 3.0 | 1.7 | 0.8 |
| Rab11a | 14.5 | 1.2 | 1.6 | 1.2 | 2.6 | 1.4 | 1.3 | 1.2 | 1.6 | 1.9 | 2.4 | 1.6 | 0.8 |
| Nucb2 | 20.0 | 1.1 | 1.5 | 1.1 | 2.6 | 1.1 | 0.8 | 1.4 | 1.6 | 2.1 | 2.9 | 2.0 | 0.9 |
| Nenf | 20.0 | 0.9 | 1.4 | 2.6 | 1.6 | 1.1 | 0.9 | 1.3 | 1.3 | 1.8 | 1.7 | 1.7 | 0.9 |
| Mboat7 | 11.2 | 1.0 |  | 1.1 | 2.6 | 1.1 | 1.1 | 1.2 | 1.6 | 1.9 | 2.3 | 1.7 | 0.9 |
| Emb | 15.8 | 1.3 | 1.8 | 1.3 | 2.6 | 1.2 | 1.1 | 1.3 | 1.7 | 1.4 | 2.2 | 1.6 | 1.0 |
| Jagn1 | 8.8 | 1.1 | 2.1 | 1.1 | 2.6 | 1.3 | 1.0 | 1.2 | 1.4 | 1.6 | 2.1 | 1.5 | 0.9 |
| Timm23 | 20.0 | 1.6 | 1.8 | 1.1 | 2.5 | 1.1 | 1.0 | 1.0 | 1.2 | 1.3 | 1.5 | 1.3 | 0.9 |
| Hsd17b12 | 15.3 | 1.1 | 2.2 | 1.7 | 2.5 | 1.3 | 0.9 | 1.2 | 1.6 | 1.7 | 2.3 | 1.7 | 0.9 |
| Cers5 | 12.0 | 1.2 | 2.1 | 1.1 | 2.5 | 1.3 | 1.3 | 1.2 | 1.8 | 2.1 | 3.0 | 1.6 | 0.9 |
| Slc25a26 | 20.0 | 1.5 | 1.0 | 0.8 | 2.5 | 1.2 | 0.7 | 0.9 | 0.7 | 0.3 | 0.4 | 0.7 | 0.6 |
| Canx | 6.8 | 1.1 | 1.6 | 1.2 | 2.5 | 1.4 | 1.2 | 1.3 | 1.7 | 1.8 | 2.6 | 1.6 | 0.9 |
| Adpgk | 16.2 | 1.2 | 1.8 | 1.2 | 2.5 | 1.3 | 1.2 | 1.4 | 1.7 | 1.5 | 2.0 | 1.5 | 0.9 |
| Ktn1 | 7.7 | 1.1 | 1.4 | 1.2 | 2.5 |  | 0.8 | 1.2 | 1.4 |  | 1.2 |  | 0.8 |
| Qil1 | 16.5 | 1.4 | 1.9 | 1.2 | 2.4 | 1.2 | 1.2 | 1.2 | 1.5 | 1.7 | 2.5 | 1.5 | 0.9 |
| Pitrm1 | 17.1 | 1.2 | 2.1 | 1.4 | 2.4 | 1.2 | 1.0 | 1.6 | 1.9 | 2.2 | 3.4 | 2.0 | 1.0 |
| Rab11b | 13.8 | 1.2 | 1.6 | 1.2 | 2.4 | 1.4 | 1.3 | 1.2 | 1.6 | 1.8 | 2.4 | 1.5 | 0.9 |
| Clptm1 | 13.3 | 1.5 | 2.3 | 1.1 | 2.3 | 1.3 | 1.2 | 1.3 | 1.6 | 1.6 | 2.5 | 1.5 | 0.9 |
| Ctage5 | 6.3 | 1.1 | 2.3 | 1.1 | 2.3 | 1.3 | 1.0 | 1.1 | 1.3 | 1.5 | 1.7 | 1.4 | 0.9 |
| Gstm1 | 20.0 | 1.3 | 2.3 | 1.5 | 2.1 |  | 1.4 | 1.7 | 1.7 | 2.1 | 2.6 | 2.2 | 1.1 |
| Lpcat3 | 18.7 | 1.0 | 1.4 | 2.3 | 2.2 | 1.2 | 1.1 | 1.2 | 1.2 | 1.4 | 1.5 | 1.3 | 1.1 |
| Gm20671 | 20.0 | 1.1 | 1.8 |  | 2.3 | 1.2 | 1.3 |  | 1.4 |  |  | 1.4 | 1.0 |
| Pisd | 20.0 | 1.1 | 1.8 |  | 2.3 | 1.2 | 1.3 |  | 1.4 |  |  | 1.4 | 1.0 |
| Creld1 | 20.0 | 1.2 | 1.8 | 1.3 | 2.3 | 1.3 | 1.4 | 1.4 | 1.8 | 2.4 | 4.2 | 1.8 | 1.0 |
| Aldh3a2 | 8.2 | 0.7 | 1.7 | 1.6 | 2.3 | 1.2 | 1.3 | 1.2 | 1.8 | 1.7 | 2.1 | 1.4 | 1.0 |
| Tusc3 | 12.8 | 1.2 | 1.7 | 1.3 | 2.3 | 1.4 | 1.2 | 1.2 | 1.6 | 1.6 | 2.6 | 1.6 | 0.9 |
| Atl2 | 5.5 | 1.3 | 2.0 | 1.1 | 2.3 |  | 1.2 | 1.1 | 1.4 | 1.6 |  | 1.3 | 0.8 |

TABLE 4B-continued

Neuro2a (AEA-DA) Competition

| Gene Name | No UV | DMSO | AEA (200 μM) | FK866 (25 μM) | Avasimibe (25 μM) | Elacridar (25 μM) | Ro 48-8071 (25 μM) | MJN228 (10 μM) | MJN228 (25 μM) | MJN228 (50 μM) | MJN228 (100 μM) | KML110 (25 μM) | KML181 (25 μM) |
|---|---|---|---|---|---|---|---|---|---|---|---|---|---|
| Ckap4 | 7.4 | 1.2 | 2.0 | 1.1 | 2.3 | 1.3 | 1.1 | 1.3 | 1.4 | 1.3 | 1.8 | 1.4 | 0.9 |
| Por | 17.1 | 1.1 | 2.0 | 1.2 | 2.2 | 1.3 | 1.5 | 1.4 | 1.8 | 2.0 | 3.1 | 1.6 | 0.9 |
| Pcyox1 | 18.2 | 1.0 | 1.7 | 1.2 | 2.2 | 1.2 | 1.8 | 1.2 | 1.4 | 1.6 | 2.2 | 1.5 | 1.0 |
| Atp2a2 | 3.9 | 1.1 | 2.2 | 1.1 | 1.8 | 1.3 | 1.2 | 1.3 | 1.4 | 1.4 | 1.9 | 1.3 | 0.9 |
| Vgf | 20.0 | 1.5 | 1.0 | 1.1 | 2.2 | 1.7 | 0.9 | 1.3 | 1.3 | 1.1 | 1.0 | 1.4 | 1.0 |
| Bri3bp | 20.0 | 1.2 | 2.0 | 1.1 | 2.2 | 1.3 | 1.1 | 1.3 | 1.5 | 1.4 | 2.1 | 1.6 | 0.8 |
| Sec22b | 5.4 | 1.3 | 1.4 | 1.2 | 2.2 | 1.1 | 1.1 | 1.5 | 1.6 | 2.0 | 2.0 | 1.4 | 0.9 |
| Nptn | 17.4 | 1.4 |  | 1.2 | 2.2 |  | 2.0 |  | 1.9 |  |  |  | 1.0 |
| Tmed7 | 4.7 | 1.1 | 1.5 | 1.1 | 2.2 |  | 1.1 | 1.0 | 1.5 |  | 2.1 | 1.6 | 1.1 |
| Kdelr3 | 20.0 | 1.3 | 1.2 | 1.1 | 2.2 |  | 0.9 | 1.2 | 1.3 | 1.3 | 1.6 | 1.2 | 1.0 |
| Kdelr2 | 20.0 | 1.2 | 1.4 | 1.2 | 2.1 | 1.1 | 0.9 | 1.2 | 1.2 | 1.3 | 1.8 | 1.3 | 1.0 |
| Tmem165 | 13.0 | 1.1 | 1.5 | 1.1 | 2.1 | 1.1 | 1.1 | 1.0 | 1.2 |  | 1.5 | 1.5 | 1.0 |
| Rtn4 | 12.7 | 1.1 | 1.8 | 1.1 | 2.1 | 1.3 | 1.0 | 1.0 | 1.3 | 1.2 | 1.4 | 1.4 | 0.8 |
| Slc2a3 | 7.3 | 1.0 | 1.0 | 1.1 |  | 2.1 | 1.0 | 1.2 | 1.4 | 1.2 | 1.2 | 1.2 | 1.0 |
| Scg3 | 20.0 | 1.5 | 1.2 | 1.0 | 2.1 | 1.2 | 0.9 | 1.0 | 1.3 | 1.0 | 0.8 | 1.0 | 0.9 |
| Ptges2 | 15.6 | 1.4 | 2.1 | 1.4 | 1.0 | 1.2 | 1.3 | 1.3 | 1.4 |  | 2.3 | 1.8 | 0.9 |
| Plec | 20.0 | 1.4 |  | 2.1 |  |  |  |  |  |  |  |  |  |
| Bnip1 | 20.0 | 1.4 | 2.1 |  |  |  | 1.0 | 1.2 | 1.1 |  |  | 1.3 |  |
| Nucb1 | 20.0 | 1.3 | 1.5 | 1.2 | 2.1 | 1.3 | 0.9 | 3.1 | 4.7 | 5.6 | 6.2 | 3.4 | 1.0 |
| Tmed1 | 20.0 | 1.2 | 2.1 | 1.3 |  |  | 1.2 | 1.1 | 1.6 | 2.1 | 2.2 | 1.6 | 0.9 |
| Ctsd | 20.0 | 1.0 | 1.2 | 1.0 | 1.2 | 2.0 | 0.5 | 1.2 | 1.2 | 1.2 | 1.1 | 1.4 | 0.9 |
| Abhd12 | 8.5 | 1.2 | 1.8 | 1.0 | 2.0 | 1.2 | 1.0 | 1.2 | 1.2 | 1.2 | 1.4 | 1.2 | 1.0 |
| Eci1 | 20.0 | 0.9 | 2.0 | 1.2 | 1.9 | 1.2 | 0.9 | 1.4 | 2.0 | 2.4 | 3.8 | 1.5 | 2.5 |
| Lbr | 3.6 | 1.2 | 2.0 | 1.0 | 1.8 | 1.4 | 1.9 | 1.1 | 1.3 | 1.5 | 1.8 | 1.2 | 0.8 |
| Tmem33 | 4.9 | 1.2 | 1.8 | 1.2 | 2.0 | 1.4 | 1.1 | 1.3 | 1.5 | 1.5 | 2.0 | 1.4 | 1.0 |
| Derl1 | 9.7 | 1.2 | 1.8 | 1.3 | 2.0 | 1.3 | 1.1 | 1.2 | 1.4 | 1.7 | 1.8 | 1.2 | 1.0 |
| Cyp20a1 | 11.9 | 1.2 | 1.8 | 1.1 | 2.0 | 1.3 | 1.1 | 1.2 | 1.3 | 1.2 | 1.6 | 1.4 | 0.8 |
| Sel11 | 14.0 | 1.2 | 1.6 | 1.4 | 2.0 |  | 1.2 | 1.2 | 1.5 | 1.5 | 1.9 | 1.5 | 1.0 |
| Calu | 20.0 | 1.0 | 1.0 | 1.0 | 2.0 |  | 0.9 | 1.1 | 1.5 |  | 1.8 | 1.1 | 1.1 |
| Vbp1 | 7.2 | 1.2 | 1.1 | 1.1 | 2.0 | 0.9 | 0.9 |  | 1.5 | 0.9 | 2.0 | 1.6 | 0.9 |
| Pmpca | 19.1 | 1.0 | 1.9 | 1.2 | 0.8 | 1.3 | 0.9 | 1.2 | 1.4 | 1.4 | 1.5 | 1.6 | 0.9 |
| Pex16 | 12.4 | 1.3 | 1.7 | 1.1 | 1.9 | 1.3 | 1.3 | 0.9 | 1.5 | 2.3 | 2.2 | 1.4 | 0.8 |
| Prkar1a | 16.4 | 1.4 | 1.2 | 1.5 | 1.9 | 1.2 | 1.0 | 1.9 | 1.9 | 2.1 | 2.8 | 1.6 | 1.0 |
| Tmed10 | 5.8 | 1.2 | 1.5 | 1.1 | 1.9 | 1.1 | 1.0 | 1.1 | 1.4 | 1.5 | 1.6 | 1.2 | 1.0 |
| Them6 | 3.8 | 1.2 | 1.9 | 1.0 | 1.5 |  | 1.0 | 1.2 | 1.3 |  | 1.3 | 1.3 | 0.8 |
| Lman2 | 12.0 | 1.1 | 1.5 | 1.1 | 1.9 |  | 0.7 | 1.2 | 1.2 | 2.1 | 1.5 | 1.3 | 0.8 |
| Tpp1 | 20.0 | 1.1 | 1.5 | 1.0 | 1.5 | 1.9 | 0.8 | 1.4 | 1.4 | 1.8 | 2.0 | 1.5 | 0.9 |
| Eif3f | 3.8 | 1.1 | 1.4 | 1.3 | 1.4 | 1.9 | 0.9 | 1.0 | 1.0 |  | 0.9 | 1.3 | 0.9 |
| Tmx4 | 4.8 | 1.1 | 1.9 | 1.0 | 1.9 | 1.2 | 1.2 | 1.0 | 1.3 | 1.3 | 1.6 | 1.4 | 0.8 |
| Sco2 | 20.0 | 1.5 |  |  | 1.9 |  | 1.0 |  |  |  | 1.5 | 1.0 |  |
| Lmf2 | 4.8 | 1.1 | 1.9 | 1.2 | 1.2 | 1.2 | 1.3 | 1.5 | 1.7 | 2.0 | 2.5 | 1.7 | 1.0 |
| Sqle | 5.0 | 1.7 | 1.9 | 1.1 | 1.6 |  | 1.0 | 1.3 | 1.5 |  | 2.1 | 1.3 | 0.7 |
| Pcyox1l | 20.0 | 1.1 | 1.5 | 1.3 | 1.9 |  | 1.0 | 1.2 | 1.8 | 1.7 | 2.5 | 2.0 | 1.1 |
| Vat1 | 4.4 | 1.2 | 1.6 | 1.9 | 0.9 | 1.2 | 1.2 | 1.2 | 1.3 | 1.0 | 1.2 | 1.4 | 1.1 |
| Acad9 | 8.6 | 1.1 |  | 1.2 | 1.5 | 1.9 | 1.3 | 1.4 | 1.2 | 1.4 | 1.4 | 1.7 | 0.8 |
| Atad3 | 7.8 | 1.2 | 1.5 | 1.2 | 1.9 | 1.6 | 1.0 | 1.1 | 1.4 | 1.3 | 1.4 | 1.2 | 0.8 |
| Slc25a33 | 12.0 | 1.3 | 1.3 | 1.2 | 1.8 | 1.3 | 1.0 | 1.2 | 1.2 | 0.9 | 0.6 | 1.4 | 0.9 |
| Cyp51a1 | 10.8 | 1.4 | 1.8 | 1.5 | 1.6 | 1.6 | 1.3 | 1.5 | 2.2 | 2.3 | 3.1 | 1.2 | 0.7 |
| Slc25a1 | 7.4 | 1.0 | 1.2 | 1.2 | 1.8 | 1.2 | 1.0 | 1.2 | 1.1 | 1.5 | 1.5 | 1.2 | 0.8 |
| Pigs | 4.4 | 1.0 | 1.6 | 1.3 | 1.8 |  | 1.1 | 1.3 | 1.6 | 1.7 | 2.0 | 1.2 | 0.9 |
| Clpp | 20.0 | 1.0 | 1.4 | 1.0 | 1.8 | 1.1 | 0.9 | 1.4 | 2.1 | 3.6 | 9.0 | 2.4 | 1.0 |
| ptplad1 | 7.5 | 1.1 | 1.8 | 1.2 | 1.8 | 1.4 | 1.4 | 1.3 | 1.7 | 1.9 | 2.3 | 1.7 | 1.0 |
| Bsg | 20.0 | 1.3 | 1.3 | 1.0 | 1.8 | 1.5 | 1.1 | 1.4 | 1.6 | 1.2 | 1.6 | 1.3 | 0.7 |
| Stip1 | 3.5 | 1.1 | 1.3 | 1.3 | 1.8 | 1.4 | 1.0 | 1.2 | 1.3 | 1.2 | 1.9 | 1.6 | 0.9 |
| Ncstn | 20.0 | 1.4 | 1.6 | 1.1 | 1.8 |  | 1.0 | 1.3 | 1.6 | 1.2 | 1.8 | 1.3 | 0.8 |
| Akr1c12 | 20.0 | 1.4 | 1.8 | 1.3 |  |  | 0.9 |  |  |  |  | 1.2 | 1.0 |
| Npepps | 20.0 | 0.9 | 1.1 |  | 1.8 |  |  |  | 1.5 |  | 4.3 |  |  |
| Tor1aip1 | 12.0 | 1.4 | 1.5 |  | 1.8 |  |  | 1.3 | 1.3 | 1.3 | 2.0 |  |  |
| Ppt1 | 20.0 | 1.2 | 1.1 | 0.8 | 1.1 | 1.8 | 1.6 | 1.5 | 1.5 | 2.1 | 4.3 | 1.2 | 0.6 |
| Mpv17l2 | 20.0 | 1.5 | 1.3 | 1.4 | 1.0 | 1.4 | 1.8 | 1.1 | 1.2 | 1.0 | 3.6 | 1.5 | 1.0 |
| Uncharacterized | 20.0 | 1.0 | 1.7 | 1.3 | 1.8 |  | 1.0 | 1.1 | 1.6 |  | 3.0 | 1.1 | 0.8 |
| Kdelr1 | 20.0 | 1.0 | 1.2 | 1.1 | 1.8 | 1.0 | 1.0 | 1.1 | 1.2 | 1.5 | 1.5 | 1.1 | 1.0 |
| Mtch2 | 10.5 | 1.3 | 1.5 | 1.1 | 1.8 | 1.1 | 0.9 | 1.2 | 1.3 | 1.1 | 1.4 | 1.3 | 0.9 |
| Cisd1 | 11.9 | 1.1 | 1.6 | 1.1 | 1.8 | 1.3 | 1.3 | 1.3 | 1.5 | 1.4 | 2.4 | 1.6 | 0.8 |
| Ndufs2 | 20.0 | 1.1 | 1.3 | 1.7 | 1.1 | 1.2 | 1.2 | 1.3 | 1.3 |  | 1.1 | 1.3 | 0.9 |
| Acsl4 | 3.4 | 1.0 | 1.6 | 1.3 | 1.7 | 1.4 | 1.1 | 1.2 | 1.4 | 1.6 | 1.7 | 1.3 | 1.0 |
| Akr1c13 | 20.0 | 1.0 | 1.7 | 1.0 | 1.0 | 1.0 | 1.0 |  | 1.0 | 1.0 |  | 1.1 | 1.0 |
| Ttll12 | 3.1 | 1.1 |  |  | 1.7 |  |  |  |  |  |  |  |  |
| Cend1 | 3.0 | 1.7 | 1.7 |  |  |  |  |  |  |  |  | 0.9 |  |
| Atp13a1 | 14.3 | 1.1 | 1.4 | 1.1 | 1.7 | 1.3 | 1.2 | 1.3 | 1.7 | 2.0 | 2.2 | 1.7 | 0.9 |
| Mtdh | 12.5 | 1.3 | 1.7 | 1.2 | 1.4 | 1.3 | 1.2 | 1.3 | 1.5 | 1.6 | 1.9 | 1.5 | 0.7 |
| Rpn2 | 3.2 | 1.1 | 1.3 | 1.1 | 1.7 | 1.2 | 1.0 | 1.2 | 1.3 | 1.4 | 1.7 | 1.2 | 0.9 |
| Psmb2 | 20.0 | 1.3 | 1.3 | 1.7 | 1.5 | 1.1 | 1.0 | 1.3 | 1.4 | 1.2 | 2.2 | 1.7 | 0.9 |

TABLE 4B-continued

| | | | | | | | | | | MJN228 | | |
|---|---|---|---|---|---|---|---|---|---|---|---|---|
| | | | | | | | Ro 48- | | | | | |
| Gene | No | | AEA (200 | FK866 | Avasimibe | Elacridar | 8071 | MJN228 | MJN228 | MJN228 | (100 | KML110 | KML181 |
| Name | UV | DMSO | μM) | (25 μM) | (25 μM) | (25 μM) | (25 μM) | (10 μM) | (25 μM) | (50 μM) | μM) | (25 μM) | (25 μM) |
|---|---|---|---|---|---|---|---|---|---|---|---|---|---|
| Spcs2 | 11.3 | 1.2 | 1.7 | 1.3 | | 1.4 | 1.2 | 1.2 | 1.4 | 1.5 | 1.8 | 1.6 | 0.9 |
| Phb2 | 5.2 | 1.2 | 1.2 | 1.1 | 1.7 | 1.3 | 0.9 | 1.3 | 1.2 | 1.4 | 1.5 | 1.3 | 0.8 |
| Lrrc59 | 3.7 | 1.3 | 1.6 | 1.2 | 1.7 | 1.2 | 1.2 | 1.3 | 1.3 | 1.5 | 2.0 | 1.3 | 0.9 |
| Atp2b1 | 11.5 | 1.2 | 1.6 | 1.2 | 1.7 | 1.3 | 1.1 | 1.1 | 1.4 | 1.4 | 1.7 | 1.8 | 0.8 |
| P4ha2 | 11.0 | 1.1 | 1.0 | 1.1 | 1.7 | | 1.0 | 1.2 | 1.3 | 1.0 | 1.0 | 1.3 | 0.8 |
| Rab1A | 3.0 | 1.1 | 1.2 | 1.1 | 1.7 | 1.1 | 1.0 | 1.1 | 1.3 | 1.3 | 1.3 | 1.3 | 0.8 |
| Zmpste24 | 11.3 | 1.3 | 1.7 | 1.1 | 1.7 | 1.2 | 1.0 | 1.1 | 1.2 | 1.3 | 1.9 | 1.4 | 0.9 |
| Mtch1 | 11.3 | 1.3 | 1.4 | 1.0 | 1.7 | 1.2 | 0.9 | 1.1 | 1.2 | 1.0 | 1.2 | 1.2 | 0.9 |
| Psmd11 | 4.9 | 1.1 | 1.2 | 1.3 | 1.7 | | 0.9 | | 1.3 | | | 1.3 | 0.9 |
| Whsc1 | 20.0 | 1.8 | 1.0 | | 1.7 | | | 1.4 | 1.2 | | 1.6 | | |
| Timm50 | 4.7 | 1.3 | 1.2 | 1.1 | 1.7 | 1.1 | 0.9 | 1.2 | 1.3 | 1.1 | 1.2 | 1.1 | |
| Surf4 | 10.5 | 1.2 | 1.4 | 1.2 | 1.7 | 1.2 | 1.1 | 1.3 | 1.4 | 1.7 | 2.0 | 1.4 | 1.0 |
| Lmna | 8.6 | 1.0 | 1.1 | 1.2 | 1.7 | 1.1 | 1.1 | 1.3 | 1.1 | 1.3 | 1.5 | 1.3 | 0.9 |
| Erlin1 | 4.5 | 1.1 | 1.7 | 1.0 | | | 1.2 | 1.4 | 1.1 | | 1.1 | | |
| Slc25a10 | 4.6 | 1.3 | 1.2 | 1.2 | 1.7 | 1.1 | 0.9 | 1.2 | 1.2 | 1.3 | 1.0 | 1.2 | 0.8 |
| Dpp7 | 20.0 | 1.0 | 1.4 | 1.0 | 1.6 | 0.8 | 0.3 | 1.0 | 0.7 | 1.0 | 0.7 | 1.5 | 1.1 |
| Rpn1 | 15.0 | 1.2 | 1.6 | 1.2 | 1.3 | 1.3 | 0.9 | 1.3 | 1.4 | 1.2 | 1.6 | 1.2 | 0.8 |
| Myl6 | 3.7 | 1.0 | 1.0 | 1.3 | 1.6 | | 0.7 | 1.1 | 1.0 | 1.3 | | 1.4 | 1.0 |
| Dld | 12.7 | 1.0 | 1.1 | 1.1 | 1.6 | 1.2 | 0.8 | 1.2 | 1.2 | 1.2 | 1.1 | 1.3 | 0.9 |
| Gaa | 18.6 | 0.9 | 1.4 | 1.1 | 1.6 | 1.0 | 0.5 | 1.0 | 1.2 | 1.4 | 1.2 | 1.6 | 1.0 |
| Eef1d | 14.2 | 1.2 | 1.1 | 1.2 | 1.6 | 1.4 | 0.9 | | 1.3 | | 1.4 | 1.4 | 0.8 |
| Slc25a20 | 19.4 | 1.0 | 1.6 | 1.4 | 1.4 | 1.3 | 1.2 | 1.4 | 1.4 | 2.4 | 3.4 | 1.5 | 1.1 |
| Psap | 20.0 | 1.1 | 1.4 | 1.0 | 1.4 | 1.6 | 1.0 | 1.1 | 1.4 | 1.4 | 1.6 | 1.3 | 0.8 |
| P4hb | 7.9 | 1.1 | 1.2 | 1.4 | 1.6 | 1.2 | 1.0 | 1.3 | 1.5 | 2.0 | 2.2 | 1.8 | 1.0 |
| Parl | 7.9 | 1.2 | 1.3 | 1.3 | 1.6 | 1.3 | 1.1 | 1.3 | 1.4 | 1.1 | 1.9 | 1.3 | 1.0 |
| Slc25a12 | 3.7 | 1.1 | 1.1 | 1.1 | 1.6 | 1.2 | 1.0 | 1.0 | 1.0 | 0.9 | 1.0 | 1.1 | 0.9 |
| Scpep1 | 20.0 | 1.0 | 1.0 | 1.2 | 1.6 | 0.9 | 0.4 | 1.2 | 1.4 | 1.5 | 1.9 | 1.6 | 1.0 |
| Icmt | 13.0 | 1.1 | 1.5 | 1.3 | 1.3 | 1.6 | 1.6 | 0.9 | 0.9 | 0.6 | 0.5 | 1.0 | 1.0 |
| Ftl1 | 13.6 | 1.3 | 1.6 | 1.6 | 1.0 | | 0.4 | | | | 1.0 | 0.9 | 0.7 |
| Tmem206 | 20.0 | 1.0 | 1.2 | 0.9 | 1.6 | | 0.6 | 1.1 | 1.3 | | 0.7 | 1.2 | 0.8 |
| Pank4 | 20.0 | 1.5 | 1.6 | | | | | | | | | | |
| Rab2a | 4.0 | 1.1 | 1.3 | 1.2 | 1.6 | 1.1 | 1.1 | 1.4 | 1.5 | 1.6 | 1.6 | 1.3 | 0.9 |
| Ociad1 | 7.8 | 1.5 | 1.6 | 1.1 | 1.4 | 1.3 | 1.0 | 1.1 | 1.4 | 1.1 | 1.5 | 1.3 | 0.9 |
| Vim | 16.0 | 1.4 | 0.9 | 1.2 | 1.6 | 1.2 | 0.8 | 1.2 | 1.2 | 0.9 | 1.0 | 1.2 | 0.8 |
| Mrpl46 | 20.0 | 1.1 | 1.3 | 1.3 | 1.6 | 1.1 | 0.9 | 1.0 | 1.3 | 1.0 | 1.3 | 1.3 | 1.0 |
| Kiaa0664 | 20.0 | 1.8 | | 1.2 | 1.6 | | 1.0 | 1.5 | 2.2 | 1.0 | 1.9 | 2.1 | 1.1 |
| Incenp | 20.0 | 1.4 | 1.4 | 0.8 | 1.6 | | | 1.4 | 1.2 | 1.8 | 1.7 | 1.2 | |
| Dhfr | 20.0 | 1.4 | 1.2 | 1.2 | 1.6 | | 0.8 | 2.0 | 1.6 | 0.4 | 1.5 | 1.4 | 0.8 |
| Naglu | 20.0 | 1.1 | 1.3 | 1.3 | 1.6 | 1.1 | 0.3 | 1.4 | 1.3 | 1.9 | 1.7 | 1.4 | 1.0 |
| Hadh | 12.8 | 1.0 | 1.2 | 1.2 | 1.6 | | 0.8 | 1.3 | 1.3 | 1.1 | 1.3 | 1.2 | 0.9 |
| Atp6v1b2 | 10.8 | 1.2 | 1.1 | 1.6 | 1.2 | | 0.6 | 1.2 | 1.1 | 0.9 | | 1.2 | 1.0 |
| P4ha1 | 9.9 | 1.1 | 1.0 | 1.1 | 1.6 | | 1.1 | 1.3 | | | | | 1.0 |
| Phgdh | 3.9 | 1.3 | 1.2 | 1.3 | 1.5 | 1.0 | 1.0 | 1.2 | 1.1 | 0.9 | 1.1 | 1.5 | 0.9 |
| Ipo4 | 20.0 | 1.2 | 1.5 | 1.3 | 1.5 | 1.1 | 1.0 | 1.0 | 1.3 | 1.0 | 1.6 | 1.4 | 0.9 |
| Kpna2 | 4.4 | 1.7 | 1.5 | 1.2 | 1.5 | 1.2 | 0.9 | 1.3 | 1.2 | 0.9 | 1.3 | 1.2 | 0.9 |
| Scarb2 | 20.0 | 1.2 | 1.5 | 1.1 | 1.3 | 1.1 | 1.1 | 1.3 | 1.5 | 1.7 | 1.9 | 1.3 | 1.0 |
| Gba | 20.0 | 1.0 | 1.5 | 1.0 | 0.8 | | 0.7 | 2.2 | | | 2.4 | | 1.1 |
| H2-L | 13.3 | 1.1 | 1.3 | 1.0 | 1.5 | 1.4 | 0.8 | 1.1 | 1.1 | 1.1 | 1.0 | 1.7 | 0.9 |
| Ptrh2 | 4.5 | 1.3 | 1.5 | 1.0 | 1.5 | 1.2 | 0.9 | 1.1 | 1.0 | 1.2 | 1.1 | 1.0 | 1.0 |
| Tfrc | 11.5 | 1.6 | 1.0 | 1.1 | 1.5 | 1.0 | 0.8 | 1.1 | 1.0 | 1.0 | 1.0 | 1.1 | 1.0 |
| Immt | 5.4 | 1.2 | 1.2 | 1.1 | 1.5 | 1.0 | | 1.1 | 1.2 | 1.1 | 1.4 | 1.3 | 0.9 |
| H2-K1 | 9.1 | 1.0 | 1.2 | 1.0 | 1.5 | | 0.9 | 1.0 | 1.1 | 0.9 | 1.0 | 1.6 | 0.9 |
| Atp5f1 | 11.3 | 1.2 | 1.5 | 1.1 | 1.5 | 1.2 | | 1.0 | 1.2 | 1.5 | 1.6 | 1.8 | 1.6 | 0.9 |
| Atp1a1 | 3.2 | 1.3 | 1.4 | 1.2 | 1.5 | 1.3 | 1.0 | 1.4 | 1.4 | 1.1 | 1.2 | 1.2 | 0.9 |
| Nup93 | 9.4 | 1.1 | 1.2 | 1.2 | 1.5 | 1.2 | 0.9 | 0.9 | 1.1 | 1.0 | 1.1 | 1.4 | 0.8 |
| Idh2 | 3.4 | 0.9 | 1.2 | 1.2 | 1.5 | 1.0 | 0.9 | 1.3 | 1.4 | 1.6 | 1.6 | 1.3 | 1.1 |
| Arl6ip1 | 20.0 | 1.2 | 1.5 | 1.0 | | | 1.1 | 0.8 | 1.6 | | 1.5 | 1.4 | 0.9 |
| Atp5l | 5.2 | 1.2 | 1.3 | 1.1 | 1.5 | | 1.0 | 1.5 | 1.5 | 1.4 | 1.3 | 1.2 | 0.9 |
| Csnk1a1 | 20.0 | 1.4 | | 1.5 | | 1.2 | 0.9 | | 1.4 | | 1.3 | 1.5 | 0.9 |
| Dhcr7 | 3.0 | 1.0 | 1.5 | 0.9 | 1.5 | 1.1 | 0.8 | 1.1 | 1.2 | 1.5 | 1.7 | 1.2 | 1.0 |
| Eif3e | 4.1 | 1.2 | 1.2 | 1.1 | 1.5 | | 0.8 | 1.1 | 1.1 | 1.0 | 1.0 | 1.4 | 0.8 |
| Hars | 20.0 | 1.1 | 1.2 | 1.3 | 1.5 | 0.9 | 0.9 | 1.6 | 1.5 | 1.0 | 1.4 | 1.5 | 0.9 |
| Mcm6 | 20.0 | 1.4 | 1.3 | 1.1 | 1.5 | | 0.8 | 1.2 | 1.4 | 1.0 | 1.6 | 2.0 | 1.0 |
| Sec63 | 7.5 | 1.0 | 1.5 | 1.1 | 1.5 | 1.1 | 1.0 | 1.4 | 1.5 | 1.8 | 1.8 | 1.5 | 0.9 |
| Psmb6 | 20.0 | 1.3 | 1.4 | 1.4 | 1.5 | 1.1 | 1.0 | 1.3 | 1.5 | 1.4 | 2.5 | 1.9 | 0.9 |
| Mest | 4.6 | 1.1 | 1.5 | 1.2 | 0.8 | 1.2 | 1.2 | 1.2 | 1.4 | 1.3 | 1.6 | 1.3 | 0.9 |
| Dctpp1 | 20.0 | 1.4 | 1.5 | 1.4 | 1.3 | 1.0 | 0.8 | | 1.2 | 1.0 | 1.0 | 1.6 | 0.8 |
| Puf60 | 10.9 | 1.4 | 1.3 | 1.3 | 1.4 | 1.5 | 1.0 | 1.4 | 1.2 | 1.0 | 1.2 | 1.3 | 1.0 |
| Slc38a2 | 3.9 | 1.4 | 1.5 | 1.0 | 1.5 | 1.2 | 0.7 | 1.2 | 1.3 | | 1.2 | 1.2 | 0.9 |
| Letm1 | 4.8 | 1.2 | 0.6 | 1.5 | | 1.4 | 1.3 | 1.3 | 1.5 | 1.2 | 1.1 | 1.1 | 1.6 |
| Chgb | 20.0 | 1.3 | 1.2 | 0.9 | 1.5 | | 0.7 | 1.2 | 0.9 | 0.4 | 0.4 | 1.1 | 0.9 |
| Cops6 | 20.0 | 1.3 | 1.4 | | 1.5 | | | | | | 1.2 | | 1.0 |
| Hspa5 | 15.9 | 1.1 | 1.2 | 1.2 | 1.5 | 1.2 | 0.9 | 1.4 | 1.4 | 1.4 | 1.5 | 1.4 | 0.9 |
| Cope | 20.0 | 1.4 | 0.9 | 1.5 | 1.4 | | | 1.1 | | 1.2 | | | 0.8 |

TABLE 4B-continued

| | | | | | | | Neuro2a (AEA-DA) Competition | | | | | |
|---|---|---|---|---|---|---|---|---|---|---|---|---|
| Gene Name | No UV | DMSO | AEA (200 μM) | FK866 (25 μM) | Avasimibe (25 μM) | Elacridar (25 μM) | Ro 48-8071 (25 μM) | MJN228 (10 μM) | MJN228 (25 μM) | MJN228 (50 μM) | MJN228 (100 μM) | KML110 (25 μM) | KML181 (25 μM) |
| Fxr1 | 11.3 | 1.2 | 1.1 | 1.4 | 1.5 | 1.2 | 0.9 | 1.2 | 1.3 | 1.1 | 1.1 | 1.5 | 1.1 |
| Myh9 | 7.7 | 1.2 | 1.1 | 1.2 | 1.5 | 1.1 | 1.0 | 1.2 | 1.3 | 1.2 | 1.6 | 1.7 | 0.9 |
| Asah1 | 20.0 | 1.2 | 0.8 | 1.3 | 1.4 | 1.5 | 1.0 | 1.4 | 1.6 | 2.2 | 2.1 | 1.2 | 0.9 |
| Hsp90b1 | 4.8 | 1.0 | 1.1 | 1.2 | 1.5 | 1.1 | 0.9 | 1.3 | 1.3 | 1.5 | 1.4 | 1.4 | 0.9 |
| Itgb1 | 11.2 | 1.1 | 1.5 | | 1.3 | | | 1.2 | 1.3 | 1.1 | 1.1 | 1.0 | 0.8 |
| Prph | 15.5 | 1.3 | 1.0 | 1.2 | 1.5 | 1.2 | 0.8 | 1.0 | 1.2 | 0.7 | 0.9 | 1.1 | 0.8 |
| Abcd3 | 11.0 | 1.1 | 1.5 | 1.3 | 1.2 | 1.1 | 0.9 | 1.2 | 1.5 | 1.3 | 1.2 | 1.2 | 0.9 |
| Eef1g | 5.1 | 1.3 | 1.4 | 1.5 | 1.4 | 1.2 | 0.9 | 1.1 | 1.1 | 1.0 | 1.3 | 1.4 | 1.1 |
| Sptbn1 | 11.0 | 1.1 | 1.1 | 1.3 | 1.5 | | 1.0 | 1.0 | 1.2 | | 1.3 | 1.2 | 0.9 |
| MLV-related | 3.6 | 1.7 | 1.4 | 1.1 | 1.5 | | 1.0 | 1.8 | 1.8 | 1.7 | 2.5 | 1.2 | 1.0 |
| Slc25a16 | 20.0 | 1.7 | 1.5 | | 1.2 | | | 1.2 | 1.1 | | | | 0.8 |
| Emc3 | 9.1 | 1.3 | | | | | 1.5 | | | | | 1.0 | |
| Ganab | 3.0 | 1.0 | 1.1 | 1.1 | 1.4 | 1.2 | 0.9 | 1.2 | 1.2 | 1.5 | 1.6 | 1.3 | 1.0 |
| Nup205 | 11.1 | 1.0 | | 0.9 | 1.4 | 1.0 | 0.9 | 1.0 | 1.2 | 1.1 | 1.2 | 1.2 | 0.9 |
| Syncrip | 6.9 | 1.1 | 1.2 | 1.1 | 1.4 | 1.2 | 0.8 | 0.9 | 1.2 | 1.3 | 1.1 | 1.4 | 0.9 |
| Mki67ip | 15.7 | 1.3 | 1.4 | 1.0 | 1.4 | 1.0 | 1.0 | 1.2 | 1.5 | 1.8 | 2.3 | 1.5 | 1.2 |
| Tpm4 | 16.2 | 1.1 | 1.1 | 1.0 | | 1.4 | 1.0 | 1.1 | 1.0 | 1.0 | 1.4 | 1.0 | 0.9 |
| Timm44 | 11.7 | 1.1 | 1.4 | 1.2 | 1.0 | 1.3 | 0.9 | 1.1 | 1.4 | 1.4 | 1.5 | 1.5 | 0.9 |
| Tomm20 | 20.0 | 1.9 | | 1.0 | 1.4 | | 0.9 | | 1.0 | | 1.1 | 1.2 | 1.0 |
| Atp5a1 | 4.0 | 1.1 | 1.2 | 1.1 | 1.4 | 1.1 | 0.9 | 1.3 | 1.3 | 1.4 | 1.4 | 1.3 | 1.0 |
| Prkra | 20.0 | 1.1 | 1.2 | | 1.4 | | | | | | 1.2 | | |
| Gstp1 | 4.0 | 1.3 | 1.4 | 1.2 | 1.4 | 1.2 | 1.0 | 1.5 | 1.4 | 1.1 | 1.7 | 1.9 | 1.1 |
| Rcn2 | 20.0 | 1.1 | 1.0 | 0.9 | 1.4 | | 1.0 | 1.2 | 1.6 | 1.8 | 1.9 | 1.8 | 0.9 |
| Mtap | 20.0 | 1.4 | 1.2 | 1.4 | 1.1 | 0.9 | 1.0 | 1.2 | 1.4 | 1.1 | 1.5 | 1.5 | 0.9 |
| Shmt2 | 6.0 | 1.1 | 1.4 | 1.0 | 1.4 | 1.2 | 0.9 | 1.1 | 1.3 | 1.1 | 1.3 | 1.3 | 0.9 |
| Psmb3 | 20.0 | 1.1 | 1.2 | 1.4 | 1.4 | | 1.1 | 1.5 | 1.2 | 0.9 | 1.3 | 1.5 | 0.8 |
| Epdr1 | 20.0 | 1.1 | 1.2 | 1.2 | 1.4 | 1.4 | 0.7 | 1.4 | 2.4 | 5.8 | 7.8 | 3.6 | 0.9 |
| Atad1 | 3.5 | 1.3 | 1.3 | 1.1 | 1.4 | | 1.0 | 1.1 | 1.1 | 1.1 | 1.4 | 1.1 | 0.8 |
| Cacybp | 3.9 | 1.3 | 1.2 | 1.3 | 1.4 | 1.3 | 0.9 | 1.1 | 1.2 | 0.8 | 1.2 | 1.3 | 0.9 |
| Tpr | 15.2 | 1.1 | 1.1 | 1.4 | | | | 1.1 | 1.0 | 1.3 | 1.1 | | 0.9 |
| Dnajc11 | 5.7 | 1.3 | 1.3 | 1.3 | 1.4 | | 0.8 | 1.0 | 1.1 | 1.1 | 1.1 | | 1.0 |
| Sv2c | 20.0 | 1.1 | | 1.1 | 1.4 | 1.4 | 1.2 | 1.1 | 1.2 | 1.1 | 3.2 | 1.3 | 0.8 |
| Stoml2 | 6.0 | 1.2 | 1.4 | 1.1 | 1.4 | 1.0 | 1.1 | 1.2 | 1.6 | 1.9 | 1.7 | 1.5 | 1.0 |
| Hnrnph2 | 3.4 | 1.2 | 1.0 | 1.0 | 1.4 | 0.8 | 1.0 | 1.0 | 1.2 | 1.0 | 1.2 | 1.2 | 1.0 |
| Prep | 6.0 | 1.2 | 1.4 | 1.3 | 1.2 | | 0.8 | 1.1 | 1.3 | 0.9 | 1.2 | 1.5 | 1.0 |
| Dhrs7b | 3.5 | 1.2 | | | 1.4 | | | 1.3 | 1.3 | 1.4 | 2.0 | | |
| Tnpo1 | 4.9 | 1.2 | 1.2 | 1.2 | 1.4 | 1.1 | 0.9 | 1.0 | 1.2 | 1.0 | 1.5 | 1.4 | 0.9 |
| Psmb7 | 20.0 | 1.0 | 1.0 | 1.0 | 1.4 | 1.0 | 1.0 | 1.0 | 1.0 | 1.0 | 1.0 | 1.0 | 1.0 |
| Ruvbl1 | 3.7 | 1.0 | 1.1 | 1.1 | 1.4 | | 0.8 | 1.5 | 1.1 | 1.4 | 1.5 | 1.4 | 0.9 |
| Ptbp1 | 7.6 | 1.1 | 1.2 | 1.1 | 1.4 | 1.1 | 1.0 | 1.1 | 1.1 | 1.1 | 1.2 | 1.3 | 1.0 |
| Slc25a22 | 5.7 | 1.2 | 1.2 | 1.0 | 1.4 | 1.0 | 1.0 | 1.3 | 1.2 | 1.3 | 1.0 | 1.3 | 0.8 |
| Ptgs1 | 11.1 | 1.3 | 0.7 | 1.1 | 1.1 | 1.1 | 1.4 | 1.5 | 1.3 | 1.3 | 1.6 | 1.5 | 1.0 |
| Pdcd5 | 20.0 | 1.2 | 1.4 | | | | | | | | | | |
| Slc25a4 | 9.7 | 1.3 | 1.2 | 1.0 | 1.4 | 1.0 | 0.8 | 1.0 | 1.0 | 0.9 | 1.0 | 1.0 | 0.9 |
| Ahcy | 4.3 | 1.1 | 1.1 | | 1.4 | | 1.0 | | 1.6 | | 1.6 | | 1.1 |
| Tpm3-rs7 | 20.0 | 1.2 | 1.0 | 1.0 | 1.2 | 1.4 | | 1.0 | 1.2 | 1.2 | 1.6 | 1.3 | 0.9 |
| Acsl1 | 3.7 | 1.3 | 1.4 | 1.0 | 1.3 | | 1.0 | 1.2 | 1.5 | | 1.1 | 1.3 | 0.8 |
| Ech1 | 17.4 | 0.7 | 1.0 | 1.1 | 1.1 | 1.0 | 1.4 | 1.4 | 1.6 | 4.2 | 13.1 | 1.3 | 1.1 |
| Hnrnph1 | 3.9 | 1.2 | 1.1 | 1.0 | 1.4 | 0.7 | 1.0 | 1.1 | 1.2 | 1.1 | 1.1 | 1.3 | 0.9 |
| Eif5 | 19.1 | 1.4 | 1.2 | 1.3 | 1.4 | 1.2 | 0.8 | 0.8 | 1.2 | 0.7 | 1.2 | 1.4 | 0.8 |
| Asns | 3.3 | 1.2 | 1.4 | 1.2 | 1.2 | 1.0 | 0.7 | 1.0 | 0.9 | 0.6 | 0.8 | 1.2 | 0.9 |
| Syne2 | 11.3 | 1.1 | 1.2 | 1.1 | 1.4 | | 0.8 | 1.0 | | | 1.2 | 1.5 | 0.8 |
| Mrpl39 | 6.2 | 1.2 | 1.4 | 1.3 | | | 0.9 | | 1.3 | | | 1.5 | 0.7 |
| Samm50 | 11.1 | 1.3 | 1.1 | 1.1 | 0.6 | 1.4 | 0.8 | 1.1 | 1.2 | 1.1 | 1.0 | 1.2 | 0.8 |
| Emc1 | 3.9 | 1.2 | | 1.4 | 1.3 | | 1.1 | 1.4 | 1.2 | 1.5 | 1.8 | 1.4 | 0.9 |
| Actn4 | 3.5 | 1.4 | 1.2 | 1.1 | 1.4 | 1.1 | 0.9 | 1.1 | 1.2 | 1.0 | 1.1 | 1.1 | 0.9 |
| Rab18 | 4.0 | 0.9 | 1.1 | 1.1 | 1.4 | | 0.9 | 1.4 | 1.7 | 1.9 | 1.7 | 1.5 | 1.0 |
| Faf2 | 5.0 | 1.1 | 1.4 | | 1.3 | | 1.1 | 1.0 | 1.5 | 1.4 | 1.3 | | 1.0 |
| Lgals1 | 4.9 | 1.3 | 1.0 | 1.2 | 1.4 | | 0.9 | | 1.5 | 1.3 | 1.5 | 1.4 | 1.1 |
| Hspa8 | 6.4 | 1.2 | 1.2 | 1.2 | 1.3 | 1.2 | 0.9 | 1.1 | 1.3 | 1.1 | 1.4 | 1.3 | 0.9 |
| Pfn1 | 11.6 | 1.5 | 1.2 | 1.1 | 1.3 | 1.1 | 0.9 | 1.3 | 1.2 | 0.9 | 1.3 | 1.4 | 0.9 |
| Tpi1 | 3.0 | 1.3 | 1.1 | 1.3 | 1.2 | 1.3 | 0.9 | 1.1 | 1.3 | 1.2 | 1.4 | 1.4 | 0.9 |
| Shmt1 | 6.0 | 1.8 | 1.3 | 1.0 | 1.3 | 1.1 | 1.0 | 1.1 | 1.0 | 1.0 | 1.0 | 1.3 | 0.9 |
| Psma6 | 11.5 | 1.3 | 1.2 | 1.3 | 1.3 | 1.2 | 0.9 | | 1.5 | 1.2 | 1.9 | 1.6 | 0.9 |
| Psmb1 | 20.0 | 1.3 | 1.0 | 1.1 | 1.3 | 1.1 | 0.9 | 1.2 | 1.3 | 1.0 | 1.4 | 1.3 | 0.8 |
| Apoo | 17.2 | 1.3 | 1.2 | 1.1 | 1.3 | 1.2 | 1.0 | 1.1 | 1.1 | 1.0 | 1.2 | 1.3 | 0.8 |
| Lmnb1 | 10.1 | 1.3 | 1.3 | 1.2 | 1.3 | 1.0 | 1.1 | 1.2 | 1.2 | 1.5 | 1.4 | 1.4 | 0.9 |
| Actn1 | 7.1 | 1.2 | 1.1 | 1.0 | 1.3 | 1.1 | 0.9 | 1.1 | 1.2 | 1.0 | 1.1 | 1.1 | 0.9 |
| Nap1l1 | 11.0 | 1.4 | 1.2 | 1.2 | 1.3 | 1.2 | 0.8 | 1.0 | 1.1 | 0.6 | 0.9 | 1.2 | 0.8 |
| Vat1l | 5.6 | 1.1 | 1.3 | 1.3 | 1.3 | | 1.0 | 1.2 | 1.5 | 0.9 | 0.9 | 1.4 | 1.0 |
| Tubb5 | 4.0 | 1.3 | 1.2 | 1.2 | 1.3 | 1.1 | 0.9 | 1.1 | 1.1 | 0.8 | 1.1 | 1.3 | 0.9 |
| Hspa1l | 4.6 | 1.1 | 1.2 | 1.3 | 1.3 | 1.2 | 0.9 | 1.2 | 1.3 | 1.2 | 1.4 | | 1.0 |
| Phb | 3.3 | 1.2 | 1.2 | 1.0 | 1.3 | 1.1 | 1.0 | 1.2 | 1.3 | 1.3 | 1.4 | 1.1 | 1.0 |

TABLE 4B-continued

| | | | | | | Neuro2a (AEA-DA) Competition | | | | | | |
|---|---|---|---|---|---|---|---|---|---|---|---|---|
| Gene Name | No UV | DMSO | AEA (200 μM) | FK866 (25 μM) | Avasimibe (25 μM) | Elacridar (25 μM) | Ro 48-8071 (25 μM) | MJN228 (10 μM) | MJN228 (25 μM) | MJN228 (50 μM) | MJN228 (100 μM) | KML110 (25 μM) | KML181 (25 μM) |
| Tomm40 | 7.1 | 1.3 | 1.2 | 1.1 | 1.3 | | 1.0 | 1.1 | 1.2 | 1.4 | 1.4 | 1.2 | 1.0 |
| Cops4 | 13.8 | 1.3 | 1.2 | 1.2 | 1.3 | | 1.0 | 1.0 | 1.0 | 0.8 | 1.0 | 1.0 | 1.0 |
| Tubb2a | 3.6 | 1.3 | 1.2 | 1.1 | 1.3 | 1.1 | 0.9 | 1.1 | 1.1 | 0.8 | 1.1 | 1.3 | 0.9 |
| Nono | 10.9 | 1.3 | 1.1 | 1.1 | 1.3 | 1.2 | 1.0 | 1.1 | 1.1 | 1.0 | 1.2 | 1.3 | 0.9 |
| Tubb6 | 3.5 | 1.3 | 1.2 | 1.1 | 1.3 | 1.1 | 0.9 | 1.1 | 1.1 | 0.8 | 1.0 | 1.3 | 0.8 |
| Ipo7 | 5.3 | 1.5 | 1.2 | 1.1 | 1.3 | 1.0 | 0.8 | 1.4 | 1.2 | 1.0 | 1.3 | 1.3 | 0.8 |
| Tubb4b | 3.7 | 1.3 | 1.2 | 1.1 | 1.3 | 1.1 | 0.9 | 1.1 | 1.1 | 0.8 | 1.0 | 1.3 | 0.9 |
| Psmb5 | 20.0 | 1.2 | 1.1 | 1.2 | 1.3 | 1.2 | 0.9 | 1.5 | 1.4 | 1.1 | 1.8 | 1.5 | 1.0 |
| Sdhb | 9.5 | 1.0 | 1.3 | 1.1 | 0.3 | 1.2 | 0.7 | 1.0 | 1.4 | 1.7 | 1.3 | 1.4 | 0.9 |
| Opa1 | 9.0 | 1.3 | 1.3 | 1.3 | | | 1.0 | 1.3 | 1.4 | 1.4 | 1.7 | 1.1 | 0.9 |
| Ipo9 | 15.3 | 1.5 | 1.2 | 1.3 | 1.3 | 1.3 | 1.0 | | 1.3 | 1.0 | 1.9 | | 0.9 |
| Plod3 | 3.3 | 1.0 | 1.1 | 1.0 | 1.3 | 1.2 | 0.9 | 1.4 | 1.4 | 1.1 | 1.6 | 1.2 | 1.0 |
| Ywhae | 7.6 | 1.2 | 1.1 | 1.3 | 1.3 | 1.1 | 0.8 | 1.2 | 1.2 | 1.0 | 1.0 | 1.3 | 1.0 |
| Ppm1l | 20.0 | 1.2 | 1.3 | 0.9 | | | 1.1 | 0.7 | 1.2 | | 1.0 | 1.4 | 0.7 |
| Slc25a5 | 8.6 | 1.3 | 1.2 | 0.9 | 1.3 | 1.0 | 0.8 | 1.0 | 1.0 | 0.9 | 1.0 | 1.0 | 0.9 |
| Arf3 | 3.6 | 1.1 | 1.1 | | 1.3 | | | 1.7 | 1.3 | | | | |
| Mtx1 | 7.4 | 1.3 | 1.2 | 1.0 | 1.3 | 1.1 | 0.9 | 1.1 | 1.2 | 1.1 | 1.3 | 1.2 | 0.9 |
| Tubb3 | 3.4 | 1.3 | 1.2 | 1.1 | 1.3 | 1.0 | 0.9 | 1.1 | 1.1 | 0.8 | 1.0 | 1.2 | 0.9 |
| Hyou1 | 3.3 | 0.9 | 1.1 | 1.2 | 1.3 | 1.3 | 1.1 | 1.2 | 1.2 | 1.2 | 1.3 | 1.3 | 1.0 |
| Echs1 | 4.4 | 1.0 | 1.2 | 0.9 | 1.3 | | 0.8 | 1.0 | 1.3 | 1.1 | 1.4 | 1.3 | 0.8 |
| Fam49b | 4.5 | 1.0 | 0.8 | 1.0 | 1.3 | | | 1.1 | 1.0 | 0.9 | 1.0 | 1.3 | |
| Elavl2 | 11.0 | 1.1 | 1.1 | | 1.3 | | 0.7 | 1.0 | 1.1 | 0.9 | 1.0 | 1.1 | |
| Ywhab | 9.9 | 1.1 | 1.1 | 1.1 | 1.3 | 1.1 | 0.7 | 1.1 | 1.2 | 1.0 | 1.1 | 1.3 | 1.0 |
| Sptan1 | 8.6 | 1.1 | 1.1 | 1.1 | 1.3 | | 1.0 | 1.2 | 1.3 | 1.3 | 1.4 | 1.2 | 1.0 |
| Hk1 | 8.1 | 1.2 | 1.2 | 1.2 | 1.2 | | 1.2 | 1.3 | 1.2 | 1.2 | 1.3 | 1.2 | 1.0 |
| Srm | 3.7 | 1.1 | 1.1 | 1.0 | 1.2 | | | | 0.8 | 1.0 | 0.9 | | |
| Psmb8 | 20.0 | 0.7 | 1.2 | | | | | | 1.3 | 0.9 | 0.7 | 1.3 | 0.9 |
| Atp6v0a1 | 14.2 | 1.2 | 1.1 | 1.1 | 1.2 | 1.0 | 0.7 | 1.0 | 1.1 | 0.9 | 1.0 | 1.3 | 0.9 |
| Arf4 | 12.1 | 1.1 | 1.1 | 1.2 | 1.2 | 1.1 | 1.1 | 1.4 | 1.5 | 1.3 | 1.6 | 1.4 | 1.0 |
| Pfkp | 4.0 | 1.1 | 1.2 | 1.0 | | | 0.5 | 0.9 | 1.1 | 0.9 | 1.5 | 1.6 | 0.8 |
| Ina | 20.0 | 1.0 | 1.2 | | | 1.2 | | | 1.3 | | | 1.1 | |
| Pfkl | 4.7 | 1.4 | 1.0 | 1.1 | 1.2 | | 1.0 | 1.2 | 1.1 | | 1.3 | 1.4 | 0.7 |
| Arf5 | 8.2 | 1.2 | 1.0 | 1.2 | 1.2 | 1.1 | 1.1 | 1.4 | 1.4 | 1.2 | 1.5 | 1.5 | 1.0 |
| Plod1 | 4.7 | 0.9 | 1.0 | | 1.2 | | 0.9 | 1.0 | | 1.4 | 1.3 | | 0.9 |
| Mcm7 | 20.0 | 1.4 | 1.2 | 1.1 | 1.2 | 1.2 | 0.9 | 1.3 | 1.2 | 0.8 | 1.2 | 1.3 | 0.8 |
| Actr2 | 3.6 | 1.1 | 1.2 | | | 1.2 | 0.7 | 1.0 | 1.1 | | 1.0 | 1.1 | 1.0 |
| Vdac1 | 20.0 | 1.1 | 1.1 | 1.0 | 1.2 | 1.0 | 1.0 | 1.1 | 1.1 | 1.1 | 1.2 | 1.2 | 0.9 |
| Psmb4 | 20.0 | 1.2 | 1.0 | 1.2 | 1.0 | 1.2 | 0.9 | 1.1 | 1.2 | 0.8 | 1.0 | 1.1 | 0.9 |
| Arf1 | 6.2 | 1.1 | 1.1 | 1.2 | 1.2 | 1.2 | 1.1 | 1.4 | 1.4 | 1.3 | 1.5 | 1.4 | 1.0 |
| Vdac2 | 16.5 | 1.2 | 1.2 | 1.0 | 1.2 | 0.9 | 1.0 | 1.0 | 1.0 | 1.0 | 1.0 | 1.1 | 0.9 |
| Ap3m1 | 20.0 | 1.8 | 1.2 | | | | | | 1.3 | 0.8 | | 1.3 | 1.1 |
| Mcee | 20.0 | 0.9 | 0.9 | 1.2 | | | 1.0 | | 1.2 | | 1.5 | | |
| Actr3 | 3.7 | 1.0 | 1.0 | 1.0 | 1.2 | | 0.8 | 1.1 | 1.2 | 1.2 | 1.1 | 1.1 | 0.9 |
| Khsrp | 3.2 | 1.0 | 1.0 | 0.9 | 1.2 | 1.0 | 1.1 | 1.0 | 1.0 | 1.0 | 1.2 | 1.2 | |
| Hm13 | 12.1 | 1.3 | 1.2 | 0.9 | 0.9 | 1.0 | 0.9 | 1.1 | 1.2 | 1.2 | 1.2 | 1.3 | 0.9 |
| Sdhc | 3.7 | 1.1 | 1.1 | 1.2 | | | 1.0 | 1.3 | 1.2 | | 1.3 | 1.3 | 1.2 |
| Apmap | 11.0 | 1.1 | | | | 1.2 | | 1.2 | | | 1.3 | | 0.8 |
| Ostc | 6.2 | 1.1 | | 1.1 | 1.0 | 1.1 | 1.2 | 1.1 | 1.2 | | 1.5 | 1.3 | 1.0 |
| Ctsb | 9.6 | 1.0 | 1.1 | 1.1 | 1.1 | 1.0 | 0.3 | 1.1 | 1.0 | 0.8 | 0.7 | 1.1 | 0.9 |
| Fah | 20.0 | 1.5 | 1.2 | | | | 1.0 | | | | | | 0.9 |
| Nap1l4 | 13.6 | 1.1 | 1.1 | 1.0 | 1.2 | | 0.9 | | 1.1 | 0.8 | 1.1 | 1.2 | 0.9 |
| Psme1 | 3.5 | 1.3 | 1.0 | | 1.2 | | 0.8 | 0.8 | 0.9 | 0.7 | 0.9 | 1.4 | 0.7 |
| Actn2 | 3.5 | 1.0 | | | 1.2 | | | | | | | | |
| Atp5c1 | 4.5 | 1.1 | 1.2 | 1.1 | 1.0 | 1.0 | 0.9 | 1.1 | 1.3 | 1.2 | 1.2 | 1.3 | 1.0 |
| Glo1 | 8.0 | 1.1 | 1.2 | | | | | | 1.5 | | | | 0.8 |
| Mif | 6.7 | 1.4 | 1.2 | 1.1 | 1.0 | 1.0 | 1.0 | 1.0 | 1.0 | 0.8 | 1.0 | 1.2 | 0.9 |
| Pmpcb | 12.1 | 1.0 | 1.1 | | | | | 0.8 | | | 1.3 | | |
| Atp5b | 3.8 | 1.1 | 1.1 | 1.1 | 1.1 | 1.1 | 0.8 | 1.2 | 1.2 | 1.2 | 1.2 | 1.3 | 0.9 |
| Plbd2 | 20.0 | 0.9 | 1.1 | 1.1 | | | | 1.1 | 0.9 | | 0.9 | 1.1 | |
| Slc25a15 | 20.0 | 1.4 | 1.1 | 1.0 | 1.0 | 1.1 | 1.0 | 1.3 | 0.9 | | 1.0 | 1.0 | 0.7 |
| Prdx3 | 6.4 | 1.0 | 1.1 | 1.0 | 1.1 | | 0.7 | 1.2 | | | 1.1 | 1.0 | 1.0 |
| Aifm1 | 11.0 | 1.4 | 1.1 | | 0.6 | 1.1 | 0.8 | 1.5 | 1.2 | | | 1.1 | 0.8 |
| Fus | 4.8 | 1.1 | 1.0 | 0.8 | 1.1 | | | 1.2 | | 1.4 | 1.0 | 1.2 | |
| Pck2 | 12.8 | 0.9 | 0.9 | 1.1 | 0.7 | 1.1 | 0.8 | 0.9 | 1.2 | 1.0 | 1.1 | 1.4 | 0.8 |
| Pitpnb | 20.0 | 1.0 | 0.3 | 1.1 | 0.2 | 1.1 | 1.0 | 1.2 | 1.9 | 2.4 | 1.8 | 1.7 | 1.2 |
| Rps27a | 6.0 | 1.2 | 1.1 | 1.1 | 0.8 | 1.1 | 0.9 | 1.3 | 1.2 | | 1.1 | 1.1 | 0.8 |
| Uba52 | 6.0 | 1.1 | 1.0 | 1.1 | 0.8 | 1.1 | 0.9 | 1.3 | 1.2 | | 1.1 | 1.1 | 0.8 |
| Ubc | 6.0 | 1.2 | 1.0 | 1.1 | 0.7 | 1.1 | | 1.3 | 1.2 | | | 1.1 | |
| Fam162a | 11.0 | 1.0 | 1.0 | | | | 1.1 | 1.1 | 1.5 | 1.2 | 1.2 | 1.4 | 1.0 |
| Mpp6 | 20.0 | 1.1 | 1.1 | 0.9 | | 1.0 | 0.9 | 1.0 | 1.0 | 1.0 | 0.9 | 1.5 | 0.9 |
| Nnt | 3.7 | 1.1 | 0.9 | 1.1 | 0.5 | | 1.1 | 1.1 | 1.5 | | 1.7 | 1.1 | 1.0 |
| Otub1 | 5.8 | 1.2 | 1.1 | | | | | | | | | | |
| Stom | 4.2 | 1.0 | 1.1 | 1.0 | | 1.0 | 1.0 | 1.0 | 1.0 | 1.0 | 1.0 | 1.0 | 1.2 |
| Nudt9 | 20.0 | 1.3 | 1.0 | | 1.0 | | | | | | | 1.9 | 0.7 |

TABLE 4B-continued

Neuro2a (AEA-DA) Competition

| Gene Name | No UV | DMSO | AEA (200 μM) | FK866 (25 μM) | Avasimibe (25 μM) | Elacridar (25 μM) | Ro 48-8071 (25 μM) | MJN228 (10 μM) | MJN228 (25 μM) | MJN228 (50 μM) | MJN228 (100 μM) | KML110 (25 μM) | KML181 (25 μM) |
|---|---|---|---|---|---|---|---|---|---|---|---|---|---|
| Rbmxl1 | 6.0 | 1.1 | 1.0 | | | | | 1.1 | 1.2 | | 1.3 | | 0.8 |
| Rtn4ip1 | 15.1 | 0.8 | 1.0 | | 0.4 | | 0.7 | 1.0 | 1.4 | | | | 0.8 |
| Cox15 | 12.3 | 1.3 | 1.0 | 0.9 | 0.7 | 1.0 | 0.8 | 0.8 | 1.0 | 0.7 | 0.6 | 1.1 | 0.9 |
| Iars2 | 20.0 | 0.8 | 0.9 | | | | 0.7 | 0.8 | 1.0 | 0.7 | | | |
| Pdp1 | 20.0 | 1.0 | | 0.9 | | | | | 1.4 | | | | |
| Micu1 | 20.0 | 1.6 | | | | | 0.9 | 1.2 | 1.5 | | | | |
| Apool | 6.4 | 1.2 | | | | | 0.9 | | | | | 1.0 | |
| Lmnb2 | 20.0 | 1.1 | | | | | | | | 1.9 | | | 0.9 |
| Fkbp2 | 5.6 | 1.1 | | | | | | 1.1 | 1.6 | | 1.1 | | |
| Dctn2 | 11.6 | 1.2 | | | | | | | | | | | 0.7 |

TABLE 4C

A549 (A-DA) Competition

| GeneName | Accession | No UV | DMSO | Flurbiprofen (25 μM) | Rofecoxib (25 μM) | FK-866 (25 μM) | Avasimibe (25 μM) | Ro 48-8071 (5.0 μM) | Ro 48-8071 (50 μM) |
|---|---|---|---|---|---|---|---|---|---|
| PNPLA6 | Q8IY17 | 14.2 | 1.2 | 1.2 | 1.5 | 1.9 | 1.6 | 1.6 | 20.0 |
| TIMM17B | O60830 | 20.0 | 1.3 | 1.2 | 1.2 | 1.3 | 1.4 | 1.8 | 20.0 |
| FAM114A2 | Q9NRY5 | 20.0 | 1.4 | 1.2 | 1.8 | 1.2 | 2.8 | 1.8 | 20.0 |
| APOL2 | Q9BQE5 | 20.0 | 1.4 | 1.3 | 1.2 | 1.3 | 2.2 | 1.4 | 20.0 |
| TMEM97 | Q5BJF2 | 20.0 | 1.4 | 1.4 | 1.1 | 1.8 | 2.0 | 20.0 | 20.0 |
| NPC1 | O15118 | 20.0 | 1.4 | 1.3 | 1.2 | 1.7 | 1.3 | 2.8 | 20.0 |
| ABHD5 | Q8WTS1 | 20.0 | 1.5 | 1.4 | 1.1 | 1.6 | 20.0 | 1.6 | 7.0 |
| LSS | P48449 | 20.0 | 1.5 | 1.5 | 2.3 | 1.7 | 2.3 | 20.0 | 20.0 |
| FA2H | Q7L5A8 | 17.2 | 1.7 | 1.4 | 1.2 | 2.2 | 2.1 | | 20.0 |
| EBP | Q15125 | 20.0 | 1.0 | 1.2 | 1.2 | | | 16.0 | 19.6 |
| AIFM2 | Q9BRQ8 | 20.0 | 1.5 | 1.4 | 1.4 | 2.0 | 16.1 | 2.2 | 7.5 |
| NAMPT | P43490 | 12.8 | 1.6 | 1.4 | 1.3 | 10.6 | 1.5 | 1.8 | 15.0 |
| PLIN3 | O60664 | 20.0 | 1.4 | 1.4 | 1.1 | 1.6 | 2.8 | 1.7 | 8.9 |
| ARFGAP1 | Q8N6T3 | 20.0 | 1.5 | 1.3 | 1.7 | 1.4 | 14.3 | 1.9 | |
| PNPLA2 | Q96AD5 | 20.0 | 1.9 | 1.6 | 1.3 | 2.2 | 8.1 | 2.0 | 10.5 |
| KDSR | Q06136 | 20.0 | 1.3 | 1.2 | 1.1 | 1.4 | 1.7 | 1.7 | 12.9 |
| DHRS1 | Q96LJ7 | 20.0 | 1.6 | 0.9 | 1.0 | 1.6 | 7.7 | 1.5 | 12.1 |
| PTGR2 | Q8N8N7 | 20.0 | 1.5 | 1.7 | 12.0 | | | 2.1 | 4.2 |
| TPD52L2 | O43399 | 18.0 | 1.6 | 1.4 | 1.3 | 2.8 | 1.6 | 8.4 | |
| TLCD1 | Q96CP7 | 20.0 | 1.1 | 1.1 | 1.2 | 1.3 | 1.6 | 1.5 | 11.7 |
| ERMP1 | Q7Z2K6 | 20.0 | 1.2 | 1.2 | 1.6 | 1.6 | 2.1 | 1.4 | 3.2 |
| PLIN2 | Q99541 | 20.0 | 1.6 | 1.5 | 1.2 | 1.6 | 9.0 | 1.7 | 9.2 |
| APMAP | Q9HDC9 | 20.0 | 1.3 | 1.2 | 1.4 | 1.6 | 2.1 | 1.8 | 8.8 |
| SLC25A20 | O43772 | 20.0 | 1.3 | 1.2 | 1.7 | 3.1 | 2.6 | 1.6 | 4.6 |
| RTN4IP1 | Q8WWV3 | 20.0 | 1.3 | 1.4 | 1.2 | 2.1 | 7.7 | 1.4 | 2.4 |
| PCYOX1 | Q9UHG3 | 20.0 | 1.2 | 1.1 | 1.1 | 2.6 | 1.4 | 2.5 | 6.9 |
| CAV1 | Q03135 | 12.7 | 1.2 | 1.1 | 1.3 | 1.2 | 1.2 | 2.2 | 6.9 |
| TTMM17A | Q99595 | 20.0 | 1.3 | 1.0 | 0.8 | 1.2 | 1.5 | 1.2 | 6.7 |
| GPR107 | Q5VW38 | 20.0 | 1.3 | 1.2 | 1.1 | 1.7 | 2.6 | 1.6 | 6.5 |
| PON2 | Q15165 | 20.0 | 1.3 | 1.2 | 1.3 | 4.3 | 2.5 | 1.5 | 3.6 |
| GPD2 | P43304 | 12.3 | 1.4 | 1.2 | 1.2 | 1.5 | 1.5 | 1.4 | 1.1 |
| NUCB1 | Q02818 | 15.2 | 1.4 | 1.2 | 1.1 | 1.4 | 1.6 | 1.5 | 1.6 |
| TRAM1 | Q15629 | 20.0 | 1.2 | 1.1 | 1.1 | 1.2 | 1.4 | 1.5 | 5.3 |
| HSD17B11 | Q8NBQ5 | 17.4 | 1.6 | 1.4 | 1.1 | 1.5 | 4.6 | 1.6 | 3.5 |
| ECH1 | Q13011 | 13.5 | 1.3 | 1.2 | 1.1 | 1.6 | 1.4 | 1.6 | 5.1 |
| HADHA | P40939 | 11.8 | 1.3 | 1.2 | 1.1 | 2.4 | 5.1 | 1.4 | 1.5 |
| POC1B-GALNT4 | F8VUJ3 | 20.0 | 1.5 | 1.4 | 1.2 | 2.1 | 2.4 | 1.8 | 5.0 |
| GALNT4 | Q8N4A0 | 20.0 | 1.5 | 1.4 | 1.2 | 2.1 | 2.4 | 1.8 | 5.0 |
| LBR | Q14739 | 15.3 | 1.4 | 1.3 | 1.2 | 1.6 | 2.1 | 2.3 | 5.0 |
| FAF2 | Q96CS3 | 20.0 | 1.6 | 1.5 | 1.3 | 1.7 | 4.9 | 2.0 | 4.1 |
| FAM82A1 | Q96LZ7 | 20.0 | 1.3 | 1.2 | 1.3 | 2.1 | 4.9 | 1.5 | |
| NDUFS2 | O75306 | 15.9 | 1.4 | 1.3 | 1.3 | 2.4 | 1.1 | 1.5 | 4.9 |
| FECH | P22830 | 13.8 | 1.4 | 1.4 | 1.9 | 4.8 | 0.3 | 1.7 | 1.9 |
| SCARB1 | Q8WTV0 | 20.0 | 1.0 | 0.9 | 1.2 | 1.3 | 1.1 | 1.9 | 4.8 |
| C2orf43 | Q9H6V9 | 20.0 | 1.3 | 1.2 | 1.1 | 1.4 | 1.6 | 1.3 | 4.6 |
| RTN3 | O95197 | 14.3 | 1.3 | 1.2 | 1.1 | 1.3 | 1.9 | 1.6 | 4.5 |
| CPT2 | P23786 | 20.0 | 1.4 | 1.2 | 1.2 | 4.4 | 1.5 | 1.4 | 2.2 |
| BSG | P35613 | 20.0 | 1.6 | 1.6 | 1.8 | 1.8 | 1.4 | 2.4 | 4.3 |
| CYB5B | O43169 | 20.0 | 1.3 | 1.2 | 1.1 | 1.4 | 2.1 | 1.5 | 4.2 |
| SCCPDH | Q8NBX0 | 20.0 | 1.5 | 1.3 | 1.2 | 2.2 | 3.4 | 1.6 | 4.1 |
| RDH10 | Q8IZV5 | 20.0 | 1.9 | 1.7 | 1.2 | 3.1 | 3.9 | 1.9 | 2.8 |
| VAT1 | Q99536 | 7.8 | 1.4 | 1.3 | 1.1 | 4.0 | 0.8 | 1.4 | 2.5 |

TABLE 4C-continued

A549 (A-DA) Competition

| GeneName | Accession | No UV | DMSO | Flurbiprofen (25 μM) | Rofecoxib (25 μM) | FK-866 (25 μM) | Avasimibe (25 μM) | Ro 48-8071 (5.0 μM) | Ro 48-8071 (50 μM) |
|---|---|---|---|---|---|---|---|---|---|
| UGT1A7 | Q9HAW7 | 20.0 | 1.5 | 1.4 | 1.5 | 2.1 | 1.7 | 1.6 | 4.0 |
| SLC39A7 | Q92504 | 14.8 | 1.1 | 1.0 | 1.5 | 2.3 | 1.7 | 1.4 | 1.5 |
| DHRS3 | O75911 | 15.6 | 1.6 | 1.5 | 1.2 | 2.0 | 3.0 | 1.8 | 3.1 |
| DNAJC1 | Q96KC8 | 20.0 | 1.3 | 1.2 | 1.1 | 1.3 | 1.3 | 1.6 | 3.9 |
| DHRSX | Q8N5I4 | 20.0 | 1.5 | 1.3 | 1.1 | 1.4 | 3.7 | 1.6 | 2.7 |
| PTGS2 | P35354 | 3.2 | 1.6 | 3.7 | 3.6 | 1.9 | 1.5 | 2.5 | 3.3 |
| FAM213A | Q9BRX8 | 3.6 | 1.3 | 1.1 | 0.9 | 1.3 | 0.9 | 1.3 | 2.3 |
| COQ5 | Q5HYK3 | 20.0 | 1.7 | 1.6 | 1.6 | | 1.4 | 2.0 | 3.4 |
| HMOX2 | P30519 | 20.0 | 1.3 | 1.2 | 1.1 | 1.3 | 1.4 | 1.3 | 3.4 |
| VDAC2 | P45880 | 19.7 | 1.2 | 1.1 | 1.1 | 1.2 | 1.4 | 1.5 | 3.4 |
| VDAC1 | P21796 | 20.0 | 1.2 | 1.1 | 1.0 | 1.3 | 1.3 | 1.4 | 3.3 |
| SQLE | Q14534 | 20.0 | 1.6 | 1.3 | 1.1 | 1.6 | 2.3 | 1.4 | 3.3 |
| LPCAT3 | Q6P1A2 | 20.0 | 1.2 | 1.1 | 1.1 | 3.3 | 2.1 | 1.3 | 2.7 |
| SEC11A | P67812 | 20.0 | 1.3 | 1.2 | 1.1 | 1.2 | 1.2 | 1.5 | 3.3 |
| NUCB2 | P80303 | 20.0 | 1.4 | 1.2 | 1.0 | 1.5 | 1.7 | 1.5 | 1.7 |
| AKR1C3 | P42330 | 3.2 | 1.6 | 2.2 | 2.2 | 3.3 | 2.8 | 1.2 | 1.4 |
| RTN4 | Q9NQC3 | 14.7 | 1.5 | 1.4 | 1.2 | 1.7 | 2.6 | 1.4 | 2.8 |
| NSDHL | Q15738 | 16.9 | 1.4 | 1.3 | 1.1 | 1.4 | 3.2 | 1.5 | 2.5 |
| PON3 | Q15166 | 20.0 | 1.3 | 1.2 | 1.2 | 1.5 | 1.7 | 1.6 | 2.9 |
| ENDOD1 | O94919 | 17.0 | 1.7 | 1.3 | 1.2 | 1.6 | 1.1 | | 1.9 |
| AUP1 | Q9Y679 | 13.8 | 1.7 | 1.4 | 1.1 | 1.7 | 2.8 | 1.7 | 2.3 |
| PSAP | P07602 | 20.0 | 1.3 | 1.1 | 1.3 | 1.2 | 1.1 | 2.3 | 3.1 |
| LPCAT1 | Q8NF37 | 20.0 | 1.5 | 1.3 | 1.1 | 1.4 | 1.9 | 1.6 | 3.1 |
| ANKLE2 | Q86XL3 | 20.0 | 1.4 | 1.2 | 1.2 | 1.3 | 1.9 | 1.7 | 3.1 |
| DHCR24 | Q15392 | 12.9 | 1.4 | 1.3 | 1.0 | 2.3 | 1.9 | 0.6 | 1.6 |
| SGPL1 | O95470 | 19.7 | 1.4 | 1.3 | 1.4 | 1.2 | 1.3 | 1.5 | 3.0 |
| NPTN | Q9Y639 | 20.0 | 1.4 | 1.4 | 1.1 | 1.4 | 1.4 | 1.3 | 3.0 |
| HSD17B12 | Q53GQ0 | 20.0 | 1.3 | 1.1 | 1.4 | 1.4 | 2.0 | 1.4 | 3.0 |
| EPHX1 | P07099 | 7.6 | 1.5 | 1.4 | 1.2 | 1.8 | 2.5 | 1.4 | 1.8 |
| CYP4F12 | Q9HCS2 | 7.3 | 1.4 | 1.3 | 1.2 | 1.8 | 1.7 | 1.4 | 1.9 |
| AGPAT9 | Q53EU6 | 20.0 | 1.4 | 1.4 | 1.2 | 1.4 | 2.7 | 1.5 | 2.9 |
| C16orf58 | Q96GQ5 | 16.3 | 1.5 | 1.4 | 1.3 | 1.6 | 1.5 | 1.7 | 2.9 |
| VMP1 | Q96GC9 | 16.6 | 1.6 | 1.5 | 1.2 | 1.8 | 1.3 | 1.7 | 2.1 |
| SLC1A5 | Q15758 | 3.4 | 1.4 | 1.5 | 1.9 | 1.7 | 1.7 | | 2.0 |
| UGCG | Q16739 | 20.0 | 1.5 | 1.4 | 1.5 | 1.6 | 1.8 | 2.0 | 2.9 |
| CYP51A1 | Q16850 | 8.3 | 1.3 | 1.2 | 1.1 | 1.6 | 1.0 | 1.0 | 2.0 |
| CYB5R3 | P00387 | 7.7 | 1.5 | 1.3 | 1.1 | 1.6 | 2.3 | 1.7 | 2.0 |
| TMPO | P42167 | 7.5 | 1.3 | 1.2 | 1.0 | 1.4 | 1.1 | 1.2 | 1.7 |
| ACSL3 | O95573 | 12.2 | 1.6 | 1.4 | 1.2 | 1.5 | 2.1 | 1.5 | 2.3 |
| FDFT1 | P37268 | 20.0 | 1.3 | 1.3 | 1.6 | 1.8 | 1.6 | 1.1 | 2.5 |
| ALDH3A2 | P51648 | 8.1 | 1.5 | 1.4 | 1.2 | 2.0 | 1.5 | 1.6 | 2.5 |
| NCEH1 | Q6PIU2 | 12.4 | 1.3 | 1.2 | 1.1 | 1.4 | 1.4 | 1.4 | 2.8 |
| TMEM48 | Q9BTX1 | 20.0 | 1.3 | 1.2 | 1.2 | 1.2 | 1.4 | 1.5 | 2.8 |
| PTGES2 | Q9H7Z7 | 12.5 | 1.2 | 1.0 | 1.2 | 1.7 | 1.3 | 1.5 | 2.7 |
| PTGR1 | Q14914 | 3.5 | 1.5 | 1.7 | 1.5 | 2.7 | 0.8 | 1.5 | 1.4 |
| EMC1 | Q8N766 | 16.4 | 1.2 | 1.1 | 1.6 | 1.5 | 1.4 | 1.7 | 1.8 |
| TUBA8 | Q9NY65 | 3.6 | 1.3 | 1.5 | 1.1 | 1.2 | 2.7 | 1.0 | 1.2 |
| CERS6 | Q6ZMG9 | 7.0 | 1.2 | 1.2 | 1.3 | 1.6 | 1.5 | 2.7 | |
| SCARB2 | Q14108 | 20.0 | 1.4 | 1.1 | 1.1 | 1.3 | 1.3 | 1.2 | 2.7 |
| CLPTM1 | O96005 | 15.7 | 1.4 | 1.3 | 1.1 | 1.6 | 1.6 | 1.4 | 2.1 |
| CYP4F11 | Q9HBI6 | 7.6 | 1.4 | 1.3 | 1.1 | 1.8 | 1.9 | 1.4 | 1.9 |
| SAR1B | Q9Y6B6 | 20.0 | 1.1 | 1.2 | 1.1 | 1.2 | 2.1 | 1.4 | 2.4 |
| CTSD | P07339 | 20.0 | 1.2 | 1.3 | 1.4 | 1.2 | 0.9 | 1.7 | 2.1 |
| NR3C1 | P04150 | 5.4 | 1.3 | 1.4 | 2.6 | | | | |
| TCIRG1 | Q13488 | 20.0 | 1.4 | 1.1 | 0.9 | 1.2 | 0.9 | | |
| SRPRB | Q9Y5M8 | 20.0 | 1.4 | 1.2 | 1.1 | 1.3 | 1.1 | 1.5 | 2.6 |
| TMED3 | Q9Y3Q3 | 20.0 | 1.3 | 1.3 | 0.6 | 1.1 | 0.4 | 2.1 | |
| MTDH | Q86UE4 | 19.3 | 1.4 | 1.3 | 1.2 | 1.3 | 1.0 | 1.3 | 2.1 |
| POR | P16435 | 20.0 | 1.5 | 1.4 | 1.2 | 1.4 | 1.2 | 1.4 | 2.6 |
| FITM2 | Q8N6M3 | 4.4 | 1.3 | 1.4 | 1.2 | 1.6 | 0.9 | 1.4 | |
| TAPBP | O15533 | 20.0 | 1.3 | 1.3 | 1.7 | | 1.9 | | |
| CDIPT | O14735 | 20.0 | 1.3 | 1.3 | 1.1 | 1.4 | 1.9 | 1.7 | 1.6 |
| TUBA4A | P68366 | 3.6 | 1.3 | 1.5 | 1.2 | 1.3 | 2.6 | 1.0 | 1.2 |
| CYP4F3 | Q08477 | 10.1 | 1.4 | 1.3 | 1.5 | 1.8 | 1.8 | | |
| TUBA1A | Q71U36 | 3.5 | 1.3 | 1.4 | 1.1 | 1.3 | 2.5 | 1.0 | 1.2 |
| UNC93B1 | Q9H1C4 | 11.0 | 1.4 | 1.3 | 1.3 | 2.1 | 1.3 | 2.0 | 2.0 |
| CERS2 | Q96G23 | 13.3 | 1.3 | 1.2 | 1.1 | 1.4 | 0.7 | 1.5 | 2.5 |
| LPCAT2 | Q7L5N7 | 20.0 | 1.4 | 1.1 | 1.7 | 1.1 | 1.7 | 1.5 | |
| MOGS | Q13724 | 6.3 | 1.5 | 1.2 | 1.7 | 1.6 | 1.5 | 1.6 | 2.5 |
| HMOX1 | P09601 | 19.3 | 1.0 | 1.5 | 2.5 | 1.5 | | 1.8 | 1.9 |
| CEPT1 | Q9Y6K0 | 14.9 | 1.2 | 1.2 | 1.5 | 1.3 | 1.3 | | 2.5 |
| ASPH | Q12797 | 4.6 | 1.6 | 1.4 | 1.1 | 1.5 | 1.4 | 1.4 | 1.4 |
| ALG5 | Q9Y673 | 20.0 | 1.3 | 1.5 | 1.6 | | 1.2 | | |
| RPS27A | P62979 | 4.8 | 1.5 | 1.2 | 1.0 | 1.6 | 0.8 | 1.4 | 1.3 |
| Uncharac- | E9PBQ3 | 20.0 | 1.4 | 1.2 | 1.3 | | 1.8 | 1.2 | 2.5 |

TABLE 4C-continued

| | | | | Flurbiprofen | Rofecoxib | FK-866 | Avasimibe | Ro 48-8071 | Ro 48-8071 |
|---|---|---|---|---|---|---|---|---|---|
| GeneName | Accession | No UV | DMSO | (25 μM) | (25 μM) | (25 μM) | (25 μM) | (5.0 μM) | (50 μM) |

A549 (A-DA) Competition

| GeneName | Accession | No UV | DMSO | Flurbiprofen (25 μM) | Rofecoxib (25 μM) | FK-866 (25 μM) | Avasimibe (25 μM) | Ro 48-8071 (5.0 μM) | Ro 48-8071 (50 μM) |
|---|---|---|---|---|---|---|---|---|---|
| terized | | | | | | | | | |
| TMEM199 | Q8N511 | 20.0 | 1.4 | 1.2 | 0.8 | 1.4 | 1.8 | 1.2 | 2.5 |
| SLC30A7 | Q8NEW0 | 9.2 | 1.2 | 1.2 | 1.0 | 1.4 | 1.5 | 1.2 | 2.1 |
| ALDH3B1 | P43353 | 6.3 | 1.6 | 1.6 | 1.3 | 2.0 | 1.7 | 1.3 | 2.1 |
| JAGN1 | Q8N5M9 | 13.5 | 1.3 | 1.3 | 1.2 | 1.3 | 1.9 | | |
| ANO10 | Q9NW15 | 20.0 | 1.2 | 1.2 | 1.0 | 1.3 | 1.2 | 1.8 | 2.0 |
| DERL1 | Q9BUN8 | 13.5 | 1.3 | 1.2 | 1.1 | 1.3 | 1.7 | 1.3 | 2.4 |
| TMX4 | Q9H1E5 | 8.6 | 1.3 | 1.4 | 1.7 | 1.3 | 1.3 | 1.5 | |
| LMF2 | Q9BU23 | 13.8 | 1.3 | 1.4 | 1.1 | 1.5 | 0.7 | 1.4 | 2.4 |
| CANX | P27824 | 8.2 | 1.6 | 1.3 | 1.2 | 1.6 | 1.6 | 1.6 | 2.1 |
| YIF1B | Q5BJH7 | 15.2 | 1.3 | 1.3 | 1.4 | 1.4 | 1.6 | 1.5 | 2.1 |
| TMCO1 | Q9UM00 | 5.8 | 1.4 | 1.3 | 1.1 | 1.5 | 1.7 | 1.7 | 2.4 |
| PIGO | Q8TEQ8 | 13.5 | 1.4 | 1.2 | 1.3 | 1.6 | 1.1 | 1.6 | 2.3 |
| GPAA1 | O43292 | 20.0 | 1.1 | 1.2 | 1.1 | 1.3 | 1.2 | 1.6 | 2.4 |
| SAR1A | Q9NR31 | 20.0 | 1.2 | 1.2 | 1.0 | 1.3 | 2.3 | 1.3 | 2.1 |
| TUBB | P07437 | 3.9 | 1.2 | 1.4 | 1.1 | 1.1 | 2.4 | 1.1 | 1.3 |
| PITRM1 | Q5JRX3 | 3.3 | 1.3 | 1.5 | 2.1 | 1.6 | 1.5 | 1.4 | 1.2 |
| CCDC47 | Q96A33 | 12.5 | 1.4 | 1.3 | 1.1 | 1.5 | 1.3 | 1.4 | 2.4 |
| COMT | P21964 | 15.5 | 1.5 | 1.3 | 1.1 | 1.4 | 1.6 | 1.4 | 2.2 |
| PGRMC1 | O00264 | 12.6 | 1.5 | 1.4 | 1.1 | 1.6 | 1.2 | 1.4 | 1.6 |
| TMEM208 | Q9BTX3 | 20.0 | 1.3 | 1.2 | 1.1 | 1.2 | 1.3 | 2.1 | |
| ITGA3 | P26006 | 20.0 | 1.2 | 1.1 | 1.0 | 1.1 | 1.3 | | 2.4 |
| cDNA | B4DNA9 | 4.7 | 1.3 | 1.4 | 1.5 | 1.6 | 1.7 | 1.3 | 1.8 |
| GALNT1 | Q10472 | 18.4 | 1.3 | 1.3 | 1.1 | 1.5 | 1.4 | 1.6 | 2.4 |
| SEL1L | Q9UBV2 | 20.0 | 1.5 | 1.2 | 1.1 | 1.3 | 1.0 | 1.3 | 1.9 |
| UBA52 | P62987 | 4.0 | 1.5 | 1.2 | 1.0 | 1.6 | 0.8 | 1.4 | 1.3 |
| AGPAT6 | Q86UL3 | 20.0 | 1.3 | 1.3 | 1.0 | 1.2 | 1.8 | | 2.4 |
| TUBB4B | P68371 | 3.8 | 1.2 | 1.3 | 1.1 | 1.1 | 2.3 | 1.1 | 1.3 |
| ACSL4 | O60488 | 4.8 | 1.9 | 1.4 | 1.5 | 1.6 | 1.6 | 1.3 | 2.0 |
| SYNGR2 | O43760 | 5.8 | 1.3 | 1.3 | 1.1 | 1.3 | 1.2 | | 2.0 |
| LCLAT1 | Q6UWP7 | 9.3 | 1.3 | 1.2 | 1.0 | 1.5 | 1.4 | 1.2 | 1.8 |
| LPGAT1 | Q92604 | 9.6 | 1.3 | 1.3 | 1.1 | 1.4 | 1.6 | 1.4 | 1.6 |
| ABHD16A | O95870 | 20.0 | 1.4 | 1.3 | 1.1 | 1.5 | 1.8 | | 1.7 |
| ABHD12 | Q8N2K0 | 20.0 | 1.4 | 1.3 | 1.3 | 1.5 | 2.1 | 1.5 | 1.8 |
| TM9SF2 | Q99805 | 20.0 | 1.6 | 1.3 | 1.2 | 1.5 | 1.8 | 1.6 | 1.7 |
| TUBB2B | Q9BVA1 | 3.9 | 1.2 | 1.3 | 1.1 | 1.1 | 2.3 | 1.1 | 1.3 |
| AGPS | O00116 | 13.6 | 1.3 | 1.3 | 1.6 | 1.7 | 1.7 | 1.5 | 2.3 |
| ICMT | O60725 | 4.8 | 1.0 | 1.3 | 1.1 | | 1.2 | 1.3 | 1.9 |
| TUBB3 | Q13509 | 3.7 | 1.2 | 1.4 | 1.1 | 1.1 | 2.3 | 1.1 | 1.2 |
| TMX1 | Q9H3N1 | 13.2 | 1.5 | 1.3 | 1.1 | 1.4 | 1.4 | 1.5 | 1.6 |
| ARSE | P51690 | 13.3 | 1.9 | 1.0 | 1.6 | 2.3 | 1.4 | 1.4 | 1.7 |
| TOR1AIP1 | Q5JTV8 | 4.1 | 1.4 | 1.2 | 1.4 | 1.2 | 1.4 | 1.6 | 2.3 |
| ANXA4 | P09525 | 3.3 | 1.6 | 1.6 | 2.1 | 2.0 | 0.7 | 1.5 | 1.1 |
| CPT1A | P50416 | 8.3 | 1.5 | 1.4 | 1.2 | 1.6 | 1.6 | 1.5 | 1.4 |
| RAB11B | Q15907 | 7.6 | 1.4 | 1.2 | 1.0 | 1.3 | 1.5 | 1.2 | 1.7 |
| FAM134C | Q86VR2 | 3.8 | 1.2 | 1.4 | 1.1 | 1.5 | 1.1 | 1.6 | 1.4 |
| CDS2 | O95674 | 12.4 | 1.4 | 1.3 | 1.1 | 1.6 | 1.7 | 1.6 | 1.5 |
| ATP2A2 | P16615 | 14.4 | 1.3 | 1.2 | 1.1 | 1.5 | 1.5 | 1.4 | 2.3 |
| MFSD5 | Q6N075 | 20.0 | 1.3 | 1.2 | 1.2 | 1.7 | 1.5 | | |
| PIGU | Q9H490 | 20.0 | 1.4 | 1.1 | 1.1 | 1.5 | 1.3 | 1.6 | 2.2 |
| TUBB6 | Q9BUF5 | 3.9 | 1.2 | 1.4 | 1.1 | 1.3 | 2.2 | 1.2 | 1.3 |
| TM9SF3 | Q9HD45 | 12.6 | 1.4 | 1.2 | 1.2 | 1.5 | 1.7 | 1.6 | 1.6 |
| CLPTM1L | Q96KA5 | 16.7 | 1.4 | 1.2 | 1.2 | 1.2 | 1.0 | 1.5 | 2.2 |
| TMEM68 | Q96MH6 | 15.1 | 1.6 | 1.1 | 1.1 | 1.6 | 1.6 | 1.4 | 1.8 |
| TAP1 | Q03518 | 15.0 | 1.8 | 1.4 | 1.1 | 1.7 | 1.3 | 1.5 | 2.0 |
| SLC30A6 | Q6NXT4 | 20.0 | 1.2 | 1.3 | 1.3 | 1.5 | 1.0 | 1.3 | |
| ATP6V0A1 | Q93050 | 12.7 | 1.7 | 1.3 | 1.2 | 1.3 | 1.0 | 1.2 | |
| LMAN2 | Q12907 | 7.9 | 1.4 | 1.3 | 1.3 | 1.7 | 2.0 | 1.5 | 1.9 |
| PTDSS1 | P48651 | 14.6 | 1.2 | 1.2 | 1.1 | 1.4 | 0.8 | 1.8 | 2.2 |
| SOAT1 | P35610 | 12.6 | 1.3 | 1.4 | 1.1 | 1.8 | 1.6 | 1.5 | 1.7 |
| RPN1 | P04843 | 7.0 | 1.3 | 1.3 | 1.1 | 1.4 | 1.3 | 1.5 | 1.2 |
| ALG1 | Q9BT22 | 6.9 | 1.3 | 1.3 | 1.1 | 1.3 | 1.4 | 1.5 | 2.2 |
| SFXN1 | Q9H9B4 | 4.5 | 1.4 | 1.3 | 1.1 | 1.6 | 1.4 | 1.4 | 1.1 |
| LETM1 | O95202 | 5.0 | 1.4 | 1.1 | 1.1 | 1.8 | 0.4 | 1.3 | 1.2 |
| EMD | P50402 | 10.3 | 1.4 | 1.2 | 1.3 | 1.3 | 1.2 | 0.6 | 0.8 |
| SEC61A1 | P61619 | 7.5 | 1.2 | 1.2 | 1.1 | 1.4 | 1.2 | 1.7 | 2.0 |
| TOMM22 | Q9NS69 | 18.4 | 1.4 | 1.2 | 1.1 | 1.3 | 1.4 | 1.4 | 1.4 |
| CYB5A | P00167 | 16.5 | 1.3 | 1.2 | 2.2 | 1.3 | 1.0 | | |
| RAB10 | P61026 | 4.1 | 1.4 | 1.3 | 1.1 | 1.6 | 1.5 | 1.2 | 1.6 |
| ERLIN1 | O75477 | 12.9 | 1.2 | 1.4 | 1.4 | 1.4 | 1.8 | | 1.7 |
| SEC63 | Q9UGP8 | 17.7 | 1.4 | 1.4 | 1.7 | 1.5 | 1.2 | 1.8 | 2.0 |
| CYP2S1 | Q96SQ9 | 4.7 | 1.6 | 1.6 | 1.2 | 1.8 | 1.2 | 1.3 | 1.3 |
| PTGES | O14684 | 3.8 | 1.1 | 1.1 | 1.1 | 1.0 | 1.1 | 1.4 | |
| LMBR1 | Q8WVP7 | 20.0 | 1.3 | 1.2 | 1.0 | 1.3 | 1.0 | 1.5 | |
| SDHB | P21912 | 18.3 | 1.4 | 1.2 | 1.0 | 1.5 | 0.8 | 1.6 | 1.6 |

TABLE 4C-continued

A549 (A-DA) Competition

| GeneName | Accession | No UV | DMSO | Flurbiprofen (25 μM) | Rofecoxib (25 μM) | FK-866 (25 μM) | Avasimibe (25 μM) | Ro 48-8071 (5.0 μM) | Ro 48-8071 (50 μM) |
|---|---|---|---|---|---|---|---|---|---|
| SQRDL | Q9Y6N5 | 5.2 | 1.4 | 1.3 | 1.1 | 1.4 | 0.9 | 1.5 | 1.6 |
| TMED2 | Q15363 | 20.0 | 1.4 | 1.2 | 1.1 | 1.4 | 1.1 | 1.7 | 1.9 |
| PGRMC2 | O15173 | 20.0 | 1.5 | 1.3 | 1.2 | 1.2 | 1.4 | 1.6 | 2.1 |
| AAAS | Q9NRG9 | 5.6 | 1.3 | 1.1 | 1.0 | 1.5 | 1.2 | 1.8 | 1.9 |
| MBOAT7 | Q96N66 | 12.8 | 1.3 | 1.2 | 1.2 | 1.5 | 0.7 | 1.5 | 2.1 |
| TMX2 | Q9Y320 | 13.6 | 1.4 | 1.2 | 1.3 | 1.5 | 0.8 | 1.7 | 2.0 |
| SPTLC1 | O15269 | 20.0 | 1.4 | 1.2 | 1.1 | 1.3 | 1.0 | 1.4 | 2.1 |
| TMEM214 | Q6NUQ4 | 13.5 | 1.4 | 1.4 | 1.2 | 1.3 | 1.1 | 1.5 | 1.3 |
| HCCS | P53701 | 4.1 | 1.1 |  | 0.7 | 1.5 | 1.4 |  |  |
| UGDH | O60701 | 3.1 | 1.6 | 1.2 | 1.2 | 1.4 | 2.1 | 1.1 | 1.6 |
| KDELR3 | O43731 | 20.0 | 1.3 | 1.1 | 1.1 | 1.5 | 2.1 | 1.4 | 1.6 |
| RETSAT | Q6NUM9 | 12.4 | 1.4 | 1.3 | 1.2 | 1.4 | 1.7 | 1.5 | 1.9 |
| PTPLB | Q6Y1H2 | 3.3 | 1.1 | 1.1 | 1.4 | 1.2 | 1.2 | 1.4 |  |
| ADPGK | Q9BRR6 | 12.2 | 1.4 | 1.2 | 1.1 | 1.3 | 1.3 | 1.4 | 2.1 |
| ITGB1 | P05556 | 5.8 | 1.5 | 1.5 | 1.4 | 1.5 | 1.8 | 1.7 | 1.7 |
| ESYT2 | A0FGR8 | 11.9 | 1.4 | 1.3 | 1.1 | 1.3 | 1.4 | 1.1 | 1.6 |
| ABCD3 | P28288 | 11.4 | 1.3 | 1.4 | 1.2 | 1.6 | 1.2 | 1.2 | 1.1 |
| PIGS | Q96S52 | 11.5 | 1.3 | 1.1 | 1.5 |  | 1.1 | 1.4 | 1.9 |
| SPTLC2 | O15270 | 14.2 | 1.4 | 1.0 | 1.7 |  |  | 1.1 | 1.4 |
| ILVBL | A1L0T0 | 13.4 | 1.4 | 1.3 | 1.2 | 1.9 | 1.5 | 1.5 | 2.1 |
| ATL3 | Q6DD88 | 9.0 | 1.4 | 1.2 | 1.1 | 1.3 | 1.3 | 1.3 | 1.3 |
| TMEM245 | Q9H330 | 16.7 | 1.9 | 1.2 | 1.1 | 1.5 | 1.0 |  | 1.7 |
| SLC25A32 | Q9H2D1 | 18.1 | 1.0 | 1.1 | 1.0 | 1.3 | 1.4 | 1.5 | 1.5 |
| SIGMAR1 | Q99720 | 14.4 | 1.0 | 1.3 | 1.6 |  |  | 1.8 | 2.1 |
| VEZT | Q9HBM0 | 12.4 | 1.1 | 1.0 | 1.5 |  | 1.3 |  |  |
| RAB11A | P62491 | 7.1 | 1.2 | 1.1 | 1.0 | 1.5 | 1.5 | 1.3 | 1.8 |
| APOO | Q9BUR5 | 10.5 | 1.4 | 1.1 | 1.1 | 1.6 | 0.7 | 1.6 | 1.2 |
| ATP2B1 | P20020 | 5.0 | 1.2 | 1.1 | 1.1 | 1.3 | 1.6 | 1.5 | 1.1 |
| ERGIC1 | Q969X5 | 8.3 | 1.5 | 1.3 | 1.1 | 1.5 | 1.5 | 1.5 | 1.4 |
| ATP13A1 | Q9HD20 | 20.0 | 1.4 | 1.2 | 1.1 | 1.5 | 1.6 | 1.4 | 1.8 |
| PPT1 | P50897 | 20.0 | 1.0 | 1.2 | 1.6 |  | 0.6 | 2.1 | 1.3 |
| MARCH5 | Q9NX47 | 4.1 | 1.3 | 1.1 | 1.5 | 1.3 | 1.5 | 1.2 |  |
| ERLIN2 | O94905 | 12.8 | 1.3 | 1.3 | 1.4 | 1.4 | 1.8 |  | 1.4 |
| STOML2 | Q9UJZ1 | 3.7 | 1.4 | 1.4 | 1.1 | 1.5 | 1.3 | 1.5 | 1.3 |
| STT3B | Q8TCJ2 | 11.3 | 1.3 | 1.2 | 1.0 | 1.3 | 1.3 | 1.4 | 1.8 |
| AGPAT5 | Q9NUQ2 | 20.0 | 1.3 | 1.1 | 1.0 | 1.3 | 1.2 | 1.2 | 2.0 |
| HM13 | Q8TCT9 | 18.9 | 1.4 | 1.3 | 1.1 | 1.2 | 0.9 | 1.5 | 1.7 |
| CYC1 | P08574 | 3.7 | 1.5 | 1.3 | 1.2 | 1.6 | 1.6 | 1.5 | 1.5 |
| SLC27A2 | O14975 | 8.3 | 1.3 | 1.3 | 1.2 | 1.5 | 1.5 | 1.4 | 1.5 |
| DDOST | P39656 | 6.1 | 1.3 | 1.3 | 1.1 | 1.5 | 1.4 | 1.3 | 2.0 |
| IMMT | Q16891 | 4.3 | 1.4 | 1.1 | 1.1 | 1.4 | 1.1 | 1.3 | 0.9 |
| PTRH2 | Q9Y3E5 | 4.9 | 1.4 | 1.4 | 1.1 | 1.5 | 1.8 | 1.4 | 1.0 |
| STT3A | P46977 | 16.6 | 1.3 | 1.2 | 1.1 | 1.3 | 1.1 | 1.5 | 2.0 |
| GHITM | Q9H3K2 | 8.5 | 1.3 | 1.2 | 1.1 | 1.3 | 1.1 | 1.2 | 1.9 |
| DHRS7 | Q9Y394 | 9.0 | 1.4 | 1.2 | 1.1 | 1.3 | 1.3 | 1.4 | 1.5 |
| TECR | Q9NZ01 | 13.2 | 1.3 | 1.2 | 1.0 | 1.3 | 1.6 | 1.4 | 2.0 |
| SSR4 | P51571 | 6.9 | 1.4 | 1.4 | 1.1 | 1.4 | 1.4 | 1.4 | 1.5 |
| TIMM50 | Q3ZCQ8 | 6.0 | 1.3 | 1.2 | 1.2 | 1.3 | 1.3 | 1.5 | 1.2 |
| FAM162A | Q96A26 | 5.5 | 1.3 | 1.3 | 1.1 | 1.3 | 0.9 | 1.7 | 1.6 |
| REEP5 | Q00765 | 4.9 | 1.3 | 1.3 | 1.2 | 1.3 | 1.3 | 1.4 | 2.0 |
| LRRC59 | Q96AG4 | 7.9 | 1.4 | 1.3 | 1.0 | 1.3 | 0.8 | 1.3 | 1.6 |
| PHB2 | Q99623 | 8.3 | 1.2 | 1.1 | 1.0 | 1.2 | 0.8 | 1.4 | 1.4 |
| SSR1 | P43307 | 20.0 | 1.3 | 1.1 | 1.1 | 1.4 | 1.0 | 1.5 | 2.0 |
| ZMPSTE24 | O75844 | 15.7 | 1.3 | 1.2 | 1.1 | 1.3 | 1.0 | 1.5 | 1.9 |
| SPCS2 | Q15005 | 12.7 | 1.3 | 1.2 | 1.1 | 1.3 | 1.3 | 1.5 | 1.6 |
| DOLK | Q9UPQ8 | 20.0 | 1.2 | 1.2 | 1.1 | 1.4 | 1.2 | 1.3 | 1.4 |
| SEC61A2 | Q9H9S3 | 11.9 | 1.1 | 1.2 | 1.6 |  |  | 1.7 | 2.0 |
| KDELR2 | P33947 | 16.1 | 1.1 | 1.0 | 1.1 | 1.3 | 1.2 | 1.3 | 1.5 |
| RPN2 | P04844 | 4.8 | 1.4 | 1.2 | 1.1 | 1.5 | 1.4 | 1.5 | 1.6 |
| TMEM205 | Q6UW68 | 5.8 | 1.5 | 1.3 | 1.2 | 1.4 | 1.2 | 1.5 | 1.2 |
| TMED7 | Q9Y3B3 | 9.6 | 1.3 | 1.2 | 1.0 | 1.3 | 1.0 | 1.3 | 1.8 |
| DHCR7 | Q9UBM7 | 5.2 | 1.4 | 1.2 | 1.0 | 1.4 | 1.4 | 1.2 | 1.5 |
| TTRAP3 | Q6JUT2 | 9.6 | 1.1 | 0.9 | 0.7 |  |  |  | 1.8 |
| PTPLAD1 | Q9P035 | 8.9 | 1.3 | 1.2 | 1.1 | 1.2 | 0.9 | 1.5 | 1.9 |
| AIFM1 | O95831 | 4.1 | 1.4 | 1.2 | 1.1 | 1.5 | 0.9 | 1.4 | 1.2 |
| TMED10 | P49755 | 5.6 | 1.3 | 1.2 | 1.1 | 1.4 | 1.6 | 1.4 | 1.7 |
| ATL2 | Q8NHH9 | 12.9 | 1.5 | 1.3 | 1.0 | 1.3 | 1.2 | 1.5 | 1.8 |
| BCAP31 | P51572 | 5.2 | 1.4 | 1.2 | 1.1 | 1.2 | 1.5 | 1.5 | 1.9 |
| SAMM50 | Q9Y512 | 10.2 | 1.3 | 1.1 | 1.1 | 1.3 | 0.3 | 1.1 | 1.0 |
| SLC25A13 | Q9UJS0 | 4.1 | 1.4 | 1.2 | 1.1 | 1.4 | 1.4 | 1.3 | 1.0 |
| SURF4 | O15260 | 8.4 | 1.2 | 1.1 | 1.0 | 1.3 | 1.3 | 1.4 | 1.8 |
| SCAMP2 | O15127 | 20.0 | 1.1 | 1.1 | 1.1 | 1.3 | 1.5 | 1.9 | 1.9 |
| TPP1 | O14773 | 5.3 | 1.2 | 1.3 | 1.1 | 1.0 | 0.9 | 1.1 | 0.6 |
| DPY19L1 | Q2PZI1 | 13.1 | 1.6 | 1.3 | 1.1 | 1.3 | 1.1 | 1.8 | 1.9 |
| SUN1 | O94901 | 11.9 | 1.4 | 1.2 | 1.7 | 1.3 | 1.3 | 1.4 | 1.7 |

TABLE 4C-continued

| | | | | A549 (A-DA) Competition | | | | |
|---|---|---|---|---|---|---|---|---|
| GeneName | Accession | No UV | DMSO | Flurbiprofen (25 μM) | Rofecoxib (25 μM) | FK-866 (25 μM) | Avasimibe (25 μM) | Ro 48-8071 (5.0 μM) | Ro 48-8071 (50 μM) |
| ATAD3A | Q9NVI7 | 3.3 | 1.2 | 1.6 | 1.9 | 1.2 | 1.2 | | |
| PEX11B | O96011 | 3.3 | 1.4 | 1.1 | 1.1 | 1.2 | 1.2 | 1.1 | |
| ACADVL | P49748 | 3.7 | 1.3 | 1.2 | 1.1 | 1.9 | 1.3 | 1.4 | 1.1 |
| TMEM33 | P57088 | 4.2 | 1.3 | 1.2 | 1.0 | 1.2 | 1.0 | 1.3 | 1.4 |
| HSD17B4 | P51659 | 3.0 | 1.4 | 1.2 | 1.1 | 1.5 | 1.9 | 1.2 | 1.5 |
| MGST1 | P10620 | 4.7 | 1.3 | 1.3 | 1.1 | 1.3 | 0.9 | 1.3 | 1.4 |
| TFRC | P02786 | 4.6 | 1.5 | 1.2 | 1.2 | 1.5 | 1.8 | 1.5 | 1.6 |
| RAB1B | Q9H0U4 | 3.8 | 1.3 | 1.2 | 1.1 | 1.5 | 1.6 | 1.3 | 1.2 |
| ITPRIP | Q8IWB1 | 13.4 | 1.4 | 1.2 | 1.7 | 1.4 | 1.0 | 1.4 | 1.8 |
| KDELR1 | P24390 | 20.0 | 1.1 | 1.0 | 1.2 | 1.3 | 1.3 | 1.2 | 1.8 |
| HTATIP2 | Q9BUP3 | 6.4 | 1.3 | 1.3 | 1.0 | 1.4 | 1.3 | 1.2 | 1.6 |
| TMEM126A | Q9H061 | 13.9 | 1.2 | 1.1 | 1.0 | 1.2 | 0.9 | 1.4 | 1.6 |
| MGST3 | O14880 | 3.5 | 1.3 | 1.2 | 1.2 | 1.5 | 1.6 | 1.3 | 1.0 |
| OPA3 | Q9H6K4 | 20.0 | 1.3 | 1.1 | 1.1 | 1.3 | 0.7 | 1.8 | |
| PHB | P35232 | 5.1 | 1.3 | 1.1 | 1.1 | 1.4 | 1.0 | 1.4 | 1.2 |
| TMEM43 | Q9BTV4 | 6.9 | 1.3 | 1.2 | 1.0 | 1.4 | 1.2 | 1.5 | 1.6 |
| ERP44 | Q9BS26 | 11.8 | 1.1 | 1.1 | 1.4 | | | | 1.8 |
| ANXA1 | P04083 | 3.8 | 1.3 | 1.3 | 1.2 | 1.5 | 1.2 | 1.1 | 1.5 |
| ARF1 | P84077 | 5.2 | 1.4 | 1.3 | 1.1 | 1.4 | 1.5 | 1.2 | 1.5 |
| ARF3 | P61204 | 5.2 | 1.5 | 1.4 | | 1.4 | 1.5 | | 1.5 |
| SFXN3 | Q9BWM7 | 4.3 | 1.2 | 1.1 | 1.5 | 1.3 | 1.1 | 1.3 | 1.2 |
| SCO1 | O75880 | 5.7 | 1.3 | 1.1 | 1.6 | | | 1.6 | 1.8 |
| HSDL1 | Q3SXM5 | 20.0 | 1.4 | 1.1 | 1.0 | 1.3 | 1.6 | 1.4 | 1.3 |
| SACM1L | Q9NTJ5 | 5.3 | 1.2 | 1.2 | 1.0 | 1.3 | 1.2 | 1.5 | 1.5 |
| CISD1 | Q9NZ45 | 3.7 | 1.1 | 1.1 | 1.1 | 1.3 | 1.0 | 1.2 | |
| ESYT1 | Q9BSJ8 | 4.3 | 1.5 | 1.2 | 1.5 | 1.4 | 1.2 | 1.4 | 1.4 |
| TMX3 | Q96JJ7 | 6.4 | 1.2 | 1.0 | 1.3 | 1.2 | 1.3 | 1.5 | 1.8 |
| GNPAT | O15228 | 4.4 | 1.2 | 1.1 | 1.2 | 1.3 | 1.5 | 1.4 | 1.6 |
| SLC25A24 | Q6NUK1 | 4.3 | 1.3 | 1.1 | 1.4 | 1.2 | 0.9 | 1.2 | 1.1 |
| ACOX1 | Q15067 | 3.6 | 1.3 | 1.2 | 1.6 | 1.5 | 1.2 | 1.2 | 1.2 |
| ARF4 | P18085 | 5.6 | 1.4 | 1.3 | 1.2 | 1.5 | 1.5 | 1.2 | 1.6 |
| LMAN1 | P49257 | 20.0 | 1.3 | 1.2 | 1.3 | 1.3 | 1.3 | 1.4 | 1.7 |
| SLC25A1 | P53007 | 3.1 | 1.3 | 1.1 | 1.0 | 1.2 | 0.9 | 1.3 | 1.0 |
| ARF5 | P84085 | 13.6 | 1.4 | 1.4 | 1.1 | 1.4 | 1.5 | 1.1 | |
| TMEM19 | Q96HH6 | 14.4 | 1.1 | 1.0 | 1.1 | | | | |
| TIMM23 | O14925 | 3.5 | 1.2 | 1.0 | 0.9 | 1.3 | 1.1 | 1.1 | 1.3 |
| TSPAN6 | O43657 | 20.0 | 1.3 | 1.1 | 0.9 | 1.3 | 0.9 | | |
| OXA1L | Q15070 | 5.8 | 1.4 | 1.4 | 1.0 | 1.3 | 0.8 | 1.6 | 1.3 |
| RDH11 | Q8TC12 | 8.6 | 1.4 | 1.3 | 1.1 | 1.3 | 1.2 | 1.5 | 1.5 |
| APOOL | Q6UXV4 | 20.0 | 1.3 | 1.1 | 1.0 | 1.1 | 1.1 | 1.6 | 1.7 |
| MPV17 | P39210 | 3.1 | 1.1 | 1.1 | 1.7 | | | 1.3 | 1.0 |
| CLN6 | Q9NWW5 | 3.6 | 1.0 | 1.1 | 1.4 | | 1.5 | | |
| MT-ND2 | P03891 | 20.0 | 1.3 | 1.1 | 1.1 | 1.3 | 1.6 | 1.5 | 1.2 |
| TOMM40 | O96008 | 3.7 | 1.2 | 1.2 | 1.1 | 1.3 | 1.5 | 1.4 | 1.1 |
| MTCH2 | Q9Y6C9 | 12.6 | 1.3 | 1.2 | 1.0 | 1.4 | 1.2 | 1.2 | 1.1 |
| CKAP4 | Q07065 | 8.1 | 1.1 | 1.1 | 0.9 | 1.0 | 1.1 | 1.2 | 1.7 |
| MTCH1 | Q9NZJ7 | 3.1 | 1.2 | 1.1 | 1.3 | 1.1 | 1.0 | 1.4 | 1.3 |
| IKBIP | Q70UQ0 | 4.7 | 1.0 | 1.1 | 1.1 | 1.3 | 1.2 | 1.4 | |
| ATP5F1 | P24539 | 5.7 | 1.2 | 1.1 | 1.1 | 1.3 | 0.9 | 1.5 | 1.1 |
| CAPN2 | P17655 | 4.4 | 1.1 | 1.1 | 1.4 | | 1.3 | 1.3 | 1.6 |
| VDAC3 | Q9Y277 | 4.9 | 1.2 | 1.1 | 1.0 | 1.2 | 1.2 | 1.2 | 1.1 |
| BRI3BP | Q8WY22 | 6.6 | 1.2 | 1.5 | 1.1 | 1.0 | 0.8 | 1.5 | 1.6 |
| SRP68 | Q9UHB9 | 4.5 | 1.2 | 1.0 | 1.6 | | | 1.4 | 1.5 |
| AGK | Q53H12 | 5.1 | 1.3 | 1.1 | 1.3 | 1.3 | 1.3 | 1.0 | 1.2 |
| NCLN | Q969V3 | 12.6 | 1.4 | 1.2 | 1.5 | 1.1 | 1.2 | 1.3 | 1.6 |
| MCU | Q8NE86 | 9.7 | 1.2 | 1.1 | 1.0 | 1.6 | 0.8 | 1.3 | 1.1 |
| Uncharacterized | H3BN98 | 4.7 | 1.3 | 1.1 | 1.0 | 1.2 | 1.0 | 1.1 | 1.4 |
| SLC25A5 | P05141 | 3.6 | 1.2 | 1.1 | 1.0 | 1.2 | 1.0 | 1.3 | 1.1 |
| ERGIC2 | Q96RQ1 | 20.0 | 1.3 | 1.1 | 1.3 | 1.3 | 1.3 | 1.2 | 1.5 |
| NNT | Q13423 | 20.0 | 1.3 | 1.1 | 0.9 | 1.4 | 0.4 | 1.0 | 0.9 |
| SLC25A4 | P12235 | 3.9 | 1.2 | 1.0 | 1.0 | 1.1 | 1.0 | 1.3 | 1.1 |
| NDUFA10 | O95299 | 4.3 | 1.5 | | 1.4 | 1.5 | 1.2 | 1.5 | 1.3 |
| SLC25A6 | P12236 | 3.6 | 1.2 | 1.0 | 1.0 | 1.1 | 1.0 | 1.3 | 1.1 |
| EIF5AL1 | Q6IS14 | 3.8 | 1.3 | 1.3 | 1.4 | | | 1.1 | 1.4 |
| UBC | P0CG48 | 4.0 | 1.3 | 1.0 | | | 0.8 | 1.4 | 1.3 |
| SUN2 | Q9UH99 | 20.0 | 1.3 | 1.1 | 1.2 | | | 1.3 | 1.3 |
| SERPINE2 | P07093 | 4.5 | 1.0 | 0.8 | 1.1 | | 0.9 | | |

TABLE 4D

A549 (AEA-DA) Competition

| Gene Name | Accession | No UV | DMSO | FK866 (25 μM) |
|---|---|---|---|---|
| NAMPT | P43490 | 20.0 | 1.3 | 20.0 |
| DHRS1 | Q96LJ7 | 20.0 | 1.3 | 20.0 |
| EPHX2 | P34913 | 20.0 | 1.3 | 20.0 |
| FECH | P22830 | 20.0 | 1.3 | 13.7 |
| AKR1C1 | Q04828 | 17.8 | 1.2 | 9.3 |
| AKR1C2 | P52895 | 17.8 | 1.3 | 9.2 |
| SCCPDH | Q8NBX0 | 20.0 | 1.1 | 8.1 |
| ALDH1A1 | P00352 | 14.9 | 1.3 | 7.6 |
| AKR1C3 | P42330 | 18.4 | 1.3 | 6.0 |
| PTGR2 | Q8N8N7 | 20.0 | 1.2 | 5.1 |
| PON2 | Q15165 | 20.0 | 1.2 | 2.9 |
| CYP4F12 | Q9HCS2 | 20.0 | 1.0 | 2.4 |
| CPT2 | P23786 | 20.0 | 1.3 | 2.3 |
| HADHA | P40939 | 20.0 | 1.3 | 1.8 |
| AKR1B15 | C9JRZ8 | 14.7 | 1.3 | 1.8 |
| AKR1B10 | O60218 | 9.9 | 1.2 | 1.7 |
| ALDH3A1 | P30838 | 20.0 | 1.2 | 1.7 |
| ACADVL | P49748 | 6.6 | 1.2 | 1.5 |
| UGT1A9 | O60656 | 20.0 | 1.3 | 1.5 |
| UGT1A7 | Q9HAW7 | 20.0 | 1.3 | 1.5 |
| NENF | Q9UMX5 | 20.0 | 1.1 | 1.4 |
| ALDH2 | P05091 | 3.8 | 1.1 | 1.4 |
| YWHAZ | P63104 | 3.0 | 1.3 | 1.3 |
| TMEM97 | Q5BJF2 | 20.0 | 1.0 | 1.3 |
| EPHX1 | P07099 | 8.1 | 1.3 | 1.2 |
| NDUFS2 | O75306 | 20.0 | 1.5 | 1.2 |
| SLC25A20 | O43772 | 20.0 | 1.2 | 1.2 |
| UGDH | O60701 | 3.6 | 1.2 | 1.1 |
| ABHD10 | Q9NUJ1 | 20.0 | 1.3 | 1.1 |
| EEF1A1 | P68104 | 3.1 | 1.3 | 1.1 |
| NQO1 | P15559 | 14.5 | 1.3 | 1.1 |
| GPX2 | P18283 | 20.0 | 1.3 | 1.0 |
| ILVBL | A1L0T0 | 20.0 | 1.5 | 1.0 |
| MGST3 | O14880 | 4.1 | 1.1 | 1.0 |
| TUBA1A | Q71U36 | 5.4 | 1.1 | 1.0 |
| ECH1 | Q13011 | 20.0 | 1.2 | 1.0 |
| TUBA4A | P68366 | 5.3 | 1.3 | 1.0 |
| CYP51A1 | Q16850 | 20.0 | 1.2 | 1.0 |
| TSPO | P30536 | 20.0 | 1.0 | 1.0 |
| CYP4F11 | Q9HBI6 | 20.0 | 1.2 | 1.0 |
| B4GALT1 | P15291 | 8.4 | 1.3 | 1.0 |
| TUBA8 | Q9NY65 | 11.3 | 1.3 | 1.0 |
| CES1 | P23141 | 5.9 | 1.0 | 1.0 |
| TUBB2B | Q9BVA1 | 8.0 | 1.1 | 1.0 |
| TUBB3 | Q13509 | 7.8 | 1.1 | 1.0 |
| TUBB4B | P68371 | 8.1 | 1.1 | 1.0 |
| CSNK1A1 | P48729 | 17.5 | 1.1 | 1.0 |
| TUBB | P07437 | 8.9 | 1.1 | 1.0 |
| PFN1 | P07737 | 6.4 | 1.2 | 1.0 |
| SLC27A2 | O14975 | 6.2 | 1.2 | 1.0 |
| MPV17 | P39210 | 15.7 | 1.7 | 0.9 |
| MGST1 | P10620 | 3.9 | 1.2 | 0.9 |
| PHB | P35232 | 6.1 | 1.2 | 0.9 |
| CTSD | P07339 | 20.0 | 1.1 | 0.9 |
| VDAC2 | P45880 | 20.0 | 1.1 | 0.9 |
| LPGAT1 | Q92604 | 7.8 | 1.1 | 0.9 |
| PITRM1 | Q5JRX3 | 20.0 | 1.3 | 0.9 |
| CLPP | Q16740 | 20.0 | 1.2 | 0.9 |
| PSMB2 | P49721 | 20.0 | 1.3 | 0.9 |
| KDELR1 | P24390 | 19.7 | 1.1 | 0.9 |
| DHCR24 | Q15392 | 20.0 | 1.1 | 0.9 |
| YWHAG | P61981 | 3.2 | 1.0 | 0.9 |
| HSP90AB1 | P08238 | 3.2 | 1.2 | 0.9 |
| ALDH1B1 | P30837 | 20.0 | 1.1 | 0.9 |
| PPT1 | P50897 | 20.0 | 1.1 | 0.9 |
| ARF1 | P84077 | 13.6 | 1.4 | 0.9 |
| ARF5 | P84085 | 15.0 | 1.4 | 0.9 |
| MYH9 | P35579 | 3.0 | 1.4 | 0.9 |
| RETSAT | Q6NUM9 | 15.5 | 1.4 | 0.9 |
| KDELR2 | P33947 | 20.0 | 1.0 | 0.9 |
| SCARB1 | Q8WTV0 | 20.0 | 1.1 | 0.9 |
| HSPA1B | P08107 | 3.4 | 1.2 | 0.8 |
| PON3 | Q15166 | 20.0 | 1.2 | 0.8 |
| SEC61A1 | P61619 | 8.4 | 1.1 | 0.8 |
| ANXA1 | P04083 | 7.0 | 1.2 | 0.8 |
| APMAP | Q9HDC9 | 15.7 | 1.2 | 0.8 |
| KDELR3 | O43731 | 20.0 | 1.1 | 0.8 |
| VDAC1 | P21796 | 20.0 | 1.1 | 0.8 |
| CCT2 | P78371 | 20.0 | 1.2 | 0.8 |
| ITGB1 | P05556 | 6.8 | 1.2 | 0.8 |
| FASN | P49327 | 3.6 | 1.4 | 0.8 |
| TIMM23 | O14925 | 20.0 | 1.2 | 0.8 |
| AIFM1 | O95831 | 6.7 | 1.3 | 0.8 |
| GPD2 | P43304 | 9.8 | 1.2 | 0.8 |
| DERL1 | Q9BUN8 | 11.6 | 1.3 | 0.8 |
| PCYOX1 | Q9UHG3 | 20.0 | 1.2 | 0.8 |
| KPNB1 | Q14974 | 3.3 | 1.1 | 0.8 |
| ANXA2 | P07355 | 3.9 | 1.1 | 0.8 |
| TMED10 | P49755 | 7.1 | 1.3 | 0.8 |
| ABHD12 | Q8N2K0 | 15.8 | 1.0 | 0.8 |
| PTPLAD1 | Q9P035 | 7.2 | 1.3 | 0.8 |
| CPT1A | P50416 | 14.8 | 1.4 | 0.8 |
| GLB1 | P16278 | 20.0 | 1.2 | 0.8 |
| HSD17B4 | P51659 | 5.3 | 1.3 | 0.8 |
| PTGES2 | Q9H7Z7 | 20.0 | 1.2 | 0.8 |
| ARF4 | P18085 | 14.8 | 1.3 | 0.8 |
| RPN2 | P04844 | 10.0 | 1.4 | 0.8 |
| ALDH3A2 | P51648 | 15.6 | 1.2 | 0.8 |
| TMED7 | Q9Y3B3 | 6.8 | 1.0 | 0.8 |
| STT3B | Q8TCJ2 | 8.8 | 1.2 | 0.8 |
| HSD17B12 | Q53GQ0 | 20.0 | 1.2 | 0.8 |
| CYB5R3 | O43169 | 9.6 | 1.3 | 0.8 |
| SURF4 | O15260 | 9.5 | 1.1 | 0.8 |
| ACOX1 | Q15067 | 4.4 | 1.3 | 0.8 |
| NCEH1 | Q6PIU2 | 8.7 | 1.2 | 0.8 |
| LRRC59 | Q96AG4 | 6.8 | 1.0 | 0.8 |
| POC1B-GALNT4 | F8VUJ3 | 20.0 | 1.0 | 0.8 |
| GALNT4 | Q8N4A0 | 20.0 | 1.0 | 0.8 |
| PABPC1 | P11940 | 4.5 | 1.5 | 0.8 |
| COMT | P21964 | 6.8 | 1.2 | 0.8 |
| GANAB | Q14697 | 4.3 | 1.4 | 0.8 |
| RCN2 | Q14257 | 20.0 | 1.4 | 0.8 |
| SGPL1 | O95470 | 20.0 | 1.3 | 0.8 |
| STT3A | P46977 | 14.2 | 1.1 | 0.8 |
| CANX | P27824 | 9.0 | 1.2 | 0.7 |
| HSD17B10 | Q99714 | 3.7 | 1.3 | 0.7 |
| STOML2 | Q9UJZ1 | 5.3 | 1.2 | 0.7 |
| ALG1 | Q9BT22 | 7.4 | 1.0 | 0.7 |
| HNRNPM | P52272 | 3.2 | 1.2 | 0.7 |
| ENDOD1 | O94919 | 20.0 | 1.3 | 0.7 |
| PGRMC2 | O15173 | 20.0 | 1.2 | 0.7 |
| KDSR | Q06136 | 20.0 | 1.3 | 0.7 |
| AUP1 | Q9Y679 | 6.6 | 1.0 | 0.7 |
| BSG | P35613 | 20.0 | 1.3 | 0.7 |
| HSP90B1 | P14625 | 3.9 | 1.1 | 0.7 |
| SQLE | Q14534 | 20.0 | 1.2 | 0.7 |
| SPTBN1 | Q01082 | 7.6 | 1.1 | 0.7 |
| KPNA2 | P52292 | 13.4 | 1.3 | 0.7 |
| SPTLC1 | O15269 | 20.0 | 1.2 | 0.7 |
| SLC25A3 | Q00325 | 3.3 | 1.1 | 0.7 |
| PCK2 | Q16822 | 15.9 | 1.3 | 0.7 |
| TRAM1 | Q15629 | 20.0 | 1.1 | 0.7 |
| TIMM17B | O60830 | 20.0 | 1.2 | 0.7 |
| SRP68 | Q9UHB9 | 12.1 | 1.3 | 0.7 |
| MT-CO2 | P00403 | 9.9 | 1.3 | 0.7 |
| TIMM50 | Q3ZCQ8 | 12.7 | 1.3 | 0.7 |
| RTN4 | Q9NQC3 | 20.0 | 1.3 | 0.7 |
| PSMB1 | P20618 | 20.0 | 1.2 | 0.7 |
| ZMPSTE24 | O75844 | 19.7 | 1.2 | 0.7 |
| PHB2 | Q99623 | 6.9 | 1.2 | 0.7 |
| ATP2A2 | P16615 | 8.2 | 1.1 | 0.7 |
| TSPAN6 | O43657 | 20.0 | 1.2 | 0.7 |
| DDOST | P39656 | 7.7 | 1.4 | 0.7 |
| ASPH | Q12797 | 6.0 | 1.2 | 0.7 |
| SLC25A11 | Q02978 | 3.9 | 1.3 | 0.7 |
| RPN1 | P04843 | 7.1 | 1.1 | 0.7 |
| ATP5B | P06576 | 4.7 | 1.3 | 0.7 |
| P4HB | P07237 | 5.2 | 1.0 | 0.7 |
| NAGLU | P54802 | 20.0 | 1.0 | 0.7 |
| ACTN1 | P12814 | 4.8 | 1.3 | 0.7 |
| PSAP | P07602 | 20.0 | 1.2 | 0.7 |
| CLPTM1 | O96005 | 17.9 | 1.3 | 0.7 |

TABLE 4D-continued

A549 (AEA-DA) Competition

| Gene Name | Accession | No UV | DMSO | FK866 (25 μM) |
|---|---|---|---|---|
| HNRNPF | P52597 | 3.8 | 1.3 | 0.7 |
| ATP5A1 | P25705 | 4.6 | 1.2 | 0.7 |
| ACTN4 | O43707 | 4.5 | 1.2 | 0.7 |
| UQCRC1 | P31930 | 5.8 | 1.3 | 0.7 |
| ATP5F1 | P24539 | 15.0 | 1.3 | 0.7 |
| CCDC47 | Q96A33 | 11.8 | 1.1 | 0.7 |
| MTCH2 | Q9Y6C9 | 12.3 | 1.2 | 0.7 |
| NUCB2 | P80303 | 20.0 | 1.3 | 0.7 |
| APOL2 | Q9BQE5 | 20.0 | 1.1 | 0.7 |
| GHITM | Q9H3K2 | 5.8 | 1.2 | 0.7 |
| POR | P16435 | 20.0 | 1.2 | 0.7 |
| HSPA1L | Q53FA3 | 11.4 | 1.2 | 0.7 |
| AGK | Q53H12 | 3.5 | 1.5 | 0.7 |
| VDAC3 | Q9Y277 | 10.9 | 1.3 | 0.7 |
| RAB2A | P61019 | 5.1 | 1.2 | 0.7 |
| SLC25A13 | Q9UJS0 | 13.2 | 1.3 | 0.7 |
| SLC25A5 | P05141 | 5.4 | 1.2 | 0.7 |
| DLD | P09622 | 3.4 | 1.2 | 0.7 |
| ACSL3 | O95573 | 6.9 | 1.2 | 0.7 |
| PRCP | P42785 | 20.0 | 1.1 | 0.7 |
| DDX3X | O00571 | 3.2 | 1.2 | 0.7 |
| HNRNPA2B1 | P22626 | 3.4 | 1.2 | 0.7 |
| SCARB2 | Q14108 | 20.0 | 1.1 | 0.7 |
| SDHB | P21912 | 20.0 | 1.3 | 0.7 |
| PRDX3 | P30048 | 3.5 | 1.3 | 0.7 |
| SEL1L | Q9UBV2 | 20.0 | 1.1 | 0.7 |
| PRKDC | P78527 | 3.5 | 1.2 | 0.7 |
| ECE1 | P42892 | 20.0 | 1.2 | 0.7 |
| UQCRC2 | P22695 | 4.4 | 1.0 | 0.7 |
| HMOX2 | P30519 | 20.0 | 1.2 | 0.7 |
| DECR1 | Q16698 | 19.3 | 1.3 | 0.7 |
| SFPQ | P23246 | 4.0 | 1.1 | 0.7 |
| EPDR1 | Q9UM22 | 20.0 | 1.1 | 0.7 |
| ITGA3 | P26006 | 18.0 | 1.7 | 0.6 |
| LNPEP | Q9UIQ6 | 20.0 | 1.4 | 0.6 |
| SLC25A6 | P12236 | 6.0 | 1.2 | 0.6 |
| SLC25A4 | P12235 | 5.9 | 1.1 | 0.6 |
| SRPRB | Q9Y5M8 | 20.0 | 1.2 | 0.6 |
| XRCC6 | P12956 | 5.8 | 1.3 | 0.6 |
| TIMM17A | Q99595 | 20.0 | 1.2 | 0.6 |
| HNRNPR | O43390 | 3.5 | 1.2 | 0.6 |
| RAB11B | Q15907 | 17.2 | 1.2 | 0.6 |
| RAB11A | P62491 | 17.2 | 1.3 | 0.6 |
| HEATR3 | Q7Z4Q2 | 20.0 | 1.4 | 0.6 |
| BRI3BP | Q8WY22 | 20.0 | 1.3 | 0.6 |
| MTDH | Q86UE4 | 20.0 | 1.1 | 0.6 |
| HSPA8 | P11142 | 6.3 | 1.2 | 0.6 |
| HNRPDL | O14979 | 3.5 | 1.2 | 0.6 |
| NUCB1 | Q02818 | 20.0 | 1.3 | 0.6 |
| IMMT | Q16891 | 12.8 | 1.4 | 0.6 |
| VIM | P08670 | 20.0 | 1.6 | 0.6 |
| CAV1 | Q03135 | 20.0 | 1.3 | 0.6 |
| PSMB5 | P28074 | 20.0 | 1.3 | 0.6 |
| GLG1 | Q92896 | 20.0 | 1.3 | 0.6 |
| ANKLE2 | Q86XL3 | 20.0 | 1.1 | 0.6 |
| CTSB | P07858 | 5.0 | 1.1 | 0.6 |
| HNRNPH1 | P31943 | 4.7 | 1.2 | 0.6 |
| HNRNPC | P07910 | 3.4 | 1.3 | 0.6 |
| ATL3 | Q6DD88 | 7.0 | 1.0 | 0.6 |
| TMEM126A | Q9H061 | 20.0 | 1.2 | 0.6 |
| ATP13A1 | Q9HD20 | 20.0 | 1.2 | 0.6 |
| SQRDL | Q9Y6N5 | 7.6 | 1.2 | 0.6 |
| SEC11A | P67812 | 14.0 | 1.0 | 0.6 |
| HSPA5 | P11021 | 11.8 | 1.3 | 0.6 |
| ESYT1 | Q9BSJ8 | 3.9 | 1.0 | 0.6 |
| SLC25A10 | B4DLN1 | 20.0 | 1.2 | 0.6 |
| SCPEP1 | Q9HB40 | 20.0 | 1.0 | 0.6 |
| NONO | Q15233 | 6.3 | 1.0 | 0.6 |
| OCIAD1 | Q9NX40 | 17.2 | 1.1 | 0.6 |
| SHMT2 | P34897 | 16.7 | 1.1 | 0.6 |
| SYNCRIP | O60506 | 4.1 | 1.3 | 0.6 |
| TOMM22 | Q9NS69 | 20.0 | 1.1 | 0.6 |
| CKAP4 | Q07065 | 9.9 | 1.1 | 0.6 |
| LMNB1 | P20700 | 6.1 | 1.2 | 0.6 |
| BZW1 | Q7L1Q6 | 20.0 | 1.2 | 0.6 |
| LMNA | P02545 | 5.6 | 1.3 | 0.5 |
| HM13 | Q8TCT9 | 20.0 | 1.3 | 0.5 |
| HNRNPH2 | P55795 | 4.5 | 1.2 | 0.5 |
| IKBIP | Q70UQ0 | 15.6 | 1.2 | 0.5 |
| SLC25A12 | O75746 | 20.0 | 1.6 | 0.4 |
| HEXA | P06865 | 20.0 | 1.5 | 0.4 |

TABLE 5

| Gene Name | Accession | Description | Neuro2a Cells AEA-DA | | | | | | | A549 Cells A-DA | |
|---|---|---|---|---|---|---|---|---|---|---|---|
| | | | NoUV | DMSO | AEA (200 uM) | FK866 (25 uM) | Avasimibe (25 uM) | Elacridar (25 uM) | Ro 48-8071 (25 uM) | MJN228 (25 uM) | NoUV | DMSO |
| ABCB1B | P06795 | Abcb1b Multidrug resistance protein 1B | 20.0 | 1.1 | 2.3 | 5.4 | 1.8 | 20.0 | 1.7 | 4.0 | — | — |
| NAMPT | P43490 | NAMPT Nicotinamide phosphoribosyl-transferase | 20.0 | 1.4 | 1.1 | 16.4 | 1.3 | 1.1 | 0.9 | 1.2 | 12.8 | 1.6 |
| LSS | P48449 | LSS Lanosterol synthase | — | — | — | — | — | — | — | — | 20.0 | 1.5 |
| SOAT1 | Q61263 | Soat1 Sterol O-acyltransferase 1 | 6.1 | 1.2 | — | 2.3 | 6.4 | 1.5 | 1.8 | 2.6 | 12.6 | 1.3 |
| NUCB1 | Q02819 | Nucb1 Nucleobindin-1 | 20.0 | 1.3 | 1.5 | 1.2 | 2.1 | 1.3 | 0.9 | 4.7 | 15.2 | 1.4 |
| EPHX2 | P34913 | EPHX2 Bifunctional epoxide hydrolase 2 | — | — | — | — | — | — | — | — | — | — |

TABLE 5-continued

| | | | | | | | | | | | |
|---|---|---|---|---|---|---|---|---|---|---|---|
| PNPLA6 | Q8IY17 | PNPLA6 Neuropathy target esterase | — | — | — | — | — | — | — | 14.2 | 1.2 |
| TMEM97 | Q8VD00 | Tmem97 Transmembrane protein 97 | 20.0 | 1.1 | 1.8 | 1.0 | 1.7 | 18.7 | 10.0 | 1.7 | 20.0 | 1.4 |
| ABHD5 | Q8WTS1 | ABHD5 1-acylglycerol-3-phosphate O-acyltransferase ABHD5 | 20.0 | 1.3 | 1.3 | 1.0 | 12.3 | 1.3 | 1.4 | 2.2 | 20.0 | 1.5 |
| DHRS1 | Q96LJ7 | DHRS1 Dehydrogenase/reductase SDR family member 1 | 20.0 | 1.1 | 18.4 | 8.0 | 2.1 | 1.5 | 9.5 | 1.8 | 20.0 | 1.6 |
| APOL2 | Q9BQE5 | APOL2 Apolipoprotein L2 | — | — | — | — | — | — | — | — | 20.0 | 1.4 |
| FAM114A2 | Q9NRY5 | FAM114A2 Protein FAM114A2 | 20.0 | 1.4 | 1.4 | 1.0 | 2.7 | 1.5 | 1.6 | 3.5 | 20.0 | 1.4 |
| TIMM17B | O60830 | TIMM17B Mitochondrial import inner membrane translocase subunit | 20.0 | 1.4 | 1.6 | 1.2 | 5.1 | 1.5 | 2.8 | 1.5 | 20.0 | 1.3 |
| FECH | P22315 | Fech Ferrochelatase, mitochondrial | 20.0 | 1.0 | 1.3 | 20.0 | 0.2 | 20.0 | 1.4 | 2.4 | 13.8 | 1.4 |
| NPC1 | O15118 | NPC1 Niemann-Pick C1 protein | — | — | — | — | — | — | — | — | 20.0 | 1.4 |
| FA2H | Q7L5A8 | FA2H Fatty acid 2-hydroxylase | — | — | — | — | — | — | — | — | 17.2 | 1.7 |
| EBP | Q15125 | EBP 3-beta-hydroxysteroid-Delta(8),Delta(7)-isomerase | — | — | — | — | — | — | — | — | 20.0 | 1.0 |
| EPHX1 | Q9D379 | Ephx1 Epoxide hydrolase 1 | 4.0 | 1.0 | 2.1 | 1.4 | 18.6 | 1.8 | 2.4 | 3.8 | 7.6 | 1.5 |
| AIFM2 | Q9BRQ8 | AIFM2 Apoptosis-inducing factor 2 | — | — | — | — | — | — | — | — | 20.0 | 1.5 |
| ARFGAP1 | Q8N6T3 | ARFGAP1 ADP-ribosylation factor GTPase-activating protein | — | — | — | — | — | — | — | — | 20.0 | 1.5 |
| KDSR | Q6GV12 | Kdsr 3-ketodihydro-sphingosine reductase | 19.4 | 1.4 | 3.6 | 1.1 | 2.1 | 1.3 | 1.6 | 1.5 | 20.0 | 1.3 |
| ZADH2 | Q8BGC4 | Zadh2 Zinc-binding alcohol dehydrogenase domain-containining 2 | 20.0 | 1.0 | 4.8 | 12.6 | 1.8 | 1.2 | 1.0 | 1.5 | — | — |
| ACADL | P51174 | Acadl Long-chain specific acyl-CoA dehydrogenase, mitochondrial | 20.0 | 1.0 | 1.1 | 12.4 | 1.0 | 1.2 | 1.3 | 1.8 | — | — |
| TLCD1 | Q96CP7 | TLCD1 TLC domain-containing protein 1 | — | — | — | — | — | — | — | — | 20.0 | 1.1 |

TABLE 5-continued

| | | | | | | | | | | | |
|---|---|---|---|---|---|---|---|---|---|---|---|
| PNPLA2 | Q96AD5 | PNPLA2 Patatin-like phospholipase domain-containing protein | — | — | — | — | — | — | — | 20.0 | 1.9 |
| PLIN2 | P43883 | Plin2 Perilipin-2 | 20.0 | 1.0 | 1.4 | 1.0 | 10.3 | 1.5 | 1.8 | 3.2 | 20.0 | 1.6 |
| AKR1C12 | Q04828/ P52895 | AKR1C1/2 Aldo-keto reductase family 1 member C1/2 | — | — | — | — | — | — | — | — | — | — |
| PLIN3 | O60664 | PLIN3 Perilipin-3 | — | — | — | — | — | — | — | — | 20.0 | 1.4 |
| APMAP | Q9HDC9 | APMAP Adipocyte plasma membrane-associated protein | 11.0 | 1.1 | — | — | — | 1.2 | — | — | 20.0 | 1.3 |
| PTGR2 | Q8VDQ1 | Ptgr2 Prostaglandin reductase 2 | 20.0 | 1.2 | 8.7 | 5.2 | 1.4 | 1.2 | 1.1 | 1.2 | 20.0 | 1.5 |
| TPD52L2 | O43399 | TPD52L2 Tumor protein D54 | — | — | — | — | — | — | — | — | 18.0 | 1.6 |
| SCCPDH | Q8NBX0 | SCCPDH Saccharopine dehydrogenase-like oxidoreductase | 20.0 | 1.1 | 3.4 | 7.3 | 2.5 | 1.3 | 1.6 | 2.1 | 20.0 | 1.5 |
| RTN4IP1 | Q8WWV3 | RTN4IP1 Reticulon-4-interacting protein 1, mitochondrial | 15.1 | 0.8 | 1.0 | — | 0.4 | — | 0.7 | — | 20.0 | 1.3 |
| AKR1B8 | P45377 | Akr1b8 Aldose reductase-related protein 2 | 20.0 | 1.3 | 7.7 | 1.7 | 2.3 | 1.2 | 1.4 | 1.9 | — | — |
| ALDH1A1 | P00352 | ALDH1A1 Retinal dehydrogenase 1 | — | — | — | — | — | — | — | — | — | — |
| PAOX | Q8C0L6 | Paox Peroxisomal N(1)-acetyl-spermine/spermidine oxidas | 20.0 | 1.2 | 7.5 | 3.2 | 1.7 | 1.5 | 2.4 | 3.2 | — | — |
| TMEM87A | A2AQJ6 | Tmem87a Transmembrane protein 87A | 20.0 | 1.4 | 1.8 | 1.1 | 7.0 | 1.4 | 2.3 | 1.9 | — | — |
| TMEM160 | Q9D938 | Tmem160 Transmembrane protein 160 | 13.4 | 1.5 | — | 1.2 | 6.9 | 1.4 | 1.2 | 1.5 | — | — |
| PCYOX1 | Q9UHG3 | PCYOX1 Prenylcysteine oxidase 1 | 18.2 | 1.0 | 1.7 | 1.2 | 2.2 | 1.2 | 1.8 | 1.4 | 20.0 | 1.2 |
| CAV1 | Q03135 | CAV1 Caveolin-1 | — | — | — | — | — | — | — | — | 12.7 | 1.2 |
| TIMM17A | Q99595 | TIMM17A Mitochondrial import inner membrane translocase subunit | 20.0 | 1.7 | 1.5 | 1.1 | 5.4 | 1.5 | 2.7 | 1.4 | 20.0 | 1.3 |
| GPR107 | Q5VW38 | GPR107 Protein GPR107 | 20.0 | 1.1 | 1.6 | 1.0 | 3.9 | 1.1 | 1.8 | 1.3 | 20.0 | 1.3 |
| HADHA | Q8BMS1 | Hadha Trifunctional enzyme subunit alpha, mitochondrial | 20.0 | 1.2 | 2.3 | 6.2 | 2.2 | 2.2 | 1.0 | 1.7 | 11.8 | 1.3 |

TABLE 5-continued

| | | | | | | | | | | | |
|---|---|---|---|---|---|---|---|---|---|---|---|
| AKR1C3 | P42330 | AKR1C3 Aldo-keto reductase family 1 member C3 | — | — | — | — | — | — | — | 3.2 | 1.6 |
| TRAM1 | Q91V04 | Tram1 Translocating chain-associated membrane protein 1 | 20.0 | 1.1 | 2.9 | 1.2 | 5.5 | 1.2 | 1.8 | 1.8 | 20.0 | 1.2 |
| ECH1 | O35459 | Ech1 Delta(3,5)-Delta(2,4)-dienoyl-CoA isomerase, mitochondrial | 17.4 | 0.7 | 1.0 | 1.1 | 1.1 | 1.0 | 1.4 | 1.6 | 13.5 | 1.3 |
| BCAP31 | Q61335 | Bcap31 B-cell receptor-associated protein 31 | 12.0 | 1.3 | 2.3 | 1.6 | 5.0 | 1.5 | 1.4 | 2.5 | 5.2 | 1.4 |
| GALNT4 | Q8N4A0 | GALNT4 Polypeptide N-acetyl-galactosaminyl-transferase 4 | — | — | — | — | — | — | — | — | 20.0 | 1.5 |
| LBR | Q14739 | LBR Lamin-B receptor | 3.6 | 1.2 | 2.0 | 1.0 | 1.8 | 1.4 | 1.9 | 1.3 | 15.3 | 1.4 |
| FAF2 | Q96CS3 | FAF2 FAS-associated factor 2 | 5.0 | 1.1 | 1.4 | — | 1.3 | — | 1.1 | 1.5 | 20.0 | 1.6 |
| FAM82A1 | Q96LZ7 | FAM82A1 Regulator of microtubule dynamics protein 2 | — | — | — | — | — | — | — | — | 20.0 | 1.3 |
| NDUFS2 | O75306 | NDUFS2 NADH dehydrogenase | 20.0 | 1.1 | 1.3 | 1.7 | 1.1 | 1.2 | 1.2 | 1.3 | 15.9 | 1.4 |
| SCARB1 | Q61009 | Scarb1 Scavenger receptor class B member 1 | 20.0 | 1.3 | 1.6 | 2.3 | 1.4 | 1.3 | 2.9 | 2.0 | 20.0 | 1.0 |
| C2ORF43 | Q9H6V9 | C2orf43 UPF0554 protein C2orf43 | — | — | — | — | — | — | — | — | 20.0 | 1.3 |
| HSD17B11 | Q8NBQ5 | HSD17B11 Estradiol 17-beta-dehydrogenase 11 | — | — | — | — | — | — | — | — | 17.4 | 1.6 |
| SLC25A20 | O43772 | SLC25A20 Mitochondrial carnitine/acylcarnitine carrier prot | 19.4 | 1.0 | 1.6 | 1.4 | 1.4 | 1.3 | 1.2 | 1.4 | 20.0 | 1.3 |
| RTN3 | O95197 | RTN3 Reticulon-3 | 4.3 | 1.0 | 2.7 | 1.1 | 1.7 | 1.3 | 1.2 | 1.4 | 14.3 | 1.3 |
| AKR1B10 | G5E895 | Akr1b10 MCG142264, isoform CRA_b | 20.0 | 1.1 | 4.5 | 1.9 | 2.4 | 1.3 | 1.5 | 2.8 | — | — |
| CPT2 | P52825 | Cpt2 Carnitine O-palmitoyl-transferase 2, mitochondrial | 20.0 | 1.1 | 1.1 | 3.1 | 1.1 | 1.3 | 2.1 | 1.7 | 20.0 | 1.4 |
| PON2 | Q15165 | PON2 Serum paraoxonase/arylesterase 2 | — | — | — | — | — | — | — | — | 20.0 | 1.3 |
| BSG | P35613 | BSG Basigin | 20.0 | 1.3 | 1.3 | 1.0 | 1.8 | 1.5 | 1.1 | 1.6 | 20.0 | 1.6 |
| CYB5B | O43169 | CYB5B Cytochrome b5 type B | — | — | — | — | — | — | — | — | 20.0 | 1.3 |

TABLE 5-continued

| | | | | | | | | | | | |
|---|---|---|---|---|---|---|---|---|---|---|---|
| SLC35B2 | Q91ZN5 | Slc35b2 Adenosine 3-phospho 5-phosphosulfate transporter | 13.4 | 1.3 | 1.9 | 1.0 | 4.2 | 1.2 | 0.9 | 1.1 | — | — |
| VAT1 | Q99536 | VAT1 Synaptic vesicle membrane protein VAT-1 homolog | 4.4 | 1.2 | 1.6 | 1.9 | 0.9 | 1.2 | 1.2 | — | 7.8 | 1.4 |
| UGT1A7 | Q9HAW7 | UGT1A7 UDP-glucuronosyl-transferase 1-7 | — | — | — | — | — | — | — | — | 20.0 | 1.5 |
| RDH10 | Q8IZV5 | RDH10 Retinol dehydrogenase 10 | — | — | — | — | — | — | — | — | 20.0 | 1.9 |
| DNAJC1 | Q96KC8 | DNAJC1 DnaJ homolog subfamily C member 1 | 20.0 | 1.3 | 2.1 | 1.4 | 2.8 | — | 1.2 | 1.6 | 20.0 | 1.3 |
| DHRSX | Q8N5I4 | DHRSX Dehydrogenase/reductase SDR family member on chromosome X | — | — | — | — | — | — | — | — | 20.0 | 1.5 |
| DCAKD | Q8BHC4 | Dcakd Dephospho-CoA kinase domain-containing protein | 9.0 | 1.2 | 1.9 | 1.1 | 3.7 | 1.2 | 1.0 | 1.4 | — | — |
| TIMM22 | Q9CQ85 | Timm22 Mitochondrial import inner membrane translocase subunit | 13.6 | 1.5 | 1.3 | 1.2 | 3.6 | 1.3 | 1.1 | 1.3 | — | — |
| COQ5 | Q5HYK3 | COQ5 2-methoxy-6-polyprenyl-1,4-benzoquinol methylase, mitochondrial | — | — | — | — | — | — | — | — | 20.0 | 1.7 |
| HMOX2 | P30519 | HMOX2 Heme oxygenase 2 | 4.0 | 1.1 | 3.2 | 1.0 | 2.1 | 1.2 | 1.3 | 1.4 | 20.0 | 1.3 |
| FADS2 | Q9Z0R9 | Fads2 Fatty acid desaturase 2 | 10.5 | 1.4 | 2.5 | 1.2 | 3.4 | 1.5 | 1.2 | 1.8 | — | — |
| VDAC2 | P45880 | VDAC2 Voltage-dependent anion-selective channel protein | 16.5 | 1.2 | 1.2 | 1.0 | 1.2 | 0.9 | 1.0 | 1.0 | 19.7 | 1.2 |
| TRABD | Q99JY4 | Trabd TraB domain-containing protein | 12.0 | 1.4 | 1.0 | 1.2 | 3.4 | 1.1 | 1.0 | 1.3 | — | — |
| VDAC1 | P21796 | VDAC1 Voltage-dependent anion-selective channel protein | 20.0 | 1.1 | 1.1 | 1.0 | 1.2 | 1.0 | 1.0 | 1.1 | 20.0 | 1.2 |
| PTGS2 | P35354 | PTGS2 Prostaglandin G/H synthase 2 | — | — | — | — | — | — | — | — | 3.2 | 1.6 |
| GM20425 | E9Q035 | Gm20425 Protein Gm20425 | 16.5 | 1.3 | 2.3 | 1.2 | 3.3 | 1.2 | 1.2 | 1.7 | — | — |
| SQLE | Q14534 | SQLE Squalene monooxygenase | 5.0 | 1.7 | 1.9 | 1.1 | 1.6 | — | 1.0 | 1.5 | 20.0 | 1.6 |

TABLE 5-continued

| | | | | | | | | | | | |
|---|---|---|---|---|---|---|---|---|---|---|---|
| TMEM48 | Q8VCB1 | Tmem48 Nucleoporin NDC1 | 14.5 | 1.3 | 1.9 | 1.2 | 3.3 | 1.2 | 1.1 | 1.5 | 20.0 | 1.3 |
| LPCAT3 | Q6P1A2 | LPCAT3 Lysophospholipid acyltransferase 5 | 18.7 | 1.0 | 1.4 | 2.3 | 2.2 | 1.2 | 1.1 | — | 20.0 | 1.2 |
| SEC11A | P67812 | SEC11A Signal peptidase complex catalytic subunit SEC11A | 5.4 | 1.2 | 1.9 | 1.1 | 3.1 | 1.3 | 1.6 | 1.6 | 20.0 | 1.3 |
| NSDHL | Q15738 | NSDHL Sterol-4-alpha-carboxylate 3-dehydrogenase, decarb | 9.4 | 1.4 | 2.0 | 1.3 | 3.0 | 1.3 | 1.3 | 2.3 | 16.9 | 1.4 |
| ERMP1 | Q7Z2K6 | ERMP1 Endoplasmic reticulum metallopeptidase 1 | — | — | — | — | — | — | — | — | 20.0 | 1.2 |
| PGRMC2 | Q80UU9 | Pgrmc2 Membrane-associated progesterone receptor component | 16.3 | 1.2 | 2.0 | 1.2 | 3.2 | 1.3 | 1.3 | 1.5 | 20.0 | 1.5 |
| MARCH5 | Q3KNM2 | March5 E3 ubiquitin-protein ligase MARCH5 | 20.0 | 1.6 | — | 1.3 | 3.1 | 1.0 | 1.1 | 1.1 | 4.1 | 1.3 |
| EMD | O08579 | Emd Emerin | 20.0 | 1.3 | 1.4 | 1.4 | 3.1 | 1.3 | 1.3 | 2.4 | 10.3 | 1.4 |
| CERS2 | Q924Z4 | Cers2 Ceramide synthase 2 | 17.1 | 1.2 | 2.4 | 1.2 | 3.0 | 1.3 | 1.6 | 3.1 | 13.3 | 1.3 |
| DHRS3 | O75911 | DHRS3 Short-chain dehydrogenase/reductase 3 | — | — | — | — | — | — | — | — | 15.6 | 1.6 |
| PSAP | P07602 | PSAP Proactivator polypeptide | 20.0 | 1.1 | 1.4 | 1.0 | 1.4 | 1.6 | 1.0 | 1.4 | 20.0 | 1.3 |
| LPCAT1 | Q8NF37 | LPCAT1 Lysophosphatidylcholine acyltransferase 1 | — | — | — | — | — | — | — | — | 20.0 | 1.5 |
| ANKLE2 | Q86XL3 | ANKLE2 Ankyrin repeat and LEM domain-containing protein 2 | — | — | — | — | — | — | — | — | 20.0 | 1.4 |
| ABHD6 | Q8R2Y0 | Abhd6 Monoacylglycerol lipase ABHD6 | 20.0 | 1.4 | 2.3 | 1.7 | 3.0 | 1.5 | 1.2 | 1.7 | — | — |
| TOMM22 | Q9CPQ3 | Tomm22 Mitochondrial import receptor subunit TOM22 homolog | 20.0 | 1.5 | 1.4 | 1.1 | 3.0 | 1.3 | 1.0 | 1.2 | 18.4 | 1.4 |
| SGPL1 | O95470 | SGPL1 Sphingosine-1-phosphate lyase 1 | 20.0 | 1.0 | 2.7 | 1.7 | 2.1 | 1.2 | 1.2 | 1.5 | 19.7 | 1.4 |
| OPA3 | Q505D7 | Opa3 Optic atrophy 3 protein homolog | 20.0 | 1.2 | — | 1.1 | 3.0 | 1.3 | 1.4 | 1.4 | 20.0 | 1.3 |

TABLE 5-continued

| | | | | | | | | | | | |
|---|---|---|---|---|---|---|---|---|---|---|---|
| NPTN | Q9Y639 | NPTN Neuroplastin | 17.4 | 1.4 | — | 1.2 | 2.2 | — | 2.0 | 1.9 | 20.0 | 1.4 |
| HSD17B12 | Q53GQ0 | HSD17B12 Estradiol 17-beta-dehydrogenase 12 | 15.3 | 1.1 | 2.2 | 1.7 | 2.5 | 1.3 | 0.9 | 1.6 | 20.0 | 1.3 |

| | A549 Cells | | | | | | | | | | |
|---|---|---|---|---|---|---|---|---|---|---|---|
| | A-DA | | | | | | AEA-DA | | | | |
| Gene Name | FK866 (25 uM) | Avasimibe (25 uM) | Ro488071 (5 uM) | Ro488071 (50 uM) | NoUV | DMSO | FK866 (25 uM) | Enzyme | Transporter | Receptor | Channel |
| ABCB1B | — | — | — | — | — | — | — | X | X | | |
| NAMPT | 10.6 | 1.5 | 1.8 | 15.0 | 20.0 | 1.3 | 20.0 | X | | | |
| LSS | 1.7 | 2.3 | 20.0 | 20.0 | — | — | — | X | | | |
| SOAT1 | 1.8 | 1.6 | 1.5 | 1.7 | — | — | — | X | | | |
| NUCB1 | 1.4 | 1.6 | 1.5 | 1.6 | 20.0 | 1.3 | 0.6 | | | | |
| EPHX2 | — | — | — | — | 20.0 | 1.3 | 20.0 | X | | | |
| PNPLA6 | 1.9 | 1.6 | 1.6 | 20.0 | — | — | — | X | | | |
| TMEM97 | 1.8 | 2.0 | 20.0 | 20.0 | 20.0 | 1.0 | 1.3 | | | | |
| ABHD5 | 1.6 | 20.0 | 1.6 | 7.0 | — | — | — | | | | |
| DHRS1 | 1.6 | 7.7 | 1.5 | 12.1 | 20.0 | 1.3 | 20.0 | X | | | |
| APOL2 | 1.3 | 2.2 | 1.4 | 20.0 | 20.0 | 1.1 | 0.7 | | X | | |
| FAM114A2 | 1.2 | 2.8 | 1.8 | 20.0 | — | — | — | | | | |
| TIMM17B | 1.3 | 1.4 | 1.8 | 20.0 | 20.0 | 1.2 | 0.7 | | X | | |
| FECH | 4.8 | 0.3 | 1.7 | 1.9 | 20.0 | 1.3 | 13.7 | X | | | |
| NPC1 | 1.7 | 1.3 | 2.8 | 20.0 | — | — | — | | | | |
| FA2H | 2.2 | 2.1 | — | 20.0 | — | — | — | X | | | |
| EBP | — | — | 16.0 | 19.6 | — | — | — | X | | | |
| EPHX1 | 1.8 | 2.5 | 1.4 | 1.8 | 8.1 | 1.3 | 1.2 | X | | | |
| AIFM2 | 2.0 | 16.1 | 2.2 | 7.5 | — | — | — | X | | | |
| ARFGAP1 | 1.4 | 14.3 | 1.9 | — | — | — | — | | X | | |
| KDSR | 1.4 | 1.7 | 1.7 | 12.9 | 20.0 | 1.3 | 0.7 | X | | | |
| ZADH2 | — | — | — | — | 20.0 | 1.8 | — | X | | | |
| ACADL | — | — | — | — | — | — | — | X | | | |
| TLCD1 | 1.3 | 1.6 | 1.5 | 11.7 | — | — | — | | | | |
| PNPLA2 | 2.2 | 8.1 | 2.0 | 10.5 | 20.0 | 1.0 | — | X | | | |
| PLIN2 | 1.6 | 9.0 | 1.7 | 9.2 | — | — | — | | | | |
| AKR1C12 | — | — | — | — | 17.8 | 1.2 | 9.3 | X | | | |
| PLIN3 | 1.6 | 2.8 | 1.7 | 8.9 | 20.0 | 1.0 | — | | X | | |
| APMAP | 1.6 | 2.1 | 1.8 | 8.8 | 15.7 | 1.2 | 0.8 | | | | |
| PTGR2 | — | — | 2.1 | 4.2 | 20.0 | 1.2 | 5.1 | X | | | |
| TPD52L2 | 1.3 | 2.8 | 1.6 | 8.4 | — | — | — | | | | |
| SCCPDH | 2.2 | 3.4 | 1.6 | 4.1 | 20.0 | 1.1 | 8.1 | X | | | |
| RTN4IP1 | 2.1 | 7.7 | 1.4 | 2.4 | 0.0 | 0.0 | 0.0 | | | | |
| AKR1B8 | — | — | — | — | — | — | — | X | | | |
| ALDH1A1 | — | — | — | — | 14.9 | 1.3 | 7.6 | X | | | |
| PAOX | — | — | — | — | — | — | — | X | | | |
| TMEM87A | — | — | — | — | — | — | — | | | | |
| TMEM160 | — | — | — | — | — | — | — | | | | |
| PCYOX1 | 2.6 | 1.4 | 2.5 | 6.9 | 20.0 | 1.2 | 0.8 | X | | | |
| CAV1 | 1.2 | 1.2 | 2.2 | 6.9 | 20.0 | 1.3 | 0.6 | | | | |
| TIMM17A | 1.2 | 1.5 | 1.2 | 6.7 | 20.0 | 1.2 | 0.6 | | X | | |
| GPR107 | 1.7 | 2.6 | 1.6 | 6.5 | — | — | — | | | X | |
| HADHA | 2.4 | 5.1 | 1.4 | 1.5 | 20.0 | 1.3 | 1.8 | X | | | |
| AKR1C3 | 3.3 | 2.8 | 1.2 | 1.4 | 18.4 | 1.3 | 6.0 | X | | | |
| TRAM1 | 1.2 | 1.4 | 1.5 | 5.3 | 20.0 | 1.1 | 0.7 | | X | | |
| ECH1 | 1.6 | 1.4 | 1.6 | 5.1 | 20.0 | 1.2 | 1.0 | X | | | |
| BCAP31 | 1.2 | 1.5 | 1.5 | 1.9 | — | — | — | | X | | |
| GALNT4 | 2.1 | 2.4 | 1.8 | 5.0 | 20.0 | 1.0 | 0.8 | X | | | |
| LBR | 1.6 | 2.1 | 2.3 | 5.0 | — | — | — | | | X | |
| FAF2 | 1.7 | 4.9 | 2.0 | 4.1 | 17.3 | 1.5 | — | | | | |
| FAM82A1 | 2.1 | 4.9 | 1.5 | — | — | — | — | | | | |
| NDUFS2 | 2.4 | 1.1 | 1.5 | 4.9 | 20.0 | 1.5 | 1.2 | X | X | | |
| SCARB1 | 1.3 | 1.1 | 1.9 | 4.8 | 20.0 | 1.1 | 0.9 | | | X | |
| C2ORF43 | 1.4 | 1.6 | 1.3 | 4.6 | — | — | — | | | | |
| HSD17B11 | 1.5 | 4.6 | 1.6 | 3.5 | — | — | — | X | | | |
| SLC25A20 | 3.1 | 2.6 | 1.6 | 4.6 | 20.0 | 1.2 | 1.2 | | X | | |
| RTN3 | 1.3 | 1.9 | 1.6 | 4.5 | — | — | — | | X | | |
| AKR1B10 | — | — | — | — | 9.9 | 1.2 | 1.7 | | | | |
| CPT2 | 4.4 | 1.5 | 1.4 | 2.2 | 20.0 | 1.3 | 2.3 | X | X | | |
| PON2 | 4.3 | 2.5 | 1.5 | 3.6 | 20.0 | 1.3 | 2.9 | X | | | |
| BSG | 1.8 | 1.4 | 2.4 | 4.3 | 20.0 | 1.3 | 0.7 | | | | |
| CYB5B | 1.4 | 2.1 | 1.5 | 4.2 | 9.6 | 1.3 | 0.8 | | X | | |
| SLC35B2 | — | — | — | — | — | — | — | | X | | |
| VAT1 | 4.0 | 0.8 | 1.4 | 2.5 | — | — | — | X | | | |
| UGT1A7 | 2.1 | 1.7 | 1.6 | 4.0 | 20.0 | 1.3 | 1.5 | X | | | |

TABLE 5-continued

| | | | | | | | | | | | |
|---|---|---|---|---|---|---|---|---|---|---|---|
| RDH10 | 3.1 | 3.9 | 1.9 | 2.8 | — | — | — | X | | | |
| DNAJC1 | 1.3 | 1.3 | 1.6 | 3.9 | — | — | — | | | | |
| DHRSX | 1.4 | 3.7 | 1.6 | 2.7 | — | — | — | X | | | |
| DCAKD | — | — | — | — | — | — | — | | | | |
| TIMM22 | — | — | — | — | — | — | — | | X | | |
| COQ5 | — | 1.4 | 2.0 | 3.4 | — | — | — | X | | | |
| HMOX2 | 1.3 | 1.4 | 1.3 | 3.4 | 20.0 | 1.2 | 0.7 | X | | | |
| FADS2 | — | — | — | — | — | — | — | X | X | | |
| VDAC2 | 1.2 | 1.4 | 1.5 | 3.4 | 20.0 | 1.1 | 0.9 | X | | | X |
| TRABD | — | — | — | — | 20.0 | 1.5 | — | | | | |
| VDAC1 | 1.3 | 1.3 | 1.4 | 3.3 | 20.0 | 1.1 | 0.8 | X | | | X |
| PTGS2 | 1.9 | 1.5 | 2.5 | 3.3 | — | — | — | X | | | |
| GM20425 | — | — | — | — | — | — | — | | | | |
| SQLE | 1.6 | 2.3 | 1.4 | 3.3 | 20.0 | 1.2 | 0.7 | X | | | |
| TMEM48 | 1.2 | 1.4 | 1.5 | 2.8 | — | — | — | | X | | |
| LPCAT3 | 3.3 | 2.1 | 1.3 | 2.7 | — | — | — | X | | | |
| SEC11A | 1.2 | 1.2 | 1.5 | 3.3 | 14.0 | 1.0 | 0.6 | X | | | |
| NSDHL | 1.4 | 3.2 | 1.5 | 2.5 | — | — | — | X | | | |
| ERMP1 | 1.6 | 2.1 | 1.4 | 3.2 | — | — | — | X | | | |
| PGRMC2 | 1.2 | 1.4 | 1.6 | 2.1 | 20.0 | 1.2 | 0.7 | | | X | |
| MARCH5 | 1.3 | 1.5 | 1.2 | — | — | — | — | X | | | |
| EMD | 1.3 | 1.2 | 0.6 | 0.8 | — | — | — | | | | |
| CERS2 | 1.4 | 0.7 | 1.5 | 2.5 | — | — | — | | | | |
| DHRS3 | 2.0 | 3.0 | 1.8 | 3.1 | — | — | — | X | | | |
| PSAP | 1.2 | 1.1 | 2.3 | 3.1 | 20.0 | 1.2 | 0.7 | | | | |
| LPCAT1 | 1.4 | 1.9 | 1.6 | 3.1 | — | — | — | X | | | |
| ANKLE2 | 1.3 | 1.9 | 1.7 | 3.1 | 20.0 | 1.1 | 0.6 | | | | |
| ABHD6 | — | — | — | — | — | — | — | X | | | |
| TOMM22 | 1.3 | 1.4 | 1.4 | 1.4 | 20.0 | 1.1 | 0.6 | X | X | | |
| SGPL1 | 1.2 | 1.3 | 1.5 | 3.0 | 20.0 | 1.3 | 0.8 | X | | | |
| OPA3 | 1.3 | 0.7 | 1.8 | — | — | — | — | | | | |
| NPTN | 1.4 | 1.4 | 1.3 | 3.0 | — | — | — | | | | |
| HSD17B12 | 1.4 | 2.0 | 1.4 | 3.0 | 20.0 | 1.2 | 0.8 | X | | | |

TABLE 6

| Gene Name | Accession # | Description | Range | SEQ ID NOs: | Sequence | Times observed |
|---|---|---|---|---|---|---|
| ABHD12 | Q99LR1 | Abhd12 Monoacylglycerol lipase ABHD12 | 263-284 | 1 | ETPPDALILESPFTNIREEAK | 2 |
| ABHD5 | Q9DBL9 | Abhd5 1-acylglycerol-3-phosphate O-acyltransferase ABHD5 | 321-343 | 2 | TIAILGAGHYVYADQPEEFNQK | 6 |
| ACSL6 | Q91WC3 | Acsl6 Long-chain-fatty-acid--CoA ligase 6 | 408-420 | 3 | NNSIWDELFFNK | 6 |
| ACTN4 | P57780 | Actn4 Alpha-actinin-4 | 839-855 | 4 | ETTDTDTADQVIASFK | 2 |
| ACTR2 | P61161 | Actr2 Actin-related protein 2 | 259-295 | 5 | FEAPEALFQPHLINVEGVGVAELLFNTIQAADIDTR | 2 |
| AKR1C12 | Q9JLI0 | Akr1c12 MCG114465, isoform CRA_a | 48-69 | 6 | HVDTAYAYQVEEEIGQAIQSK | 4 |
| AKR1C13 | Q8VC28 | Akr1c13 Aldo-keto reductase family 1 member C13 | 48-69 | 7 | HVDTAYAYQVEEEIGQAIQSK | 4 |
| ALDH1B1 | Q9CZS1 | Aldh1b1 Aldehyde dehydrogenase X, mitochondrial | 119-147 | 8 | VYLASLETLDNGKPFQESYVLDLDEVIK | 4 |
| APOO | Q9DCZ4 | Apoo Apolipoprotein O | 187-197 | 9 | GYIVIEDLWK | 2 |
| ARF1 | P84078 | Arf1 ADP-ribosylation factor 1 | 39-60 | 10 | LGEIVTTIPTIGFNVETVEYK | 9 |
| ARF3 | P61205 | Arf3 ADP-ribosylation factor 3 | 39-60 | 11 | LGEIVTTIPTIGFNVETVEYK | 9 |

TABLE 6-continued

| Gene Name | Accession # | Description | Range | SEQ ID NOs: | Sequence | Times observed |
|---|---|---|---|---|---|---|
| ARF4 | P61750 | Arf4 ADP-ribosylation factor 4 | 110-128 | 12 | MLLEDELQDAVLLLFANK | 2 |
| ARF4 | P61750 | Arf4 ADP-ribosylation factor 4 | 39-60 | 13 | LGEIVTTIPTIGFNVETVEYK | 9 |
| ARF5 | P84084 | Arf5 ADP-ribosylation factor 5 | 39-60 | 14 | LGEIVTTIPTIGFNVETVEYK | 9 |
| ARL6IP1 | Q9JKW0 | Arl6ip1 ADP-ribosylation factor-like protein 6-interacting | 8-36 | 15 | SSNLLAVETASLEEQLQGWGEVMLMADK | 2 |
| ATAD3 | Q925I1 | Atad3 ATPase family AAA domain-containing protein 3 | 238-246 | 16 | AFVTDWDK | 3 |
| ATP1A1 | Q8VDN2 | Atp1a1 Sodium/potassium-transporting ATPase subunit alpha | 360-386 | 17 | NLEAVETLGSTSTICSDKTGTLTQNR | 2 |
| ATP1A3 | Q6PIC6 | Atp1a3 Sodium/potassium-transporting ATPase subunit alpha | 350-376 | 18 | NLEAVETLGSTSTICSDKTGTLTQNR | 2 |
| ATP5L | Q9CPQ8 | Atp5l ATP synthase subunit g, mitochondrial | 36-55 | 19 | VELVPPTPAEIPTAIQSVK | 3 |
| ATP6V1B2 | P62814 | Atp6v1b2 V-type proton ATPase subunit B, brain isoform | 68-82 | 20 | YAEIVHLTLPDGTK | 3 |
| BCAP31 | Q61335 | Bcap31 B-cell receptor-associated protein 31 | 73-80 | 21 | YDDVTEK | 2 |
| CCDC56 | Q9D2R6 | Ccdc56 Cytochrome C oxidase assembly factor 3 homolog, mitochondrial | 84-94 | 22 | FLDELEDEAK | 2 |
| CKAP4 | Q8BMK4 | Ckap4 Cytoskeleton-associated protein 4 | 292-307 | 23 | SSLQTMESDVY1EVR | 7 |
| COPS6 | O88545 | Cops6 COP9 signalosome complex subunit 6 | 274-295 | 24 | TDFYDQCNDVGLMAYLGTITK | 8 |
| COX15 | Q8BJ03 | Cox15 Cytochrome c oxidase assembly protein COX15 homolog | 317-331 | 25 | NVFENPTMVQFDHR | 2 |
| CPT2 | P52825 | Cpt2 Carnitine O-palmitoyltransferase 2, mitochondrial | 363-383 | 26 | DGTAAVHFEHAWGDGVAVLR | 6 |
| CTSD | P18242 | Ctsd Cathepsin D | 312-330 | 27 | AIGAVPLIQGEYMIPCEK | 12 |
| CYB5B | Q9CQX2 | Cyb5b Cytochrome b5 type B | 138-145 | 28 | HFWADSK | 2 |
| CYP20A1 | Q8BKE6 | Cyp20a1 Cytochrome P450 20A1 | 397-414 | 29 | VFSSLGFSGTWECPELR | 8 |
| DHFR | P00375 | Dhfr Dihydrofolate reductase | 20-34 | 30 | NGDLPWPPLRNEFK | 4 |
| DHRS7B | Q99J47 | Dhrs7b Dehydrogenase/reductase SDR family member 7B | 284-300 | 31 | DVLLTDFVPSMAVYIR | 2 |

TABLE 6-continued

| Gene Name | Accession # | Description | Range | SEQ ID NOs: | Sequence | Times observed |
|---|---|---|---|---|---|---|
| ECH1 | O35459 | Ech1 Delta(3,5)-Delta(2,4)-dienoyl-CoA isomerase, mitochondrial | 185-211 | 32 | YCTQDAFFQIKEVDMGLAADVGTLQR | 4 |
| ECH1 | O35459 | Ech1 Delta(3,5)-Delta(2,4)-dienoyl-CoA isomerase, mitochondrial | 196-211 | 33 | EVDMGLAADVGTLQR | 8 |
| ECI1 | P42125 | Eci1 Enoyl-CoA delta isomerase 1, mitochondrial | 276-284 | 34 | SLHMYLEK | 2 |
| EEF1D | P57776 | Eef1d Elongation factor 1-delta | 25-39 | 35 | FYEQMNGPVTSGSR | 10 |
| EIF5 | P59325 | Eif5 Eukaryotic translation initiation factor 5 | 272-287 | 36 | AMGPLVLTEVLFDEK | 12 |
| EMD | O08579 | Emd Emerin | 176-205 | 37 | SSLGLSYYPTSSTSSVSSSSSSPSSWLTR | 2 |
| EPDR1 | Q99M71 | Epdr1 Mammalian ependymin-related protein 1 | 171-182 | 38 | DCYPVQETFIR | 3 |
| EPHX1 | Q9D379 | Ephx1 Epoxide hydrolase 1 | 296-329 | 39 | ESGYLHIQATKPDTVGCALNDSPVGLAAYILEK | 8 |
| FAH | P35505 | Fah Fumarylacetoacetase | 238-254 | 40 | DIQQWEYVPLGPFLGK | 8 |
| GAA | P70699 | Gaa Lysosomal alpha-glucosidase | 904-935 | 41 | EVTVLGVATAPTQVLSNGIPVSNFTYSPDNK | 11 |
| GLO1 | Q9CPU0 | Glo1 Lactoylglutathione lyase | 160-180 | 42 | GLAFIQDPDGYWIEILNPNK | 2 |
| GM20425 | E9Q035 | Gm20425 Protein Gm20425 | 718-741 | 43 | VGDGAGGAFQPYLDSLRQELQQR | 7 |
| GSTM1 | P10649 | Gstm1 Glutathione S-transferase Mu 1 | 109-123 | 44 | MQLIMLCYNPDFEK | 4 |
| GSTM2 | P15626 | Gstm2 Glutathione S-transferase Mu 2 | 109-123 | 45 | IQLAMVCYSPDFEK | 5 |
| GSTP1 | P19157 | Gstp1 Glutathione S-transferase P 1 | 104-117 | 46 | YVTLIYTNYENGK | 4 |
| HADH | Q61425 | Hadh Hydroxyacyl-coenzyme A dehydrogenase, mitochondrial | 250-272 | 47 | LGAGYPMGPFELLDYVGLDTTK | 10 |
| HM13 | Q9D8V0 | Hm13 Minor histocompatibility antigen H13 | 62-74 | 48 | SSSDMPETITSR | 12 |
| HNRNPH1 | O35737 | Hnrnph1 Heterogeneous nuclear ribonucleoprotein H | 50-69 | 49 | EGRPSGEAFVELESEDEVK | 9 |
| HNRNPH2 | P70333 | Hnrnph2 Heterogeneous nuclear ribonucleoprotein H2 | 50-69 | 50 | EGRPSGEAFVELESEDEVK | 9 |
| HSP90B1 | P08113 | Hsp90b1 Endoplasmin | 664-672 | 51 | AQAYQTGK | 4 |
| HSPA5 | P20029 | Hspa5 78 kDa glucose-regulated protein | 466-476 | 52 | VYEGERPLTK | 8 |

TABLE 6-continued

| Gene Name | Accession # | Description | Range | SEQ ID NOs: | Sequence | Times observed |
|---|---|---|---|---|---|---|
| HSPA5 | P20029 | Hspa5 78 kDa glucose-regulated protein | 635-656 | 53 | LYGSGGPPPTGEEDTSEKDEL | 4 |
| IPO9 | Q91YE6 | Ipo9 Importin-9 | 777-788 | 54 | ELGENLDQILR | 3 |
| LMNA | P48678 | Lmna Prelamin-A/C | 281-297 | 55 | NSNLVGAAHEELQQSR | 2 |
| LMNB1 | P14733 | Lmnb1 Lamin-B1 | 159-183 | 56 | SLEGDLEDLKDQIAQLEASLSAAK | 2 |
| LMNB2 | P21619 | Lmnb2 Lamin-B2 | 137-160 | 57 | SEAELATALSDKQGLETEVAELR | 5 |
| LPCAT3 | Q91V01 | Lpcat3 Lysophospholipid acyltransferase 5 | 18-31 | 58 | GLWPGVEDLSLNK | 2 |
| MCM6 | P97311 | Mcm6 DNA replication licensing factor MCM6 | 59-86 | 59 | NTLVVSFADLEQFNQQLSTTIQEEFYR | 3 |
| MIF | P34884 | Mif Macrophage migration inhibitory factor | 13-38 | 60 | ASVPEGFLSELTQQLAQATGKPAQY | 4 |
| MRPL39 | Q9JKF7 | Mrpl39 39S ribosomal protein L39, mitochondrial | 154-166 | 61 | AFKDDYVVSLVR | 4 |
| MTCH2 | Q791V5 | Mtch2 Mitochondrial carrier homolog 2 | 91-112 | 62 | VLQYYQESEKPEELGSVTVQK | 2 |
| MTX1 | P47802 | Mtx1 Metaxin-1 | 89-104 | 63 | QGADTLAFMSLLEEK | 2 |
| NAMPT | Q99KQ4 | Nampt Nicotinamide phosphoribosyltransferase | 175-190 | 64 | YLLETSGNLDGLEYK | 10 |
| NAMPT | Q99KQ4 | Nampt Nicotinamide phosphoribosyltransferase | 303-324 | 65 | STEAPLIIRPDSGNPLDTVLK | 2 |
| NAP1L4 | Q78ZA7 | Nap1l4 Nucleosome assembly protein 1-like 4 | 84-94 | 66 | FYEEVHDLER | 3 |
| NDUFS2 | Q91WD5 | Ndufs2 NADH dehydrogenase | 36-57 | 67 | QWQPDIEWAEQFSGAVMYPSK | 3 |
| NENF | Q9CQ45 | Nenf Neudesin | 84-94 | 68 | GAPYNALAGK | 4 |
| NONO | Q99K48 | Nono Non-POU domain-containing octamer-binding protein | 122-138 | 69 | TLAEIAKVELDNMPLR | 3 |
| NUCB1 | Q02819 | Nucb1 Nucleobindin-1 | 246-275 | 70 | TFFILHDINSDGVLDEQELEALFTKELEK | 4 |
| NUCB1 | Q02819 | Nucb1 Nucleobindin-1 | 53-69 | 71 | YLQEVINVLETDGHFR | 11 |
| NUCB2 | P81117 | Nucb2 Nucleobindin-2 | 60-73 | 72 | QVIEVLETDPHFR | 4 |
| NUDT9 | Q8BVU5 | Nudt9 ADP-ribose pyrophosphatase, mitochondrial | 230-242 | 73 | EFGEEALNSLQK | 7 |
| OPA1 | P58281 | Opa1 Dynamin-like 120 kDa protein, mitochondrial | 801-819 | 74 | VNDEHPAYLASDEITTVR | 2 |
| ORF61 | Q8CIV2 | ORF61 Membralin | 245-263 | 75 | LLLDEFLGYDDILMSSVK | 4 |
| P4HA2 | Q60716 | P4ha2 Prolyl 4-hydroxylase subunit alpha-2 | 177-197 | 76 | SAYNEGDYYHTVLWMEQVLK | 3 |

TABLE 6-continued

| Gene Name | Accession # | Description | Range | SEQ ID NOs: | Sequence | Times observed |
|---|---|---|---|---|---|---|
| P4HB | P09103 | P4hb Protein disulfide-isomerase | 135-165 | 77 | TGPAATTLSDTAAAESLVDSSEVTVIGFFK | 3 |
| P4HB | P09103 | P4hb Protein disulfide-isomerase | 233-250 | 78 | HNQLPLVIEFTEQTAPK | 10 |
| PCK2 | Q8BH04 | Pck2 Phosphoenolpyruvate carboxykinase | 245-262 | 79 | EIVSFGSGYGGNSLLGK | 12 |
| PDCD5 | P56812 | Pdcd5 Programmed cell death protein 5 | 69-80 | 80 | AVENYLIQMAR | 5 |
| PGRMC1 | O55022 | Pgrmc1 Membrane-associated progesterone receptor component | 106-120 | 81 | FYGPEGPYGVFAGR | 12 |
| PGRMC1 | O55022 | Pgrmc1 Membrane-associated progesterone receptor component | 48-68 | 82 | GDQPGASGDNDDDEPPPLPR | 2 |
| PGRMC2 | Q80UU9 | Pgrmc2 Membrane-associated progesterone receptor component | 130-144 | 83 | FYGPAGPYGIFAGR | 9 |
| PGRMC2 | Q80UU9 | Pgrmc2 Membrane-associated progesterone receptor component | 74-92 | 84 | LCSGPGAGEESPAATLPR | 2 |
| PHB | P67778 | Phb Prohibitin | 5-12 | 85 | VFESIGK | 2 |
| PITPNB | P53811 | Pitpnb Phosphatidylinositol transfer protein beta isoform | 32-45 | 86 | NETGGGEGIEVLK | 4 |
| PITRM1 | Q8K411 | Pitrm1 Presequence protease, mitochondrial | 364-386 | 87 | ALIESGLGTDFSPDVGYNGYTR | 2 |
| PMPCA | Q9DC61 | Pmpca Mitochondrial-processing peptidase subunit alpha | 428-451 | 88 | TQLMSMLMMNLESRPVIFEDVGR | 7 |
| PSMA6 | Q9QUM9 | Psma6 Proteasome subunit alpha type-6 | 103-117 | 89 | YKYGYEIPVDMLCK | 8 |
| PSMB1 | O09061 | Psmb1 Proteasome subunit beta type-1 | 127-146 | 90 | RFFPYYVYNIIGGLDEEGK | 8 |
| PSMB5 | O55234 | Psmb5 Proteasome subunit beta type-5 | 141-151 | 91 | LLANMVYQYK | 11 |
| PTGES2 | Q8BWM0 | Ptges2 Prostaglandin E synthase 2 | 269-279 | 92 | FGAVEAAMAK | 3 |
| PTRH2 | Q8R2Y8 | Ptrh2 Peptidyl-tRNA hydrolase 2, mitochondrial | 35-69 | 93 | SHLGMFPQNSTSEANRDTETGTEASILGESGEYK | 2 |
| RTN4 | Q99P72 | Rtn4 Reticulon-4 | 1045-106 | 94 | AYLESEVAISEELVQK | 7 |
| SAR1A | P36536 | Sar1a GTP-binding protein SAR1a | 192-199 | 95 | WLSQYID | 6 |
| SCCPDH | Q8R127 | Sccpdh Saccharopine dehydrogenase-like oxidoreductase | 145-168 | 96 | GVYIIGSSGFDSIPADLGVLYTR | 11 |
| SCG3 | P47867 | Scg3 Secretogranin-3 | 178-203 | 97 | LLNLGLIIESQAHTLEDEVAEALQK | 4 |
| SEPT2 | P42208 | Sept2 Septin-2 | 78-92 | 98 | TVQIEASTVEIEER | 2 |
| SGPL1 | Q8R0X7 | Sgpl1 Sphingosine-1-phosphate lyase 1 | 519-536 | 99 | TTGMGAIYGMAQATIDR | 12 |

TABLE 6-continued

| Gene Name | Accession # | Description | Range | SEQ ID NOs: | Sequence | Times observed |
|---|---|---|---|---|---|---|
| SGPL1 | Q8R0X7 | Sgpl1 Sphingosine-1-phosphate lyase 1 | 9-26 | 100 | LKDFEPYLEILESYSTK | 4 |
| SHMT2 | Q9CZN7 | Shmt2 Protein Shmt2 | 105-122 | 101 | YYGGAEVVDEIELLCQR | 9 |
| SHMT2 | Q9CZN7 | Shmt2 Protein Shmt2 | 161-182 | 102 | IMGLDLPDGGHLTHGYMSDVK | 3 |
| SLC25A20 | Q9Z2Z6 | Slc25a20 Mitochondrial carnitine/acylcarnitine carrier protein | 179-195 | 103 | DVPASGMYFMTYEWLK | 4 |
| SLC25A32 | Q8BMG8 | Slc25a32 Mitochondrial folate transporter/carrier | 115-146 | 104 | AEQLEPLEYLVSAAEAGAMTLCITNPLWVTK | 6 |
| SLC38A2 | Q8CFE6 | Slc38a2 Sodium-coupled neutral amino acid transporter 2 | 171-179 | 105 | YELPLVIK | 4 |
| STIP1 | Q60864 | Stip1 Stress-induced-phosphoprotein 1 | 506-514 | 106 | LILEQMQK | 3 |
| STOML2 | Q99JB2 | Stoml2 Stomatin-like protein 2 | 292-322 | 107 | DSNTVLLPSNPSDVTSMVAQAMGVYGALTK | 2 |
| SURF4 | Q64310 | Surf4 Surfeit locus protein 4 | 2-20 | 108 | GQNDLMGTAEDFADQFLR | 10 |
| SURF4 | Q64310 | Surf4 Surfeit locus protein 4 | 31-44 | 109 | LCLISTFLEDGIR | 3 |
| TFRC | Q62351 | Tfrc Transferrin receptor protein 1 | 7-23 | 110 | SAFSNLFGGEPLSYTR | 2 |
| TIMM17A | Q9Z0V8 | Timm17a Mitochondrial import inner membrane translocase subunit | 13-36 | 111 | IVDDCGGAFTMGTIGGGIFQAFK | 9 |
| TIMM17A | Q9Z0V8 | Timm17a Mitochondrial import inner membrane translocase subunit | 85-107 | 112 | GKEDPWNSITSGALTGAILAAR | 4 |
| TMEM206 | Q9D771 | Tmem206 Transmembrane protein 206 | 247-260 | 113 | TKEEDGREAVEFR | 2 |
| TNPO1 | Q8BFY9 | Tnpo1 Transportin-1 | 45-65 | 114 | LEQLNQYPDFNNYLIFVLTK | 5 |
| TOMM20 | Q9DCC8 | Tomm20 Mitochondrial import receptor subunit TOM20 homolog | 69-89 | 115 | FFLEEIQLGEELLAQGDYEK | 7 |
| TRABD | Q99JY4 | Trabd TraB domain-containing protein | 234-253 | 116 | DLLEQMMAEMIGEFPDLHR | 4 |
| UNC119 | Q9Z2R6 | Unc119 Protein unc-119 homolog A | 131-140 | 117 | YQFTPAFLR | 3 |
| UNC119B | Q8C4B4 | Unc119b Protein unc-119 homolog B | 142-151 | 118 | YQFTPAFLR | 3 |
| VBP1 | P61759 | Vbp1 Prefoldin subunit 3 | 153-178 | 119 | NLDSLEEDLDFLRDQFTTTEVNMAR | 2 |
| YWHAB | Q9CQV8 | Ywhab 14-3-3 protein beta/alpha | 196-225 | 120 | TAFDEAIAELDTLNEESYKDSTLIMQLLR | 8 |
| YWHAE | P62259 | Ywhae 14-3-3 protein epsilon | 197-226 | 121 | AAFDDAIAELDTLSEESYKDSTLIMQLLR | 8 |

TABLE 6-continued

| Gene Name | Accession # | Description | Range | SEQ ID NOs: | Sequence | Times observed |
|---|---|---|---|---|---|---|
| ZADH2 | Q8BGC4 | Zadh2 Zinc-binding alcohol dehydrogenase domain-containing 2 | 86-115 | 122 | YDPSLKPPFDIGFEGI GEVVALGLSASAR | 8 |

TABLE 7

Representative features of untargeted lipidomic profiling of MJN228- or KML181-treated Neuro2a cells

| | | | | Significant Change (≥2 fold, P value < 0.0001, n = 5) | | | | | |
|---|---|---|---|---|---|---|---|---|---|
| | | | | *No Change* | | | | | |
| | | | | DMSO versus MJN228 (10 µM) | | | DMSO versus KML181 (10 µM) | | |
| Polarity | Proposed Species | m/z | RT (min) | Fold Change | P Value | Change | Fold Change | P Value | Change |
| Pos | NAE 18:1 | 326.30 | 8.36 | 2.91 | 0.00002310 | UP | *1.04* | *0.4111233* | *DOWN* |
| Pos | NAE 18:0 | 328.32 | 12.20 | 2.00 | 0.00003157 | UP | *1.01* | *0.9264302* | *UP* |
| Neg | NAT 24:1 | 444.31 | 9.31 | 2.51 | 0.00000712 | UP | *1.03* | *0.5309418* | *UP* |
| Neg | NAT 24:0 | 446.33 | 13.76 | 2.29 | 0.00003429 | UP | *1.07* | *0.0445628* | *DOWN* |
| Neg | NAT 26:0 | 474.36 | 19.60 | 2.75 | 0.00005251 | UP | *1.26* | *0.1518409* | *UP* |
| Neg | — | 596.39 | 12.00 | 2.02 | 0.00000067 | UP | *1.13* | *0.0492851* | *UP* |
| Neg | — | 622.41 | 12.66 | 2.06 | 0.00004036 | UP | *1.24* | *0.0014807* | *UP* |
| Pos | — | 371.10 | 13.51 | 2.00 | 0.00000288 | UP | 2.14 | 0.0000026 | UP |
| Pos | — | 669.22 | 13.52 | 2.15 | 0.00002090 | UP | 2.18 | 0.0000231 | UP |
| Pos | — | 704.21 | 19.42 | 2.45 | 0.00007397 | UP | 2.83 | 0.0000142 | UP |
| Pos | — | 705.21 | 19.44 | 2.63 | 0.00001587 | UP | 3.19 | 0.0000028 | UP |
| Pos | — | 743.24 | 19.42 | 2.56 | 0.00000040 | UP | 3.00 | 0.0000191 | UP |
| Pos | — | 744.24 | 19.44 | 2.88 | 0.00000012 | UP | 3.29 | 0.0000206 | UP |
| Pos | — | 745.24 | 19.44 | 2.81 | 0.00000099 | UP | 3.35 | 0.0000042 | UP |
| Pos | — | 776.23 | 25.46 | 2.50 | 0.00002404 | UP | 3.08 | 0.0000594 | UP |
| Pos | — | 777.23 | 25.48 | 2.52 | 0.00008462 | UP | 3.10 | 0.0002452 | UP |
| Pos | — | 778.23 | 25.47 | 2.41 | 0.00006253 | UP | 2.93 | 0.0000148 | UP |
| Pos | — | 779.23 | 25.47 | 2.59 | 0.00002455 | UP | 3.16 | 0.0000966 | UP |
| Pos | — | 817.26 | 25.47 | 2.35 | 0.00000278 | UP | 3.01 | 0.0000837 | UP |
| Pos | — | 818.26 | 25.47 | 2.51 | 0.00000074 | UP | 3.00 | 0.0000629 | UP |
| Pos | — | 819.26 | 25.46 | 2.85 | 0.00000789 | UP | 3.46 | 0.0000863 | UP |
| Pos | — | 820.26 | 25.47 | 2.79 | 0.00000004 | UP | 3.35 | 0.0000638 | UP |
| Pos | — | 850.25 | 30.92 | 2.42 | 0.00000034 | UP | 3.10 | 0.0000175 | UP |
| Pos | — | 851.25 | 30.92 | 2.41 | 0.00000045 | UP | 3.02 | 0.0000089 | UP |
| Pos | — | 852.25 | 30.92 | 2.46 | 0.00000054 | UP | 3.18 | 0.0000085 | UP |
| Pos | — | 853.25 | 30.92 | 2.61 | 0.00000115 | UP | 3.33 | 0.0000019 | UP |
| Pos | — | 924.27 | 33.83 | 2.14 | 0.00000891 | UP | 2.68 | 0.0000139 | UP |
| Pos | — | 925.27 | 33.83 | 2.19 | 0.00000319 | UP | 2.71 | 0.0000170 | UP |
| Pos | — | 926.27 | 33.84 | 2.27 | 0.00000741 | UP | 2.75 | 0.0000223 | UP |
| Pos | — | 927.27 | 33.83 | 2.19 | 0.00000877 | UP | 2.66 | 0.0000837 | UP |
| Pos | MAG 16:0 | 331.28 | 8.51 | *1.67* | *0.00521131* | *UP* | *1.08* | *0.4349426* | *DOWN* |
| Pos | MAG 18:1 | 358.30 | 9.68 | *1.37* | *0.05789544* | *UP* | *1.01* | *0.9416353* | *UP* |
| Pos | PC 34:0 | 762.60 | 36.86 | *1.00* | *0.96044809* | *UP* | *1.03* | *0.5656804* | *DOWN* |
| Pos | PC 36:1 | 788.61 | 35.81 | *1.04* | *0.61030901* | *DOWN* | *1.02* | *0.7290154* | *DOWN* |
| Pos | LPC 18:0 | 524.37 | 7.49 | *1.48* | *0.00162470* | *UP* | *1.06* | *0.3699929* | *UP* |
| Pos | LPC 18:1 | 522.35 | 5.29 | *1.24* | *0.04379242* | *UP* | *1.15* | *0.1837608* | *DOWN* |
| Pos | LPC 20:4 | 544.34 | 5.29 | *1.69* | *0.03896284* | *UP* | *1.10* | *0.5096613* | *UP* |
| Neg | FFA 16:0 | 255.23 | 14.24 | *1.17* | *0.07086814* | *UP* | *1.05* | *0.8357592* | *UP* |
| Neg | FFA 18:1 | 281.25 | 15.75 | *1.23* | *0.03283308* | *UP* | *1.13* | *0.1567142* | *UP* |
| Neg | FFA 18:0 | 283.26 | 20.89 | *1.22* | *0.01893619* | *UP* | *1.11* | *0.5950044* | *UP* |
| Neg | FFA 20:4 | 303.23 | 12.39 | *1.17* | *0.03905025* | *UP* | *1.35* | *0.0096387* | *UP* |
| Neg | PE 34:1 | 716.52 | 32.28 | *1.35* | *0.19422170* | *DOWN* | *1.26* | *0.3113366* | *DOWN* |
| Neg | PE 36:4 | 738.51 | 33.92 | *1.46* | *0.17404098* | *UP* | *1.09* | *0.1400935* | *UP* |
| Neg | PE 38:5 | 764.52 | 35.18 | *1.02* | *0.61002735* | *UP* | *1.02* | *0.5388540* | *UP* |
| Neg | PE 38:4 | 766.54 | 36.76 | *1.01* | *0.83525337* | *UP* | *1.03* | *0.3995352* | *UP* |
| Neg | LPE 16:0 | 452.28 | 5.02 | *1.25* | *0.01607387* | *UP* | *1.03* | *0.6772790* | *DOWN* |
| Neg | LPE 18:1 | 478.29 | 5.66 | *1.50* | *0.08340579* | *UP* | *1.26* | *0.1805840* | *UP* |
| Neg | LPE 18:0 | 480.31 | 7.96 | *1.43* | *0.00005535* | *UP* | *1.19* | *0.0032877* | *UP* |
| Neg | PA 34:1 | 673.48 | 33.41 | *1.01* | *0.91354827* | *UP* | *1.27* | *0.0631068* | *DOWN* |
| Neg | PS 34:1 | 760.51 | 31.80 | *1.07* | *0.35575526* | *UP* | *1.08* | *0.4901641* | *DOWN* |
| Neg | PS 36:2 | 786.53 | 31.97 | *1.11* | *0.61545091* | *DOWN* | *1.29* | *0.1609645* | *DOWN* |
| Neg | PS 36:1 | 788.54 | 34.16 | *1.03* | *0.46607524* | *DOWN* | *1.04* | *0.2746587* | *UP* |
| Neg | PS 38:5 | 808.51 | 30.14 | *1.05* | *0.80187768* | *DOWN* | *1.03* | *0.8723866* | *DOWN* |
| Neg | PG 32:0 | 721.50 | 30.94 | *1.26* | *0.25029036* | *DOWN* | *1.07* | *0.7705510* | *DOWN* |
| Neg | PG 34:1 | 747.52 | 32.95 | *1.22* | *0.19905052* | *UP* | *1.09* | *0.1738809* | *DOWN* |

TABLE 7-continued

Representative features of untargeted lipidomic profiling of MJN228- or KML181-treated Neuro2a cells Significant Change (≥2 fold, P value < 0.0001, n = 5)
*No Change*

| | | | | DMSO versus MJN228 (10 µM) | | | DMSO versus KML181 (10 µM) | | |
|---|---|---|---|---|---|---|---|---|---|
| Polarity | Proposed Species | m/z | RT (min) | Fold Change | P Value | Change | Fold Change | P Value | Change |
| Neg | PG 34:0 | 749.53 | 34.04 | *1.24* | *0.00415650* | *UP* | *1.06* | *0.2788134* | *UP* |
| Neg | PG 36:1 | 775.55 | 34.70 | *1.02* | *0.73375155* | *UP* | *1.01* | *0.7979934* | *UP* |

The examples and embodiments described herein are for illustrative purposes only and various modifications or changes suggested to persons skilled in the art are to be included within the spirit and purview of this application and scope of the appended claims.

---

What is claimed is:

1. A process of generating a lipid probe-protein composition, comprising:
   contacting a sample comprising a protein with a lipid probe; and
   treating the sample and the lipid probe by a photoreactive means to generate the lipid probe-protein composition, wherein the treating time is from about 5 minutes to about 1 hour; and
   wherein the lipid probe is a lipid probe of Formula (I):

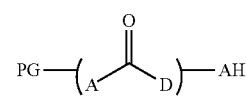

Formula (I)

wherein:
A is $C_{16}$-$C_{20}$alkyl or $C_{16}$-$C_{20}$alkenyl;
D is —$NH_2$, —$NHR^7$, or —$OR^8$;
$R^7$ is $C_1$-$C_4$alkyl, ($C_1$-$C_5$alkyl)OH, or ($C_1$-$C_5$)$SO_3$M;
$R^8$ is $(CH_2OH)n$;
M is monovalent or divalent cation;
n is 1, 2, or 3;
PG is a photoreactive group; and
AH is an affinity handle; and
wherein PG is attached to A or D and AH is attached to A or D.

2. The process of claim 1, wherein the treating time is about 10 minutes.

3. The process of claim 1, wherein the photoreactive group comprises azides, benzophenone, diazo compounds, diazirines, diazonium salts, or diaryl ketones.

4. The process of claim 1, wherein the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group.

5. The process of claim 1, wherein the protein is an enzyme, a transporter, a receptor, an adaptor, a channel protein, or a chaperone.

6. The process of claim 1, wherein the protein is encoded by a gene of Table 3, a protein encoded by a gene of Table 4, or a protein encoded by a gene of Table 5.

7. The process of claim 1, wherein the photoreactive means comprises ultraviolet light.

8. The process of claim 1, wherein the treating occurs at a temperature of from about 0° C. to about 40° C.

9. The process of claim 1, wherein the treating occurs at a temperature of about 4° C.

10. A lipid probe-protein composition generated by the process of claim 2.

11. A process of generating a lipid probe-protein composition, comprising:
contacting a sample comprising a protein with a lipid probe, wherein the lipid probe is selected from lipid probes 1, 3-10, 12-15, 17-21 and 23 of Table 1; and
treating the sample and the lipid probe by a photoreactive means to generate the lipid probe-protein composition, wherein the treating time is from about 5 minutes to about 1 hour.

12. The process of claim 11, wherein the treating time is about 10 minutes.

13. The process of claim 11, wherein the photoreactive group comprises azides, benzophenone, diazo compounds, diazirines, diazonium salts, or diaryl ketones.

14. The process of claim 11, wherein the affinity handle comprises a carbodiimide, N-hydroxysuccinimide (NHS) ester, imidoester, pentafluorophenyl ester, hydroxymethyl phosphine, maleimide, haloacetyl, pyridyl disulfide, thiosulfonate, vinylsulfone, hydrazide, alkoxyamine, alkyne, azide, or isocyanate group.

15. The process of claim 11, wherein the protein is an enzyme, a transporter, a receptor, an adaptor, a channel protein, or a chaperone.

16. The process of claim 11, wherein the protein is encoded by a gene of Table 3, a protein encoded by a gene of Table 4, or a protein encoded by a gene of Table 5.

17. The process of claim 11, wherein the photoreactive means comprises ultraviolet light.

18. The process of claim 11, wherein the treating occurs at a temperature of from about 0° C. to about 40° C.

19. The process of claim 11, wherein the treating occurs at a temperature of about 4° C.

20. A lipid probe-protein composition generated by the process of claim 11.

* * * * *

SEQUENCE LISTING

<160> NUMBER OF SEQ ID NOS: 122

<210> SEQ ID NO 1
<211> LENGTH: 21
<212> TYPE: PRT
<213> ORGANISM: Mus musculus

<400> SEQUENCE: 1

Glu Thr Pro Pro Asp Ala Leu Ile Leu Glu Ser Pro Phe Thr Asn Ile
1               5                   10                  15

Arg Glu Glu Ala Lys
            20

<210> SEQ ID NO 2
<211> LENGTH: 22
<212> TYPE: PRT
<213> ORGANISM: Mus musculus

<400> SEQUENCE: 2

Thr Ile Ala Ile Leu Gly Ala Gly His Tyr Val Tyr Ala Asp Gln Pro
1               5                   10                  15

Glu Glu Phe Asn Gln Lys
            20

<210> SEQ ID NO 3
<211> LENGTH: 12
<212> TYPE: PRT
<213> ORGANISM: Mus musculus

<400> SEQUENCE: 3

Asn Asn Ser Ile Trp Asp Glu Leu Phe Phe Asn Lys
1               5                   10

<210> SEQ ID NO 4
<211> LENGTH: 16
<212> TYPE: PRT
<213> ORGANISM: Mus musculus

<400> SEQUENCE: 4

Glu Thr Thr Asp Thr Asp Thr Ala Asp Gln Val Ile Ala Ser Phe Lys
1               5                   10                  15

```
<210> SEQ ID NO 5
<211> LENGTH: 36
<212> TYPE: PRT
<213> ORGANISM: Mus musculus

<400> SEQUENCE: 5

Phe Glu Ala Pro Glu Ala Leu Phe Gln Pro His Leu Ile Asn Val Glu
1               5                   10                  15

Gly Val Gly Val Ala Glu Leu Leu Phe Asn Thr Ile Gln Ala Ala Asp
            20                  25                  30

Ile Asp Thr Arg
        35

<210> SEQ ID NO 6
<211> LENGTH: 21
<212> TYPE: PRT
<213> ORGANISM: Mus musculus

<400> SEQUENCE: 6

His Val Asp Thr Ala Tyr Ala Tyr Gln Val Glu Glu Glu Ile Gly Gln
1               5                   10                  15

Ala Ile Gln Ser Lys
            20

<210> SEQ ID NO 7
<211> LENGTH: 21
<212> TYPE: PRT
<213> ORGANISM: Mus musculus

<400> SEQUENCE: 7

His Val Asp Thr Ala Tyr Ala Tyr Gln Val Glu Glu Glu Ile Gly Gln
1               5                   10                  15

Ala Ile Gln Ser Lys
            20

<210> SEQ ID NO 8
<211> LENGTH: 28
<212> TYPE: PRT
<213> ORGANISM: Mus musculus

<400> SEQUENCE: 8

Val Tyr Leu Ala Ser Leu Glu Thr Leu Asp Asn Gly Lys Pro Phe Gln
1               5                   10                  15

Glu Ser Tyr Val Leu Asp Leu Asp Glu Val Ile Lys
            20                  25

<210> SEQ ID NO 9
<211> LENGTH: 10
<212> TYPE: PRT
<213> ORGANISM: Mus musculus

<400> SEQUENCE: 9

Gly Tyr Ile Val Ile Glu Asp Leu Trp Lys
1               5                   10

<210> SEQ ID NO 10
<211> LENGTH: 21
<212> TYPE: PRT
<213> ORGANISM: Mus musculus

<400> SEQUENCE: 10

Leu Gly Glu Ile Val Thr Thr Ile Pro Thr Ile Gly Phe Asn Val Glu
1               5                   10                  15
```

Thr Val Glu Tyr Lys
            20

<210> SEQ ID NO 11
<211> LENGTH: 21
<212> TYPE: PRT
<213> ORGANISM: Mus musculus

<400> SEQUENCE: 11

Leu Gly Glu Ile Val Thr Thr Ile Pro Thr Ile Gly Phe Asn Val Glu
1               5                   10                  15

Thr Val Glu Tyr Lys
            20

<210> SEQ ID NO 12
<211> LENGTH: 18
<212> TYPE: PRT
<213> ORGANISM: Mus musculus

<400> SEQUENCE: 12

Met Leu Leu Glu Asp Glu Leu Gln Asp Ala Val Leu Leu Leu Phe Ala
1               5                   10                  15

Asn Lys

<210> SEQ ID NO 13
<211> LENGTH: 21
<212> TYPE: PRT
<213> ORGANISM: Mus musculus

<400> SEQUENCE: 13

Leu Gly Glu Ile Val Thr Thr Ile Pro Thr Ile Gly Phe Asn Val Glu
1               5                   10                  15

Thr Val Glu Tyr Lys
            20

<210> SEQ ID NO 14
<211> LENGTH: 21
<212> TYPE: PRT
<213> ORGANISM: Mus musculus

<400> SEQUENCE: 14

Leu Gly Glu Ile Val Thr Thr Ile Pro Thr Ile Gly Phe Asn Val Glu
1               5                   10                  15

Thr Val Glu Tyr Lys
            20

<210> SEQ ID NO 15
<211> LENGTH: 28
<212> TYPE: PRT
<213> ORGANISM: Mus musculus

<400> SEQUENCE: 15

Ser Ser Asn Leu Leu Ala Val Glu Thr Ala Ser Leu Glu Glu Gln Leu
1               5                   10                  15

Gln Gly Trp Gly Glu Val Met Leu Met Ala Asp Lys
            20                  25

<210> SEQ ID NO 16
<211> LENGTH: 8
<212> TYPE: PRT
<213> ORGANISM: Mus musculus

```
<400> SEQUENCE: 16

Ala Phe Val Thr Asp Trp Asp Lys
1               5

<210> SEQ ID NO 17
<211> LENGTH: 26
<212> TYPE: PRT
<213> ORGANISM: Mus musculus

<400> SEQUENCE: 17

Asn Leu Glu Ala Val Glu Thr Leu Gly Ser Thr Ser Thr Ile Cys Ser
1               5                   10                  15

Asp Lys Thr Gly Thr Leu Thr Gln Asn Arg
            20                  25

<210> SEQ ID NO 18
<211> LENGTH: 26
<212> TYPE: PRT
<213> ORGANISM: Mus musculus

<400> SEQUENCE: 18

Asn Leu Glu Ala Val Glu Thr Leu Gly Ser Thr Ser Thr Ile Cys Ser
1               5                   10                  15

Asp Lys Thr Gly Thr Leu Thr Gln Asn Arg
            20                  25

<210> SEQ ID NO 19
<211> LENGTH: 19
<212> TYPE: PRT
<213> ORGANISM: Mus musculus

<400> SEQUENCE: 19

Val Glu Leu Val Pro Pro Thr Pro Ala Glu Ile Pro Thr Ala Ile Gln
1               5                   10                  15

Ser Val Lys

<210> SEQ ID NO 20
<211> LENGTH: 14
<212> TYPE: PRT
<213> ORGANISM: Mus musculus

<400> SEQUENCE: 20

Tyr Ala Glu Ile Val His Leu Thr Leu Pro Asp Gly Thr Lys
1               5                   10

<210> SEQ ID NO 21
<211> LENGTH: 7
<212> TYPE: PRT
<213> ORGANISM: Mus musculus

<400> SEQUENCE: 21

Tyr Asp Asp Val Thr Glu Lys
1               5

<210> SEQ ID NO 22
<211> LENGTH: 10
<212> TYPE: PRT
<213> ORGANISM: Mus musculus

<400> SEQUENCE: 22

Phe Leu Asp Glu Leu Glu Asp Glu Ala Lys
1               5                   10
```

<210> SEQ ID NO 23
<211> LENGTH: 15
<212> TYPE: PRT
<213> ORGANISM: Mus musculus

<400> SEQUENCE: 23

Ser Ser Leu Gln Thr Met Glu Ser Asp Val Tyr Thr Glu Val Arg
1               5                   10                  15

<210> SEQ ID NO 24
<211> LENGTH: 21
<212> TYPE: PRT
<213> ORGANISM: Mus musculus

<400> SEQUENCE: 24

Thr Asp Phe Tyr Asp Gln Cys Asn Asp Val Gly Leu Met Ala Tyr Leu
1               5                   10                  15

Gly Thr Ile Thr Lys
            20

<210> SEQ ID NO 25
<211> LENGTH: 14
<212> TYPE: PRT
<213> ORGANISM: Mus musculus

<400> SEQUENCE: 25

Asn Val Phe Glu Asn Pro Thr Met Val Gln Phe Asp His Arg
1               5                   10

<210> SEQ ID NO 26
<211> LENGTH: 20
<212> TYPE: PRT
<213> ORGANISM: Mus musculus

<400> SEQUENCE: 26

Asp Gly Thr Ala Ala Val His Phe Glu His Ala Trp Gly Asp Gly Val
1               5                   10                  15

Ala Val Leu Arg
            20

<210> SEQ ID NO 27
<211> LENGTH: 18
<212> TYPE: PRT
<213> ORGANISM: Mus musculus

<400> SEQUENCE: 27

Ala Ile Gly Ala Val Pro Leu Ile Gln Gly Glu Tyr Met Ile Pro Cys
1               5                   10                  15

Glu Lys

<210> SEQ ID NO 28
<211> LENGTH: 7
<212> TYPE: PRT
<213> ORGANISM: Mus musculus

<400> SEQUENCE: 28

His Phe Trp Ala Asp Ser Lys
1               5

<210> SEQ ID NO 29
<211> LENGTH: 17
<212> TYPE: PRT
<213> ORGANISM: Mus musculus

<400> SEQUENCE: 29

Val Phe Ser Ser Leu Gly Phe Ser Gly Thr Trp Glu Cys Pro Glu Leu
1               5                   10                  15
Arg

<210> SEQ ID NO 30
<211> LENGTH: 14
<212> TYPE: PRT
<213> ORGANISM: Mus musculus

<400> SEQUENCE: 30

Asn Gly Asp Leu Pro Trp Pro Pro Leu Arg Asn Glu Phe Lys
1               5                   10

<210> SEQ ID NO 31
<211> LENGTH: 16
<212> TYPE: PRT
<213> ORGANISM: Mus musculus

<400> SEQUENCE: 31

Asp Val Leu Leu Thr Asp Phe Val Pro Ser Met Ala Val Tyr Ile Arg
1               5                   10                  15

<210> SEQ ID NO 32
<211> LENGTH: 26
<212> TYPE: PRT
<213> ORGANISM: Mus musculus

<400> SEQUENCE: 32

Tyr Cys Thr Gln Asp Ala Phe Phe Gln Ile Lys Glu Val Asp Met Gly
1               5                   10                  15

Leu Ala Ala Asp Val Gly Thr Leu Gln Arg
            20                  25

<210> SEQ ID NO 33
<211> LENGTH: 15
<212> TYPE: PRT
<213> ORGANISM: Mus musculus

<400> SEQUENCE: 33

Glu Val Asp Met Gly Leu Ala Ala Asp Val Gly Thr Leu Gln Arg
1               5                   10                  15

<210> SEQ ID NO 34
<211> LENGTH: 8
<212> TYPE: PRT
<213> ORGANISM: Mus musculus

<400> SEQUENCE: 34

Ser Leu His Met Tyr Leu Glu Lys
1               5

<210> SEQ ID NO 35
<211> LENGTH: 14
<212> TYPE: PRT
<213> ORGANISM: Mus musculus

<400> SEQUENCE: 35

Phe Tyr Glu Gln Met Asn Gly Pro Val Thr Ser Gly Ser Arg
1               5                   10

<210> SEQ ID NO 36

```
<211> LENGTH: 15
<212> TYPE: PRT
<213> ORGANISM: Mus musculus

<400> SEQUENCE: 36

Ala Met Gly Pro Leu Val Leu Thr Glu Val Leu Phe Asp Glu Lys
1               5                   10                  15

<210> SEQ ID NO 37
<211> LENGTH: 29
<212> TYPE: PRT
<213> ORGANISM: Mus musculus

<400> SEQUENCE: 37

Ser Ser Leu Gly Leu Ser Tyr Tyr Pro Thr Ser Ser Thr Ser Val
1               5                   10                  15

Ser Ser Ser Ser Ser Ser Pro Ser Ser Trp Leu Thr Arg
            20                  25

<210> SEQ ID NO 38
<211> LENGTH: 11
<212> TYPE: PRT
<213> ORGANISM: Mus musculus

<400> SEQUENCE: 38

Asp Cys Tyr Pro Val Gln Glu Thr Phe Ile Arg
1               5                   10

<210> SEQ ID NO 39
<211> LENGTH: 33
<212> TYPE: PRT
<213> ORGANISM: Mus musculus

<400> SEQUENCE: 39

Glu Ser Gly Tyr Leu His Ile Gln Ala Thr Lys Pro Asp Thr Val Gly
1               5                   10                  15

Cys Ala Leu Asn Asp Ser Pro Val Gly Leu Ala Ala Tyr Ile Leu Glu
            20                  25                  30

Lys

<210> SEQ ID NO 40
<211> LENGTH: 16
<212> TYPE: PRT
<213> ORGANISM: Mus musculus

<400> SEQUENCE: 40

Asp Ile Gln Gln Trp Glu Tyr Val Pro Leu Gly Pro Phe Leu Gly Lys
1               5                   10                  15

<210> SEQ ID NO 41
<211> LENGTH: 31
<212> TYPE: PRT
<213> ORGANISM: Mus musculus

<400> SEQUENCE: 41

Glu Val Thr Val Leu Gly Val Ala Thr Ala Pro Thr Gln Val Leu Ser
1               5                   10                  15

Asn Gly Ile Pro Val Ser Asn Phe Thr Tyr Ser Pro Asp Asn Lys
            20                  25                  30

<210> SEQ ID NO 42
<211> LENGTH: 20
<212> TYPE: PRT
```

```
<213> ORGANISM: Mus musculus

<400> SEQUENCE: 42

Gly Leu Ala Phe Ile Gln Asp Pro Asp Gly Tyr Trp Ile Glu Ile Leu
1               5                   10                  15

Asn Pro Asn Lys
            20

<210> SEQ ID NO 43
<211> LENGTH: 23
<212> TYPE: PRT
<213> ORGANISM: Mus musculus

<400> SEQUENCE: 43

Val Gly Asp Gly Ala Gly Gly Ala Phe Gln Pro Tyr Leu Asp Ser Leu
1               5                   10                  15

Arg Gln Glu Leu Gln Gln Arg
            20

<210> SEQ ID NO 44
<211> LENGTH: 14
<212> TYPE: PRT
<213> ORGANISM: Mus musculus

<400> SEQUENCE: 44

Met Gln Leu Ile Met Leu Cys Tyr Asn Pro Asp Phe Glu Lys
1               5                   10

<210> SEQ ID NO 45
<211> LENGTH: 14
<212> TYPE: PRT
<213> ORGANISM: Mus musculus

<400> SEQUENCE: 45

Ile Gln Leu Ala Met Val Cys Tyr Ser Pro Asp Phe Glu Lys
1               5                   10

<210> SEQ ID NO 46
<211> LENGTH: 13
<212> TYPE: PRT
<213> ORGANISM: Mus musculus

<400> SEQUENCE: 46

Tyr Val Thr Leu Ile Tyr Thr Asn Tyr Glu Asn Gly Lys
1               5                   10

<210> SEQ ID NO 47
<211> LENGTH: 22
<212> TYPE: PRT
<213> ORGANISM: Mus musculus

<400> SEQUENCE: 47

Leu Gly Ala Gly Tyr Pro Met Gly Pro Phe Glu Leu Leu Asp Tyr Val
1               5                   10                  15

Gly Leu Asp Thr Thr Lys
            20

<210> SEQ ID NO 48
<211> LENGTH: 12
<212> TYPE: PRT
<213> ORGANISM: Mus musculus

<400> SEQUENCE: 48
```

-continued

Ser Ser Ser Asp Met Pro Glu Thr Ile Thr Ser Arg
1               5                   10

<210> SEQ ID NO 49
<211> LENGTH: 19
<212> TYPE: PRT
<213> ORGANISM: Mus musculus

<400> SEQUENCE: 49

Glu Gly Arg Pro Ser Gly Glu Ala Phe Val Glu Leu Glu Ser Glu Asp
1               5                   10                  15

Glu Val Lys

<210> SEQ ID NO 50
<211> LENGTH: 19
<212> TYPE: PRT
<213> ORGANISM: Mus musculus

<400> SEQUENCE: 50

Glu Gly Arg Pro Ser Gly Glu Ala Phe Val Glu Leu Glu Ser Glu Asp
1               5                   10                  15

Glu Val Lys

<210> SEQ ID NO 51
<211> LENGTH: 8
<212> TYPE: PRT
<213> ORGANISM: Mus musculus

<400> SEQUENCE: 51

Ala Gln Ala Tyr Gln Thr Gly Lys
1               5

<210> SEQ ID NO 52
<211> LENGTH: 10
<212> TYPE: PRT
<213> ORGANISM: Mus musculus

<400> SEQUENCE: 52

Val Tyr Glu Gly Glu Arg Pro Leu Thr Lys
1               5                   10

<210> SEQ ID NO 53
<211> LENGTH: 21
<212> TYPE: PRT
<213> ORGANISM: Mus musculus

<400> SEQUENCE: 53

Leu Tyr Gly Ser Gly Gly Pro Pro Thr Gly Glu Glu Asp Thr Ser
1               5                   10                  15

Glu Lys Asp Glu Leu
            20

<210> SEQ ID NO 54
<211> LENGTH: 11
<212> TYPE: PRT
<213> ORGANISM: Mus musculus

<400> SEQUENCE: 54

Glu Leu Gly Glu Asn Leu Asp Gln Ile Leu Arg
1               5                   10

<210> SEQ ID NO 55
<211> LENGTH: 16

-continued

```
<212> TYPE: PRT
<213> ORGANISM: Mus musculus

<400> SEQUENCE: 55

Asn Ser Asn Leu Val Gly Ala Ala His Glu Glu Leu Gln Gln Ser Arg
1               5                   10                  15

<210> SEQ ID NO 56
<211> LENGTH: 24
<212> TYPE: PRT
<213> ORGANISM: Mus musculus

<400> SEQUENCE: 56

Ser Leu Glu Gly Asp Leu Glu Asp Leu Lys Asp Gln Ile Ala Gln Leu
1               5                   10                  15

Glu Ala Ser Leu Ser Ala Ala Lys
            20

<210> SEQ ID NO 57
<211> LENGTH: 23
<212> TYPE: PRT
<213> ORGANISM: Mus musculus

<400> SEQUENCE: 57

Ser Glu Ala Glu Leu Ala Thr Ala Leu Ser Asp Lys Gln Gly Leu Glu
1               5                   10                  15

Thr Glu Val Ala Glu Leu Arg
            20

<210> SEQ ID NO 58
<211> LENGTH: 13
<212> TYPE: PRT
<213> ORGANISM: Mus musculus

<400> SEQUENCE: 58

Gly Leu Trp Pro Gly Val Glu Asp Leu Ser Leu Asn Lys
1               5                   10

<210> SEQ ID NO 59
<211> LENGTH: 27
<212> TYPE: PRT
<213> ORGANISM: Mus musculus

<400> SEQUENCE: 59

Asn Thr Leu Val Val Ser Phe Ala Asp Leu Glu Gln Phe Asn Gln Gln
1               5                   10                  15

Leu Ser Thr Thr Ile Gln Glu Glu Phe Tyr Arg
            20                  25

<210> SEQ ID NO 60
<211> LENGTH: 25
<212> TYPE: PRT
<213> ORGANISM: Mus musculus

<400> SEQUENCE: 60

Ala Ser Val Pro Glu Gly Phe Leu Ser Glu Leu Thr Gln Gln Leu Ala
1               5                   10                  15

Gln Ala Thr Gly Lys Pro Ala Gln Tyr
            20                  25

<210> SEQ ID NO 61
<211> LENGTH: 12
<212> TYPE: PRT
```

<213> ORGANISM: Mus musculus

<400> SEQUENCE: 61

Ala Phe Lys Asp Asp Tyr Val Val Ser Leu Val Arg
1               5                   10

<210> SEQ ID NO 62
<211> LENGTH: 21
<212> TYPE: PRT
<213> ORGANISM: Mus musculus

<400> SEQUENCE: 62

Val Leu Gln Tyr Tyr Gln Glu Ser Glu Lys Pro Glu Glu Leu Gly Ser
1               5                   10                  15

Val Thr Val Gln Lys
            20

<210> SEQ ID NO 63
<211> LENGTH: 15
<212> TYPE: PRT
<213> ORGANISM: Mus musculus

<400> SEQUENCE: 63

Gln Gly Ala Asp Thr Leu Ala Phe Met Ser Leu Leu Glu Glu Lys
1               5                   10                  15

<210> SEQ ID NO 64
<211> LENGTH: 15
<212> TYPE: PRT
<213> ORGANISM: Mus musculus

<400> SEQUENCE: 64

Tyr Leu Leu Glu Thr Ser Gly Asn Leu Asp Gly Leu Glu Tyr Lys
1               5                   10                  15

<210> SEQ ID NO 65
<211> LENGTH: 21
<212> TYPE: PRT
<213> ORGANISM: Mus musculus

<400> SEQUENCE: 65

Ser Thr Glu Ala Pro Leu Ile Ile Arg Pro Asp Ser Gly Asn Pro Leu
1               5                   10                  15

Asp Thr Val Leu Lys
            20

<210> SEQ ID NO 66
<211> LENGTH: 10
<212> TYPE: PRT
<213> ORGANISM: Mus musculus

<400> SEQUENCE: 66

Phe Tyr Glu Glu Val His Asp Leu Glu Arg
1               5                   10

<210> SEQ ID NO 67
<211> LENGTH: 21
<212> TYPE: PRT
<213> ORGANISM: Mus musculus

<400> SEQUENCE: 67

Gln Trp Gln Pro Asp Ile Glu Trp Ala Glu Gln Phe Ser Gly Ala Val
1               5                   10                  15

Met Tyr Pro Ser Lys
            20

<210> SEQ ID NO 68
<211> LENGTH: 10
<212> TYPE: PRT
<213> ORGANISM: Mus musculus

<400> SEQUENCE: 68

Gly Ala Pro Tyr Asn Ala Leu Ala Gly Lys
1               5                   10

<210> SEQ ID NO 69
<211> LENGTH: 16
<212> TYPE: PRT
<213> ORGANISM: Mus musculus

<400> SEQUENCE: 69

Thr Leu Ala Glu Ile Ala Lys Val Glu Leu Asp Asn Met Pro Leu Arg
1               5                   10                  15

<210> SEQ ID NO 70
<211> LENGTH: 29
<212> TYPE: PRT
<213> ORGANISM: Mus musculus

<400> SEQUENCE: 70

Thr Phe Phe Ile Leu His Asp Ile Asn Ser Asp Gly Val Leu Asp Glu
1               5                   10                  15

Gln Glu Leu Glu Ala Leu Phe Thr Lys Glu Leu Glu Lys
            20                  25

<210> SEQ ID NO 71
<211> LENGTH: 16
<212> TYPE: PRT
<213> ORGANISM: Mus musculus

<400> SEQUENCE: 71

Tyr Leu Gln Glu Val Ile Asn Val Leu Glu Thr Asp Gly His Phe Arg
1               5                   10                  15

<210> SEQ ID NO 72
<211> LENGTH: 13
<212> TYPE: PRT
<213> ORGANISM: Mus musculus

<400> SEQUENCE: 72

Gln Val Ile Glu Val Leu Glu Thr Asp Pro His Phe Arg
1               5                   10

<210> SEQ ID NO 73
<211> LENGTH: 12
<212> TYPE: PRT
<213> ORGANISM: Mus musculus

<400> SEQUENCE: 73

Glu Phe Gly Glu Glu Ala Leu Asn Ser Leu Gln Lys
1               5                   10

<210> SEQ ID NO 74
<211> LENGTH: 18
<212> TYPE: PRT
<213> ORGANISM: Mus musculus

<400> SEQUENCE: 74

```
Val Asn Asp Glu His Pro Ala Tyr Leu Ala Ser Asp Glu Ile Thr Thr
1               5                   10                  15
Val Arg
```

<210> SEQ ID NO 75
<211> LENGTH: 18
<212> TYPE: PRT
<213> ORGANISM: Mus musculus

<400> SEQUENCE: 75

```
Leu Leu Leu Asp Glu Phe Leu Gly Tyr Asp Asp Ile Leu Met Ser Ser
1               5                   10                  15
Val Lys
```

<210> SEQ ID NO 76
<211> LENGTH: 20
<212> TYPE: PRT
<213> ORGANISM: Mus musculus

<400> SEQUENCE: 76

```
Ser Ala Tyr Asn Glu Gly Asp Tyr Tyr His Thr Val Leu Trp Met Glu
1               5                   10                  15
Gln Val Leu Lys
            20
```

<210> SEQ ID NO 77
<211> LENGTH: 30
<212> TYPE: PRT
<213> ORGANISM: Mus musculus

<400> SEQUENCE: 77

```
Thr Gly Pro Ala Ala Thr Thr Leu Ser Asp Thr Ala Ala Ala Glu Ser
1               5                   10                  15
Leu Val Asp Ser Ser Glu Val Thr Val Ile Gly Phe Phe Lys
            20                  25                  30
```

<210> SEQ ID NO 78
<211> LENGTH: 17
<212> TYPE: PRT
<213> ORGANISM: Mus musculus

<400> SEQUENCE: 78

```
His Asn Gln Leu Pro Leu Val Ile Glu Phe Thr Glu Gln Thr Ala Pro
1               5                   10                  15
Lys
```

<210> SEQ ID NO 79
<211> LENGTH: 17
<212> TYPE: PRT
<213> ORGANISM: Mus musculus

<400> SEQUENCE: 79

```
Glu Ile Val Ser Phe Gly Ser Gly Tyr Gly Gly Asn Ser Leu Leu Gly
1               5                   10                  15
Lys
```

<210> SEQ ID NO 80
<211> LENGTH: 11
<212> TYPE: PRT
<213> ORGANISM: Mus musculus

```
<400> SEQUENCE: 80

Ala Val Glu Asn Tyr Leu Ile Gln Met Ala Arg
1               5                   10

<210> SEQ ID NO 81
<211> LENGTH: 14
<212> TYPE: PRT
<213> ORGANISM: Mus musculus

<400> SEQUENCE: 81

Phe Tyr Gly Pro Glu Gly Pro Tyr Gly Val Phe Ala Gly Arg
1               5                   10

<210> SEQ ID NO 82
<211> LENGTH: 20
<212> TYPE: PRT
<213> ORGANISM: Mus musculus

<400> SEQUENCE: 82

Gly Asp Gln Pro Gly Ala Ser Gly Asp Asn Asp Asp Glu Pro Pro
1               5                   10                  15

Pro Leu Pro Arg
            20

<210> SEQ ID NO 83
<211> LENGTH: 14
<212> TYPE: PRT
<213> ORGANISM: Mus musculus

<400> SEQUENCE: 83

Phe Tyr Gly Pro Ala Gly Pro Tyr Gly Ile Phe Ala Gly Arg
1               5                   10

<210> SEQ ID NO 84
<211> LENGTH: 18
<212> TYPE: PRT
<213> ORGANISM: Mus musculus

<400> SEQUENCE: 84

Leu Cys Ser Gly Pro Gly Ala Gly Glu Glu Ser Pro Ala Ala Thr Leu
1               5                   10                  15

Pro Arg

<210> SEQ ID NO 85
<211> LENGTH: 7
<212> TYPE: PRT
<213> ORGANISM: Mus musculus

<400> SEQUENCE: 85

Val Phe Glu Ser Ile Gly Lys
1               5

<210> SEQ ID NO 86
<211> LENGTH: 13
<212> TYPE: PRT
<213> ORGANISM: Mus musculus

<400> SEQUENCE: 86

Asn Glu Thr Gly Gly Gly Glu Gly Ile Glu Val Leu Lys
1               5                   10

<210> SEQ ID NO 87
<211> LENGTH: 22
```

```
<212> TYPE: PRT
<213> ORGANISM: Mus musculus

<400> SEQUENCE: 87

Ala Leu Ile Glu Ser Gly Leu Gly Thr Asp Phe Ser Pro Asp Val Gly
1               5                   10                  15

Tyr Asn Gly Tyr Thr Arg
            20

<210> SEQ ID NO 88
<211> LENGTH: 23
<212> TYPE: PRT
<213> ORGANISM: Mus musculus

<400> SEQUENCE: 88

Thr Gln Leu Met Ser Met Leu Met Met Asn Leu Glu Ser Arg Pro Val
1               5                   10                  15

Ile Phe Glu Asp Val Gly Arg
            20

<210> SEQ ID NO 89
<211> LENGTH: 14
<212> TYPE: PRT
<213> ORGANISM: Mus musculus

<400> SEQUENCE: 89

Tyr Lys Tyr Gly Tyr Glu Ile Pro Val Asp Met Leu Cys Lys
1               5                   10

<210> SEQ ID NO 90
<211> LENGTH: 19
<212> TYPE: PRT
<213> ORGANISM: Mus musculus

<400> SEQUENCE: 90

Arg Phe Phe Pro Tyr Tyr Val Tyr Asn Ile Ile Gly Gly Leu Asp Glu
1               5                   10                  15

Glu Gly Lys

<210> SEQ ID NO 91
<211> LENGTH: 10
<212> TYPE: PRT
<213> ORGANISM: Mus musculus

<400> SEQUENCE: 91

Leu Leu Ala Asn Met Val Tyr Gln Tyr Lys
1               5                   10

<210> SEQ ID NO 92
<211> LENGTH: 10
<212> TYPE: PRT
<213> ORGANISM: Mus musculus

<400> SEQUENCE: 92

Phe Gly Ala Val Glu Ala Ala Met Ala Lys
1               5                   10

<210> SEQ ID NO 93
<211> LENGTH: 34
<212> TYPE: PRT
<213> ORGANISM: Mus musculus

<400> SEQUENCE: 93
```

-continued

```
Ser His Leu Gly Met Phe Pro Gln Asn Ser Thr Glu Ala Asn Arg
1               5                   10                  15

Asp Thr Glu Thr Gly Thr Glu Ala Ser Ile Leu Gly Ser Gly Glu
            20                  25                  30

Tyr Lys

<210> SEQ ID NO 94
<211> LENGTH: 16
<212> TYPE: PRT
<213> ORGANISM: Mus musculus

<400> SEQUENCE: 94

Ala Tyr Leu Glu Ser Glu Val Ala Ile Ser Glu Glu Leu Val Gln Lys
1               5                   10                  15

<210> SEQ ID NO 95
<211> LENGTH: 7
<212> TYPE: PRT
<213> ORGANISM: Mus musculus

<400> SEQUENCE: 95

Trp Leu Ser Gln Tyr Ile Asp
1               5

<210> SEQ ID NO 96
<211> LENGTH: 23
<212> TYPE: PRT
<213> ORGANISM: Mus musculus

<400> SEQUENCE: 96

Gly Val Tyr Ile Ile Gly Ser Ser Gly Phe Asp Ser Ile Pro Ala Asp
1               5                   10                  15

Leu Gly Val Leu Tyr Thr Arg
            20

<210> SEQ ID NO 97
<211> LENGTH: 25
<212> TYPE: PRT
<213> ORGANISM: Mus musculus

<400> SEQUENCE: 97

Leu Leu Asn Leu Gly Leu Ile Thr Glu Ser Gln Ala His Thr Leu Glu
1               5                   10                  15

Asp Glu Val Ala Glu Ala Leu Gln Lys
            20                  25

<210> SEQ ID NO 98
<211> LENGTH: 14
<212> TYPE: PRT
<213> ORGANISM: Mus musculus

<400> SEQUENCE: 98

Thr Val Gln Ile Glu Ala Ser Thr Val Glu Ile Glu Glu Arg
1               5                   10

<210> SEQ ID NO 99
<211> LENGTH: 17
<212> TYPE: PRT
<213> ORGANISM: Mus musculus

<400> SEQUENCE: 99

Thr Thr Gly Met Gly Ala Ile Tyr Gly Met Ala Gln Ala Thr Ile Asp
1               5                   10                  15
```

Arg

<210> SEQ ID NO 100
<211> LENGTH: 17
<212> TYPE: PRT
<213> ORGANISM: Mus musculus

<400> SEQUENCE: 100

Leu Lys Asp Phe Glu Pro Tyr Leu Glu Ile Leu Glu Ser Tyr Ser Thr
1               5                   10                  15

Lys

<210> SEQ ID NO 101
<211> LENGTH: 17
<212> TYPE: PRT
<213> ORGANISM: Mus musculus

<400> SEQUENCE: 101

Tyr Tyr Gly Gly Ala Glu Val Val Asp Glu Ile Glu Leu Leu Cys Gln
1               5                   10                  15

Arg

<210> SEQ ID NO 102
<211> LENGTH: 21
<212> TYPE: PRT
<213> ORGANISM: Mus musculus

<400> SEQUENCE: 102

Ile Met Gly Leu Asp Leu Pro Asp Gly Gly His Leu Thr His Gly Tyr
1               5                   10                  15

Met Ser Asp Val Lys
                20

<210> SEQ ID NO 103
<211> LENGTH: 16
<212> TYPE: PRT
<213> ORGANISM: Mus musculus

<400> SEQUENCE: 103

Asp Val Pro Ala Ser Gly Met Tyr Phe Met Thr Tyr Glu Trp Leu Lys
1               5                   10                  15

<210> SEQ ID NO 104
<211> LENGTH: 31
<212> TYPE: PRT
<213> ORGANISM: Mus musculus

<400> SEQUENCE: 104

Ala Glu Gln Leu Glu Pro Leu Glu Tyr Leu Val Ser Ala Ala Glu Ala
1               5                   10                  15

Gly Ala Met Thr Leu Cys Ile Thr Asn Pro Leu Trp Val Thr Lys
                20                  25                  30

<210> SEQ ID NO 105
<211> LENGTH: 8
<212> TYPE: PRT
<213> ORGANISM: Mus musculus

<400> SEQUENCE: 105

Tyr Glu Leu Pro Leu Val Ile Lys
1               5

-continued

<210> SEQ ID NO 106
<211> LENGTH: 8
<212> TYPE: PRT
<213> ORGANISM: Mus musculus

<400> SEQUENCE: 106

Leu Ile Leu Glu Gln Met Gln Lys
1               5

<210> SEQ ID NO 107
<211> LENGTH: 30
<212> TYPE: PRT
<213> ORGANISM: Mus musculus

<400> SEQUENCE: 107

Asp Ser Asn Thr Val Leu Leu Pro Ser Asn Pro Ser Asp Val Thr Ser
1               5                   10                  15

Met Val Ala Gln Ala Met Gly Val Tyr Gly Ala Leu Thr Lys
            20                  25                  30

<210> SEQ ID NO 108
<211> LENGTH: 18
<212> TYPE: PRT
<213> ORGANISM: Mus musculus

<400> SEQUENCE: 108

Gly Gln Asn Asp Leu Met Gly Thr Ala Glu Asp Phe Ala Asp Gln Phe
1               5                   10                  15

Leu Arg

<210> SEQ ID NO 109
<211> LENGTH: 13
<212> TYPE: PRT
<213> ORGANISM: Mus musculus

<400> SEQUENCE: 109

Leu Cys Leu Ile Ser Thr Phe Leu Glu Asp Gly Ile Arg
1               5                   10

<210> SEQ ID NO 110
<211> LENGTH: 16
<212> TYPE: PRT
<213> ORGANISM: Mus musculus

<400> SEQUENCE: 110

Ser Ala Phe Ser Asn Leu Phe Gly Gly Glu Pro Leu Ser Tyr Thr Arg
1               5                   10                  15

<210> SEQ ID NO 111
<211> LENGTH: 23
<212> TYPE: PRT
<213> ORGANISM: Mus musculus

<400> SEQUENCE: 111

Ile Val Asp Asp Cys Gly Gly Ala Phe Thr Met Gly Thr Ile Gly Gly
1               5                   10                  15

Gly Ile Phe Gln Ala Phe Lys
            20

<210> SEQ ID NO 112
<211> LENGTH: 22
<212> TYPE: PRT
<213> ORGANISM: Mus musculus

<400> SEQUENCE: 112

Gly Lys Glu Asp Pro Trp Asn Ser Ile Thr Ser Gly Ala Leu Thr Gly
1               5                   10                  15

Ala Ile Leu Ala Ala Arg
            20

<210> SEQ ID NO 113
<211> LENGTH: 13
<212> TYPE: PRT
<213> ORGANISM: Mus musculus

<400> SEQUENCE: 113

Thr Lys Glu Glu Asp Gly Arg Glu Ala Val Glu Phe Arg
1               5                   10

<210> SEQ ID NO 114
<211> LENGTH: 20
<212> TYPE: PRT
<213> ORGANISM: Mus musculus

<400> SEQUENCE: 114

Leu Glu Gln Leu Asn Gln Tyr Pro Asp Phe Asn Asn Tyr Leu Ile Phe
1               5                   10                  15

Val Leu Thr Lys
            20

<210> SEQ ID NO 115
<211> LENGTH: 20
<212> TYPE: PRT
<213> ORGANISM: Mus musculus

<400> SEQUENCE: 115

Phe Phe Leu Glu Glu Ile Gln Leu Gly Glu Glu Leu Leu Ala Gln Gly
1               5                   10                  15

Asp Tyr Glu Lys
            20

<210> SEQ ID NO 116
<211> LENGTH: 19
<212> TYPE: PRT
<213> ORGANISM: Mus musculus

<400> SEQUENCE: 116

Asp Leu Leu Glu Gln Met Met Ala Glu Met Ile Gly Glu Phe Pro Asp
1               5                   10                  15

Leu His Arg

<210> SEQ ID NO 117
<211> LENGTH: 9
<212> TYPE: PRT
<213> ORGANISM: Mus musculus

<400> SEQUENCE: 117

Tyr Gln Phe Thr Pro Ala Phe Leu Arg
1               5

```
<210> SEQ ID NO 118
<211> LENGTH: 9
<212> TYPE: PRT
<213> ORGANISM: Mus musculus

<400> SEQUENCE: 118

Tyr Gln Phe Thr Pro Ala Phe Leu Arg
1               5

<210> SEQ ID NO 119
<211> LENGTH: 25
<212> TYPE: PRT
<213> ORGANISM: Mus musculus

<400> SEQUENCE: 119

Asn Leu Asp Ser Leu Glu Glu Asp Leu Asp Phe Leu Arg Asp Gln Phe
1               5                   10                  15

Thr Thr Thr Glu Val Asn Met Ala Arg
            20                  25

<210> SEQ ID NO 120
<211> LENGTH: 29
<212> TYPE: PRT
<213> ORGANISM: Mus musculus

<400> SEQUENCE: 120

Thr Ala Phe Asp Glu Ala Ile Ala Glu Leu Asp Thr Leu Asn Glu Glu
1               5                   10                  15

Ser Tyr Lys Asp Ser Thr Leu Ile Met Gln Leu Leu Arg
            20                  25

<210> SEQ ID NO 121
<211> LENGTH: 29
<212> TYPE: PRT
<213> ORGANISM: Mus musculus

<400> SEQUENCE: 121

Ala Ala Phe Asp Asp Ala Ile Ala Glu Leu Asp Thr Leu Ser Glu Glu
1               5                   10                  15

Ser Tyr Lys Asp Ser Thr Leu Ile Met Gln Leu Leu Arg
            20                  25

<210> SEQ ID NO 122
<211> LENGTH: 29
<212> TYPE: PRT
<213> ORGANISM: Mus musculus

<400> SEQUENCE: 122

Tyr Asp Pro Ser Leu Lys Pro Pro Phe Asp Ile Gly Phe Glu Gly Ile
1               5                   10                  15

Gly Glu Val Val Ala Leu Gly Leu Ser Ala Ser Ala Arg
            20                  25
```